US009150556B2

(12) United States Patent
Abeywardane et al.

(10) Patent No.: US 9,150,556 B2
(45) Date of Patent: Oct. 6, 2015

(54) BENZIMIDAZOLONE CHYMASE INHIBITORS

(75) Inventors: Asitha Abeywardane, Danbury, CT (US); Brian Nicholas Cook, Danbury, CT (US); Stephane De Lombaert, Madison, CT (US); Michel Jose Emmanuel, New Fairfield, CT (US); Xin Guo, Danbury, CT (US); Ming-Hong Hao, Ridgefield, CT (US); Jin Mi Kim, Sandy Hook, CT (US); Ho Yin Lo, Bethel, CT (US); Chuk Chui Man, Ridgefield, CT (US); Tina Marie Morwick, New Milford, CT (US); Peter Allen Nemoto, Southbury, CT (US); Kevin Chungeng Qian, New Milford, CT (US); Hidenori Takahashi, LaGrangeville, NY (US); Steven John Taylor, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 926 days.

(21) Appl. No.: 12/596,152

(22) PCT Filed: May 15, 2008

(86) PCT No.: PCT/US2008/063630
§ 371 (c)(1),
(2), (4) Date: Oct. 26, 2009

(87) PCT Pub. No.: WO2008/147697
PCT Pub. Date: Dec. 4, 2008

(65) Prior Publication Data
US 2010/0240702 A1 Sep. 23, 2010

Related U.S. Application Data

(60) Provisional application No. 60/939,452, filed on May 22, 2007.

(51) Int. Cl.
| | |
|---|---|
| C07D 235/26 | (2006.01) |
| C07D 401/14 | (2006.01) |
| C07D 403/06 | (2006.01) |
| C07D 403/14 | (2006.01) |
| C07D 405/12 | (2006.01) |
| C07D 409/06 | (2006.01) |
| C07D 409/12 | (2006.01) |
| C07D 409/14 | (2006.01) |
| C07D 413/06 | (2006.01) |
| C07D 417/06 | (2006.01) |
| C07D 417/14 | (2006.01) |
| C07D 471/04 | (2006.01) |

(52) U.S. Cl.
CPC ............ *C07D 409/06* (2013.01); *C07D 235/26* (2013.01); *C07D 401/14* (2013.01); *C07D 403/06* (2013.01); *C07D 403/14* (2013.01); *C07D 405/12* (2013.01); *C07D 409/12* (2013.01); *C07D 409/14* (2013.01); *C07D 413/06* (2013.01); *C07D 417/06* (2013.01); *C07D 417/14* (2013.01); *C07D 471/04* (2013.01)

(58) Field of Classification Search
CPC .. C07D 235/22; C07D 135/26; C07D 235/26; C07D 401/14; C07D 403/06; C07D 403/14; C07D 405/12; C07D 409/06; C07D 409/12; C07D 409/14; C07D 413/06; C07D 17/06; C07D 17/14; C07D 71/04; A61K 31/4184
USPC ........................................ 514/387; 548/304.4
See application file for complete search history.

(56) References Cited

U.S. PATENT DOCUMENTS

| | | | |
|---|---|---|---|
| 4,130,560 A | 12/1978 | Habermeier | |
| 4,209,527 A * | 6/1980 | Sarges ........................... 514/387 |
| 4,377,695 A | 3/1983 | Lautenschlager et al. | |
| 6,248,770 B1 | 6/2001 | Ries et al. | |
| 6,420,410 B1 | 7/2002 | Sperl et al. | |
| 6,919,331 B2 | 7/2005 | Yu et al. | |
| 2003/0207868 A1 | 11/2003 | Yu et al. | |

FOREIGN PATENT DOCUMENTS

| | | | |
|---|---|---|---|
| EP | 1249450 A1 | 10/2002 |
| JP | 57108074 A | 7/1982 |
| JP | 2001507679 A | 6/2001 |
| JP | 2003505376 A | 2/2003 |
| JP | 2006520383 A | 9/2006 |
| WO | 9824806 A2 | 6/1998 |
| WO | WO 0105770 A1 * | 1/2001 |
| WO | 0226228 A1 | 4/2002 |
| WO | 2004082605 A2 | 9/2004 |
| WO | 2006078698 A1 | 7/2006 |

(Continued)

OTHER PUBLICATIONS

Howard, H.R. et al., "Synthesis and aldose reductase inhibitory activity of substituted 2(1H)-benzimidazolone-and oxoindole-1-acetic acids". European Journal of Medicinal Chemistry, vol. 27, 1992, pp. 779-789.
International Search Report for PCT/US08/063630 mailed Aug. 27, 2009.
Wang, X.A. et al., "Respiratory syncytial virus fusion inhibitors. Part 5: Optimization of benzimidazole substitution patterns towards derivatives with improved activity." Bioorganic and Medicinal Chemistry Letters, vol. 17, 2007, pp. 4592-4598.
Yu, K-L, et al., "Respiratory syncytial virus fusion inhibitors. Part 3: Water soluble benzimidazol-2-one derivatives with antiviral activity in vivor". Bioorganic and Mediciinal Chemistry Letters, vol. 16, 2006, pp. 1115-1121.

(Continued)

*Primary Examiner* — Sarah Pihonak
(74) *Attorney, Agent, or Firm* — Michael P. Morris; Anthony P. Bottino; Usha R. Patel

(57) ABSTRACT

Disclosed are small molecule inhibitors which are useful in treating various diseases and conditions involving chymase.

2 Claims, No Drawings

(56) References Cited

FOREIGN PATENT DOCUMENTS

| WO | 2007061692 | A2 | 5/2007 |
| WO | 2007061694 | A2 | 5/2007 |
| WO | 2007061696 | A2 | 5/2007 |
| WO | 20080147697 | A1 | 12/2008 |

OTHER PUBLICATIONS

Yu, K-L, et al., "Respiratory syncytial virus fusion inhibitors. Part 4: Optimization for oral bioavailability". Bioorganic and Medicinal Chemistry Letters, vol. 17, 2007, pp. 895-901.

Yu, K-L, et al., "Respiratory syncytial virus inhibitors. Part 2: Benzimidazole-2-one-derivatives". Bioorganic and Medicinal Chemistry Letters, vol. 14, 2004, pp. 1133-1137.

* cited by examiner

BENZIMIDAZOLONE CHYMASE INHIBITORS

APPLICATION DATA

This application is a 371 National Stage filing of PCT/US2008/063630 filed on May 15, 2008. This application also claims benefit to U.S. provisional application Ser. No. 60/939,452 filed on May 22, 2007.

FIELD OF THE INVENTION

The invention relates to small molecule inhibitors which are useful in treating various diseases and conditions involving Chymase.

BACKGROUND OF THE INVENTION

In cardiac tissue of cardiomyopathic patients, transforming growth factor-β (TGF-β), which has been demonstrated to stimulate cardiac fibrosis in animal models (Kuwahara, et al. Circulation, 2002, 106, 130), is increased (Li et al., Circulation, 1997, 96, 874). In the myocardial fibrotic area, it is known that mast cells are increased in number and may contribute to the development of fibroblast proliferation in cardiac tissues of patients with cardiomyopathy (Patella et al., Circulation, 1998, 97, 971). Chymase is a chymotrypsin-like serine protease contained in the secretory granules of mast cells. Although the precise physiological roles of Chymase have not been completely revealed, Chymase is known to transform angiotensin I to angiotensin II and may contribute to activation of TGF-β, matrix proteases, and cytokines (Taipale et al., J. Biol. Chem., 1995, 270, 4689; Takai et al., Life Sci., 1996, 58, 591; Takai et al., Circulation, 1999, 100, 654).

A potent and selective Chymase inhibitor may have potential use as a treatment of chronic heart failure, atherosclerosis, restenosis, and myocardial infarction by inhibiting local production of angiotensin II in the heart and release of TGF-β, two independent mediators of cardiac remodeling. An inhibitor may also have potential use for treatment of mast cell mediated diseases such as dermatitis, asthma, chronic obstructive pulmonary disease (COPD), and pulmonary inflammation, since Chymase is implicated in microvascular leakage, neutrophil accumulation, the stimulation of mucus secretion, and the modulation of cytokines (He et al., Eur. J. Pharmacol., 1998, 352, 91).

Several small molecule Chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061). Additionally, a Chymase inhibitor has been demonstrated to be efficacious in a sheep asthma model (WO 2005/073214). However, there is no example of commercialization of a Chymase inhibitor as a medicament.

SUMMARY OF THE INVENTION

It is therefore an object of the invention to provide a small molecule a Chymase inhibitor as defined herein, and pharmaceutical compositions thereof.

It is also an object of the invention to provide methods of using said Chymase inhibitors to treat various diseases and conditions related thereto.

It is a further object of the invention to provide processes of preparing said Chymase inhibitors.

DETAILED DESCRIPTION OF THE INVENTION

In a first generic embodiment, there is provided a compound of the formula (I):

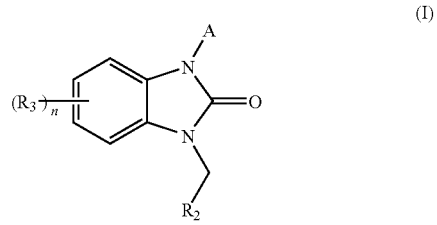

(I)

wherein:

A is $C_1$-$C_8$ linear or branched alkyl, $C_2$-$C_8$ linear or branched alkenyl, $(CH_2)_m$-aryl-$(CH_2)_m$, $(CH_2)_m$—$C_3$-$C_8$ cycloalkyl-$(CH_2)_m$ or $(CH_2)_m$—$C_3$-$C_8$ cycloalkenyl-$(CH_2)_m$, each optionally interrupted at each possible occurrence by one or more —O—, —S—, —SO—, —SO$_2$— or —NRa—, and A is substituted with $R_1$ and further optionally substituted with 1 to 5 substituents independently chosen at each possible occurrence from $C_{1-5}$ linear or branched alkyl, $C_{2-5}$ linear or branched alkenyl, $C_3$-$C_7$ cycloalkyl, $C_3$-$C_7$ cycloalkenyl, $C_{1-4}$ alkoxy, $C_{1-4}$ alkoxycarbonyl, carboxyl, ($C_{1-4}$ alkyl)sulfonyl, hydroxyl, halogen, $C_1$-$C_6$ haloalkyl, trifluromethylsulfonyl, trifluoromethoxy, difluoromethoxy, cyano, heterocycloalkyl, aryl, heteroaryl and carboxamido or sulfonamido wherein the nitrogen atom of the said carboxamide or sulfonamide is optionally independently mono or disubstituted with $C_{1-3}$ linear or branched alkyl, or the nitrogen atom of the said carboxamide or sulfonamide is part of a pyrrolidinyl, piperdinyl, morpholinyl or piperazinyl ring;

$R_1$ is —C(O)—$R_4$, —C(O)—N($R_5$)—SO$_2$$R_6$, or —C(O)—NR$_5$R$_7$, wherein $R_4$ is chosen from hydroxyl, $C_1$-$C_4$ alkoxy and aryloxy; $R_5$ is chosen from hydrogen or $C_1$-$C_3$ alkyl; $R_6$ is chosen from aryl and heteroaryl; or $R_6$ is chosen from $C_1$-$C_6$ linear or branched alkyl, amino and $C_3$-$C_6$ cycloalkyl, each optionally independently substituted with 1-5 substituents chosen from $C_{1-5}$ alkyl, $C_{1-4}$ alkoxy, halogen, cyano, aryl and heteroaryl; $R_7$ is chosen from hydrogen, cyano, aryl and heteroaryl; or $R_7$ is chosen from $C_1$-$C_6$ linear or branched alkyl and $C_3$-$C_6$ cycloalkyl, each optionally independently substituted with 1-5 substituents chosen from $C_{1-5}$ alkyl, $C_{1-4}$ alkoxy, halogen, cyano, aryl and heteroaryl;

or $R_1$ is —SO$_2$$R_8$ or —SO$_2$—NH—C(O)$R_9$, wherein $R_8$ is chosen from hydroxyl, amino, $C_1$-$C_3$ alkoxy, aryloxy, trifluoromethyl, $C_1$-$C_3$ alkylamino, $C_1$-$C_3$ dialkylamino, 1-pyrrolidino, 1-piperidino and 1-morpholino; $R_9$ is chosen from aryl and heteroaryl; or $R_9$ is chosen from $C_1$-$C_6$ linear or branched alkyl and $C_3$-$C_6$ cycloalkyl, each optionally independently substituted with 1-5 substituents chosen from $C_{1-5}$ alkyl, $C_{1-4}$ alkoxy, halogen, cyano, aryl and heteroaryl;

or $R_1$ is —NH—C(O)—N($R_5$)—SO$_2$$R_{10}$ wherein $R_{10}$ is chosen from $C_{1-5}$ alkyl, aryl and heteroaryl; or $R_1$ is tetrazolyl or dioxothiadiazolidinone;

$R_2$ is aryl or heteroaryl;

$R_3$ is carboxyl, halogen, cyano, $C_{1-3}$ alkyl, —NHR$_{11}$, pyrrolidino, piperidino, morpholino, —C(O)—R$_{12}$ or —C(O)—NR$_{13}$R$_{14}$, R$_{11}$ is chosen from hydrogen, carboxamido, $C_1$-$C_4$ alkyl, $C_1$-$C_4$ alkoxycarbonyl, aryl, benzyl and heteroaryl; $R_{12}$ is $C_1$-$C_4$ alkoxy; $R_{13}$ is heteroaryl, heterocyclyl or $C_1$-$C_4$ alkyl, each optionally substituted with 1-3 substituents chosen from aryl, heteroaryl, heterocyclyl, hydroxy, $C_{1-3}$ alkoxy, oxo, thioalkyl and dimethylamino; $R_{14}$ is chosen from hydrogen and $C_1$-$C_4$ alkyl optionally substituted with 1-2 hydroxyl groups; or $R_{13}$ and $R_{14}$ together with the nitrogen atom to which they are attached form a 5-6 membered heterocyclic ring optionally substituted with 1-3 substituents chosen from halogen, $C_{1-3}$ alkyl, $C_{1-3}$ alkoxy, hydroxyl, hydroxymethyl, carboxamido, N-acetyl-N-methyl amino and cyano;

n=0-3
and
m=0-6;

wherein all aryl or heteroaryl groups are optionally substituted with 1-5 substitutents chosen from halogen, hydroxyl, cyano, $C_{1-6}$ linear or branched alkyl, $C_{1-6}$ linear or branched alkoxy, $C_{1-6}$ linear or branched alkylthio, $C_{1-6}$ linear or branched alkylsulfonyl, phenylsulfonyl, $C_{1-6}$ linear or branched acyl, $C_{1-6}$ linear or branched acylamino, polyhalomethyl, polyhalomethoxy, phenyl, oxo, —COORa, —CON(Rc)Ra, $SO_2N(Rc)Ra$, —N(Rc)Ra and phenoxy optionally substituted by one or more halogens;

Ra and Rc are each independently C1-3 alkyl or hydrogen; with the proviso that when A is $C_1$-$C_3$ linear or branched alkyl, and $R_1$ is —C(O)—OH, —C(O)—$NH_2$, or —C(O)—$OC_2H_3$ and $R_3$ is lower alkyl, lower alkoxy or halogen, and n=0-2, then $R_2$ is not unsubstituted naphthyl, unsubstituted thienyl, unsubstituted furanyl, or phenyl with 0-2 substituents selected from halogen, trifluoromethyl, lower alkyl or lower alkoxy;

or a pharmaceutically acceptable salt thereof.

In another embodiment, there is provided a compound as described herein above and wherein:

A is $C_1$-$C_8$ linear or branched alkyl, $C_2$-$C_8$ linear or branched alkenyl, $(CH_2)_m$-phenyl-$(CH_2)_m$, $(CH_2)_m$—$C_3$-$C_6$ cycloalkyl-$(CH_2)_m$, or $(CH_2)_m$—$C_3$-$C_6$ cycloalkenyl-$(CH_2)_m$;

and

A is substituted with $R_1$ and further optionally substituted with 1 to 5 substituents independently chosen at each possible occurrence from $C_{1-5}$ linear or branched alkyl, $C_{1-4}$ alkoxy, $C_{1-4}$ alkoxycarbonyl, carboxyl, hydroxyl, halogen, $C_1$-$C_6$ haloalkyl, cyano and carboxamido wherein the nitrogen atom of the said carboxamide is optionally independently mono or disubstituted with $C_{1-3}$ linear or branched alkyl; A is further optionally substituted with phenyl, pyridinyl, pyrimidinyl, pyrazinyl, pyridazinyl, pyrazolyl, imidazolyl, oxazolyl, thiazolyl, thienyl, furanyl or tetrazolyl, each optionally independently substituted with 1-3 substitutents chosen from halogen, hydroxyl, cyano, $C_{1-6}$ linear or branched alkyl, $C_{1-4}$ linear or branched alkoxy, $C_{1-6}$ linear or branched alkylthio, $C_{1-6}$ linear or branched alkylsulfonyl, phenylsulfonyl, $C_{1-6}$ linear or branched acyl, $C_{1-6}$ linear or branched acylamino, polyhalomethyl, polyhalomethoxy, phenyl, —COORa, —CON(Rc)Ra, $SO_2N(Rc)Ra$, —N(Rc)Ra and phenoxy optionally substituted by one or more halogens;

Ra and Rc are each independently C1-3 alkyl or hydrogen;

$R_1$ is —C(O)—$R_4$, —C(O)—N($R_5$)—$SO_2R_6$, or —C(O)—$NR_5R_7$, wherein $R_4$ is chosen from hydroxyl and $C_1$-$C_4$ alkoxy; $R_5$ is chosen from hydrogen and $C_1$-$C_3$ alkyl; $R_6$ is chosen from phenyl, pyridinyl, pyrimidinyl, pyrazinyl, pyridazinyl, pyrazolyl, imidazolyl, oxazolyl, thiazolyl, thienyl and furanyl, each optionally independently substituted with 1-5 substituents chosen from $C_{1-5}$ alkyl, $C_{1-4}$ alkoxy, halogen, or cyano; or $R_6$ is chosen from $C_1$-$C_6$ linear or branched alkyl, amino and $C_3$-$C_6$ cycloalkyl,; $R_7$ is chosen from hydrogen, cyano and benzyl;

or $R_1$ is —$SO_2R_8$ or —$SO_2$—NH—C(O)$R_9$, wherein $R_8$ is chosen from hydroxyl, amino, $C_1$-$C_3$ alkoxy, phenoxy, $C_1$-$C_3$ alkylamino and $C_1$-$C_3$ dialkylamino; $R_9$ is chosen from phenyl, pyridinyl, pyrimidinyl, pyrazinyl, pyridazinyl, pyrazolyl, imidazolyl, oxazolyl, thiazolyl, thienyl and furanyl, each optionally independently substituted with 1-5 substituents chosen from $C_{1-5}$ alkyl, $C_{1-4}$ alkoxy, halogen and cyano; or $R_9$ is chosen from $C_1$-$C_6$ linear or branched alkyl and $C_3$-$C_6$ cycloalkyl;

or $R_1$ is —NH—C(O)—N($R_5$)—$SO_2R_{10}$ wherein $R_{10}$ is chosen from $C_{1-5}$ alkyl and phenyl;

or $R_1$ is tetrazolyl or dioxothiadiazolidinone;

$R_2$ is phenyl, naphthyl or a heteroaryl ring chosen from benzothienyl, benzothiazolyl, benzoisothiazolyl, benzoxazolyl, benzisoxazolyl, indolyl, indolizinyl, dihydroindolyl, pyrazolopyridinyl, benzoxazolinyl and benzothiazolinyl, wherein each ring is optionally independently substituted with 1-5 substituents chosen from halogen, $C_{1-3}$ alkyl, $C_{1-3}$ alkoxy, hydroxy, cyano, oxo, $C_{1-3}$ alkoxycarbonyl, amino, trifluormethyl, difluoromethoxy and trifluoromethoxy;

$R_3$ is carboxyl, halogen, cyano, $C_{1-3}$ alkyl, —$NHR_{11}$, —C(O)—$R_{12}$ or —C(O)—$NR_{13}R_{14}$; $R_{11}$ is chosen from hydrogen, carboxamido, $C_1$-$C_4$ alkyl, $C_1$-$C_4$ alkoxycarbonyl, phenyl, thiazolyl, oxazolyl, imidazolyl, thienyl and furanyl; $R_{12}$ is $C_1$-$C_4$ alkoxy; $R_{13}$ is 1,1-dioxotetrahydrothienyl, oxotetrahydrofuranyl or $C_1$-$C_3$ alkyl, each optionally substituted with 1-3 substituents chosen from phenyl optionally mono- or di-substituted with methoxy, hydroxyl, thiomethoxy or halogen, tetrahydrofuranyl, dioxolanyl, hydroxyl, $C_{1-3}$ alkoxy, thioalkyl and dimethylamino; $R_{14}$ is chosen from hydrogen and $C_1$-$C_4$ alkyl optionally substituted with 1-2 hydroxyl groups; or $R_{13}$ and $R_{14}$ together with the nitrogen atom to which they are attached form a 5-6 membered heterocyclic ring chosen from piperidinyl and pyrrolidinyl, optionally substituted with 1-3 substituents chosen from halogen, $C_{1-3}$ alkyl, $C_{1-3}$ alkoxy, hydroxyl, hydroxymethyl, carboxamido, N-acetyl-N-methyl amino and cyano;

and
n=0-3
m=0-3.

In another embodiment, there is provide a compound as described hereinabove and wherein:

A is $C_1$-$C_4$ linear or branched alkyl, $C_2$-$C_4$ linear or branched alkenyl, $(CH_2)_m$-phenyl, $(CH_2)_m$—$C_3$-$C_6$ cycloalkyl-$(CH_2)_m$, or cyclopentenyl;

and

A is substituted with $R_1$ and further optionally substituted with 1 to 3 substituents independently chosen at each possible occurrence from $C_{1-5}$ linear or branched alkyl, $C_{1-4}$ alkoxy, $C_{1-4}$ alkoxycarbonyl, carboxyl, hydroxyl, $C_1$-$C_6$ haloalkyl, phenyl, pyridinyl and carboxamido wherein the nitrogen atom of the said carboxamide is optionally independently mono or disubstituted with $C_{1-3}$ linear or branched alkyl;

$R_1$ is —C(O)—OH, —C(O)—N($R_5$)—$SO_2R_6$, or —C(O)—$NR_5R_7$; $R_5$ is chosen from hydrogen and methyl; $R_6$ is chosen from phenyl, pyridyl, imidazolyl, each optionally independently substituted with 1-3 substituents chosen from $C_{1-5}$ alkyl, $C_{1-4}$ alkoxy and halogen; or $R_6$ is chosen from $C_1$-$C_6$ linear or branched alkyl, amino and $C_3$-$C_6$ cycloalkyl,; $R_7$ is chosen from hydrogen, cyano and benzyl;

or

R$_1$ is —SO$_2$R$_4$ or —SO$_2$—NH—C(O)R$_9$, wherein R$_8$ is chosen from hydroxyl, amino and C$_1$-C$_3$ alkylamino; R$_9$ is chosen from C$_{1-4}$ alkyl and phenyl;

or

R$_1$ is —NH—C(O)—N(R$_5$)—SO$_2$R$_{10}$ wherein R$_{10}$ is phenyl;

or

R$_1$ is tetrazolyl or dioxothiadiazolidinone;

R$_2$ is phenyl, naphthyl or a heteroaryl ring chosen from benzothienyl, benzoisothiazolyl, indolyl, indolizinyl, dihydroindolyl, benzoxazolinyl and benzothiazolinyl, wherein each ring is optionally independently substituted with 1-4 substituents chosen from halogen, C$_{1-3}$ alkyl, methoxy, hydroxy, cyano, oxo and trifluoromethyl;

R$_3$ is halogen, cyano, methyl, —NHR$_{11}$, —C(O)—R$_{12}$ or —C(O)—NR$_{13}$R$_{14}$; R$_{11}$ is chosen from carboxamido, C$_1$-C$_4$ alkoxycarbonyl, phenyl and thiazolyl; R$_{12}$ is C$_1$-C$_4$ alkyl; R$_{13}$ is 1,1-dioxotetrahydrothienyl, oxotetrahydrofuranyl or C$_1$-C$_3$ alkyl, each optionally substituted with 1-3 substituents chosen from phenyl optionally mono- or di-substituted with methoxy, hydroxyl, thiomethoxy or halogen, tetrahydrofuranyl, dioxolanyl and hydroxy; R$_{14}$ is hydrogen; or R$_{13}$ and R$_{14}$ together with the nitrogen atom to which they are attached form a piperidinyl or pyrrolidinyl ring optionally substituted with hydroxyl, hydroxymethyl, carboxamido or N-acetyl-N-methyl amino;

n=0-2 and m=0-2.

In another embodiment, there is provide a compound as described hereinabove and wherein:

A is C$_1$-C$_4$ linear or branched alkyl, ethenyl, phenyl, (CH$_2$)$_m$—C$_3$-C$_6$ cycloalkyl-(CH$_2$)$_m$ or cyclopentenyl;

and

A is substituted with R$_1$ and further optionally substituted with 1 to 3 substituents independently chosen at each possible occurrence from C$_{1-5}$ linear or branched alkyl, C$_{1-4}$ alkoxy, C$_{1-4}$ alkoxycarbonyl, carboxyl, hydroxyl, phenyl and pyridinyl;

R$_1$ is —C(O)—OH, —C(O)—N(R$_5$)—SO$_2$R$_6$ or —C(O)—NR$_5$R$_7$; R$_5$ is hydrogen; R$_6$ is chosen from phenyl, pyridyl and imidazolyl, each optionally independently substituted with 1-3 substituents chosen from methyl, methoxy and fluoro; or R6 is chosen from C$_1$-C$_6$ linear or branched alkyl, amino and C$_3$-C$_6$ cycloalkyl; R$_7$ is cyano;

or

R$_1$ is —SO$_3$H or —SO$_2$—NH—C(O)R$_9$; R$_9$ is chosen from methyl and phenyl;

or

R$_1$ is —NH—C(O)—N(R$_5$)—SO$_2$R$_{10}$ wherein R$_{10}$ is phenyl;

or

R$_1$ is tetrazolyl or dioxothiadiazolidinone;

R$_2$ is phenyl, naphthyl or a heteroaryl ring chosen from benzothienyl, benzoisothiazolyl, indolyl, indolizinyl and dihydroindolyl, wherein each ring is optionally independently substituted with 1-4 substituents chosen from halogen, C$_{1-2}$ alkyl, hydroxy, cyano and oxo;

R$_3$ is bromo, methyl or —NHR$_{11}$, R$_{11}$ is thiazolyl;

n=0-2 and m=0-1.

In another embodiment, there is provided compound as described in Table I which can be made as described in the schemes and examples herein below, and by methods apparent to those of ordinary skill in the art:

TABLE I

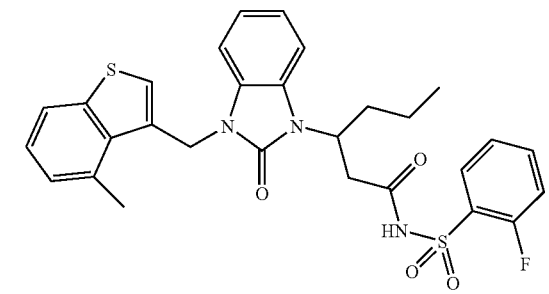 [SMILES: CCCC(CC(=O)NS(=O)(=O)c1ccccc1F)n1c(=O)n(Cc2csc3cccc(C)c23)c2ccccc21]

N-[(2-fluorophenyl)sulfonlyl]-3-{3-[(4-methyl-1-benzothien-3-yl)methyl]-2-oxo-2,3-dihydro-1H-benzimidazol-1-yl}hexanamide

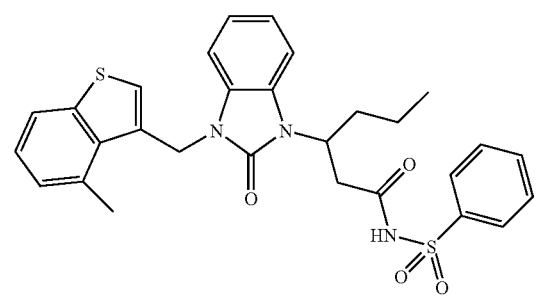

3-{3-[(4-methyl-1-benzothien-3-yl)methyl]-2-oxo-2,3-dihydro-1H-benzimidazol-1-yl}-N-(phenylsulfonyl)hexanamide TABLE I-continued

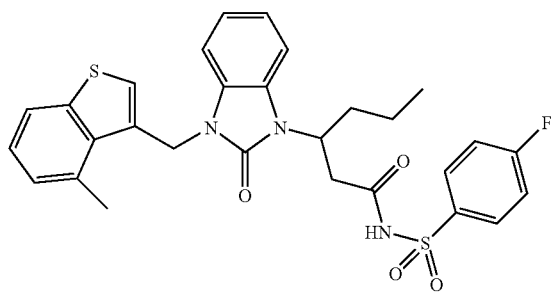 [SMILES: CCCC(CC(=O)NS(=O)(=O)c1ccc(F)cc1)n1c(=O)n(Cc2csc3cccc(C)c23)c2ccccc21] N-[(4-fluorophenyl)sulfonyl]-3-{3-[(4-methyl-1-benzothien-3-yl)methyl]-2-oxo-2,3-dihydro-1H-benzimidazol-1-yl}hexanamide Chiral 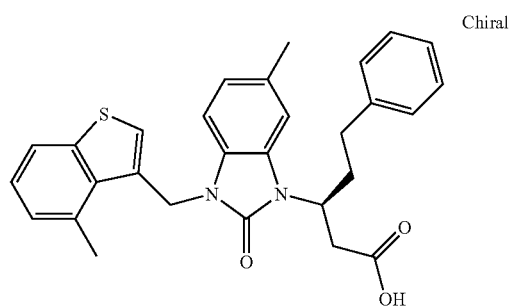 [SMILES: Cc1ccc2c(c1)n([C@@H](CCc1ccccc1)CC(=O)O)c(=O)n2Cc1csc2cccc(C)c12] (3S)-3-{6-methyl-3-[(4-methyl-1-benzothien-3-yl)methyl]-2-oxo-2,3-dihydro-1H-benzimidazol-1-yl}-5-phenylpentanoic acid

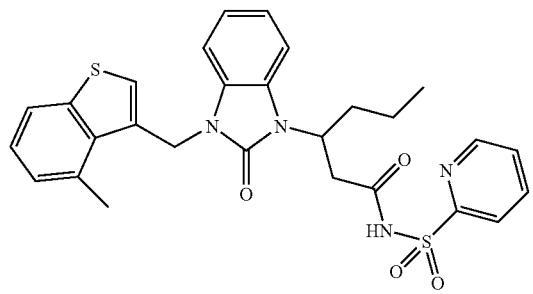 3-{3-[(4-methyl-1-benzothien-3-yl)methyl]-2-oxo-2,3-dihydro-1H-benzimidazol-1-yl}-N-(pyridin-2-ylsulfonyl)hexanamide

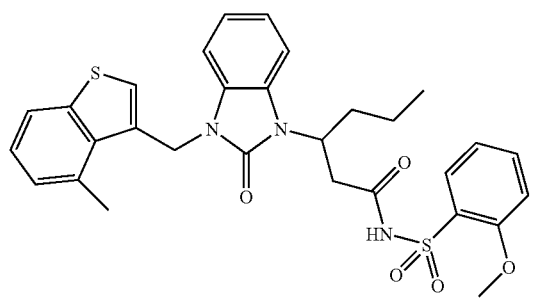 [SMILES: CCCC(CC(=O)NS(=O)(=O)c1ccccc1OC)n1c(=O)n(Cc2csc3cccc(C)c23)c2ccccc21] N-[(2-methoxyphenyl)sulfonyl]-3-{3-[(4-methyl-1-benzothien-3-yl)methyl]-2-oxo-2,3-dihydro-1H-benzimidazol-1-yl}hexanamide

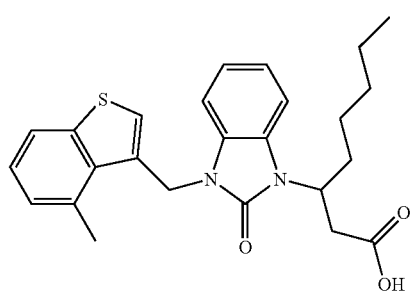 [SMILES: CCCCCC(CC(=O)O)n1c(=O)n(Cc2csc3cccc(C)c23)c2ccccc21] 3-{3-[(4-methyl-1-benzothien-3-yl)methyl]-2-oxo-2,3-dihydro-1H-benzimidazol-1-yl}octanoic acid TABLE I-continued

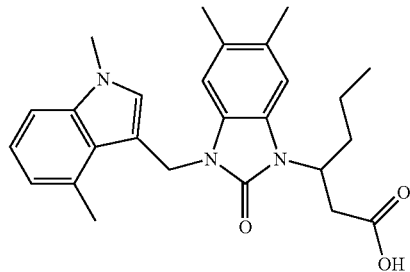 [SMILES: CCCC(CC(=O)O)n1c(=O)n(Cc2cn(C)c3cccc(C)c23)c2cc(C)c(C)cc21]

3-{3-[(1,4-dimethyl-1H-indol-3-yl)methyl]-5,6-dimethyl-2-oxo-2-3-dihydro-1H-bezimidazol-1-yl}hexanoic acid

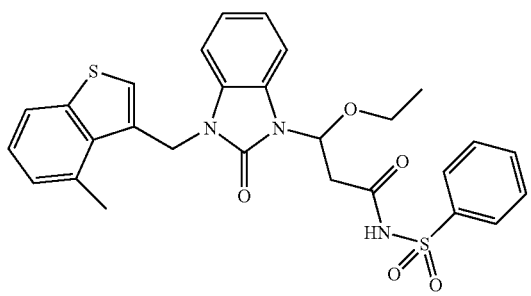

3-ethoxy-3-{3-[(4-methyl-1-benzothien-3-yl)methyl]-2-oxo-2,3-dihydro-1H-benzimidazol-1-yl}-N-(phenylsulfonyl)propanamide

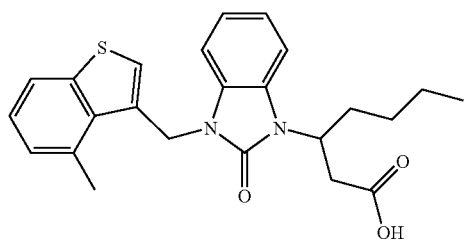 [SMILES: CCCCC(CC(=O)O)n1c(=O)n(Cc2csc3cccc(C)c23)c2ccccc21]

3-{3-[(4-methyl-1-benzothien-3-yl)methyl]-2-oxo-2,3-dihydro-1H-benzimidazol-1-yl}heptanoic acid

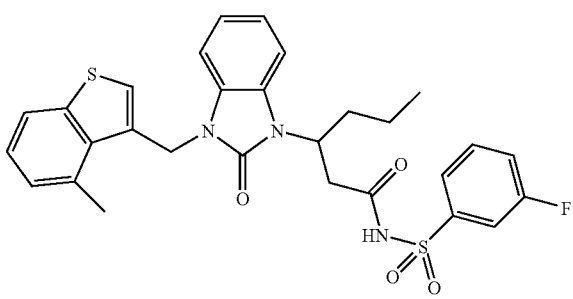 [SMILES: CCCC(CC(=O)NS(=O)(=O)c1cccc(F)c1)n1c(=O)n(Cc2csc3cccc(C)c23)c2ccccc21]

N-[(3-fluorophenyl)sulfonyl]-3-{3-[(4-methyl-1-benzothien-3-yl)methyl]-2-oxo-2,3-dihydro-1H-benzimidazol-1-yl}hexanamide

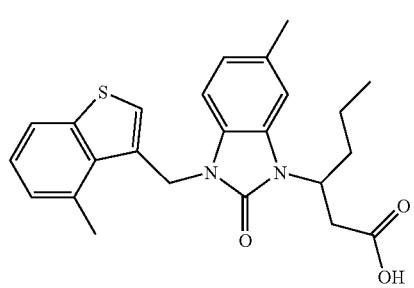 [SMILES: CCCC(CC(=O)O)n1c(=O)n(Cc2csc3cccc(C)c23)c2ccc(C)cc21]

3-{6-methyl-3-[(4-methyl-1-benzothien-3-yl)methyl]-2-oxo-2,3-dihydro-1H-benzimidazol-1-yl}hexanoic acid TABLE I-continued

| Structure | Name |
|---|---|
| | 3-ethoxy-3-{6-methyl-3-[(4-methyl-1-benzothien-3-yl)methyl]-2-oxo-2,3-dihydro-1H-benzimidazol-1-yl}propanoic acid |
| | 3-{5,6-dimethyl-3-[(4-methyl-1-benzothien-3-yl)methyl]-2-oxo-2,3-dihydro-1H-benzimidazol-1-yl}-3-ethoxypropanoic acid |
| Chiral | (3S)-3-{3-[(4-methyl-1-benzothien-3-yl)methyl]-2-oxo-2,3-dihydro-1H-benzimidazol-1-yl}hexanoic acid |
| | N-[(4-methoxyphenyl)sulfonyl]-3-{3-[(4-methyl-1-benzothien-3-yl)methyl]-2-oxo-2,3-dihydro-1H-benzimidazol-1-yl}hexanamide |
| | 3-{3-[(1,4-dimethyl-1H-indol-3-yl)methyl]-6-methyl-2-oxo-2,3-dihydro-1H-benzimidazol-1-yl}hexanoic acid |

TABLE I-continued

| Structure | Name |
|---|---|
| | 3-ethoxy-3-{3-[(4-methyl-1-benzothien-3-yl)methyl]-2-oxo-2,3-dihydro-1H-benzimidazol-1-yl}propanoic acid |
| | N-[(3-methoxyphenyl)sulfonyl]-3-{3-[(4-methyl-1-benzothien-3-yl)methyl]-2-oxo-2,3-dihydro-1H-benzimidazol-1-yl}hexanamide |
| Chiral | (3S)-3-{3-[(1,4-dimethyl-1H-indol-3-yl)methyl]-2-oxo-2,3-dihydro-1H-benzimidazol-1-yl}hexanoic acid |
| | 3-{3-[(4-methyl-1-benzothien-3-yl)methyl]-2-oxo-2,3-dihydro-1H-benzimidazol-1-yl}hexanoic acid |
| | 3-{3-[(4-methyl-1-benzothien-3-yl)methyl]-2-oxo-2,3-dihydro-1H-benzimidazol-1-yl}-N-(pyridin-3-ylsulfonyl)hexanamide |
| | 3-{3-[(1,4-dimethyl-1H-indol-3-yl)methyl]-2-oxo-2,3-dihydro-1H-benzimidazol-1-yl}hexanoic acid |

TABLE I-continued

| | |
|---|---|
| 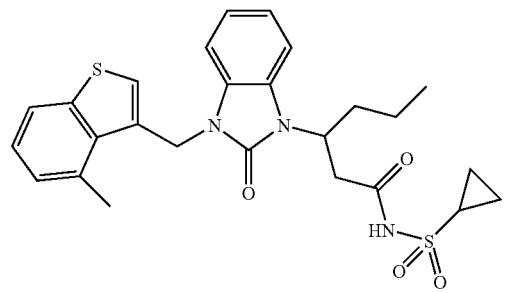 [SMILES: CCCC(CC(=O)NS(=O)(=O)C1CC1)n1c(=O)n(Cc2csc3cccc(C)c23)c2ccccc21] | N-(cyclopropylsulfonyl)-3-{3-[(4-methyl-1-benzothien-3-yl)methyl]-2-oxo-2,3-dihydro-1H-benzimidazol-1-yl}hexanamide |
| 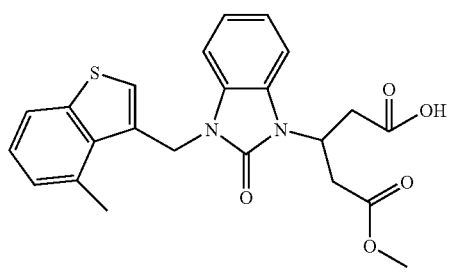 [SMILES: COC(=O)CC(CC(=O)O)n1c(=O)n(Cc2csc3cccc(C)c23)c2ccccc21] | 5-methoxy-3-{3-[(4-methyl-1-benzothien-3-yl)methyl]-2-oxo-2,3-dihydro-1H-benzimidazol-1-yl}-5-oxopentanoic acid |
| 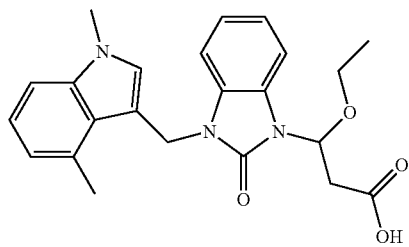 [SMILES: CCOC(CC(=O)O)n1c(=O)n(Cc2cn(C)c3cccc(C)c23)c2ccccc21] | 3-{3-[(1,4-dimethyl-1H-indol-3-yl)methyl]-2-oxo-2,3-dihydro-1H-benzimidazol-1-yl}-3-ethoxypropanoic acid |
| 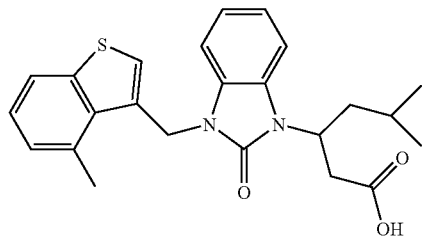 [SMILES: Cc1cccc2scc(Cn3c(=O)n(C(CC(=O)O)CC(C)C)c4ccccc43)c12] | 5-methyl-3-{3-[(4-methyl-1-benzothien-3-yl)methyl]-2-oxo-2,3-dihydro-1H-benzimidazol-1-yl}hexanoic acid |
| 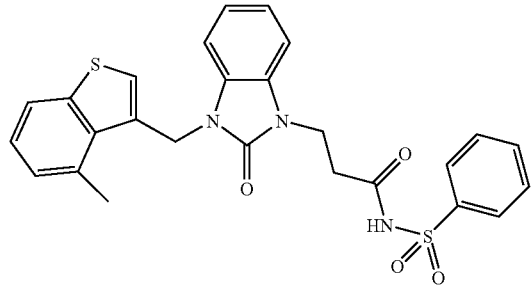 [SMILES: Cc1cccc2scc(Cn3c(=O)n(CCC(=O)NS(=O)(=O)c4ccccc4)c4ccccc43)c12] | 3-{3-[(4-methyl-1-benzothien-3-yl)methyl]-2-oxo-2,3-dihydro-1H-benzimidazol-1-yl}-N-(phenylsulfonyl)propanamide |
| 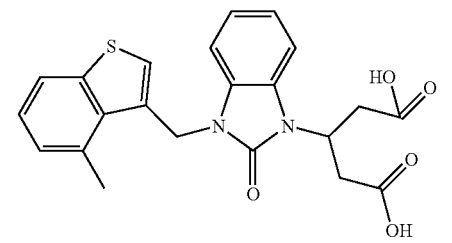 [SMILES: Cc1cccc2scc(Cn3c(=O)n(C(CC(=O)O)CC(=O)O)c4ccccc43)c12] | 3-{3-[(4-methyl-1-benzothien-3-yl)methyl]-2-oxo-2,3-dihydro-1H-benzimidazol-1-yl}pentanedioic acid |

TABLE I-continued

| | |
|---|---|
| 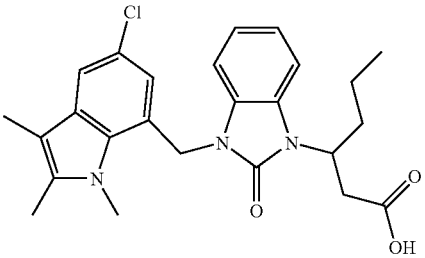 [SMILES: CCCC(CC(=O)O)n1c(=O)n(Cc2cc(Cl)cc3c(C)c(C)n(C)c23)c2ccccc21] | 3-{3-[(5-chloro-1,2,3-trimethyl-1H-indol-7-yl)methyl]-2-oxo-2,3-dihydro-1H-benzimidazol-1-yl}hexanoic acid |
| 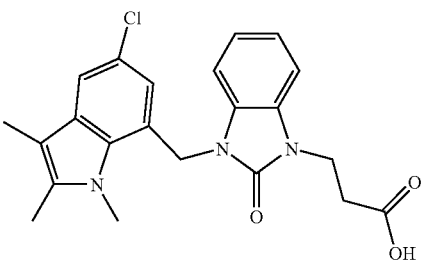 [SMILES: Cc1c(C)n(C)c2c(Cn3c(=O)n(CCC(=O)O)c4ccccc43)cc(Cl)cc12] | 3-{3-[(5-chloro-1,2,3-trimethyl-1H-indol-7-yl)methyl]-2-oxo-2,3-dihydro-1H-benzimidazol-1-yl}propanoic acid |
| 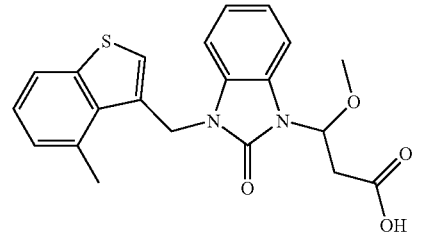 [SMILES: COC(CC(=O)O)n1c(=O)n(Cc2csc3cccc(C)c23)c2ccccc21] | 3-methoxy-3-{3-[(4-methyl-1-benzothien-3-yl)methyl]-2-oxo-2,3-dihydro-1H-benzimidazol-1-yl}propanoic acid |
| 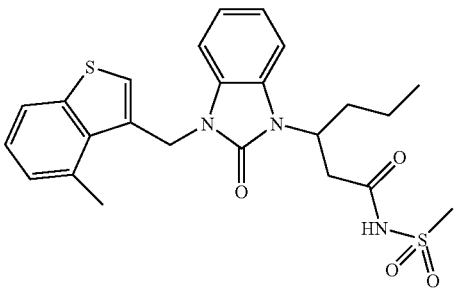 [SMILES: CCCC(CC(=O)NS(C)(=O)=O)n1c(=O)n(Cc2csc3cccc(C)c23)c2ccccc21] | 3-{3-[(4-methyl-1-benzothien-3-yl)methyl]-2-oxo-2,3-dihydro-1H-benzimidazol-1-yl}-N-(methylsulfonyl)hexanamide |
| 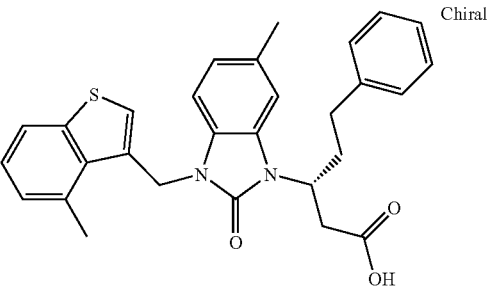 [SMILES: Cc1ccc2c(c1)n([C@H](CCc1ccccc1)CC(=O)O)c(=O)n2Cc1csc2cccc(C)c12] | (3R)-3-{6-methyl-3-[(4-methyl-1-benzothien-3-yl)methyl]-2-oxo-2,3-dihydro-1H-benzimidazol-1-yl}-5-phenylpentanoic acid |

TABLE I-continued

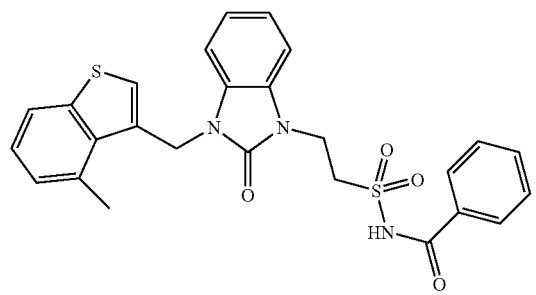 [SMILES: Cc1cccc2scc(Cn3c(=O)n(CCS(=O)(=O)NC(=O)c4ccccc4)c4ccccc43)c12]

N-[(2-{3-[(4-methyl-1-benzothien-3-yl)methyl]-2-oxo-2,3-dihydro-1H-benzimidazol-1-yl}ethyl)sulfonyl]benzamide

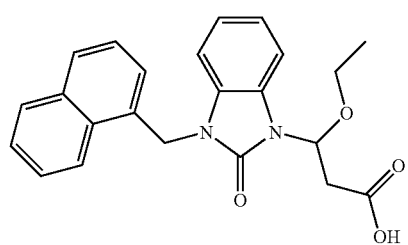

3-ethoxy-3-[3-(1-naphthylmethyl)-2-oxo-2,3-dihydro-1H-benzimidazol-1-yl]propanoic acid Chiral

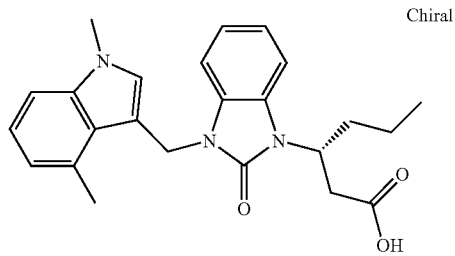 [SMILES: CCC[C@H](CC(=O)O)n1c(=O)n(Cc2cn(C)c3cccc(C)c23)c2ccccc21]

(3R)-3-{3-[(1,4-dimethyl-1H-indol-3-yl)methyl]-2-oxo-2,3-dihydro-1H-benzimidazol-1-yl}hexanoic acid Chiral

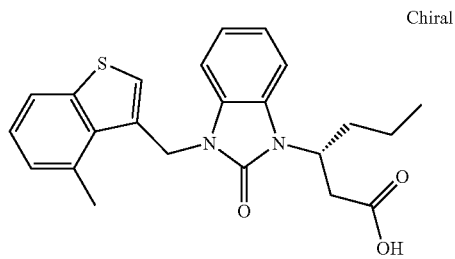 [SMILES: CCC[C@H](CC(=O)O)n1c(=O)n(Cc2csc3cccc(C)c23)c2ccccc21]

(3R)-3-{3-[(4-methyl-1-benzothien-3-yl)methyl]-2-oxo-2,3-dihydro-1H-benzimidazol-1-yl}hexanoic acid

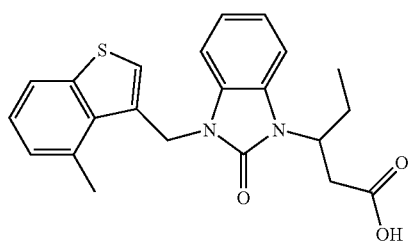 [SMILES: CCC(CC(=O)O)n1c(=O)n(Cc2csc3cccc(C)c23)c2ccccc21]

3-{3-[(4-methyl-1-benzothien-3-yl)methyl]-2-oxo-2,3-dihydro-1H-benzimidazol-1-yl}pentanoic acid

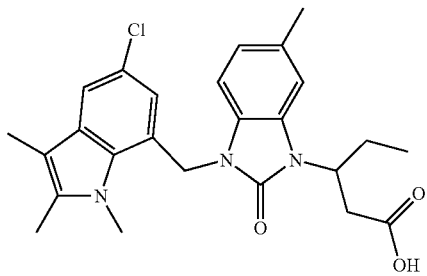 [SMILES: CCC(CC(=O)O)n1c(=O)n(Cc2cc(Cl)cc3c(C)c(C)n(C)c23)c2ccc(C)cc21]

3-{3-[(5-chloro-1,2,3-trimethyl-1H-indol-7-yl)methyl]-6-methyl-2-oxo-2,3-dihydro-1H-benzimidazol-1-yl}pentanoic acid TABLE I-continued

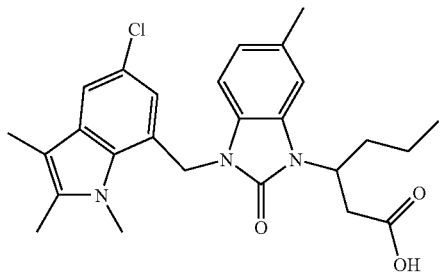 [SMILES: CCCC(CC(=O)O)n1c(=O)n(Cc2cc(Cl)cc3c(C)c(C)n(C)c23)c2ccc(C)cc21]

3-{3-[(5-chloro-1,2,3-trimethyl-1H-indol-7-yl)methyl]-6-methyl-2-oxo-2,3-dihydro-1H-benzimidazol-1-yl}hexanoic acid

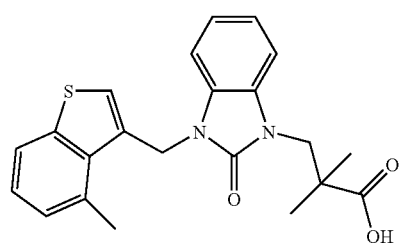 [SMILES: Cc1cccc2scc(Cn3c(=O)n(CC(C)(C)C(=O)O)c4ccccc43)c12]

2,2-dimethyl-3-{3-[(4-methyl-1-benzothien-3-yl)methyl]-2-oxo-2,3-dihydro-1H-benzimidazol-1-yl}propanoic acid

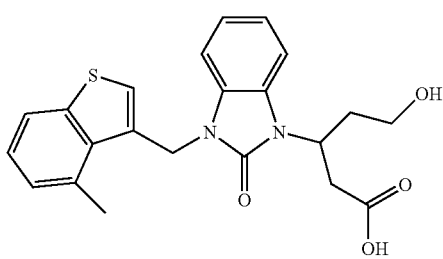 [SMILES: Cc1cccc2scc(Cn3c(=O)n(C(CCO)CC(=O)O)c4ccccc43)c12]

5-hydroxy-3-{3-[(4-methyl-1-benzothien-3-yl)methyl]-2-oxo-2,3-dihydro-1H-benzimidazol-1-yl)}pentanoic acid

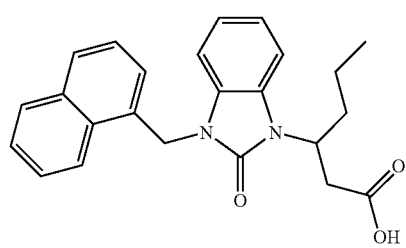

3-[3-(1-naphthylmethyl)-2-oxo-2,3-dihydro-1H-benzimidazol-1-yl]hexanoic acid

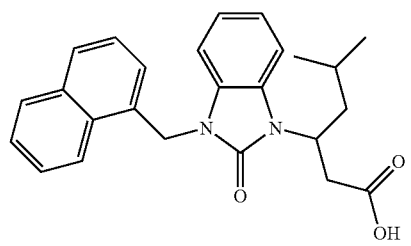 [SMILES: CC(C)CC(CC(=O)O)n1c(=O)n(Cc2cccc3ccccc23)c2ccccc21]

5-methyl-3-[3-(1-naphthylmethyl)-2-oxo-2,3-dihydro-1H-benzimidazol-1-yl]hexanoic acid

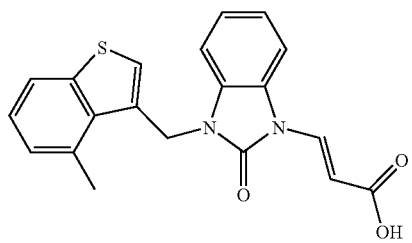 [SMILES: Cc1cccc2scc(Cn3c(=O)n(/C=C/C(=O)O)c4ccccc43)c12]

(2E)-3-{3-[(4-methyl-1-benzothien-3-yl)methyl]-2-oxo-2,3-dihydro-1H-benzimidazol-1-yl}acrylic acid TABLE I-continued

| | |
|---|---|
| 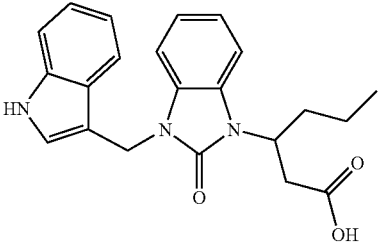 [SMILES: CCCC(CC(=O)O)n1c(=O)n(Cc2c[nH]c3ccccc23)c2ccccc21] | 3-[3-(1H-indol-3-ylmethyl)-2-oxo-2,3-dihydro-1H-benzimidazol-1-yl]hexanoic acid |
| 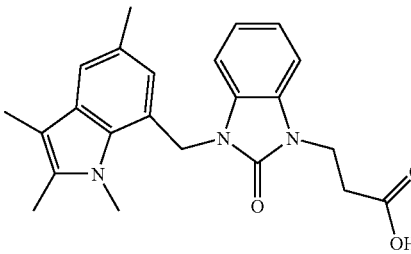 | 3-{2-oxo-3-[(1,2,3,5-tetramethyl-1H-indol-7-yl)methyl]-2,3-dihydro-1H-benzimidazol-1-yl}propanoic acid |
| 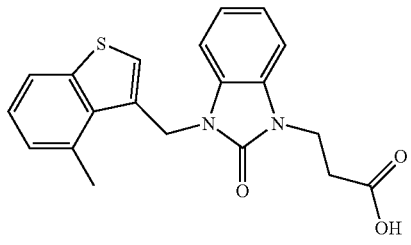 [SMILES: Cc1cccc2scc(Cn3c(=O)n(CCC(=O)O)c4ccccc43)c12] | 3-{3-[(4-methyl-1-benzothien-3-yl)methyl]-2-oxo-2,3-dihydro-1H-benzimidazol-1-yl}propanoic acid |
| 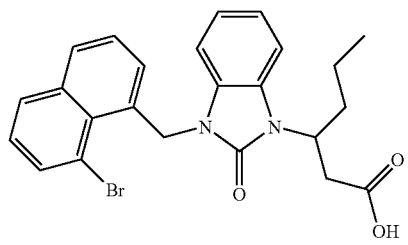 [SMILES: CCCC(CC(=O)O)n1c(=O)n(Cc2cccc3cccc(Br)c23)c2ccccc21] | 3-{3-[(8-bromo-1-naphthyl)methyl]-2-oxo-2,3-dihydro-1H-benzimidazol-1-yl}hexanoic acid |
| 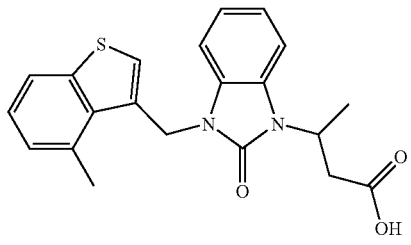 [SMILES: Cc1cccc2scc(Cn3c(=O)n(C(C)CC(=O)O)c4ccccc43)c12] | 3-{3-[(4-methyl-1-benzothien-3-yl)methyl]-2-oxo-2,3-dihydro-1H-benzimidazol-1-yl}butanoic acid |
| 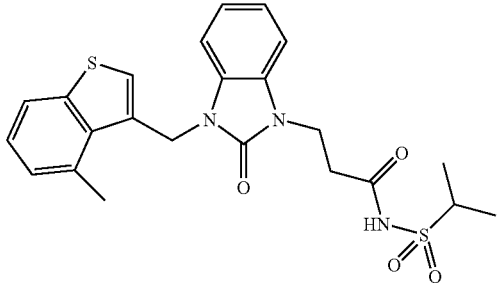 [SMILES: Cc1cccc2scc(Cn3c(=O)n(CCC(=O)NS(=O)(=O)C(C)C)c4ccccc43)c12] | N-(isopropylsulfonyl)-3-{3-[(4-methyl-1-benzothien-3-yl)methyl]-2-oxo-2,3-dihydro-1H-benzimidazol-1-yl}propanamide |

TABLE I-continued

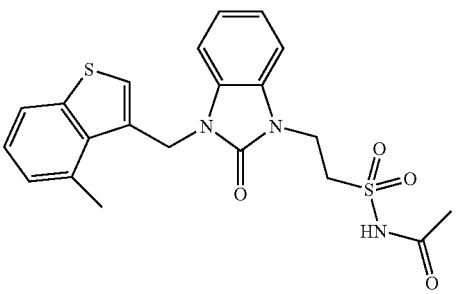 [SMILES: CC(=O)NS(=O)(=O)CCn1c(=O)n(Cc2csc3cccc(C)c23)c2ccccc21]

N-[(2-{3-[(4-methyl-1-benzothien-3-yl)methyl]-2-oxo-2,3-dihydro-1H-benzimidazol-1-yl}ethyl)sulfonyl]acetamide

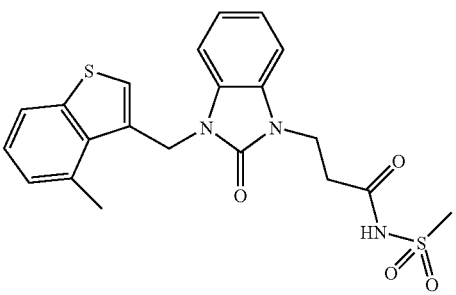 [SMILES: Cc1cccc2scc(Cn3c(=O)n(CCC(=O)NS(C)(=O)=O)c4ccccc43)c12]

3-{3-[(4-methyl-1-benzothien-3-yl)methyl]-2-oxo-2,3-dihydro-1H-benzimidazol-1-yl}-N-(methylsulfony)propanamide

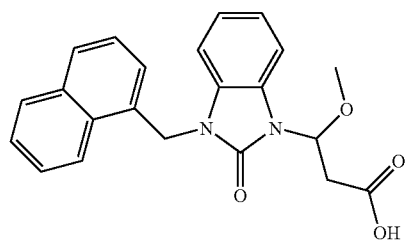 [SMILES: COC(CC(=O)O)n1c(=O)n(Cc2cccc3ccccc23)c2ccccc21]

3-methoxy-3-[3-(1-naphthylmethyl)-2-oxo-2,3-dihydro-1H-benzimidazol-1-yl]propanoic acid

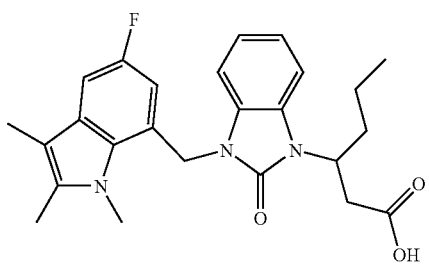 [SMILES: CCCC(CC(=O)O)n1c(=O)n(Cc2cc(F)cc3c(C)c(C)n(C)c23)c2ccccc21]

3-{3-[(5-fluoro-1,2,3-trimethyl-1H-indol-7-yl)methyl]-2-oxo-2,3-dihydro-1H-benzimidazol-1-yl}hexanoic acid

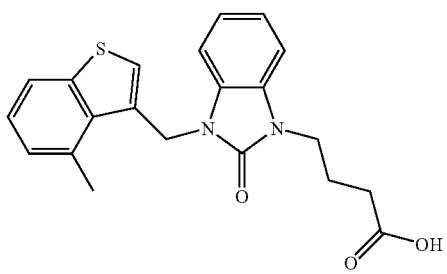 [SMILES: Cc1cccc2scc(Cn3c(=O)n(CCCC(=O)O)c4ccccc43)c12]

4-{3-[(4-methyl-1-benzothien-3-yl)methyl]-2-oxo-2,3-dihydro-1H-benzimidazol-1-yl}butanoic acid

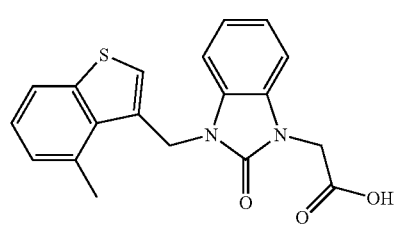 [SMILES: Cc1cccc2scc(Cn3c(=O)n(CC(=O)O)c4ccccc43)c12]

{3-[(4-methyl-1-benzothien-3-yl)methyl]-2-oxo-2,3-dihydro-1H-benzimidazol-1-yl}acetic acid TABLE I-continued

| | |
|---|---|
| 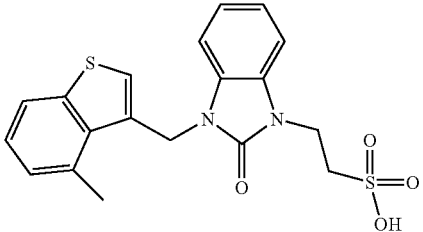 [SMILES: Cc1cccc2scc(Cn3c(=O)n(CCS(=O)(=O)O)c4ccccc43)c12] | 2-{3-[(4-methyl-1-benzothien-3-yl)methyl]-2-oxo-2,3-dihydro-1H-benzimidazol-1-yl}ethanesulfonic acid |
| 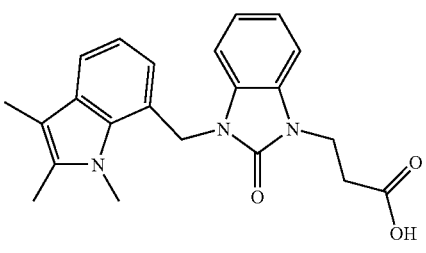 [SMILES: Cc1c(C)n(C)c2c(Cn3c(=O)n(CCC(=O)O)c4ccccc43)cccc12] | 3-{2-oxo-3-[(1,2,3-trimethyl-1H-indol-7-yl)methyl]-2,3-dihydro-1H-benzimidazol-1-yl}propanoic acid |
| 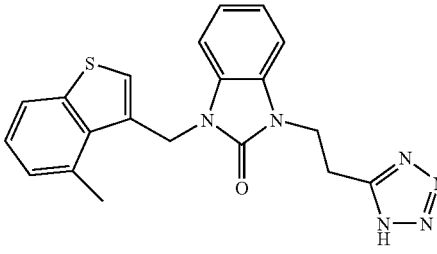 | 1-[(4-methyl-1-benzothien-3-yl)methyl]-3-[2-(1H-tetrazol-5-yl)ethyl]-1,3-dihydro-2H-benzimidazol-2-one |
| 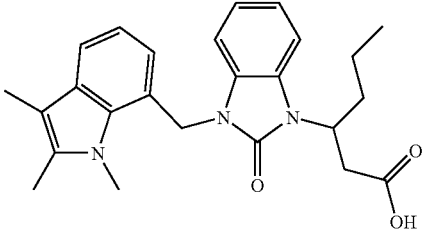 [SMILES: CCCC(CC(=O)O)n1c(=O)n(Cc2cccc3c(C)c(C)n(C)c23)c2ccccc21] | 3-{2-oxo-3-[(1,2,3-trimethyl-1H-indol-7-yl)methyl]-2,3-dihydro-1H-benzimidazol-1-yl}hexanoic acid |
| 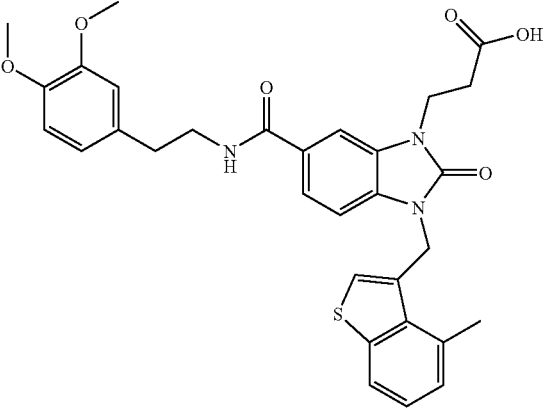 [SMILES: COc1ccc(CCNC(=O)c2ccc3c(c2)n(CCC(=O)O)c(=O)n3Cc2csc3cccc(C)c23)cc1OC] | 3-(6-{[2-(3,4-dimethoxyphenyl)ethyl]carbamoyl}-3-[(4-methyl-1-benzothien-3-yl)methyl]-2-oxo-2,3-dihydro-1H-benzimidazol-1-yl)propanoic acid |

TABLE I-continued

| | |
|---|---|
| 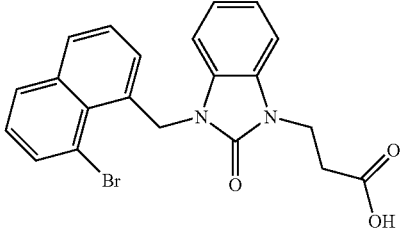 [SMILES: O=C(O)CCn1c(=O)n(Cc2cccc3cccc(Br)c23)c2ccccc21] | 3-{3-[(8-bromo-1-naphthyl)methyl]-2-oxo-2,3-dihydro-1H-benzimidazol-1-yl}propanoic acid |
| 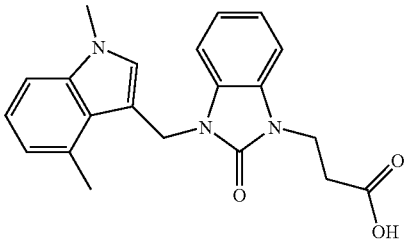 [SMILES: Cc1cccc2c1c(Cn1c(=O)n(CCC(=O)O)c3ccccc31)cn2C] | 3-{3-[(1,4-dimethyl-1H-indol-3-yl)methyl]-2-oxo-2,3-dihydro-1H-benzimidazol-1-yl}propanoic acid |
| 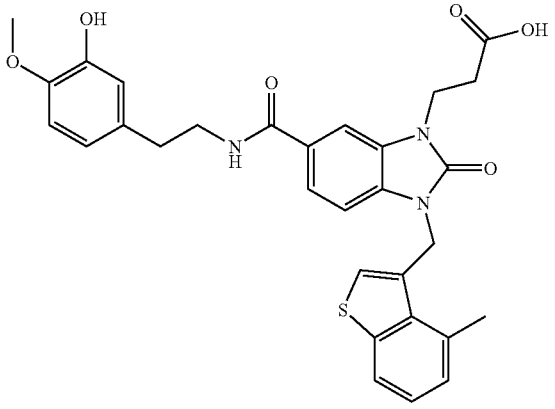 [SMILES: COc1ccc(CCNC(=O)c2ccc3c(c2)n(CCC(=O)O)c(=O)n3Cc2csc3cccc(C)c23)cc1O] | 3-(6-{[2-(3-hydroxy-4-methoxyphenyl)ethyl]carbamoyl}-3-[(4-methyl-1-benzothien-3-yl)methyl]-2-oxo-2,3-dihydro-1H-benzimidazol-1-yl)propanoic acid |
| 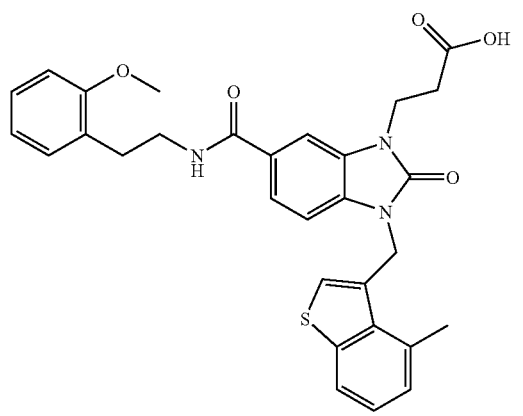 [SMILES: COc1ccccc1CCNC(=O)c1ccc2c(c1)n(CCC(=O)O)c(=O)n2Cc1csc2cccc(C)c12] | 3-(6-{[2-(2-methoxyphenyl)ethyl]carbamoyl}-3-[(4-methyl-1-benzothien-3-yl)methyl]-2-oxo-2,3-dihydro-1H-benzimidazol-1-yl)propanoic acid |
| 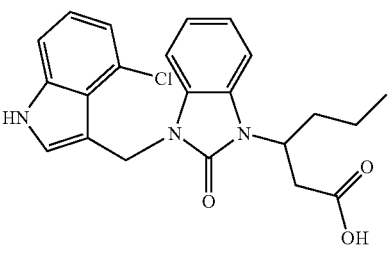 | 3-{3-[(4-chloro-1H-indol-3-yl)methyl]-2-oxo-2,3-dihydro-1H-benzimidazol-1-yl}hexanoic acid |

TABLE I-continued

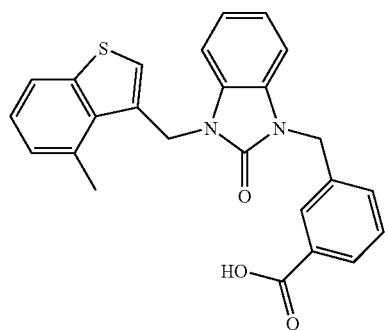 [SMILES: Cc1cccc2scc(Cn3c(=O)n(Cc4cccc(C(=O)O)c4)c4ccccc43)c12]

3-({3-[(4-methyl-1-benzothien-3-yl)methyl]-2-oxo-2,3-dihydro-1H-benzimidazol-1-yl}methyl)benzoic acid

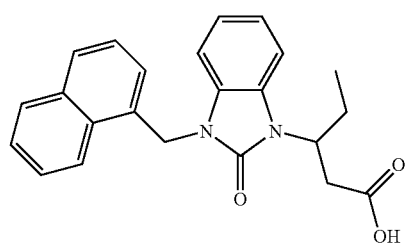 [SMILES: CCC(CC(=O)O)n1c(=O)n(Cc2cccc3ccccc23)c2ccccc21]

3-[3-(1-naphthylmethyl)-2-oxo-2,3-dihydro-1H-benzimidazol-1-yl]pentanoic acid

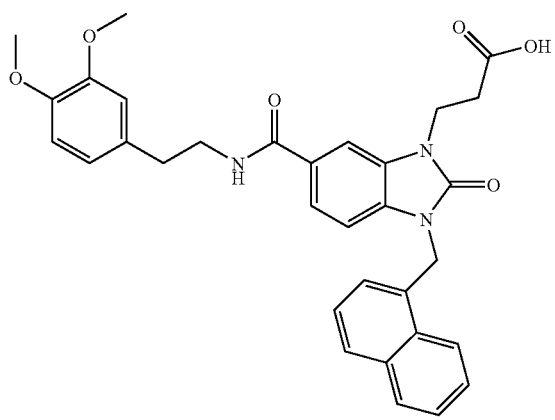 [SMILES: COc1ccc(CCNC(=O)c2ccc3c(c2)n(CCC(=O)O)c(=O)n3Cc2cccc3ccccc23)cc1OC]

3-[6-{[2-(3,4-dimethoxyphenyl)ethyl]carbamoyl}-3-(1-naphthylmethyl)-2-oxo-2,3-dihydro-1H-benzimidazol-1-yl]propanoic acid

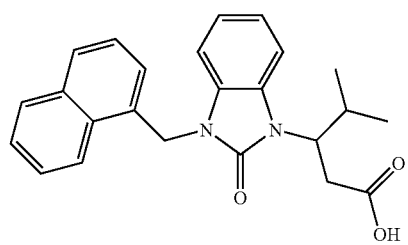 [SMILES: CC(C)C(CC(=O)O)n1c(=O)n(Cc2cccc3ccccc23)c2ccccc21]

4-methyl-3-[3-(1-naphthylmethyl)-2-oxo-2,3-dihydro-1H-benzimidazol-1-yl]pentanoic acid

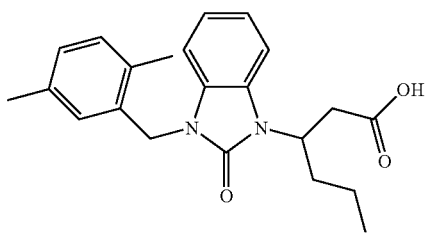 [SMILES: CCCC(CC(=O)O)n1c(=O)n(Cc2cc(C)ccc2C)c2ccccc21]

3-[3-(2,5-dimethylbenzyl)-2-oxo-2,3-dihydro-1H-benzimidazol-1-yl]hexanoic acid

TABLE I-continued

| | |
|---|---|
| 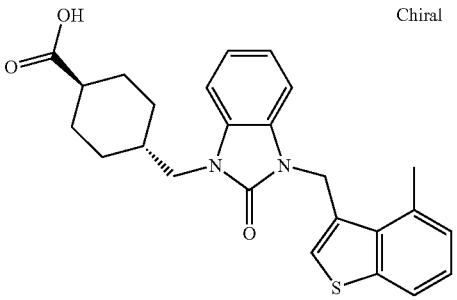 [SMILES: Cc1cccc2scc(Cn3c(=O)n(C[C@H]4CC[C@H](C(=O)O)CC4)c4ccccc43)c12] | trans-4-({3-[(4-methyl-1-benzothien-3-yl)methyl]-2-oxo-2,3-dihydro-1H-benzimidazol-1-yl}methyl)cyclohexanecarboxylic acid (Chiral) |
| 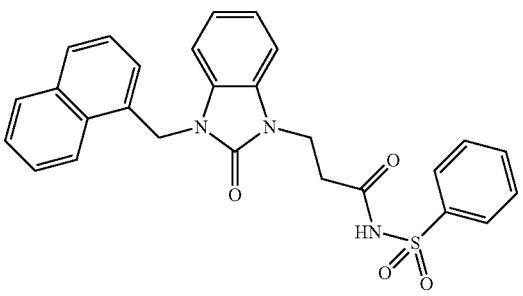 [SMILES: O=C(CCn1c(=O)n(Cc2cccc3ccccc23)c2ccccc21)NS(=O)(=O)c1ccccc1] | 3-[3-(1-naphthylmethyl)-2-oxo-2,3-dihydro-1H-benzimidazol-1-yl]-N-(phenylsulfonyl)propanamide |
| 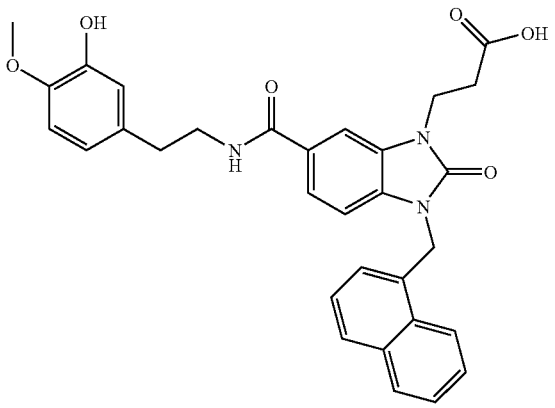 [SMILES: COc1ccc(CCNC(=O)c2ccc3c(c2)n(CCC(=O)O)c(=O)n3Cc2cccc3ccccc23)cc1O] | 3-[6-{[2-(3-hydroxy-4-methoxyphenyl)ethyl]carbamoyl}-3-(1-naphthylmethyl)-2-oxo-2,3-dihydro-1H-benzimidazol-1-yl]propanoic acid |
| 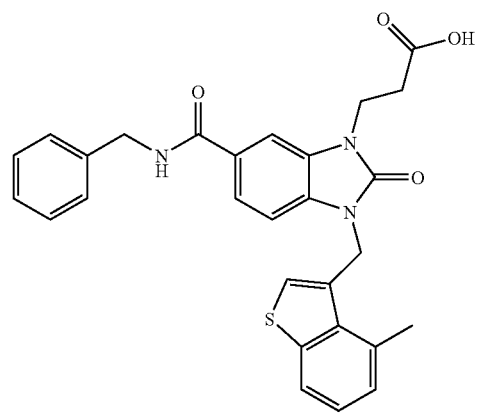 [SMILES: Cc1cccc2scc(Cn3c(=O)n(CCC(=O)O)c4cc(C(=O)NCc5ccccc5)ccc43)c12] | 3-{6-(benzylcarbamoyl)-3-[(4-methyl-1-benzothien-3-yl)methyl]-2-oxo-2,3-dihydro-1H-benzimidazol-1-yl}propanoic acid |

TABLE I-continued

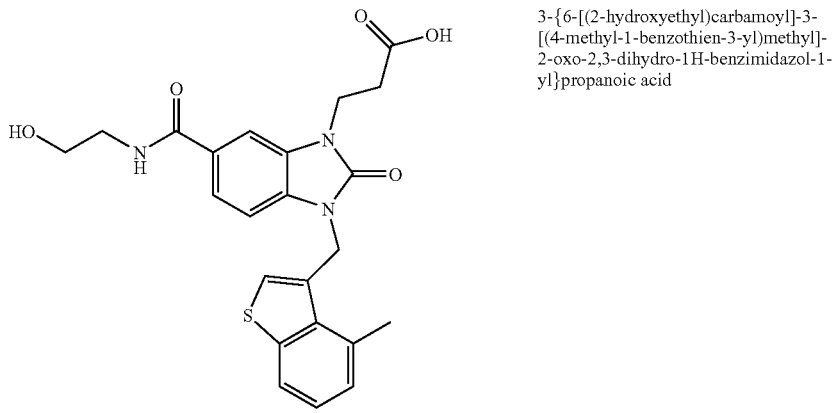

3-{6-[(2-hydroxyethyl)carbamoyl]-3-
[(4-methyl-1-benzothien-3-yl)methyl]-
2-oxo-2,3-dihydro-1H-benzimidazol-1-
yl}propanoic acid

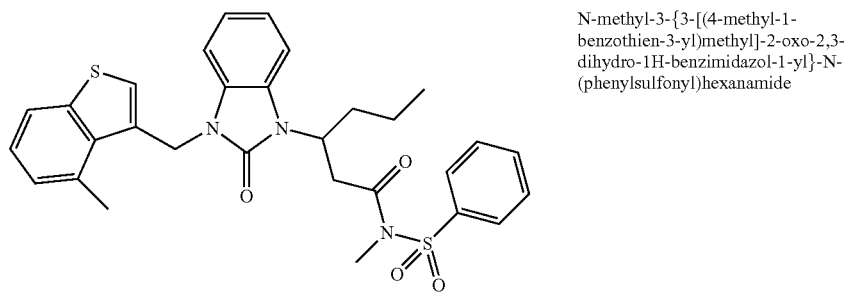

N-methyl-3-{3-[(4-methyl-1-
benzothien-3-yl)methyl]-2-oxo-2,3-
dihydro-1H-benzimidazol-1-yl}-N-
(phenylsulfonyl)hexanamide

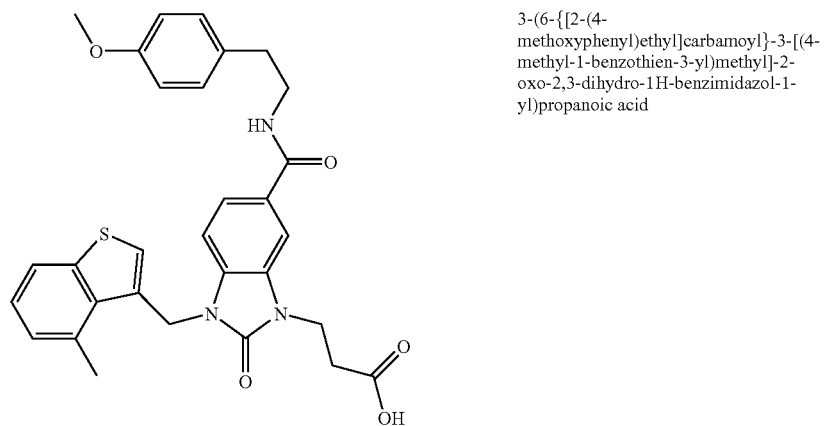

3-(6-{[2-(4-
methoxyphenyl)ethyl]carbamoyl}-3-[(4-
methyl-1-benzothien-3-yl)methyl]-2-
oxo-2,3-dihydro-1H-benzimidazol-1-
yl)propanoic acid

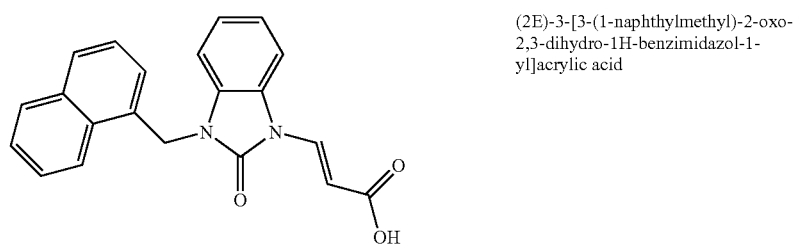

(2E)-3-[3-(1-naphthylmethyl)-2-oxo-
2,3-dihydro-1H-benzimidazol-1-
yl]acrylic acid TABLE I-continued

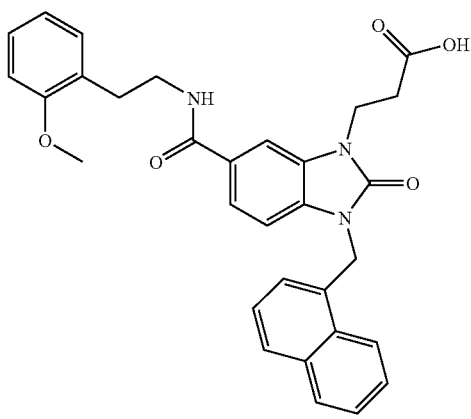 [SMILES: COc1ccccc1CCNC(=O)c1ccc2c(c1)n(CCC(=O)O)c(=O)n2Cc1cccc2ccccc12]

3-[6-{[2-(2-methoxyphenyl)ethyl]carbamoyl}-3-(1-naphthylmethyl)-2-oxo-2,3-dihydro-1H-benzimidazol-1-yl]propanoic acid

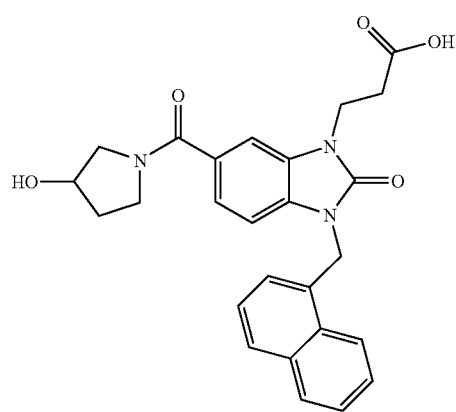 [SMILES: O=C(O)CCn1c(=O)n(Cc2cccc3ccccc23)c2ccc(C(=O)N3CCC(O)C3)cc21]

3-{6-[(3-hydroxypyrrolidin-1-yl)carbonyl]-3-(1-naphthylmethyl)-2-oxo-2,3-dihydro-1H-benzimidazol-1-yl}propanoic acid

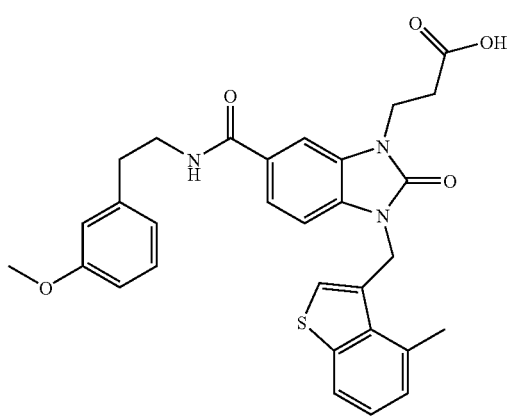 [SMILES: COc1cccc(CCNC(=O)c2ccc3c(c2)n(CCC(=O)O)c(=O)n3Cc2csc3cccc(C)c23)c1]

3-(6-{[2-(3-methoxyphenyl)ethyl]carbamoyl}-3-[(4-methyl-1-benzothien-3-yl)methyl]-2-oxo-2,3-dihydro-1H-benzimidazol-1-yl)propanoic acid

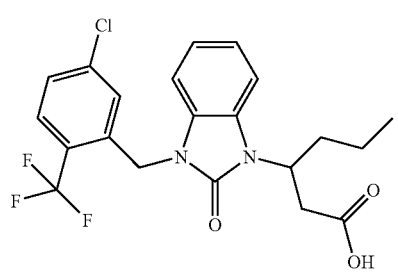 [SMILES: CCCC(CC(=O)O)n1c(=O)n(Cc2cc(Cl)ccc2C(F)(F)F)c2ccccc21]

3-{3-[5-chloro-2-(trifluoromethyl)benzyl]-2-oxo-2,3-dihydro-1H-benzimidazol-1-yl}hexanoic acid TABLE I-continued
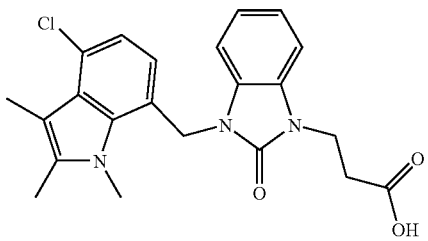 [SMILES: Cc1c(C)n(C)c2c(Cn3c(=O)n(CCC(=O)O)c4ccccc43)ccc(Cl)c12]
3-{3-[(4-chloro-1,2,3-trimethyl-1H-indol-7-yl)methyl]-2-oxo-2,3-dihydro-1H-benzimidazol-1-yl}propanoic acid
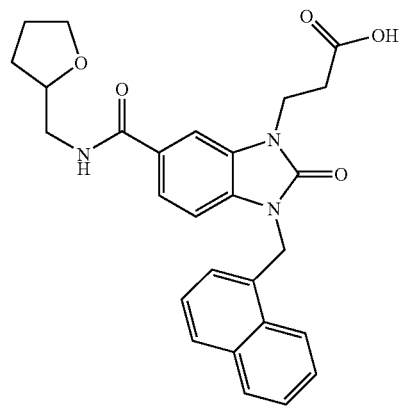 [SMILES: O=C(O)CCn1c(=O)n(Cc2cccc3ccccc23)c2ccc(C(=O)NCC3CCCO3)cc21]
3-{3-(1-naphthylmethyl)-2-oxo-6-[(tetrahydrofuran-2-ylmethyl)carbamoyl]-2,3-dihydro-1H-benzimidazol-1-yl}propanoic acid
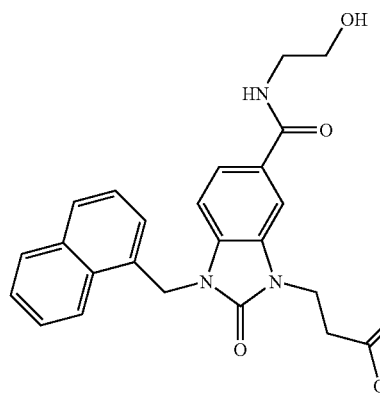
3-{6-[(2-hydroxyethyl)carbamoyl]-3-(1-naphthylmethyl)-2-oxo-2,3-dihydro-1H-benzimidazol-1-yl}propanoic acid
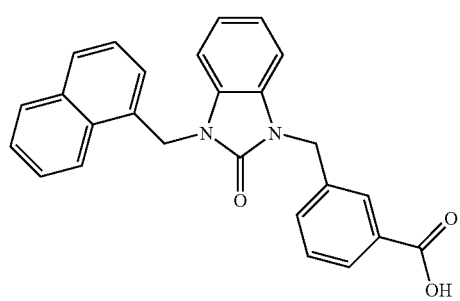 [SMILES: O=C(O)c1cccc(Cn2c(=O)n(Cc3cccc4ccccc34)c3ccccc32)c1]
3-{[3-(1-naphthylmethyl)-2-oxo-2,3-dihydro-1H-benzimidazol-1-yl]methyl}benzoic acid

| | |
|---|---|
| 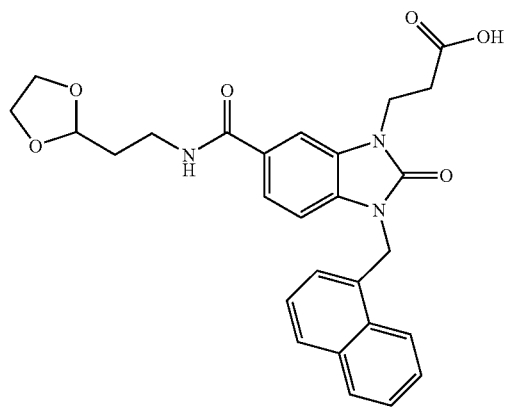 [SMILES: O=C(O)CCn1c(=O)n(Cc2cccc3ccccc23)c2ccc(C(=O)NCCC3OCCO3)cc21] | 3-[6-{[2-(1,3-dioxolan-2-yl)ethyl]carbamoyl}-3-(1-naphthylmethyl)-2-oxo-2,3-dihydro-1H-benzimidazol-1-yl]propanoic acid |
| 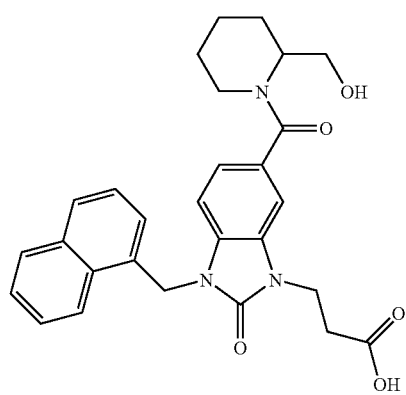 [SMILES: O=C(O)CCn1c(=O)n(Cc2cccc3ccccc23)c2ccc(C(=O)N3CCCCC3CO)cc21] | 3-[6-{[2-(hydroxymethyl)piperidin-1-yl]carbonyl}-3-(1-naphthylmelhyl)-2-oxo-2,3-dihydro-1H-benzimidazol-1-yl]propanoic acid |
| 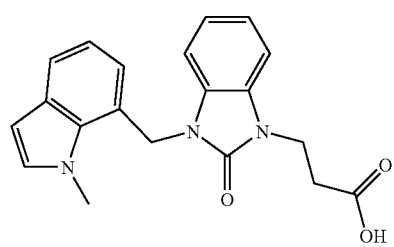 [SMILES: Cn1ccc2cccc(Cn3c(=O)n(CCC(=O)O)c4ccccc43)c21] | 3-{3-[(1-methyl-1H-indol-7-yl)methyl]-2-oxo-2,3-dihydro-1H-benzimidazol-1-yl}propanoic acid |
| 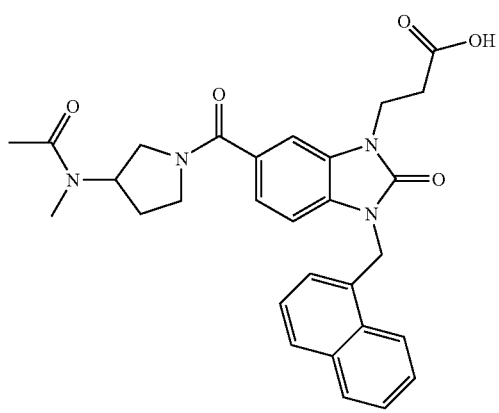 [SMILES: CC(=O)N(C)C1CCN(C(=O)c2ccc3c(c2)n(CCC(=O)O)c(=O)n3Cc2cccc3ccccc23)C1] | 3-[6-({3-[acetyl(methyl)amino]pyrrolidin-1-yl}carbonyl)-3-(1-naphthylmethyl)-2-oxo-2,3-dihydro-1H-benzimidazol-1-yl]propanoic acid |

TABLE I-continued

| | |
|---|---|
| 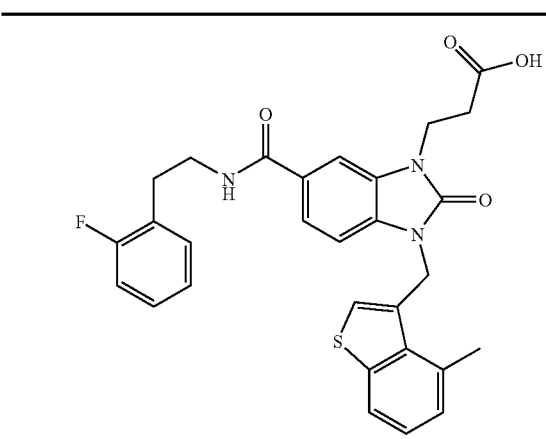 | 3-(6-{[2-(2-fluorophenyl)ethyl]carbamoyl}-3-[(4-methyl-1-benzothien-3-yl)methyl]-2-oxo-2,3-dihydro-1H-benzimidazol-1-yl)propanoic acid |
| Chiral 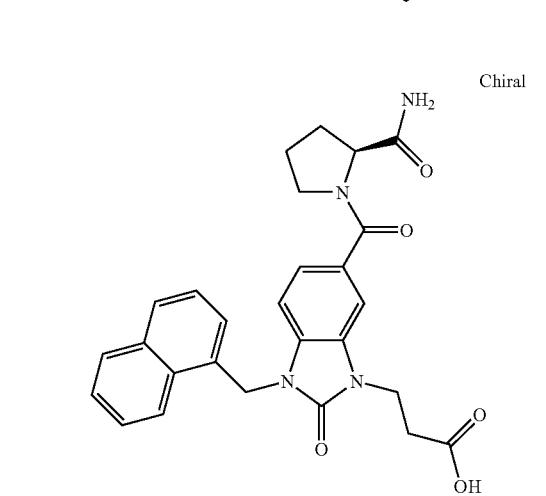 | 3-[6-{[(2S)-2-carbamoylpyrrolidin-1-yl]carbonyl}-3-(1-naphthylmethyl)-2-oxo-2,3-dihydro-1H-benzimidazol-1-yl]propanoic acid |
| 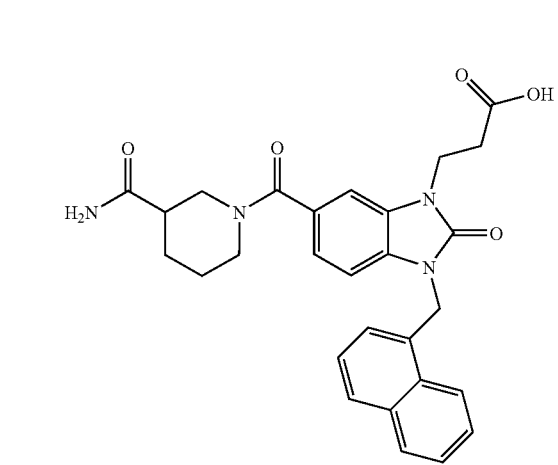 [SMILES: NC(=O)C1CCCN(C(=O)c2ccc3c(c2)n(CCC(=O)O)c(=O)n3Cc2cccc3ccccc23)C1] | 3-{6-[(3-carbamoylpiperidin-1-yl)carbonyl]-3-(1-naphthylmethyl)-2-oxo-2,3-dihydro-1H-benzimidazol-1-yl}propanoic acid |
| 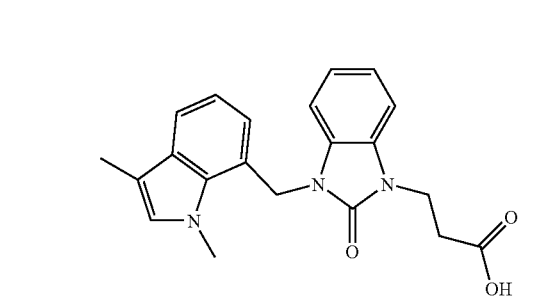 [SMILES: Cc1cn(C)c2c(Cn3c(=O)n(CCC(=O)O)c4ccccc43)cccc12] | 3-{3-[(1,3-dimethyl-1H-indol-7-yl)methyl]-2-oxo-2,3-dihydro-1H-benzimidazol-1-yl}propanoic acid |

| | |
|---|---|
| 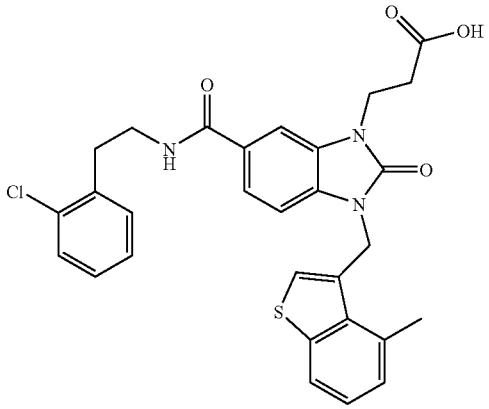 [SMILES: Cc1cccc2scc(Cn3c(=O)n(CCC(=O)O)c4cc(C(=O)NCCc5ccccc5Cl)ccc43)c12] | 3-(6-{[2-(2-chlorophenyl)ethyl]carbamoyl}-3-[(4-methyl-1-benzothien-3-yl)methyl]-2-oxo-2,3-dihydro-1H-benzimidazol-1-yl)propanoic acid |
| 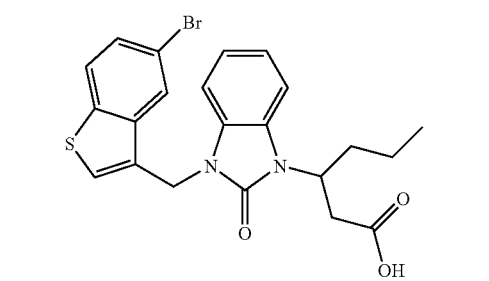 [SMILES: CCCC(CC(=O)O)n1c(=O)n(Cc2csc3ccc(Br)cc23)c2ccccc21] | 3-{3-[(5-bromo-1-benzothien-3-yl)methyl]-2-oxo-2,3-dihydro-1H-benzimidazol-1-yl}hexanoic acid |
| 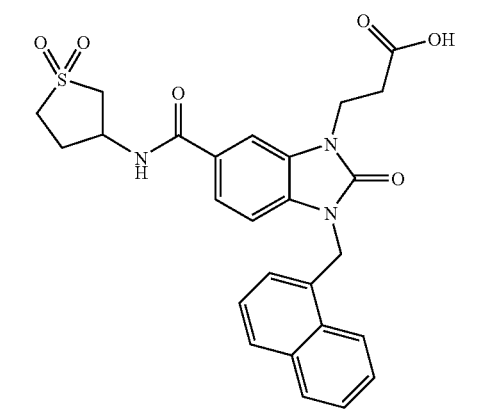 [SMILES: O=C(O)CCn1c(=O)n(Cc2cccc3ccccc23)c2ccc(C(=O)NC3CCS(=O)(=O)C3)cc21] | 3-{6-[(1,1-dioxidotetrahydro-3-thienyl)carbamoyl]-3-(1-naphthylmethyl)-2-oxo-2,3-dihydro-1H-benzimidazol-1-yl}propanoic acid |
| 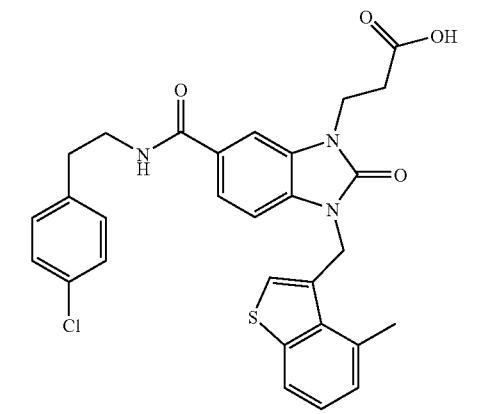 [SMILES: Cc1cccc2scc(Cn3c(=O)n(CCC(=O)O)c4cc(C(=O)NCCc5ccc(Cl)cc5)ccc43)c12] | 3-(6-{[2-(4-chlorophenyl)ethyl]carbamoyl}-3-[(4-methyl-1-benzothien-3-yl)methyl]-2-oxo-2,3-dihydro-1H-benzimidazol-1-yl)propanoic acid |

TABLE I-continued

| | |
|---|---|
| 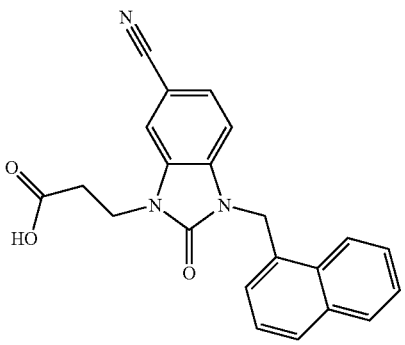 [SMILES: N#Cc1ccc2c(c1)n(CCC(=O)O)c(=O)n2Cc1cccc2ccccc12] | 3-[6-cyano-3-(1-naphthylmethyl)-2-oxo-2,3-dihydro-1H-benzimidazol-1-yl]propanoic acid |
| 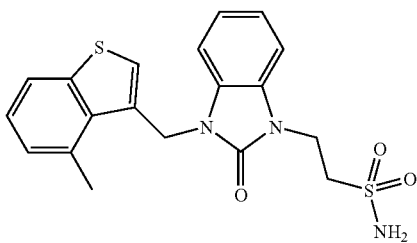 [SMILES: Cc1cccc2scc(Cn3c(=O)n(CCS(N)(=O)=O)c4ccccc43)c12] | 2 {3-[(4-methyl-1-benzothien-3-yl)methyl]-2-oxo-2,3-dihydro-1H-benzimidazol-1-yl}ethanesulfonamide |
| 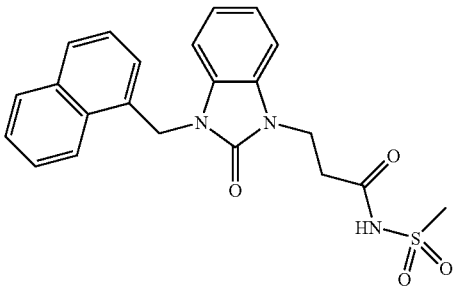 [SMILES: CS(=O)(=O)NC(=O)CCn1c(=O)n(Cc2cccc3ccccc23)c2ccccc21] | N-(methylsulfonyl)-3-[3-(1-naphthylmethyl)-2-oxo-2,3-dihydro-1H-benzimidazol-1-yl]propanamide |
| 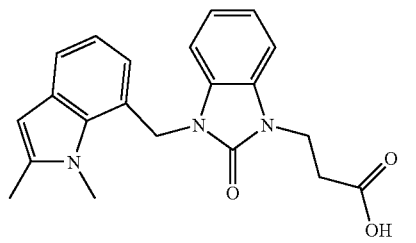 [SMILES: Cc1cc2cccc(Cn3c(=O)n(CCC(=O)O)c4ccccc43)c2n1C] | 3-{3-[(1,2-dimethyl-1H-indol-7-yl)methyl]-2-oxo-2,3-dihydro-1H-benzimidazol-1-yl}propanoic acid |
| 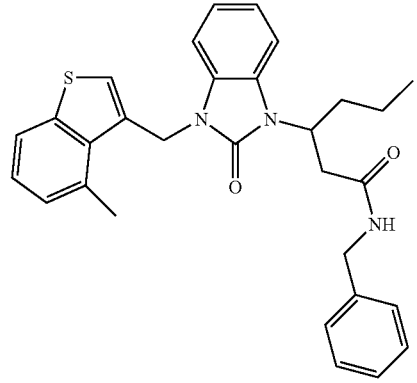 [SMILES: CCCC(CC(=O)NCc1ccccc1)n1c(=O)n(Cc2csc3cccc(C)c23)c2ccccc21] | N-benzyl-3-{3-[(4-methyl-1-benzothien-3-yl)methyl]-2-oxo-2,3-dihydro-1H-benzimidazol-1-yl}hexanamide |

TABLE I-continued

| | |
|---|---|
| 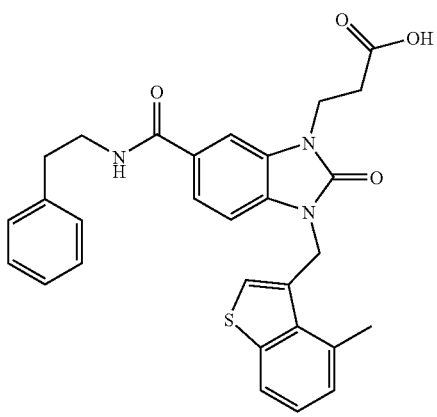 [SMILES: Cc1cccc2scc(Cn3c(=O)n(CCC(=O)O)c4cc(C(=O)NCCc5ccccc5)ccc43)c12] | 3-{3-[(4-methyl-1-benzothien-3-yl)methyl]-2-oxo-6-[(2-phenylethyl)carbamoyl]-2,3-dihydro-1H-benzimidazol-1-yl}propanoic acid |
| 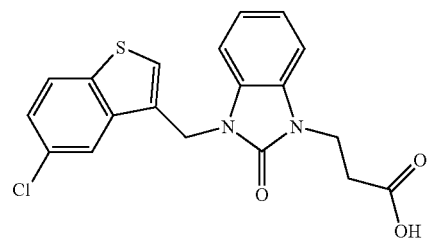 [SMILES: O=C(O)CCn1c(=O)n(Cc2csc3ccc(Cl)cc23)c2ccccc21] | 3-{3-[(5-chloro-1-benzothien-3-yl)methyl]-2-oxo-2,3-dihydro-1H-benzimidazol-1-yl}propanoic acid |
| 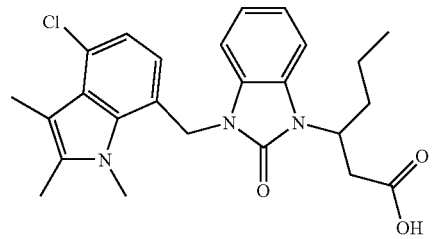 [SMILES: CCCC(CC(=O)O)n1c(=O)n(Cc2ccc(Cl)c3c(C)c(C)n(C)c23)c2ccccc21] | 3-{3-[(4-chloro-1,2,3-trimethyl-1H-indol-7-yl)methyl]-2-oxo-2,3-dihydro-1H-benzimidazol-1-yl}hexanoic acid |
| 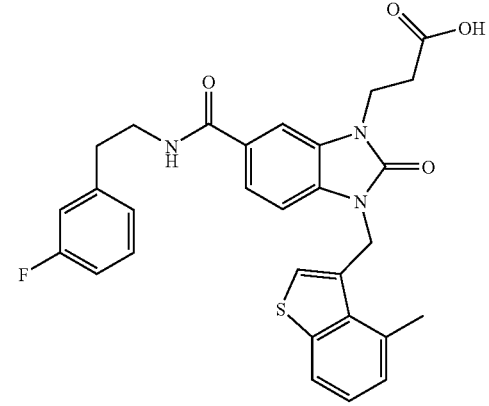 [SMILES: Cc1cccc2scc(Cn3c(=O)n(CCC(=O)O)c4cc(C(=O)NCCc5cccc(F)c5)ccc43)c12] | 3-(6-{[2-(3-fluorophenyl)ethyl]carbamoyl}-3-[(4-methyl-1-benzothien-3-yl)methyl]-2-oxo-2,3-dihydro-1H-benzimidazol-1-yl)propanoic acid |
| 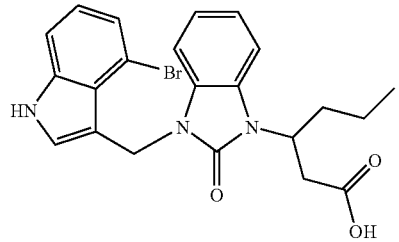 [SMILES: CCCC(CC(=O)O)n1c(=O)n(Cc2c[nH]c3cccc(Br)c23)c2ccccc21] | 3-{3-[(4-bromo-1H-indol-3-yl)methyl]-2-oxo-2,3-dihydro-1H-benzimidazol-1-yl}hexanoic acid |

TABLE I-continued
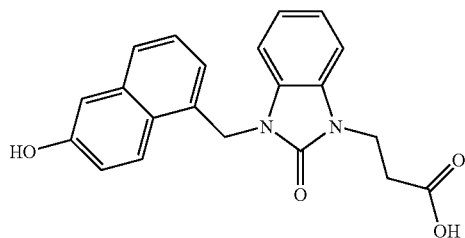 [SMILES: O=C(O)CCn1c(=O)n(Cc2cccc3cc(O)ccc23)c2ccccc21]
3-{3-[(6-hydroxy-1-naphthyl)methyl]-2-oxo-2,3-dihydro-1H-benzimidazol-1-yl}propanoic acid
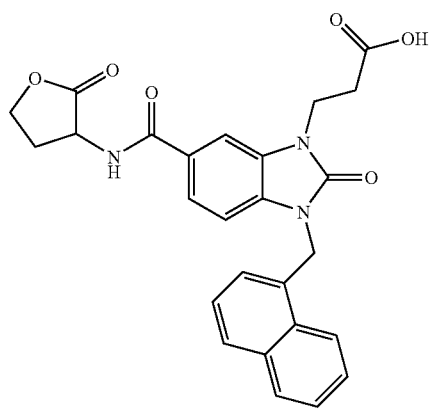 [SMILES: O=C(O)CCn1c(=O)n(Cc2cccc3ccccc23)c2ccc(C(=O)NC3CCOC3=O)cc21]
3-{3-(1-naphthylmethyl)-2-oxo-6-[(2-oxotetrahydrofuran-3-yl)carbamoyl]-2,3-dihydro-1H-benzimidazol-1-yl}propanoic acid
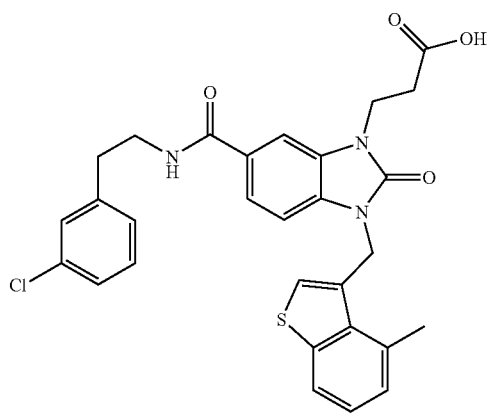 [SMILES: Cc1cccc2scc(Cn3c(=O)n(CCC(=O)O)c4cc(C(=O)NCCc5cccc(Cl)c5)ccc43)c12]
3-(6-{[2-(3-chlorophenyl)ethyl]carbamoyl}-3-[(4-methyl-1-benzothien-3-yl)methyl]-2-oxo-2,3-dihydro-1H-benzimidazol-1-yl)propanoic acid
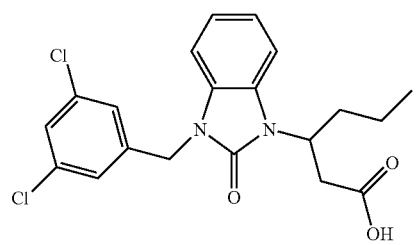 [SMILES: CCCC(CC(=O)O)n1c(=O)n(Cc2cc(Cl)cc(Cl)c2)c2ccccc21]
3-[3-(3,5-dichlorobenzyl)-2-oxo-2,3-dihydro-1H-benzimidazol-1-yl]hexanoic acid TABLE I-continued

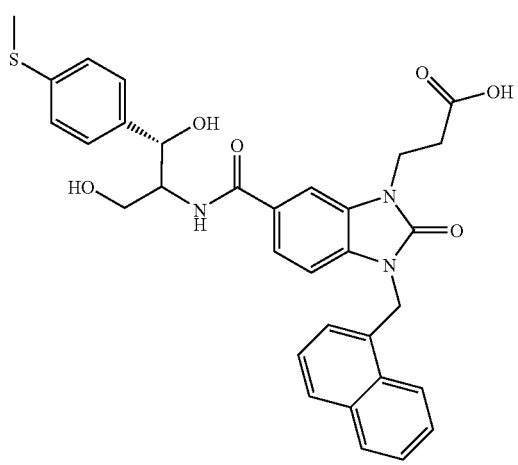

3-[6-({(2S)-2-hydroxy-1-(hydroxymethyl)-2-[4-(methylthio)phenyl]ethyl}carbamoyl)-3-(1-naphthylmethyl)-2-oxo-2,3-dihydro-1H-benzimidazol-1-yl]propanoic acid

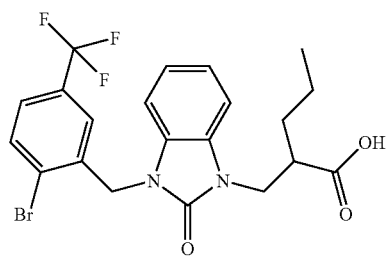 [SMILES: CCCC(Cn1c(=O)n(Cc2cc(C(F)(F)F)ccc2Br)c2ccccc21)C(=O)O]

2-({3-[2-bromo-5-(trifluoromethyl)benzyl]-2-oxo-2,3-dihydro-1H-benzimidazol-1-yl}methyl)pentanoic acid

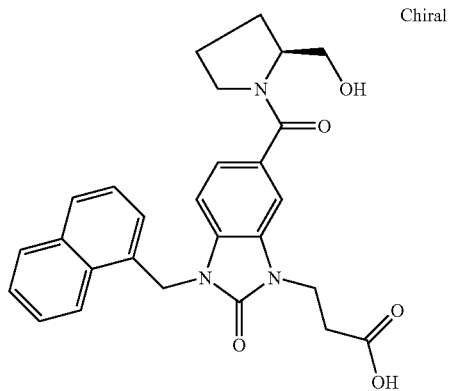 [SMILES: O=C(O)CCn1c(=O)n(Cc2cccc3ccccc23)c2ccc(C(=O)N3CCC[C@H]3CO)cc21]

3-[6-{[2S)-2-(hydroxymethyl)pyrrolidin-1-yl]carbonyl}-3-(1-naphthylmethyl)-2-oxo-2,3-dihydro-1H-benzimidazol-1-yl]propanoic acid

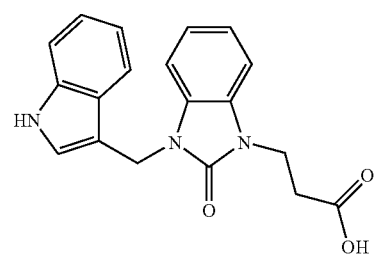 [SMILES: O=C(O)CCn1c(=O)n(Cc2c[nH]c3ccccc23)c2ccccc21]

3-[3-(1H-indol-3-ylmethyl)-2-oxo-2,3-dihydro-1H-benzimidazol-1-yl]propanoic acid TABLE I-continued
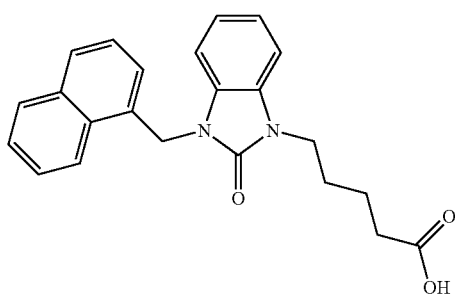 [SMILES: O=C(O)CCCCn1c(=O)n(Cc2cccc3ccccc23)c2ccccc21]
5-[3-(1-naphthylmethyl)-2-oxo-2,3-dihydro-1H-benzimidazol-1-yl]pentanoic acid
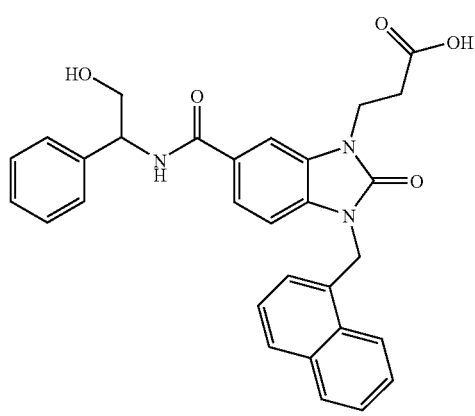 [SMILES: O=C(O)CCn1c(=O)n(Cc2cccc3ccccc23)c2ccc(C(=O)NC(CO)c3ccccc3)cc21]
3-{6-[(2-hydroxy-1-phenylethyl)carbamoyl]-3-(1-naphthylmethyl)-2-oxo-2,3-dihydro-1H-benzimidazol-1-yl}propanoic acid
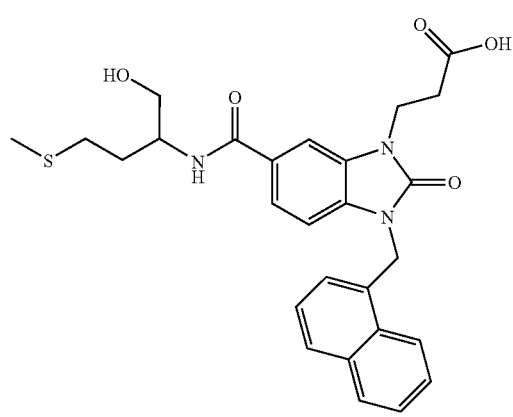 [SMILES: CSCCC(CO)NC(=O)c1ccc2c(c1)n(CCC(=O)O)c(=O)n2Cc1cccc2ccccc12]
3-[6-{[1-(hydroxymethyl)-3-(methylthio)propyl]carbamoyl}-3-(1-naphthylmethyl)-2-oxo-2,3-dihydro-1H-benzimidazol-1-yl]propanoic acid
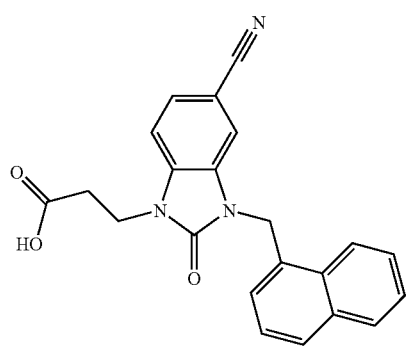 [SMILES: N#Cc1ccc2c(c1)n(Cc1cccc3ccccc13)c(=O)n2CCC(=O)O]
3-[5-cyano-3-(1-naphthylmethyl)-2-oxo-2,3-dihydro-1H-benzimidazol-1-yl]propanoic acid TABLE I-continued

| | |
|---|---|
| 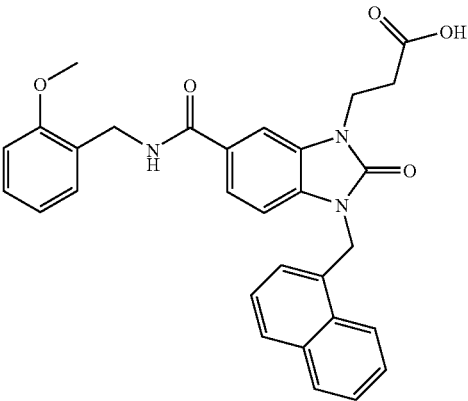 [SMILES: COc1ccccc1CNC(=O)c1ccc2c(c1)n(CCC(=O)O)c(=O)n2Cc1cccc2ccccc12] | 3-{6-[(2-methoxybenzyl)carbamoyl]-3-(1-naphthylmethyl)-2-oxo-2,3-dihydro-1H-benzimidazol-1-yl}propanoic acid |
| 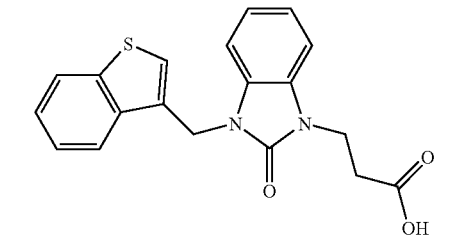 [SMILES: O=C(O)CCn1c(=O)n(Cc2csc3ccccc23)c2ccccc21] | 3-[3-(1-benzothien-3-ylmethyl)-2-oxo-2,3-dihydro-1H-benzimidazol-1-yl]propanoic acid |
| 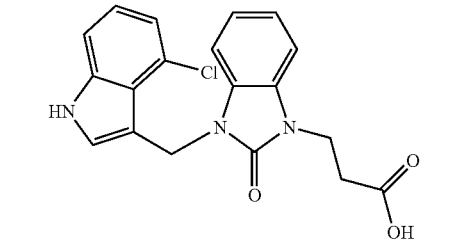 [SMILES: O=C(O)CCn1c(=O)n(Cc2c[nH]c3cccc(Cl)c23)c2ccccc21] | 3-{3-[(4-chloro-1H-indol-3-yl)methyl]-2-oxo-2,3-dihydro-1H-benzimidazol-1-yl}propanoic acid |
| Chiral<br>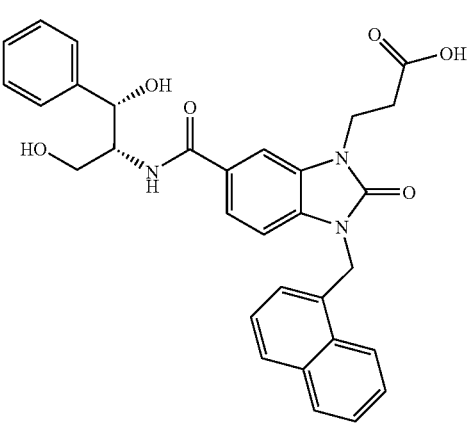 | 3-[6-{[(1R,2S)-2-hydroxy-1-(hydroxymethyl)-2-phenylethyl]carbamoyl}-3-(1-naphthylmethyl)-2-oxo-2,3-dihydro-1H-benzimidazol-1-yl]propanoic acid |
| 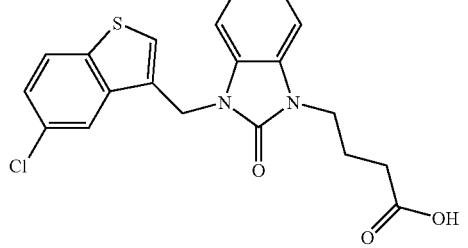 | 4-{3-[(5-chloro-1-benzothien-3-yl)methyl]-2-oxo-2,3-dihydro-1H-benzimidazol-1-yl}butanoic acid |

TABLE I-continued

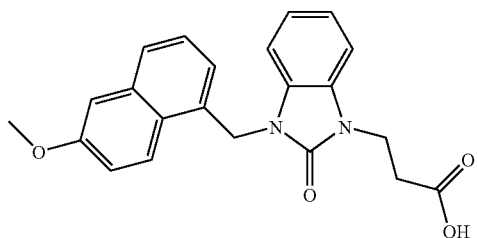 [SMILES: COc1ccc2c(Cn3c(=O)n(CCC(=O)O)c4ccccc43)cccc2c1]

3-{3-[(6-methoxy-1-naphthyl)methyl]-2-oxo-2,3-dihydro-1H-benzimidazol-1-yl}propanoic acid Chiral

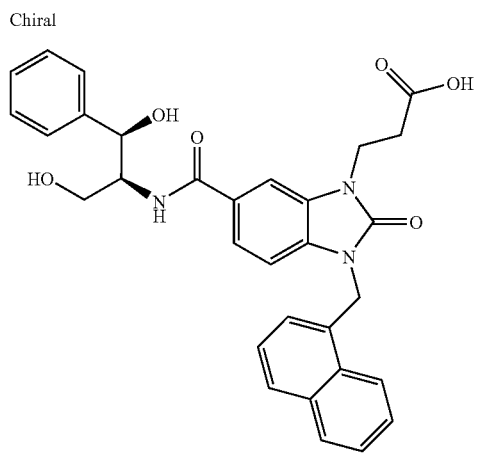 [SMILES: O=C(O)CCn1c(=O)n(Cc2cccc3ccccc23)c2ccc(C(=O)N[C@@H](CO)[C@H](O)c3ccccc3)cc21]

3-[6-{[(1S,2R)-2-hydroxy-1-(hydroxymethyl)-2-phenylethyl]carbamoyl}-3-(1-naphthylmethyl)-2-oxo-2,3-dihydro-1H-benzimidazol-1-yl]propanoic acid

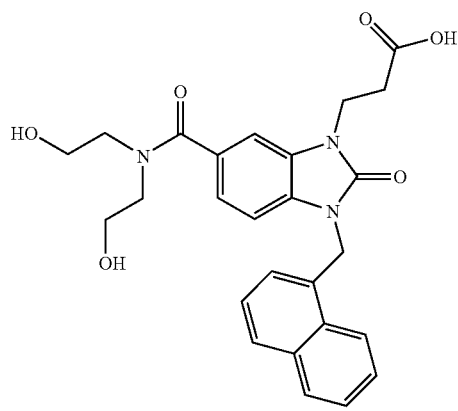 [SMILES: O=C(O)CCn1c(=O)n(Cc2cccc3ccccc23)c2ccc(C(=O)N(CCO)CCO)cc21]

3-{6-[bis(2-hydroxyethyl)carbamoyl]-3-(1-naphthylmethyl)-2-oxo-2,3-dihydro-1H-benzimidazol-1-yl}propanoic acid

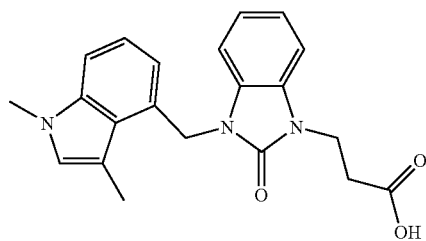 [SMILES: Cc1cn(C)c2cccc(Cn3c(=O)n(CCC(=O)O)c4ccccc43)c12]

3-{3-[(1,3-dimethyl-1H-indol-4-yl)methyl]-2-oxo-2,3-dihydro-1H-benzimidazol-1-yl}propanoic acid

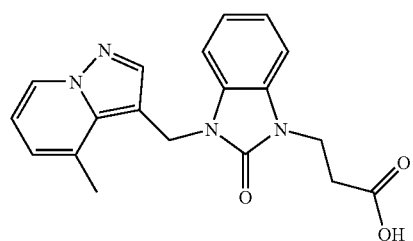 [SMILES: Cc1cccn2ncc(Cn3c(=O)n(CCC(=O)O)c4ccccc43)c12]

3-{3-[(4-methylpyrazolo[1,5-a]pyridin-3-yl)methyl]-2-oxo-2,3-dihydro-1H-benzimidazol-1-yl}propanoic acid TABLE I-continued

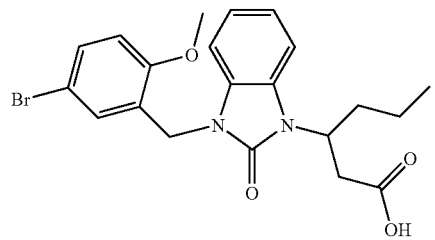 [SMILES: CCCC(CC(=O)O)n1c(=O)n(Cc2cc(Br)ccc2OC)c2ccccc21]
3-[3-(5-bromo-2-methoxybenzyl)-2-oxo-2,3-dihydro-1H-benzimidazol-1-yl]hexanoic acid

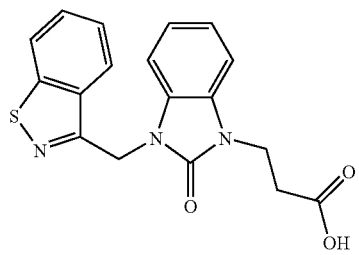 [SMILES: O=C(O)CCn1c(=O)n(Cc2nsc3ccccc23)c2ccccc21]
3-[3-(1,2-benzisothiazol-3-ylmethyl)-2-oxo-2,3-dihydro-1H-benzimidazol-1-yl]propanoic acid

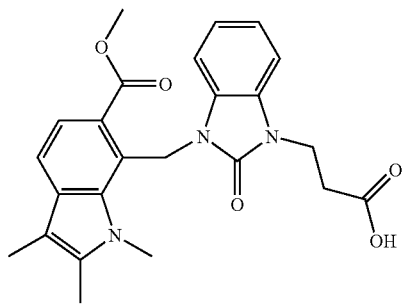 [SMILES: COC(=O)c1ccc2c(C)c(C)n(C)c2c1Cn1c(=O)n(CCC(=O)O)c2ccccc21]
3-(3-{[6-(methoxycarbonyl)-1,2,3-trimethyl-1H-indol-7-yl]methyl}-2-oxo-2,3-dihydro-1H-benzimidazol-1-yl)propanoic acid

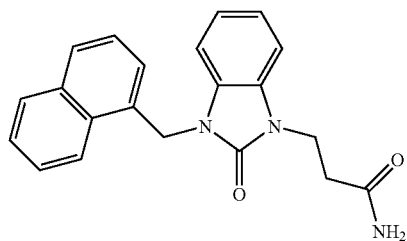 [SMILES: NC(=O)CCn1c(=O)n(Cc2cccc3ccccc23)c2ccccc21]
3-[3-(1-naphthylmethyl)-2-oxo-2,3-dihydro-1H-benzimidazol-1-yl]propanamide

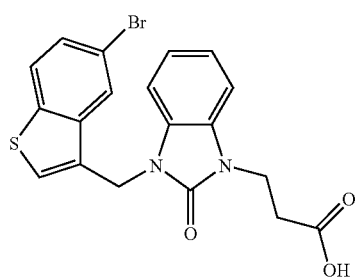 [SMILES: O=C(O)CCn1c(=O)n(Cc2csc3ccc(Br)cc23)c2ccccc21]
3-{3-[(5-bromo-1-benzothien-3-yl)methyl]-2-oxo-2,3-dihydro-1H-benzimidazol-1-yl}propanoic acid

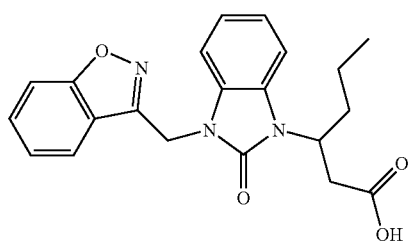 [SMILES: CCCC(CC(=O)O)n1c(=O)n(Cc2noc3ccccc23)c2ccccc21]
3-[3-(1,2-benzisoxazol-3-ylmethyl)-2-oxo-2,3-dihydro-1H-benzimidazol-1-yl]hexanoic acid TABLE I-continued

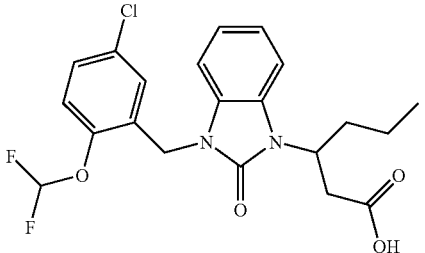 [SMILES: CCCC(CC(=O)O)n1c(=O)n(Cc2cc(Cl)ccc2OC(F)F)c2ccccc21] 3-{3-[5-chloro-2-(difluoromethoxy)benzyl]-2-oxo-2,3-dihydro-1H-benzimidazol-1-yl}hexanoic acid

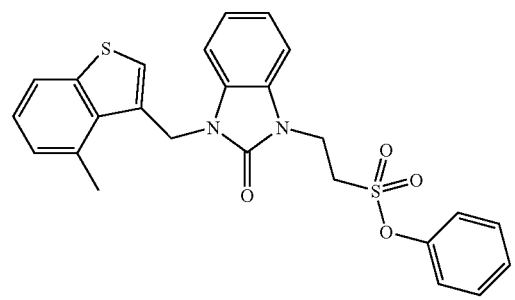 [SMILES: Cc1cccc2scc(Cn3c(=O)n(CCS(=O)(=O)Oc4ccccc4)c4ccccc43)c12] phenyl 2-{3-[(4-methyl-1-benzothien-3-yl)methyl]-2-oxo-2,3-dihydro-1H-benzimidazol-1-yl}ethanesulfonate

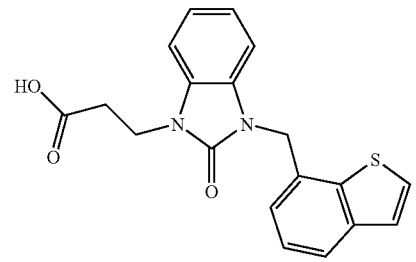 [SMILES: O=C(O)CCn1c(=O)n(Cc2cccc3ccsc23)c2ccccc21] 3-[3-(1-benzothien-7-ylmethyl)-2-oxo-2,3-dihydro-1H-benzimidazol-1-yl]propanoic acid

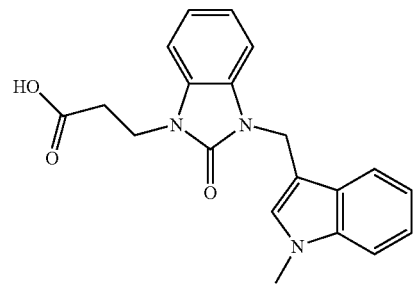 [SMILES: Cn1cc(Cn2c(=O)n(CCC(=O)O)c3ccccc32)c2ccccc21] 3-{3-[(1-methyl-1H-indol-3-yl)methyl]-2-oxo-2,3-dihydro-1H-benzimidazol-1-yl}propanoic acid

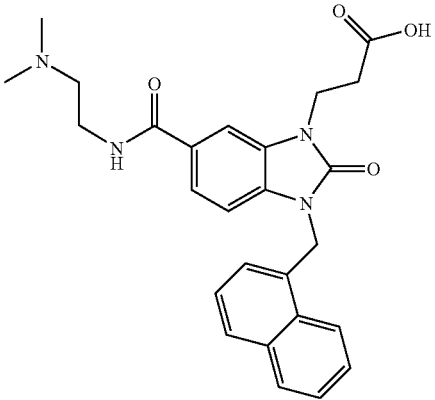 [SMILES: CN(C)CCNC(=O)c1ccc2c(c1)n(CCC(=O)O)c(=O)n2Cc1cccc2ccccc12] 3-[6-{[2-(dimethylamino)ethyl]carbamoyl}-3-(1-naphthylmethyl)-2-oxo-2,3-dihydro-1H-benzimidazol-1-yl]propanoic acid TABLE I-continued

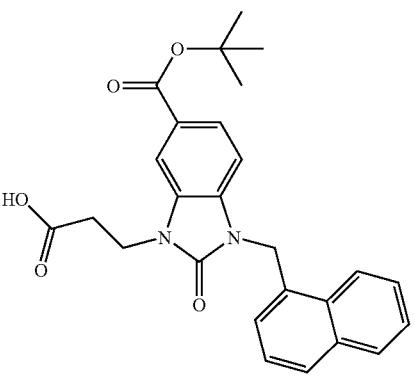 [SMILES: CC(C)(C)OC(=O)c1ccc2c(c1)n(CCC(=O)O)c(=O)n2Cc1cccc2ccccc12]

3-[6-(tert-butoxycarbonyl)-3-(1-naphthylmethyl)-2-oxo-2,3-dihydro-1H-benzimidazol-1-yl]propanoic acid

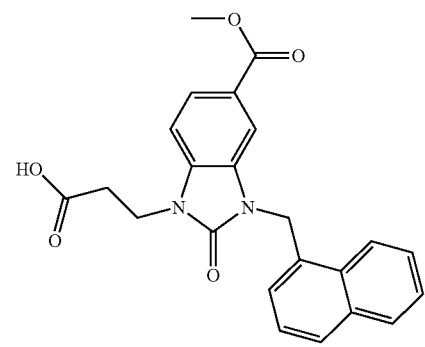 [SMILES: COC(=O)c1ccc2c(c1)n(Cc1cccc3ccccc13)c(=O)n2CCC(=O)O]

3-[5-(methoxycarbonyl)-3-(1-naphthylmethyl)-2-oxo-2,3-dihydro-1H-benzimidazol-1-yl]propanoic acid

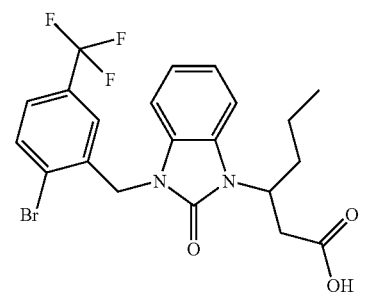 [SMILES: CCCC(CC(=O)O)n1c(=O)n(Cc2cc(C(F)(F)F)ccc2Br)c2ccccc21]

3-{3-[2-bromo-5-(trifluoromethyl)benzyl]-2-oxo-2,3-dihydro-1H-benzimidazol-1-yl}hexanoic acid

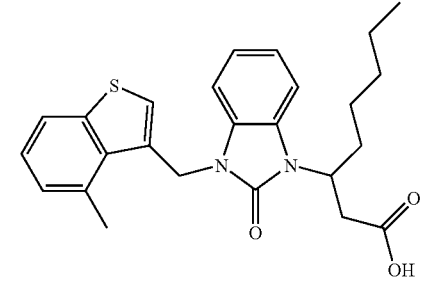 [SMILES: CCCCCC(CC(=O)O)n1c(=O)n(Cc2csc3cccc(C)c23)c2ccccc21]

3-{3-[(4-methyl-1-benzothien-3-yl)methyl]-2-oxo-2,3-dihydro-1H-benzimidazol-1-yl}octanoic acid

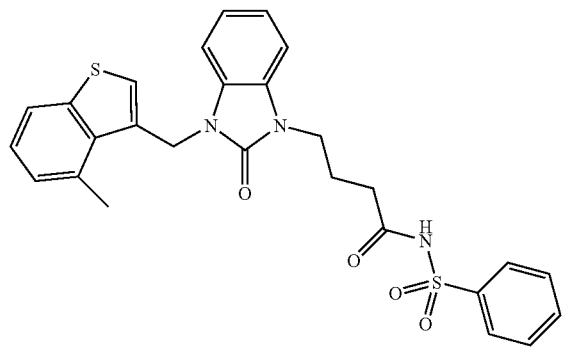 [SMILES: Cc1cccc2scc(Cn3c(=O)n(CCCC(=O)NS(=O)(=O)c4ccccc4)c4ccccc43)c12]

4-{3-[(4-methyl-1-benzothien-3-yl)methyl]-2-oxo-2,3-dihydro-1H-benzimidazol-1-yl}-N-(phenylsulfonyl)butanamide TABLE I-continued
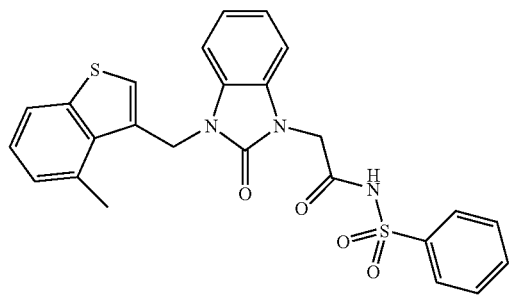 [SMILES: Cc1cccc2scc(Cn3c(=O)n(CC(=O)NS(=O)(=O)c4ccccc4)c4ccccc43)c12]
2-{3-[(4-methyl-1-benzothien-3-yl)methyl]-2-oxo-2,3-dihydro-1H-benzimidazol-1-yl}-N-(phenylsulfonyl)acetamide
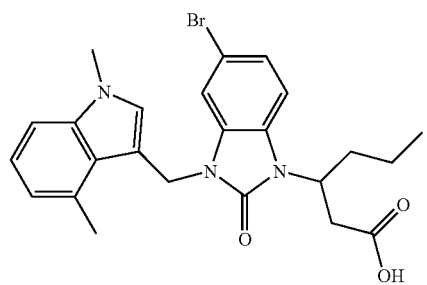 [SMILES: CCCC(CC(=O)O)n1c(=O)n(Cc2cn(C)c3cccc(C)c23)c2cc(Br)ccc21]
3-{5-bromo-3-[(1,4-dimethyl-1H-indol-3-yl)methyl]-2-oxo-2,3-dihydro-1H-benzimidazol-1-yl}hexanoic acid
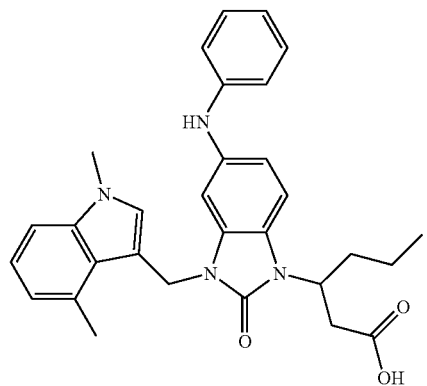 [SMILES: CCCC(CC(=O)O)n1c(=O)n(Cc2cn(C)c3cccc(C)c23)c2cc(Nc3ccccc3)ccc21]
3-{5-anilino-3-[(1,4-dimethyl-1H-indol-3-yl)methyl]-2-oxo-2,3-dihydro-1H-benzimidazol-1-yl}hexanoic acid
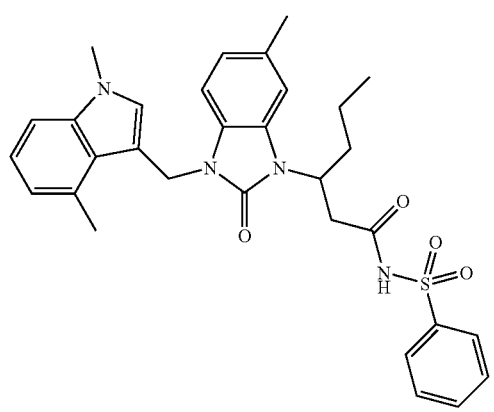 [SMILES: CCCC(CC(=O)NS(=O)(=O)c1ccccc1)n1c(=O)n(Cc2cn(C)c3cccc(C)c23)c2ccc(C)cc21]
3-{3-[(1,4-dimethyl-1H-indol-3-yl)methyl]-6-methyl-2-oxo-2,3-dihydro-1H-benzimidazol-1-yl}-N-(phenylsulfonyl)hexanamide

| | |
|---|---|
| 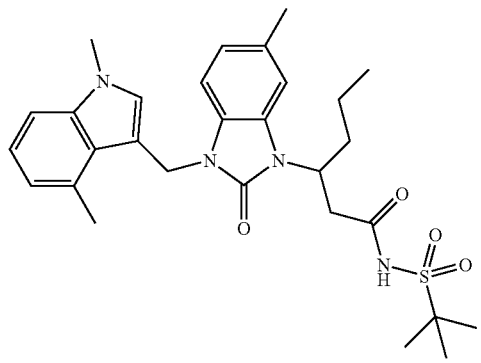 [SMILES: CCCC(CC(=O)NS(=O)(=O)C(C)(C)C)n1c(=O)n(Cc2cn(C)c3cccc(C)c23)c2ccc(C)cc21] | N-(tert-butylsulfonyl)-3-{3-[(1,4-dimethyl-1H-indol-3-yl)methyl]-6-methyl-2-oxo-2,3-dihydro-1H-benzimidazol-1-yl}hexanamide |
| 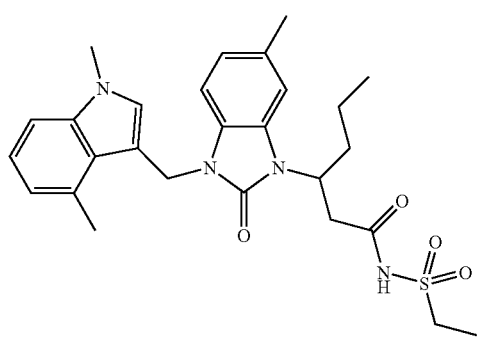 [SMILES: CCCC(CC(=O)NS(=O)(=O)CC)n1c(=O)n(Cc2cn(C)c3cccc(C)c23)c2ccc(C)cc21] | 3-{3-[(1,4-dimethyl-1H-indol-3-yl)methyl]-6-methyl-2-oxo-2,3-dihydro-1H-benzimidazol-1-yl}-N-(ethylsulfonyl)hexanamide |
| 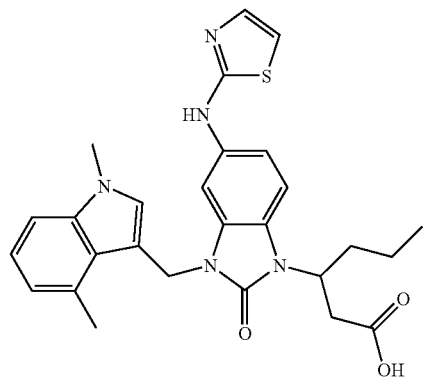 [SMILES: CCCC(CC(=O)O)n1c(=O)n(Cc2cn(C)c3cccc(C)c23)c2cc(Nc3nccs3)ccc21] | 3-{3-[(1,4-dimethyl-1H-indol-3-yl)methyl]-2-oxo-5-(1,3-thiazol-2-ylamino)-2,3-dihydro-1H-benzimidazol-1-yl}hexanoic acid |
| 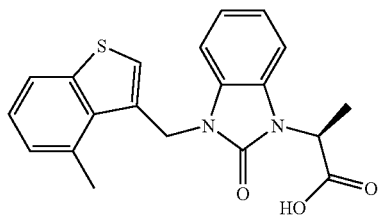 | (2S)-2-{3-[(4-methyl-1-benzothien-3-yl)methyl]-2-oxo-2,3-dihydro-1H-benzimidazol-1-yl}propanoic acid |
| 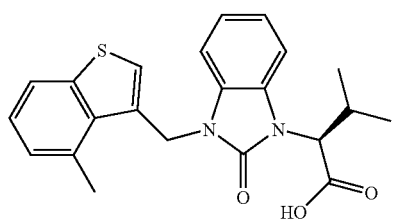 | (2S)-3-methyl-2-{3-[(4-methyl-1-benzothien-3-yl)methyl]-2-oxo-2,3-dihydro-1H-benzimidazol-1-yl}butanoic acid |

TABLE I-continued

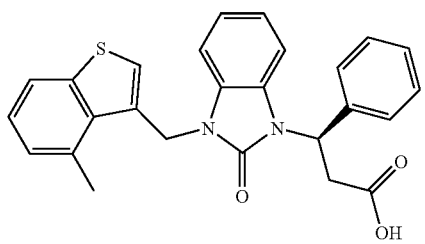
Chiral (3R)-3-{3-[(4-methyl-1-benzothien-3-yl)methyl]-2-oxo-2,3-dihydro-1H-benzimidazol-1-yl}-3-phenylpropanoic acid

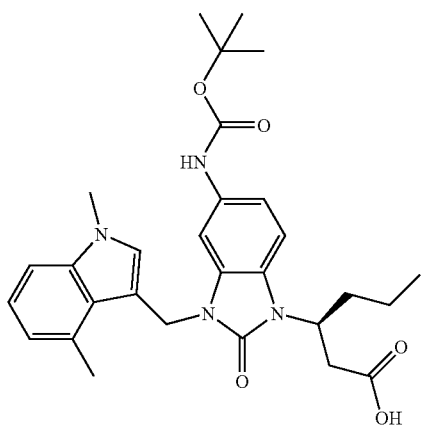
Chiral (3S)-3-{5-[(tert-butoxycarbonyl)amino]3-[(1,4-dimethyl-1H-indol-3-yl)methyl]-2-oxo-2,3-dihydro-1H-benzimidazol-1-yl}hexanoic acid

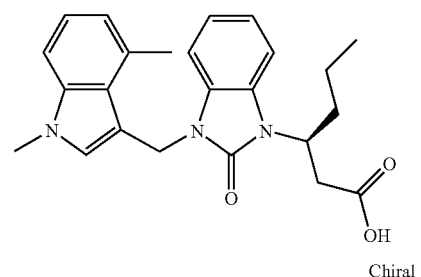 [SMILES: CCC[C@@H](CC(=O)O)n1c(=O)n(Cc2cn(C)c3cccc(C)c23)c2ccccc21]
Chiral (3S)-3-{3-[(1,4-dimethyl-1H-indol-3-yl)methyl]-2-oxo-2,3-dihydro-1H-benzimidazol-1-yl}hexanoic acid

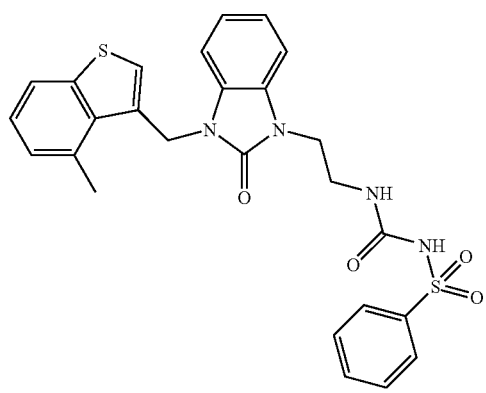 [SMILES: Cc1cccc2scc(Cn3c(=O)n(CCNC(=O)NS(=O)(=O)c4ccccc4)c4ccccc43)c12]

N-[(2-{3-[(4-methyl-1-benzothien-3-yl)methyl]-2-oxo-2,3-dihydro-1H-benzimidazol-1-yl}ethyl)carbamoyl]benzenesulfonamide TABLE I-continued

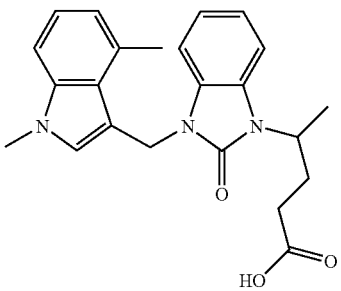 [SMILES: Cc1cccc2c1c(Cn1c(=O)n(C(C)CCC(=O)O)c3ccccc31)cn2C]
4-{3-[(1,4-dimethyl-1H-indol-3-yl)methyl]-2-oxo-2,3-dihydro-1H-benzimidazol-1-yl}pentanoic acid

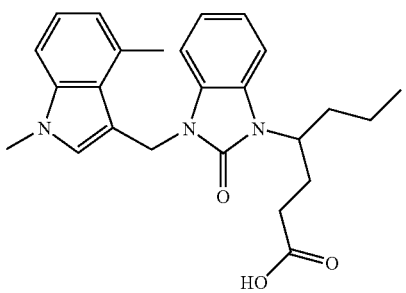 [SMILES: CCCC(CCC(=O)O)n1c(=O)n(Cc2cn(C)c3cccc(C)c23)c2ccccc21]
4-{3-[(1,4-dimethyl-1H-indol-3-yl)methyl]-2-oxo-2,3-dihydro-1H-benzimidazol-1-yl}heptanoic acid

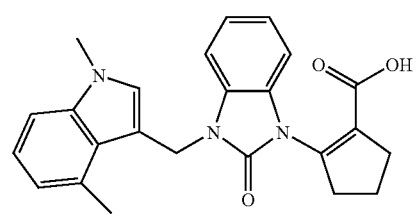 [SMILES: Cc1cccc2c1c(Cn1c(=O)n(C3=C(C(=O)O)CCC3)c3ccccc31)cn2C]
2-{3-[(1,4-dimethyl-1H-indol-3-yl)methyl]-2-oxo-2,3-dihydro-1H-benzimidazol-1-yl}cyclopent-1-ene-1-carboxylic acid

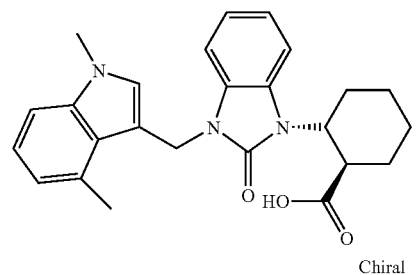
Chiral (1R,2R)-2-{3-[(1,4-dimethyl-1H-indol-3-yl)methyl]-2-oxo-2,3-dihydro-1H-benzimidazol-1-yl}cyclohexanecarboxylic acid

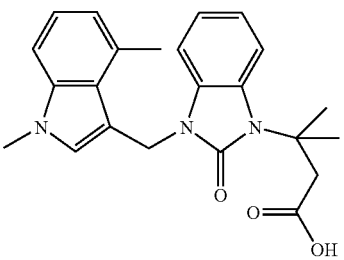 [SMILES: Cc1cccc2c1c(Cn1c(=O)n(C(C)(C)CC(=O)O)c3ccccc31)cn2C]
3-{3-[(1,4-dimethyl-1H-indol-3-yl)methyl]-2-oxo-2,3-dihydro-1H-benzimidazol-1-yl}-3-methylbutanoic acid

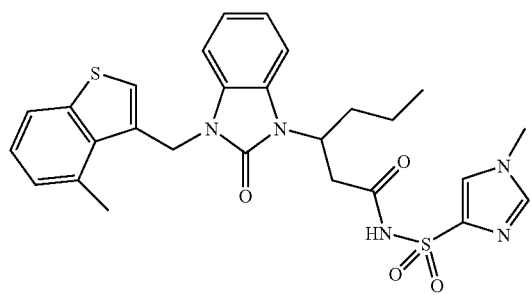 [SMILES: CCCC(CC(=O)NS(=O)(=O)c1cn(C)cn1)n1c(=O)n(Cc2csc3cccc(C)c23)c2ccccc21]
3-{3-[(4-methyl-1-benzothien-3-yl)methyl]-2-oxo-2,3-dihydro-1H-benzimidazol-1-yl}-N-[(1-methyl-1H-imidazol-4-yl)sulfonyl]hexanamide TABLE I-continued

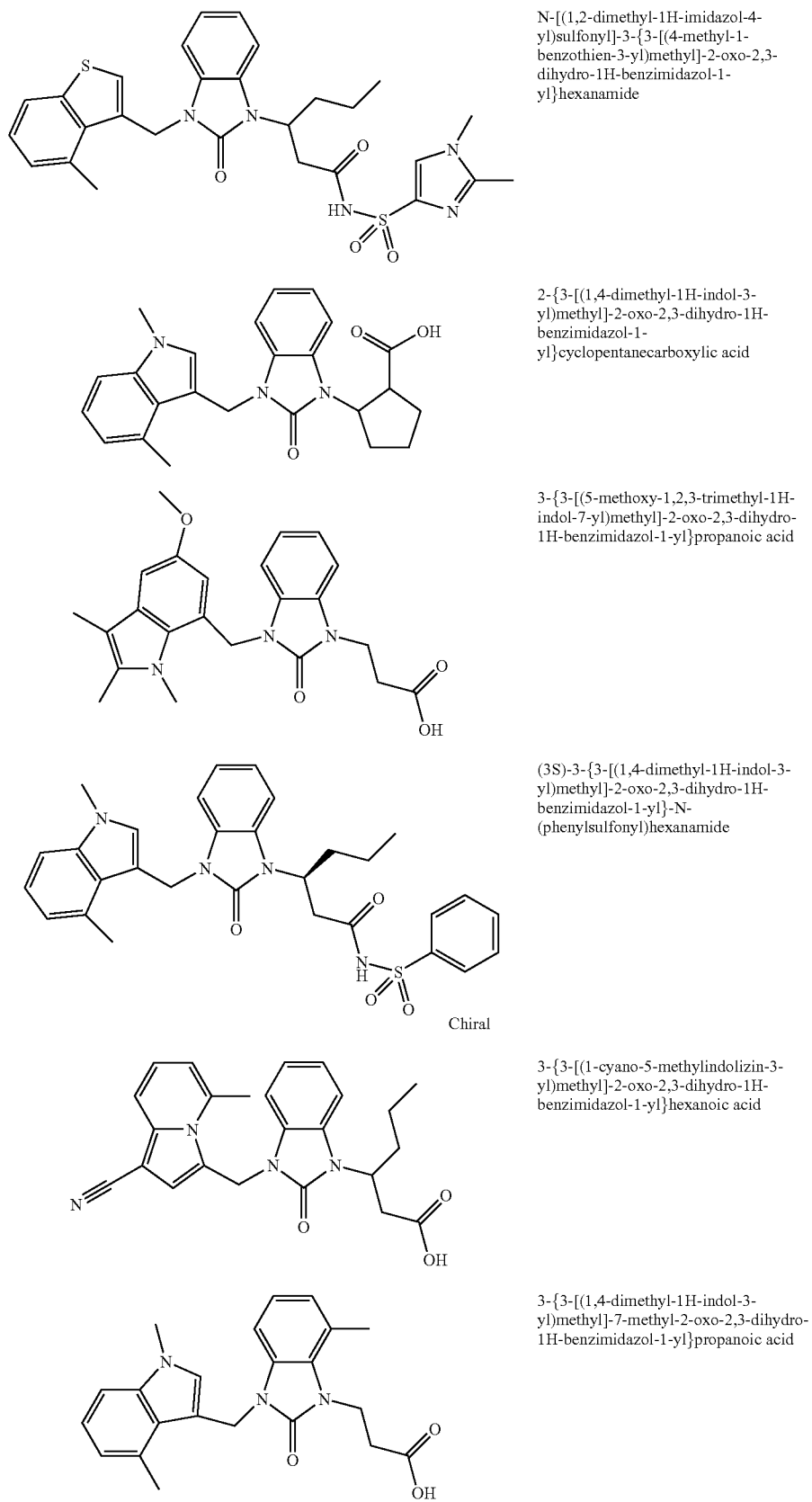

N-[(1,2-dimethyl-1H-imidazol-4-yl)sulfonyl]-3-{3-[(4-methyl-1-benzothien-3-yl)methyl]-2-oxo-2,3-dihydro-1H-benzimidazol-1-yl}hexanamide 2-{3-[(1,4-dimethyl-1H-indol-3-yl)methyl]-2-oxo-2,3-dihydro-1H-benzimidazol-1-yl}cyclopentanecarboxylic acid 3-{3-[(5-methoxy-1,2,3-trimethyl-1H-indol-7-yl)methyl]-2-oxo-2,3-dihydro-1H-benzimidazol-1-yl}propanoic acid (3S)-3-{3-[(1,4-dimethyl-1H-indol-3-yl)methyl]-2-oxo-2,3-dihydro-1H-benzimidazol-1-yl}-N-(phenylsulfonyl)hexanamide 3-{3-[(1-cyano-5-methylindolizin-3-yl)methyl]-2-oxo-2,3-dihydro-1H-benzimidazol-1-yl}hexanoic acid 3-{3-[(1,4-dimethyl-1H-indol-3-yl)methyl]-7-methyl-2-oxo-2,3-dihydro-1H-benzimidazol-1-yl}propanoic acid TABLE I-continued

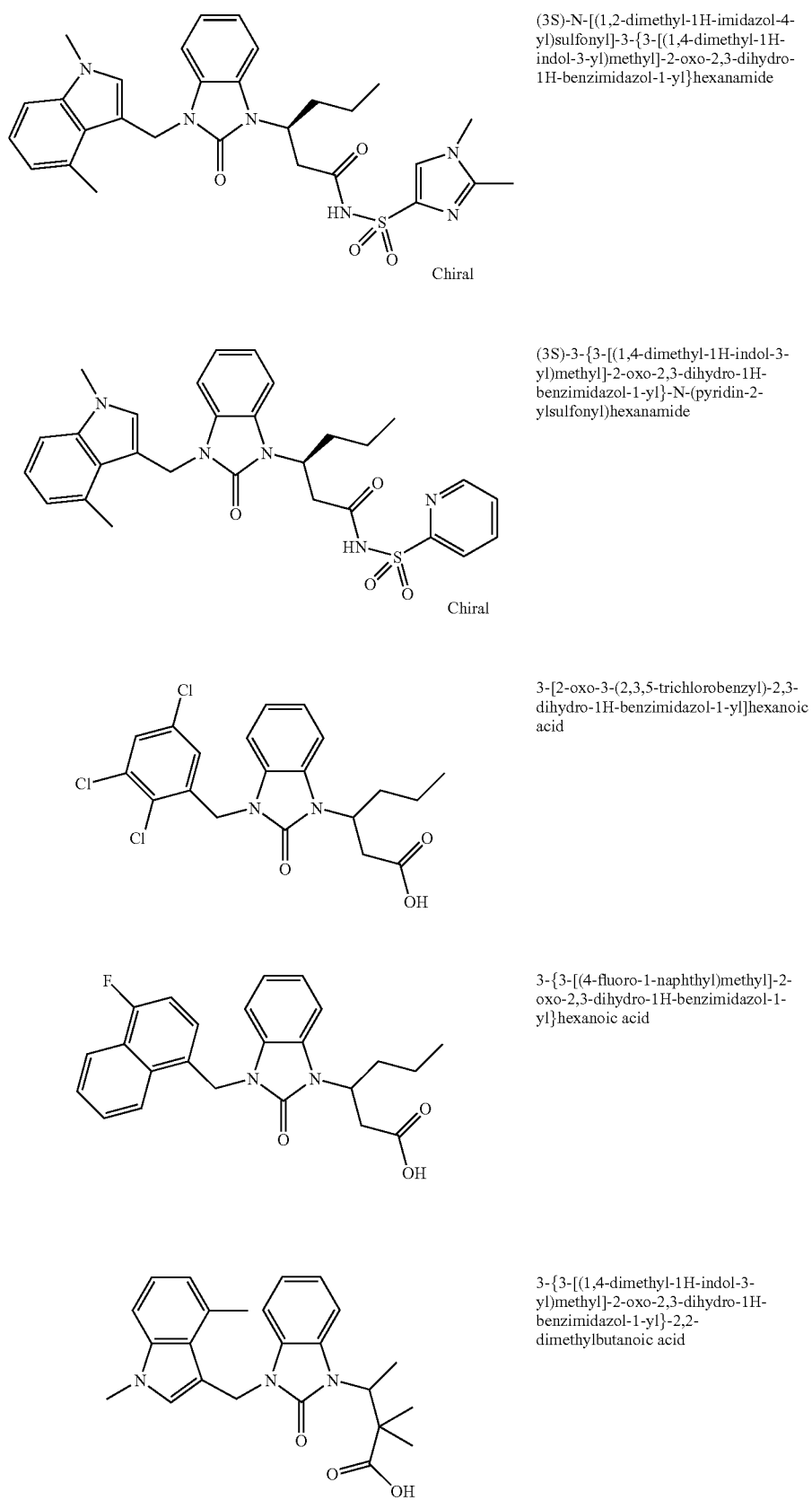

(3S)-N-[(1,2-dimethyl-1H-imidazol-4-yl)sulfonyl]-3-{3-[(1,4-dimethyl-1H-indol-3-yl)methyl]-2-oxo-2,3-dihydro-1H-benzimidazol-1-yl}hexanamide (3S)-3-{3-[(1,4-dimethyl-1H-indol-3-yl)methyl]-2-oxo-2,3-dihydro-1H-benzimidazol-1-yl}-N-(pyridin-2-ylsulfonyl)hexanamide 3-[2-oxo-3-(2,3,5-trichlorobenzyl)-2,3-dihydro-1H-benzimidazol-1-yl]hexanoic acid 3-{3-[(4-fluoro-1-naphthyl)methyl]-2-oxo-2,3-dihydro-1H-benzimidazol-1-yl}hexanoic acid 3-{3-[(1,4-dimethyl-1H-indol-3-yl)methyl]-2-oxo-2,3-dihydro-1H-benzimidazol-1-yl}-2,2-dimethylbutanoic acid TABLE I-continued

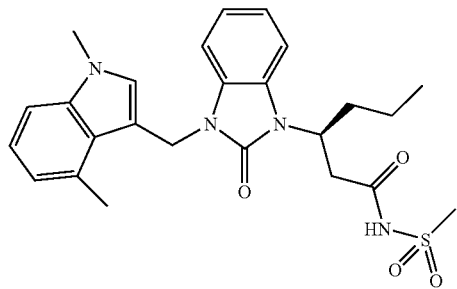
Chiral (3S)-3-{3-[(1,4-dimethyl-1H-indol-3-yl)methyl]-2-oxo-2,3-dihydro-1H-benzimidazol-1-yl}-N-(methylsulfonyl)hexanamide

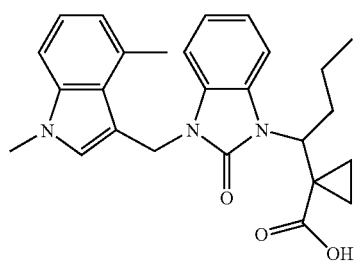 [SMILES: CCCC(n1c(=O)n(Cc2cn(C)c3cccc(C)c23)c2ccccc21)C1(C(=O)O)CC1]

1-(1-{3-[(1,4-dimethyl-1H-indol-3-yl)methyl]-2-oxo-2,3-dihydro-1H-benzimidazol-1-yl}butyl)cyclopropanecarboxylic acid

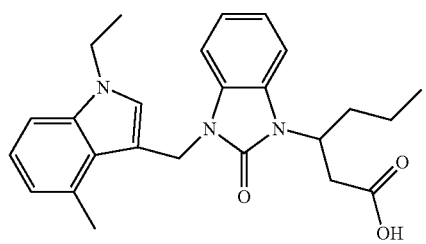 [SMILES: CCCC(CC(=O)O)n1c(=O)n(Cc2cn(CC)c3cccc(C)c23)c2ccccc21]

3-{3-[(1-ethyl-4-methyl-1H-indol-3-yl)methyl]-2-oxo-2,3-dihydro-1H-benzimidazol-1-yl}hexanoic acid

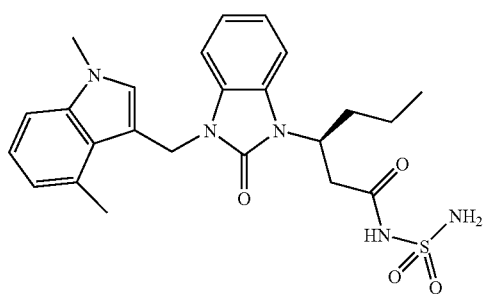
Chiral (3S)-N-(aminosulfonyl)-3-{3-[(1,4-dimethyl-1H-indol-3-yl)methyl]-2-oxo-2,3-dihydro-1H-benzimidazol-1-yl}hexanamide

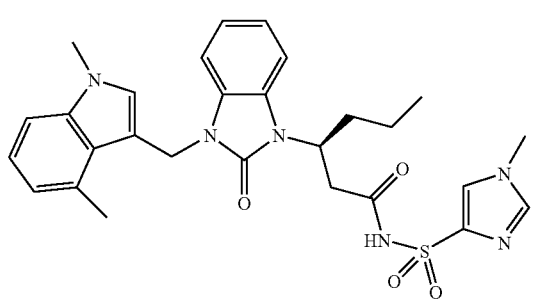
Chiral (3S)-3-{3-[(1,4-dimethyl-1H-indol-3-yl)methyl]-2-oxo-2,3-dihydro-1H-benzimidazol-1-yl}-N-[(1-methyl-1H-imidazol-4-yl)sulfonyl]hexanamide TABLE I-continued

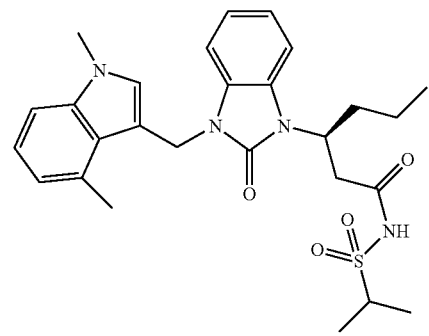

Chiral (3S)-3-{3-[(1,4-dimethyl-1H-indol-3-yl)methyl]-2-oxo-2,3-dihydro-1H-benzimidazol-1-yl}-N-(isopropylsulfonyl)hexanamide

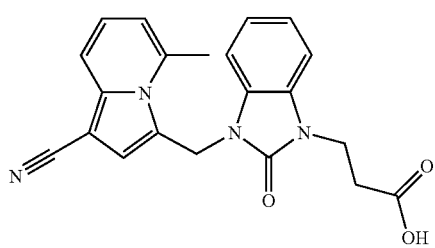 [SMILES: Cc1cccc2c(C#N)cc(Cn3c(=O)n(CCC(=O)O)c4ccccc43)n12]

3-{3-[(1-cyano-5-methylindolizin-3-yl)methyl]-2-oxo-2,3-dihydro-1H-benzimidazol-1-yl}propanoic acid

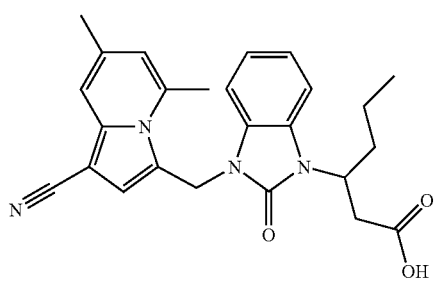 [SMILES: CCCC(CC(=O)O)n1c(=O)n(Cc2cc(C#N)c3cc(C)cc(C)n23)c2ccccc21]

3-{3-[(1-cyano-5,7-dimethylindolizin-3-yl)methyl]-2-oxo-2,3-dihydro-1H-benzimidazol-1-yl}hexanoic acid

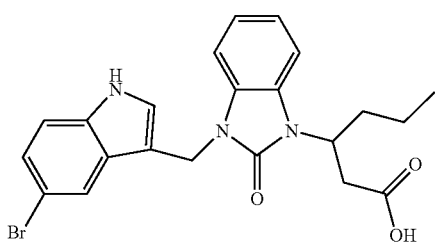 [SMILES: CCCC(CC(=O)O)n1c(=O)n(Cc2c[nH]c3ccc(Br)cc23)c2ccccc21]

3-{3-[(5-bromo-1H-indol-3-yl)methyl]-2-oxo-2,3-dihydro-1H-benzimidazol-1-yl}hexanoic acid

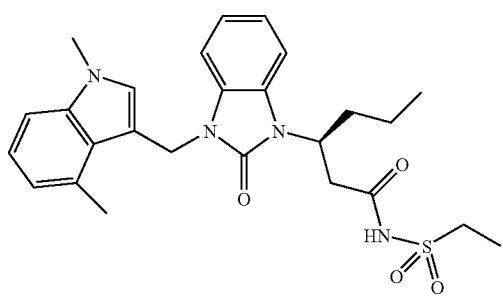

Chiral (3S)-3-{3-[(1,4-dimethyl-1H-indol-3-yl)methyl]-2-oxo-2,3-dihydro-1H-benzimidazol-1-yl}-N-(ethylsulfonyl)hexanamide TABLE I-continued

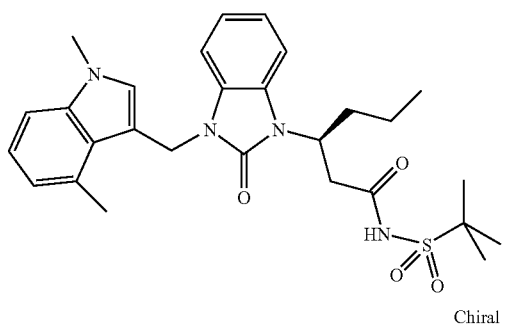 [SMILES: CCC[C@@H](CC(=O)NS(=O)(=O)C(C)(C)C)n1c(=O)n(Cc2cn(C)c3cccc(C)c23)c2ccccc21]
Chiral (3S)-N-(tert-butylsulfonyl)-3-{3-[(1,4-dimethyl-1H-indol-3-yl)methyl]-2-oxo-2,3-dihydro-1H-benzimidazol-1-yl}hexanamide

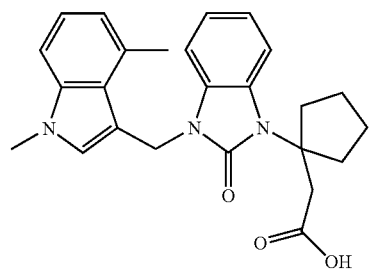 [SMILES: Cc1cccc2c1c(Cn1c(=O)n(C3(CC(=O)O)CCCC3)c3ccccc31)cn2C]

(1-{3-[(1,4-dimethyl-1H-indol-3-yl)methyl]-2-oxo-2,3-dihydro-1H-benzimidazol-1-yl}cyclopentyl)acetic acid

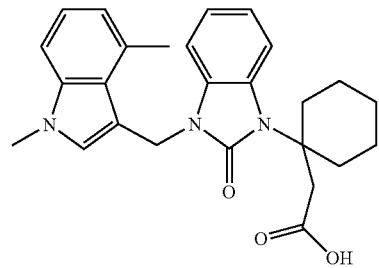 [SMILES: Cc1cccc2c1c(Cn1c(=O)n(C3(CC(=O)O)CCCCC3)c3ccccc31)cn2C]

(1-{3-[(1,4-dimethyl-1H-indol-3-yl)methyl]-2-oxo-2,3-dihydro-1H-benzimidazol-1-yl}cyclohexyl)acetic acid

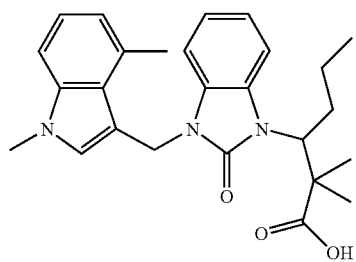

3-{3-[(1,4-dimethyl-1H-indol-3-yl)methyl]-2-oxo-2,3-dihydro-1H-benzimidazol-1-yl}-2,2-dimethylhexanoic acid

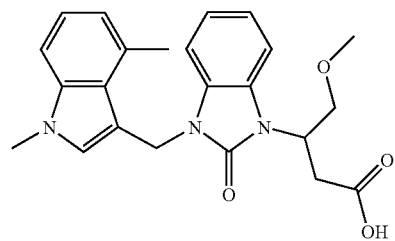 [SMILES: COCC(CC(=O)O)n1c(=O)n(Cc2cn(C)c3cccc(C)c23)c2ccccc21]

3-{3-[(1,4-dimethyl-1H-indol-3-yl)methyl]-2-oxo-2,3-dihydro-1H-benzimidazol-1-yl}-4-methoxybutanoic acid TABLE I-continued

| | |
|---|---|
| 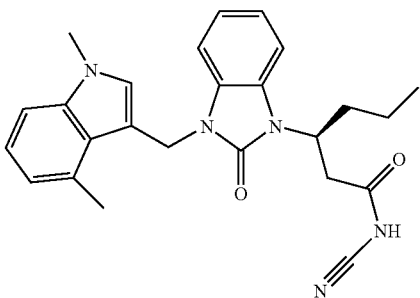<br>Chiral | (3S)-N-cyano-3-{3-[(1,4-dimethyl-1H-indol-3-yl)methyl]-2-oxo-2,3-dihydro-1H-benzimidazol-1-yl}hexanamide |
| 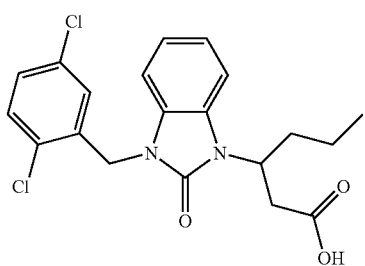 [SMILES: CCCC(CC(=O)O)n1c(=O)n(Cc2cc(Cl)ccc2Cl)c2ccccc21] | 3-[3-(2,5-dichlorobenzyl)-2-oxo-2,3-dihydro-1H-benzimidazol-1H-yl]hexanoic acid |
| 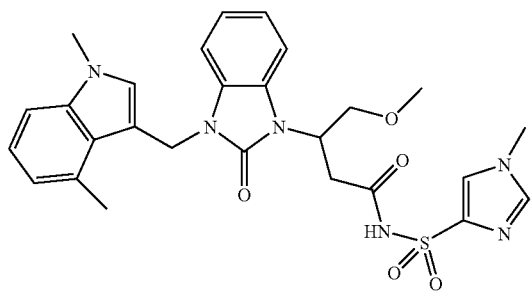 [SMILES: COCC(CC(=O)NS(=O)(=O)c1cn(C)cn1)n1c(=O)n(Cc2cn(C)c3cccc(C)c23)c2ccccc21] | 3-{3-[(1,4-dimethyl-1H-indol-3-yl)methyl]-2-oxo-2,3-dihydro-1H-benzimidazol-1-yl}-4-methoxy-N-[(1-methyl-1H-imidazol-4-yl)sulfonyl]butanamide |
| 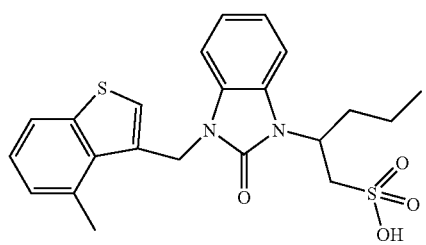 [SMILES: CCCC(CS(=O)(=O)O)n1c(=O)n(Cc2csc3cccc(C)c23)c2ccccc21] | 2-{3-[(4-methyl-1-benzothien-3-yl)methyl]-2-oxo-2,3-dihydro-1H-benzimidazol-1-yl}pentane-1-sulfonic acid |
| 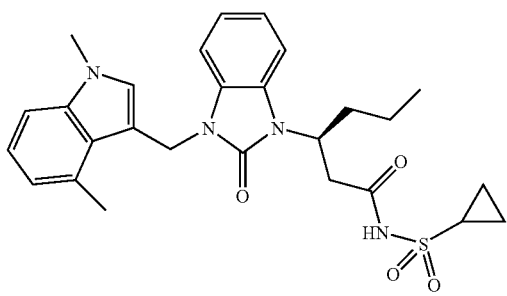<br>Chiral | (3S)-N-(cyclopropylsulfonyl)-3-{3-[(1,4-dimethyl-1H-indol-3-yl)methyl]-2-oxo-2,3-dihydro-1H-benzimidazol-1-yl}hexanamide |

TABLE I-continued

| | |
|---|---|
| 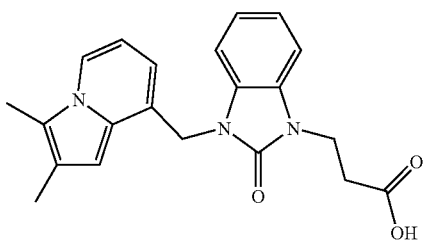 [SMILES: Cc1cc2c(Cn3c(=O)n(CCC(=O)O)c4ccccc43)cccn2c1C] | 3-{3-[(2,3-dimethylindolizin-8-yl)methyl]-2-oxo-2,3-dihydro-1H-benzimidazol-1-yl}propanoic acid |
| 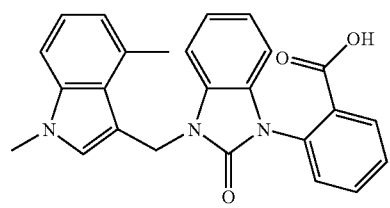 [SMILES: Cc1cccc2c1c(Cn1c(=O)n(-c3ccccc3C(=O)O)c3ccccc31)cn2C] | 2-{3-[(1,4-dimethyl-1H-indol-3-yl)methyl]-2-oxo-2,3-dihydro-1H-benzimidazol-1-yl}benzoic acid |
| 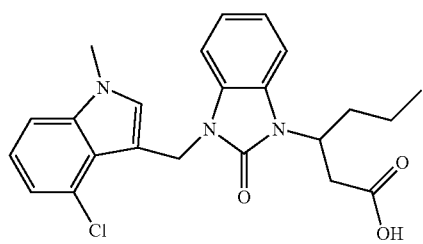 [SMILES: CCCC(CC(=O)O)n1c(=O)n(Cc2cn(C)c3cccc(Cl)c23)c2ccccc21] | 3-{3-[(4-chloro-1-methyl-1H-indol-3-yl)methyl]-2-oxo-2,3-dihydro-1H-benzimidazol-1-yl}hexanoic acid |
| 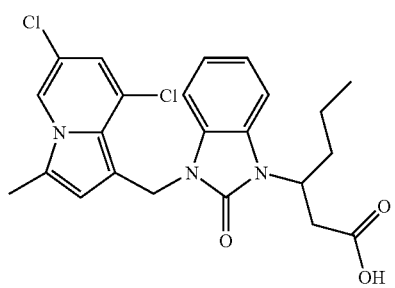 [SMILES: CCCC(CC(=O)O)n1c(=O)n(Cc2cc(C)n3cc(Cl)cc(Cl)c23)c2ccccc21] | 3-{3-[(6,8-dichloro-3-methylindolizin-1-yl)methyl]-2-oxo-2,3-dihydro-1H-benzimidazol-1-yl}hexanoic acid |
| 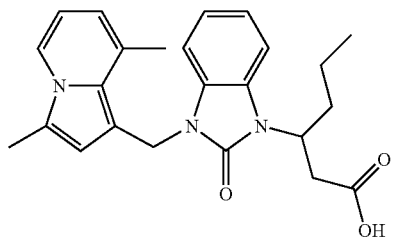 [SMILES: CCCC(CC(=O)O)n1c(=O)n(Cc2cc(C)n3cccc(C)c23)c2ccccc21] | 3-{3-[(3,8-dimethylindolizin-1-yl)methyl]-2-oxo-2,3-dihydro-1H-benzimidazol-1-yl}hexanoic acid |
| 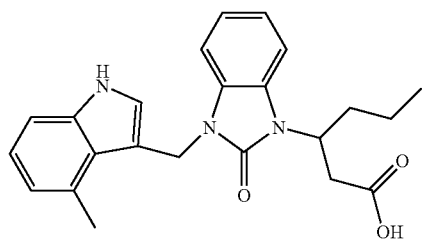 [SMILES: CCCC(CC(=O)O)n1c(=O)n(Cc2c[nH]c3cccc(C)c23)c2ccccc21] | 3-{3-[(4-methyl-1H-indol-3-yl)methyl]-2-oxo-2,3-dihydro-1H-benzimidazol-1-yl}hexanoic acid |

| | |
|---|---|
| 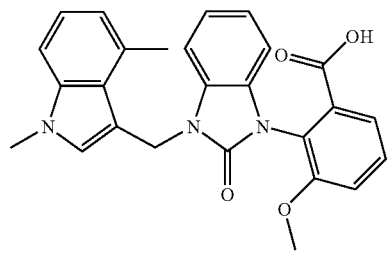 [SMILES: COc1cccc(C(=O)O)c1-n1c(=O)n(Cc2cn(C)c3cccc(C)c23)c2ccccc21] | 2-{3-[(1,4-dimethyl-1H-indol-3-yl)methyl]-2-oxo-2,3-dihydro-1H-benzimidazol-1-yl}-3-methoxybenzoic acid |
| 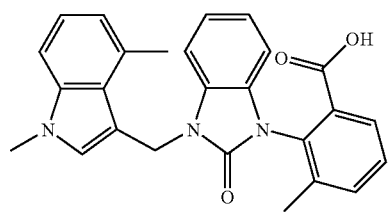 [SMILES: Cc1cccc(C(=O)O)c1-n1c(=O)n(Cc2cn(C)c3cccc(C)c23)c2ccccc21] | 2-{3-[(1,4-dimethyl-1H-indol-3-yl)methyl]-2-oxo-2,3-dihydro-1H-benzimidazol-1-yl}-3-methylbenzoic acid |
| 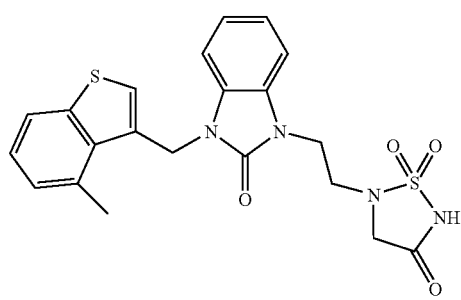 [SMILES: Cc1cccc2scc(Cn3c(=O)n(CCN4CC(=O)NS4(=O)=O)c4ccccc43)c12] | 1-[2-(1,1-dioxido-4-oxo-1,2,5-thiadiazolidin-2-yl)ethyl]-3-[(4-methyl-1-benzothien-3-yl)methyl]-1,3-dihydro-2H-benzimidazol-2-one |
| 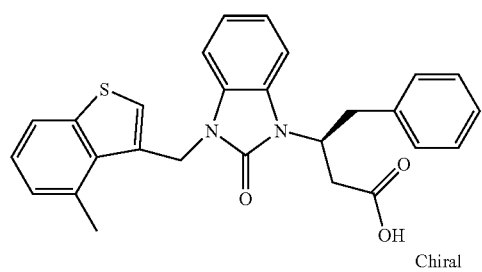 [SMILES: Cc1cccc2scc(Cn3c(=O)n([C@H](CC(=O)O)Cc4ccccc4)c4ccccc43)c12] | (3S)-3-{3-[(4-methyl-1-benzothien-3-yl)methyl]-2-oxo-2,3-dihydro-1H-benzimidazol-1-yl}-4-phenylbutanoic acid |
| 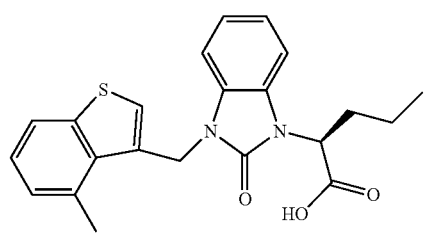 | (2S)-2-{3-[(4-methyl-1-benzothien-3-yl)methyl]-2-oxo-2,3-dihydro-1H-benzimidazol-1-yl}pentanoic acid |
| 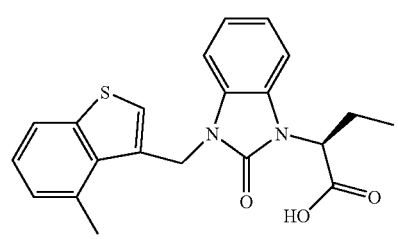 | (2S)-2-{3-[(4-methyl-1-benzothien-3-yl)methyl]-2-oxo-2,3-dihydro-1H-benzimidazol-1-yl}butanoic acid |

TABLE I-continued

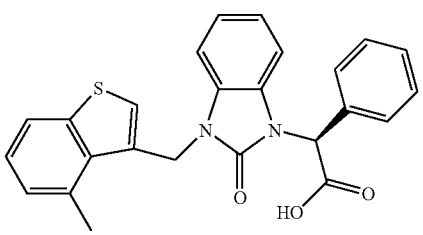

Chiral (2S)-{3-[(4-methyl-1-benzothien-3-yl)methyl]-2-oxo-2,3-dihydro-1H-benzimidazol-1-yl}(phenyl)acetic acid

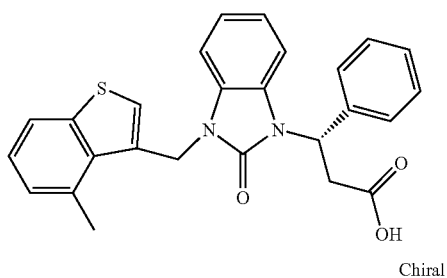 [SMILES: Cc1cccc2scc(Cn3c(=O)n([C@@H](CC(=O)O)c4ccccc4)c4ccccc43)c12]

Chiral (3S)-3-{3-[(4-methyl-1-benzothien-3-yl)methyl]-2-oxo-2,3-dihydro-1H-benzimidazol-1-yl}-3-phenylpropanoic acid

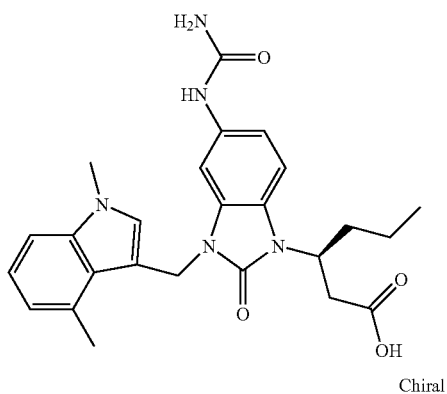 [SMILES: CCC[C@@H](CC(=O)O)n1c(=O)n(Cc2cn(C)c3cccc(C)c23)c2cc(NC(N)=O)ccc21]

Chiral (3S)-3-{5-(carbamoylamino)-3-[(1,4-dimethyl-1H-indol-3-yl)methyl]-2-oxo-2,3-dihydro-1H-benzimidazol-1-yl}hexanoic acid

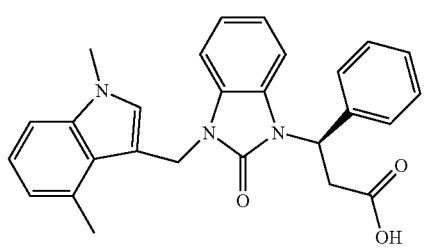

Chiral (3R)-3-{3-[(1,4-dimethyl-1H-indol-3-yl)methyl]-2-oxo-2,3-dihydro-1H-benzimidazol-1-yl}-3-phenylpropanoic acid

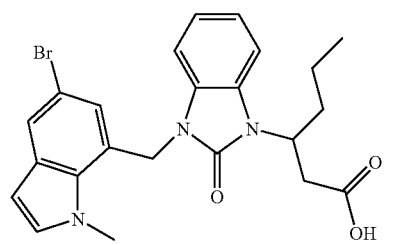 [SMILES: CCCC(CC(=O)O)n1c(=O)n(Cc2cc(Br)cc3ccn(C)c23)c2ccccc21]

3-{3-[(5-bromo-1-methyl-1H-indol-7-yl)methyl]-2-oxo-2,3-dihydro-1H-benzimidazol-1-yl}hexanoic acid TABLE I-continued

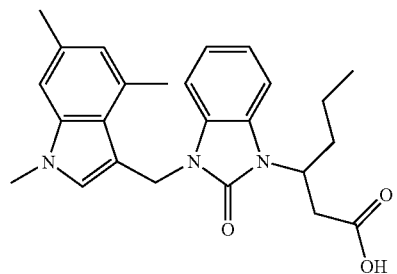 [SMILES: CCCC(CC(=O)O)n1c(=O)n(Cc2cn(C)c3cc(C)cc(C)c23)c2ccccc21]

3-{2-oxo-3-[(1,4,6-trimethyl-1H-indol-3-yl)methyl]-2,3-dihydro-1H-benzimidazol-1-yl}hexanoic acid

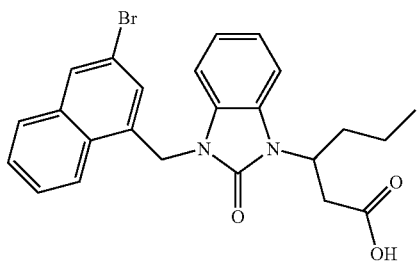 [SMILES: CCCC(CC(=O)O)n1c(=O)n(Cc2cc(Br)cc3ccccc23)c2ccccc21]

3-{3-[(3-bromo-1-naphthyl)methyl]-2-oxo-2,3-dihydro-1H-benzimidazol-1-yl}hexanoic acid

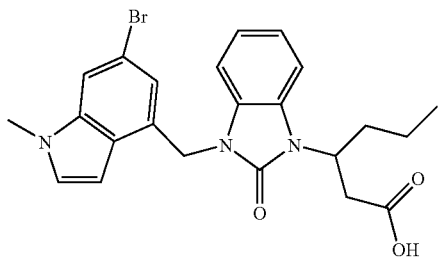 [SMILES: CCCC(CC(=O)O)n1c(=O)n(Cc2cc(Br)cc3c2ccn3C)c2ccccc21]

3-{3-[(6-bromo-1-methyl-1H-indol-4-yl)methyl]-2-oxo-2,3-dihydro-1H-benzimidazol-1-yl}hexanoic acid

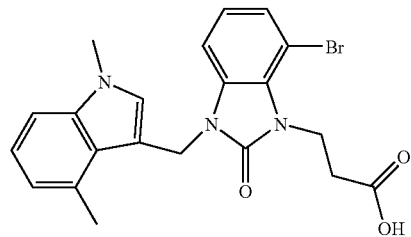 [SMILES: Cc1cccc2c1c(Cn1c(=O)n(CCC(=O)O)c3c(Br)cccc31)cn2C]

3-{7-bromo-3-[(1,4-dimethyl-1H-indol-3-yl)methyl]-2-oxo-2,3-dihydro-1H-benzimidazol-1-yl}propanoic acid

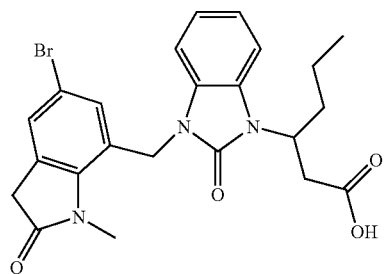 [SMILES: CCCC(CC(=O)O)n1c(=O)n(Cc2cc(Br)cc3c2N(C)C(=O)C3)c2ccccc21]

3-{3-[(5-bromo-1-methyl-2-oxo-2,3-dihydro-1H-indol-7-yl)methyl]-2-oxo-2,3-dihydro-1H-benzimidazol-1-yl}hexanoic acid

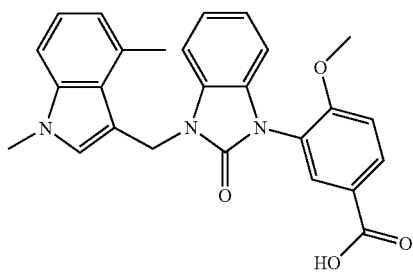 [SMILES: COc1ccc(C(=O)O)cc1-n1c(=O)n(Cc2cn(C)c3cccc(C)c23)c2ccccc21]

3-{3-[(1,4-dimethyl-1H-indol-3-yl)methyl]-2-oxo-2,3-dihydro-1H-benzimidazol-1-yl}-4-methoxybenzoic acid TABLE I-continued

| | |
|---|---|
| 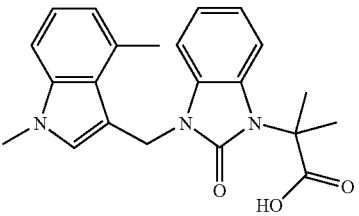 [SMILES: Cc1cccc2c1c(Cn1c(=O)n(C(C)(C)C(=O)O)c3ccccc31)cn2C] | 2-{3-[(1,4-dimethyl-1H-indol-3-yl)methyl]-2-oxo-2,3-dihydro-1H-benzimidazol-1-yl}-2-methylpropanoic acid |
| 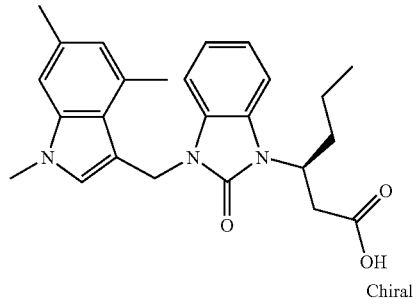 [SMILES: CCC[C@@H](CC(=O)O)n1c(=O)n(Cc2cn(C)c3cc(C)cc(C)c23)c2ccccc21]  Chiral | (3S)-3-{2-oxo-3-[(1,4,6-trimethyl-1H-indol-3-yl)methyl]-2,3-dihydro-1H-benzimidazol-1-yl}hexanoic acid |
| 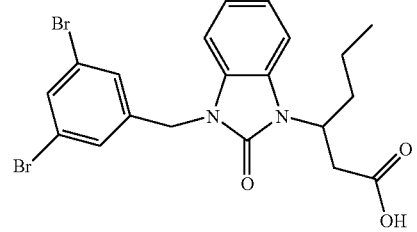 [SMILES: CCCC(CC(=O)O)n1c(=O)n(Cc2cc(Br)cc(Br)c2)c2ccccc21] | 3-[3-(3,5-dibromobenzyl)-2-oxo-2,3-dihydro-1H-benzimidazol-1-yl]hexanoic acid |
| 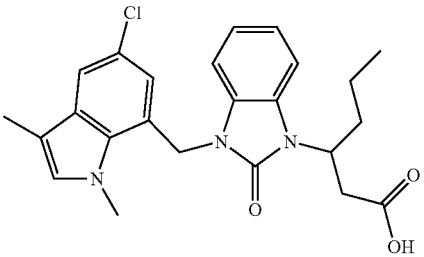 [SMILES: CCCC(CC(=O)O)n1c(=O)n(Cc2cc(Cl)cc3c(C)cn(C)c23)c2ccccc21] | 3-{3-[(5-chloro-1,3-dimethyl-1H-indol-7-yl)methyl]-2-oxo-2,3-dihydro-1H-benzimidazol-1-yl}hexanoic acid |
| 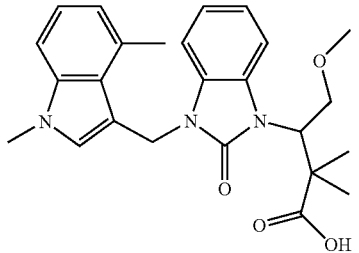 | 3-{3-[(1,4-dimethyl-1H-indol-3-yl)methyl]-2-oxo-2,3-dihydro-1H-benzimidazol-1-yl}-4-methoxy-2,2-dimethylbutanoic acid |
| 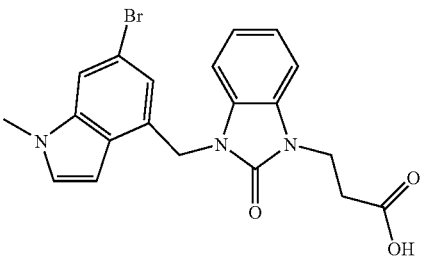 [SMILES: Cn1ccc2c(Cn3c(=O)n(CCC(=O)O)c4ccccc43)cc(Br)cc21] | 3-{3-[(6-bromo-1-methyl-1H-indol-4-yl)methyl]-2-oxo-2,3-dihydro-1H-benzimidazol-1-yl}propanoic acid |

TABLE I-continued

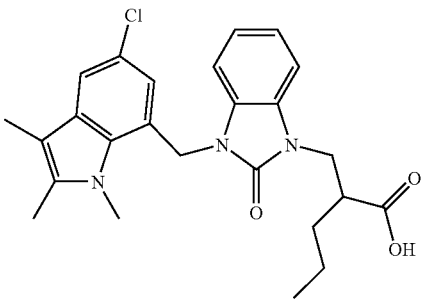 [SMILES: CCCC(Cn1c(=O)n(Cc2cc(Cl)cc3c(C)c(C)n(C)c23)c2ccccc21)C(=O)O]

2-({3-[(5-chloro-1,2,3-trimethyl-1H-indol-7-yl)methyl]-2-oxo-2,3-dihydro-1H-benzimidazol-1-yl}methyl)pentanoic acid

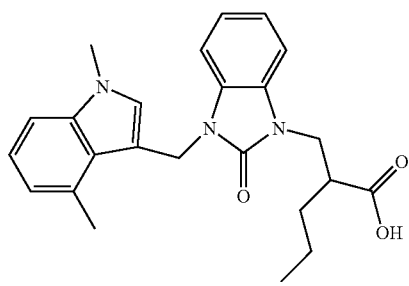 [SMILES: CCCC(Cn1c(=O)n(Cc2cn(C)c3cccc(C)c23)c2ccccc21)C(=O)O]

2-({3-[(1,4-dimethyl-1H-indol-3-yl)methyl]-2-oxo-2,3-dihydro-1H-benzimidazol-1-yl}methyl)pentanoic acid

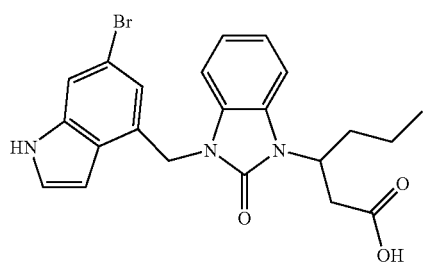 [SMILES: CCCC(CC(=O)O)n1c(=O)n(Cc2cc(Br)cc3[nH]ccc23)c2ccccc21]

3-{3-[(6-bromo-1H-indol-4-yl)methyl]-2-oxo-2,3-dihydro-1H-benzimidazol-1-yl}hexanoic acid

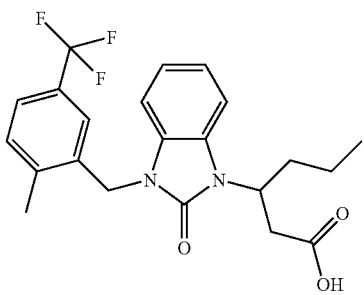 [SMILES: CCCC(CC(=O)O)n1c(=O)n(Cc2cc(C(F)(F)F)ccc2C)c2ccccc21]

3-{3-[2-methyl-5-(trifluoromethyl)benzyl]-2-oxo-2,3-dihydro-1H-benzimidazol-1-yl}hexanoic acid

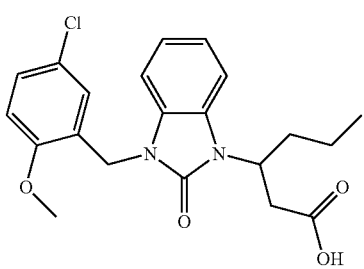 [SMILES: CCCC(CC(=O)O)n1c(=O)n(Cc2cc(Cl)ccc2OC)c2ccccc21]

3-[3-(5-chloro-2-methoxybenzyl)-2-oxo-2,3-dihydro-1H-benzimidazol-1-yl]hexanoic acid TABLE I-continued

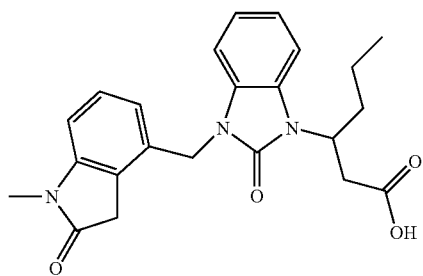 [SMILES: CCCC(CC(=O)O)n1c(=O)n(Cc2cccc3c2CC(=O)N3C)c2ccccc21]
3-{3-[(1-methyl-2-oxo-2,3-dihydro-1H-indol-4-yl)methyl]-2-oxo-2,3-dihydro-1H-benzimidazol-1-yl}hexanoic acid

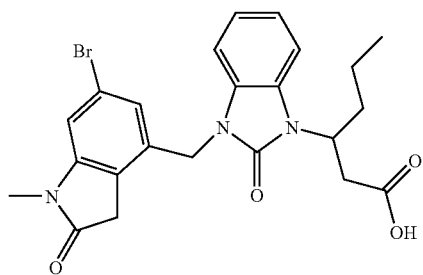 [SMILES: CCCC(CC(=O)O)n1c(=O)n(Cc2cc(Br)cc3c2CC(=O)N3C)c2ccccc21]
3-{3-[(6-bromo-1-methyl-2-oxo-2,3-dihydro-1H-indol-4-yl)methyl]-2-oxo-2,3-dihydro-1H-benzimidazol-1-yl}hexanoic acid

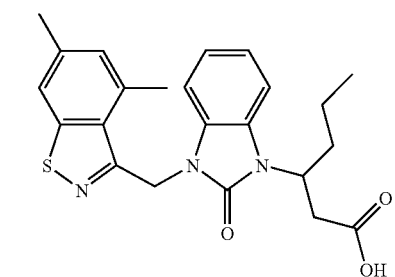 [SMILES: CCCC(CC(=O)O)n1c(=O)n(Cc2nsc3cc(C)cc(C)c23)c2ccccc21]
3-{3-[(4,6-dimethyl-1,2-benzisothiazol-3-yl)methyl]-2-oxo-2,3-dihydro-1H-benzimidazol-1-yl}hexanoic acid

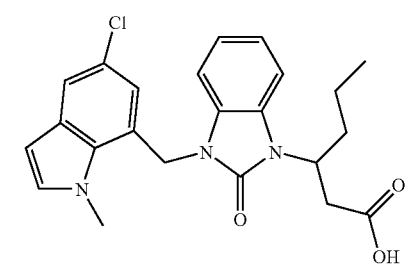 [SMILES: CCCC(CC(=O)O)n1c(=O)n(Cc2cc(Cl)cc3ccn(C)c23)c2ccccc21]
3-{3-[(5-chloro-1-methyl-1H-indol-7-yl)methyl]-2-oxo-2,3-dihydro-1H-benzimidazol-1-yl}hexanoic acid

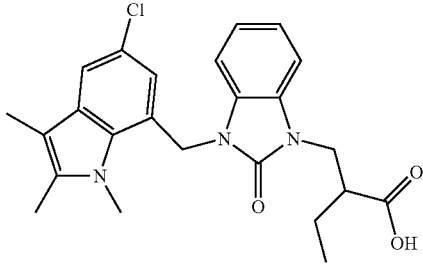 [SMILES: CCC(Cn1c(=O)n(Cc2cc(Cl)cc3c(C)c(C)n(C)c23)c2ccccc21)C(=O)O]
2-({3-[(5-chloro-1,2,3-trimethyl-1H-indol-7-yl)methyl]-2-oxo-2,3-dihydro-1H-benzimidazol-1-yl}methyl)butanoic acid

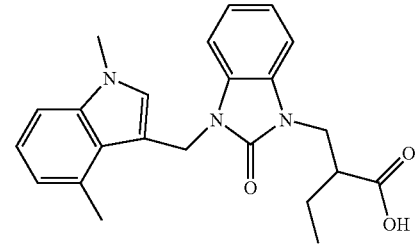 [SMILES: CCC(Cn1c(=O)n(Cc2cn(C)c3cccc(C)c23)c2ccccc21)C(=O)O]
2-({3-[(1,4-dimethyl-1H-indol-3-yl)methyl]-2-oxo-2,3-dihydro-1H-benzimidazol-1-yl}methyl)butanoic acid

| | |
|---|---|
| 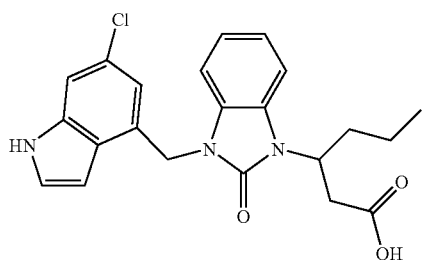 [SMILES: CCCC(CC(=O)O)n1c(=O)n(Cc2cc(Cl)cc3[nH]ccc23)c2ccccc21] | 3-{3-[(6-chloro-1H-indol-4-yl)methyl]-2-oxo-2,3-dihydro-1H-benzimidazol-1-yl}hexanoic acid |
| 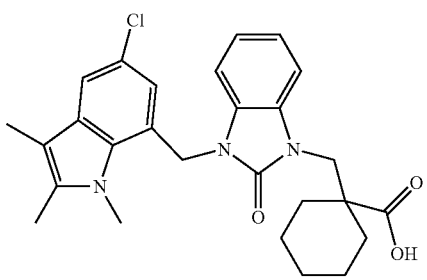 [SMILES: Cc1c(C)n(C)c2c(Cn3c(=O)n(CC4(C(=O)O)CCCCC4)c4ccccc43)cc(Cl)cc12] | 1-({3-[(5-chloro-1,2,3-trimethyl-1H-indol-7-yl)methyl]-2-oxo-2,3-dihydro-1H-benzimidazol-1-yl}methyl)cyclohexanecarboxylic acid |
| 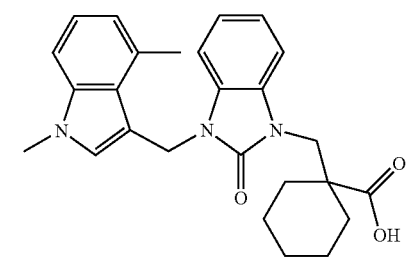 [SMILES: Cc1cccc2c1c(Cn1c(=O)n(CC3(C(=O)O)CCCCC3)c3ccccc31)cn2C] | 1-({3-[(1,4-dimethyl-1H-indol-3-yl)methyl]-2-oxo-2,3-dihydro-1H-benzimidazol-1-yl}methyl)cyclohexanecarboxylic acid |
| 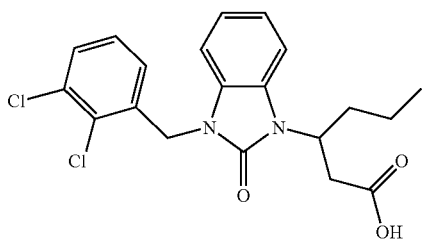 [SMILES: CCCC(CC(=O)O)n1c(=O)n(Cc2cccc(Cl)c2Cl)c2ccccc21] | 3-[3-(2,3-dichlorobenzyl)-2-oxo-2,3-dihydro-1H-benzimidazol-1-yl]hexanoic acid |
| 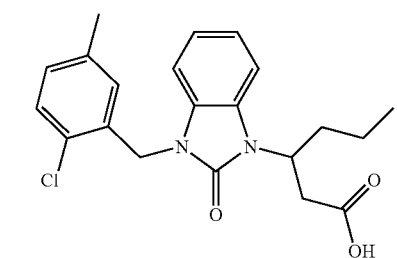 [SMILES: CCCC(CC(=O)O)n1c(=O)n(Cc2cc(C)ccc2Cl)c2ccccc21] | 3-[3-(2-chloro-5-methylbenzyl)-2-oxo-2,3-dihydro-1H-benzimidazol-1-yl]hexanoic acid |
| 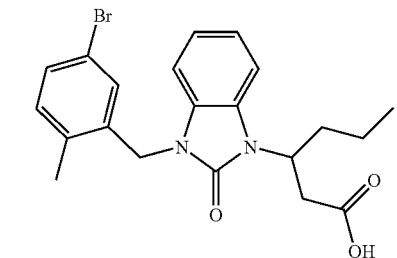 [SMILES: CCCC(CC(=O)O)n1c(=O)n(Cc2cc(Br)ccc2C)c2ccccc21] | 3-[3-(5-bromo-2-methylbenzyl)-2-oxo-2,3-dihydro-1H-benzimidazol-1-yl]hexanoic acid |

TABLE I-continued

| | |
|---|---|
| 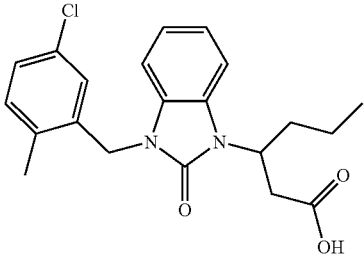 [SMILES: CCCC(CC(=O)O)n1c(=O)n(Cc2cc(Cl)ccc2C)c2ccccc21] | 3-[3-(5-chloro-2-methylbenzyl)-2-oxo-2,3-dihydro-1H-benzimidazol-1-yl]hexanoic acid |
| 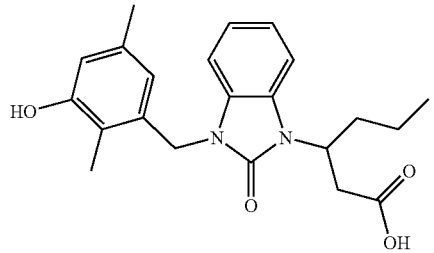 [SMILES: CCCC(CC(=O)O)n1c(=O)n(Cc2cc(C)cc(O)c2C)c2ccccc21] | 3-[3-(3-hydroxy-2,5-dimethylbenzyl)-2-oxo-2,3-dihydro-1H-benzimidazol-1-yl]hexanoic acid |
| 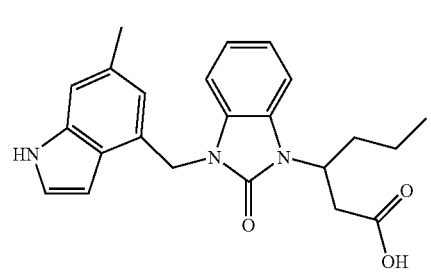 [SMILES: CCCC(CC(=O)O)n1c(=O)n(Cc2cc(C)cc3[nH]ccc23)c2ccccc21] | 3-{3-[(6-methyl-1H-indol-4-yl)methyl]-2-oxo-2,3-dihydro-1H-benzimidazol-1-yl}hexanoic acid |
| 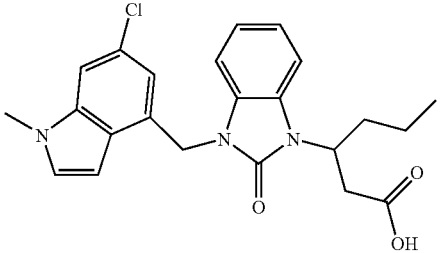 [SMILES: CCCC(CC(=O)O)n1c(=O)n(Cc2cc(Cl)cc3c2ccn3C)c2ccccc21] | 3-{3-[(6-chloro-1-methyl-H-indol-4-yl)methyl]-2-oxo-2,3-dihydro-1H-benzimidazol-1-yl}hexanoic acid |
| 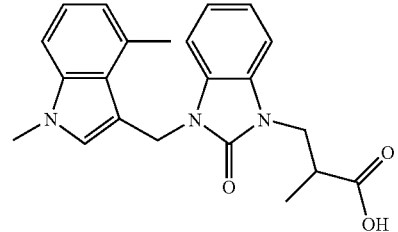 [SMILES: Cc1cccc2c1c(Cn1c(=O)n(CC(C)C(=O)O)c3ccccc31)cn2C] | 3-{3-[(1,4-dimethyl-1H-indol-3-yl)methyl]-2-oxo-2,3-dihydro-1H-benzimidazol-1-yl}-2-methylpropanoic acid |
| 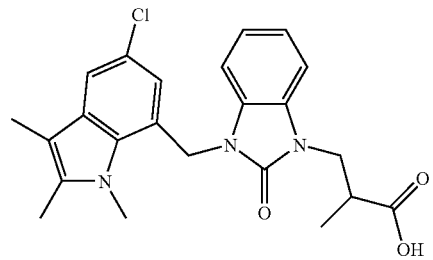 [SMILES: Cc1c(C)n(C)c2c(Cn3c(=O)n(CC(C)C(=O)O)c4ccccc43)cc(Cl)cc12] | 3-{3-[(5-chloro-1,2,3-trimethyl-1H-indol-7-yl)methyl]-2-oxo-2,3-dihydro-1H-benzimidazol-1-yl}-2-methylpropanoic acid |

TABLE I-continued

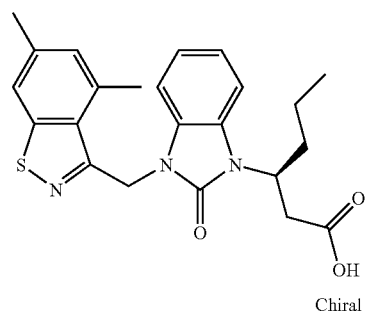 [SMILES: CCC[C@@H](CC(=O)O)n1c(=O)n(Cc2nsc3cc(C)cc(C)c23)c2ccccc21]

Chiral (3S)-3-{3-[(4,6-dimethyl-1,2-benzisothiazol-3-yl)methyl]-2-oxo-2,3-dihydro-1H-benzimidazol-1-yl}hexanoic acid

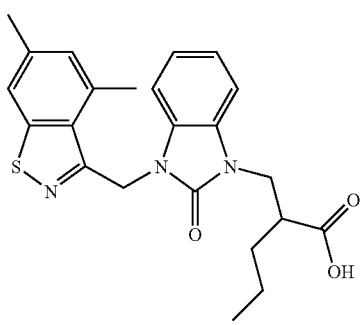 [SMILES: CCCC(Cn1c(=O)n(Cc2nsc3cc(C)cc(C)c23)c2ccccc21)C(=O)O]

2-({3-[(4,6-dimethyl-1,2-benzisothiazol-3-yl)methyl]-2-oxo-2,3-dihydro-1H-benzimidazol-1-yl}methyl)pentanoic acid

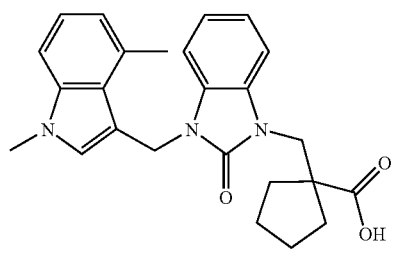 [SMILES: Cc1cccc2c1c(Cn1c(=O)n(CC3(C(=O)O)CCCC3)c3ccccc31)cn2C]

1-({3-[(1,4-dimethyl-1H-indol-3-yl)methyl]-2-oxo-2,3-dihydro-1H-benzimidazol-1-yl}methyl)cyclopentanecarboxylic acid

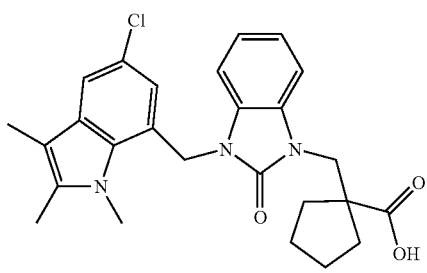

1-({3-[(5-chloro-1,2,3-trimethyl-1H-indol-7-yl)methyl]-2-oxo-2,3-dihydro-1H-benzimidazol-1-yl}methyl)cyclopentanecarboxylic acid

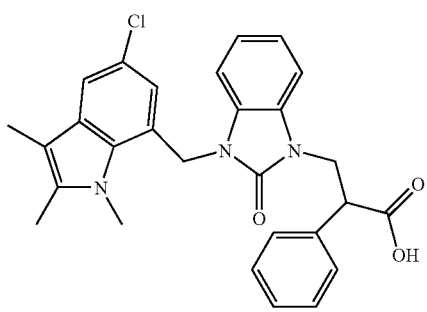 [SMILES: Cc1c(C)n(C)c2c(Cn3c(=O)n(CC(C(=O)O)c4ccccc4)c4ccccc43)cc(Cl)cc12]

3-{3-[(5-chloro-1,2,3-trimethyl-1H-indol-7-yl)methyl]-2-oxo-2,3-dihydro-1H-benzimidazol-1-yl}-2-phenylpropanoic acid

TABLE I-continued

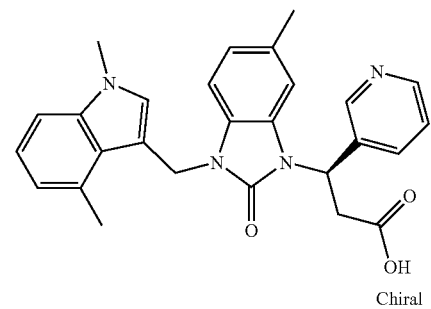 [SMILES: Cc1ccc2c(c1)n([C@H](CC(=O)O)c1cccnc1)c(=O)n2Cc1cn(C)c2cccc(C)c12]
Chiral (3R)-3-{3-[(1,4-dimethyl-1H-indol-3-yl)methyl]-6-methyl-2-oxo-2,3-dihydro-1H-benzimidazol-1-yl}-3-pyridin-3-ylpropanoic acid

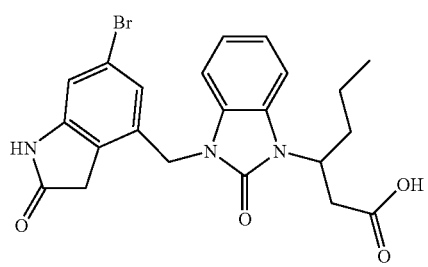 [SMILES: CCCC(CC(=O)O)n1c(=O)n(Cc2cc(Br)cc3c2CC(=O)N3)c2ccccc21]

3-{3-[(6-bromo-2-oxo-2,3-dihydro-1H-indol-4-yl)methyl]-2-oxo-2,3-dihydro-1H-benzimidazol-1-yl}hexanoic acid

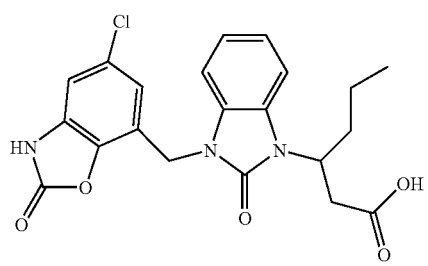 [SMILES: CCCC(CC(=O)O)n1c(=O)n(Cc2cc(Cl)cc3[nH]c(=O)oc23)c2ccccc21]

3-{3-[(5-chloro-2-oxo-2,3-dihydro-1,3-benzoxazol-7-yl)methyl]-2-oxo-2,3-dihydro-1H-benzimidazol-1-yl}hexanoic acid

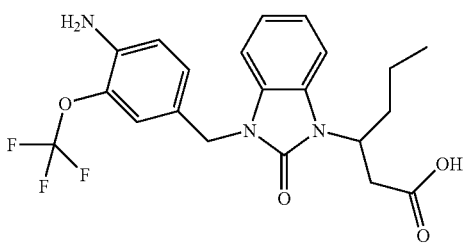 [SMILES: CCCC(CC(=O)O)n1c(=O)n(Cc2ccc(N)c(OC(F)(F)F)c2)c2ccccc21]

3-{3-[4-amino-3-(trifluoromethoxy)benzyl]-2-oxo-2,3-dihydro-1H-benzimidazol-1-yl}hexanoic acid

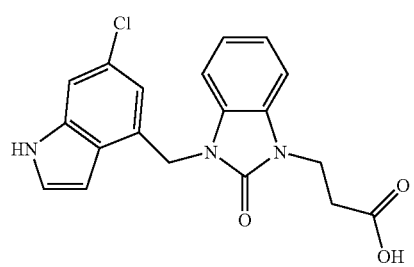 [SMILES: O=C(O)CCn1c(=O)n(Cc2cc(Cl)cc3[nH]ccc23)c2ccccc21]

3-{3-[(6-chloro-1H-indol-4-yl)methyl]-2-oxo-2,3-dihydro-1H-benzimidazol-1-yl}propanoic acid

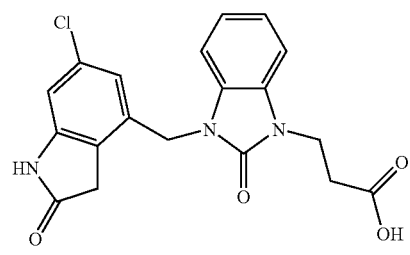 [SMILES: O=C(O)CCn1c(=O)n(Cc2cc(Cl)cc3c2CC(=O)N3)c2ccccc21]

3-{3-[(6-chloro-2-oxo-2,3-dihydro-1H-indol-4-yl)methyl]-2-oxo-2,3-dihydro-1H-benzimidazol-1-yl}propanoic acid TABLE I-continued

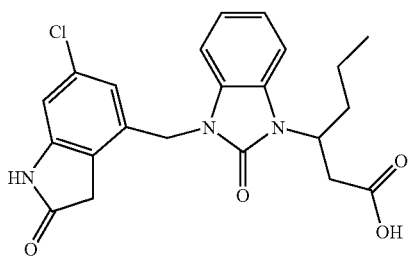 [SMILES: CCCC(CC(=O)O)n1c(=O)n(Cc2cc(Cl)cc3c2CC(=O)N3)c2ccccc21]

3-{3-[(6-chloro-2-oxo-2,3-dihydro-1H-indol-4-yl)methyl]2-oxo-2,3-dihydro-1H-benzimidazol-1-yl}hexanoic acid

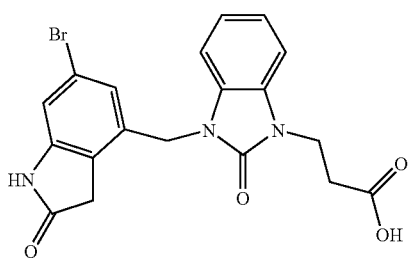 [SMILES: O=C(O)CCn1c(=O)n(Cc2cc(Br)cc3c2CC(=O)N3)c2ccccc21]

3-{3-[(6-bromo-2-oxo-2,3-dihydro-1H-indol-4-yl)methyl]-2-oxo-2,3-dihydro-1H-benzimidazol-1-yl}propanoic acid

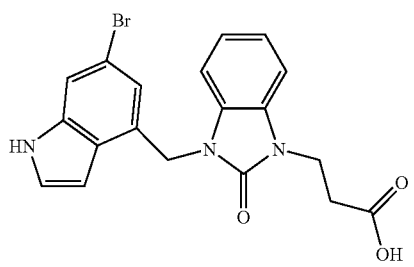 [SMILES: O=C(O)CCn1c(=O)n(Cc2cc(Br)cc3[nH]ccc23)c2ccccc21]

3-{3-[(6-bromo-1H-indol-4-yl)methyl]-2-oxo-2,3-dihydro-1H-benzimidazol-1-yl}propanoic acid

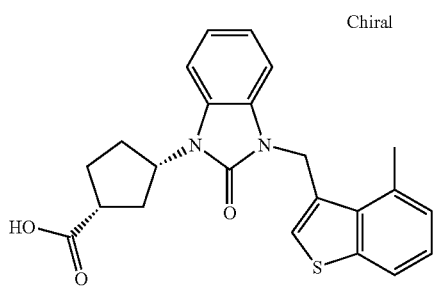 [SMILES: Cc1cccc2scc(Cn3c(=O)n([C@H]4CC[C@@H](C(=O)O)C4)c4ccccc43)c12]

Chiral (1R,3S)-3-(3-[(4-methyl-1-benzothien-3-yl)methyl]-2-oxo-2,3-dihydro-1H-benzimidazol-1-yl}cyclopentanecarboxylic acid

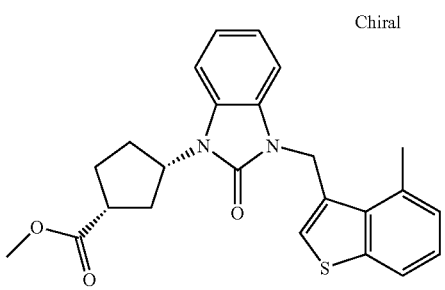 [SMILES: COC(=O)[C@@H]1CC[C@H](n2c(=O)n(Cc3csc4cccc(C)c34)c3ccccc32)C1]

Chiral methyl (1R,3S)-3-{3-[(4-methyl-1-benzothien-3-yl)methyl]-2-oxo-2,3-dihydro-1H-benzimidazol-1-yl}cyclopentanecarboxylate TABLE I-continued
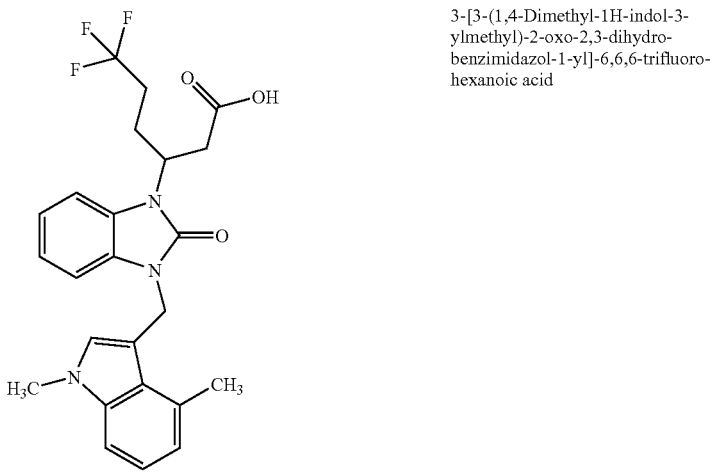
3-[3-(1,4-Dimethyl-1H-indol-3-ylmethyl)-2-oxo-2,3-dihydro-benzimidazol-1-yl]-6,6,6-trifluoro-hexanoic acid
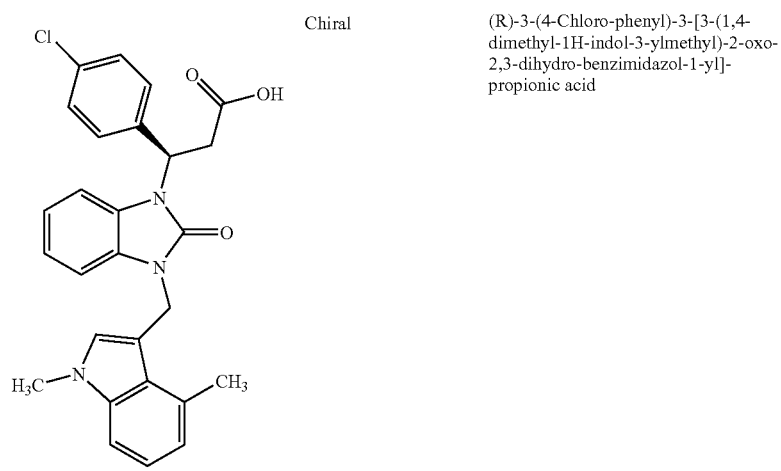
Chiral
(R)-3-(4-Chloro-phenyl)-3-[3-(1,4-dimethyl-1H-indol-3-ylmethyl)-2-oxo-2,3-dihydro-benzimidazol-1-yl]-propionic acid
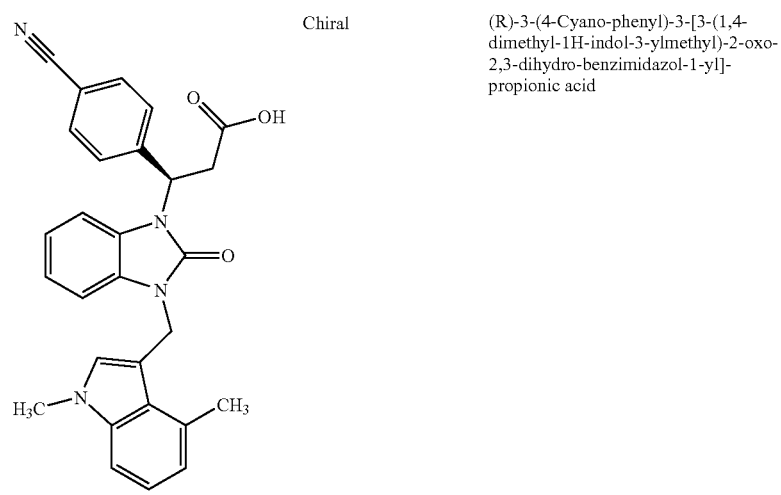
Chiral
(R)-3-(4-Cyano-phenyl)-3-[3-(1,4-dimethyl-1H-indol-3-ylmethyl)-2-oxo-2,3-dihydro-benzimidazol-1-yl]-propionic acid TABLE I-continued
| | | |
|---|---|---|
| 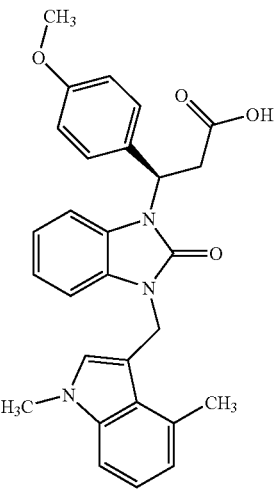 | Chiral | (R)-3-[3-(1,4-Dimethyl-1H-indol-3-ylmethyl)-2-oxo-2,3-dihydro-benzimidazol-1-yl]-3-(4-methoxy-phenyl)-propionic acid |
| 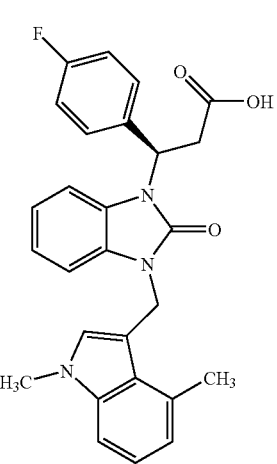 | Chiral | (R)-3-[3-(1,4-Dimethyl-1H-indol-3-ylmethyl)-2-oxo-2,3-dihydro-benzimidazol-1-yl]-3-(4-fluoro-phenyl)-propionic acid |
| 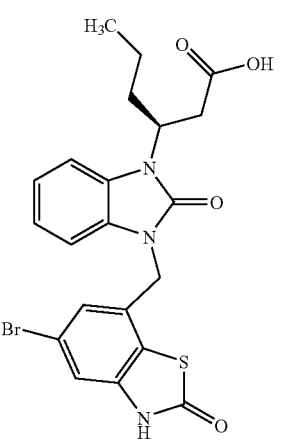 | Chiral | (S)-3-[3-(5-Bromo-2-oxo-2,3-dihydro-benzothiazol-7-ylmethyl)-2-oxo-2,3-dihydro-benzimidazol-1-yl]-hexanoic acid |

TABLE I-continued
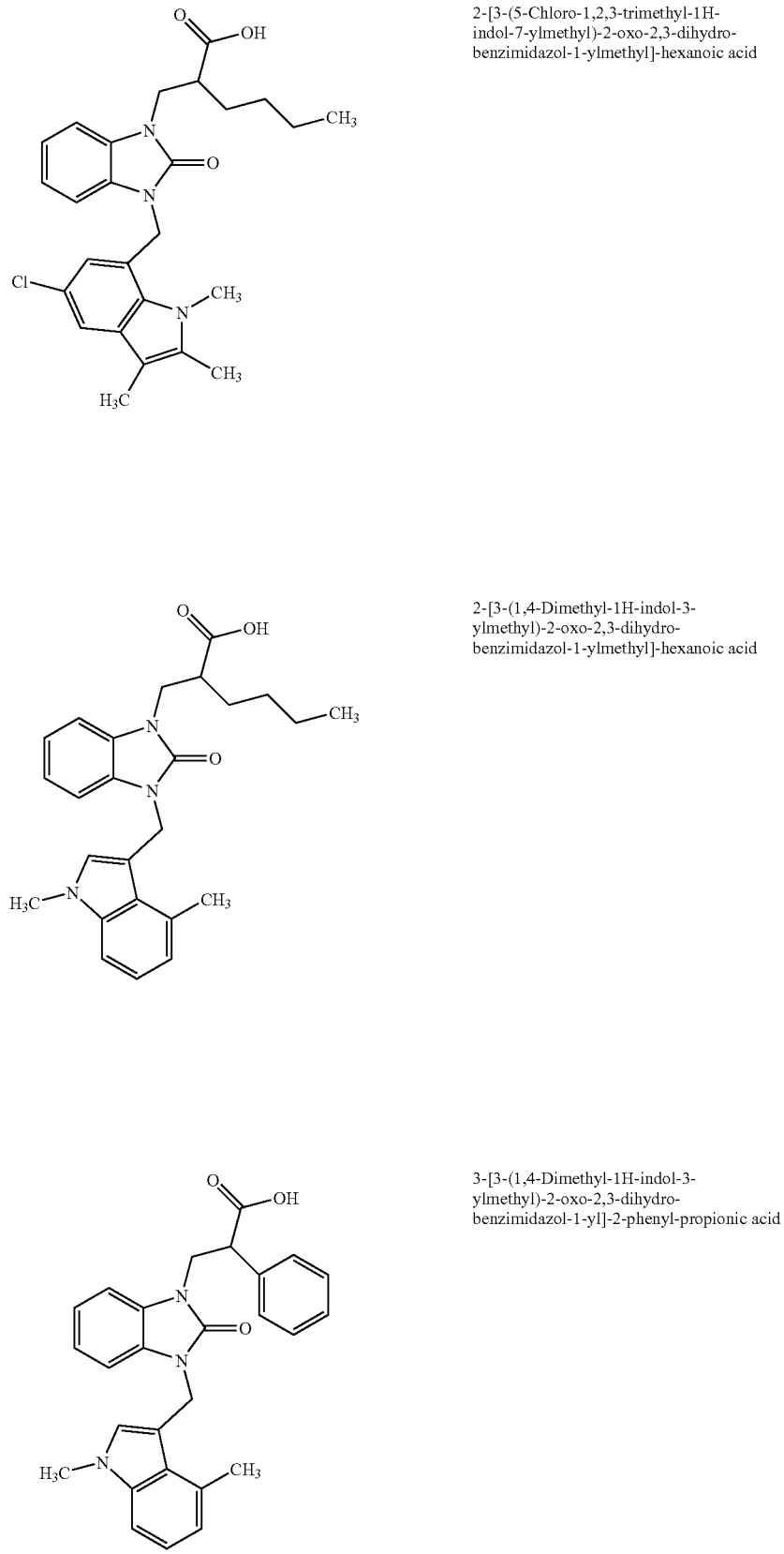
2-[3-(5-Chloro-1,2,3-trimethyl-1H-indol-7-ylmethyl)-2-oxo-2,3-dihydro-benzimidazol-1-ylmethyl]-hexanoic acid
2-[3-(1,4-Dimethyl-1H-indol-3-ylmethyl)-2-oxo-2,3-dihydro-benzimidazol-1-ylmethyl]-hexanoic acid
3-[3-(1,4-Dimethyl-1H-indol-3-ylmethyl)-2-oxo-2,3-dihydro-benzimidazol-1-yl]-2-phenyl-propionic acid TABLE I-continued

| | |
|---|---|
| 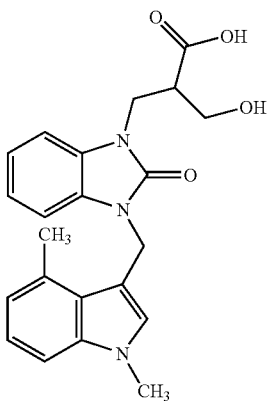 [SMILES: Cc1cccc2c1c(Cn1c(=O)n(CC(CO)C(=O)O)c3ccccc31)cn2C] | 3-[3-(1,4-Dimethyl-1H-indol-3-ylmethyl)-2-oxo-2,3-dihydro-benzimidazol-1-yl]-2-hydroxymethyl-propionic acid |
| 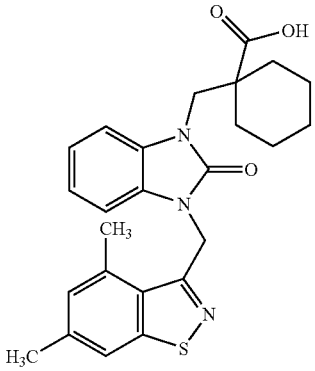 [SMILES: Cc1cc(C)c2c(Cn3c(=O)n(CC4(C(=O)O)CCCCC4)c4ccccc43)nsc2c1] | 1-[3-(4,6-Dimethyl-1,2-benzisothiazol-3-ylmethyl)-2-oxo-2,3-dihydro-benzimidazol-1-ylmethyl]-cyclohexanecarboxylic acid |
| 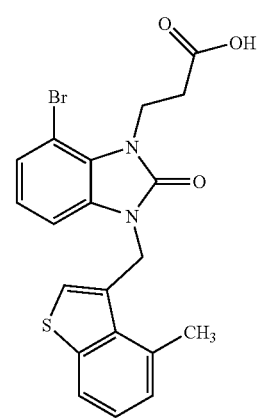 [SMILES: Cc1cccc2scc(Cn3c(=O)n(CCC(=O)O)c4c(Br)cccc43)c12] | 3-[7-Bromo-3-(4-methyl-benzo[b]thiophen-3-ylmethyl)-2-oxo-2,3-dihydro-benzimidazol-1-yl]-propionic acid |
| 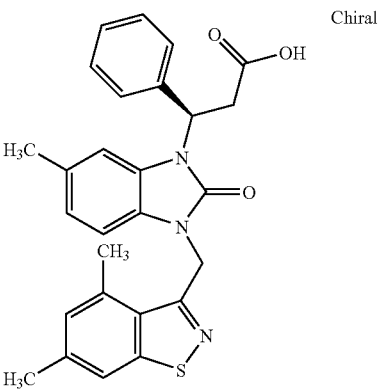 [SMILES: Cc1cc(C)c2c(Cn3c(=O)n([C@H](CC(=O)O)c4ccccc4)c4cc(C)ccc43)nsc2c1] Chiral | (R)-3-[3-(4,6-Dimethyl-1,2-benzisothiazol-3-ylmethyl)-6-methyl-2-oxo-2,3-dihydro-benzimidazol-1-yl]-3-phenyl-propionic acid |

TABLE I-continued
| | |
|---|---|
| 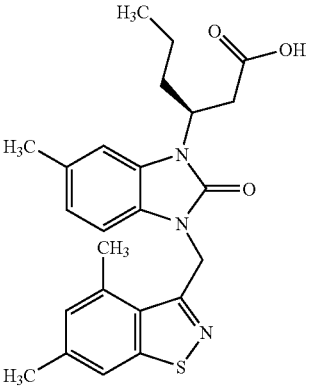 | (S)-3-[3-(4,6-Dimethyl-1,2-benzisothiazol-3-ylmethyl)-6-methyl-2-oxo-2,3-dihydro-benzimidazol-1-yl]-hexanoic acid |
| 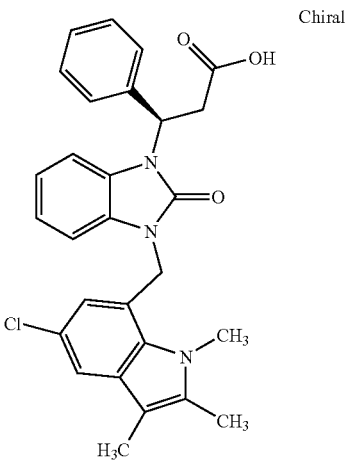 [SMILES: Cc1c(C)n(C)c2c(Cn3c(=O)n([C@H](CC(=O)O)c4ccccc4)c4ccccc43)cc(Cl)cc12] | (R)-3-[3-(5-Chloro-1,2,3-trimethyl-1H-indol-7-ylmethyl)-2-oxo-2,3-dihydro-benzimidazol-1-yl]-3-phenyl-propionic acid |
| 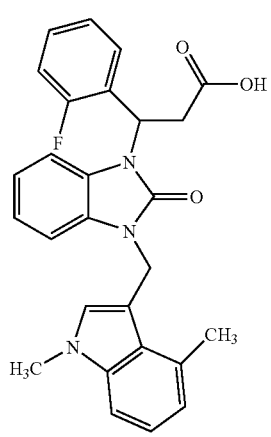 [SMILES: Cc1cccc2c1c(Cn1c(=O)n(C(CC(=O)O)c3ccccc3F)c3ccccc31)cn2C] | 3-[3-(1,4-Dimethyl-1H-indol-3-ylmethyl)-2-oxo-2,3-dihydro-benzimidazol-1-yl]-3-(2-fluoro-phenyl)-propionic acid |

TABLE I-continued
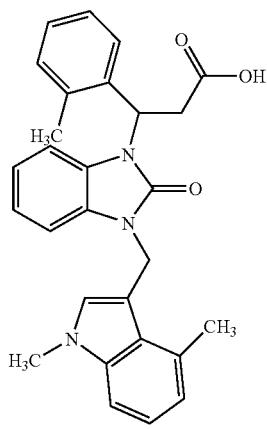 [SMILES: Cc1ccccc1C(CC(=O)O)n1c(=O)n(Cc2cn(C)c3cccc(C)c23)c2ccccc21]
3-[3-(1,4-Dimethyl-1H-indol-3-ylmethyl)-2-oxo-2,3-dihydro-benzimidazol-1-yl]-3-o-tolyl-propionic acid
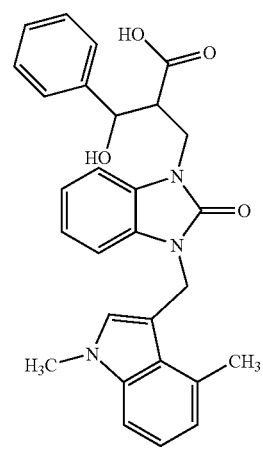 [SMILES: Cc1cccc2c1c(Cn1c(=O)n(CC(C(=O)O)C(O)c3ccccc3)c3ccccc31)cn2C]
2-[3-(1,4-Dimethyl-1H-indol-3-ylmethyl)-2-oxo-2,3-dihydro-benzimidazol-1-ylmethyl]-3-hydroxy-3-phenyl-propionic acid
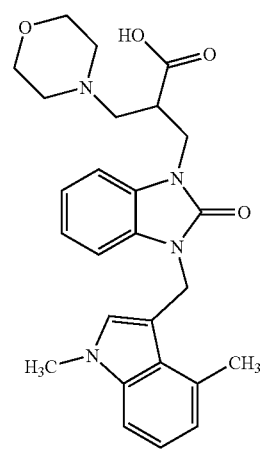 [SMILES: Cc1cccc2c1c(Cn1c(=O)n(CC(CN3CCOCC3)C(=O)O)c3ccccc31)cn2C]
3-[3-(1,4-Dimethyl-1H-indol-3-ylmethyl)-2-oxo-2,3-dihydro-benzimidazol-1-yl]-2-morpholin-4-ylmethyl-propionic acid TABLE I-continued
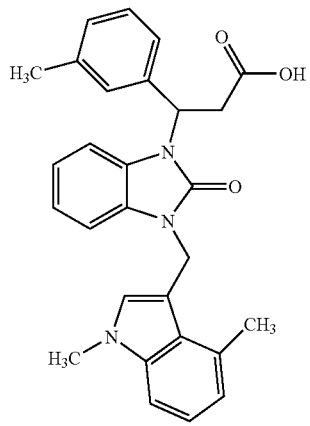 [SMILES: Cc1cccc(C(CC(=O)O)n2c(=O)n(Cc3cn(C)c4cccc(C)c34)c3ccccc32)c1]
3-[3-(1,4-Dimethyl-1H-indol-3-ylmethyl)-2-oxo-2,3-dihydro-benzimidazol-1-yl]-3-m-tolyl-propionic acid
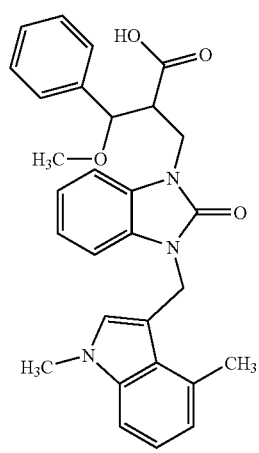 [SMILES: COC(c1ccccc1)C(Cn1c(=O)n(Cc2cn(C)c3cccc(C)c23)c2ccccc21)C(=O)O]
2-[3-(1,4-Dimethyl-1H-indol-3-ylmethyl)-2-oxo-2,3-dihydro-benzimidazol-1-ylmethyl]-3-methoxy-3-phenyl-propionic acid
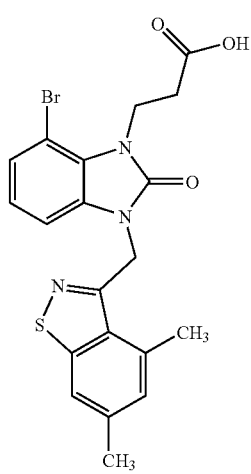 [SMILES: Cc1cc(C)c2c(Cn3c(=O)n(CCC(=O)O)c4c(Br)cccc43)nsc2c1]
3-[7-Bromo-3-(4,6-dimethyl-1,2-benzisothiazol-3-ylmethyl)-2-oxo-2,3-dihydro-benzimidazol-1-yl]-propionic acid TABLE I-continued
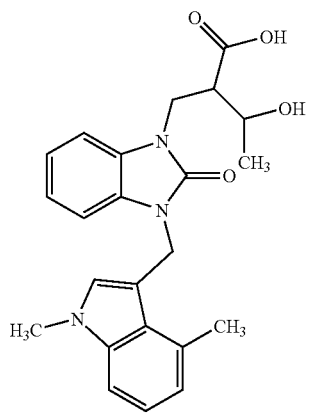 [SMILES: Cc1cccc2c1c(Cn1c(=O)n(CC(C(=O)O)C(C)O)c3ccccc31)cn2C]
2-[3-(1,4-Dimethyl-1H-indol-3-ylmethyl)-2-oxo-2,3-dihydro-benzimidazol-1-ylmethyl]-3-hydroxy-butyric acid
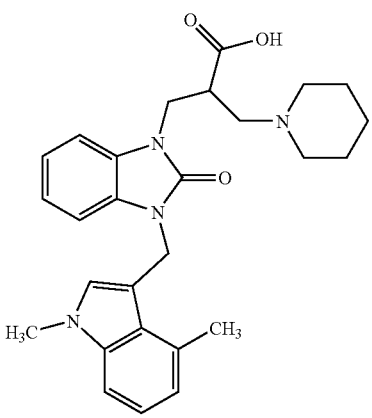 [SMILES: Cc1cccc2c1c(Cn1c(=O)n(CC(CN3CCCCC3)C(=O)O)c3ccccc31)cn2C]
3-[3-(1,4-Dimethyl-1H-indol-3-ylmethyl)-2-oxo-2,3-dihydro-benzimidazol-1-yl]-2-piperidin-1-ylmethyl-propionic acid
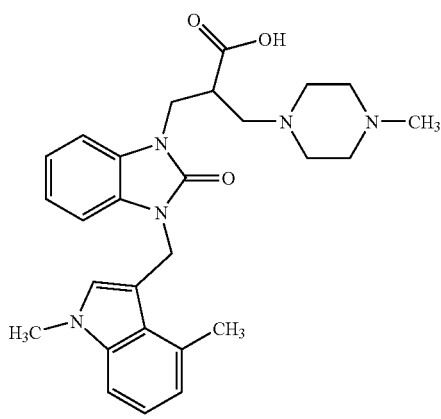
3-[3-(1,4-Dimethyl-1H-indol-3-ylmethyl)-2-oxo-2,3-dihydro-benzimidazol-1-yl]-2-(4-methyl-piperazin-1-ylmethyl)-propionic acid TABLE I-continued
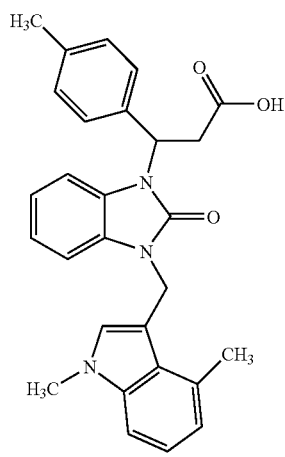 [SMILES: Cc1ccc(C(CC(=O)O)n2c(=O)n(Cc3cn(C)c4cccc(C)c34)c3ccccc32)cc1]
3-[3-(1,4-Dimethyl-1H-indol-3-ylmethyl)-2-oxo-2,3-dihydro-benzimidazol-1-yl]-3-p-tolyl-propionic acid
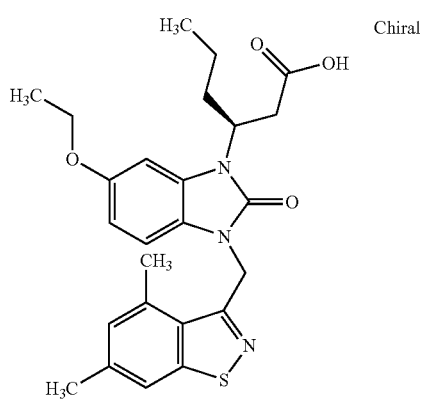 [SMILES: CCC[C@@H](CC(=O)O)n1c(=O)n(Cc2nsc3cc(C)cc(C)c23)c2ccc(OCC)cc21]
(S)-3-[3-(4,6-Dimethyl-1,2-benzisothiazol-3-ylmethyl)-6-ethoxy-2-oxo-2,3-dihydro-benzimidazol-1-yl]-hexanoic acid
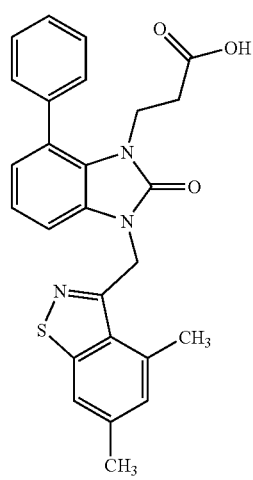 [SMILES: Cc1cc(C)c2c(Cn3c(=O)n(CCC(=O)O)c4c(-c5ccccc5)cccc43)nsc2c1]
3-[3-(4,6-Dimethyl-1,2-benzisothiazol-3-ylmethyl)-2-oxo-7-phenyl-2,3-dihydro-benzimidazol-1-yl]-propionic acid TABLE I-continued
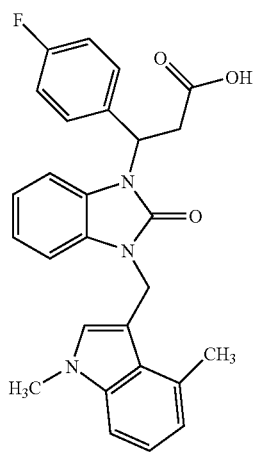 [SMILES: Cc1cccc2c1c(Cn1c(=O)n(C(CC(=O)O)c3ccc(F)cc3)c3ccccc31)cn2C]
3-[3-(1,4-Dimethyl-1H-indol-3-ylmethyl)-2-oxo-2,3-dihydro-benzimidazol-1-yl]-3-(4-fluoro-phenyl)-propionic acid
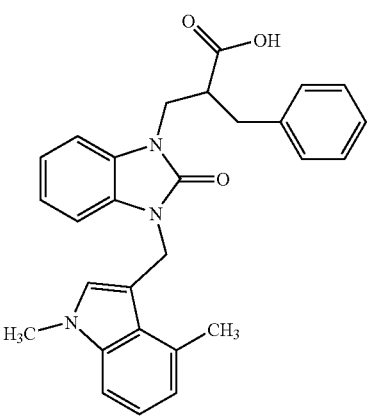 [SMILES: Cc1cccc2c1c(Cn1c(=O)n(CC(Cc3ccccc3)C(=O)O)c3ccccc31)cn2C]
2-Benzyl-3-[3-(1,4-dimethyl-1H-indol-3-ylmethyl)-2-oxo-2,3-dihydro-benzimidazol-1-yl]-propionic acid
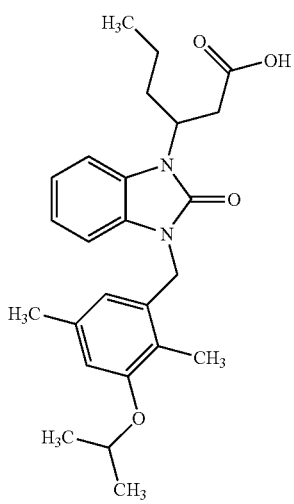 [SMILES: CCCC(CC(=O)O)n1c(=O)n(Cc2cc(C)cc(OC(C)C)c2C)c2ccccc21]
3-[3-(3-Isopropoxy-2,5-dimethyl-benzyl)-2-oxo-2,3-dihydro-benzimidazol-1-yl]-hexanoic acid TABLE I-continued
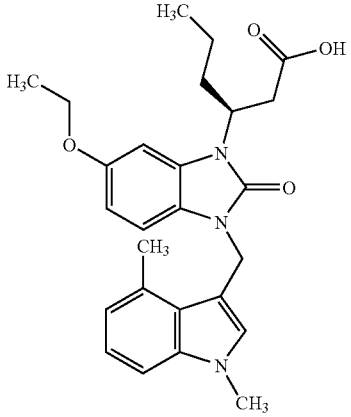
(S)-3-[3-(1,4-Dimethyl-1H-indol-3-ylmethyl)-6-ethoxy-2-oxo-2,3-dihydro-benzimidazol-1-yl]-hexanoic acid
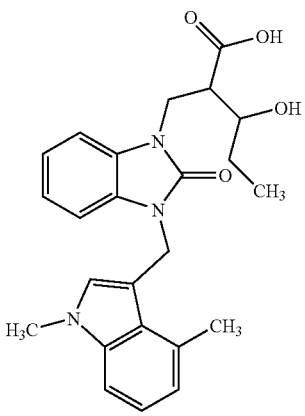 [SMILES: CCC(O)C(Cn1c(=O)n(Cc2cn(C)c3cccc(C)c23)c2ccccc21)C(=O)O]
2-[3-(1,4-Dimethyl-1H-indol-3-ylmethyl)-2-oxo-2,3-dihydro-benzimidazol-1-ylmethyl]-3-hydroxy-pentanoic acid
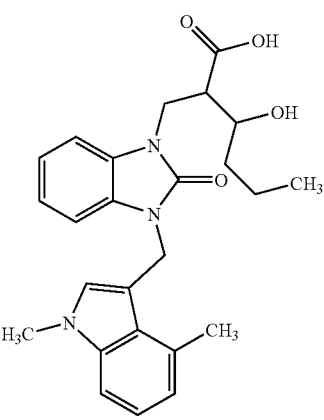 [SMILES: CCCC(O)C(Cn1c(=O)n(Cc2cn(C)c3cccc(C)c23)c2ccccc21)C(=O)O]
2-[3-(1,4-Dimethyl-1H-indol-3-ylmethyl)-2-oxo-2,3-dihydro-benzimidazol-1-ylmethyl]-3-hydroxy-hexanoic acid TABLE I-continued
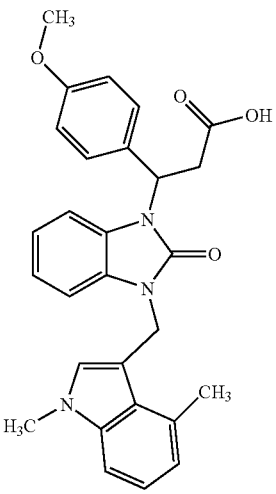 [SMILES: COc1ccc(C(CC(=O)O)n2c(=O)n(Cc3cn(C)c4cccc(C)c34)c3ccccc32)cc1]
3-[3-(1,4-Dimethyl-1H-indol-3-ylmethyl)-2-oxo-2,3-dihydro-benzimidazol-1-yl]-3-(4-methoxy-phenyl)-propionic acid
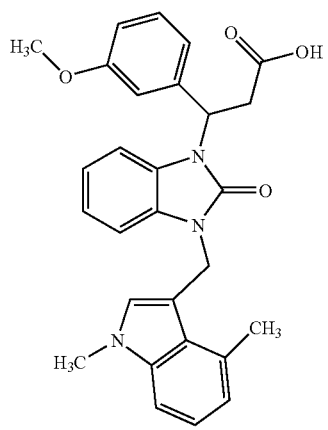 [SMILES: COc1cccc(C(CC(=O)O)n2c(=O)n(Cc3cn(C)c4cccc(C)c34)c3ccccc32)c1]
3-[3-(1,4-Dimethyl-1H-indol-3-ylmethyl)-2-oxo-2,3-dihydro-benzimidazol-1-yl]-3-(3-methoxy-phenyl)-propionic acid
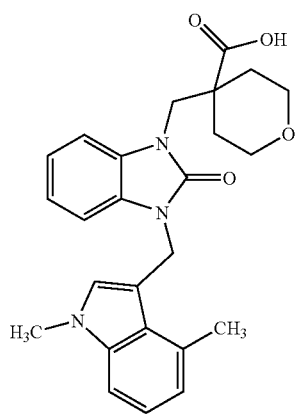 [SMILES: Cc1cccc2c1c(Cn1c(=O)n(CC3(C(=O)O)CCOCC3)c3ccccc31)cn2C]
4-[3-(1,4-Dimethyl-1H-indol-3-ylmethyl)-2-oxo-2,3-dihydro-benzimidazol-1-ylmethyl]-tetrahydro-pyran-4-carboxylic acid TABLE I-continued
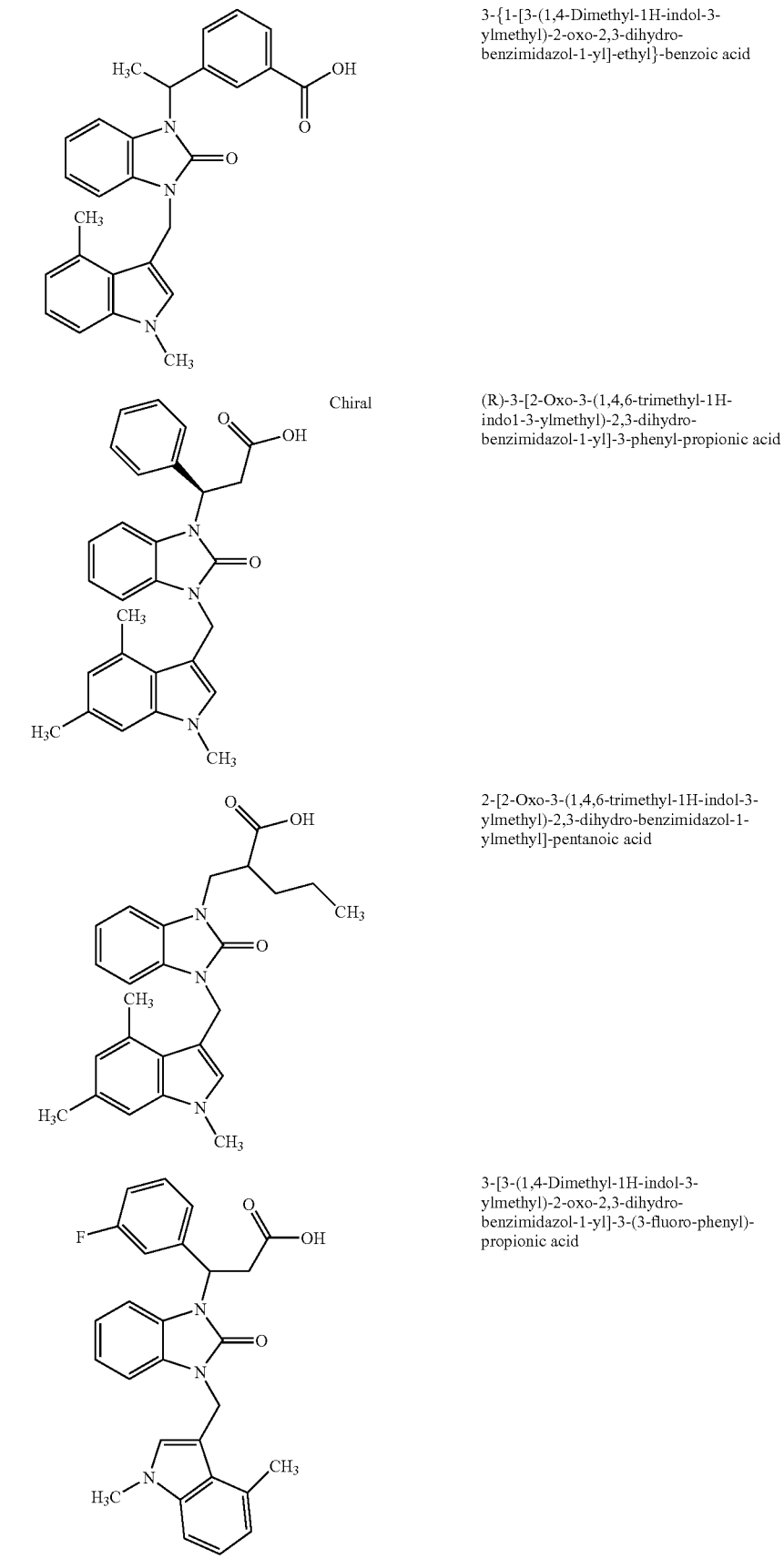
3-{1-[3-(1,4-Dimethyl-1H-indol-3-ylmethyl)-2-oxo-2,3-dihydro-benzimidazol-1-yl]-ethyl}-benzoic acid
(R)-3-[2-Oxo-3-(1,4,6-trimethyl-1H-indol-3-ylmethyl)-2,3-dihydro-benzimidazol-1-yl]-3-phenyl-propionic acid
2-[2-Oxo-3-(1,4,6-trimethyl-1H-indol-3-ylmethyl)-2,3-dihydro-benzimidazol-1-ylmethyl]-pentanoic acid
3-[3-(1,4-Dimethyl-1H-indol-3-ylmethyl)-2-oxo-2,3-dihydro-benzimidazol-1-yl]-3-(3-fluoro-phenyl)-propionic acid

TABLE I-continued
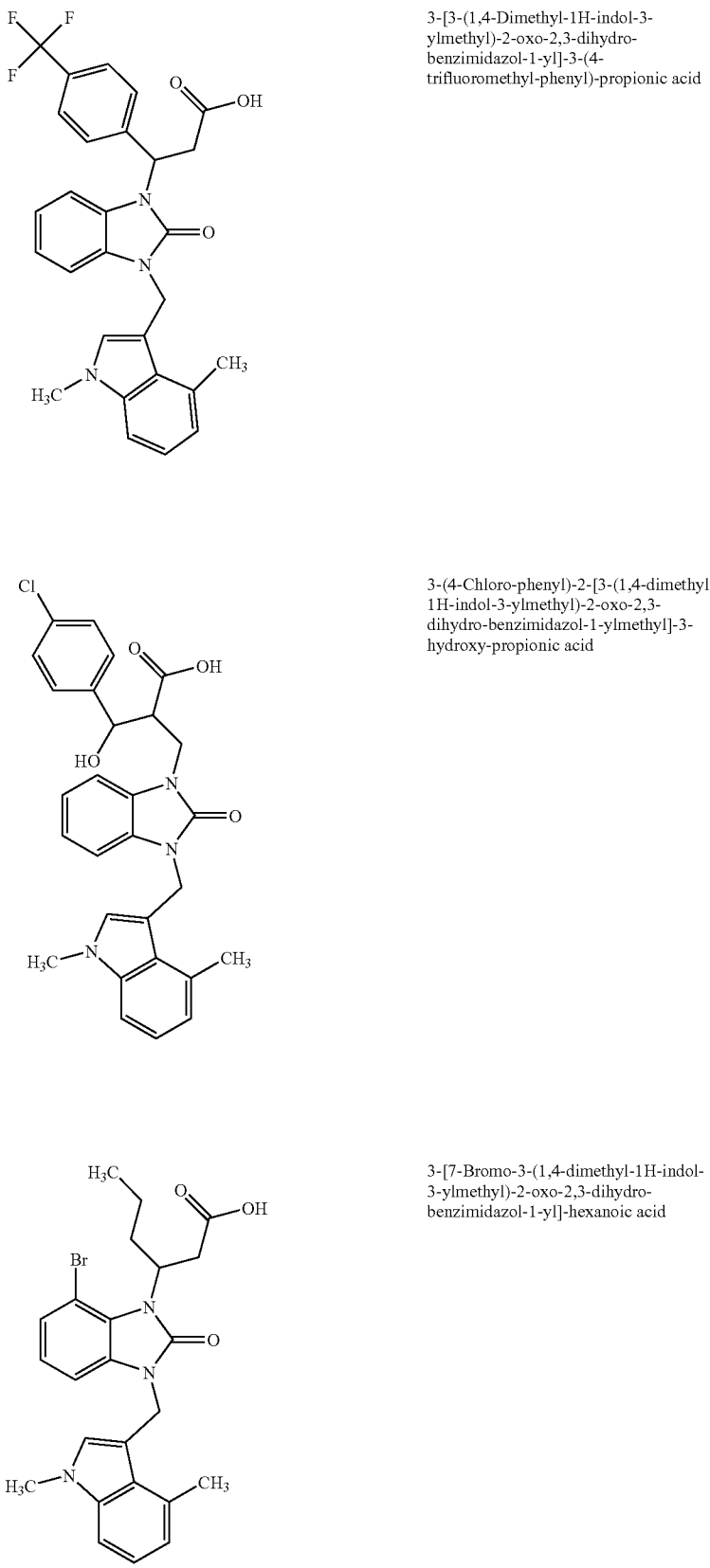
3-[3-(1,4-Dimethyl-1H-indol-3-ylmethyl)-2-oxo-2,3-dihydro-benzimidazol-1-yl]-3-(4-trifluoromethyl-phenyl)-propionic acid
3-(4-Chloro-phenyl)-2-[3-(1,4-dimethyl-1H-indol-3-ylmethyl)-2-oxo-2,3-dihydro-benzimidazol-1-ylmethyl]-3-hydroxy-propionic acid
3-[7-Bromo-3-(1,4-dimethyl-1H-indol-3-ylmethyl)-2-oxo-2,3-dihydro-benzimidazol-1-yl]-hexanoic acid TABLE I-continued
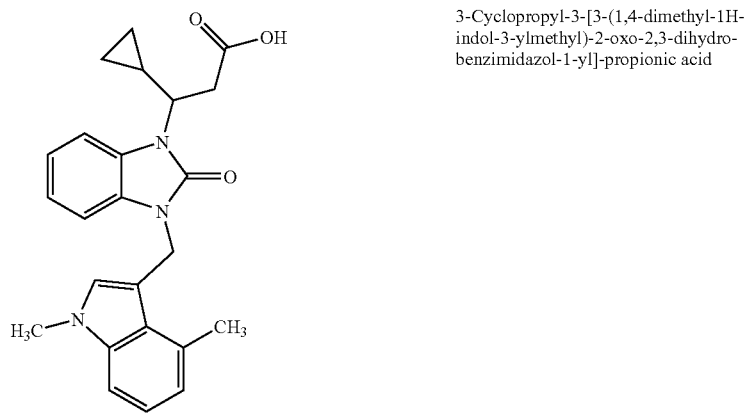
3-Cyclopropyl-3-[3-(1,4-dimethyl-1H-indol-3-ylmethyl)-2-oxo-2,3-dihydro-benzimidazol-1-yl]-propionic acid
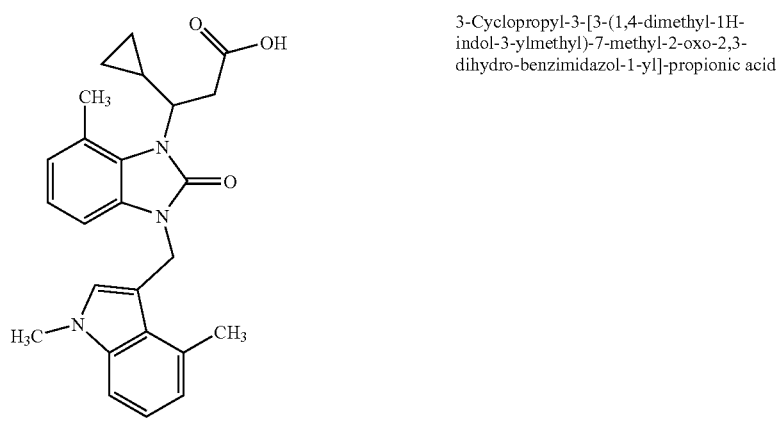
3-Cyclopropyl-3-[3-(1,4-dimethyl-1H-indol-3-ylmethyl)-7-methyl-2-oxo-2,3-dihydro-benzimidazol-1-yl]-propionic acid
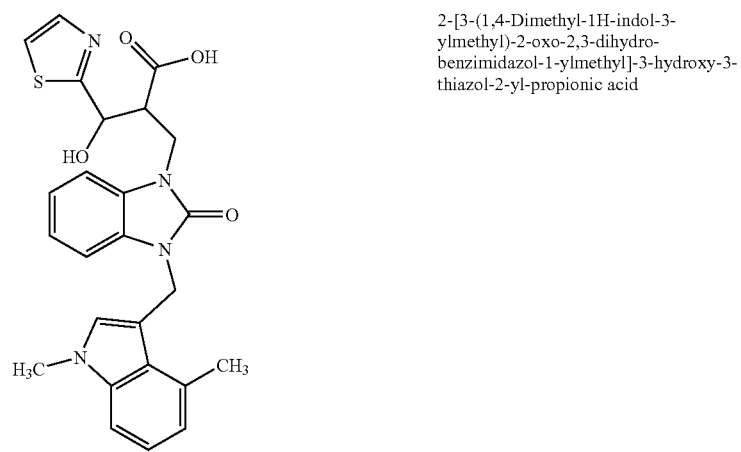
2-[3-(1,4-Dimethyl-1H-indol-3-ylmethyl)-2-oxo-2,3-dihydro-benzimidazol-1-ylmethyl]-3-hydroxy-3-thiazol-2-yl-propionic acid TABLE I-continued
| | |
|---|---|
| 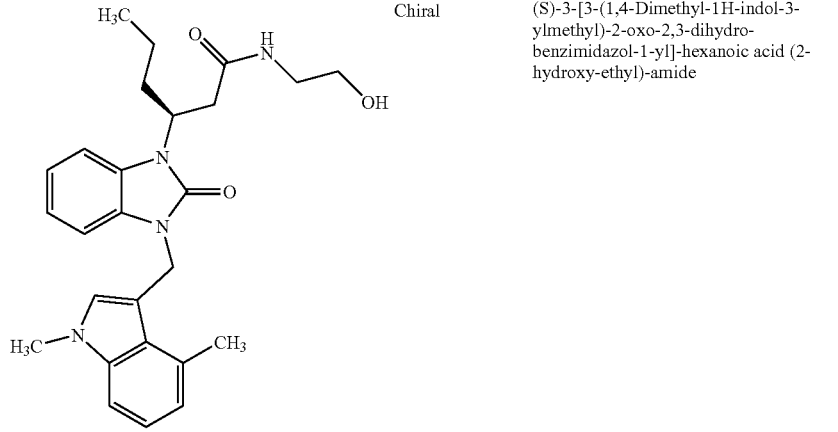 Chiral | (S)-3-[3-(1,4-Dimethyl-1H-indol-3-ylmethyl)-2-oxo-2,3-dihydro-benzimidazol-1-yl]-hexanoic acid (2-hydroxy-ethyl)-amide |
| 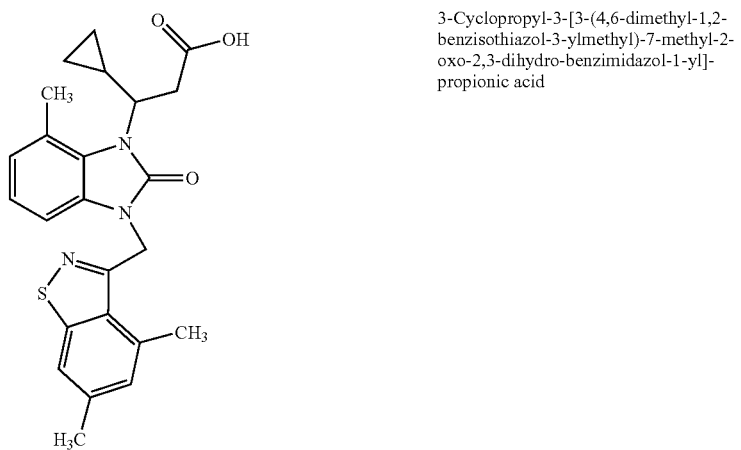 | 3-Cyclopropyl-3-[3-(4,6-dimethyl-1,2-benzisothiazol-3-ylmethyl)-7-methyl-2-oxo-2,3-dihydro-benzimidazol-1-yl]-propionic acid |
| 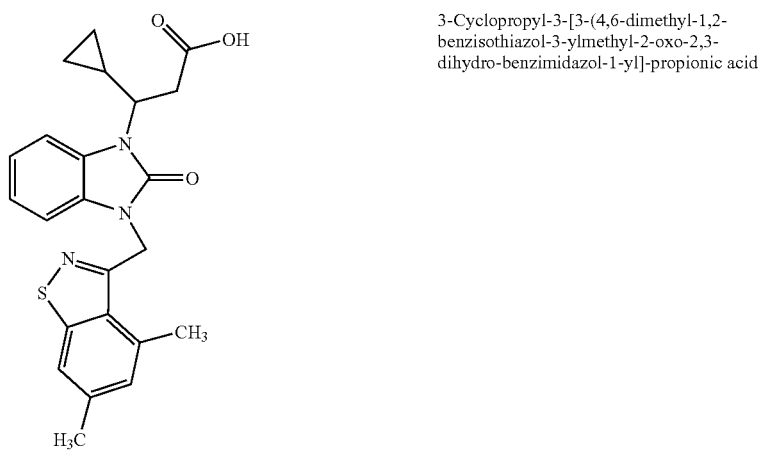 | 3-Cyclopropyl-3-[3-(4,6-dimethyl-1,2-benzisothiazol-3-ylmethyl-2-oxo-2,3-dihydro-benzimidazol-1-yl]-propionic acid |

| | |
|---|---|
| 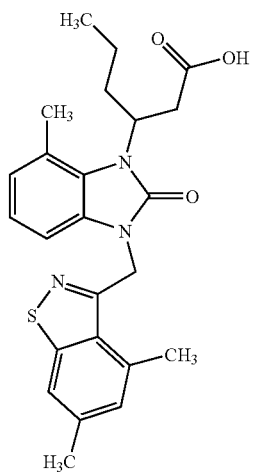 [SMILES: CCCC(CC(=O)O)n1c(=O)n(Cc2nsc3cc(C)cc(C)c23)c2cccc(C)c21] | 3-[3-(4,6-Dimethyl-1,2-benzisothiazol-3-ylmethyl)-7-methyl-2-oxo-2,3-dihydro-benzimidazol-1-yl]-hexanoic acid |
| 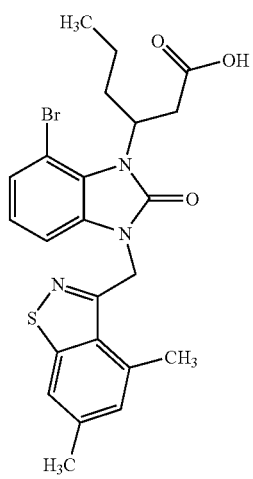 [SMILES: CCCC(CC(=O)O)n1c(=O)n(Cc2nsc3cc(C)cc(C)c23)c2cccc(Br)c21] | 3-[7-Bromo-3-(4,6-dimethyl-1,2-benzisothiazol-3-ylmethyl)-2-oxo-2,3-dihydro-benzimidazol-1-yl]-hexanoic acid |
| 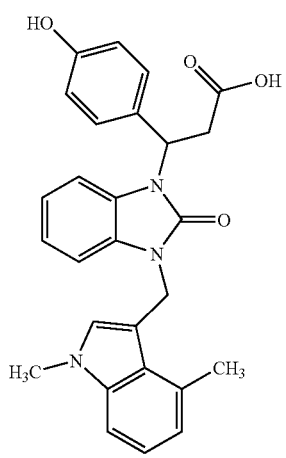 [SMILES: Cc1cccc2c1c(Cn1c(=O)n(C(CC(=O)O)c3ccc(O)cc3)c3ccccc31)cn2C] | 3-[3-(1,4-Dimethyl-1H-indol-3-ylmethyl)-2-oxo-2,3-dihydro-benzimidazol-1-yl]-3-(4-hydroxy-phenyl)-propionic acid |

TABLE I-continued
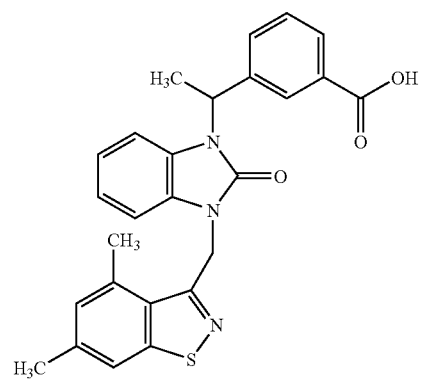 [SMILES: Cc1cc(C)c2c(Cn3c(=O)n(C(C)c4cccc(C(=O)O)c4)c4ccccc43)nsc2c1]
3-{1-[3-(4,6-Dimethyl-1,2-benzisothiazol-3-ylmethyl)-2-oxo-2,3-dihydro-benzimidazol-1-yl]-ethyl}-benzoic acid
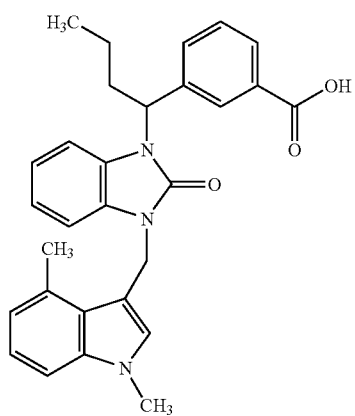 [SMILES: CCCC(c1cccc(C(=O)O)c1)n1c(=O)n(Cc2cn(C)c3cccc(C)c23)c2ccccc21]
3-{1-[3-(1,4-Dimethyl-1H-indol-3-ylmethyl)-2-oxo-2,3-dihydro-benzimidazol-1-yl]-butyl}-benzoic acid
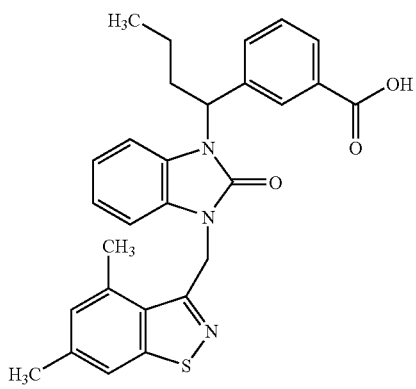 [SMILES: CCCC(c1cccc(C(=O)O)c1)n1c(=O)n(Cc2nsc3cc(C)cc(C)c23)c2ccccc21]
3-{1-[3-(4,6-Dimethyl-1,2-benzisothiazol-3-ylmethyl)-2-oxo-2,3-dihydro-benzimidazol-1-yl]-butyl}-benzoic acid
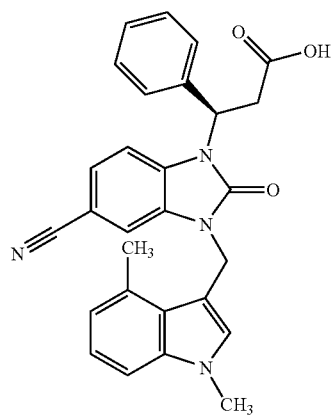 [SMILES: Cc1cccc2c1c(Cn1c(=O)n([C@H](CC(=O)O)c3ccccc3)c3ccc(C#N)cc31)cn2C]
(R)-3-[5-Cyano-3-(1,4-dimethyl-1H-indol-3-ylmethyl)-2-oxo-2,3-dihydro-benzimidazol-1-yl]-3-phenyl-propionic acid

| | |
|---|---|
| 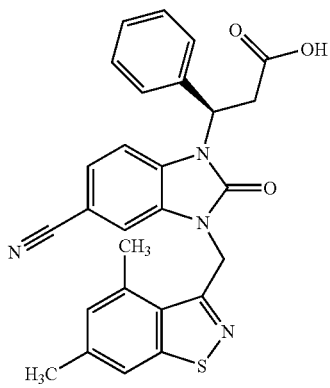 [SMILES: Cc1cc(C)c2c(Cn3c(=O)n([C@H](CC(=O)O)c4ccccc4)c4ccc(C#N)cc43)nsc2c1] | (R)-3-[5-Cyano-3-(4,6-dimethyl-1,2-benzisothiazol-3-ylmethyl)-2-oxo-2,3-dihydro-benzimidazol-1-yl]-3-phenyl-propionic acid |
| 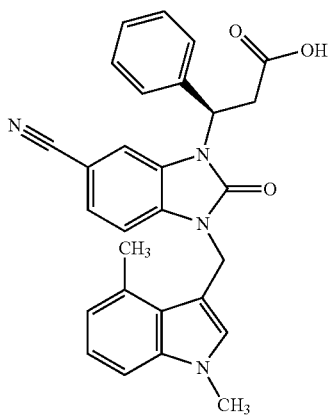 [SMILES: Cc1cccc2c1c(Cn1c(=O)n([C@H](CC(=O)O)c3ccccc3)c3cc(C#N)ccc31)cn2C] | (R)-3-[6-Cyano-3-(1,4-dimethyl-1H-indol-3-ylmethyl)-2-oxo-2,3-dihydro-benzimidazol-1-yl]-3-phenyl-propionic acid |
| 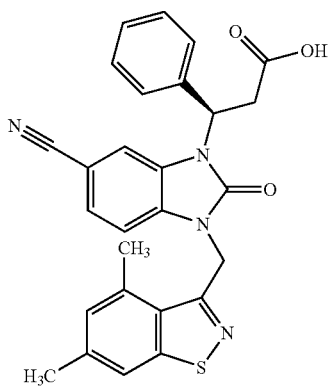 [SMILES: Cc1cc(C)c2c(Cn3c(=O)n([C@H](CC(=O)O)c4ccccc4)c4cc(C#N)ccc43)nsc2c1] | (R)-3-[6-Cyano-3-(4,6-dimethyl-1,2-benzisothiazol-3-ylmethyl)-2-oxo-2,3-dihydro-benzimidazol-1-yl]-3-phenyl-propionic acid |
| 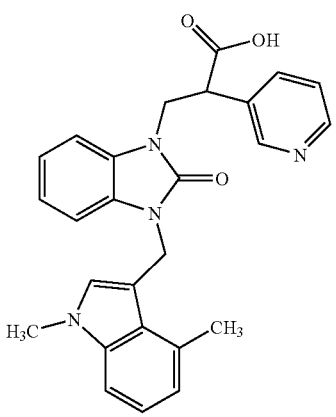 [SMILES: Cc1cccc2c1c(Cn1c(=O)n(CC(C(=O)O)c3cccnc3)c3ccccc31)cn2C] | 3-[3-(1,4-Dimethyl-1H-indol-3-ylmethyl)-2-oxo-2,3-dihydro-benzimidazol-1-yl]-2-pyridin-3-yl-propionic acid |

TABLE I-continued
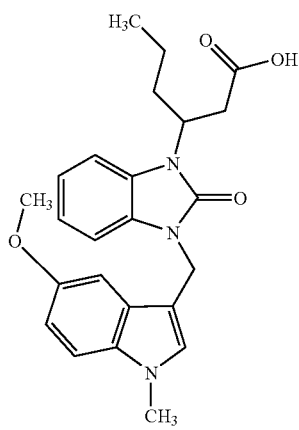 [SMILES: CCCC(CC(=O)O)n1c(=O)n(Cc2cn(C)c3ccc(OC)cc23)c2ccccc21]
3-[3-(5-Methoxy-1-methyl-1H-indol-3-ylmethyl)-2-oxo-2,3-dihydro-benzimidazol-1-yl]-hexanoic acid
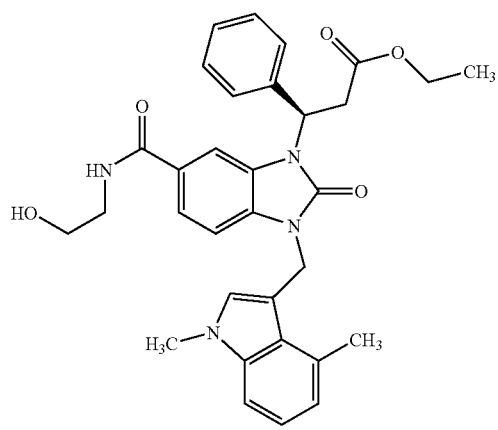 [SMILES: CCOC(=O)C[C@H](c1ccccc1)n1c(=O)n(Cc2cn(C)c3cccc(C)c23)c2ccc(C(=O)NCCO)cc21]
(R)-3-[3-(1,4-Dimethyl-1H-indol-3-ylmethyl)-6-(2-hydroxy-ethylcarbamoyl)-2-oxo-2,3-dihydro-benzimidazol-1-yl]-3-phenyl-propionic acid ethyl ester
Chiral
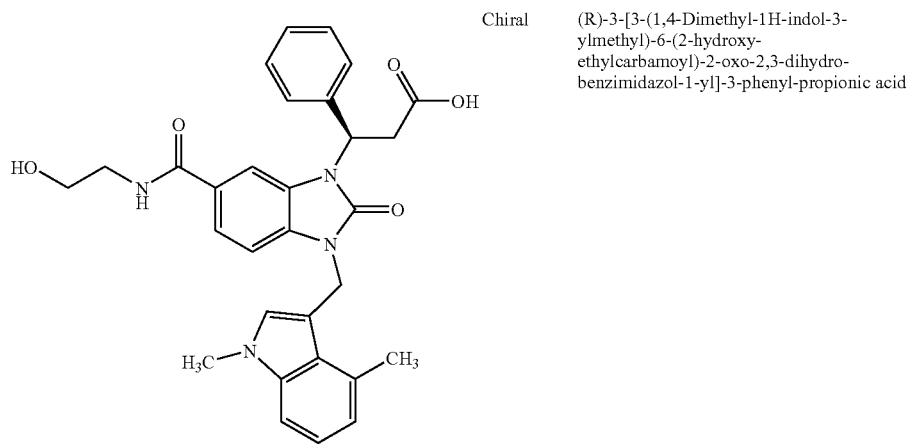
(R)-3-[3-(1,4-Dimethyl-1H-indol-3-ylmethyl)-6-(2-hydroxy-ethylcarbamoyl)-2-oxo-2,3-dihydro-benzimidazol-1-yl]-3-phenyl-propionic acid TABLE I-continued
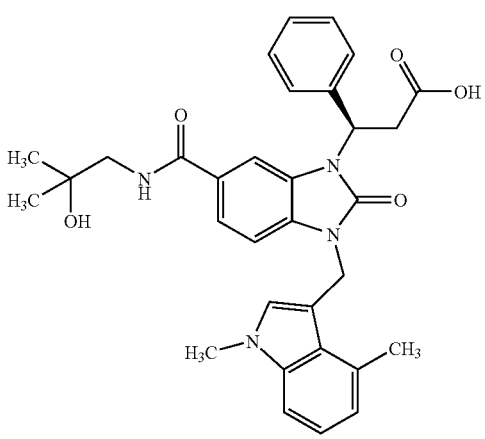
Chiral
(R)-3-[3-(1,4-Dimethyl-1H-indol-3-ylmethyl)-6-(2-hydroxy-2-methyl-propylcarbamoyl)-2-oxo-2,3-dihydro-benzimidazol-1-yl]-3-phenyl-propionic acid
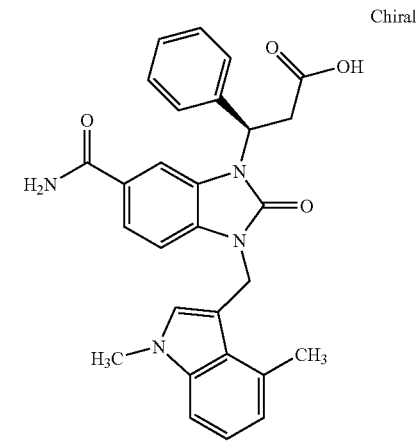 [SMILES: Cc1cccc2c1c(Cn1c(=O)n([C@H](CC(=O)O)c3ccccc3)c3cc(C(N)=O)ccc31)cn2C]
Chiral
(R)-3-[6-Carbamoyl-3-(1,4-dimethyl-1H-indol-3-ylmethyl)-2-oxo-2,3-dihydro-benzimidazol-1-yl]-3-phenyl-propionic acid
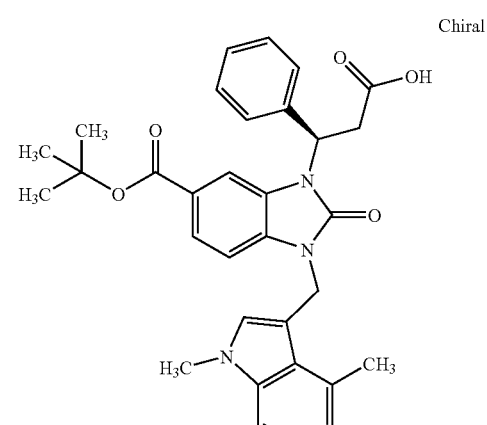
Chiral
3-((R)-2-Carboxy-1-phenyl-ethyl)-1-(1,4-dimethyl-1H-indol-3-ylmethyl)-2-oxo-2,3-dihydro-1H-benzimidazole-5-carboxylic acid tert-butyl ester TABLE I-continued

| Structure | Chirality | Name |
|---|---|---|
| 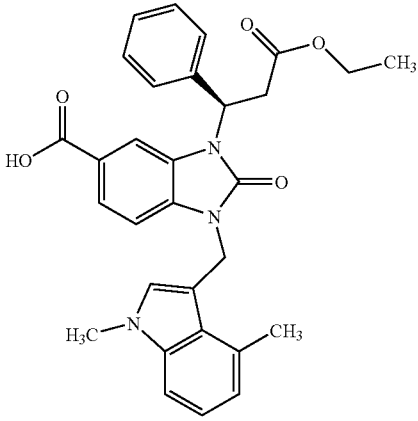 | Chiral | 1-(1,4-Dimethyl-1H-indol-3-ylmethyl)-3-((R)-2-ethoxycarbonyl-1-phenyl-ethyl)-2-oxo-2,3-dihydro-1H-benzimidazole-5-carboxylic acid |
| 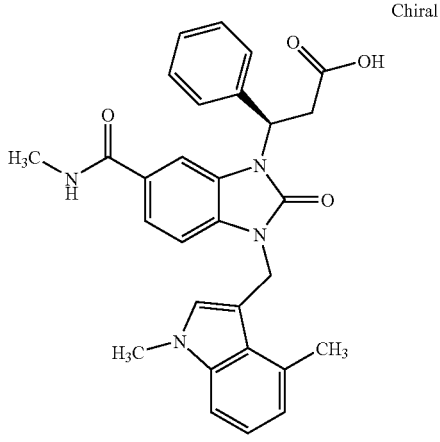 [SMILES: CNC(=O)c1ccc2c(c1)n([C@H](CC(=O)O)c1ccccc1)c(=O)n2Cc1cn(C)c2cccc(C)c12] | Chiral | (R)-3-[3-(1,4-Dimethyl-1H-indol-3-ylmethyl)-6-methylcarbamoyl-2-oxo-2,3-dihydro-benzimidazol-1-yl]-3-phenyl-propionic acid |
| 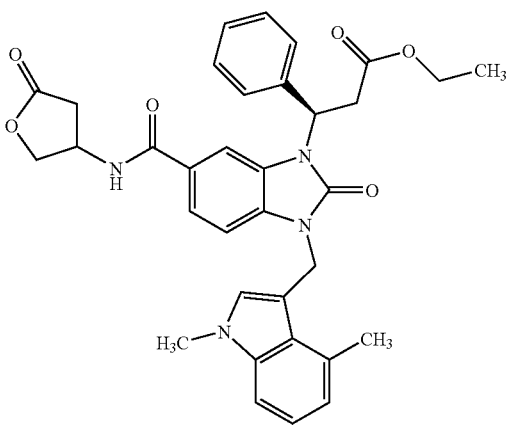 [SMILES: CCOC(=O)C[C@H](c1ccccc1)n1c(=O)n(Cc2cn(C)c3cccc(C)c23)c2ccc(C(=O)NC3COC(=O)C3)cc21] | | (R)-3-[3-(1,4-Dimethyl-1H-indol-3-ylmethyl)-2-oxo-6-(5-oxo-tetrahydro-furan-3-ylcarbamoyl)-2,3-dihydro-benzimidazol-1-yl]-3-phenyl-propionic acid ethyl ester |

TABLE I-continued
| | |
|---|---|
| 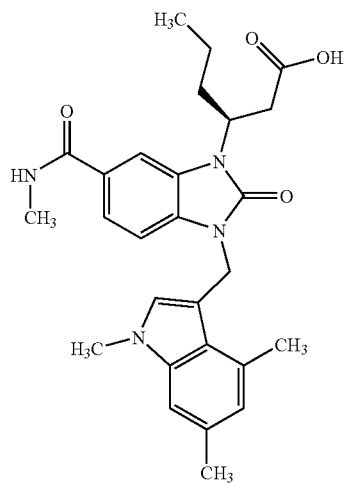 | (S)-3-[6-Methylcarbamoyl-2-oxo-3-(1,4,6-trimethyl-1H-indol-3-ylmethyl)-2,3-dihydro-benzimidazol-1-yl]-hexanoic acid |
| 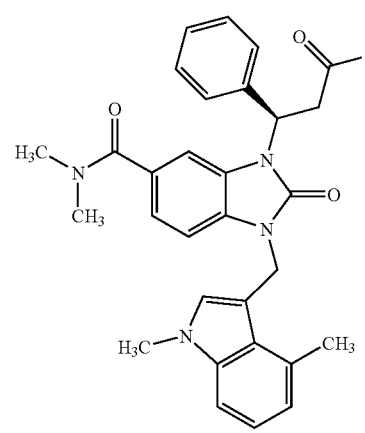 | (R)-3-[6-Dimethylcarbamoyl-3-(1,4-dimethyl-1H-indol-3-ylmethyl)-2-oxo-2,3-dihydro-benzimidazol-1-yl]-3-phenyl-propionic acid |
| 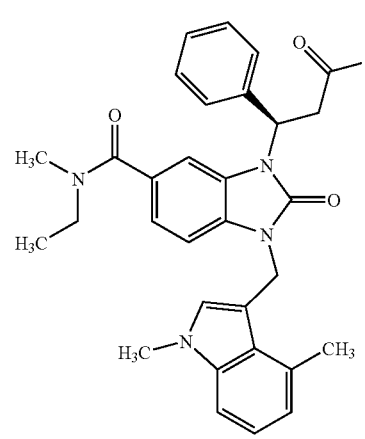 | (R)-3-[3-(1,4-Dimethyl-1H-indol-3-ylmethyl)-6-(ethyl-methyl-carbamoyl)-2-oxo-2,3-dihydro-benzimidazol-1-yl]-3-phenyl-propionic acid |

| | |
|---|---|
| 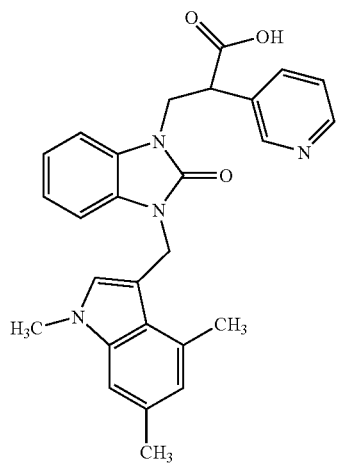 [SMILES: Cc1cc(C)c2c(Cn3c(=O)n(CC(C(=O)O)c4cccnc4)c4ccccc43)cn(C)c2c1] | 3-[2-Oxo-3-(1,4,6-trimelhyl-1H-indol-3-ylmethyl)-2,3-dihydro-benzimidazol-1-yl]-2-pyridin-3-yl-propionic acid |
| 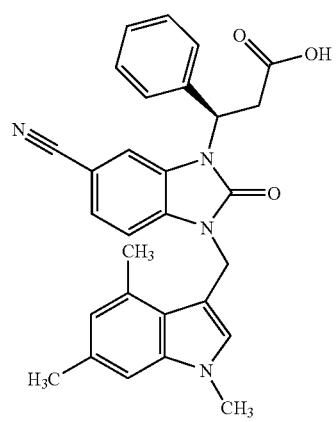 [SMILES: Cc1cc(C)c2c(Cn3c(=O)n([C@H](CC(=O)O)c4ccccc4)c4cc(C#N)ccc43)cn(C)c2c1] | (R)-3-[6-Cyano-2-oxo-3-(1,4,6-trimethyl-1H-indol-3-ylmethyl)-2,3-dihydro-benzimidazol-1-yl]-3-phenyl-propionic acid |
| 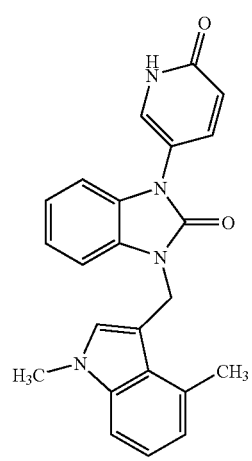 [SMILES: Cc1cccc2c1c(Cn1c(=O)n(-c3ccc(=O)[nH]c3)c3ccccc31)cn2C] | 1-(1,4-Dimethyl-1H-indol-3-ylmethyl)-3-(6-oxo-1,6-dihydro-pyridin-3-yl)-1,3-dihydro-benzimidazol-2-one |

TABLE I-continued
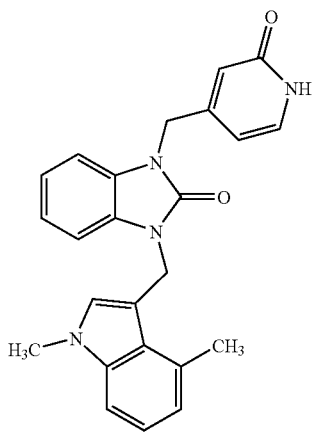 [SMILES: Cc1cccc2c1c(Cn1c(=O)n(Cc3cc[nH]c(=O)c3)c3ccccc31)cn2C]
1-(1,4-Dimethyl-1H-indol-3-ylmethyl)-3-(2-oxo-1,2-dihydro-pyridin-4-ylmethyl)-1,3-dihydro-benzimidazol-2-one
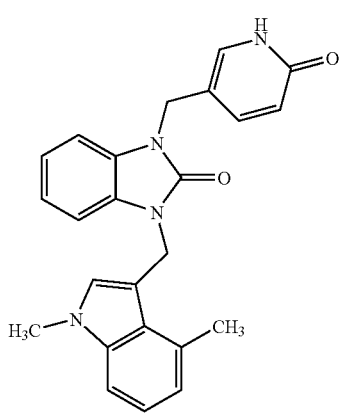 [SMILES: Cc1cccc2c1c(Cn1c(=O)n(Cc3ccc(=O)[nH]c3)c3ccccc31)cn2C]
1-(1,4-Dimethyl-1H-indol-3-ylmethyl)-3-(6-oxo-1,6-dihydxo-pyridin-3-ylmethyl)-1,3-dihydro-benzimidazol-2-one
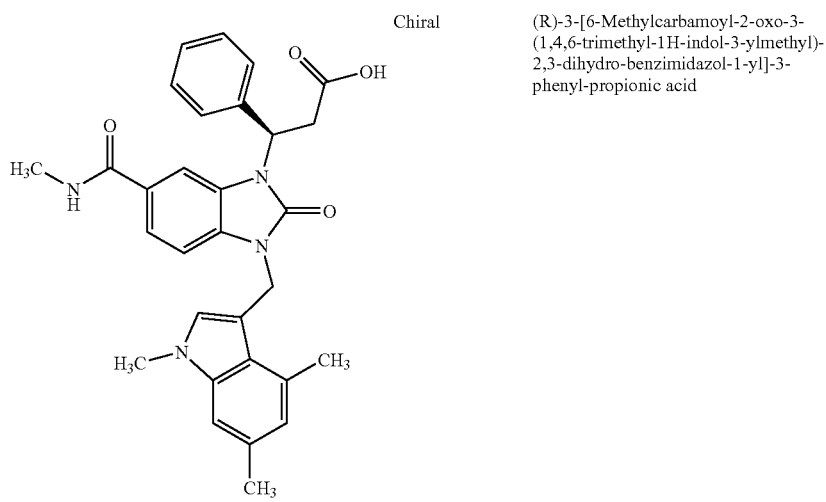
(R)-3-[6-Methylcarbamoyl-2-oxo-3-(1,4,6-trimethyl-1H-indol-3-ylmethyl)-2,3-dihydro-benzimidazol-1-yl]-3-phenyl-propionic acid TABLE I-continued
| | | |
|---|---|---|
| 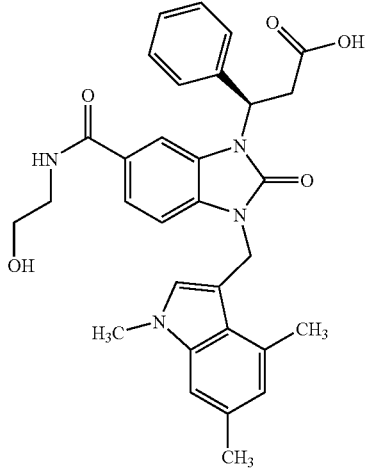 | Chiral | (R)-3-[6-(2-Hydroxy-ethylcarbamoyl)-2-oxo-3-(1,4,6-trimethyl-1H-indol-3-ylmethyl)-2,3-dihydro-benzimidazol-1-yl]-3-phenyl-propionic acid |
| 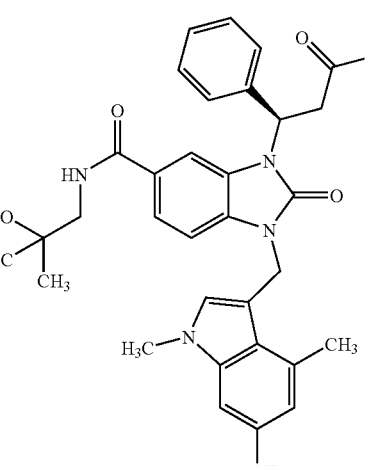 | Chiral | (R)-3-[6-(2-Hydroxy-2-methyl-propylcarbamoyl)-2-oxo-3-(1,4,6-trimethyl-1H-indol-3-ylmethyl)-2,3-dihydro-benzimidazol-1-yl]-3-phenyl-propionic acid |
| 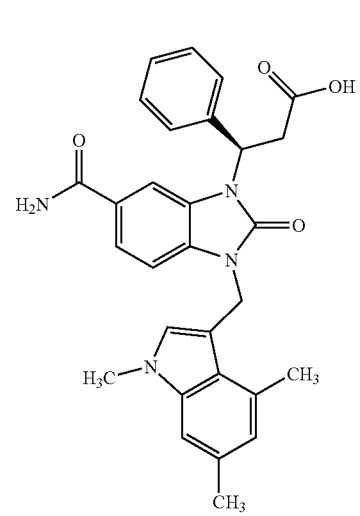 | Chiral | (R)-3-[6-Carbamoyl-2-oxo-3-(1,4,6-trimethyl-1H-indol-3-ylmethyl)-2,3-dihydro-benzimidazol-1-yl]-3-phenyl-propionic acid |

TABLE I-continued
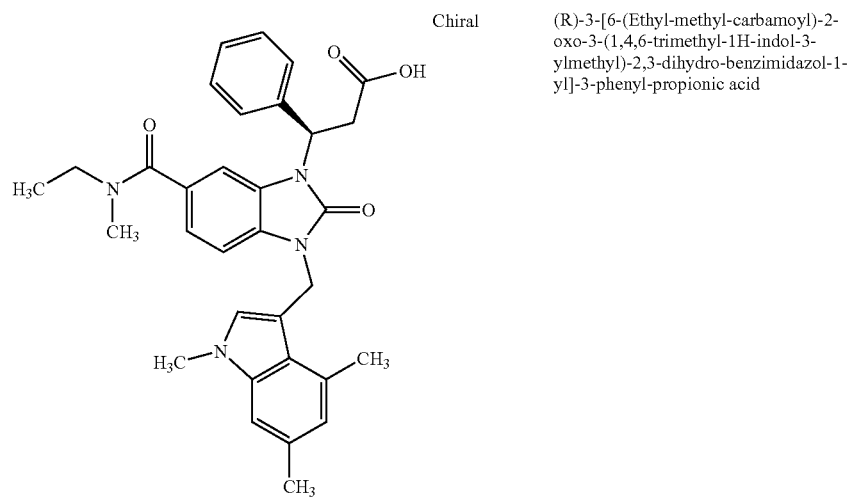
Chiral
(R)-3-[6-(Ethyl-methyl-carbamoyl)-2-oxo-3-(1,4,6-trimethyl-1H-indol-3-ylmethyl)-2,3-dihydro-benzimidazol-1-yl]-3-phenyl-propionic acid
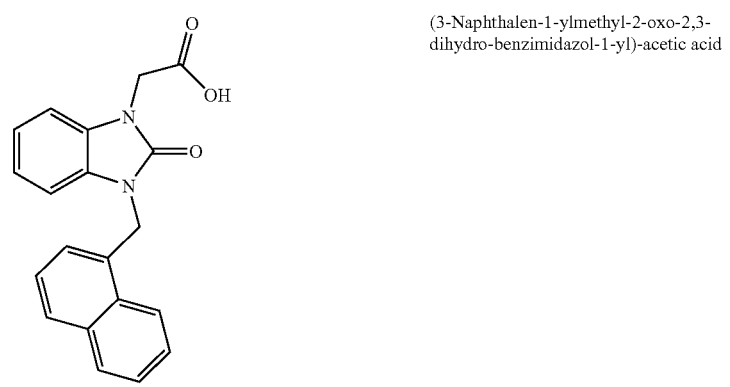
(3-Naphthalen-1-ylmethyl-2-oxo-2,3-dihydro-benzimidazol-1-yl)-acetic acid
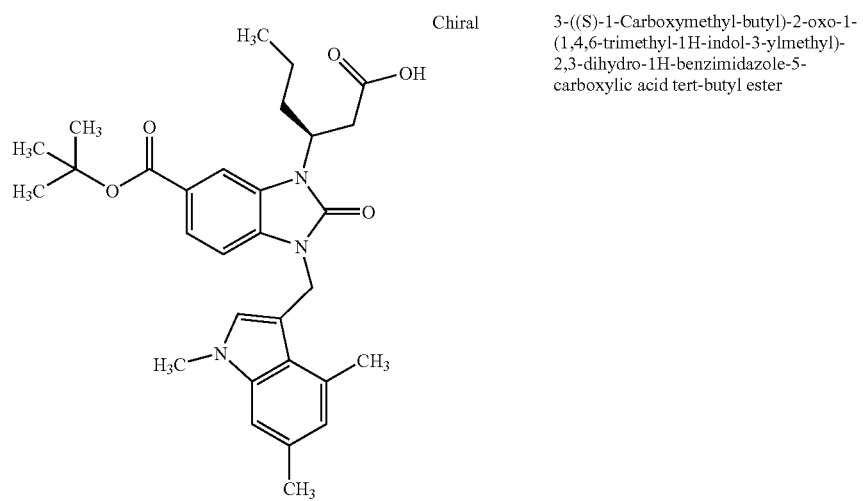
Chiral
3-((S)-1-Carboxymethyl-butyl)-2-oxo-1-(1,4,6-trimethyl-1H-indol-3-ylmethyl)-2,3-dihydro-1H-benzimidazole-5-carboxylic acid tert-butyl ester TABLE I-continued
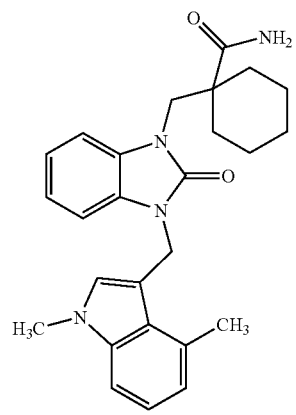 [SMILES: Cc1cccc2c1c(Cn1c(=O)n(CC3(C(N)=O)CCCCC3)c3ccccc31)cn2C]
1-[3-(1,4-Dimethyl-1H-indol-3-ylmethyl)-2-oxo-2,3-dihydro-benzimidazol-1-ylmethyl]-cyclohexanecarboxylic acid amide
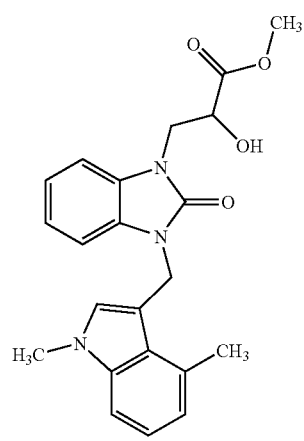
3-[3-(1,4-Dimethyl-1H-indol-3-ylmethyl)-2-oxo-2,3-dihydro-benzimidazol-1-yl]-2-hydroxy-propionic acid methyl ester
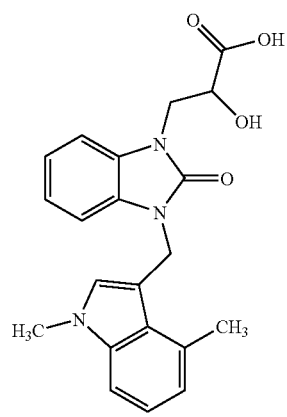 [SMILES: Cc1cccc2c1c(Cn1c(=O)n(CC(O)C(=O)O)c3ccccc31)cn2C]
3-[3-(1,4-Dimethyl-1H-indol-3-ylmethyl)-2-oxo-2,3-dihydro-benzimidazol-1-yl]-2-hydroxy-propionic acid

TABLE I-continued
| | | |
|---|---|---|
| 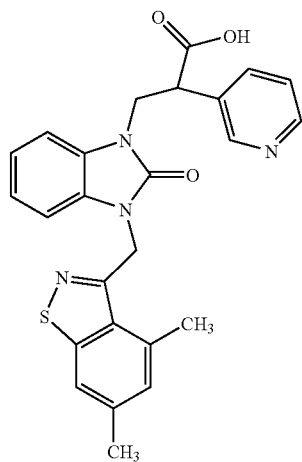 [SMILES: Cc1cc(C)c2c(Cn3c(=O)n(CC(C(=O)O)c4cccnc4)c4ccccc43)nsc2c1] | | 3-[3-(4,6-Dimethyl-1,2-benzisothiazol-3-ylmethyl)-2-oxo-2,3-dihydro-benzimidazol-1-yl]-2-pyridin-3-yl-propionic acid |
| 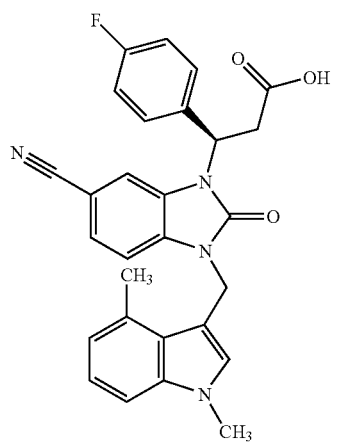 | Chiral | (R)-3-[6-Cyano-3-(1,4-dimethyl-1H-indol-3-ylmethyl)-2-oxo-2,3-dihydro-benzimidazol-1-yl]-3-(4-fluoro-phenyl)-propionic acid |
| 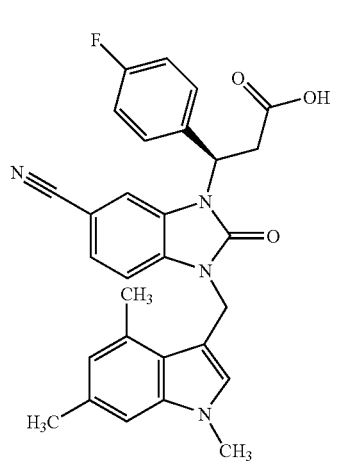 | Chiral | (R)-3-[6-Cyano-2-oxo-3-(1,4,6-trimethyl-1H-indol-3-ylmethyl)-2,3-dihydro-benzimidazol-1-yl]-3-(4-fluoro-phenyl)-propionic acid |

TABLE I-continued
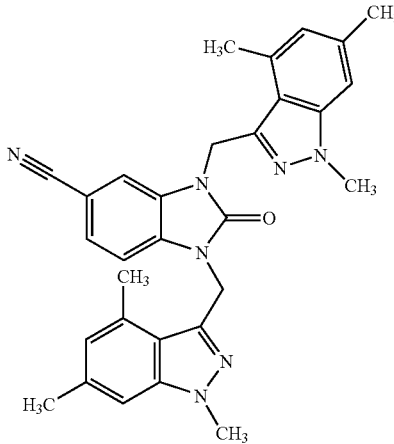
2-Oxo-1,3-bis-(1,4,6-trimethyl-1H-indazol-3-ylmethyl)-2,3-dihydro-1H-benzimidazole-5-carbonitrile
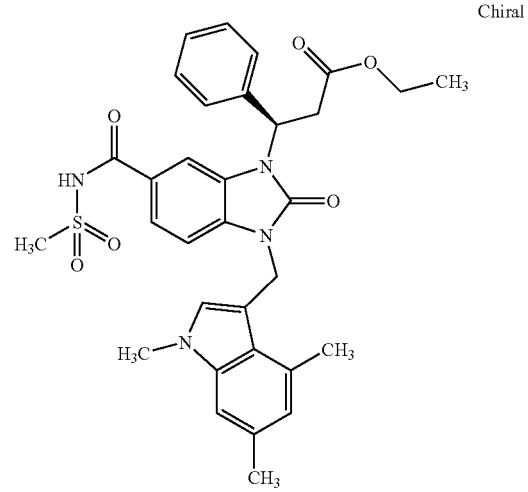 [SMILES: CCOC(=O)C[C@H](c1ccccc1)n1c(=O)n(Cc2cn(C)c3cc(C)cc(C)c23)c2ccc(C(=O)NS(C)(=O)=O)cc21]
Chiral
(R)-3-[6-Methanesulfonylaminocarbonyl-2-oxo-3-(1,4,6-trimethyl-1H-indol-3-ylmethyl)-2,3-dihydro-benzimidazol-1-yl]-3-phenyl-propionic acid ethyl ester
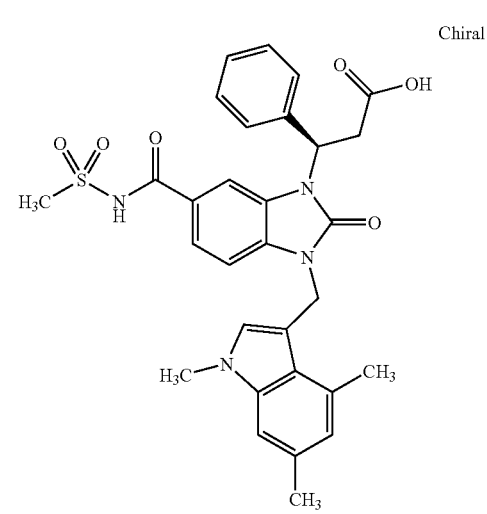 [SMILES: Cc1cc(C)c2c(Cn3c(=O)n([C@H](CC(=O)O)c4ccccc4)c4cc(C(=O)NS(C)(=O)=O)ccc43)cn(C)c2c1]
Chiral
(R)-3-[6-Methanesulfonylaminocarbonyl-2-oxo-3-(1,4,6-trimethyl-1H-indol-3-ylmethyl)-2,3-dihydro-benzimidazol-1-yl]-3-phenyl-propionic acid TABLE I-continued
| Structure | | Name |
|---|---|---|
| 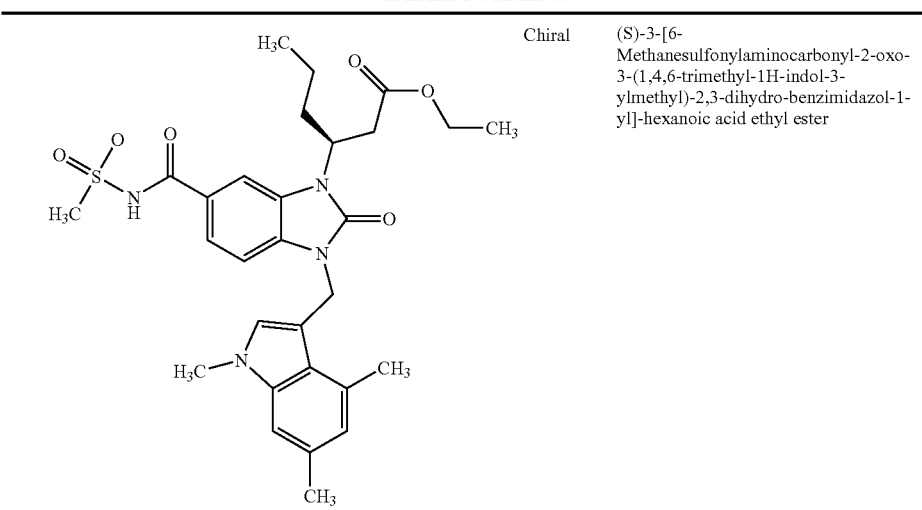 | Chiral | (S)-3-[6-Methanesulfonylaminocarbonyl-2-oxo-3-(1,4,6-trimethyl-1H-indol-3-ylmethyl)-2,3-dihydro-benzimidazol-1-yl]-hexanoic acid ethyl ester |
| 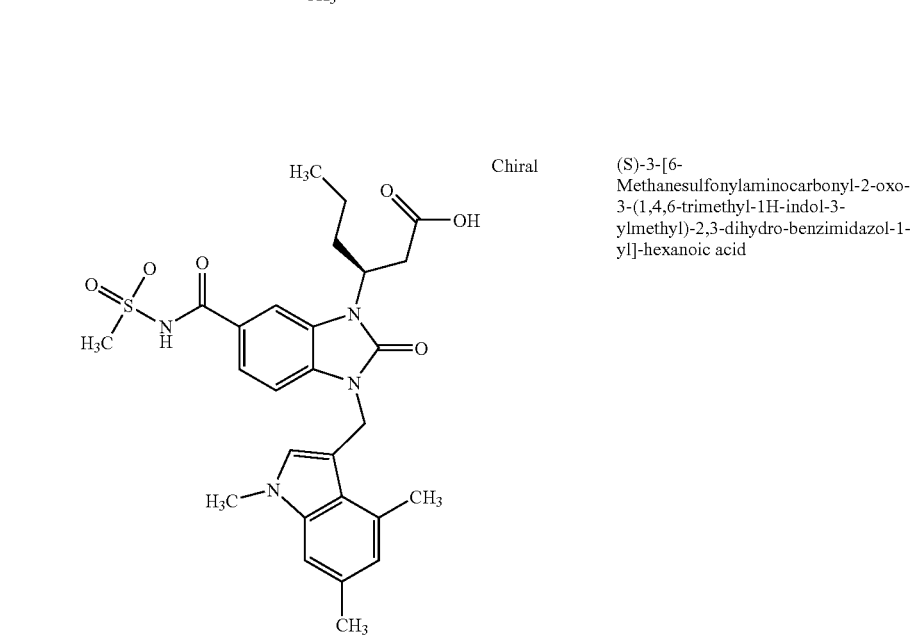 | Chiral | (S)-3-[6-Methanesulfonylaminocarbonyl-2-oxo-3-(1,4,6-trimethyl-1H-indol-3-ylmethyl)-2,3-dihydro-benzimidazol-1-yl]-hexanoic acid |
| 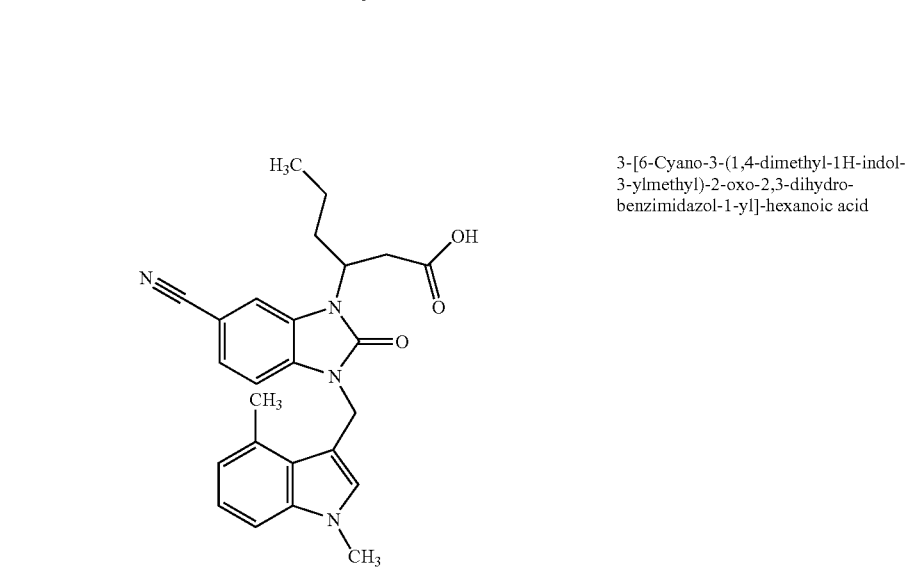 | | 3-[6-Cyano-3-(1,4-dimethyl-1H-indol-3-ylmethyl)-2-oxo-2,3-dihydro-benzimidazol-1-yl]-hexanoic acid |

TABLE I-continued
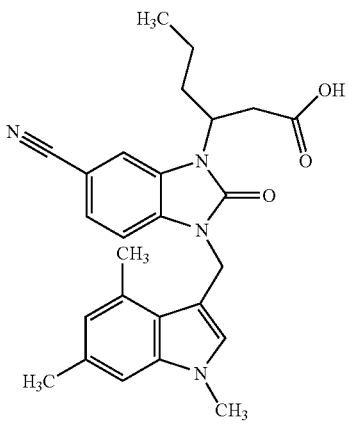 [SMILES: CCCC(CC(=O)O)n1c(=O)n(Cc2cn(C)c3cc(C)cc(C)c23)c2ccc(C#N)cc21]
3-[6-Cyano-2-oxo-3-(1,4,6-trimethyl-1H-indol-3-ylmethyl)-2,3-dihydro-benzimidazol-1-yl]-hexanoic acid
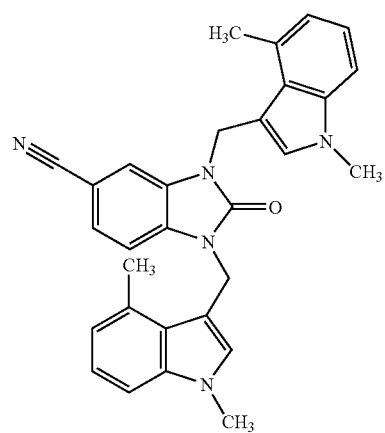 [SMILES: Cc1cccc2c1c(Cn1c(=O)n(Cc3cn(C)c4cccc(C)c34)c3cc(C#N)ccc31)cn2C]
1,3-Bis-(1,4-dimethyl-1H-indol-3-ylmethyl)-2-oxo-2,3-dihydro-1H-benzimidazole-5-carbonitrile
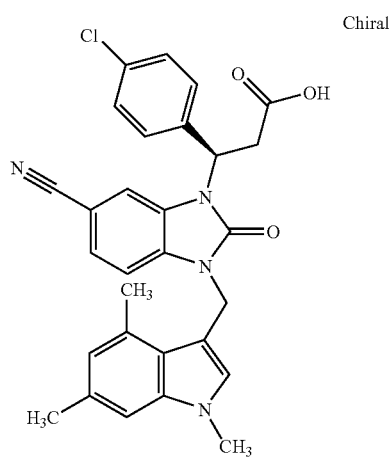 [SMILES: Cc1cc(C)c2c(Cn3c(=O)n([C@H](CC(=O)O)c4ccc(Cl)cc4)c4cc(C#N)ccc43)cn(C)c2c1]
Chiral
(R)-3-(4-Chloro-phenyl)-3-[6-cyano-2-oxo-3-(1,4,6-trimethyl-1H-indol-3-ylmethyl)-2,3-dihydro-benzimidazol-1-yl]-propionic acid TABLE I-continued
| | |
|---|---|
| 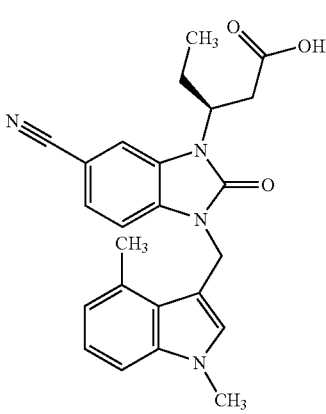 Chiral | (S)-3-[6-Cyano-3-(1,4-dimethyl-1H-indol-3-ylmethyl)-2-oxo-2,3-dihydro-benzimidazol-1-yl]-pentanoic acid |
| 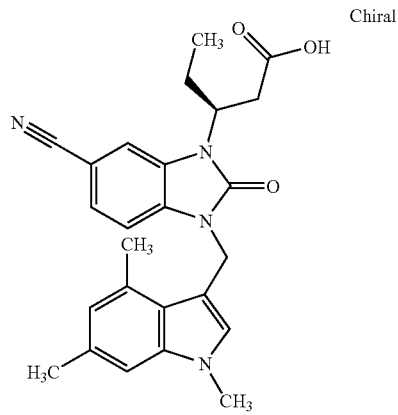 [SMILES: CC[C@@H](CC(=O)O)n1c(=O)n(Cc2cn(C)c3cc(C)cc(C)c23)c2ccc(C#N)cc21] Chiral | (S)-3-[6-Cyano-2-oxo-3-(1,4,6-trimethyl-1H-indol-3-ylmethyl)-2,3-dihydro-benzimidazol-1-yl]-pentanoic acid |
| 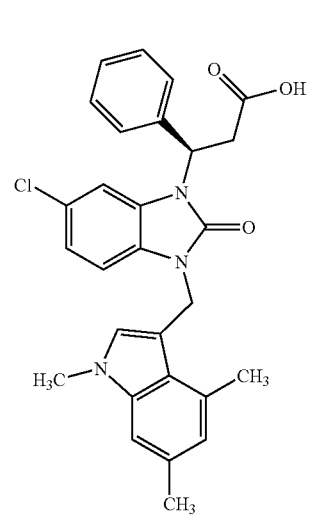 Chiral | (R)-3-[6-Chloro-2-oxo-3-(1,4,6-trimethyl-1H-indol-3-ylmethyl)-2,3-dihydro-benzimidazol-1-yl]-3-phenyl-propionic acid |

TABLE I-continued
| Structure | | Name |
|---|---|---|
| 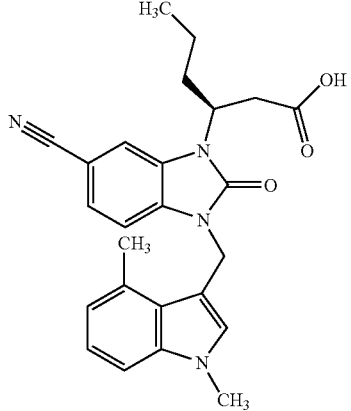 | Chiral | (S)-3-[6-Cyano-3-(1,4-dimethyl-1H-indol-3-ylmethyl)-2-oxo-2,3-dihydro-benzimidazol-1-yl]-hexanoic acid |
| 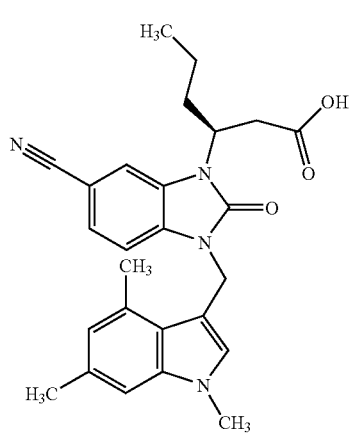 | Chiral | (S)-3-[6-Cyano-2-oxo-3-(1,4,6-trimethyl-1H-indol-3-ylmethyl)-2,3-dihydro-benzimidazol-1-yl]-hexanoic acid |
| 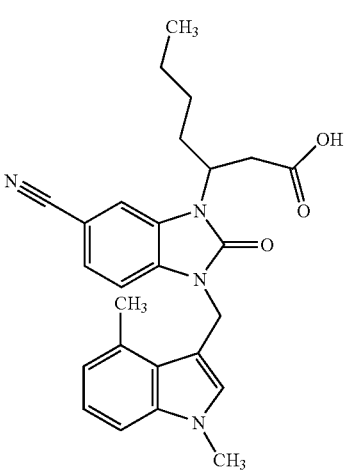 [SMILES: CCCCC(CC(=O)O)n1c(=O)n(Cc2cn(C)c3cccc(C)c23)c2ccc(C#N)cc21] | | 3-[6-Cyano-3-(1,4-dimethyl-1H-indol-3-ylmethyl)-2-oxo-2,3-dihydro-benzimidazol-1-yl]-heptanoic acid |

TABLE I-continued
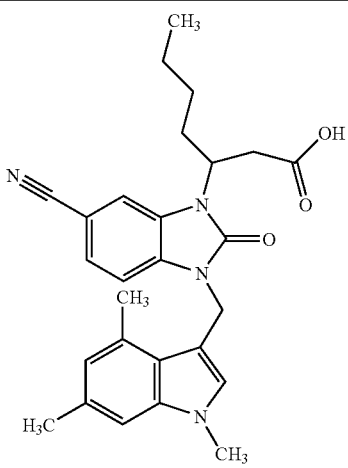
3-[6-Cyano-2-oxo-3-(1,4,6-trimethyl-1H-indol-3-ylmethyl)-2,3-dihydro-benzimidazol-1-yl]-heptanoic acid
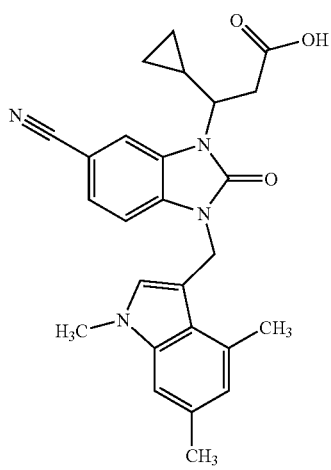 [SMILES: Cc1cc(C)c2c(Cn3c(=O)n(C(CC(=O)O)C4CC4)c4cc(C#N)ccc43)cn(C)c2c1]
3-[6-Cyano-2-oxo-3-(1,4,6-trimethyl-1H-indol-3-ylmethyl)-2,3-dihydro-benzimidazol-1-yl]-3-cyclopropyl-propionic acid
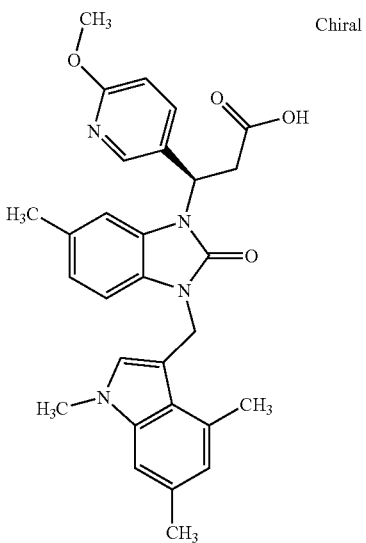 [SMILES: COc1ccc([C@@H](CC(=O)O)n2c(=O)n(Cc3cn(C)c4cc(C)cc(C)c34)c3ccc(C)cc32)cn1]
Chiral
(R)-3-(6-Methoxy-pyridin-3-yl)-3-[6-methyl-2-oxo-3-(1,4,6-trimethyl-1H-indol-3-ylmethyl)-2,3-dihydro-benzimidazol-1-yl]-propionic acid TABLE I-continued
| | |
|---|---|
| 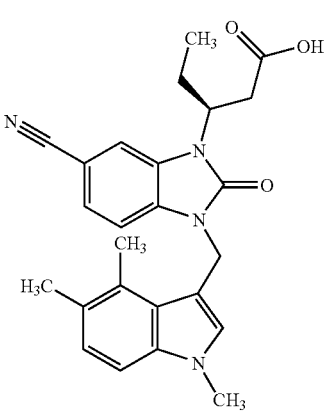 Chiral | (S)-3-[6-Cyano-2-oxo-3-(1,4,5-trimethyl-1H-indol-3-ylmethyl)-2,3-dihydro-benzimidazol-1-yl]-pentanoic acid |
| 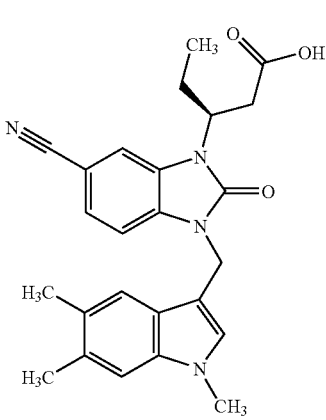 Chiral | (S)-3-[6-Cyano-2-oxo-3-(1,5,6-trimethyl-1H-indol-3-ylmethyl)-2,3-dihydro-benzimidazol-1-yl]-pentanoic acid |
| 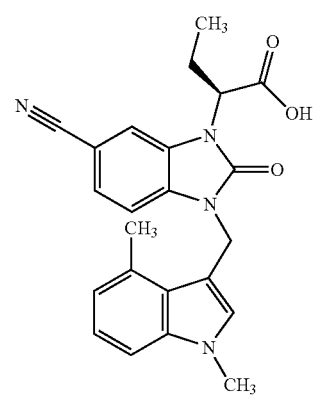 Chiral | (S)-2-[6-Cyano-3-(1,4-dimethyl-1H-indol-3-ylmethyl)-2-oxo-2,3-dihydro-benzimidazol-1-yl]-butyric acid |

TABLE I-continued
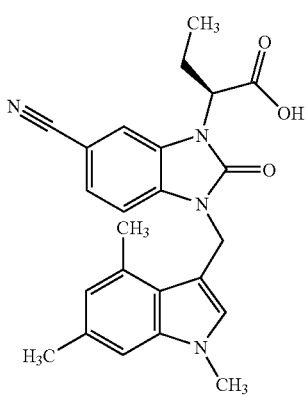
Chiral
(S)-2-[6-Cyano-2-oxo-3-(1,4,6-trimethyl-1H-indol-3-ylmethyl)-2,3-dihydro-benzimidazol-1-yl]-butyric acid
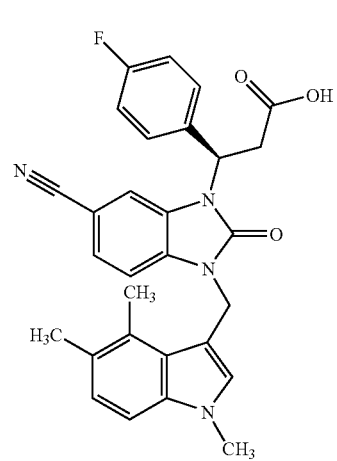
Chiral
(R)-3-[6-Cyano-2-oxo-3-(1,4,5-trimethyl-1H-indol-3-ylmethyl)-2,3-dihydro-benzimidazol-1-yl]-3-(4-fluoro-phenyl)-propionic acid
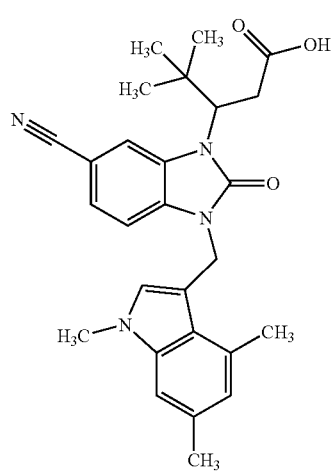 [SMILES: Cc1cc(C)c2c(Cn3c(=O)n(C(CC(=O)O)C(C)(C)C)c4cc(C#N)ccc43)cn(C)c2c1]
3-[6-Cyano-2-oxo-3-(1,4,6-trimethyl-1H-indol-3-ylmethyl)-2,3-dihydro-benzimidazol-1-yl]-4,4-dimethyl-pentanoic acid TABLE I-continued
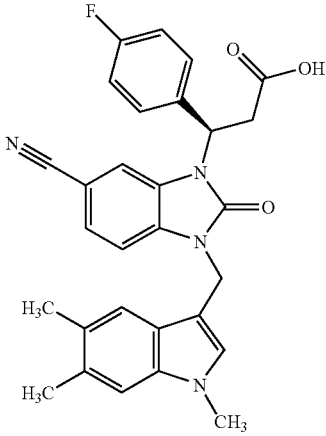
Chiral
(R)-3-[6-Cyano-2-oxo-3-(1,5,6-trimethyl-1H-indol-3-ylmethyl)-2,3-dihydro-benzimidazol-1-yl]-3-(4-fluoro-phenyl)-propionic acid
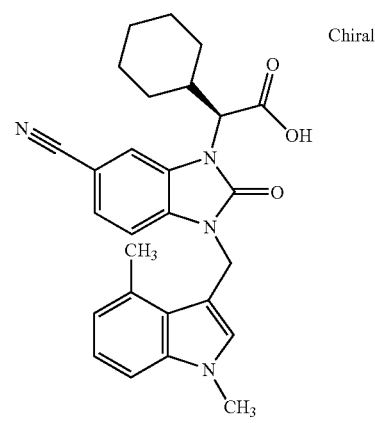 [SMILES: Cc1cccc2c1c(Cn1c(=O)n([C@H](C(=O)O)C3CCCCC3)c3cc(C#N)ccc31)cn2C]
Chiral
(S)-[6-Cyano-3-(1,4-dimethyl-1H-indol-3-ylmethyl)-2-oxo-2,3-dihydro-benzimidazol-1-yl]-cyclohexyl-acetic acid
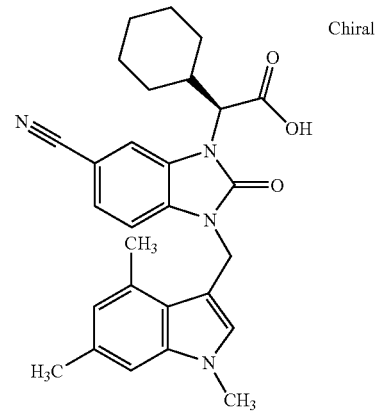 [SMILES: Cc1cc(C)c2c(Cn3c(=O)n([C@H](C(=O)O)C4CCCCC4)c4cc(C#N)ccc43)cn(C)c2c1]
Chiral
(S)-[6-Cyano-2-oxo-3-(1,4,6-trimethyl-1H-indol-3-ylmethyl)-2,3-dihydro-benzimidazol-1-yl]-cyclohexyl-acetic acid TABLE I-continued
| Structure | Chirality | Name |
|---|---|---|
| 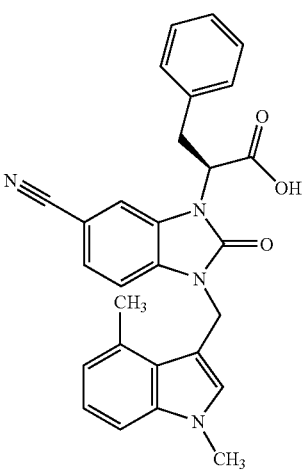 | Chiral | (S)-2-[6-Cyano-3-(1,4-dimethyl-1H-indol-3-ylmethyl)-2-oxo-2,3-dihydro-benzimidazol-1-yl]-3-phenyl-propionic acid |
| 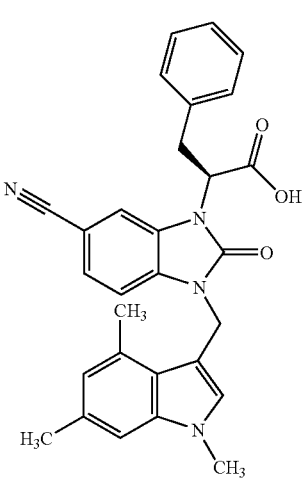 | Chiral | (S)-2-[6-Cyano-2-oxo-3-(1,4,6-trimethyl-1H-indol-3-ylmethyl)-2,3-dihydro-benzimidazol-1-yl]-3-phenyl-propionic acid |
| 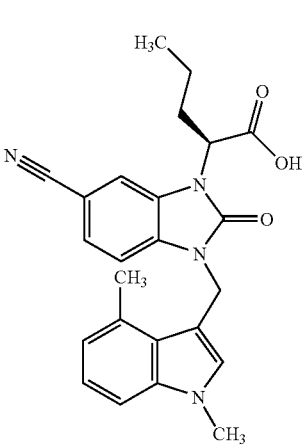 | Chiral | (S)-2-[6-Cyano-3-(1,4-dimethyl-1H-indol-3-ylmethyl)-2-oxo-2,3-dihydro-benzimidazol-1-yl]-pentanoic acid |

TABLE I-continued

| Structure | | Name |
|---|---|---|
| (structure) | Chiral | (S)-2-[6-Cyano-2-oxo-3-(1,4,6-trimethyl-1H-indol-3-ylmethyl)-2,3-dihydro-benzimidazol-1-yl]-pentanoic acid |
| (structure) | | 2-[3-(5-Bromo-2-oxo-2,3-dihydro-benzothiazol-7-ylmethyl)-2-oxo-2,3-dihydro-benzimidazol-1-ylmethyl]-pentanoic acid |
| (structure) | | 2-[3-(6-Bromo-2-oxo-2,3-dihydro-1H-indol-4-ylmethyl)-2-oxo-2,3-dihydro-benzimidazol-1-ylmethyl]-pentanoic acid |

TABLE I-continued

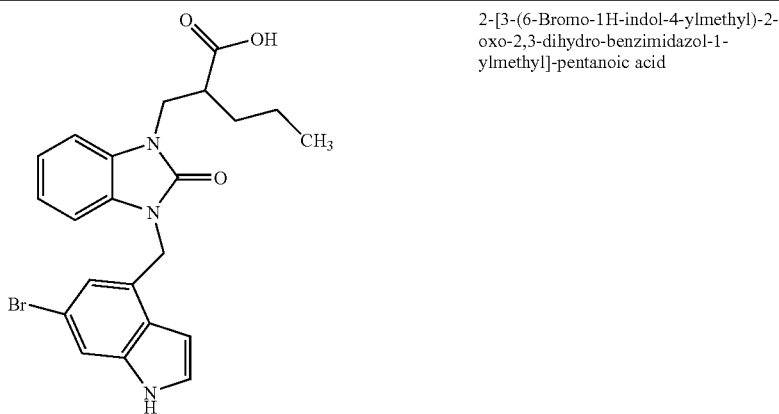

2-[3-(6-Bromo-1H-indol-4-ylmethyl)-2-oxo-2,3-dihydro-benzimidazol-1-ylmethyl]-pentanoic acid or a pharmaceutically acceptable salt thereof.

The following are preferred compounds of the invention:

TABLE II

N-[(2-fluorophenyl)sulfonyl]-3-{3-[(4-methyl-1-benzothien-3-yl)methyl]-2-oxo-2,3-dihydro-1H-benzimidazol-1-yl}hexanamide
(3R)-3-{3-[(4-methyl-1-benzothien-3-yl)methyl]-2-oxo-2,3-dihydro-1H-benzimidazol-1-yl}-3-phenylpropanoic acid
N-[(1,2-dimethyl-1H-imidazol-4-yl)sulfonyl]-3-{3-[(4-methyl-1-benzothien-3-yl)methyl]-2-oxo-2,3-dihydro-1H-benzimidazol-1-yl}hexanamide
3-{3-[(4-methyl-1-benzothien-3-yl)methyl]-2-oxo-2,3-dihydro-1H-benzimidazol-1-yl}-N-(phenylsulfonyl)hexanamide
(3S)—N-[(1,2-dimethyl-1H-imidazol-4-yl)sulfonyl]-3-{3-[(1,4-dimethyl-1H-indol-3-yl)methyl]-2-oxo-2,3-dihydro-1H-benzimidazol-1-yl}hexanamide
(3S)-3-{3-[(1,4-dimethyl-1H-indol-3-yl)methyl]-2-oxo-2,3-dihydro-1H-benzimidazol-1-yl}-N-(pyridin-2-ylsulfonyl)hexanamide
2-({3-[(5-chloro-1,2,3-trimethyl-1H-indol-7-yl)methyl]-2-oxo-2,3-dihydxo-1H-benzimidazol-1-yl}methyl)pentanoic acid
3-{3-[(5-chloro-1,2,3-trimethyl-1H-indol-7-yl)methyl]-2-oxo-2,3-dihydro-1H-benzimidazol-1-yl}-2-phenylpropanoic acid
(2S)-{3-[(4-methyl-1-benzothien-3-yl)methyl]-2-oxo-2,3-dihydro-1H-benzimidazol-1-yl}(phenyl)acetic acid
N-[(4-fluorophenyl)sulfonyl]-3-{3-[(4-methyl-1-benzothien-3-yl)methyl]-2-oxo-2,3-dihydro-1H-benzimidazol-1-yl}hexanamide
3-{3-[(4-methyl-1-benzothien-3-yl)methyl]-2-oxo-2,3-dihydro-1H-benzimidazol-1-yl}-N-[(1-methyl-1H-imidazol-4-yl)sulfonyl]hexanamide
(3S)-3-{3-[(1,4-dimethyl-1H-indol-3-yl)methyl]-2-oxo-2,3-dihydro-1H-benzimidazol-1-yl}-N-[(1-methyl-1H-imidazol-4-yl)sulfonyl]hexanamide
(3R)-3-{3-[(1,4-dimethyl-1H-indol-3-yl)methyl]-2-oxo-2,3-dihydro-1H-benzimidazol-1-yl}-3-phenylpropanoic acid
(3S)-3-{6-methyl-3-[(4-methyl-1-benzothien-3-yl)methyl]-2-oxo-2,3-dihydro-1H-benzimidazol-1-yl}-5-phenylpentanoic acid
3-{3-[(1,4-dimethyl-1H-indol-3-yl)methyl]-6-methyl-2-oxo-2,3-dihydro-1H-benzimidazol-1-yl}-N-(phenylsulfonyl)hexanamide
3-{3-[(4-methyl-1-benzothien-3-yl)methyl]-2-oxo-2,3-dihydro-1H-benzimidazol-1-yl}-N-(pyridin-2-ylsulfonyl)hexanamide
N-[(2-methoxyphenyl)sulfonyl]-3-{3-[(4-methyl-1-benzothien-3-yl)methyl]-2-oxo-2,3-dihydro-1H-benzimidazol-1-yl}hexanamide
3-{3-[(4-methyl-1-benzothien-3-yl)methyl]-2-oxo-2,3-dihydro-1H-benzimidazol-1-yl}octanoic acid
(3S)-3-{3-[(1,4-dimethyl-1H-indol-3-yl)methyl]-2-oxo-2,3-dihydro-1H-benzimidazol-1-yl}-N-(phenylsulfonyl)hexanamide
(3R)-3-{3-[(1,4-dimethyl-1H-indol-3-yl)methyl]-6-methyl-2-oxo-2,3-dihydro-1H-benzimidazol-1-yl}-3-pyridin-3-ylpropanoic acid
3-{3-[(4-methyl-1-benzothien-3-yl)methyl]-2-oxo-2,3-dihydro-1H-benzimidazol-1-yl}octanoic acid
3-{3-[(1,4-dimethyl-1H-indol-3-yl)methyl]-5,6-dimethyl-2-oxo-2,3-dihydro-1H-benzimidazol-1-yl}hexanoic acid
3-ethoxy-3-{3-[(4-methyl-1-benzothien-3-yl)methyl]-2-oxo-2,3-dihydro-1H-benzimidazol-1-yl}-N-(phenylsulfonyl)propanamide
(3S)-3-{3-[(4-methyl-1-benzothien-3-yl)methyl]-2-oxo-2,3-dihydro-1H-benzimidazol-1-yl}-3-phenylpropanoic acid
(3S)—N-(tert-butylsulfonyl)-3-{3-[(1,4-dimethyl-1H-indol-3-yl)methyl]-2-oxo-2,3-dihydro-1H-benzimidazol-1-yl}hexanamide
2-({3-[(1,4-dimethyl-1H-indol-3-yl)methyl]-2-oxo-2,3-dihydro-1H-benzimidazol-1-yl}methyl)pentanoic acid
(3S)-3-{2-oxo-3-[(1,4,6-trimethyl-1H-indol-3-yl)methyl]-2,3-dihydro-1H-benzimidazol-1-yl}hexanoic acid TABLE II-continued 3-{3-[(4-methyl-1-benzothien-3-yl)methyl]-2-oxo-2,3-dihydro-1H-benzimidazol-1-yl}heptanoic acid
N-[(3-fluorophenyl)sulfonyl]-3-{3-[(4-methyl-1-benzothien-3-yl)methyl]-2-oxo-2,3-dihydro-1H-benzimidazol-1-yl}hexanamide
3-{6-methyl-3-[(4-methyl-1-benzothien-3-yl)methyl]-2-oxo-2,3-dihydro-1H-benzimidazol-1-yl}hexanoic acid
3-ethoxy-3-{6-methyl-3-[(4-methyl-1-benzothien-3-yl)methyl]-2-oxo-2,3-dihydro-1H-benzimidazol-1-yl}propanoic acid
3-{5,6-dimethyl-3-[(4-methyl-1-benzothien-3-yl)methyl]-2-oxo-2,3-dihydro-1H-benzimidazol-1-yl}-3-ethoxypropanoic acid
(3S)-3-{3-[(4-methyl-1-benzothien-3-yl)methyl]-2-oxo-2,3-dihydro-1H-benzimidazol-1-yl}hexanoic acid
3-{2-oxo-3-[(1,4,6-trimethyl-1H-indol-3-yl)methyl]-2,3-dihydro-1H-benzimidazol-1-yl}hexanoic acid
N-[(4-methoxyphenyl)sulfonyl]-3-{3-[(4-methyl-1-benzothien-3-yl)methyl]-2-oxo-2,3-dihydro-1H-benzimidazol-1-yl}hexanamide
3-{3-[(1,4-dimethyl-1H-indol-3-yl)methyl]-6-methyl-2-oxo-2,3-dihydro-1H-benzimidazol-1-yl}hexanoic acid
N-(tert-butylsulfonyl)-3-{3-[(1,4-dimethyl-1H-indol-3-yl)methyl]-6-methyl-2-oxo-2,3-dihydro-1H-benzimidazol-1-yl}hexanamide
3-{3-[(1,4-dimethyl-1H-indol-3-yl)methyl]-2-oxo-2,3-dihydro-1H-benzimidazol-1-yl}-2,2-dimethylhexanoic acid
1-({3-[(1,4-dimethyl-1H-indol-3-yl)methyl]-2-oxo-2,3-dihydro-1H-benzimidazol-1-yl}methyl)cyclohexanecarboxylic acid
3-ethoxy-3-{3-[(4-methyl-1-benzothien-3-yl)methyl]-2-oxo-2,3-dihydro-1H-benzimidazol-1-yl}propanoic acid
N-[(3-methoxyphenyl)sulfonyl]-3-{3-[(4-methyl-1-benzothien-3-yl)methyl]-2-oxo-2,3-dihydro-1H-benzimidazol-1-yl}hexanamide
3-{3-[(6-bromo-1H-indol-4-yl)methyl]-2-oxo-2,3-dihydro-1H-benzimidazol-1-yl}hexanoic acid
2-({3-[(4,6-dimethyl-1,2-benzisothiazol-3-yl)methyl]-2-oxo-2,3-dihydro-1H-benzimidazol-1-yl}methyl)pentanoic acid
(3S)-3-{3-[(1,4-dimethyl-1H-indol-3-yl)methyl]-2-oxo-2,3-dihydro-1H-benzimidazol-1-yl}hexanoic acid
3-{3-[(1,4-dimethyl-1H-indol-3-yl)methyl]-2-oxo-2,3-dihydro-1H-benzimidazol-1-yl}-4-methoxy-N-[(1-methyl-1H-imidazol-4-yl)sulfonyl]butanamide
3-{3-[(6-chloro-1H-indol-4-yl)methyl]-2-oxo-2,3-dihydro-1H-benzimidazol-1-yl}hexanoic acid
(3S)-3-{3-[(4-methyl-1-benzothien-3-yl)methyl]-2-oxo-2,3-dihydro-1H-benzimidazol-1-yl}-4-phenylbutanoic acid
3-{3-[(4-methyl-1-benzothien-3-yl)methyl]-2-oxo-2,3-dihydro-1H-benzimidazol-1-yl}hexanoic acid
3-{3-[(4-methyl-1-benzothien-3-yl)methyl]-2-oxo-2,3-dihydro-1H-benzimidazol-1-yl}-N-(pyridin-3-ylsulfonyl)hexanamide
2-({3-[(5-chloro-1,2,3-trimethyl-1H-indol-7-yl)methyl]-2-oxo-2,3-dihydro-1H-benzimidazol-1-yl}methyl)butanoic acid
2-{3-[(4-methyl-1-benzothien-3-yl)methyl]-2-oxo-2,3-dihydro-1H-benzimidazol-1-yl}pentane-1-sulfonic acid
(3S)-3-{3-[(1,4-dimethyl-1H-indol-3-yl)methyl]-2-oxo-2,3-dihydro-1H-benzimidazol-1-yl}-N-(isopropylsulfonyl)hexanamide
3-{3-[(1,4-dimethyl-1H-indol-3-yl)methyl]-2-oxo-2,3-dihydro-1H-benzimidazol-1-yl}hexanoic acid
3-{3-[(1,4-dimethyl-1H-indol-3-yl)methyl]-2-oxo-5-(1,3-thiazol-2-ylamino)-2,3-dihydro-1H-benzimidazol-1-yl}hexanoic acid
1-({3-[(5-chloro-1,2,3-trimethyl-1H-indol-7-yl)methyl]-2-oxo-2,3-dihydro-1H-benzimidazol-1-yl}methyl)cyclohexanecarboxylic acid
N-(cyclopropylsulfonyl)-3-{3-[(4-methyl-1-benzothien-3-yl)methyl]-2-oxo-2,3-dihydro-1H-benzimidazol-1-yl}hexanamide
5-methoxy-3-{3-[(4-methyl-1-benzothien-3-yl)methyl]-2-oxo-2,3-dihydro-1H-benzimidazol-1-yl}-5-oxopentanoic acid
(3S)—N-cyano-3-{3-[(1,4-dimethyl-1H-indol-3-yl)methyl]-2-oxo-2,3-dihydro-1H-benzimidazol-1-yl}hexanamide
3-{3-[(1,4-dimethyl-1H-indol-3-yl)methyl]-2-oxo-2,3-dihydro-1H-benzimidazol-1-yl}-3-ethoxypropanoic acid
3-{5-bromo-3-[(1,4-dimethyl-1H-indol-3-yl)methyl]-2-oxo-2,3-dihydro-1H-benzimidazol-1-yl}hexanoic acid
5-methyl-3-{3-[(4-methyl-1-benzothien-3-yl)methyl]-2-oxo-2,3-dihydro-1H-benzimidazol-1-yl}hexanoic acid
(3S)-3-{3-[(1,4-dimethyl-1H-indol-3-yl)methyl]-2-oxo-2,3-dihydro-1H-benzimidazol-1-yl}-N-(ethylsulfonyl)hexanamide
3-{3-[(4-methyl-1-benzothien-3-yl)methyl]-2-oxo-2,3-dihydro-1H-benzimidazol-1-yl}-N-(phenylsulfonyl)propanamide
(3S)—N-(cyclopropylsulfonyl)-3-{3-[(1,4-dimethyl-1H-indol-3-yl)methyl]-2-oxo-2,3-dihydro-1H-benzimidazol-1-yl}hexanamide
3-{3-[(4-methyl-1-benzothien-3-yl)methyl]-2-oxo-2,3-dihydro-1H-benzimidazol-1-yl}pentanedioic acid
3-{3-[(5-chloro-1,2,3-trimethyl-1H-indol-7-yl)methyl]-2-oxo-2,3-dihydro-1H-benzimidazol-1-yl}hexanoic acid
1-(1-{3-[(1,4-dimethyl-1H-indol-3-yl)methyl]-2-oxo-2,3-dihydro-1H-benzimidazol-1-yl}butyl)cyclopropanecarboxylic acid
3-{3-[(3-bromo-1-naphthyl)methyl]-2-oxo-2,3-dihydro-1H-benzimidazol-1-yl}hexanoic acid
3-{3-[(1-cyano-5,7-dimethylindolizin-3-yl)methyl]-2-oxo-2,3-dihydro-1H-benzimidazol-1-yl}hexanoic acid
3-{3-[(5-chloro-1,2,3-trimethyl-1H-indol-7-yl)methyl]-2-oxo-2,3-dihydro-1H-benzimidazol-1-yl}propanoic acid TABLE II-continued N-[(2-{3-[(4-methyl-1-benzothien-3-yl)methyl]-2-oxo-2,3-dihydro-1H-benzimidazol-1-yl}ethyl)carbamoyl]benzenesulfonamide
3-methoxy-3-{3-[(4-methyl-1-benzothien-3-yl)methyl]-2-oxo-2,3-dihydro-1H-benzimidazol-1-yl}propanoic acid
3-{3-[(4-methyl-1-benzothien-3-yl)methyl]-2-oxo-2,3-dihydro-1H-benzimidazol-1-yl}-N-(methylsulfonyl)hexanamide
(1-{3-[(1,4-dimethyl-1H-indol-3-yl)methyl]-2-oxo-2,3-dihydro-1H-benzimidazol-1-yl}cyclohexyl)acetic acid
3-{3-[(5-chloro-1,3-dimethyl-1H-indol-7-yl)methyl]-2-oxo-2,3-dihydro-1H-benzimidazol-1-yl}hexanoic acid
(3R)-3-{6-methyl-3-[(4-methyl-1-benzothien-3-yl)methyl]-2-oxo-2,3-dihydro-1H-benzimidazol-1-yl}-5-phenylpentanoic acid
3-{3-[(1,4-dimethyl-1H-indol-3-yl)methyl]-6-methyl-2-oxo-2,3-dihydro-1H-benzimidazol-1-yl}-N-(ethylsulfonyl)hexanamide
(3S)-3-{3-[(4,6-dimethyl-1,2-benzisothiazol-3-yl)methyl]-2-oxo-2,3-dihydro-1H-benzimidazol-1-yl}hexanoic acid
N-[(2-{3-[(4-melhyl-1-benzothien-3-yl)methyl]-2-oxo-2,3-dihydro-1H-benzimidazol-1-yl}ethyl)sulfonyl]benzamide
(2S)-2-{3-[(4-methyl-1-benzothien-3-yl)methyl]-2-oxo-2,3-dihydro-1H-benzimidazol-1-yl}pentanoic acid
3-{3-[(3,8-dimethylindolizin-1-yl)methyl]-2-oxo-2,3-dihydro-1H-benzimidazol-1-yl}hexanoic acid
(3S)—N-(aminosulfonyl)-3-{3-[(1,4-dimethyl-1H-indol-3-yl)methyl]-2-oxo-2,3-dihydro-1H-benzimidazol-1-yl}hexanamide
3-ethoxy-3-[3-(1-naphthylmethyl)-2-oxo-2,3-dihydro-1H-benzimidazol-1-yl]propanoic acid
(3R)-3-{3-[(1,4-dimethyl-1H-indol-3-yl)methyl]-2-oxo-2,3-dihydro-1H-benzimidazol-1-yl}hexanoic acid
(3R)-3-{3-[(4-methyl-1-benzothien-3-yl)methyl]-2-oxo-2,3-dihydro-1H-benzimidazol-1-yl}hexanoic acid
2-({3-[(1,4-dimethyl-1H-indol-3-yl)methyl]-2-oxo-2,3-dihydro-1H-benzimidazol-1-yl}methyl)butanoic acid
3-{3-[(4,6-dimethyl-1,2-benzisothiazol-3-yl)methyl]-2-oxo-2,3-dihydro-1H-benzimidazol-1-yl}hexanoic acid
3-{3-[(4-methyl-1-benzothien-3-yl)methyl]-2-oxo-2,3-dihydro-1H-benzimidazol-1-yl}pentanoic acid
1-({3-[(1,4-dimethyl-1H-indol-3-yl)methyl]-2-oxo-2,3-dihydro-1H-benzimidazol-1-yl}methyl)cyclopentanecarboxylic acid
2-{3-[(4-methyl-1-benzothien-3-yl)methyl]-2-oxo-2,3-dihydro-1H-benzimidazol-1-yl}-N-(phenylsulfonyl)acetamide
3-{3-[(1-ethyl-4-methyl-1H-indol-3-yl)methyl]-2-oxo-2,3-dihydro-1H-benzimidazol-1-yl}hexanoic acid
3-{3-[(5-bromo-1-methyl-1H-indol-7-yl)methyl]-2-oxo-2,3-dihydro-1H-benzimidazol-1-yl}hexanoic acid
3-{3-[(5-chloro-1,2,3-trimethyl-1H-indol-7-yl)methyl]-6-methyl-2-oxo-2,3-dihydro-1H-benzimidazol-1-yl}pentanoic acid
3-{3-[(5-chloro-1,2,3-trimethyl-1H-indol-7-yl)methyl]-6-methyl-2-oxo-2,3-dihydro-1H-benzimidazol-1-yl}hexanoic acid
(3S)-3-{3-[(1,4-dimethyl-1H-indol-3-yl)methyl]-2-oxo-2,3-dihydro-1H-benzimidazol-1-yl}-N-(methylsulfonyl)hexanamide
3-{3-[(6,8-dichloro-3-methylindolizin-1-yl)methyl]-2-oxo-2,3-dihydro-1H-benzimidazol-1-yl}hexanoic acid
4-{3-[(1,4-dimethyl-1H-indol-3-yl)methyl]-2-oxo-2,3-dihydro-1H-benzimidazol-1-yl}heptanoic acid
(2S)-2-{3-[(4-methyl-1-benzothien-3-yl)methyl]-2-oxo-2,3-dihydro-1H-benzimidazol-1-yl}butanoic acid
1-({3-[(5-chloro-1,2,3-trimethyl-1H-indol-7-yl)methyl]-2-oxo-2,3-dihydro-1H-benzimidazol-1-yl}methyl)cyclopentanecarboxylic acid
2,2-dimethyl-3-{3-[(4-methyl-1-benzothien-3-yl)methyl]-2-oxo-2,3-dihydro-1H-benzimidazol-1-yl}propanoic acid
5-hydroxy-3-{3-[(4-methyl-1-benzothien-3-yl)methyl]-2-oxo-2,3-dihydro-1H-benzimidazol-1-yl}pentanoic acid
3-{3-[(6-bromo-2-oxo-2,3-dihydro-1H-indol-4-yl)methyl]-2-oxo-2,3-dihydro-1H-benzimidazol-1-yl}hexanoic acid
3-[3-(1-naphthylmethyl)-2-oxo-2,3-dihydro-1H-benzimidazol-1-yl]hexanoic acid
3-{3-[(6-bromo-1-methyl-1H-indol-4-yl)methyl]-2-oxo-2,3-dihydro-1H-benzimidazol-1-yl}hexanoic acid
2-{3-[(1,4-dimethyl-1H-indol-3-yl)methyl]-2-oxo-2,3-dihydro-1H-benzimidazol-1-yl}cyclopent-1-ene-1-carboxylic acid
3-{3-[(1,4-dimethyl-1H-indol-3-yl)methyl]-2-oxo-2,3-dihydro-1H-benzimidazol-1-yl}-4-methoxybutanoic acid
3-{3-[(5-chloro-1,2,3-trimethyl-1H-indol-7-yl)methyl]-2-oxo-2,3-dihydro-1H-benzimidazol-1-yl}-2-methylpropanoic acid
(1-{3-[(1,4-dimethyl-1H-indol-3-yl)methyl]-2-oxo-2,3-dihydro-1H-benzimidazol-1-yl}cyclopentyl)acetic acid
3-{3-[(1-cyano-5-methylindolizin-3-yl)methyl]-2-oxo-2,3-dihydro-1H-benzimidazol-1-yl}hexanoic acid
2-{3-[(1,4-dimethyl-1H-indol-3-yl)methyl]-2-oxo-2,3-dihydro-1H-benzimidazol-1-yl}-3-methoxybenzoic acid
3-{3-[(5-chloro-1-methyl-1H-indol-7-yl)methyl]-2-oxo-2,3-dihydro-1H-benzimidazol-1-yl}hexanoic acid
3-{7-bromo-3-[(1,4-dimethyl-1H-indol-3-yl)methyl]-2-oxo-2,3-dihydro-1H-benzimidazol-1-yl}propanoic acid
5-methyl-3-[3-(1-naphthylmethyl)-2-oxo-2,3-dihydro-1H-benzimidazol-1-yl]hexanoic acid TABLE II-continued 3-{3-[(6-methyl-1H-indol-4-yl)methyl]-2-oxo-2,3-dihydro-1H-benzimidazol-1-yl}hexanoic acid
4-{3-[(4-methyl-1-benzothien-3-yl)methyl]-2-oxo-2,3-dihydro-1H-benzimidazol-1-yl}-N-(phenylsulfonyl)butanamide
(2E)-3-{3-[(4-methyl-1-benzothien-3-yl)methyl]-2-oxo-2,3-dihydro-1H-benzimidazol-1-yl}acrylic acid
3-{3-[(1,4-dimethyl-1H-indol-3-yl)methyl]-2-oxo-2,3-dihydro-1H-benzimidazol-1-yl}-2,2-dimethylbutanoic acid
(2S)-3-methyl-2-{3-[(4-methyl-1-benzothien-3-yl)methyl]-2-oxo-2,3-dihydro-1H-benzimidazol-1-yl}butanoic acid
3-{3-[(1,4-dimethyl-1H-indol-3-yl)methyl]-2-oxo-2,3-dihydro-1H-benzimidazol-1-yl}-4-methoxy-2,2-dimethylbutanoic acid
3-[3-(1H-indol-3-ylmethyl)-2-oxo-2,3-dihydro-1H-benzimidazol-1-yl]hexanoic acid
3-{3-[(1,4-dimethyl-1H-indol-3-yl)methyl]-2-oxo-2,3-dihydro-1H-benzimidazol-1-yl}-4-methoxybenzoic acid
3-{2-oxo-3-[(1,2,3,5-tetramethyl-1H-indol-7-yl)methyl]-2,3-dihydro-1H-benzimidazol-1-yl}propanoic acid
3-{3-[(4-methyl-1-benzothien-3-yl)methyl]-2-oxo-2,3-dihydro-1H-benzimidazol-1-yl}propanoic acid
2-{3-[(1,4-dimethyl-1H-indol-3-yl)methyl]-2-oxo-2,3-dihydro-1H-benzimidazol-1-yl}benzoic acid
3-{3-[(8-bromo-1-naphthyl)methyl]-2-oxo-2,3-dihydro-1H-benzimidazol-1-yl}hexanoic acid
3-{3-[(4-methyl-1-benzothien-3-yl)methyl]-2-oxo-2,3-dihydro-1H-benzimidazol-1-yl}butanoic acid
N-(isopropylsulfonyl)-3-{3-[(4-methyl-1-benzothien-3-yl)methyl]-2-oxo-2,3-dihydro-1H-benzimidazol-1-yl}propanamide
N-[(2-{3-[(4-methyl-1-benzothien-3-yl)methyl]-2-oxo-2,3-dihydro-1H-benzimidazol-1-yl}ethyl)sulfonyl]acetamide
3-{3-[(4-methyl-1H-indol-3-yl)methyl]-2-oxo-2,3-dihydro-1H-benzimidazol-1-yl}hexanoic acid
(2S)-2-{3-[(4-methyl-1-benzothien-3-yl)methyl]-2-oxo-2,3-dihydro-1H-benzimidazol-1-yl}propanoic acid
2-{3-[(1,4-dimethyl-1H-indol-3-yl)methyl]-2-oxo-2,3-dihydro-1H-benzimidazol-1-yl}-3-methylbenzoic acid
3-{3-[(6-bromo-1H-indol-4-yl)methyl]-2-oxo-2,3-dihydro-1H-benzimidazol-1-yl}propanoic acid
3-{3-[(4-methyl-1-benzothien-3-yl)methyl]-2-oxo-2,3-dihydro-1H-benzimidazol-1-yl}-N-(methylsulfonyl)propanamide
3-{3-[(4-chloro-1-methyl-1H-indol-3-yl)methyl]-2-oxo-2,3-dihydro-1H-benzimidazol-1-yl}hexanoic acid
3-{3-[(6-chloro-1H-indol-4-yl)methyl]-2-oxo-2,3-dihydro-1H-benzimidazol-1-yl}propanoic acid
3-methoxy-3-[3-(1-naphthylmethyl)-2-oxo-2,3-dihydro-1H-benzimidazol-1-yl]propanoic acid
4-{3-[(1,4-dimethyl-1H-indol-3-yl)methyl]-2-oxo-2,3-dihydro-1H-benzimidazol-1-yl}pentanoic acid
3-{3-[(5-fluoro-1,2,3-trimethyl-1H-indol-7-yl)methyl]-2-oxo-2,3-dihydro-1H-benzimidazol-1-yl}hexanoic acid
4-{3-[(4-methyl-1-benzothien-3-yl)methyl]-2-oxo-2,3-dihydro-1H-benzimidazol-1-yl}butanoic acid
3-[3-(3-hydroxy-2,5-dimethylbenzyl)-2-oxo-2,3-dihydro-1H-benzimidazol-1-yl]hexanoic acid
{3-[(4-methyl-1-benzothien-3-yl)methyl]-2-oxo-2,3-dihydro-1H-benzimidazol-1-yl}acetic acid
2-{3-[(4-methyl-1-benzothien-3-yl)methyl]-2-oxo-2,3-dihydro-1H-benzimidazol-1-yl}ethanesulfonic acid
3-{2-oxo-3-[(1,2,3-trimethyl-1H-indol-7-yl)methyl]-2,3-dihydro-1H-benzimidazol-1-yl}propanoic acid
1-[(4-methyl-1-benzothien-3-yl)methyl]-3-[2-(1H-tetrazol-5-yl)ethyl]-1,3-dihydro-2H-benzimidazol-2-one
3-{3-[(6-bromo-1-methyl-2-oxo-2,3-dihydro-1H-indol-4-yl)methyl]-2-oxo-2,3-dihydro-1H-benzimidazol-1-yl}hexanoic acid
3-[2-oxo-3-(2,3,5-trichlorobenzyl)-2,3-dihydro-1H-benzimidazol-1-yl]hexanoic acid
3-{2-oxo-3-[(1,2,3-trimethyl-1H-indol-7-yl)methyl]-2,3-dihydro-1H-benzimidazol-1-yl}hexanoic acid
(1R,2R)-2-{3-[(1,4-dimethyl-1H-indol-3-yl)methyl]-2-oxo-2,3-dihydro-1H-benzimidazol-1-yl}cyclohexanecarboxylic acid
3-(6-{[2-(3,4-dimethoxyphenyl)ethyl]carbamoyl}-3-[(4-methyl-1-benzothien-3-yl)methyl]-2-oxo-2,3-dihydro-1H-benzimidazol-1-yl)propanoic acid
3-{3-[(1,4-dimethyl-1H-indol-3-yl)methyl]-2-oxo-2,3-dihydro-1H-benzimidazol-1-yl}-3-methylbutanoic acid
3-{3-[(1,4-dimethyl-1H-indol-3-yl)methyl]-7-methyl-2-oxo-2,3-dihydro-1H-benzimidazol-1-yl}propanoic acid
3-{3-[(8-bromo-1-naphthyl)methyl]-2-oxo-2,3-dihydro-1H-benzimidazol-1-yl}propanoic acid
3-{3-[(1,4-dimethyl-1H-indol-3-yl)methyl]-2-oxo-2,3-dihydro-1H-benzimidazol-1-yl}propanoic acid
2-{3-[(1,4-dimethyl-1H-indol-3-yl)methyl]-2-oxo-2,3-dihydro-1H-benzimidazol-1-yl}-2-methylpropanoic acid
3-(6-{[2-(3-hydroxy-4-methoxyphenyl)ethyl]carbamoyl}-3-[(4-methyl-1-benzothien-3-yl)methyl]-2-oxo-2,3-dihydro-1H-benzimidazol-1-yl)propanoic acid
3-{3-[(1,4-dimethyl-1H-indol-3-yl)methyl]-2-oxo-2,3-dihydro-1H-benzimidazol-1-yl}-2-methylpropanoic acid
3-{3-[(6-chloro-1-methyl-1H-indol-4-yl)methyl]-2-oxo-2,3-dihydro-1H-benzimidazol-1-yl}hexanoic acid
3-(6-{[2-(2-methoxyphenyl)ethyl]carbamoyl}-3-[(4-methyl-1-benzothien-3-yl)methyl]-2-oxo-2,3-dihydro-1H-benzimidazol-1-yl)propanoic acid
3-{3-[(4-chloro-1H-indol-3-yl)methyl]-2-oxo-2,3-dihydro-1H-benzimidazol-1-yl}hexanoic acid
3-({3-[(4-methyl-1-benzothien-3-yl)methyl]-2-oxo-2,3-dihydro-1H-benzimidazol-1-yl}methyl)benzoic acid
2-{3-[(1,4-dimethyl-1H-indol-3-yl)methyl]-2-oxo-2,3-dihydro-1H-benzimidazol-1-yl}cyclopentanecarboxylic acid
1-[2-(1,1-dioxido-4-oxo-1,2,5-thiadiazolidin-2-yl)ethyl]-3-[(4-methyl-1-benzothien-3-yl)methyl]-1,3-dihydro-2H-benzimidazol-2-one TABLE II-continued 3-[3-(1-naphthylmethyl)-2-oxo-2,3-dihydro-1H-benzimidazol-1-yl]pentanoic acid
3-[6-{[2-(3,4-dimethoxyphenyl)ethyl]carbamoyl}-3-(1-naphthylmethyl)-2-oxo-2,3-dihydro-1H-benzimidazol-1-yl]propanoic acid
4-methyl-3-[3-(1-naphthylmethyl)-2-oxo-2,3-dihydro-1H-benzimidazol-1-yl]pentanoic acid
3-[3-(5-bromo-2-methylbenzyl)-2-oxo-2,3-dihydro-1H-benzimidazol-1-yl]hexanoic acid
3-[3-(2,5-dimethylbenzyl)-2-oxo-2,3-dihydro-1H-benzimidazol-1-yl]hexanoic acid
3-{3-[(5-methoxy-1,2,3-trimethyl-1H-indol-7-yl)methyl]-2-oxo-2,3-dihydro-1H-benzimidazol-1-yl}propanoic acid
trans-4-({3-[(4-methyl-1-benzothien-3-yl)methyl]-2-oxo-2,3-dihydro-1H-benzimidazol-1-yl}methyl)cyclohexanecarboxylic acid
3-[3-(2,5-dichlorobenzyl)-2-oxo-2,3-dihydro-1H-benzimidazol-1-yl]hexanoic acid
3-{3-[(6-chloro-2-oxo-2,3-dihydro-1H-indol-4-yl)methyl]-2-oxo-2,3-dihydro-1H-benzimidazol-1-yl}hexanoic acid
3-{3-[(5-bromo-1-methyl-2-oxo-2,3-dihydro-1H-indol-7-yl)methyl]-2-oxo-2,3-dihydro-1H-benzimidazol-1-yl}hexanoic acid
3-[3-(1-naphthylmethyl)-2-oxo-2,3-dihydro-1H-benzimidazol-1-yl]-N-(phenylsulfonyl)propanamide
3-[6-{[2-(3-hydroxy-4-methoxyphenyl)ethyl]carbamoyl}-3-(1-naphthylmethyl)-2-oxo-2,3-dihydro-1H-benzimidazol-1-yl]propanoic acid
(3S)-3-{5-(carbamoylamino)-3-[(1,4-dimethyl-1H-indol-3-yl)methyl]-2-oxo-2,3-dihydro-1H-benzimidazol-1-yl}hexanoic acid
(3S)-3-{5-[(tert-butoxycarbonyl)amino]-3-[(1,4-dimethyl-1H-indol-3-yl)methyl]-2-oxo-2,3-dihydro-1H-benzimidazol-1-yl}hexanoic acid
3-{6-(benzylcarbamoyl)-3-[(4-methyl-1-benzothien-3-yl)methyl]-2-oxo-2,3-dihydro-1H-benzimidazol-1-yl}propanoic acid
3-{6-[(2-hydroxyethyl)carbamoyl]-3-[(4-methyl-1-benzothien-3-yl)methyl]-2-oxo-2,3-dihydro-1H-benzimidazol-1-yl}propanoic acid
3-[3-(5-chloro-2-methylbenzyl)-2-oxo-2,3-dihydro-1H-benzimidazol-1-yl]hexanoic acid
N-methyl-3-{3-[(4-methyl-1-benzothien-3-yl)methyl]-2-oxo-2,3-dihydro-1H-benzimidazol-1-yl}-N-(phenylsulfonyl)hexanamide
3-(6-{[2-(4-methoxyphenyl)ethyl]carbamoyl}-3-[(4-methyl-1-benzothien-3-yl)methyl]-2-oxo-2,3-dihydro-1H-benzimidazol-1-yl)propanoic acid
(2E)-3-[3-(1-naphthylmethyl)-2-oxo-2,3-dihydro-1H-benzimidazol-1-yl]acrylic acid
3-[6-{[2-(2-methoxyphenyl)ethyl]carbamoyl}-3-(1-naphthylmethyl)-2-oxo-2,3-dihydro-1H-benzimidazol-1-yl]propanoic acid
3-{6-[(3-hydroxypyrrolidin-1-yl)carbonyl]-3-(1-naphthylmethyl)-2-oxo-2,3-dihydro-1H-benzimidazol-1-yl}propanoic acid
3-{3-[(4-fluoro-1-naphthyl)methyl]-2-oxo-2,3-dihydro-1H-benzimidazol-1-yl}hexanoic acid
3-(6-{[2-(3-methoxyphenyl)ethyl]carbamoyl}-3-[(4-methyl-1-benzothien-3-yl)methyl]-2-oxo-2,3-dihydro-1H-benzimidazol-1-yl)propanoic acid
3-{3-[5-chloro-2-(trifluoromethyl)benzyl]-2-oxo-2,3-dihydro-1H-benzimidazol-1-yl}hexanoic acid
3-{3-[(4-chloro-1,2,3-trimethyl-1H-indol-7-yl)methyl]-2-oxo-2,3-dihydro-1H-benzimidazol-1-yl}propanoic acid
3-{3-(1-naphthylmethyl)-2-oxo-6-[(tetrahydrofuran-2-ylmethyl)carbamoyl]-2,3-dihydro-1H-benzimidazol-1-yl}propanoic acid
3-{6-[(2-hydroxyethyl)carbamoyl]-3-(1-naphthylmethyl)-2-oxo-2,3-dihydro-1H-benzimidazol-1-yl}propanoic acid
3-{[3-(1-naphthylmethyl)-2-oxo-2,3-dihydro-1H-benzimidazol-1-yl]methyl}benzoic acid
3-[6-{[2-(1,3-dioxolan-2-yl)ethyl]carbamoyl}-3-(1-naphthylmethyl)-2-oxo-2,3-dihydro-1H-benzimidazol-1-yl]propanoic acid
3-[6-{[2-(hydroxymethyl)piperidin-1-yl]carbonyl}-3-(1-naphthylmethyl)-2-oxo-2,3-dihydro-1H-benzimidazol-1-yl]propanoic acid
3-{5-anilino-3-[(1,4-dimethyl-1H-indol-3-yl)methyl]-2-oxo-2,3-dihydro-1H-benzimidazol-1-yl}hexanoic acid
3-{3-[(1-methyl-1H-indol-7-yl)methyl]-2-oxo-2,3-dihydro-1H-benzimidazol-1-yl}propanoic acid
3-[6-({3-[acetyl(methyl)amino]pyrrolidin-1-yl}carbonyl)-3-(1-naphthylmethyl)-2-oxo-2,3-dihydro-1H-benzimidazol-1-yl]propanoic acid
3-(6-{[2-(2-fluorophenyl)ethyl]carbamoyl}-3-[(4-methyl-1-benzothien-3-yl)methyl]-2-oxo-2,3-dihydro-1H-benzimidazol-1-yl)propanoic acid
3-[6-{[(2S)-2-carbamoylpyrrolidin-1-yl]carbonyl}-3-(1-naphthylmethyl)-2-oxo-2,3-dihydro-1H-benzimidazol-1-yl]propanoic acid
3-{6-[(3-carbamoylpiperidin-1-yl)carbonyl]-3-(1-naphthylmethyl)-2-oxo-2,3-dihydro-1H-benzimidazol-1-yl}propanoic acid
3-{3-[2-methyl-5-(trifluoromethyl)benzyl]-2-oxo-2,3-dihydro-1H-benzimidazol-1-yl}hexanoic acid
3-{3-[(1,3-dimethyl-1H-indol-7-yl)methyl]-2-oxo-2,3-dihydro-1H-benzimidazol-1-yl}propanoic acid
3-(6-{[2-(2-chlorophenyl)ethyl]carbamoyl}-3-[(4-methyl-1-benzothien-3-yl)methyl]-2-oxo-2,3-dihydro-1H-benzimidazol-1-yl)propanoic acid
3-{3-[(5-bromo-1-benzothien-3-yl)methyl]-2-oxo-2,3-dihydro-1H-benzimidazol-1-yl}hexanoic acid
3-{6-[(1,1-dioxidotetrahydro-3-thienyl)carbamoyl]-3-(1-naphthylmethyl)-2-oxo-2,3-dihydro-1H-benzimidazol-1-yl}propanoic acid
3-(6-{[2-(4-chlorophenyl)ethyl]carbamoyl}-3-[(4-methyl-1-benzothien-3-yl)methyl]-2-oxo-2,3-dihydro-1H-benzimidazol-1-yl)propanoic acid
3-[6-cyano-3-(1-naphthylmethyl)-2-oxo-2,3-dihydro-1H-benzimidazol-1-yl]propanoic acid
2-{3-[(4-methyl-1-benzothien-3-yl)methyl]-2-oxo-2,3-dihydro-1H-benzimidazol-1-yl}ethanesulfonamide
N-(methylsulfonyl)-3-[3-(1-naphthylmethyl)-2-oxo-2,3-dihydro-1H-benzimidazol-1-yl]propanamide
3-{3-[(1,2-dimethyl-1H-indol-7-yl)methyl]-2-oxo-2,3-dihydro-1H-benzimidazol-1-yl}propanoic acid
N-benzyl-3-{3-[(4-methyl-1-benzothien-3-yl)methyl]-2-oxo-2,3-dihydro-1H-benzimidazol-1-yl}hexanamide
3-{3-[(4-methyl-1-benzothien-3-yl)methyl]-2-oxo-6-[(2-phenylethyl)carbamoyl]-2,3-dihydro-1H-benzimidazol-1-yl}propanoic acid TABLE II-continued 3-{3-[(1-cyano-5-methylindolizin-3-yl)methyl]-2-oxo-2,3-dihydro-1H-benzimidazol-1-yl}propanoic acid
3-{3-[(5-chloro-1-benzothien-3-yl)methyl]-2-oxo-2,3-dihydro-1H-benzimidazol-1-yl}propanoic acid
3-{3-[(4-chloro-1,2,3-trimethyl-1H-indol-7-yl)methyl]-2-oxo-2,3-dihydro-1H-benzimidazol-1-yl}hexanoic acid
3-(6-{[2-(3-fluorophenyl)ethyl]carbamoyl}-3-[(4-methyl-1-benzothien-3-yl)methyl]-2-oxo-2,3-dihydro-1H-benzimidazol-1-yl)propanoic acid
3-{3-[(4-bromo-1H-indol-3-yl)methyl]-2-oxo-2,3-dihydro-1H-benzimidazol-1-yl}hexanoic acid
3-{3-[(6-bromo-1-methyl-1H-indol-4-yl)methyl]-2-oxo-2,3-dihydro-1H-benzimidazol-1-yl}propanoic acid
3-{3-[(6-hydroxy-1-naphthyl)methyl]-2-oxo-2,3-dihydro-1H-benzimidazol-1-yl}propanoic acid
3-{3-(1-naphthylmethyl)-2-oxo-6-[(2-oxotetrahydrofuran-3-yl)carbamoyl]-2,3-dihydro-1H-benzimidazol-1-yl}propanoic acid
3-(6-{[2-(3-chlorophenyl)ethyl]carbamoyl}-3-[(4-methyl-1-benzothien-3-yl)methyl]-2-oxo-2,3-dihydro-1H-benzimidazol-1-yl)propanoic acid
3-[3-(3,5-dibromobenzyl)-2-oxo-2,3-dihydro-1H-benzimidazol-1-yl]hexanoic acid
3-[3-(3,5-dichlorobenzyl)-2-oxo-2,3-dihydro-1H-benzimidazol-1-yl]hexanoic acid
3-[6-({(2S)-2-hydroxy-1-(hydroxymethyl)-2-[4-(methylthio)phenyl]ethyl}carbamoyl)-3-(1-naphthylmethyl)-2-oxo-2,3-dihydro-1H-benzimidazol-1-yl]propanoic acid
3-{3-[(5-chloro-2-oxo-2,3-dihydro-1,3-benzoxazol-7-yl)methyl]-2-oxo-2,3-dihydro-1H-benzimidazol-1-yl}hexanoic acid
2-({3-[2-bromo-5-(trifluoromethyl)benzyl]-2-oxo-2,3-dihydro-1H-benzimidazol-1-yl}methyl)pentanoic acid
3-{3-[2-bromo-5-(trifluoromethyl)benzyl]-2-oxo-2,3-dihydro-1H-benzimidazol-1-yl}hexanoic acid
3-[6-{[(2S)-2-(hydroxymethyl)pyrrolidin-1-yl]carbonyl}-3-(1-naphthylmethyl)-2-oxo-2,3-dihydro-1H-benzimidazol-1-yl]propanoic acid
3-[3-(1H-indol-3-ylmethyl)-2-oxo-2,3-dihydro-1H-benzimidazol-1-yl]propanoic acid
5-[3-(1-naphthylmethyl)-2-oxo-2,3-dihydro-1H-benzimidazol-1-yl]pentanoic acid
3-{3-[(4-chloro-1H-indol-3-yl)methyl]-2-oxo-2,3-dihydro-1H-benzimidazol-1-yl}propanoic acid
(R)-3-(4-Chloro-phenyl)-3-[3-(1,4-dimethyl-1H-indol-3-ylmethyl)-2-oxo-2,3-dihydro-benzimidazol-1-yl]-propionic acid
3-[3-(1,4-Dimethyl-1H-indol-3-ylmethyl)-2-oxo-2,3-dihydro-benzimidazol-1-yl]-2-hydroxymethyl-propionic acid
3-[2-Oxo-3-(1,4,6-trimethyl-1H-indol-3-ylmethyl)-2,3-dihydro-benzimidazol-1-yl]-2-pyridin-3-yl-propionic acid
(R)-3-[6-Cyano-2-oxo-3-(1,4,6-trimethyl-1H-indol-3-ylmethyl)-2,3-dihydro-benzimidazol-1-yl]-3-phenyl-propionic acid
(R)-3-[6-Carbamoyl-2-oxo-3-(1,4,6-trimethyl-1H-indol-3-ylmethyl)-2,3-dihydro-benzimidazol-1-yl]-3-phenyl-propionic acid
(R)-3-[6-Cyano-2-oxo-3-(1,4,6-trimethyl-1H-indol-3-ylmethyl)-2,3-dihydro-benzimidazol-1-yl]-3-(4-fluoro-phenyl)-propionic acid
(R)-3-[6-Cyano-2-oxo-3-(1,4,5-trimethyl-1H-indol-3-ylmethyl)-2,3-dihydro-benzimidazol-1-yl]-3-(4-fluoro-phenyl)-propionic acid or a pharmaceutically acceptable salt thereof.

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures, and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, $C_{1-4}$alkoxy includes the organic radical $C_{1-4}$alkyl with a terminal oxygen, such as methoxy, ethoxy, propoxy, butoxy.

All organic radicals: alkyl, alkenyl and alkynyl groups, or such groups which are incorporated in other radicals such as acyl and alkoxy, shall be understood as being branched or unbranched where structurally possible and unless otherwise specified, and may be partially or fully halogenated.

The term "lower" referred to above and hereinafter in connection with organic radicals or compounds respectively defines such as branched or unbranched with up to and including 7, preferably up to and including 4 and advantageously one or two carbon atoms.

A cyclic group shall be understood to mean carbocycle, heterocycle or heteroaryl, each may be partially or fully halogenated.

An acyl group is a radical defined as —C(O)—R, where R is an organic radical or a cyclic group. Acyl represents, for example, carbocyclic or heterocyclic aroyl, cycloalkylcarbonyl, (oxa or thia)-cycloalkylcarbonyl, lower alkanoyl, (lower alkoxy, hydroxy or acyloxy)-lower alkanoyl, (mono- or di-carbocyclic or heterocyclic)-(lower alkanoyl or lower alkoxy-, hydroxy- or acyloxy-substituted lower alkanoyl), or biaroyl.

Carbocycles include hydrocarbon rings containing from three to fourteen carbon atoms. These carbocycles may be either aromatic either aromatic or non-aromatic ring systems. The non-aromatic ring systems may be mono- or polyunsaturated, monocyclic, bicyclic or tricyclic and may be bridged. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, benzyl, indanyl, indenyl, benzocyclobutanyl, dihydronaphthyl, tetrahydronaphthyl, naphthyl, decahydronaphthyl, benzocycloheptanyl, adamantyl, norbornyl, fluorene, and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or non-aromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzopyrrolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, tetrazol-5-yl, 5-oxo-1,2,4-oxadiazol-3-yl, 5-oxo-1,2,4-thiadiazol-3-yl, 5-thioxo-1,2,4-oxadiazol-3-yl, 5-thioxo-1,2,4-thiadiazol-3-yl, 3-oxo-1,2,4-oxadiazol-5-yl, N3,5-dioxo-5-oxadiazolidino, 2-oxo1,3,4-oxadiazol-2-yl, 3-oxo1,2,4-triazol-5-yl, 2,dioxo-benzothiadiazin-6-yl, 1,2-dioxo-3-hydroxy-3-cyclobuten-4-yl, and imidazo[4,5-b]pyridinyl.

The term "heteroatom" as used herein shall be understood to mean atoms other than carbon such as oxygen, nitrogen, sulfur and phosphorous.

As used herein, "nitrogen" and "sulfur" include any oxidized form of nitrogen and sulfur and the quaternized form of any basic nitrogen. All heteroatoms in open chain or cyclic radicals include all oxidized forms.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative and/or is partially or fully halogenated. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1\text{-}C_4 \text{ alkyl})_4^+$ salts.

In addition, within the scope of the invention is use of prodrugs of compounds of the formula (1). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds described herein are either commercially available or can be made by methods and any necessary intermediates well known in the art.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

GENERAL SYNTHETIC METHODS

The invention also provides processes for making compounds of Formula (I). In all schemes, unless specified otherwise, $R_1$, $R_2$, $R_3$ and n in the formulas below shall have the meaning of $R_1$, $R_2$, $R_3$ and n in Formula (1) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the schemes below, are either commercially available or easily prepared from commercially available materials by those skilled in the art.

The compounds in this application may be synthesized according to schemes 1, 2 and 3 below:

provides a compound of formula (I). Alternatively, intermediate IV may be reacted with an alkene or alkyne, such as $CH_2CH_2C(O)-R_2$ or $CHC-C(O)-R_2$ a suitable solvent to provide a compound of formula (I)

Further modification of the initial product of formula (I) by methods known in the art and illustrated in the Examples below, may be used to prepare additional compounds of this invention

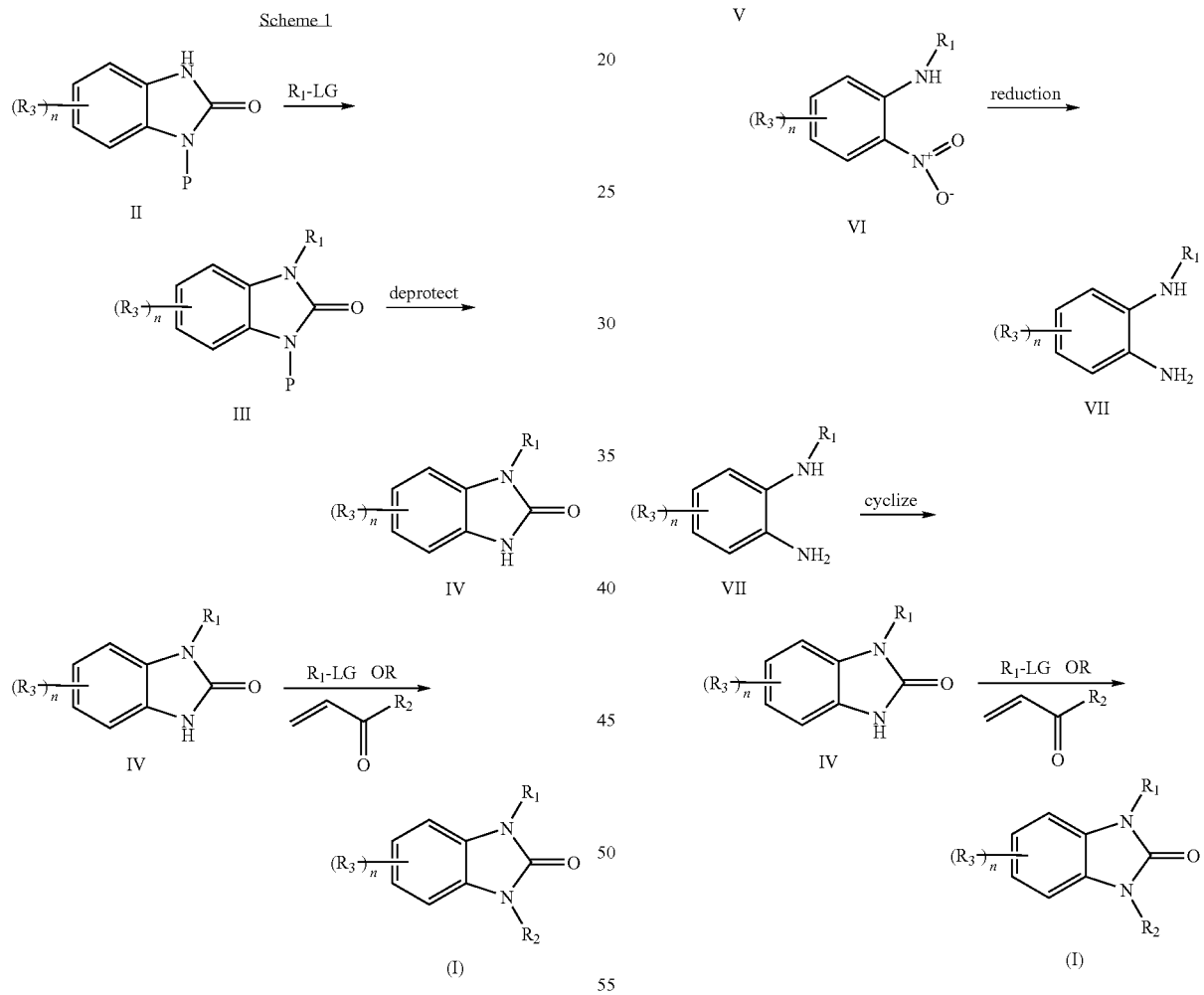

As illustrated in scheme 1, reacting an appropriately substituted benzimidazolone of formula II (wherein P is a protecting group) with an alkylating agent $R_1$-LG (wherein LG is a leaving group such as halogen, alkylammonium salt, tosylate, an activated alcohol) provides a N-alkylated benzimidazolone of formula III. Deprotection of the compound of formula III with a suitable reagent, in a suitable solvent, provides a compound of formula IV, N-alkylation of the compound of formula IV with a suitable alkylating agent such as $R_2$-LG (wherein LG is a leaving group such as halogen, alkylammonium salt, tosylate, an activated alcohol), in a suitable solvent As outlined in scheme 2, reacting an appropriately substituted starting material of formula V (wherein Hal is F, Cl, Br or I) with an amine $R_1NH_2$ in a suitable solvent provides a compound of formula VI. Reducing the compound of formula VI with a suitable reducing agent, in a suitable solvent, provides a diamine of formula VII. Cyclization of the diamine of formula VII with a reagent such as N,N'-carbonyldimidazole (CDI) provides a cyclized compound of formula IV. N-alkylation of the compound of formula IV with a suitable alkylating agent such as $R_2$-LG (wherein LG is a leaving group such as halogen, alkylammonium salt, tosylate, an activated alcohol), in a suitable solvent provides a compound of formula (I). Alternatively, intermediate IV may be reacted with an alkene or alkyne, such as $CH_2CH_2C(O)$—$R_2$ or CHC—C(O)—$R_2$, in a suitable solvent to provide a compound of formula (I)

Compounds of formula (I) may also be made using the method outlined in scheme 3.

Scheme 3

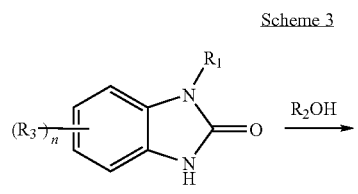

As shown in scheme 3, alkylation of a compound of formula (IV) with an alcohol $R_2OH$ under Mitsunobu reaction conditions gives a compound of formula (I).

Further modification of the initial product of formula (I) by methods known in the art and illustrated in the Examples below, may be used to prepare additional compounds of this invention The experimental procedures described below are included as examples.

Example 1

3-{3-[(5-chloro-1-benzothien-3-yl)methyl]-2-oxo-2,3-dihydro-1H-benzimidazol-1-yl}propanoic acid

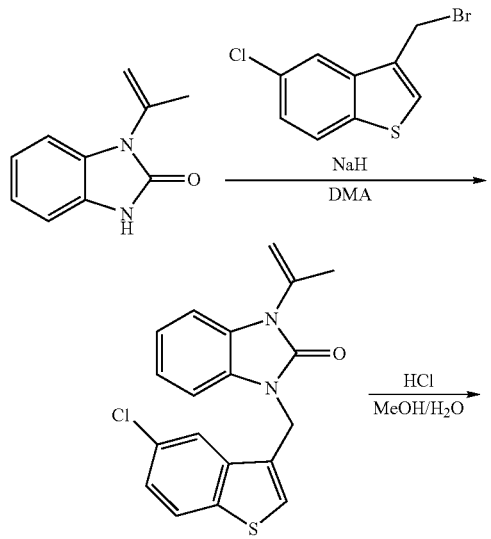

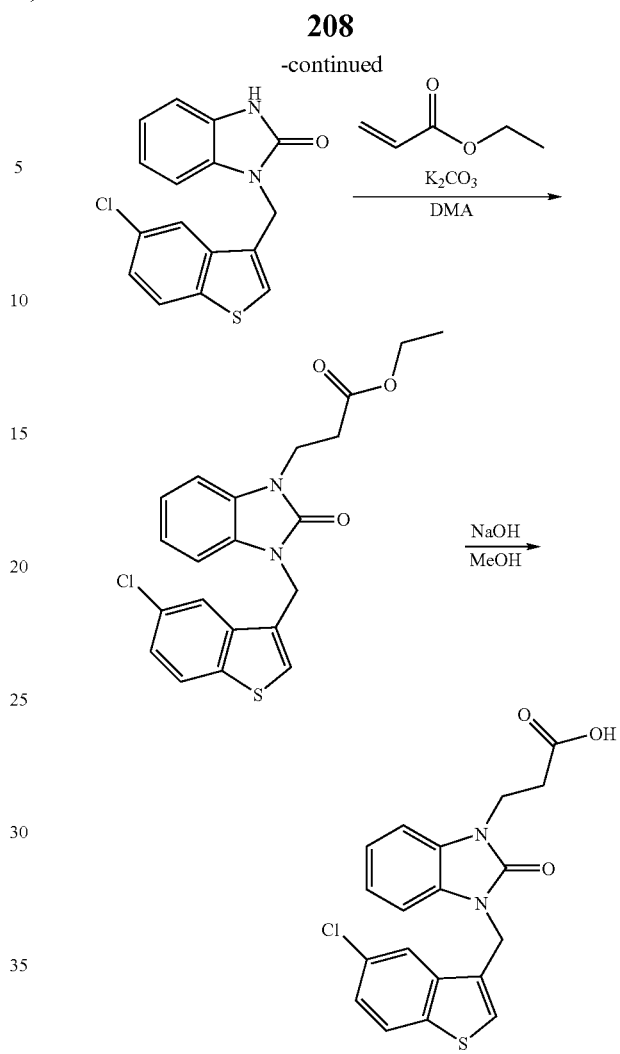

1-(5-Chloro-benzo[b]thiophen-3-ylmethyl)-3-isopropenyl-1,3-dihydro-benzimidazol-2-one To a solution of 1-isopropenylbenzimidazolone (0.3 g, 1.72 mmol) in DMF (5 mL) was added 60% NaH (0.1 g, 2.6 mmol). The reaction mixture was stirred at room temperature for 15 min and added 3-(Bromomethyl)-5-chlorobenzo[b]thiophene (0.54 g, 2.07 mmol). The reaction mixture was heated to 65° C. and stirred at that temperature for 2 h. When the reaction was complete, the mixture was treated with water. The mixture was then diluted with ethyl acetate and washed with water (×4). The organic phase was dried over $Na_2SO_4$ and concentrated. The resulting residue was purified by silica gel prep TLC to afford 0.53 g (87%) of the desired product.

1-(5-Chloro-benzo[b]thiophen-3-ylmethyl)-1,3-dihydro-benzimidazol-2-one 1-(5-Chloro-benzo[b]thiophen-3-ylmethyl)-3-isopropenyl-1,3-dihydro-benzimidazol-2-one (0.53 g, 1.56 mmol) was treated with MeOH (5 mL) followed by water (5 mL). To this heterogeneous reaction mixture was added 37% hydrochloric acid (4 mL). This heterogeneous reaction mixture was heated to 80° C. for 30 min. A white solid was precipitated out. TLC indicated that reaction was complete (starting material Rf 0.8, product Rf 0.4, CH₂Cl₂:MeOH 95:5). The reaction mixture was diluted with CH₂Cl₂ (at this point a white precipitate was completely soluble in CH₂Cl₂) and washed with water. The organic phase was dried over Na₂SO₄ and concentrated to afford 0.44 g (89%) of the desired product as a white solid. This product was used for the next reaction without further purification. LCMS (ESMS): m/z 315.79 (M+H⁺).

3-[3-(5-Chloro-benzo[b]thiophen-3-ylmethyl)-2-oxo-2,3-dihydro-benzimidazol-1-yl]-propionic acid ethyl ester To a solution of 1-(5-Chloro-benzo[b]thiophen-3-ylmethyl)-1,3-dihydro-benzimidazol-2-one (50 mg, 0.16 mmol) in DMF (2 mL) were added ethyl acrylate (0.02 mL) and benzyltrimethyl ammonium hydroxide (20 mg, 0.01 mmol). The resulting mixture was stirred at room temperature overnight. When the reaction was complete, the reaction mixture was diluted with ethyl acetate and washed with water (×4). The organic phase was dried over Na₂SO₄ and concentrated. The resulting residue was purified by silica gel prep TLC using 95:5 CH₂Cl₂:MeOH as an eluent to afford 50 mg of the desired product as a colorless oil. LCMS (ESMS): m/z 415.78 (M+H⁺).

3-{3-[(5-chloro-1-benzothien-3-yl)methyl]-2-oxo-2,3-dihydro-1H-benzimidazol-1-yl}propanoic acid A solution of 3-[3-(5-Chloro-benzo[b]thiophen-3-ylmethyl)-2-oxo-2,3-dihydro-benzimidazol-1-yl]-propionic acid ethyl ester (50 mg, 0.12 mmol) in MeOH (3 mL) was added 2N NaOH (1 mL). The reaction mixture was stirred at room temperature for 1 h. The solution was then treated with 1M HCl solution until pH ~4 and extracted with CH₂Cl₂. The organic phase was dried over Na₂SO₄ and concentrated. The resulting residue was purified by silica gel prep TLC using 95:5 CH₂Cl₂:MeOH as an eluent to afford 20 mg (42%) of the desired product as a white solid. LCMS (ESMS): m/z 387.89 (M+H⁺).

Following compounds were synthesized using a similar procedure.

3-[3-(1-naphthylmethyl)-2-oxo-2,3-dihydro-1H-benzimidazol-1-yl]pentanoic acid. LCMS (ESMS): m/z 375.07 (M+H⁺)

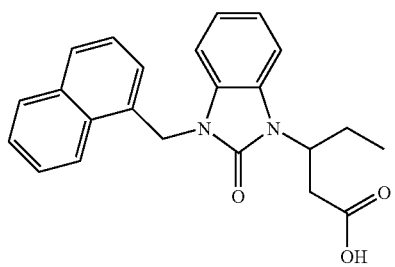 [SMILES: CCC(CC(=O)O)n1c(=O)n(Cc2cccc3ccccc23)c2ccccc21]

4-methyl-3-[3-(1-naphthylmethyl)-2-oxo-2,3-dihydro-1H-benzimidazol-1-yl]pentanoic acid. LCMS (ESMS): m/z 389.66 (M+H⁺)

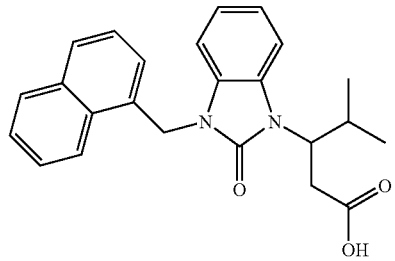 [SMILES: CC(C)C(CC(=O)O)n1c(=O)n(Cc2cccc3ccccc23)c2ccccc21]

5-methyl-3-[3-(1-naphthylmethyl)-2-oxo-2,3-dihydro-1H-benzimidazol-1-yl]hexanoic acid. LCMS (ESMS): m/z 403.64 (M+H⁺)

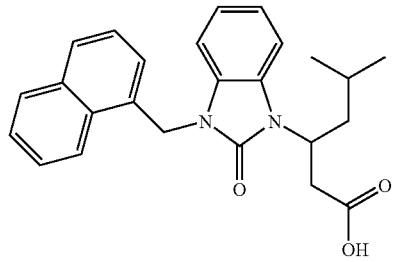 [SMILES: CC(C)CC(CC(=O)O)n1c(=O)n(Cc2cccc3ccccc23)c2ccccc21]

3-[3-(1-naphthylmethyl)-2-oxo-2,3-dihydro-1H-benzimidazol-1-yl]hexanoic acid. LCMS (ESMS): m/z 389.05 (M+H⁺)

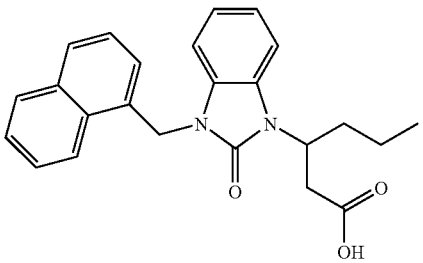 [SMILES: CCCC(CC(=O)O)n1c(=O)n(Cc2cccc3ccccc23)c2ccccc21]

3-ethoxy-3-[3-(1-naphthylmethyl)-2-oxo-2,3-dihydro-1H-benzimidazol-1-yl]propanoic acid. LCMS (ESMS): m/z 391.35 (M+H⁺)

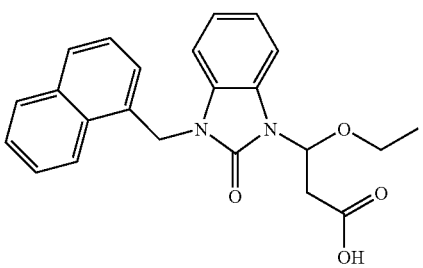 [SMILES: CCOC(CC(=O)O)n1c(=O)n(Cc2cccc3ccccc23)c2ccccc21]

211

3-[3-(3,5-dibromobenzyl)-2-oxo-2,3-dihydro-1H-benzimidazol-1-yl]hexanoic acid. LCMS (ESMS): m/z 497.06 (M+H⁺)

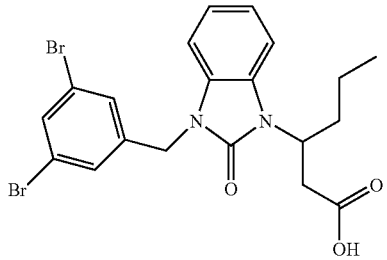 [SMILES: CCCC(CC(=O)O)n1c(=O)n(Cc2cc(Br)cc(Br)c2)c2ccccc21]

Example 2

3-{3-[(4-methyl-1-benzothien-3-yl)methyl]-2-oxo-2,3-dihydro-1H-benzimidazol-1-yl}propanoic acid

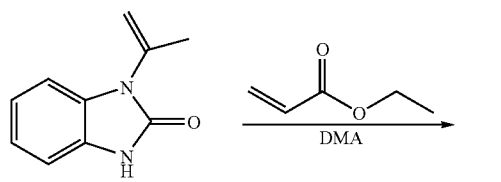

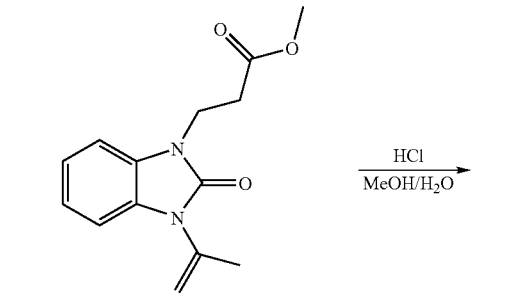

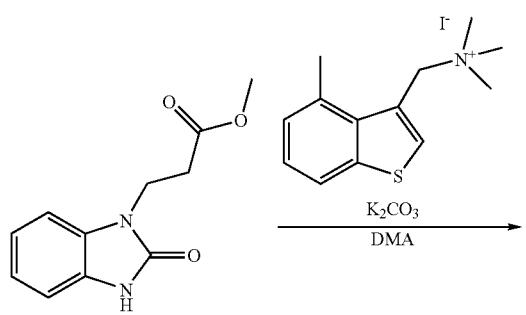

-continued

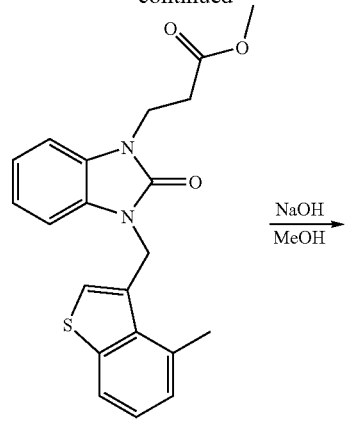

3-(3-Isopropenyl-2-oxo-2,3-dihydro-benzimidazol-1-yl)-propionic acid ethyl ester To a solution of 1-Isopropenyl-2-benzimidazolidinone (2.5 g, 14.4 mmol) in DMF (10 mL) were added ethyl acrylate (1.7 mL, 15.8 mmol) and benzyltrimethyl ammonium hydroxide in MeOH (1.4 g, 8.6 mmol). The resulting mixture was stirred at room temperature for 1.5 h. When the reaction was complete, the reaction mixture was diluted with ethyl acetate and washed with water (×4). The organic phase was dried over Na₂SO₄ and concentrated. The resulting residue was purified by silica gel prep TLC using 1:1 Hexanes:Ethyl acetate as an eluent to afford 3.0 g (76%) of the desired product along with methyl ester. Since the methyl ester was the major product, this product was used for the next reaction.

3-(2-Oxo-2,3-dihydro-benzimidazol-1-yl)-propionic acid methyl ester 3-(3-Isopropenyl-2-oxo-2,3-dihydro-benzimidazol-1-yl)-propionic acid methyl ester (2.2 g, 8.3 mmol) was treated with MeOH (5 mL) followed by water (5 mL) To this heterogeneous reaction mixture was added 37% hydrochloric acid (4 mL). This reaction mixture was heated to 60° C. for 20 min. The reaction remained as a clear homogeneous solution after heating. The reaction mixture was diluted with CH₂Cl₂ and washed with water. The organic phase was dried over Na₂SO₄ and concentrated to afford 1.7 g of the desired product as a white solid. This product was used for the next reaction without further purification.

3-(4-Methyl-benzo[b]thiophen-3-ylmethyl)-2-oxo-2,3-dihydro-benzimidazol-1-yl]propionic acid methyl ester To a solution of 3-(2-Oxo-2,3-dihydro-benzimidazol-1-yl)-propionic acid methyl ester (0.1 g, 0.45 mmol) in DMA (2 mL) were added $K_2CO_3$ (0.1 g, 0.68 mmol) and trimethyl-(4-methyl-benzo[b]thiophen-3-ylmethyl)-ammonium; iodide (0.17 g, 0.50 mmol). The reaction mixture was heated to 150° C. for 15 min in the microwave. When the reaction was complete, the mixture was diluted with ethyl acetate and washed with water (×4). The organic phase was dried over $Na_2SO_4$ and concentrated. The resulting oily residue was purified by silica gel prep TLC using 98:2 $CH_2Cl_2$:MeOH as an eluent to afford 0.1 g of the desired product. LCMS (ESMS): m/z 381.21 (M+H$^+$).

3-{3-[(4-methyl-1-benzothien-3-yl)methyl]-2-oxo-2,3-dihydro-1H-benzimidazol-1-yl}propanoic acid To a solution of 3-(4-Methyl-benzo[b]thiophen-3-ylmethyl)-2-oxo-2,3-dihydro-benzimidazol-1-yl]-propionic acid methyl ester (0.1 g, 0.26 mmol) in MeOH (2 mL) was added 2 N NaOH (2 mL). The reaction mixture was stirred at room temperature for 2 h. The solution was then treated with 1M HCl until pH ~2 and extracted with $CH_2Cl_2$ (×2). The organic phase was dried over $Na_2SO_4$ and concentrated. The resulting residue was purified by silica gel prep TLC using 95:5 $CH_2Cl_2$:MeOH as an eluent to afford 48 mg of the title compound as an off-white solid. LCMS (ESMS): m/z 367.20 (M+H$^+$).

The following compounds were synthesized by a similar procedure.

3-{3-[(1,4-dimethyl-1H-indol-3-yl)methyl]-2-oxo-2,3-dihydro-1H-benzimidazol-1-yl}propanoic acid. LCMS (ESMS): m/z 367.20 (M+H$^+$)

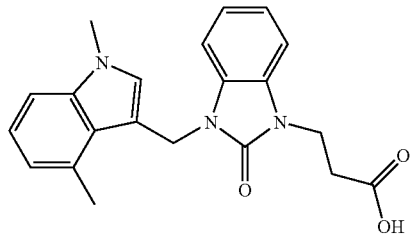 [SMILES: Cc1cccc2c1c(Cn1c(=O)n(CCC(=O)O)c3ccccc31)cn2C]

3-[3-(1-benzothien-3-ylmethyl)-2-oxo-2,3-dihydro-1H-benzimidazol-1-yl]propanoic acid. LCMS (ESMS): m/z 353.08 (M+H$^+$)

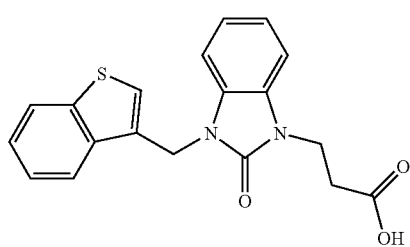 [SMILES: O=C(O)CCn1c(=O)n(Cc2csc3ccccc23)c2ccccc21]

2-({3-[(1,4-dimethyl-1H-indol-3-yl)methyl]-2-oxo-2,3-dihydro-1H-benzimidazol-1-yl}methyl)pentanoic acid. LCMS (ESMS): m/z 406.27 (M+H$^+$)

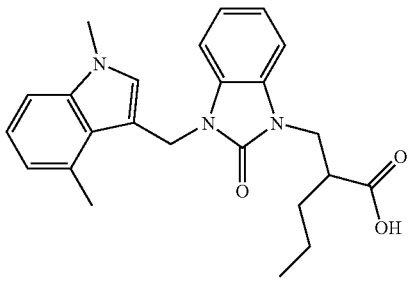 [SMILES: CCCC(Cn1c(=O)n(Cc2cn(C)c3cccc(C)c23)c2ccccc21)C(=O)O]

2-({3-[(1,4-dimethyl-1H-indol-3-yl)methyl]-2-oxo-2,3-dihydro-1H-benzimidazol-1-yl}methyl)butanoic acid. LCMS (ESMS): m/z 392.02 (M+H$^+$)

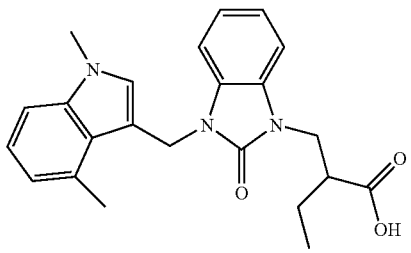 [SMILES: CCC(Cn1c(=O)n(Cc2cn(C)c3cccc(C)c23)c2ccccc21)C(=O)O]

3-{3-[(1,4-dimethyl-1H-indol-3-yl)methyl]-2-oxo-2,3-dihydro-1H-benzimidazol-1-yl)-2-methylpropanoic acid. LCMS (ESMS): m/z 378.23 (M+H$^+$)

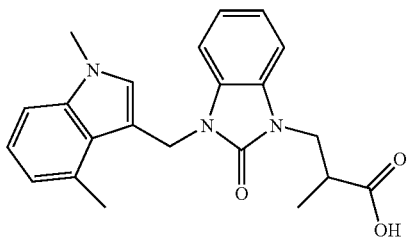 [SMILES: Cc1cccc2c1c(Cn1c(=O)n(CC(C)C(=O)O)c3ccccc31)cn2C]

2-({3-[(4,6-dimethyl-1,2-benzisothiazol-3-yl)methyl]-2-oxo-2,3-dihydro-1H-benzimidazol-1-yl}methyl)pentanoic acid. LCMS (ESMS): m/z 424.18 (M+H$^+$)

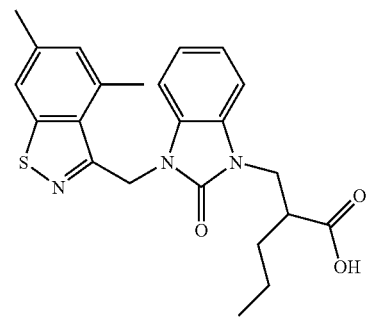 [SMILES: CCCC(Cn1c(=O)n(Cc2nsc3cc(C)cc(C)c23)c2ccccc21)C(=O)O]

Example 3

3-{3-[(4-methyl-1-benzothien-3-yl)methyl]-2-oxo-2,3-dihydro-1H-benzimidazol-1-yl}hexanoic acid

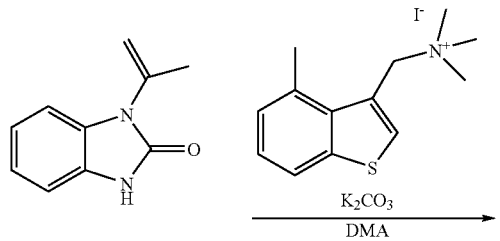

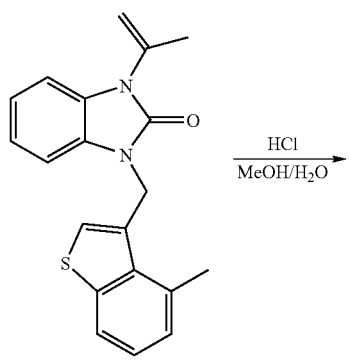

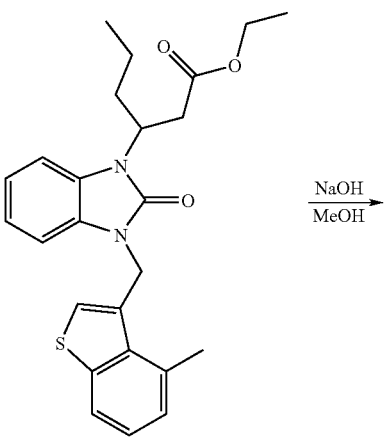

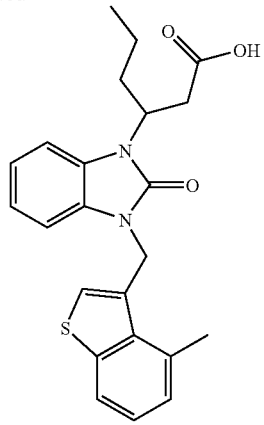 [SMILES: CCCC(CC(=O)O)n1c(=O)n(Cc2csc3cccc(C)c23)c2ccccc21]

1-Isopropenyl-3-(4-methyl-benzo[b]thiophen-3-ylmethyl)-1,3-dihydro-benzimidazol-2-one 1-isopropenylbenzimidazolone (0.5 g, 2.9 mmol) in DMA (8 mL) was added and trimethyl-(4-methyl-benzo[b]thiophen-3-ylmethyl)-ammonium; iodide (1.0 g, 2.9 mmol) and $K_2CO_3$ (0.80 g, 5.74 mmol). The reaction mixture was heated to 120° C. for 15 min in a microwave and then 150° C. for another 5 min. The mixture was diluted with ethyl acetate and washed with water (×4). The organic phase was dried over $Na_2SO_4$ and concentrated. The resulting residue was purified by silica gel prep TLC using 98:2 $CH_2Cl_2$:MeOH as an eluent to afford 0.7 g of the desired product as a white solid

1-(4-Methyl-benzo[b]thiophen-3-ylmethyl)-1,3-dihydro-benzimidazol-2-one

1-Isopropenyl-3-(4-methyl-benzo[b]thiophen-3-ylmethyl)-1,3-dihydro-benzimidazol-2-one (0.70 g, 2.1 mmol) was treated with MeOH (10 mL) followed by water (10 mL). To this heterogeneous reaction mixture was added 37% hydrochloric acid (5 mL). This reaction mixture was heated to 65° C. for 3 h. The reaction mixture maintained as a heterogeneous mixture with white precipitates. The reaction mixture was extracted with $CH_2Cl_2$ (×2). The combined organic phase was washed with water. The organic phase was dried over $Na_2SO_4$ and concentrated to afford 0.7 g of the desired product as a white scaly solid.

3-[3-(4-Methyl-benzo[b]thiophen-3-ylmethyl)-2-oxo-2,3-dihydro-benzimidazol-1-yl]-hexanoic acid ethyl ester To a solution of 1-(4-Methyl-benzo[b]thiophen-3-ylmethyl)-1,3-dihydro-benzimidazol-2-one (0.2 g, 0.68 mmol) in DMA (5 mL) were added ethyl trans-2-hexanoate (0.19 g, 1.4 mmol) and benzyltrimethyl ammonium hydroxide in MeOH (0.43 g, 1.0 mmol) (Benzyltrimethyl ammonium hydroxide in MeOH can be replaced with $K_2CO_3$ (2eq) as a base). The reaction mixture was heated to 60° C. for 20 h. The reaction mixture was diluted with ethyl acetate and washed with water (×4). The organic phase was dried over $Na_2SO_4$ and concentrated. The resulting residue was attempted to dissolve in a mixture of $CH_2Cl_2$ and MeOH to load to a prep TLC. However, some insoluble material was present. This insoluble solid was filtered, however, the structure of the filtered solid couldn't be characterized (no aliphatic region in NMR). The filtrate was concentrated and resulting residue was purified by silica gel prep TLC using 98:2 CH$_2$Cl$_2$:MeOH as an eluent to afford 0.2 g of the desired product (with methyl ester instead of ethyl ester) as an oil. LCMS (ESMS): m/z 423.46 (M+H$^+$).

3-{3-[(4-methyl-1-benzothien-3-yl)methyl]-2-oxo-2,3-dihydro-1H-benzimidazol-1-yl}hexanoic acid To a solution of the ester (0.1 g, 0.23 mmol) in MeOH (5 mL) was added 2N NaOH (3 mL). The reaction mixture was stirred at room temperature for 2 h. When all the starting material was consumed, the reaction mixture was acidified with 1N HCl. The reaction mixture was extracted with CH$_2$Cl$_2$ (×2). The combined organic phase was dried over Na$_2$SO$_4$ and concentrated. The resulting residue was purified by silica gel prep TLC using 95:5 CH$_2$Cl$_2$:MeOH as an eluent to afford 66 mg of the title compound as an off-white powder. LCMS (ESMS): m/z 409.18 (M+H$^+$).

Two enantiomers of 3-[3-(4-Methyl-benzo[b]thiophen-3-ylmethyl)-2-oxo-2,3-dihydro-benzimidazol-1-yl]-hexanoic acid ethyl ester were separated by chiral column chromatography (85:15 Hexanes:iPA, 8.5 mL/min, AD-H column) to afford (R) and (S) enantiomers. These (R) and (S) esters were hydrolyzed using 2N NaOH in MeOH to afford (R) and (S) acids.

(3S)-3-{3-[(4-methyl-1-benzothien-3-yl)methyl]-2-oxo-2,3-dihydro-1H-benzimidazol-1-yl}hexanoic acid. LCMS (ESMS): m/z 409.59(M+H$^+$)

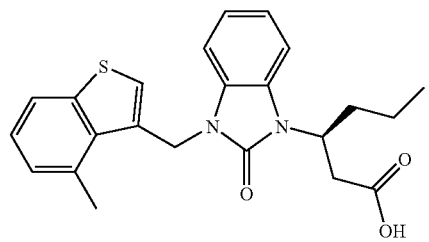 [SMILES: CCC[C@@H](CC(=O)O)n1c(=O)n(Cc2csc3cccc(C)c23)c2ccccc21]

(3R)-3-{3-[(4-methyl-1-benzothien-3-yl)methyl]-2-oxo-2,3-dihydro-1H-benzimidazol-1-yl}hexanoic acid. LCMS (ESMS): m/z 409.24 (M+H$^+$)

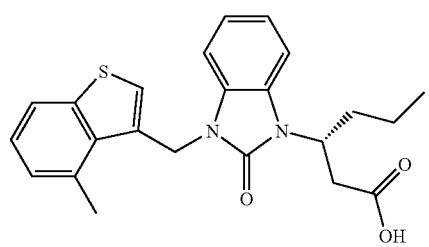 [SMILES: CCC[C@H](CC(=O)O)n1c(=O)n(Cc2csc3cccc(C)c23)c2ccccc21]

The following compounds were synthesized using a similar procedure.

3-{3-[(4-methyl-1-benzothien-3-yl)methyl]-2-oxo-2,3-dihydro-1H-benzimidazol-1-yl}butanoic acid.
LCMS (ESMS): m/z 381.15 (M+H$^+$)

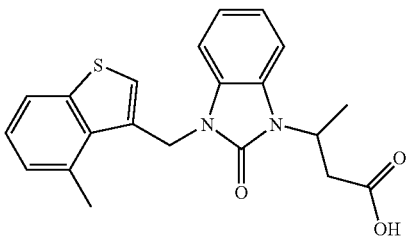 [SMILES: Cc1cccc2scc(Cn3c(=O)n(C(C)CC(=O)O)c4ccccc43)c12]

3-{3-[(4-methyl-1-benzothien-3-yl)methyl]-2-oxo-2,3-dihydro-1H-benzimidazol-1yl}pentanoic acid.
LCMS (ESMS): m/z 395.10 (M+H$^+$)

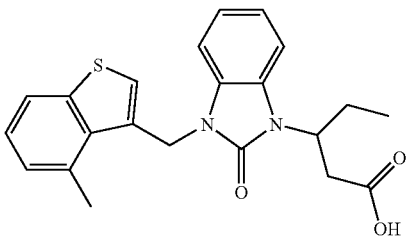 [SMILES: CCC(CC(=O)O)n1c(=O)n(Cc2csc3cccc(C)c23)c2ccccc21]

3-{3-[(4-methyl-1-benzothien-3-yl)methyl]-2-oxo-2,3-dihydro-1H-benzimidazol-1-yl}octanoic acid.
LCMS (ESMS): m/z 437.33 (M+H$^+$)

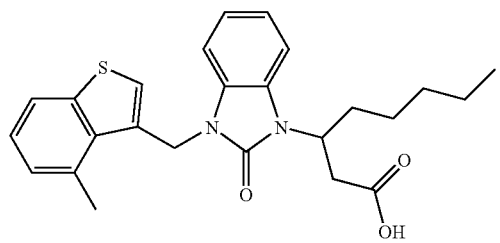 [SMILES: CCCCCC(CC(=O)O)n1c(=O)n(Cc2csc3cccc(C)c23)c2ccccc21]

3-{3-[(4-methyl-1-benzothien-3-yl)methyl]-2-oxo-2,3-dihydro-1H-benzimidazol-1-yl}heptanoic acid.
LCMS (ESMS): m/z 423.43 (M+H$^+$)

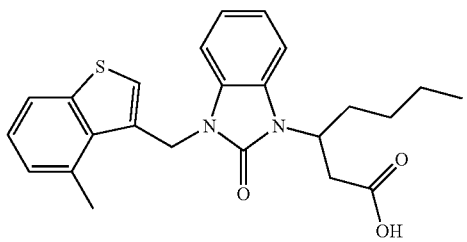 [SMILES: CCCCC(CC(=O)O)n1c(=O)n(Cc2csc3cccc(C)c23)c2ccccc21]

3-ethoxy-3-{3-[(4-methyl-1-benzothien-3-yl)methyl]-2-oxo-2,3-dihydro-1H-benzimidazol-1-yl}propanoic acid. LCMS (ESMS): m/z 411.40 (M+H$^+$)

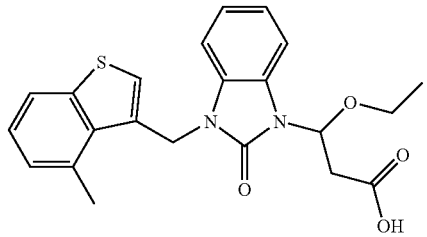 [SMILES: CCOC(CC(=O)O)n1c(=O)n(Cc2csc3cccc(C)c23)c2ccccc21]

5-methyl-3-{3-[(4-methyl-1-benzothien-3-yl)methyl]-2-oxo-2,3-dihydro-1H-benzimidazol-1-yl}hexanoic acid. LCMS (ESMS): m/z 423.70 (M+H$^+$)

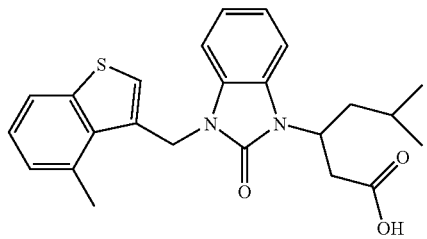 [SMILES: Cc1cccc2scc(Cn3c(=O)n(C(CC(=O)O)CC(C)C)c4ccccc43)c12]

3-{3-[(1,4-dimethyl-1H-indol-3-yl)methyl]-2-oxo-2,3-dihydro-1H-benzimidazol-1-yl}hexanoic acid. LCMS (ESMS): m/z 406.48 (M+H$^+$)

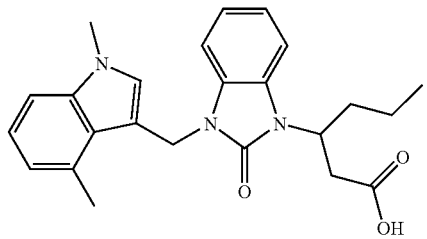 [SMILES: CCCC(CC(=O)O)n1c(=O)n(Cc2cn(C)c3cccc(C)c23)c2ccccc21]

3-{3-[(1,4-dimethyl-1H-indol-3-yl)methyl]-2-oxo-2,3-dihydro-1H-benzimidazol-1-yl}-3-ethoxypropanoic acid. LCMS (ESMS): m/z 408.49 (M+H$^+$)

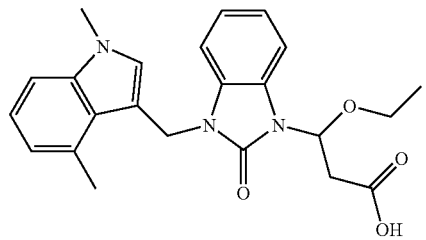 [SMILES: CCOC(CC(=O)O)n1c(=O)n(Cc2cn(C)c3cccc(C)c23)c2ccccc21]

3-{3-[(4-methyl-1-benzothien-3-yl)methyl]-2-oxo-2,3-dihydro-1H-benzimidazol-1-yl}octanoic acid. LCMS (ESMS): m/z 437.33 (M+H$^+$)

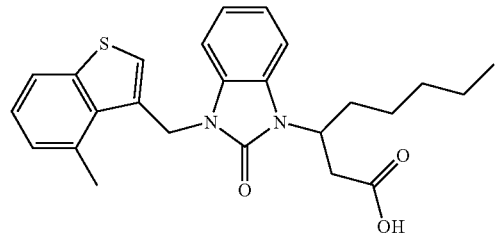 [SMILES: CCCCCC(CC(=O)O)n1c(=O)n(Cc2csc3cccc(C)c23)c2ccccc21]

3-{2-oxo-3-[(1,4,6-trimethyl-1H-indol-3-yl)methyl]-2,3-dihydro-1H-benzimidazol-1-yl}hexanoic acid. LCMS (ESMS): m/z 420.28 (M+H$^+$)

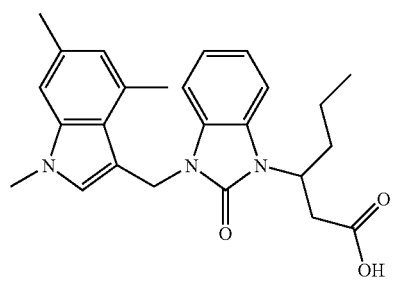 [SMILES: CCCC(CC(=O)O)n1c(=O)n(Cc2cn(C)c3cc(C)cc(C)c23)c2ccccc21]

Example 4

3-methoxy-3-[3-(1-naphthylmethyl)-2-oxo-2,3-dihydro-1H-benzimidazol-1-yl]propanoic acid

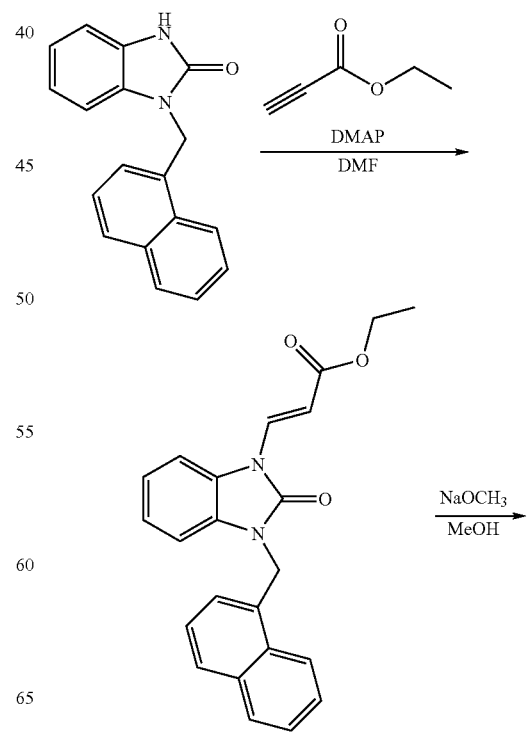

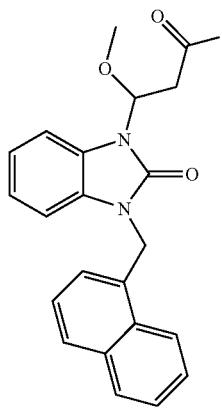

(E)-3-(3-Naphthalen-1-ylmethyl-2-oxo-2,3-dihydro-benzimidazol-1-yl)-acrylic acid ethyl ester To a solution of 1-Naphthalen-1-ylmethyl-1,3-dihydro-benzimidazol-2-one (0.5 g, 1.8 mmol) in DMF (4 mL) were added ethyl propiolate (0.28 mL, 2.7 mmol) and DMAP (0.22 mL), 1.8 mmol). The reaction mixture was stirred at room temperature for 10 min. The reaction mixture turned dark brown in color. The reaction mixture was diluted with ethyl acetate and washed with water (×4). The organic phase was dried over $Na_2SO_4$ and concentrated to afford 0.68 g of the desired product as a dark brown foam. This crude product was used for the next reaction without further purification. LCMS (ESMS): m/z 373.33 (M+H$^+$).

3-methoxy-3-[3-(1-naphthylmethyl)-2-oxo-2,3-dihydro-1H-benzimidazol-1-yl]propanoic acid To a solution of (E)-3-(3-Naphthalen-1-ylmethyl-2-oxo-2,3-dihydro-benzimidazol-1-yl)-acrylic acid ethyl ester (0.1 g, 0.27 mmol) in DMF (1 mL) was added $NaOCH_3$ (1.1 mL, 0.5 M in MeOH). The reaction mixture was stirred at 60° C. for 2 h (due to poor solubility, the reaction was heated). The reaction mixture was concentrated. The reaction mixture was diluted with 1N HCl and then extracted with $CH_2Cl_2$. The organic phase was dried over $Na_2SO_4$ and concentrated. Since LCMS indicated that there was a small amount of the product in methyl ester form, the resulting residue was diluted with methanol and treated with 2N NaOH for 30 min. The mixture was acidified by adding 1N HCl and extracted with $CH_2Cl_2$. The organic phase was dried over $Na_2SO_4$ and concentrated. The resulting residue was purified by silica gel prep TLC using 95:5 $CH_2Cl_2$:MeOH as an eluent to afford 39 mg of the title compound as an off-white solid. LCMS (ESMS): m/z 377.31 (M+H$^+$).

Example 5

(2E)-3-[3-(1-naphthylmethyl)-2-oxo-2,3-dihydro-1H-benzimidazol-1-yl]acrylic acid

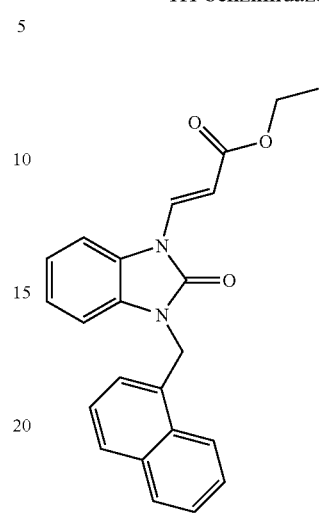

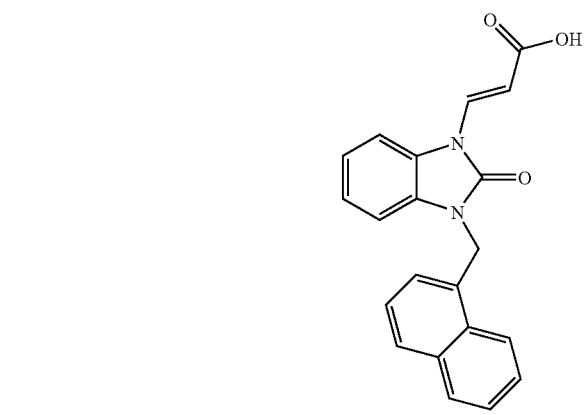

To a solution of (E)-3-(3-Naphthalen-1-ylmethyl-2-oxo-2,3-dihydro-benzimidazol-1-yl)-acrylic acid ethyl ester (0.1 g, 0.30 mmol) in MeOH (10 mL) was added 2N NaOH (5 mL). The reaction mixture was stirred at room temperature for 3 h. Since the mixture was heterogeneous, the mixture was heated to 60° C. for 2 h. The reaction mixture was then treated with 1N HCl and extracted with $CH_2Cl_2$. The organic phase was dried over $Na_2SO_4$ and concentrated. The resulting residue was purified by silica gel prep TLC using 10:1 $CH_2Cl_2$:MeOH as an eluent to afford 30 mg of the title compound as an off-white solid. LCMS (ESMS): m/z 345.12 (M+H$^+$).

Example 6

3-{[3-(1-naphthylmethyl)-2-oxo-2,3-dihydro-1H-benzimidazol-1-yl]methyl}benzoic acid

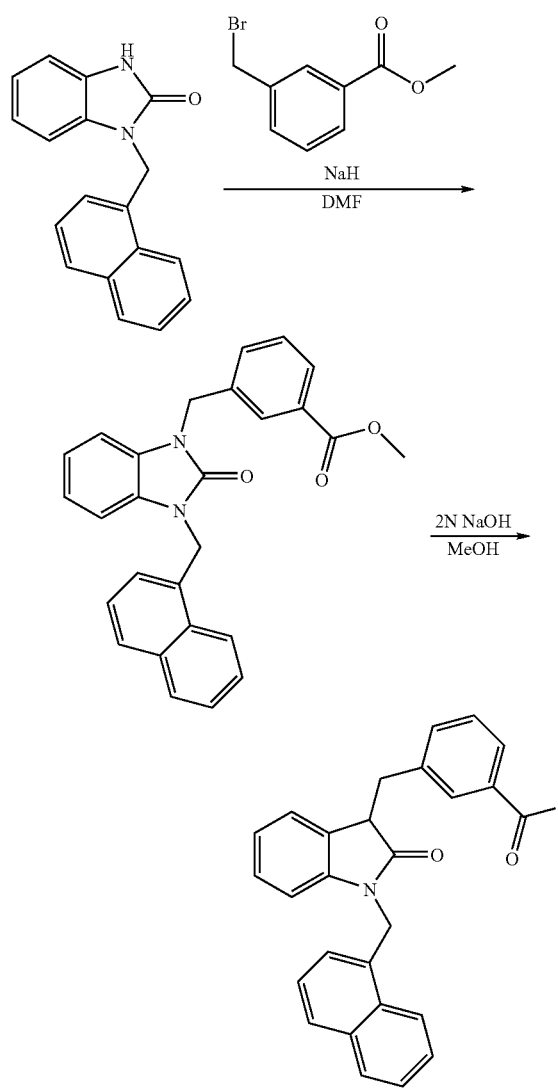

3-(3-Naphthalen-1-ylmethyl-2-oxo-2,3-dihydro-benzimidazol-1-ylmethyl)-benzoic acid methyl ester To a solution of 1-Naphthalen-1-ylmethyl-1,3-dihydro-benzimidazol-2-one (0.1 g, 0.37 mmol) in DMF (3 mL) was added 60% NaH (22 mg, 0.55 mmol). The reaction mixture was stirred at room temperature for 10 min and then Methyl 3-(bromomethyl)benzoate (0.1 g, 0.44 mmol) was added to the reaction mixture. The reaction mixture was stirred at room temperature for 2 h. When the reaction was complete, the mixture was diluted with ethyl acetate and washed with water (×4). The organic phase was then dried over $Na_2SO_4$ and concentrated. The resulting residue was purified by silica gel prep TLC using 100% $CH_2Cl_2$ as an elunet to afford 0.14 g of the desired product as a white foam. LCMS (ESMS): m/z 423.84 (M+H$^+$).

3-{[3-(1-naphthylmethyl)-2-oxo-2,3-dihydro-1H-benzimidazol-1-yl]methyl}benzoic acid To a solution of the ester (0.14 g, 0.34 mmol) in MeOH (3 mL), 2N NaOH (2 mL) was added. The reaction mixture was stirred at room temperature for 1 h until all the starting material was consumed. The mixture was then acidified by adding 1M HCl and extracted with $CH_2Cl_2$ (×2). The organic phase was dried over $Na_2SO_4$ and concentrated. The resulting white solid was not soluble in $CH_2Cl_2$. This white solid was therefore filtered to afford 0.1 g of the title compound. LCMS (ESMS): m/z 407.70 (M–H$^+$).

The following compounds were synthesized using a similar procedure.

5-[3-(1-naphthylmethyl)-2-oxo-2,3-dihydro-1H-benzimidazol-1-yl]pentanoic acid. LCMS (ESMS): m/z 375.84 (M+H$^+$)

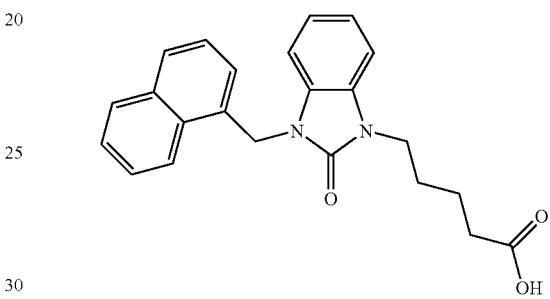

4-{3-[(5-chloro-1-benzothien-3-yl)methyl]-2-oxo-2,3-dihydro-1H-benzimidazol-1-yl}butanoic acid. LCMS (ESMS): m/z 401.75 (M+H$^+$)

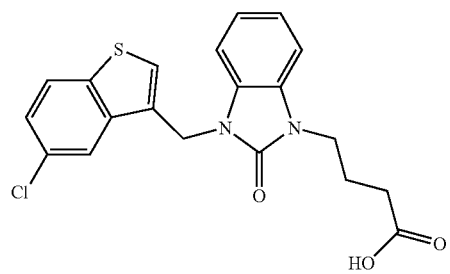 [SMILES: O=C(O)CCCn1c(=O)n(Cc2csc3ccc(Cl)cc23)c2ccccc21]

3-({3-[(4-methyl-1-benzothien-3-yl)methyl]-2-oxo-2,3-dihydro-1H-benzimidazol-1-yl}methyl)benzoic acid. LCMS (ESMS): m/z 429.09 (M+H$^+$)

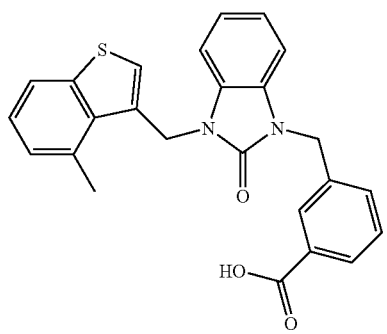 [SMILES: Cc1cccc2scc(Cn3c(=O)n(Cc4cccc(C(=O)O)c4)c4ccccc43)c12]

225
{3-[(4-methyl-1-benzothien-3-yl)methyl]-2-oxo-2,3-dihydro-1H-benzimidazol-1yl}acetic acid. LCMS (ESMS): m/z 353.28 (M+H$^+$)
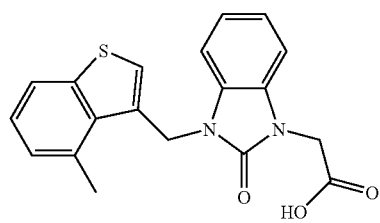 [SMILES: Cc1cccc2scc(Cn3c(=O)n(CC(=O)O)c4ccccc43)c12]
4-{3-[(4-methyl-1-benzothien-3-yl)methyl]-2-oxo-2,3-dihydro-1H-benzimidazol-1-yl}butanoic acid. LCMS (ESMS): m/z 381.81 (M+H$^+$)
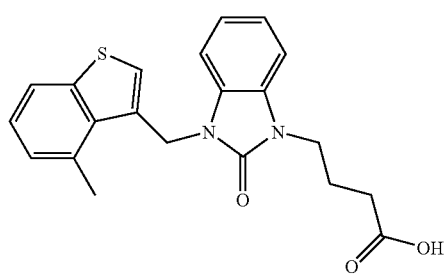 [SMILES: Cc1cccc2scc(Cn3c(=O)n(CCCC(=O)O)c4ccccc43)c12]
Example 7
(3S)-3-{6-methyl-3-[(4-methyl-1-benzothien-3-yl)methyl]-2-oxo-2,3-dihydro-1H-benzimidazol-1-yl}-5-phenylpentanoic acid
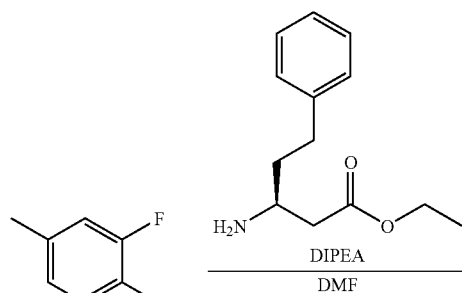
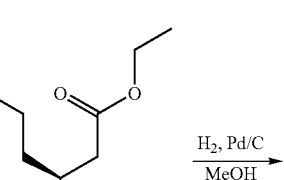
226
-continued
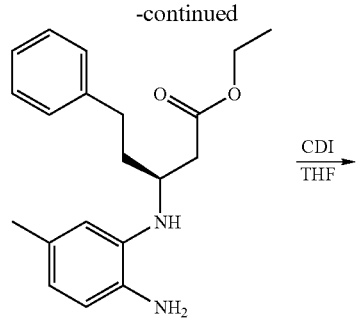
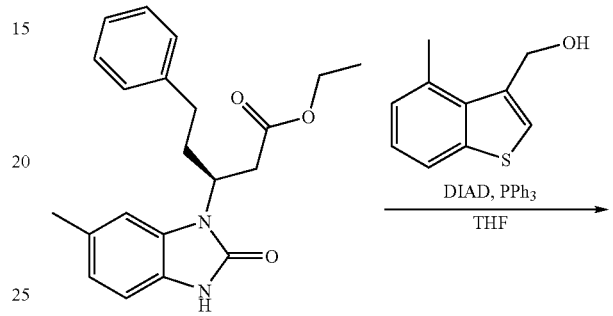
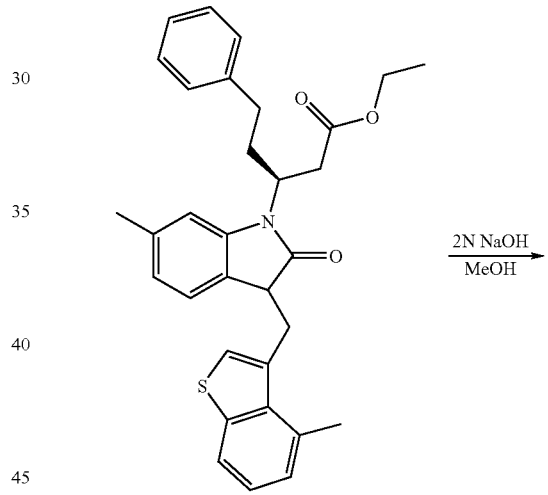
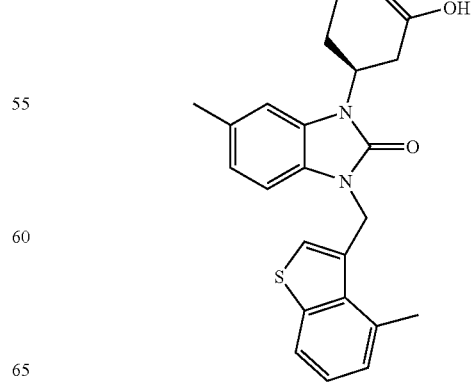

(S)-3-(5-Methyl-2-nitro-phenylamino)-5-phenyl-pentanoic acid ethyl ester

To a solution of 3-Fluoro-4-nitrotoluene (0.7 g, 4.5 mmol) in DMF (5 mL) were added (S)-3-Amino-5-phenyl-pentanoic acid ethyl ester hydrochloride (1.2 g, 4.5 mmol) and DIPEA (1.6 g, 9.0 mmol). The reaction mixture was stirred at room temperature for 48 h. The reaction mixture was then diluted with ethyl acetate and washed with water (×4). The organic phase was then dried over $Na_2SO_4$ and concentrated to afford an orange solid. The resulting residue was Purified by silica gel prep TLC using 4:1 Hexanes:ethyl acetate as an eluent to afford 0.9 g of the desired product.

(S)-3-(2-Amino-5-methyl-phenylamino)-5-phenyl-pentanoic acid ethyl ester

To a solution of (S)-3-(5-Methyl-2-nitro-phenylamino)-5-phenyl-pentanoic acid ethyl ester (0.9 g, 2.5 mmol) in MeOH (20 mL) was added slurry of Pd/C (0.2 g) in MeOH. The reaction mixture was de-gassed using house vacuum. The reaction mixture was stirred under $H_2$ balloon for 3 h. When the reaction color changed from orange to colorless, the reaction mixture was filtered through a pad of celite. The filtrate was concentrated to afford 0.84 g the desired product. This product was used for the next reaction without further purification.

(S)-3-(6-Methyl-2-oxo-2,3-dihydro-benzimidazol-1-yl)-5-phenyl-pentanoic acid ethyl ester To a solution of (S)-3-(2-Amino-5-methyl-phenylamino)-5-phenyl-pentanoic acid ethyl ester (0.84 g, 2.6 mmol) in THF (15 mL) was added CDI (0.50 g, 3.1 mmol). The reaction mixture was stirred at room temperature for 16 h. When the reaction was complete, the reaction mixture was diluted with $CH_2Cl_2$ and washed with water. The organic phase was dried over $Na_2SO_4$ and concentrated to afford 0.75 g of the desired product as a dark brown solid. The resulting residue was used for the next reaction without further purification.

(S)-3-[6-Methyl-3-(4-methyl-benzo[b]thiophen-3-ylmethyl)-2-oxo-2,3-dihydro-benzimidazol-1-yl]-5-phenyl-pentanoic acid ethyl ester To a solution of (S)-3-(6-Methyl-2-oxo-2,3-dihydro-benzimidazol-1-yl)-5-phenyl-pentanoic acid ethyl ester (0.2 g, 0.57 mmol), (4-Methyl-benzo[b]thiophen-3-yl)-methanol (0.10 g, 0.57 mmol), and triphenylphosphine (0.18 g, 0.68 mmol) was added dropwise DIAD (0.14 g, 0.68 mmol). The mixture was stirred at room temperature for 1 h. The reaction mixture was diluted with ethyl acetate and washed with water. The organic phase was dried over $Na_2SO_4$ and concentrated. The resulting oily residue was purified by prep TLC using 4:1 Hexane:EtOAc as an eluent to afford 0.12 g of the desired product as a brown oil.

(3S)-3-{6-methyl-3-[(4-methyl-1-benzothien-3-yl)methyl]-2-oxo-2,3-dihydro-1H-benzimidazol-1-yl}-5-phenylpentanoic acid To a solution of (S)-3-[6-Methyl-3-(4-methyl-benzo[b]thiophen-3-ylmethyl)-2-oxo-2,3-dihydro-benzimidazol-1-yl]-hexanoic acid ethyl ester (0.12 g, 0.23 mmol) in MeOH (5 mL) was added 2N NaOH (2 mL). The reaction mixture was stirred at room temperature for 2 h. When the reaction was complete, the reaction mixture was treated with 1N HCl and extracted with $CH_2Cl_2$ (×2). The organic phase was dried over $Na_2SO_4$ and concentrated. The resulting residue was purified by silica gel prep TLC using 10:1 $CH_2Cl_2$:MeOH as an eluent to afford 0.1 g of the title compound as a white solid. LCMS (ESMS): m/z 485.54 (M+H$^+$).

The following compounds were synthesized following a similar procedure using appropriate starting materials.

(3R)-3-{6-methyl-3-[(4-methyl-1-benzothien-3-yl)methyl]-2-oxo-2,3-dihydro-1H-benzimidazol-1-yl}-5-phenylpentanoic acid. LCMS (ESMS): m/z 485.28 (M+H$^+$)

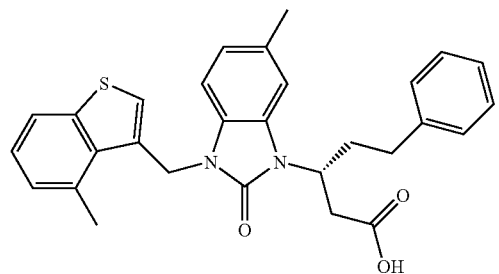 [SMILES: Cc1ccc2c(c1)n([C@H](CCc1ccccc1)CC(=O)O)c(=O)n2Cc1csc2cccc(C)c12]

3-{6-methyl-3-[(4-methyl-1-benzothien-3-yl)methyl]-2-oxo-2,3-dihydro-1H-benzimidazol-1-yl}hexanoic acid. LCMS (ESMS): m/z 423.21 (M+H$^+$)

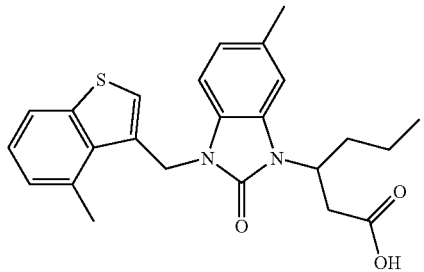 [SMILES: CCCC(CC(=O)O)n1c(=O)n(Cc2csc3cccc(C)c23)c2ccc(C)cc21]

3-{3-[(5-chloro-1,2,3-trimethyl-1H-indol-7-yl)methyl]-6-methyl-2-oxo-2,3-dihydro-1H-benzimidazol-1-yl}hexanoic acid. LCMS (ESMS): m/z 468.34 (M+H$^+$)

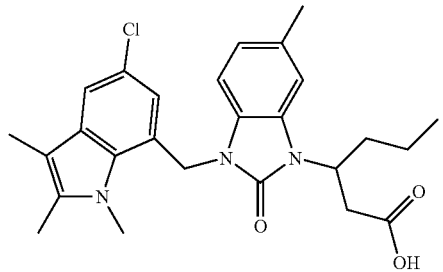 [SMILES: CCCC(CC(=O)O)n1c(=O)n(Cc2cc(Cl)cc3c(C)c(C)n(C)c23)c2ccc(C)cc21]

229

(3R)-3-{3-[(4-methyl-1-benzothien-3-yl)methyl]-2-oxo-2,3-dihydro-1H-benzimidazol-1-yl}-3-phenyl-propanoic acid. LCMS (ESMS): m/z 443.27 (M+H$^+$)

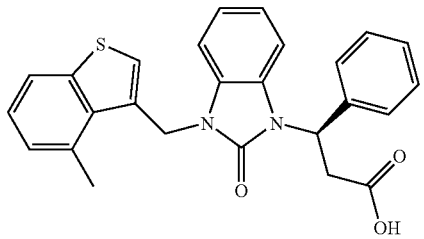 [SMILES: Cc1cccc2scc(Cn3c(=O)n([C@H](CC(=O)O)c4ccccc4)c4ccccc43)c12]

(3S)-3-{3-[(4-methyl-1-benzothien-3-yl)methyl]-2-oxo-2,3-dihydro-1H-benzimidazol-1-yl}-4-phenylbutanoic acid. LCMS (ESMS): m/z 457.28 (M+H$^+$)

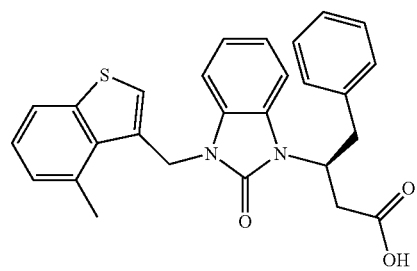 [SMILES: Cc1cccc2scc(Cn3c(=O)n([C@H](CC(=O)O)Cc4ccccc4)c4ccccc43)c12]

(3S)-3-{3-[(4-methyl-1-benzothien-3-yl)methyl]-2-oxo-2,3-dihydro-1H-benzimidazol-1-yl}-3-phenyl-propanoic acid. LCMS (ESMS): m/z 443.23 (M+H$^+$)

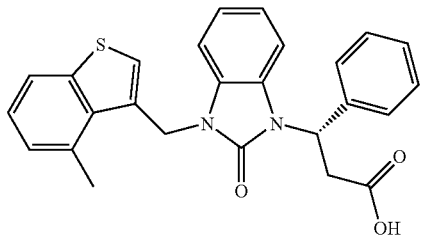 [SMILES: Cc1cccc2scc(Cn3c(=O)n([C@@H](CC(=O)O)c4ccccc4)c4ccccc43)c12]

1-({3-[(5-chloro-1,2,3-trimethyl-1H-indol-7-yl)methyl]-2-oxo-2,3-dihydro-1H-benzimidazol-1-yl}methyl)cyclohexanecarboxylic acid. LCMS (ESMS): m/z 480.24 (M+H$^+$)

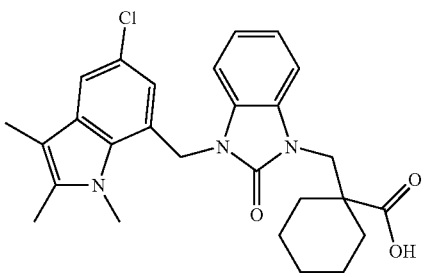 [SMILES: Cc1c(C)n(C)c2c(Cn3c(=O)n(CC4(C(=O)O)CCCCC4)c4ccccc43)cc(Cl)cc12]

230

1-({3-[(5-chloro-1,2,3-trimethyl-1H-indol-7-yl)methyl]-2-oxo-2,3-dihydro-1H-benzimidazol-1-yl}methyl)cyclopentanecarboxylic acid. LCMS (ESMS): m/z 466.16 (M+H$^+$)

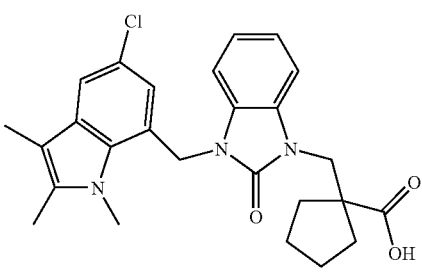 [SMILES: Cc1c(C)n(C)c2c(Cn3c(=O)n(CC4(C(=O)O)CCCC4)c4ccccc43)cc(Cl)cc12]

Example 8

3-[6-cyano-3-(1-naphthylmethyl)-2-oxo-2,3-dihydro-1H-benzimidazol-1-yl]propanoic acid

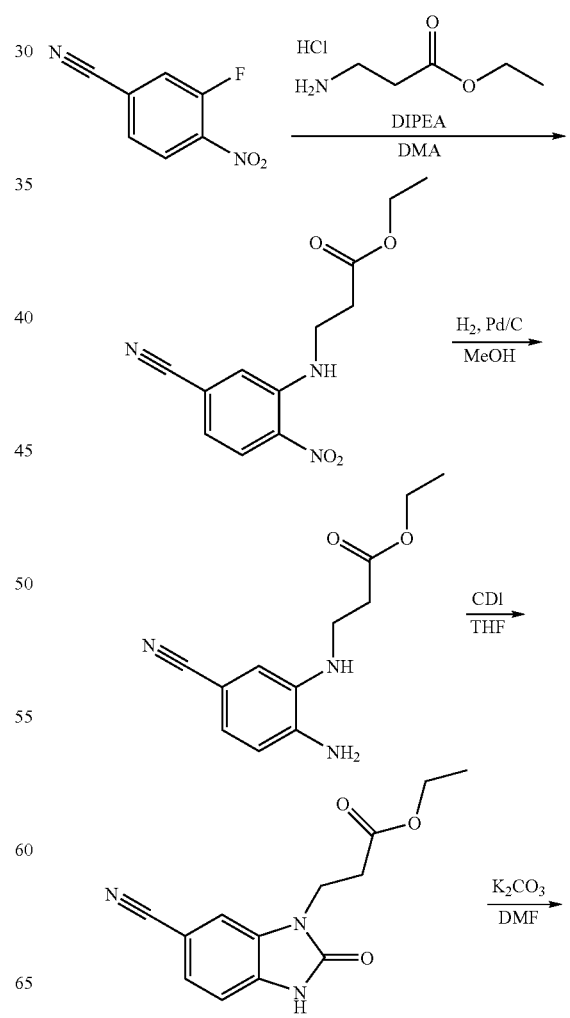

-continued

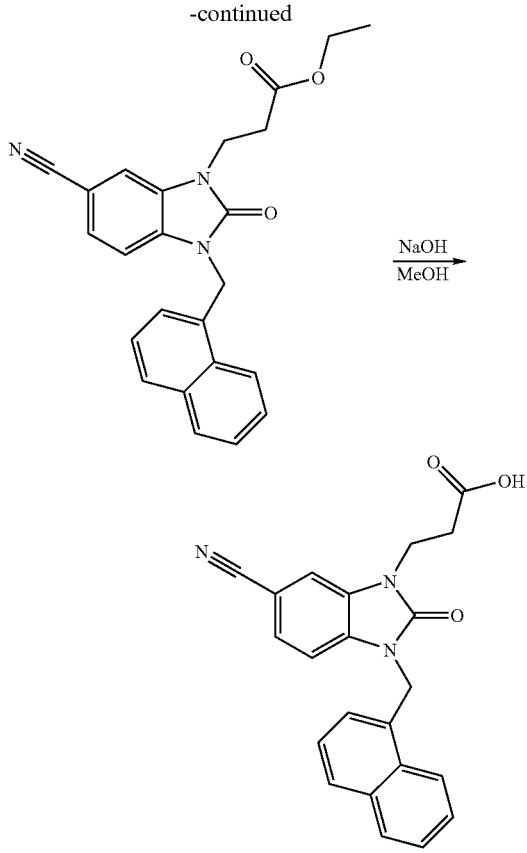

3-(5-Cyano-2-nitro-phenylamino)-propionic acid ethyl ester

To a solution of 3-Fluoro-4-nitrobenzonitrile (1.0 g, 6.0 mmol) in DMA (5 mL) were added Beta-Alanine ethyl ester HCl (1.4 g, 9.03 mmol) and DIPEA (1.6 mL, 9.03 mmol). The reaction mixture was stirred at room temperature for 16 h (the reaction was completed; the reaction mixture turned to orange from yellow in color). The reaction mixture was then diluted with ethyl acetate and washed with water (×4). The organic phase was then dried over $Na_2SO_4$ and concentrated to afford 1.53 g (96%) of the desired product as yellow solid.

3-(2-Amino-5-cyano-phenylamino)-propionic acid ethyl ester

To a solution of 3-(5-Cyano-2-nitro-phenylamino)-propionic acid ethyl ester (1.53 g, 5.8 mmol) in MeOH (10 mL) was added a slurry of Pd/C (0.3 g) in MeOH. The reaction mixture was saturated with $H_2$ and stirred for 2 h. When the reaction was complete, the reaction mixture was filtered and the filtrate was concentrated to afford 0.65 g (48%) of the desired product as a brown solid. The resulting residue was used for the next reaction without further purification. LCMS (ESMS): m/z 233.66 (M+H$^+$).

3-(6-Cyano-2-oxo-2,3-dihydro-benzimidazol-1-yl)-propionic acid ethyl ester

To a solution of 3-(2-Amino-5-cyano-phenylamino)-propionic acid ethyl ester (0.65 g, 2.8 mmol) in $CHCl_3$ (10 mL) was added CDI (0.68 g, 4.2 mmol). The reaction mixture was stirred at room temperature for 16 h. When the reaction was complete, the reaction mixture was diluted with $CH_2Cl_2$ and washed with water. The organic phase was dried over $Na_2SO_4$ and concentrated to afford 0.6 g (83%) of the desired priduct as a brown solid. The resulting residue was used for the next reaction without further purification.

3-(6-Cyano-3-naphthalen-1-ylmethyl-2-oxo-2,3-dihydro-benzimidazol-1-yl)-propionic acid ethyl ester To a solution of 3-(6-Cyano-2-oxo-2,3-dihydro-benzimidazol-1-yl)-propionic acid ethyl ester (0.1 g, 0.39 mmol) in DMA (3 mL) were added 1-(chloromethyl)naphthalene (0.1 g, 0.58 mmol) and $K_2CO_3$ (0.11 g, 0.81 mmol). The reaction mixture was stirred at 65° C. for 16 h. When the reaction was complete, the reaction mixture was diluted with ethyl acetate and washed with water (×4). The organic phase was dried over $Na_2SO_4$ and concentrated. The resulting residue was purified by silica gel prep TLC using 98:2 $CH_2Cl_2$:MeOH as an eluent to afford 20 mg (13%) of the desired product.

3-[6-cyano-3-(1-naphthylmethyl)-2-oxo-2,3-dihydro-1H-benzimidazol-1-yl]propanoic acid To a solution of 3-(6-Cyano-3-naphthalen-1-ylmethyl-2-oxo-2,3-dihydro-benzimidazol-1-yl)-propionic acid ethyl ester (20 mg, 0.05 mmol) in MeOH (5 mL) was added 2N NaOH (3 mL). The reaction mixture was stirred at room temperature for 16 h. When all the starting material was consumed, the reaction mixture was acidified with 1N HCl. The reaction mixture was extracted with $CH_2Cl_2$ (×2). The combined organic phase was dried over $Na_2SO_4$ and concentrated. The resulting residue was purified by silica gel prep TLC using 10:1 $CH_2Cl_2$:MeOH as an eluent to afford 4 mg (22%) of the desired product as an off-white solid. LCMS (ESMS): m/z 372.11 (M+H$^+$).

The following compounds were synthesized by a similar procedure.

3-[5-cyano-3-(1-naphthylmethyl)-2-oxo-2,3-dihydro-1H-benzimidazol-1-yl]propanoic acid. LCMS (ESMS): m/z 372.10 (M+H$^+$)

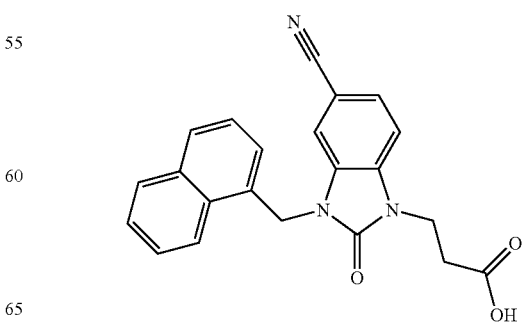

Example 9

3-{3-[(1,4-dimethyl-1H-indol-3-yl)methyl]-5,6-dimethyl-2-oxo-2,3-dihydro-1H-benzimidazol-1-yl}hexanoic acid

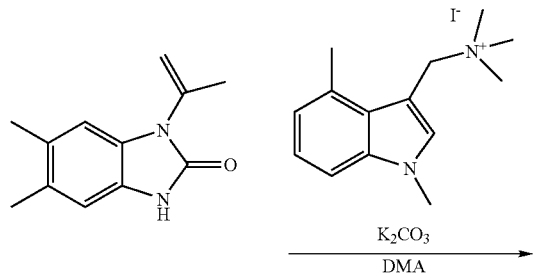

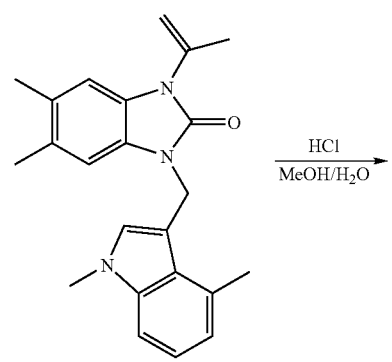

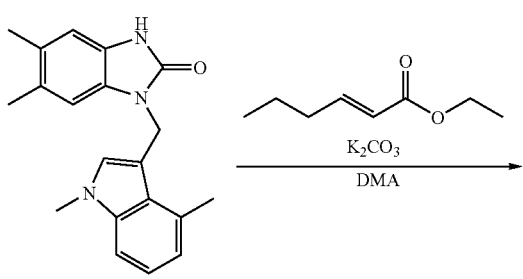

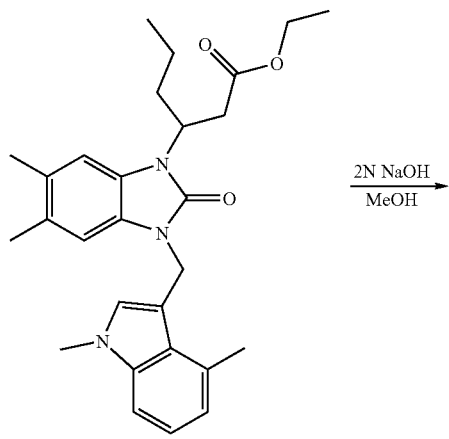

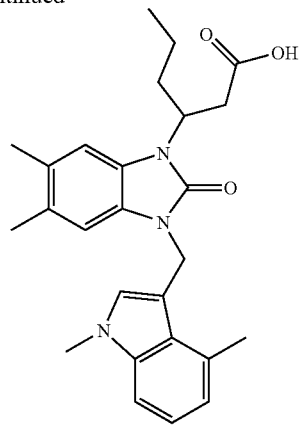

1-(1,4-Dimethyl-1H-indol-3-ylmethyl)-3-isopropenyl-5,6-dimethyl-1,3-dihydro-benzimidazol-2-one To a solution of 1-Isopropenyl-5,6-dimethyl-1,3-dihydro-benzimidazol-2-one (0.25 g, 1.2 mmol) in DMF (10 mL) was added $K_2CO_3$ (0.51 g, 3.7 mmol). The reaction mixture was heated to 90° C. and stirred for 20 min. (1,4-Dimethyl-1H-indol-3-ylmethyl)-trimethyl-ammonium; iodide (0.64 g, 1.8 mmol) was then added to the reaction mixture and stirred for another 3 h. The reaction mixture was treated with ethyl acetate and washed with water. The resulting residue was purified by silica gel prep TLC using 4:1 Hexane:ethyl acetate as an eluent to afford 0.35 g the desired product as an off-white solid. LCMS (ESMS): m/z 360.33 (M+H$^+$).

1-(1,4-Dimethyl-1H-indol-3-ylmethyl)-5,6-dimethyl-1,3-dihydro-benzimidazol-2-one To 1-(1,4-Dimethyl-1H-indol-3-ylmethyl)-3-isopropenyl-5,6-dimethyl-1,3-dihydro-benzimidazol-2-one (0.35 mmol) in MeOH (5 mL) was added water (5 mL) and conc. HCl (3 mL). The reaction mixture was heated to 60° C. for 2 h. The reaction mixture turned into pink in color and heterogeneous (milky solution). The TLC indicated that the reaction was complete and clean. The reaction mixture was therefore diluted with $CH_2Cl_2$ and washed with water. The organic phase remained heterogeneous (milky with fine powder). The organic phase was filtered through a fine filter to collect some of the solid which was partially soluble in DMSO-d6. 1H-NMR indicated this filtered solid being the desired product. Therefore, the organic phase was concentrated without drying with $Na_2SO_4$ to afford a pink solid. 1H-NMR of this product in DMSO-d6 matched well with the previous filtered solid.

3-[3-(1,4-Dimethyl-1H-indol-3-ylmethyl)-5,6-dimethyl-2-oxo-2,3-dihydro-benzimidazol-1-yl]-hexanoic acid ethyl ester A mixture of 1-(1,4-Dimethyl-1H-indol-3-ylmethyl)-5,6-dimethyl-1,3-dihydro-benzimidazol-2-one (0.1 g, 0.31 mmol), $K_2CO_3$ (87 mg, 0.63 mmol) and ethyl trans-2-hexenoate (0.45 g, 3.1 mmol) was heated to 130° C. for 20 min in a microwave. Since the starting material was not soluble in ethyl trans-2-hexenoate even after heating, DMA (2 mL) was added to the reaction mixture and heated again at 150° C. for 30 min. Although the un-reacted starting material was present, the reaction mixture was diluted with ethyl acetate and washed with water (×4). The organic phase was dried over Na$_2$SO$_4$ and concentrated. The resulting heterogeneous residue was purified by silica gel prep TLC using 4:1 hexanes: ethyl acetate as an eluent to afford 25 mg of the desired product as an oil. LCMS (ESMS): m/z 462.88 (M+H$^+$).

3-{3-[(1,4-dimethyl-1H-indol-3-yl)methyl]-5,6-dimethyl-2-oxo-2,3-dihydro-1H-benzimidazol-1-yl}hexanoic acid To a solution of the ester (25 mg, 0.05 mmol) in MeOH (5 mL) was added 2N NaOH (5 mL). The reaction mixture was stirred at room temperature for 3 h. When the reaction was complete, the mixture was treated with 1N HCl and extracted with CH$_2$Cl$_2$. The organic phase was dried over Na$_2$SO$_4$ and concentrated. The resulting residue was purified by silica gel prep TLC using 10:1 CH$_2$Cl$_2$:MeOH as an eluent to afford 22 mg of the title compound as a pale gray solid. LCMS (ESMS): m/z 434.72 (M+H$^+$).

The following compounds were synthesized using a similar procedure.

3-ethoxy-3-{6-methyl-3-[(4-methyl-1-benzothien-3-yl)methyl]-2-oxo-2,3-dihydro-1H-benzimidazol-1-yl}propanoic acid. LCMS (ESMS): m/z 434.72 (M+H$^+$)

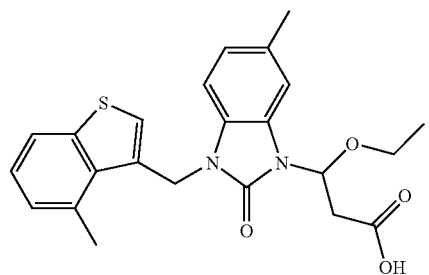 [SMILES: CCOC(CC(=O)O)n1c(=O)n(Cc2csc3cccc(C)c23)c2ccc(C)cc21]

Example 10

3-{5,6-dimethyl-3-[(4-methyl-1-benzothien-3-yl)methyl]-2-oxo-2,3-dihydro-1H-benzimidazol-1-yl}-3-ethoxypropanoic acid

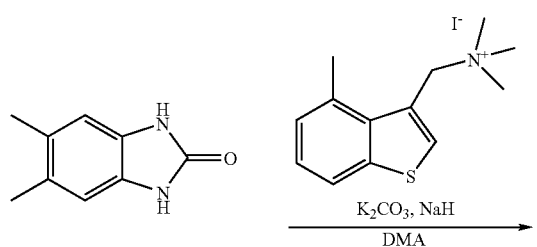

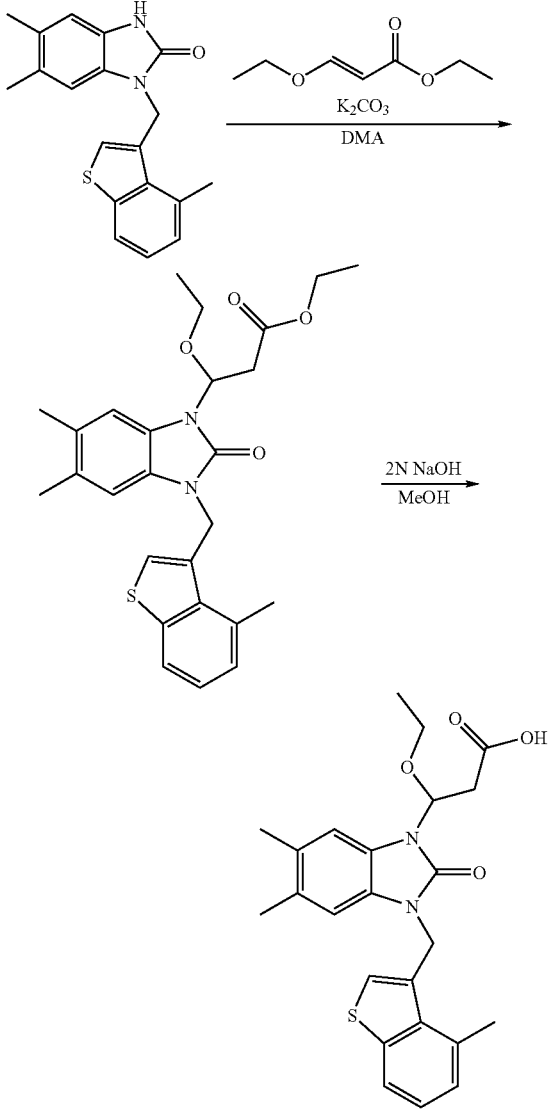

5,6-Dimethyl-1-(4-methyl-benzo[b]thiophen-3-ylmethyl)-1,3-dihydro-benzimidazol-2-one To a slurry of 5,6-Dimethyl-2-benzimidazolinone (0.2 g, 1.2 mmol) in DMA (2 mL) (poor solubility) were added K$_2$CO$_3$ (0.10 g, 0.74 mmol) and trimethyl-(4-methyl-benzo[b]thiophen-3-ylmethyl)-ammonium; iodide (0.21 g, 0.62 mmol). The heterogeneous reaction mixture was heated to 130° C. for 10 min. Since there was still un-reacted starting material left, NaH (15 mg, 0.38 mmol) was added to the reaction mixture and heated to 150° C. for 10 min. The reaction was complete. The reaction mixture was then diluted with ethyl acetate (some MeOH was added to solubilize the reaction mixture into the organic phase) and washed with water (×5). The organic phase was dried over Na$_2$SO$_4$ and concentrated. The resulting solid had poor solubility. To the solid, CH$_2$Cl$_2$ was added and the resulting solid was filtered. The filtered solid was identified as the desired product (with a minimal amount of excess 5,6-Dimethyl-2-benzimidazolinone). Therefore, this filtered solid was used for the next reaction. LCMS (ESMS): m/z 323.13 (M+H$^+$).

3-[5,6-Dimethyl-3-(4-methyl-benzo[b]thiophen-3-ylmethyl)-2-oxo-2,3-dihydro-benzimidazol-1-yl]-3-ethoxy-propionic acid ethyl ester To a mixture of 5,6-Dimethyl-1-(4-methyl-benzo[b]thiophen-3-ylmethyl)-1,3-dihydro-benzimidazol-2-one (0.1 g, 0.31 mmol) and $K_2CO_3$ (86 mg, 0.62 mmol) in a microwave vial was added Ethyl 3-ethoxyacrylate (0.45 g, 3.1 mmol). The reaction mixture was heated to 130° C. for 20 min in a microwave. The reaction mixture was then diluted with ethyl acetate (since there was some insoluble material left, MeOH was added to the solution mixture to solubilize the material). This organic phase was washed with water (×2). The organic phase was dried over $Na_2SO_4$ and concentrated. The resulting residue was purified by silica gel prep TLC using 4:1 Hexane:ethyl acetate as an eluent to afford 45 mg of the desired product as an oily foam. LCMS (ESMS): m/z 467.32 (M+H$^+$).

3-{5,6-dimethyl-3-[(4-methyl-1-benzothien-3-yl)methyl]-2-oxo-2,3-dihydro-1H-benzimidazol-1-yl}-3-ethoxypropanoic acid To a solution of the ester (45 mg, 0.1 mmol) in MeOH (5 mL) was added 2N NaOH (2 mL). The reaction mixture was stirred at room temperature for 2 h. The reaction mixture was then acidified with 1N HCl. The reaction mixture was extracted with $CH_2Cl_2$ and the combined organic phase was dried over $Na_2SO_4$ and concentrated. The resulting residue was purified by silica gel prep TLC using 10:1 $CH_2Cl_2$:MeOH as an eluent to afford 37 mg of the title compound as an off-white solid. LCMS (ESMS): m/z 439.48 (M+H$^+$).

Example 11

3-{3-[(1,4-dimethyl-1H-indol-3-yl)methyl]-6-methyl-2-oxo-2,3-dihydro-1H-benzimidazol-1-yl}hexanoic acid

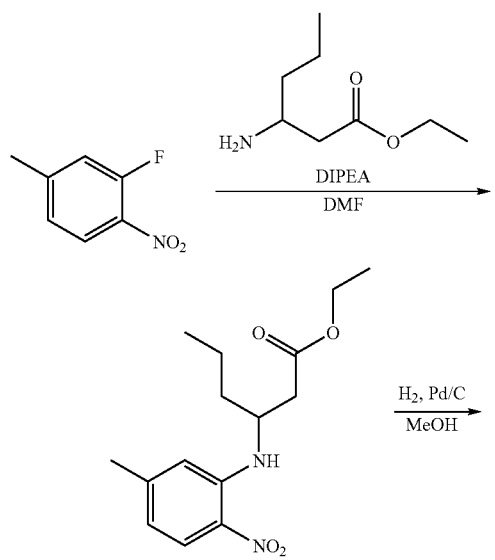

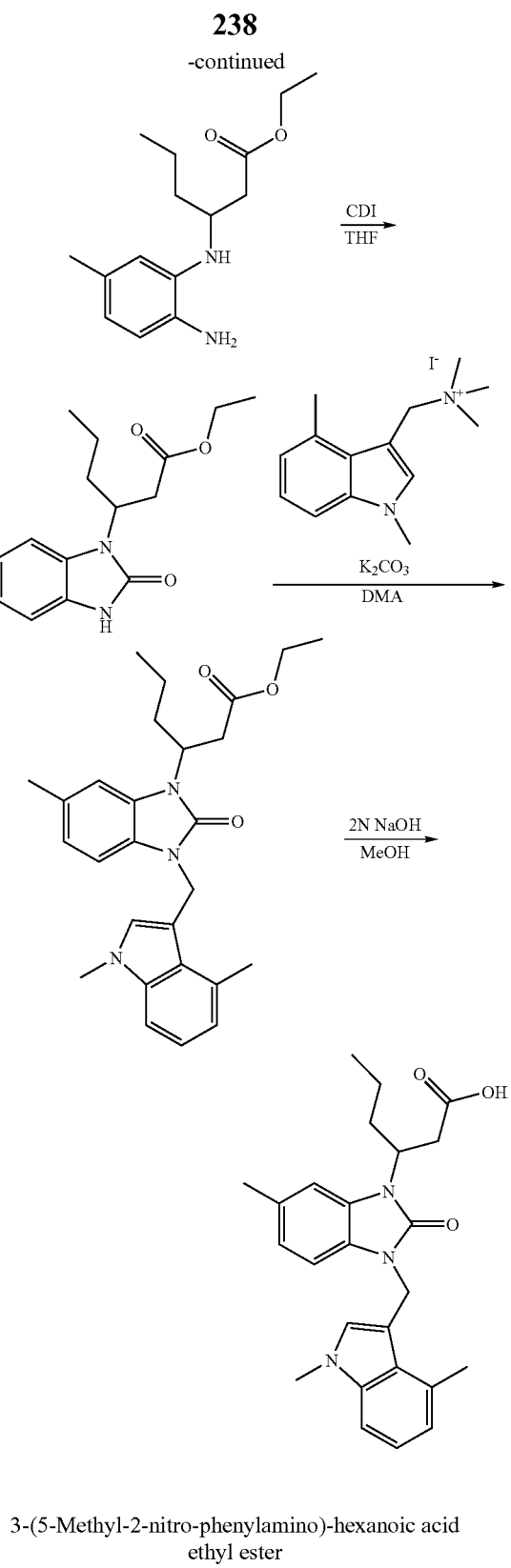

3-(5-Methyl-2-nitro-phenylamino)-hexanoic acid ethyl ester

To a solution of 3-Fluoro-4-nitrotoluene (1.0 g, 6.5 mmol) in DMF (5 mL) were: 3-Amino-hexanoic acid ethyl ester hydrochloride (1.3 g, 6.7 mmol) and DIPEA (2.2 mL, 12.9 mmol). The reaction mixture was stirred at room temperature for 48 h. The reaction mixture was then diluted with ethyl acetate and washed with water (×4). The organic phase was then dried over Na$_2$SO$_4$ and concentrated. The resulting residue was purified by Combiflash using hexane and ethyl acetate (10% gradient) as an eluent to afford 1.4 g of the desired product as orange oil.

3-(2-Amino-5-methyl-phenylamino)-hexanoic acid ethyl ester

To a solution of 3-(5-Methyl-2-nitro-phenylamino)-hexanoic acid ethyl ester (1.4 g, 4.8 mmol) in MeOH (10 mL) was added a slurry of Pd/C (wet) (0.25 g) in MeOH. The reaction mixture was saturated with H$_2$ balloon and stirred at room temperature for 2 h. When the reaction was complete, the reaction mixture was filtered through a pad of celite. The filtrate was concentrated to afford 1.4 g of the desired product as dark purplish oil. This product was used for the next reaction without further purification.

3-(6-Methyl-2-oxo-2,3-dihydro-benzimidazol-1-yl)-hexanoic acid ethyl ester

To a solution of 3-(2-Amino-5-methyl-phenylamino)-hexanoic acid ethyl ester (1.4 g, 5.3 mmol) in THF (20 mL) was added CDI (1.0 g, 6.4 mmol). The reaction mixture was stirred at room temperature for 16 h. When the reaction was complete, the reaction mixture was diluted with ethyl acetate and washed with water. The organic phase was dried over Na$_2$SO$_4$ and concentrated to afford 1.3 g of the desired product as dark brown solid. The resulting residue was used for the next reaction without further purification. LCMS (ESMS): m/z 291.40 (M+H$^+$).

3-[3-(1,4-Dimethyl-1H-indol-3-ylmethyl)-6-methyl-2-oxo-2,3-dihydro-benzimidazol-1-yl]-hexanoic acid ethyl ester To a solution of 3-(6-Methyl-2-oxo-2,3-dihydro-benzimidazol-1-yl)-hexanoic acid ethyl ester (50 mg, 0.17 mmol) in DMF (2 mL) were added K$_2$CO$_3$ (71 mg, 0.52 mmol) and (1,4-Dimethyl-1H-indol-3-ylmethyl)-trimethyl-ammonium; iodide (90 mg, 0.26 mmol). The reaction mixture was heated to 80° C. for 16 h. The reaction mixture was then diluted with ethyl acetate and washed with water (×4). The organic phase was then dried over Na$_2$SO$_4$ and concentrated. The resulting residue was purified by silica gel prep TLC using 4:1 Hexanes:ethyl acetate as an eluent to afford 35 mg of the desired product as oil. LCMS (ESMS): m/z 448.82 (M+H$^+$).

3-{3-[(1,4-dimethyl-1H-indol-3-yl)methyl]-6-methyl-2-oxo-2,3-dihydro-1H-benzimidazol-1-yl}hexanoic acid To a solution of the ester (35 mg, 0.078 mmol) in MeOH (5 mL) was added 2N NaOH (5 mL). The reaction mixture was stirred at room temperature for 3 h. When the reaction was complete, the mixture was treated with 1N HCl and extracted with CH$_2$Cl$_2$. The organic phase was dried over Na$_2$SO$_4$ and concentrated. The resulting residue was purified by silica gel prep TLC using 10:1 CH$_2$Cl$_2$:MeOH as an eluent to afford 27 mg of the title compound as an off-white solid. LCMS (ESMS): m/z 420.63 (M+H$^+$).

The following compounds were prepared following a similar procedure using appropriate starting materials.

(3R)-3-{3-[(1,4-dimethyl-1H-indol-3-yl)methyl]-2-oxo-2,3-dihydro-1H-benzimidazol-1-yl}-3-phenyl-propanoic acid. LCMS (ESMS): m/z 440.17 (M+H$^+$)

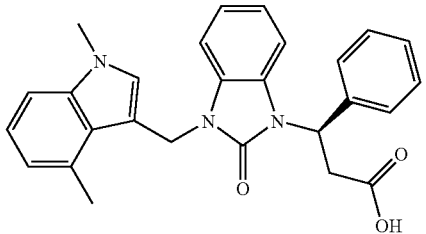 [SMILES: Cc1cccc2c1c(Cn1c(=O)n([C@H](CC(=O)O)c3ccccc3)c3ccccc31)cn2C]

(3R)-3-{3-[(1,4-dimethyl-1H-indol-3-yl)methyl]-6-methyl-2-oxo-2,3-dihydro-1H-benzimidazol-1-yl)-3-pyridin-3-ylpropanoic acid. LCMS (ESMS): m/z 455.51 (M+H$^+$)

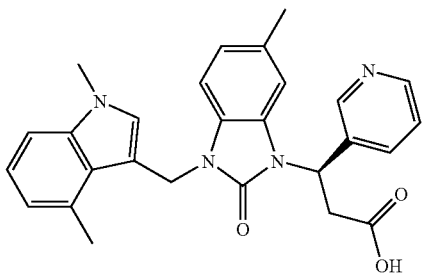 [SMILES: Cc1ccc2c(c1)n([C@H](CC(=O)O)c1cccnc1)c(=O)n2Cc1cn(C)c2cccc(C)c12]

3-{5-bromo-3-[(1,4-dimethyl-1H-indol-3-yl)methyl]-2-oxo-2,3-dihydro-1H-benzimidazol-1-yl}hexanoic acid. LCMS (ESMS): m/z 484.38 (M+H$^+$)

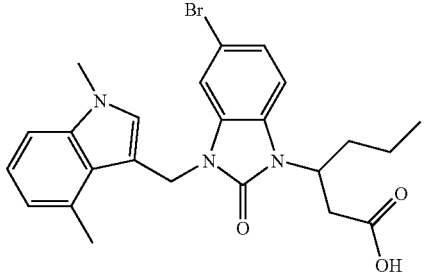 [SMILES: CCCC(CC(=O)O)n1c(=O)n(Cc2cn(C)c3cccc(C)c23)c2cc(Br)ccc21]

(3S)-3-{5-[(tert-butoxycarbonyl)amino]-3-[(1,4-dimethyl-1H-indol-3-yl)methyl]-2-oxo-2,3-dihydro-1H-benzimidazol-1-yl}hexanoic acid. LCMS (ESMS): m/z 520.62 (M+H$^+$)

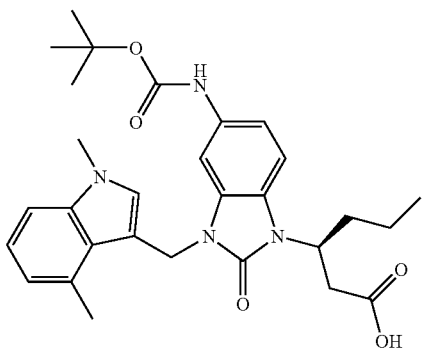 [SMILES: CCC[C@@H](CC(=O)O)n1c(=O)n(Cc2cn(C)c3cccc(C)c23)c2cc(NC(=O)OC(C)(C)C)ccc21]

241

(1R,2R)-2-{3-[(1,4-dimethyl-1H-indol-3-yl)methyl]-2-oxo-2,3-dihydro-1H-benzimidazol-1-yl}cyclohexanecarboxylic acid LCMS (ESMS): m/z 418 (M+H$^+$)

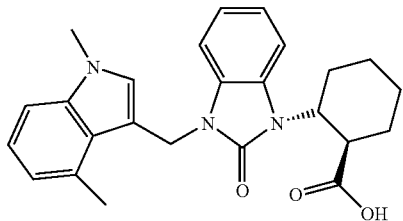

1-({3-[(1,4-dimethyl-1H-indol-3-yl)methyl]-2-oxo-2,3-dihydro-1H-benzimidazol-1-yl}methyl)cyclohexanecarboxylic acid. LCMS (ESMS): m/z 432.25 (M+H$^+$)

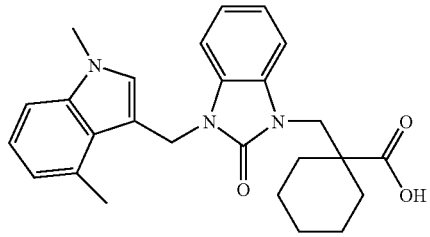 [SMILES: Cc1cccc2c1c(Cn1c(=O)n(CC3(C(=O)O)CCCCC3)c3ccccc31)cn2C]

1-({3-[(1,4-dimethyl-1H-indol-3-yl)methyl]-2-oxo-2,3-dihydro-1H-benzimidazol-1-yl}methyl)cyclopentanecarboxylic acid. LCMS (ESMS): m/z 418.23 (M+H$^+$)

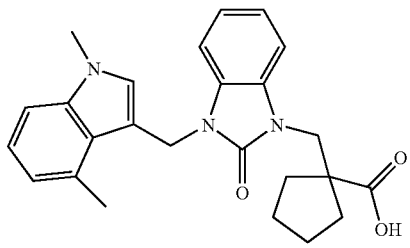 [SMILES: Cc1cccc2c1c(Cn1c(=O)n(CC3(C(=O)O)CCCC3)c3ccccc31)cn2C]

Example 12

(2E)-3-{3-[(4-methyl-1-benzothien-3-yl)methyl]-2-oxo-2,3-dihydro-1H-benzimidazol-1-yl}acrylic acid

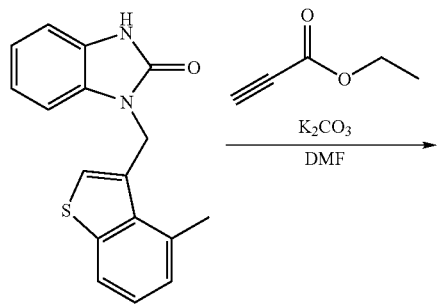

-continued

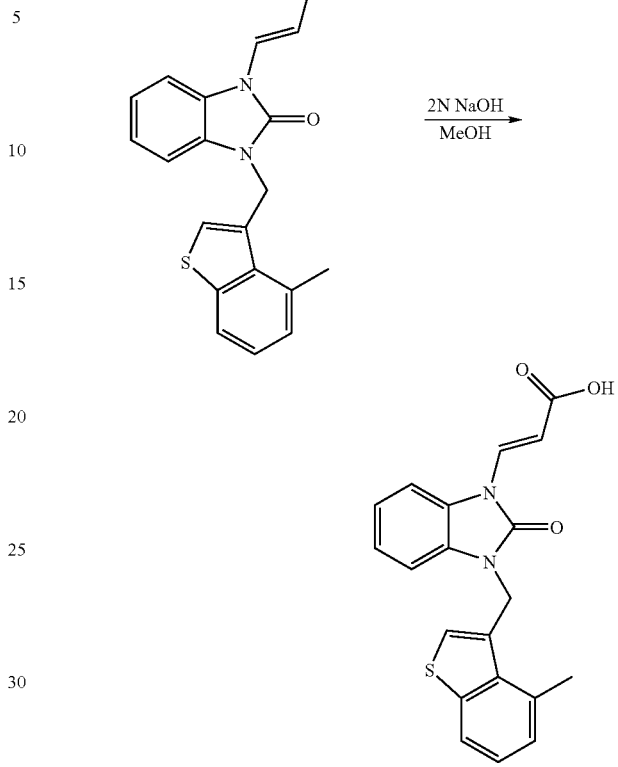

(E)-3-[3-(4-Methyl-benzo[b]thiophen-3-ylmethyl)-2-oxo-2,3-dihydro-benzimidazol-1-yl]-acrylic acid ethyl ester To a solution of 1-(4-Methyl-benzo[b]thiophen-3-ylmethyl)-1,3-dihydro-benzimidazol-2-one (0.1 g, 0.34 mmol) in AcCN (2 mL) and DMF (1 mL) were added ethyl propiolate (0.04 mL, 0.34 mmol) and DMAP (0.02 mL, 0.17 mmol). The reaction mixture was stirred at room temperature for 2 h. When the reaction was complete, the reaction mixture was diluted with CH$_2$Cl$_2$ and washed with water. The organic phase was dried over Na$_2$SO$_4$ and concentrated. The resulting residue was purified by silica gel prep TLC using 95:5 CH$_2$Cl$_2$:MeOH as an eluent to afford 0.11 g of the desired product as a white solid. LCMS (ESMS): m/z 393.13 (M+H$^+$).

(2E)-3-{3-[(4-methyl-1-benzothien-3-yl)methyl]-2-oxo-2,3-dihydro-1H-benzimidazol-1-yl}acrylic acid To a solution of the ester (0.11 g, 0.28 mmol) in MeOH (10 mL) was added 2N NaOH (5 mL). The reaction mixture was stirred at 60° C. for 2 h until all the starting material was consumed. The reaction mixture was then treated with 1M HCl to pH ~2 and extracted with CH$_2$Cl$_2$ (×2).

The organic phase was dried over Na$_2$SO$_4$ and concentrated. The resulting residue was purified by silica gel prep TLC using 10:1 CH$_2$Cl$_2$:MeOH as an eluent to afford 20 mg of the title compound as an off-white solid. LCMS (ESMS): m/z 365.03 (M+H$^+$).

The by-product was obtained during hydrolysis of (E)-3-[3-(4-Methyl-benzo[b]thiophen-3-ylmethyl)-2-oxo-2,3-dihydro-benzimidazol-1-yl]-acrylic acid ethyl ester.

243

3-methoxy-3-{3-[(4-methyl-1-benzothien-3-yl)methyl]-2-oxo-2,3-dihydro-1H-benzimidazol-1-yl}propanoic acid LCMS (ESMS): m/z 397.04 (M+H⁺)

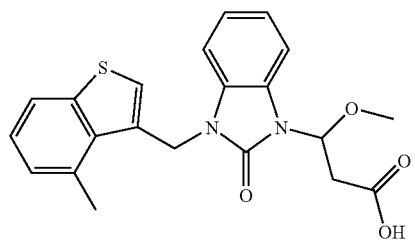

Example 13

3-{3-[(5-chloro-1,2,3-trimethyl-1H-indol-7-yl)methyl]-6-methyl-2-oxo-2,3-dihydro-1H-benzimidazol-1-yl}pentanoic acid

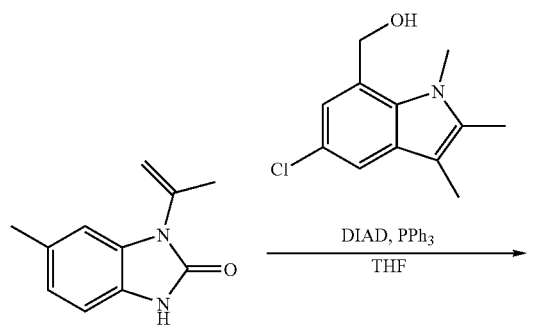

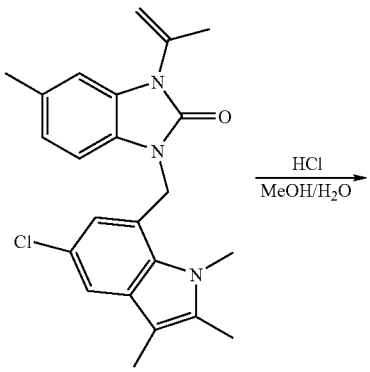

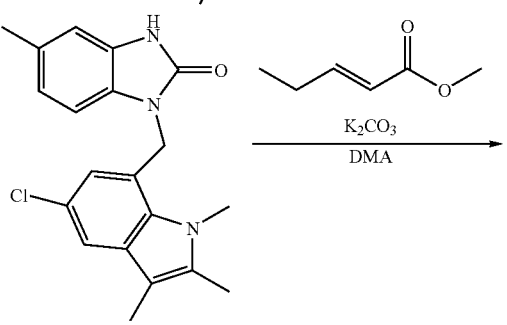

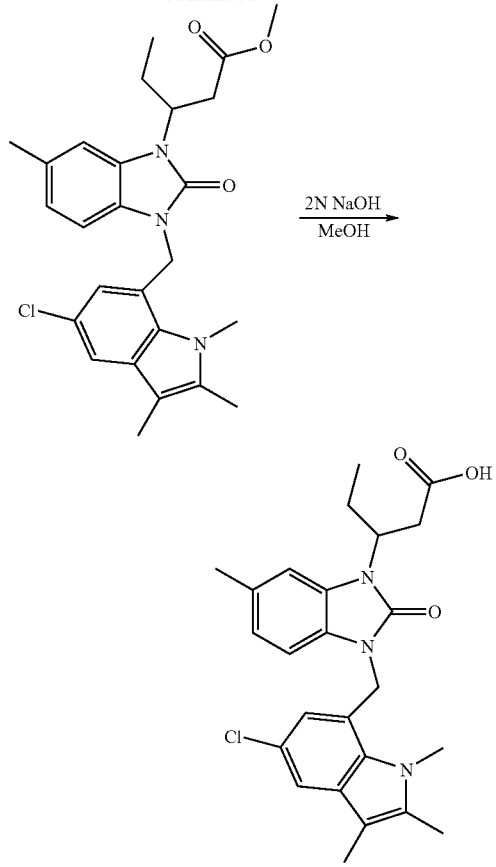

1-(5-Chloro-1,2,3-trimethyl-1H-indol-7-ylmethyl)-3-isopropenyl-5-methyl-1,3-dihydro-benzimidazol-2-one To a solution of 1-Isopropenyl-6-methyl-1,3-dihydro-benzimidazol-2-one (50 mg, 0.27 mmol) and (5-Chloro-1,2,3-trimethyl-1H-indol-7-yl)-methanol (60 mg, 0.27 mmol), triphenylphosphine (84 mg, 0.32 mmol) in THF (2 mL) was added dropwise DIAD (0.06 mL, 0.32 mmol). The mixture was stirred at room temperature for 1 h. The reaction mixture was diluted with ethyl acetate and washed with water (×2). The organic phase was dried over Na₂SO₄ and concentrated. The resulting residue was purified by silica gel prep TLC using 4:1 Hexanes:ethyl acetate as an eluent to afford 60 mg of the desired product as a brownish oil. LCMS (ESMS): m/z 394.28 (M+H⁺).

1-(5-Chloro-1,2,3-trimethyl-1H-indol-7-ylmethyl)-5-methyl-1,3-dihydro-benzimidazol-2-one To a solution of 1-(5-Chloro-1,2,3-trimethyl-1H-indol-7-ylmethyl)-3-isopropenyl-5-methyl-1,3-dihydro-benzimidazol-2-one (60 mg, 0.15 mmol) in a mixture of MeOH (3 mL) and water (3 mL), was added 1N HCl (2 mL). The reaction mixture was heated to 60° C. for 2 h. When the reaction was completed, the mixture was extracted with CH₂Cl₂ (×2). The organic phase was dried over Na₂SO₄ and concentrated to afford 40 mg of the desired product. The resulting residue was used for the next reaction without further purification.

3-[3-(5-Chloro-1,2,3-trimethyl-1H-indol-7-ylm-ethyl)-6-methyl-2-oxo-2,3-dihydro-benzimidazol-1-yl]-pentanoic acid methyl ester To a solution of 1-(5-Chloro-1,2,3-trimethyl-1H-indol-7-ylmethyl)-5-methyl-1,3-dihydro-benzimidazol-2-one (40 mg, 0.11 mmol) in DMA (2 mL) were added Methyl 2-pentenoate (26 mg, 0.23 mmol) and K$_2$CO$_3$ (31 mg, 0.23 mmol). The reaction mixture was heated to 120° C. for 20 min in a microwave. When the reaction was completed, the reaction mixture was diluted with ethyl acetate and washed with water (×4). The organic phase was dried over Na$_2$SO$_4$ and concentrated. The resulting residue was purified by silica gel prep TLC using 4:1 Hexane:ethyl acetate to afford 40 mg of the desired product. LCMS (ESMS): m/z 468.36 (M+H$^+$).

3-{3-[(5-chloro-1,2,3-trimethyl-1H-indol-7-yl)methyl]-6-methyl-2-oxo-2,3-dihydro-1H-benzimidazol-1-yl}pentanoic acid To a solution of the ester (40 mg, 0.09 mmol) in MeOH (2 mL) was added 2N NaOH (2 mL). The reaction mixture was not homogeneous at room temperature. The reaction mixture was therefore heated to 60° C. for 1 h. When the reaction was complete, the mixture was treated with 1N HCl and extracted with CH$_2$Cl$_2$ (×2). The organic phase was dried over Na$_2$SO$_4$ and concentrated. The resulting residue was purified by silica gel prep TLC using 10:1 CH$_2$Cl$_2$:MeOH as an eluent to afford the title compound as an off-white solid. LCMS (ESMS): m/z 454.20 (M+H$^+$). However, this product also contains approximately 50% of the other isomer, 3-{3-[(5-chloro-1,2,3-trimethyl-1H-indol-7-yl)methyl]-5-methyl-2-oxo-2,3-dihydro-1H-benzimidazol-1-yl}pentanoic acid.

Example 14

N-[3-(3-Naphthalen-1-ylmethyl-2-oxo-2,3-dihydro-benzimidazol-1-yl)-propionyl]-benzenesulfonamide

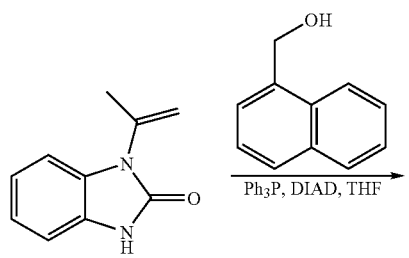

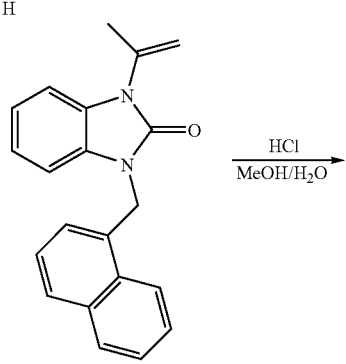

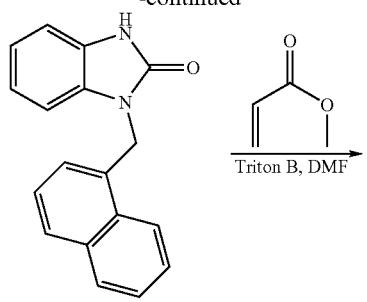

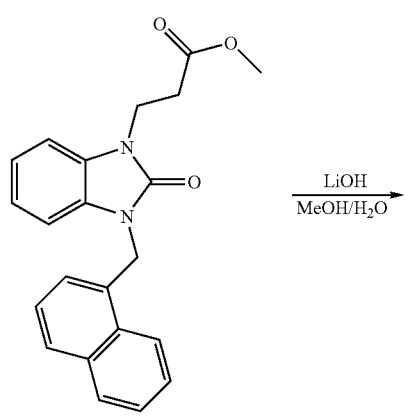

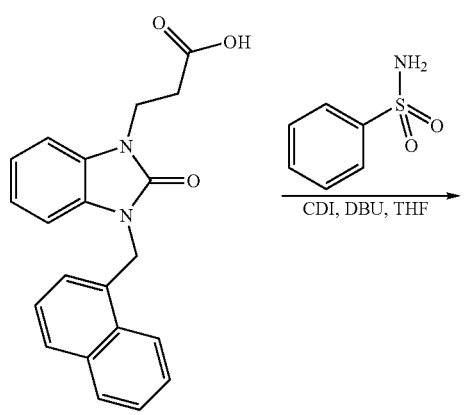

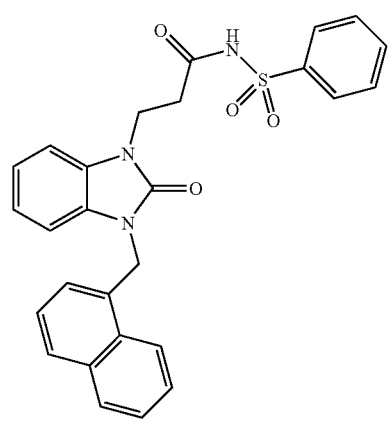 [SMILES: O=C(CCn1c(=O)n(Cc2cccc3ccccc23)c2ccccc21)NS(=O)(=O)c1ccccc1]

1-Isopropenyl-3-naphthalen-1-ylmethyl-1,3-dihydro-benzimidazol-2-one

To a solution of 1-isopropenylbenzimidazolone (1.0 g, 5.7 mmol) in dry THF (80 mL) are added triphenylphosphine (1.8 g, 6.9 mmol) and naphthalen-1-yl-methanol (1.1 g, 6.9 mmol). Then diisopropyl azodicarboxylate (1.4 mL, 6.9 mmol) is added drop wise into the above solution at room temperature. The mixture is stirred for 16 hrs and then the solvent is removed under vacuum. The residue is purified by flash column chromatography using 10% EtOAc in hexanes to give 1.6 g (89%) of 1-isopropenyl-3-naphthalen-1-ylmethyl-1,3-dihydro-benzimidazol-2-one.

1-Naphthalen-1-ylmethyl-1,3-dihydro-benzimidazol-2-one

1-Isopropenyl-3-naphthalen-1-ylmethyl-1,3-dihydro-benzimidazol-2-one (1.6 g, 5.1 mmol) is dissolved in MeOH (5.0 mL) and water (5.0 mL) is added into the solution. To this heterogeneous reaction mixture is added 37% hydrochloric acid (4.0 mL). The reaction mixture is heated to 60° C. for 30 min and then water (50 mL) and CH$_2$Cl$_2$ (50 mL) are added. The organic layer is separated and the aqueous layer is extracted with CH$_2$Cl$_2$ (3×50 mL). The organic layers are combined, washed with Sat. NaHCO$_3$ (100 mL), Sat. NH$_4$Cl (100 mL) and water (3×100 mL), dried over MgSO$_4$ and concentrated to give 1.3 g (93%) of crude product which is pure enough for the next step.

3-(3-Naphthalen-1-ylmethyl-2-oxo-2,3-dihydro-benzimidazol-1-yl)-propionic acid methyl ester To a solution of 1-naphthalen-1-ylmethyl-1,3-dihydro-benzimidazol-2-one (200 mg, 0.73 mmol) in DMF (3.0 mL) are added methyl acrylate (0.07 mL, 0.8 mmol) and 40% benzyltrimethyl ammonium hydroxide in MeOH (0.03 mL, 0.073 mmol). The resulting mixture is stirred at room temperature for 1.5 h and then Sat. NH$_4$Cl (5 mL) and water (20 mL) are added. The mixture is extracted with EtOAc (3×50 mL) and the organic layers are combined, washed with water (3×75 dried over MgSO$_4$ and concentrated to give crude product. Purification by flash column chromatography using 30% EtOAc in Hexanes affords 220 mg (84%) of 3-(3-naphthalen-1-ylmethyl-2-oxo-2,3-dihydro-benzimidazol-1-yl)-propionic acid methyl ester.

3-(3-Naphthalen-1-ylmethyl-2-oxo-2,3-dihydro-benzimidazol-1-yl)-propionic acid Lithium hydroxide monohydrate (31 mg, 0.75 mmol) is dissolved in water (3.5 mL) and this solution is added into 3-(3-naphthalen-1-ylmethyl-2-oxo-2,3-dihydro-benzimidazol-1-yl)-propionic acid methyl ester (180 mg, 0.5 mmol) in methanol (3.5 mL) at room temperature. The mixture is stirred for 6 hr and 1.0 M HCl aqueous solution (1.5 mL) is added along with water (25 mL). Then the mixture is extracted with EtOAc (3×50 mL) and the organic layers are combined, dried over MgSO$_4$ and concentrated to give 170 mg of crude 3-(3-Naphthalen-1-ylmethyl-2-oxo-2,3-dihydro-benzimidazol-1-yl)-propionic acid which is used in the following step without further purification.

N-[3-(3-Naphthalen-1-ylmethyl-2-oxo-2,3-dihydro-benzimidazol-1-yl)-propionyl]-benzenesulfonamide 3-(3-Naphthalen-1-ylmethyl-2-oxo-2,3-dihydro-benzimidazol-1-yl)-propionic acid (80 mg, 0.23 mmol) is dissolved in dry THF (3.0 mL) and 1,1'-carbonyl diimidazole (84 mg, 0.52 mmol) is added into it. The mixture is stirred for 30 min at room temperature and then it is heated at 55° C. for 1 hr. After the mixture is cooled down to room temperature, benzenesulfonamide (73 mg, 0.46 mmol) is added and after 10 min, 1,8-diazabicyclo[5,4,0]undec-7-ene (0.07 mL, 0.46 mmol) is added. The mixture is again stirred for 8 heat room temperature. 1.0 M HCl aqueous solution (3 mL) is added followed by water (30 mL). The mixture is extracted with EtOAc (3×50 mL) and the organic layers are combined, dried and concentrated to give crude product. Purification by preparative TLC using 55% EtOAc in Hexanes affords 66 mg (59%) of N-[3-(3-Naphthalen-1-ylmethyl-2-oxo-2,3-dihydro-benzimidazol-1-yl)-propionyl]-benzenesulfonamide. LCMS (ESMS): m/z 486.05 (M+H$^+$)

The following compound is synthesized using the same procedure as Example 1 by replacing benzenesulfonamide with commercially available methane sulfonamide:

N-[3-(3-Naphthalen-1-ylmethyl-2-oxo-2,3-dihydro-benzimidazol-1-yl)-propionyl]-methanesulfonamide. LCMS (ESMS): m/z 424.06 (M+H$^+$)

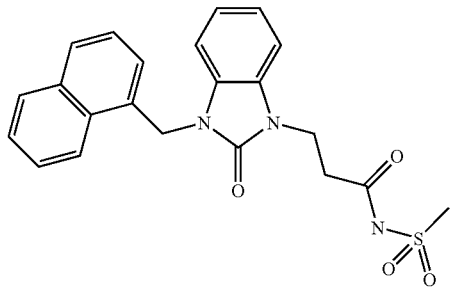 [SMILES: CS(=O)(=O)NC(=O)CCn1c(=O)n(Cc2cccc3ccccc23)c2ccccc21]

Example 15

3-(3-Naphthalen-1-ylmethyl-2-oxo-2,3-dihydro-benzimidazol-1-yl)-propionamide

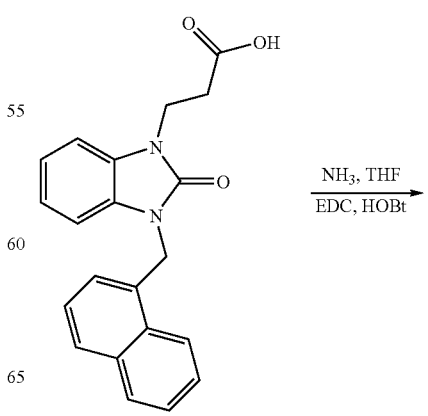

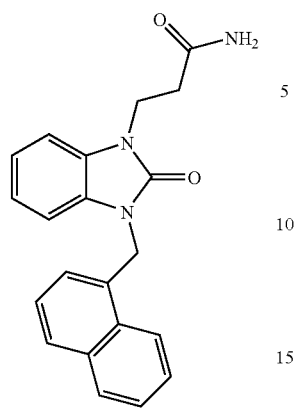

To the THF (1.0 mL) suspension of 3-(3-Naphthalen-1-ylmethyl-2-oxo-2,3-dihydro-benzimidazol-1-yl)-propionic acid (50 mg, 0.14 mmol) at room temperature are added ammonia 0.5 M solution in dioxane (1.4 mL, 0.72 mmol) and 1-hydroxybenzotriazole (94 mg, 0.7 mmol). Then N-(3-dimethylaminopropyl)-N'-ethylcarbodiimide (118 mg, 0.61 mmol) is added in small portions. The reaction mixture is stirred for 20 hr and then water (5 mL) is added and the mixture is extracted with EtOAc (3×10 mL). The organic layers are combined, dried over MgSO₄ and concentrated to give crude product. Purification by preparative TLC using 5% MeOH in CH₂Cl₂ affords 37 mg (74%) of 3-(3-Naphthalen-1-ylmethyl-2-oxo-2,3-dihydro-benzimidazol-1-yl)-propionamide. LCMS (ESMS): m/z 346.12 (M+H⁺).

Example 16

N-{3-[3-(4-Methyl-benzo[b]thiophen-3-ylmethyl)-2-oxo-2,3-dihydro-benzimidazol-1-yl]-propionyl}-benzenesulfonamide

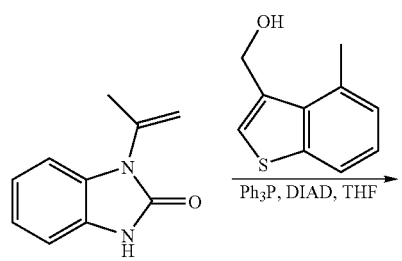

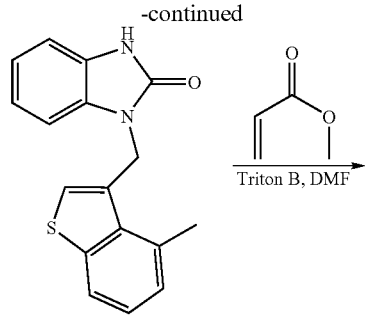

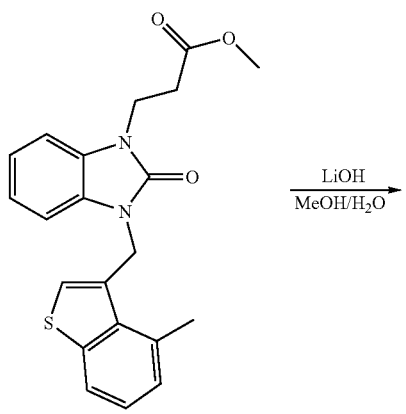

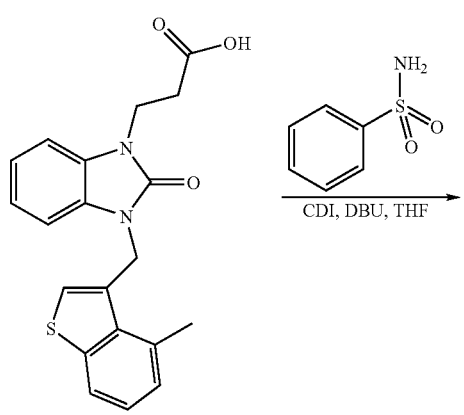

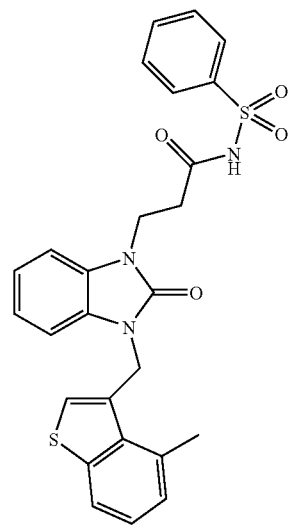 [SMILES: Cc1cccc2scc(Cn3c(=O)n(CCC(=O)NS(=O)(=O)c4ccccc4)c4ccccc43)c12]

1-Isopropenyl-3-(4-methyl-benzo[b]thiophen-3-ylmethyl)-1,3-dihydro-benzimidazol-2-one To a solution of 1-isopropenylbenzimidazolone (500 mg, 2.8 mmol) in dry THF (40 mL) are added triphenylphosphine (902 mg, 3.4 mmol) and (4-Methyl-benzo[b]thiophen-3-yl)-methanol (563 mg, 3.2 mmol). Then diisopropyl azodicarboxylate (0.70 mL, 3.4 mmol) is added drop wise into the above solution after it is cooled down to 0° C. The mixture is then stirred at room temperature for 5 hr and then the solvent is removed under vacuum and the residue is purified by flash column chromatography using gradient EtOAc/Hexane from 0% to 20% to give 630 mg (66%) of 1-isopropenyl-3-(4-methyl-benzo[b]thiophen-3-ylmethyl)-1,3-dihydro-benzimidazol-2-one.

1-(4-Methyl-benzo[b]thiophen-3-ylmethyl)-1,3-dihydro-benzimidazol-2-one

1-Isopropenyl-3-(4-methyl-benzo[b]thiophen-3-ylmethyl)-1,3-dihydro-benzimidazol-2-one (630 mg, 1.9 mmol) is dissolved in methanol (2.0 mL), 1,4-dioxane (10 mL) and water (2.0 mL). Then 37% HCl (1.6 mL) is added and the reaction mixture is heated at 65° C. for 6 hr. A white solid is formed during the heating. Then water (80 mL) and CH$_2$Cl$_2$ (80 mL) are added. The organic layer is separated and the aqueous layer is extracted with CH$_2$Cl$_2$ (3×50 mL). The organic layers are combined, washed with Sat. NaHCO$_3$ (100 mL), Sat. NH$_4$Cl (100 mL) and water (3×100 mL), dried over MgSO$_4$ and concentrated to give 560 mg (99%) of 1-(4-methyl-benzo[b]thiophen-3-ylmethyl)-1,3-dihydro-benzimidazol-2-one which is used for the next step without further purification.

3-[3-(4-Methyl-benzo[b]thiophen-3-ylmethyl)-2-oxo-2,3-dihydro-benzimidazol-1-yl]-propionic acid methyl ester To a solution of 1-(4-methyl-benzo[b]thiophen-3-ylmethyl)-1,3-dihydro-benzimidazol-2-one (560 mg, 1.9 mmol) in DMF (9.0 mL) are added methyl acrylate (0.19 mL, 2.1 mmol) and 40% benzyltrimethyl ammonium hydroxide in MeOH (0.09 mL, 0.19 mmol). The resulting mixture is stirred at room temperature for 3 hr. Then Sat. NH$_4$Cl (5 mL) and water (50 mL) are added and the mixture is extracted with EtOAc (3×50 mL). The organic layers are combined, washed with water (3×75 mL), dried over MgSO$_4$ and concentrated to give crude product. Purification by flash column chromatography using 30% EtOAc in hexanes affords 600 mg (83%) of 3-[3-(4-Methyl-benzo[b]thiophen-3-ylmethyl)-2-oxo-2,3-dihydro-benzimidazol-1-yl]-propionic acid methyl ester.

3-[3-(4-Methyl-benzo[b]thiophen-3-ylmethyl)-2-oxo-2,3-dihydro-benzimidazol-1-yl]-propionic acid Lithium hydroxide monohydrate (99 mg, 2.4 mmol) is dissolved in water (12 mL) and this solution is added into 3-[3-(4-Methyl-benzo[b]thiophen-3-ylmethyl)-2-oxo-2,3-dihydro-benzimidazol-1-yl]-propionic acid methyl ester (600 mg, 1.6 mmol) in methanol (12 mL) at room temperature. The mixture is stirred for 2 hr and then 1.0 M HCl aqueous solution (3 mL) is added along with water (100 mL). Then the mixture is extracted with EtOAc (3×100 mL) and the organic layers are combined, dried over MgSO$_4$ and concentrated to give about 560 mg (97%) of 3-[3-(4-Methyl-benzo[b]thiophen-3-ylmethyl)-2-oxo-2,3-dihydro-benzimidazol-1-yl]-propionic acid which is used in the next step without further purification.

N-{3-[3-(4-Methyl-benzo[b]thiophen-3-ylmethyl)-2-oxo-2,3-dihydro-benzimidazol-1-yl]-propionyl}-benzenesulfonamide 3-[3-(4-Methyl-benzo[b]thiophen-3-ylmethyl)-2-oxo-2,3-dihydro-benzimidazol-1-yl]-propionic acid (150 mg, 0.41 mmol) is dissolved in dry THF (3.0 mL) and 1,1'-carbonyl diimidazole (150 mg, 0.92 mmol) is added into it at room temperature. The mixture is stirred for 30 min and then it is heated at 55° C. for 1 hr. After the mixture is cooled down to room temperature, benzenesulfonamide (130 mg, 0.82 mmol) is added and after 10 min, 1,8-diazabicyclo[5,4,0]undec-7-ene (0.12 mL, 0.82 mmol) is added. The mixture is stirred for 5 hr at room temperature and then 1.0 M HCl (3 mL) is added followed by water (30 mL). The mixture is extracted with EtOAc (3×50 mL) and the organic layers are combined, dried and concentrated to give crude product. Purification by preparative TLC using 75% EtOAc in Hexanes affords 123 mg (60%) of N-{3-[3-(4-Methyl-benzo[b]thiophen-3-ylmethyl)-2-oxo-2,3-dihydro-benzimidazol-1-yl]-propionyl}-benzenesulfonamide. LCMS (ESMS): m/z 506.18 (M+H$^+$).

The following compounds are synthesized using the same procedure.

N-{3-[3-(4-Methyl-benzo[b]thiophen-3-ylmethyl)-2-oxo-2,3-dihydro-benzimidazol-1-yl]-propionyl}-methanesulfonamide. LCMS (ESMS): m/z 444.00 (M+H$^+$)

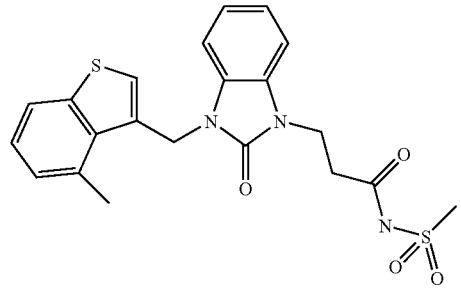 [SMILES: Cc1cccc2scc(Cn3c(=O)n(CCC(=O)NS(C)(=O)=O)c4ccccc43)c12]

Propane-2-sulfonic acid {3-[3-(4-methyl-benzo[b]thiophen-3-ylmethyl)-2-oxo-2,3-dihydro-benzimidazol-1-yl]-propionyl}-amide. LCMS (ESMS): m/z 472.07 (M+H$^+$)

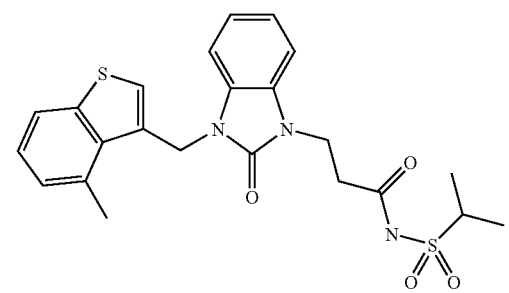

Propane-2-sulfonic acid amide

Propane-2-sulfonyl chloride (0.11 mL, 0.98 mmol) is added drop wise into the mixture of 28% NH$_4$OH in H$_2$O (2.0 mL) and CHCl$_3$ (2.0 mL) at room temperature. The mixture is stirred for 2 hrs at that temperature and then the solvents are removed under vacuum. THF (50 mL) is added into the residue to form a white suspension. The solid is filtered and the filtrate is concentrated to give 86 mg of propane-2-sulfonic acid amide which is used in the next step without further purification.

Example 17

2,2-Dimethyl-3-[3-(4-methyl-benzo[b]thiophen-3-ylmethyl)-2-oxo-2,3-dihydro-benzimidazol-1-yl]-propionic acid

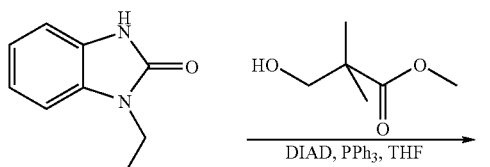

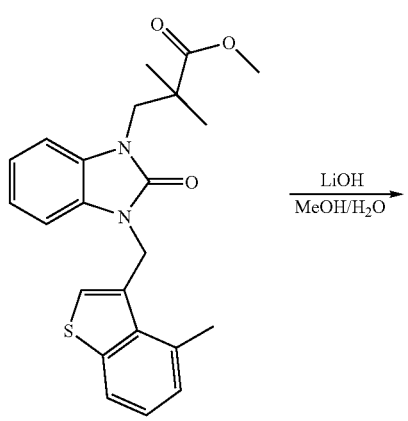

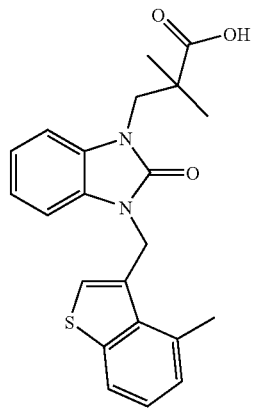

2,2-Dimethyl-3-[3-(4-methyl-benzo[b]thiophen-3-ylmethyl)-2-oxo-2,3-dihydro-benzimidazol-1-yl]-propionic acid methyl ester To a stirred solution of 1-(4-Methyl-benzo[b]thiophen-3-ylmethyl)-1,3-dihydro-benzimidazol-2-one (50 mg, 0.17 mmol), 3-Hydroxy-2,2-dimethyl-propionic acid methyl ester (0.026 mL, 0.20 mmol) and triphenylphosphine (53 mg, 0.20 mmol) in dry THF (1.5 mL) is added diisopropyl azodicarboxylate (0.041 mL, 0.20 mmol) in a drop wise manner. The mixture is stirred at room temperature for 40 hrs. Then the solvent is removed under vacuum and the residue is purified by two preparative TLC's (first one is developed with 30% EtOAc in Hexanes, second one is developed with 1% MeOH in CH$_2$Cl$_2$) to give 28 mg (41%) of 2,2-Dimethyl-3-[3-(4-methyl-benzo[b]thiophen-3-ylmethyl)-2-oxo-2,3-dihydro-benzimidazol-1-yl]-propionic acid methyl ester.

2,2-Dimethyl-3-[3-(4-methyl-benzo[b]thiophen-3-ylmethyl)-2-oxo-2,3-dihydro-benzimidazol-1-yl]-propionic acid Lithium hydroxide monohydrate (4.3 mg, 0.10 mmol) is dissolved in water (1.0 mL) and it is added into the solution of 2,2-Dimethyl-3-[3-(4-methyl-benzo[b]thiophen-3-ylmethyl)-2-oxo-2,3-dihydro-benzimidazol-1-yl]-propionic acid methyl ester (28 mg, 0.069 mmol) in 1,4-dioxane (2.0 mL) at room temperature. The mixture is stirred for 60 hr and LCMS then 1.0 M HCl solution (1.0 mL) is added followed by water (15 mL). Then the mixture is extracted with EtOAc (3×30 mL) and the organic layers are combined, dried over MgSO$_4$ and concentrated to give 25 mg (90%) of 2,2-Dimethyl-3-[3-(4-methyl-benzo[b]thiophen-3-ylmethyl)-2-oxo-2,3dihydro-benzimidazol-1-yl]propionic acid. LCMS (ESMS): m/z 395.17 (M+H$^+$).

Example 18

N-{3-[3-(4-Methyl-benzo[b]thiophen-3-ylmethyl)-2-oxo-2,3-dihydro-benzimidazol-1-yl]-hexanoyl}-benzenesulfonamide

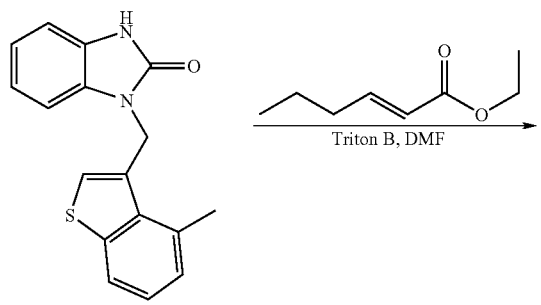

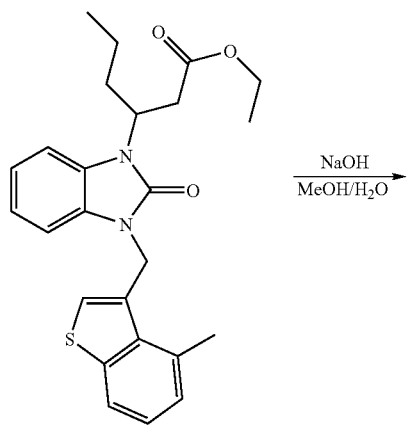

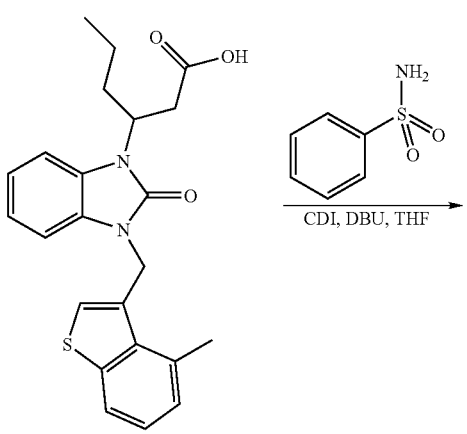

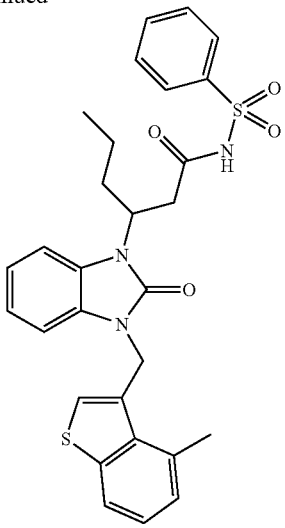

3-[3-(4-Methyl-benzo[b]thiophen-3-ylmethyl)-2-oxo-2,3-dihydro-benzimidazol-1-yl]hexanoic acid ethyl ester To a solution of 1-(4-Methyl-benzo[b]thiophen-3-ylmethyl)-1,3-dihydro-benzimidazol-2-one (50 mg, 0.17 mmol) in dry DMF (1.0 mL) are added (E)-Hex-2-enoic acid ethyl ester (27 mg, 0.19 mmol) and 40% benzyltrimethyl ammonium hydroxide in MeOH (0.008 mL, 0.017 mmol). The resulting mixture is warmed up to 60° C. for 16 hr. Then another 27 mg of (E)-Hex-2-enoic acid ethyl ester is added the heating is continued for another 8 hr. Then saturated NH$_4$Cl (2 mL) and water (10 mL) are added and the mixture is extracted with EtOAc (3×25 mL). The organic layers are combined, dried over MgSO$_4$ and concentrated to give the crude product. Purification with flash column chromatography using 20% EtOAc in Hexanes affords 70 mg (95%) of 3-[3-(4-Methyl-benzo[b]thiophen-3-ylmethyl)-2-oxo-2,3-dihydro-benzimidazol-1-yl]-hexanoic acid ethyl ester.

3-[3-(4-Methyl-benzo[b]thiophen-3-ylmethyl)-2-oxo-2,3-dihydro-benzimidazol-1-yl]-hexanoic acid To a solution of 3-[3-(4-Methyl-benzo[b]thiophen-3-ylmethyl)-2-oxo-2,3-dihydro-benzimidazol-1-yl]-hexanoic acid ethyl ester (65 mg, 0.15 mmol) in MeOH (3.0 mL) is added 2.0 N NaOH (0.5 mL). The reaction mixture is stirred at room temperature for 3.5 h and then 1.0M HCl (1.5 mL) and water (50 mL) are added. The mixture is extracted with EtOAc (3×50 mL). The organic layers are combined, dried over MgSO$_4$ and concentrated to give crude product. Purification by flash column chromatography affords 56 mg (92%) of 3-[3-(4-Methyl-benzo[b]thiophen-3-ylmethyl)-2-oxo-2,3-dihydro-benzimidazol-1-yl]-hexanoic acid.

N-{3-[3-(4-Methyl-benzo[b]thiophen-3-ylmethyl)-2-oxo-2,3-dihydro-benzimidazol-1-yl]-hexanoyl-benzenesulfonamide 3-[3-(4-Methyl-benzo[b]thiophen-3-ylmethyl)-2-oxo-2,3-dihydro-benzimidazol-1-yl]-hexanoic acid (56 mg, 0.14 mmol) is dissolved in dry THF (1.0 mL) and 1,1'-carbonyl diimidazole (50 mg, 0.29 mmol) is added into it at room temperature. The mixture is stirred for 30 min and then it is heated at 55° C. for 1 hr. After the mixture is cooled down to room temperature, benzenesulfonamide (46 mg, 0.29 mmol)

is added and after 10 min, 1,8-diazabicyclo[5,4,0]undec-7-ene (0.044 mL, 0.29 mmol) is added. The mixture is stirred for 3 hr at room temperature. Then 1.0 M HCl (3 mL) is added followed by water (30 mL). The mixture is extracted with EtOAc (3×50 mL) and the organic layers are combined, dried and concentrated to give crude product. Purification by preparative TLC using 2% MeOH in CH$_2$Cl$_2$ affords 63 mg (84%) of N-{3-[3-(4-Methyl-benzo[b]thiophen-3-ylmethyl)-2-oxo-2,3-dihydro-benzimidazol-1-yl]hexanoyl}-benzenesulfonamide. LCMS (ESMS): m/z 548.11 (M+H$^+$).

The following compounds are synthesized using the same procedure.

N-{3-[3-(4-Methyl-benzo[b]thiophen-3-ylmethyl)-2-oxo-2,3-dihydro-benzimidazol-1-yl]-hexanoyl}-methanesulfonamide. LCMS (ESMS): m/z 486.29 (M+H$^+$)

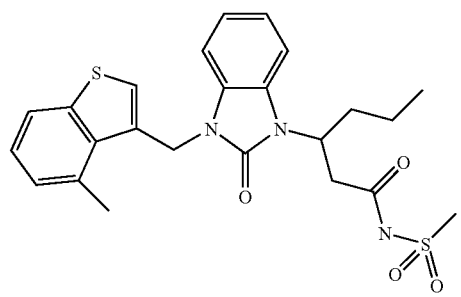 [SMILES: CCCC(CC(=O)NS(C)(=O)=O)n1c(=O)n(Cc2csc3cccc(C)c23)c2ccccc21]

Cyclopropanesulfonic acid {3-[3-(4-methyl-benzo[b]thiophen-3-ylmethyl)-2-oxo-2,3-dihydro-benzimidazol-1-yl]-hexanoyl}-amide. LCMS (ESMS): m/z 512.26 (M+H$^+$)

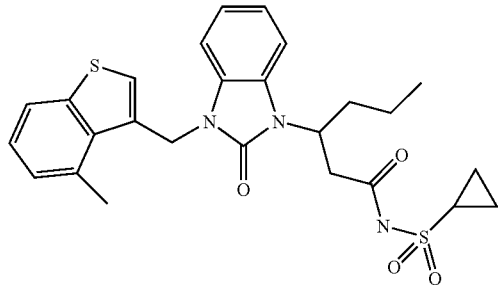 [SMILES: CCCC(CC(=O)NS(=O)(=O)C1CC1)n1c(=O)n(Cc2csc3cccc(C)c23)c2ccccc21]

Pyridine-3-sulfonic acid (3-[3-(4-methyl-benzo[b]thiophen-3-ylmethyl)-2-oxo-2,3-dihydro-benzimidazol-1-yl]-hexanoyl}-amide. LCMS (ESMS): m/z 549.16 (M+H$^+$)

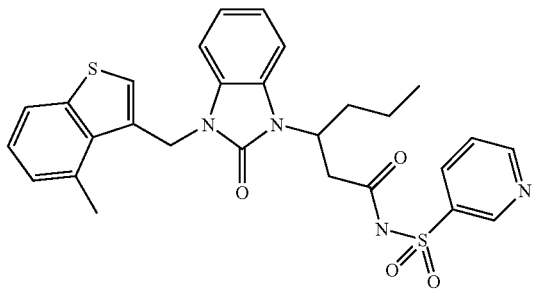 [SMILES: CCCC(CC(=O)NS(=O)(=O)c1cccnc1)n1c(=O)n(Cc2csc3cccc(C)c23)c2ccccc21]

4-Methoxy-N-{3-[3-(4-methyl-benzo[b]thiophen-3-ylmethyl)-2-oxo-2,3-dihydro-benzimidazol-1-yl]-hexanoyl}-benzenesulfonamide. LCMS (ESMS): m/z 578.21 (M+H$^+$)

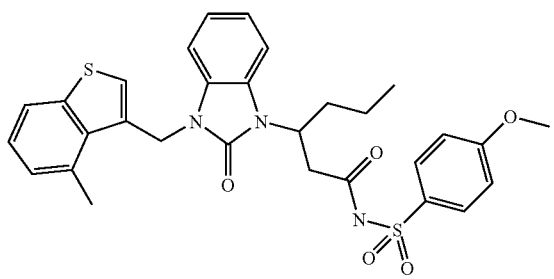 [SMILES: CCCC(CC(=O)NS(=O)(=O)c1ccc(OC)cc1)n1c(=O)n(Cc2csc3cccc(C)c23)c2ccccc21]

3-Methoxy-N-{3-[3-(4-methyl-benzo[b]thiophen-3-ylmethyl)-2-oxo-2,3-dihydro-benzimidazol-1-yl]-hexanoyl}-benzenesulfonamide. LCMS (ESMS): m/z 578.19 (M+H$^+$)

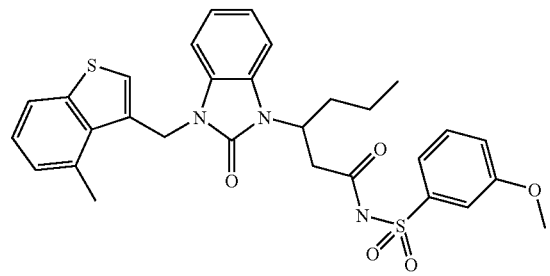 [SMILES: CCCC(CC(=O)NS(=O)(=O)c1cccc(OC)c1)n1c(=O)n(Cc2csc3cccc(C)c23)c2ccccc21]

Pyridine-2-sulfonic acid {3-[3-(4-methyl-benzo[b]thiophen-3-ylmethyl)-2-oxo-2,3-dihydro-benzimidazol-1-yl]-hexanoyl}-amide. LCMS (ESMS): m/z 549.25 (M+H$^+$)

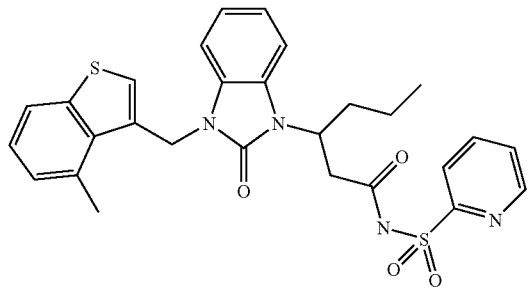 [SMILES: CCCC(CC(=O)NS(=O)(=O)c1ccccn1)n1c(=O)n(Cc2csc3cccc(C)c23)c2ccccc21]

259

2-Methoxy-N-{3-[3-(4-methyl-benzo[b]thiophen-3-ylmethyl)-2-oxo-2,3-dihydro-benzimidazol-1-yl]-hexanoyl}-benzenesulfonamide. LCMS (ESMS): m/z 578.35 (M+H$^+$)

260

3-Fluoro-N-(3-{3-[4-((Z)-1-methyl-propenyl)-5-vinyl-thiophen-3-ylmethyl]-2-oxo-2,3-dihydro-benzimidazol-1-yl}-hexanoyl)-benzenesulfonamide. LCMS (ESMS): m/z 566.17 (M+H$^+$)

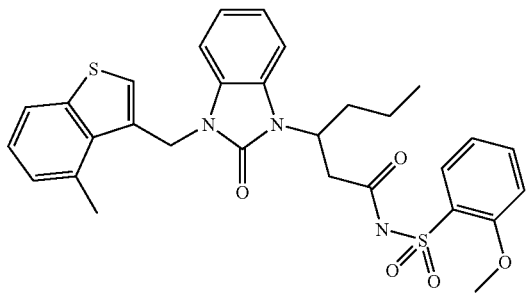 [SMILES: CCCC(CC(=O)NS(=O)(=O)c1ccccc1OC)n1c(=O)n(Cc2csc3cccc(C)c23)c2ccccc21]

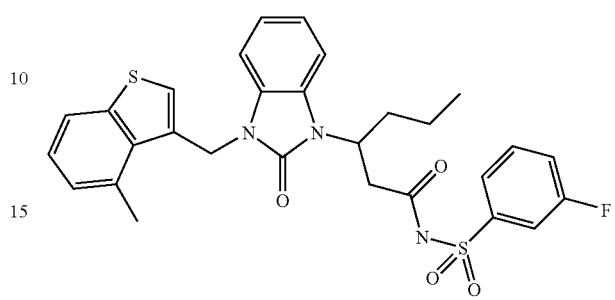

2-Fluoro-N-{3-[3-(4-methyl-benzo[b]thiophen-3-ylmethyl)-2-oxo-2,3-dihydro-benzimidazol-1-yl]-hexanoyl}-benzenesulfonamide. LCMS (ESMS): m/z 566.28 (M+H$^+$)

3-{3-[(4-methyl-1-benzothien-3-yl)methyl]-2-oxo-2,3-dihydro-1H-benzimidazol-1-yl}-N-[(1-methyl-1H-imidazol-4-yl)sulfonyl]hexanamide. LCMS (ESMS): m/z 552.20 (M+H$^+$)

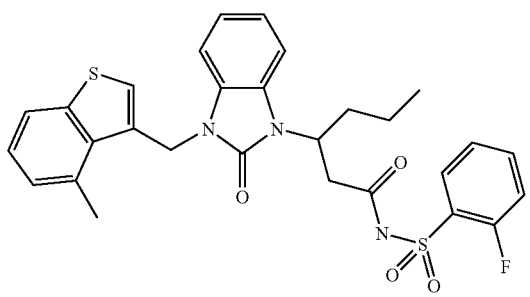 [SMILES: CCCC(CC(=O)NS(=O)(=O)c1ccccc1F)n1c(=O)n(Cc2csc3cccc(C)c23)c2ccccc21]

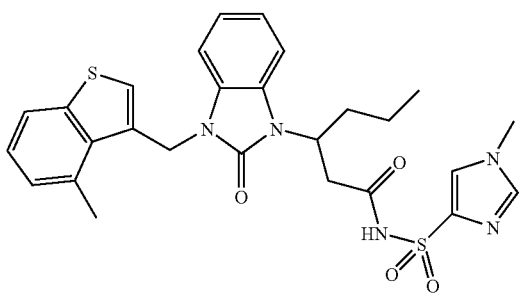 [SMILES: CCCC(CC(=O)NS(=O)(=O)c1cn(C)cn1)n1c(=O)n(Cc2csc3cccc(C)c23)c2ccccc21]

N-[(1,2-dimethyl-1H-imidazol-4-yl)sulfonyl]-3-{3-[(4-methyl-1-benzothien-3-yl)methyl]-2-oxo-2,3-dihydro-1H-benzimidazol-1-yl}hexanamide. LCMS (ESMS): m/z 566.24 (M+H$^+$)

4-Fluoro-N-{3-[3-(4-methyl-benzo[b]thiophen-3-ylmethyl)-2-oxo-2,3-dihydro-benzimidazol-1-yl]-hexanoyl}-benzenesulfonamide. LCMS (ESMS): m/z 566.17 (M+H$^+$)

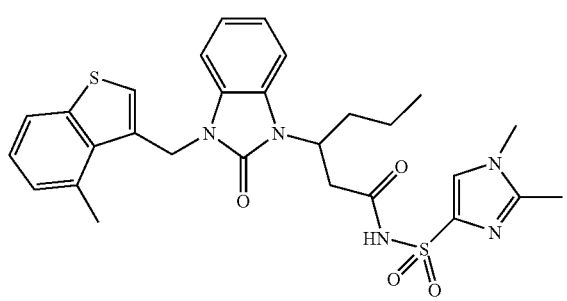 [SMILES: CCCC(CC(=O)NS(=O)(=O)c1cn(C)c(C)n1)n1c(=O)n(Cc2csc3cccc(C)c23)c2ccccc21]

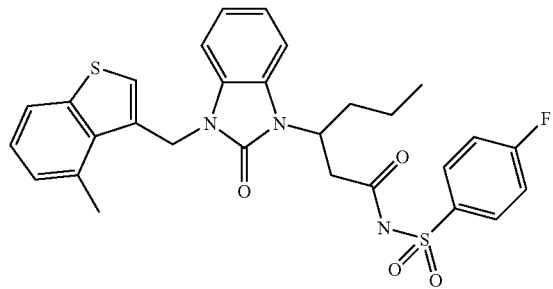

The following compounds were prepared following the same procedure using the acids that were synthesized in Example 6.

261

4-{3-[(4-methyl-1-benzothien-3-yl)methyl]-2-oxo-2,3-dihydro-1H-benzimidazol-1-yl}-N-(phenylsulfonyl)butanamide. LCMS (ESMS): m/z 520.09 (M+H$^+$)

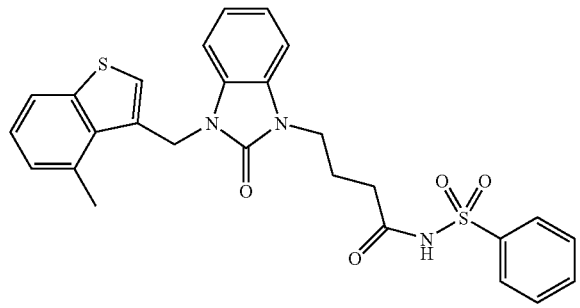 [SMILES: Cc1cccc2scc(Cn3c(=O)n(CCCC(=O)NS(=O)(=O)c4ccccc4)c4ccccc43)c12]

2-{3-[(4-methyl-1-benzothien-3-yl)methyl]-2-oxo-2,3-dihydro-1H-benzimidazol-1-yl}-N-(phenylsulfonyl)acetamide. LCMS (ESMS): m/z 492.15 (M+H$^+$)

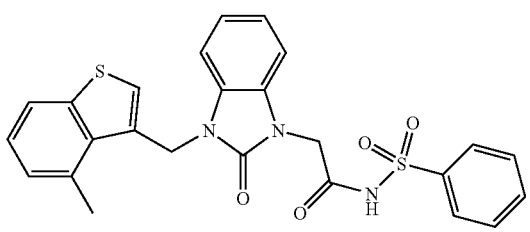 [SMILES: Cc1cccc2scc(Cn3c(=O)n(CC(=O)NS(=O)(=O)c4ccccc4)c4ccccc43)c12]

The following compounds were prepared following the same procedure using the acids that were synthesized in Example 11.

3-{3-[(1,4-dimethyl-1H-indol-3-yl)methyl]-6-methyl-2-oxo-2,3-dihydro-1H-benzimidazol-1-yl}-N-(phenylsulfonyl)hexanamide. LCMS (ESMS): m/z 559.31 (M+H$^+$)

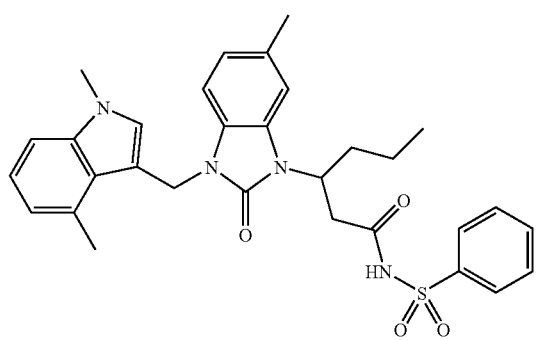 [SMILES: CCCC(CC(=O)NS(=O)(=O)c1ccccc1)n1c(=O)n(Cc2cn(C)c3cccc(C)c23)c2ccc(C)cc21]

262

N-(tert-butylsulfonyl)-3-{3-[(1,4-dimethyl-1H-indol-3-yl)methyl]-6-methyl-2-oxo-2,3-dihydro-1H-benzimidazol-1-yl}hexanamide. LCMS (ESMS): m/z 539.36 (M+H$^+$)

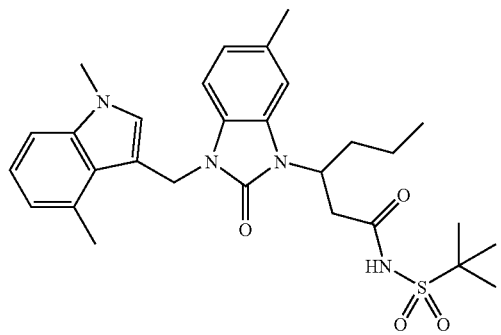 [SMILES: CCCC(CC(=O)NS(=O)(=O)C(C)(C)C)n1c(=O)n(Cc2cn(C)c3cccc(C)c23)c2ccc(C)cc21]

3-{3-[(1,4-dimethyl-1H-indol-3-yl)methyl]-6-methyl-2-oxo-2,3-dihydro-1H-benzimidazol-1-yl}-N-(ethylsulfonyl)hexanamide. LCMS (ESMS): m/z 511.25 (M+H$^+$)

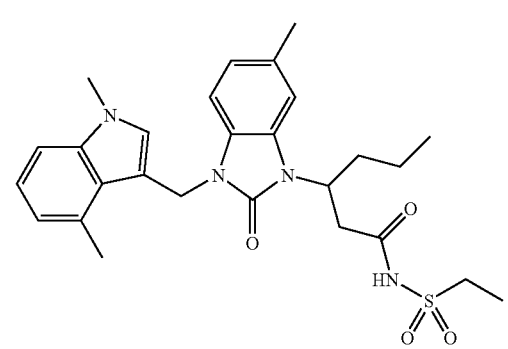 [SMILES: CCCC(CC(=O)NS(=O)(=O)CC)n1c(=O)n(Cc2cn(C)c3cccc(C)c23)c2ccc(C)cc21]

Example 19

1-(4-Methyl-benzo[b]thiophen-3-ylmethyl)-3-[2-(1H-tetrazol-5-yl)-ethyl]-1,3-dihydro-benzimidazol-2-one

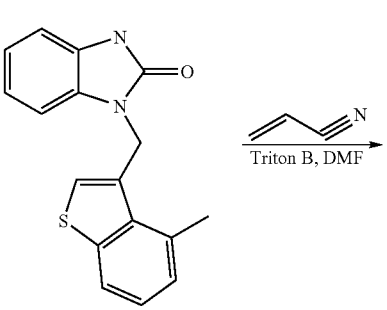

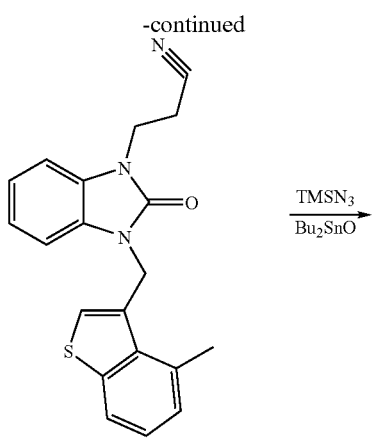

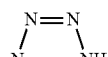

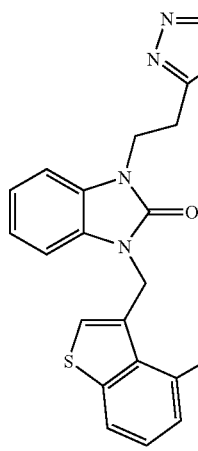

3-[3-(4-Methyl-benzo[b]thiophen-3-ylmethyl)-2-oxo-2,3-dihydro-benzimidazol-1-yl]-propionitrile To a solution of 1-(4-Methyl-benzo[b]thiophen-3-ylmethyl)-1,3-dihydro-benzimidazol-2-one (50 mg, 0.17 mmol) in dry DMF (1.0 mL) are added acrylonitrile (0.012 mL, 0.19 mmol) and 40% benzyltrimethyl ammonium hydroxide in MeOH (0.008 mL, 0.017 mmol). The resulting mixture is stirred at room temperature for 2 hr and then Sat. NH$_4$Cl (2 mL) is added along with water (30 mL). Then the mixture is extracted with EtOAc (3×30 mL). The organic layers are combined, dried over MgSO$_4$ and concentrated to give crude product. Purification by flash column chromatography affords 58 mg (98%) of 3-[3-(4-Methyl-benzo[b]thiophen-3-ylmethyl)-2-oxo-2,3-dihydro-benzimidazol-1-yl]-propionitrile.

1-(4-Methyl-benzo[b]thiophen-3-ylmethyl)-3-[2-(1H-tetrazol-5-yl)-ethyl]-1,3-dihydro-benzimidazol-2-one 3-[3-(4-Methyl-benzo[b]thiophen-3-ylmethyl)-2-oxo-2,3-dihydro-benzimidazol-1-yl]-propionitrile (58 mg, 0.17 mmol), azidotrimethylsilane (0.047 mL, 0.33 mmol) and dibutyltin oxide (4.2 mg, 0.017 mmol) are dissolved in dry DMF (2.0 mL) in microwave vial. It is then heated at 150° C. for 2 hrs in microwave reactor. Then another 0.05 mL of azidotrimethylsilane and 4.0 mg of dibutyltin oxide are added and the mixture is heated for another 2 hr at 150° C. in microwave reactor. Then water (2 mL) is added and the mixture is extracted with EtOAc (2×30 mL). The organic layers are combined and extracted with 2.0M NaOH (2×30 mL). The NaOH layers are combined and washed with EtOAc (30 mL). Then the NaOH layers are acidified with 1.0M HCl to pH=3 and it is then extracted with EtOAc (2×30 mL). All the organic layers are combined, dried (MgSO$_4$) and concentrated to give crude product. Purification by preparative TLC using 3% MeOH in CH$_2$Cl$_2$ affords 15 mg (65%) of 1-(4-Methyl-benzo[b]thiophen-3-ylmethyl)-3-[2-(1H-tetrazol-5-yl)-ethyl]-1,3-dihydro-benzimidazol-2-one. LCMS (ESMS): m/z 391.07 (M+H$^+$).

Example 20

5-Hydroxy-3-[3-(4-methyl-benzo[b]thiophen-3-ylmethyl)-2-oxo-2,3-dihydro-benzimidazol-1-yl]-pentanoic acid

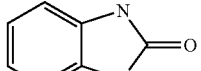

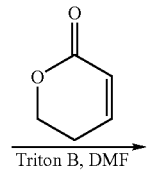

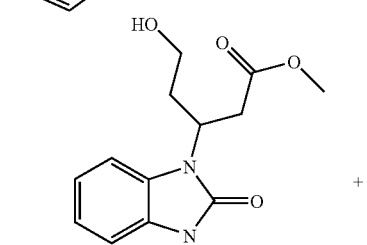

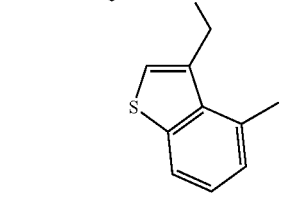

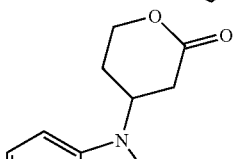

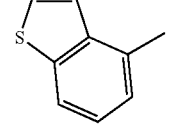

-continued

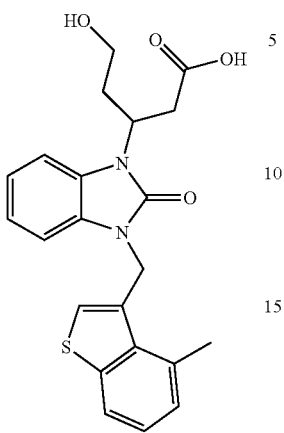

5-Hydroxy-3-[3-(4-methyl-benzo[b]thiophen-3-ylmethyl)-2-oxo-2,3-dihydro-benzimidazol-1-yl]-pentanoic acid methyl ester and 1-(4-Methyl-benzo[b]thiophen-3-ylmethyl)-3-(2-oxo-tetrahydro-pyran-4-yl)-1,3-dihydro-benzimidazol-2-one To a solution of 1-(4-Methyl-benzo[b]thiophen-3-ylmethyl)-1,3-dihydro-benzimidazol-2-one (50 mg, 0.17 mmol) in DMF (0.7 mL) are added 5,6-Dihydro-pyran-2-one (0.059 mL, 0.68 mmol) and 40% benzyltrimethyl ammonium hydroxide in MeOH (0.008 mL, 0.017 mmol). The resulting mixture is stirred for 5 days and then saturated NH$_4$Cl (2 mL) and water (30 mL) are added. The mixture is extracted with EtOAc (3×35 mL). The organic layers are combined, dried over MgSO$_4$ and concentrated to give the crude product. Purification with flash column chromatography using EtOAc in Hexane afforded 51 mg of mixture of 5-Hydroxy-3-[3-(4-methyl-benzo[b]thiophen-3-ylmethyl)-2-oxo-2,3-dihydro-benzimidazol-1-yl]-pentanoic acid methyl ester and 1-(4-Methyl-benzo[b]thiophen-3-ylmethyl)-3-(2-oxo-tetrahydro-pyran-4-yl)-1,3-dihydro-benzimidazol-2-one. They are used in the next step without further separation.

5-Hydroxy-3-[3-(4-methyl-benzo[b]thiophen-3-ylmethyl)-2-oxo-2,3-dihydro-benzimidazol-1-yl]-pentanoic acid 5-Hydroxy-3-[3-(4-methyl-benzo[b]thiophen-3-ylmethyl)-2-oxo-2,3-dihydro-benzimidazol-1-yl]-pentanoic acid methyl ester and 1-(4-Methyl-benzo[b]thiophen-3-ylmethyl)-3-(2-oxo-tetrahydro-pyran-4-yl)-1,3-dihydro-benzimidazol-2-one (51 mg) are dissolved in 1,4-dioxane (2.5 mL). Then 1.0 N NaOH solution (2.0 mL) is added and the mixture is stirred for 2 hr. Then 1.0 M HCl (3.0 mL) is added to make it acidic and the mixture is extracted with EtOAc (3×35 mL). The organic layers are combined, dried and concentrated to give crude product. Purification by preparative TLC using 7.5% MeOH in CH$_2$Cl$_2$ affords 43 mg (62% for two steps) of 5-Hydroxy-3-[3-(4-methyl-benzo[b]thiophen-3-ylmethyl)-2-oxo-2,3-dihydro-benzimidazol-1-yl]-pentanoic acid. LCMS (ESMS): m/z 411.07 (M+H$^+$).

Example 21

3-[3-(4-Methyl-benzo[b]thiophen-3-ylmethyl)-2-oxo-2,3-dihydro-benzimidazol-1-yl]-pentanedioic acid monomethyl ester

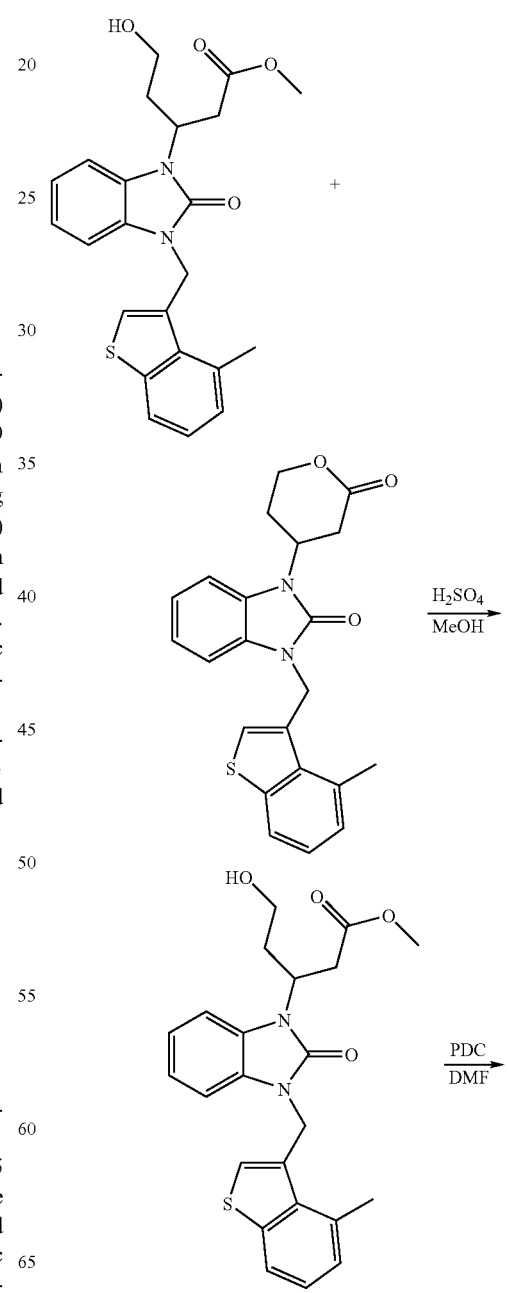

-continued

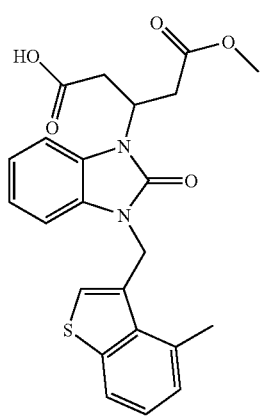

5-Hydroxy-3-[3-(4-methyl-benzo[b]thiophen-3-ylmethyl)-2-oxo-2,3-dihydro-benzimidazol-1-yl]-pentanoic acid methyl ester The crude mixture of 5-Hydroxy-3-[3-(4-methyl-benzo[b]thiophen-3-ylmethyl)-2-oxo-2,3-dihydro-benzimidazol-1-yl]-pentanoic acid methyl ester and 1-(4-Methyl-benzo[b]thiophen-3-ylmethyl)-3-(2-oxo-tetrahydro-pyran-4-yl)-1,3-dihydro-benzimidazol-2-one (320 mg) is dissolved in MeOH (30 mL) and then one drop of concentrated $H_2SO_4$ is added. The mixture is stirred at room temperature for 30 min, and sat. $NaHCO_3$ (2 mL) along with water (20 mL) are added. The mixture is then extracted with EtOAc (3×40 mL). The organic layers are combined, dried ($MgSO_4$) and concentrated to give crude product. Purification by flash column chromatography using EtOAc in Hexane affords 70 mg (25% for two steps) of 5-Hydroxy-3-[3-(4-methyl-benzo[b]thiophen-3-ylmethyl)-2-oxo-2,3-dihydro-benzimidazol-1-yl]-pentanoic acid methyl ester.

3-[3-(4-Methyl-benzo[b]thiophen-3-ylmethyl)-2-oxo-2,3-dihydro-benzimidazol-1-yl]-pentanedioic acid monomethyl ester 5-Hydroxy-3-[3-(4-methyl-benzo[b]thiophen-3-ylmethyl)-2-oxo-2,3-dihydro-benzimidazol-1-yl]pentanoic acid methyl ester (70 mg, 0.17 mmol) is dissolved in DMF (1.5 mL) at room temperature and pyridinium dichromate (250 mg, 0.66 mmol) is added into it. The mixture is stirred for 20 hr and water (25 mL) is added. The pH of the solution is adjusted to pH 5 by adding acetic acids and the mixture is extracted with EtOAc (3×50 mL). The organic layers are combined, dried and concentrated to give crude product. Purification by preparative TLC using 80% EtOAc in Hexanes with 1% acetic acid affords 48 mg (66%) of 3-[3-(4-Methyl-benzo[b]thiophen-3-ylmethyl)-2-oxo-2,3-dihydro-benzimidazol-1-yl]-pentanedioic acid monomethyl ester. LCMS (ESMS): m/z 439.17 (M+H$^+$).

Example 22

3-[3-(4-Methyl-benzo[b]thiophen-3-ylmethyl)-2-oxo-2,3-dihydro-benzimidazol-1-yl]-pentanedioic acid

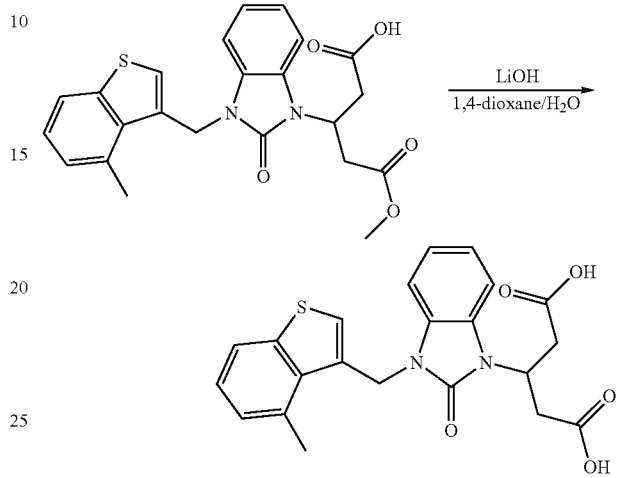

3-[3-(4-Methyl-benzo[b]thiophen-3-ylmethyl)-2-oxo-2,3-dihydro-benzimidazol-1-yl]-pentanedioic acid Lithium hydroxide monohydrate (7.2 mg, 0.17 mmol) is dissolved in water (1.0 mL) and it is added into the solution of 3-[3-(4-Methyl-benzo[b]thiophen-3-ylmethyl)-2-oxo-2,3-dihydro-benzimidazol-1-yl]-pentanedioic acid monomethyl ester (25 mg, 0.057 mmol) in methanol (1.0 mL) at room temperature. The mixture is stirred for 2 hr and then 1.0 M HCl solution (0.5 mL) is added along with water (10 mL). The mixture is extracted with EtOAc (3×10 mL) and the organic layers are combined, dried over $MgSO_4$ and concentrated to give crude product. Purification by preparative TLC using 5% MeOH in $CH_2Cl_2$ with 1% acetic acid afforded 21 mg (87%) of 3-[3-(4-Methyl-benzo[b]thiophen-3-ylmethyl)-2-oxo-2,3-dihydro-benzimidazol-1-yl]-pentanedioic acid. LCMS (ESMS): m/z 425.22 (M+H$^+$).

Example 23

3-[3-(4-Methyl-benzo[b]thiophen-3-ylmethyl)-2-oxo-2,3-dihydro-benzimidazol-1-yl]-hexanoic acid benzylamide

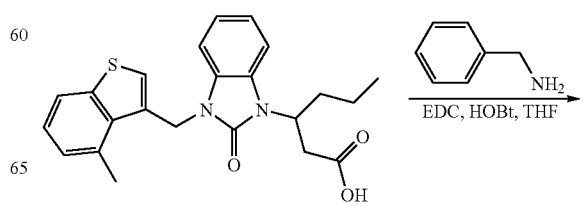

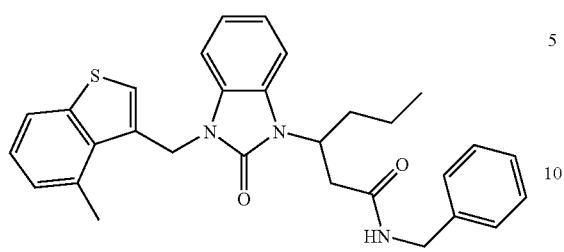

3-[3-(4-Methyl-benzo[b]thiophen-3-ylmethyl)-2-oxo-2,3-dihydro-benzimidazol-1-yl]-hexanoic acid benzylamide To the suspension of 3-[3-(4-Methyl-benzo[b]thiophen-3-ylmethyl)-2-oxo-2,3-dihydro-benzimidazol-1-yl]-hexanoic acid (20 mg, 0.049 mmol) in THF (1.0 mL) at room temperature are added benzyl amine (0.027 mL, 0.245 mmol) and 1-hydroxybenzotriazole (32 mg, 0.24 mmol). Then N-(3-dimethylaminopropyl)-N'-ethylcarbodiimide (40 mg, 0.21 mmol) is added and the reaction mixture is stirred for 16 hr. Water (5 mL) is added and the mixture is extracted with EtOAc (3×10 mL). The organic layers are combined, dried over MgSO$_4$ and concentrated to give crude product. The crude is filtered through a short path of silica gel eluting first with CH$_2$Cl$_2$ then with 50% EtOAc in hexanes to give 23 mg (95%) of 3-[3-(4-Methyl-benzo[b]thiophen-3-ylmethyl)-2-oxo-2,3-dihydro-benzimidazol-1-yl]-hexanoic acid benzylamide. LCMS (ESMS): m/z 498.22 (M+H$^+$).

Example 24

N-{3-Ethoxy-3-[3-(4-methyl-benzo[b]thiophen-3-ylmethyl)-2-oxo-2,3-dihydro-benzimidazol-1-yl]propionyl}-benzenesulfonamide

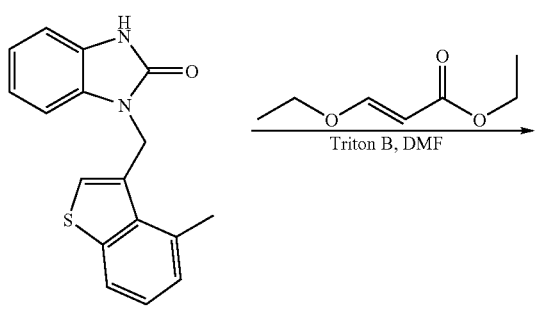

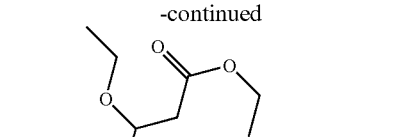

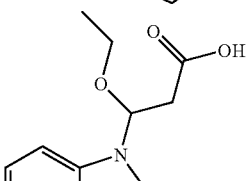

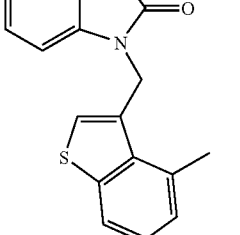

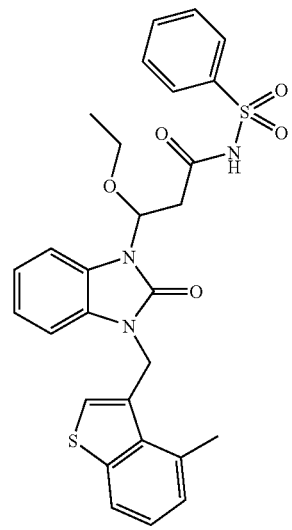

3-Ethoxy-3-[3-(4-methyl-benzo[b]thiophen-3-ylmethyl)-2-oxo-2,3-dihydro-benzimidazol-1-yl]-propionic acid ethyl ester To a solution of 1-(4-Methyl-benzo[b]thiophen-3-ylmethyl)-1,3-dihydro-benzimidazol-2-one (50 mg, 0.17 mmol) in dry DMF (0.7 mL) are added (E)-3-Ethoxy-acrylic acid ethyl ester (0.049 mL, 0.34 mmol) and 40% benzyltrimethyl ammonium hydroxide in MeOH (0.008 mL, 0.017 mmol). The resulting mixture is warmed up to 60° C. for 16 hr and then saturated NH$_4$Cl solution (1 mL) is added followed by water (5 mL). The mixture is extracted with EtOAc (3×10 mL). The organic layers are combined, dried and concentrated to give crude product. Purification by flash column chromatography using EtOAc in hexane (from 0% to 30%)

affords 50 mg (67%) of 3-Ethoxy-3-[3-(4-methyl-benzo[b]thiophen-3-ylmethyl)-2-oxo-2,3-dihydro-benzimidazol-1-yl]-propionic acid ethyl ester.

3-Ethoxy-3-[3-(4-methyl-benzo[b]thiophen-3-ylmethyl)-2-oxo-2,3-dihydro-benzimidazol-1-yl]-propionic acid To a solution of 3-Ethoxy-3-[3-(4-methyl-benzo[b]thiophen-3-ylmethyl)-2-oxo-2,3-dihydro-benzimidazol-1-yl]-propionic acid ethyl ester (50 mg, 0.11 mmol) in MeOH (3.0 mL) is added 2.0 N NaOH solution (1.0 mL). The reaction mixture is stirred at room temperature for 2 h. Then 1.0 M HCl solution (3.0 mL) and water (10 mL) are added and the reaction mixture is extracted with EtOAc (3×20 mL). The organic layers are combined, dried and concentrated to give 45 mg (96%) of the crude 3-Ethoxy-3-[3-(4-methyl-benzo[b]thiophen-3-ylmethyl)-2-oxo-2,3-dihydro-benzimidazol-1-yl]-propionic acid which is used in the next step without further purification.

N-{3-Ethoxy-3-[3-(4-methyl-benzo[b]thiophen-3-ylmethyl)-2-oxo-2,3-dihydro-benzimidazol-1-yl]-propionyl}-benzenesulfonamide 3-Ethoxy-3-[3-(4-methyl-benzo[b]thiophen-3-ylmethyl)-2-oxo-2,3-dihydro-benzimidazol-1-yl]-propionic acid (45 mg, 0.11 mmol) is dissolved in dry THF (1.0 mL) and 1,1'-carbonyl diimidazole (40 mg, 0.25 mmol) is added into it at room temperature. The mixture is stirred for 30 min and then it is heated at 55° C. for 1 hr. After the mixture is cooled down to room temperature, benzenesulfonamide (34 mg, 0.22 mmol) is added and after 10 min, 1,8-diazabicyclo[5,4,0]undec-7-ene (0.033 mL, 0.22 mmol) is added. The mixture is stirred for 4 hr at room temperature and 1.0 M HCl solution (3 mL) is added followed by water (30 mL). The mixture is extracted with EtOAc (3×50 mL) and the organic layers are combined, dried and concentrated to give crude product. Purification by preparative TLC using 6% MeOH in $CH_2Cl_2$ with 1.0% concentrated aqueous $NH_4OH$ solution (28%) affords 22 mg (36%) of N-{3-Ethoxy-3-[3-(4-methyl-benzo[b]thiophen-3-ylmethyl)-2-oxo-2,3-dihydro-benzimidazol-1-yl]-propionyl}-benzenesulfonamide. LCMS (ESMS): m/z 550.15 (M+H$^+$).

Example 25

2-[3-(4-Methyl-benzo[b]thiophen-3-ylmethyl)-2-oxo-2,3-dihydro-benzimidazol-1-yl]-ethanesulfonic acid phenyl ester

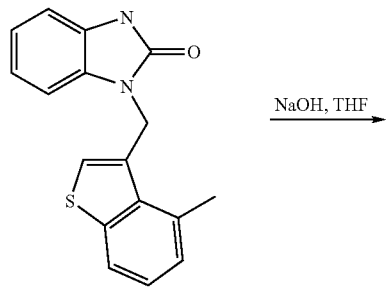

NaOH, THF

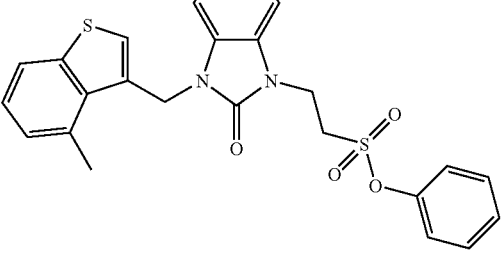

2-[3-(4-Methyl-benzo[b]thiophen-3-ylmethyl)-2-oxo-2,3-dihydro-benzimidazol-1-yl]-ethanesulfonic acid phenyl ester To a solution of 1-(4-Methyl-benzo[b]thiophen-3-ylmethyl)-1,3-dihydro-benzimidazol-2-one (50 mg, 0.17 mmol) in THF (1.0 mL) are added Ethenesulfonic acid phenyl ester (63 mg, 0.34 mmol) and solid NaOH (14 mg, 0.34 mmol). The resulting suspension is stirred at room temperature for 0.5 hr and it turned into clear solution in about 10 min. Then saturated $NH_4Cl$ solution (5.0 mL) is added along with water (5 mL). The mixture is extracted with EtOAc (3×20 mL). The organic layers are combined, dried ($MgSO_4$) and concentrated to give crude product. Purification by flash column chromatography using EtOAc in Hexanes (from 0% to 30%) affords 61 mg (75%) of 2-[3-(4-Methyl-benzo[b]thiophen-3-ylmethyl)-2-oxo-2,3-dihydro-benzimidazol-1-yl]-ethanesulfonic acid phenyl ester. LCMS (ESMS): m/z 479.11 (M+H$^+$).

Example 26

N-Methyl-N-{3-[3-(4-methyl-benzo[b]thiophen-3-ylmethyl)-2-oxo-2,3-dihydro-benzimidazol-1-yl]-hexanoyl}-benzenesulfonamide

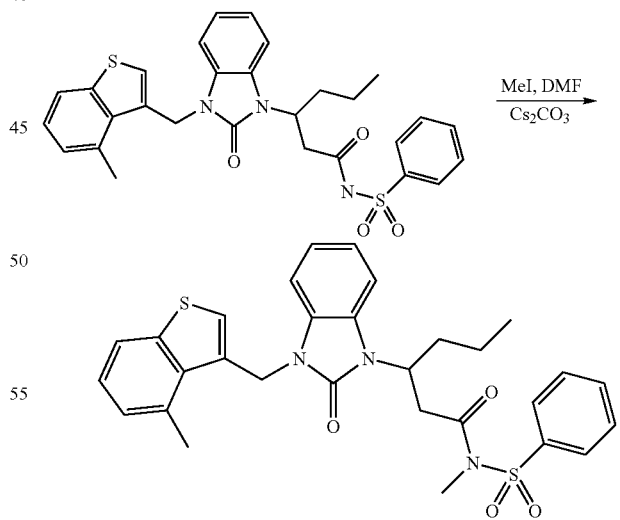

N-Methyl-N-{3-[3-(4-methyl-benzo[b]thiophen-3-ylmethyl)-2-oxo-2,3-dihydro-benzimidazol-1-yl]-hexanoyl}-benzenesulfonamide N-{3-[3-(4-Methyl-benzo[b]thiophen-3-ylmethyl)-2-oxo-2,3-dihydro-benzimidazol-1-yl]-hexanoyl}-benzenesulfonamide (33 mg, 0.061 mmol) and Iodomethane (0.015 mL, 0.24 mmol) are added into DMF (1.0 mL) at room temperature. Then cesium carbonate (80 mg, 0.24 mmol) is added and the mixture is warmed up to 65° C. for 10 min. Then it is cooled down to room temperature for 16 hrs. Saturated NH₄Cl solution (3.0 mL) and water (10 mL) are added and the mixture is extracted with EtOAc (3×20 mL). The organic layers are combined, dried (MgSO₄) and concentrated to give crude product. Purification by flash column chromatography using EtOAc in hexanes (from 0% to 30%) affords 24 mg (71%) of N-Methyl-N-{3-[3-(4-methyl-benzo[b]thiophen-3-ylmethyl)-2-oxo-2,3-dihydro-benzimidazol-1-yl]-hexanoyl}-benzenesulfonamide. LCMS (ESMS): m/z 562.19 (M+H⁺).

Example 27

2-[3-(4-Methyl-benzo[b]thiophen-3-ylmethyl)-2-oxo-2,3-dihydro-benzimidazol-1-yl]-ethanesulfonic acid

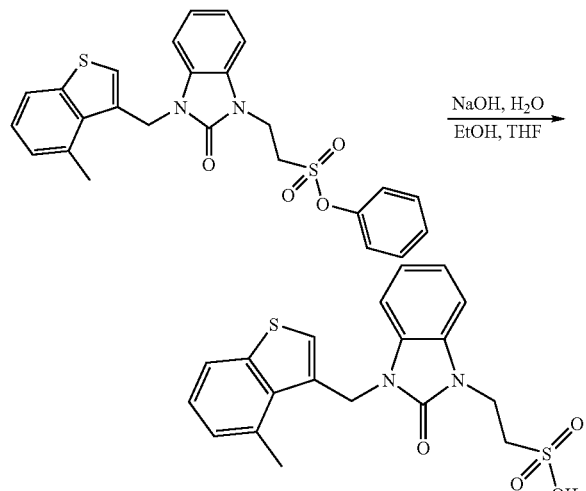

2-[3-(4-Methyl-benzo[b]thiophen-3-ylmethyl)-2-oxo-2,3-dihydro-benzimidazol-1-yl]-ethanesulfonic acid 2-[3-(4-Methyl-benzo[b]thiophen-3-ylmethyl)-2-oxo-2,3-dihydro-benzimidazol-1-yl]-ethanesulfonic acid phenyl ester (25 mg, 0.052 mmol) is dissolved in ethanol (1.0 mL) and THF (1.0 mL), 2.0N NaOH solution (1.0 mL) is added into it and the mixture is warmed up to 80° C. for 3 hr. Then 1.0 M HCl solution (5.0 mL) is added along with water (15 mL). The mixture is extracted with EtOAc (3×35 mL) and the organic layers are combined, dried (MgSO₄) and concentrated to give crude product. The crude is then dissolved in 10% MeOH in CH₂Cl₂ and purified by column chromatography eluting with 10% MeOH in CH₂Cl₂ to give 12 mg (58%) of 2-[3-(4-Methyl-benzo[b]thiophen-3-ylmethyl)-2-oxo-2,3-dihydro-benzimidazol-1-yl]-ethanesulfonic acid. LCMS (ESMS): m/z 403.08 (M+H⁺).

Example 28

2-[3-(4-Methyl-benzo[b]thiophen-3-ylmethyl)-2-oxo-2,3-dihydro-benzimidazol-1-yl]-ethanesulfonic acid amide

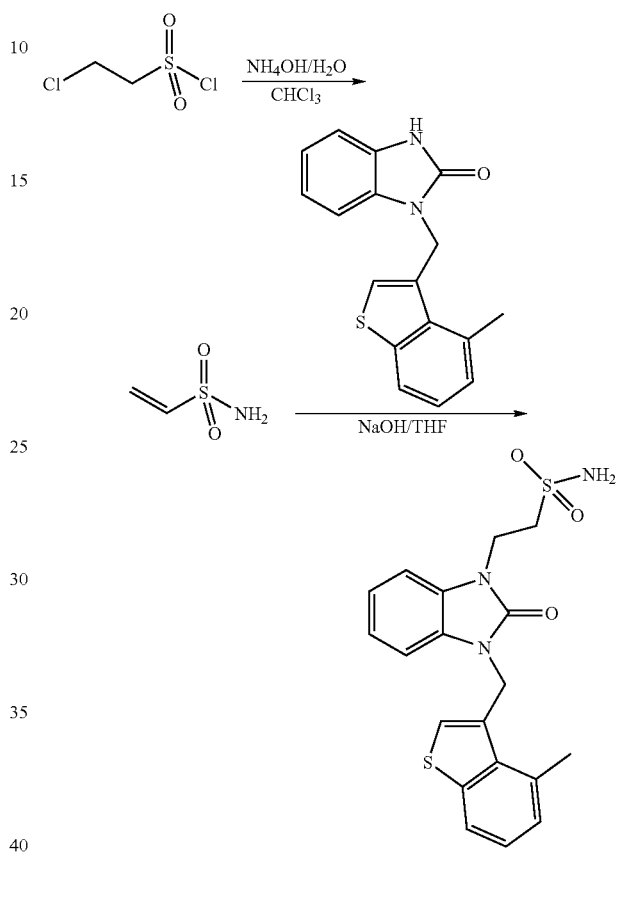

Ethenesulfonic acid amide

2-Chloro-ethanesulfonyl chloride (0.32 mL, 3.1 mmol) is added into the mixture of CHCl₃ (1.0 mL) and 28% ammonium hydroxide aqueous solution (0.85 mL, 6.2 mmol) at room temperature. The mixture is stirred for 1.5 hr and then the solvents are removed under vacuum. THF (50 mL) is added to dissolve the organic portion of the crude. The mixture is filtered and the filtrate is concentrated to give 100 mg (31%) of ethenesulfonic acid amide.

2-[3-(4-Methyl-benzo[b]thiophen-3-ylmethyl)-2-oxo-2,3-dihydro-benzimidazol-1-yl]-ethanesulfonic acid amide To the solution of 1-(4-methyl-benzo[b]thiophen-3-ylmethyl)-1,3-dihydro-benzimidazol-2-one (50 mg, 0.17 mmol) in THF (1.0 mL) are added ethenesulfonic acid amide (40 mg, 0.34 mmol) and solid NaOH (14 mg, 0.34 mmol). The mixture is warmed up to 65° C. for 24 hr and then saturated NH₄Cl solution (5.0 mL) is added along with water (5.0 mL). The mixture is extracted with EtOAc (3×20 mL). The organic layers are combined, dried (Na₂SO₄) and concentrated to give crude product. Purification by preparative TLC using 4% MeOH in CH₂Cl₂ affords 31 mg (46%) of 2-[3-(4-Methylbenzo[b]thiophen-3-ylmethyl)-2-oxo-2,3-dihydro-benzimidazol-1-yl]-ethanesulfonic acid amide. LCMS (ESMS): m/z 402.10 (M+H+).

Example 29

2-[3-(4-Methyl-benzo[b]thiophen-3-ylmethyl)-2-oxo-2,3-dihydro-benzimidazol-1-yl]-ethanesulfonic acid benzoylamide

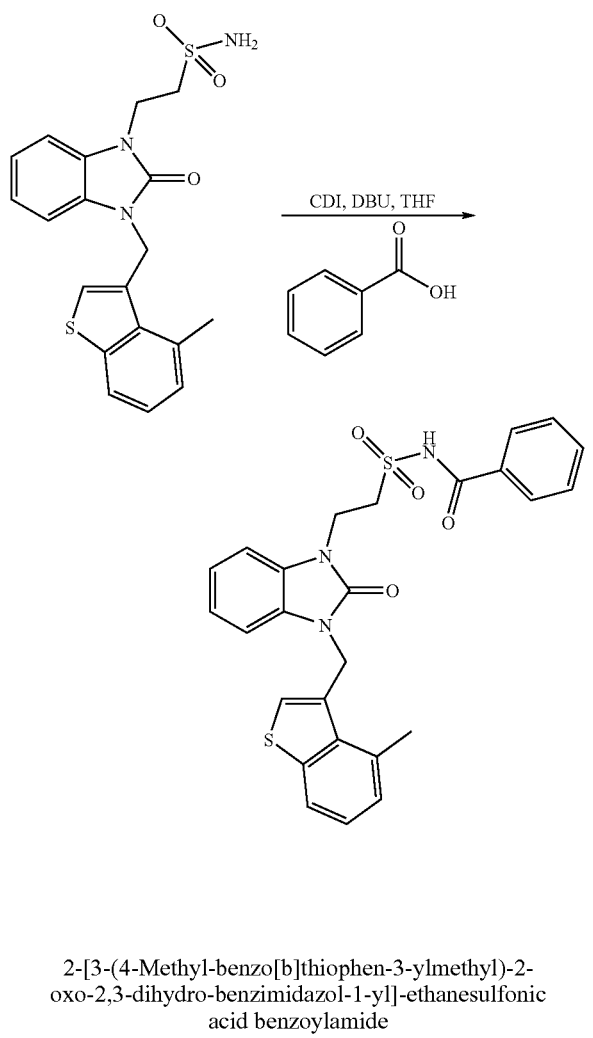

2-[3-(4-Methyl-benzo[b]thiophen-3-ylmethyl)-2-oxo-2,3-dihydro-benzimidazol-1-yl]-ethanesulfonic acid benzoylamide Benzoic acid (6.1 mg, 0.050 mmol) is dissolved THF (0.50 mL) and 1,1'-carbonyl diimidazole (9.1 mg, 0.056 mmol) is added into it at room temperature. The mixture is stirred for 30 min and then it is heated at 55° C. for 1 hr. After the mixture is cooled down to room temperature, 2-[3-(4-Methyl-benzo[b]thiophen-3-ylmethyl)-2-oxo-2,3-dihydro-benzimidazol-1-yl]-ethanesulfonic acid amide (10 mg, 0.025 mmol) is added and after 10 min, 1,8-diazabicyclo[5,4,0]undec-7-ene (0.007 mL, 0.050 mmol) is added. The mixture is stirred for 16 hr at room temperature. 1.0 M HCl solution (1.0 mL) is added followed by water (10 mL). The mixture is extracted with EtOAc (3×20 mL) and the organic layers are combined, dried and concentrated to give crude product. Purification by preparative TLC using 6% MeOH in EtOAc affords 11 mg (85%) of 2-[3-(4-Methyl-benzo[b]thiophen-3-ylmethyl)-2-oxo-2,3-dihydro-benzimidazol-1-yl]-ethanesulfonic acid benzoylamide. LCMS (ESMS): m/z 506.25 (M+H+).

The following compound is synthesized using the same procedure.

2-[3-(4-Methyl-benzo[b]thiophen-3-ylmethyl)-2-oxo-2,3-dihydro-benzimidazol-1-yl]-ethanesulfonic acid acetyl-amide. LCMS (ESMS): m/z 444.07 (M+H+)

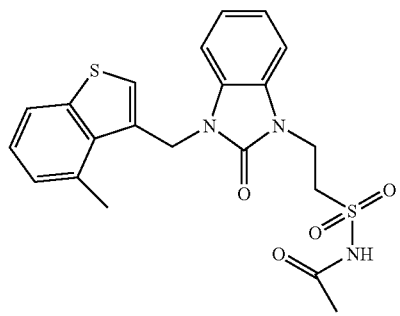 [SMILES: CC(=O)NS(=O)(=O)CCn1c(=O)n(Cc2csc3cccc(C)c23)c2ccccc21]

Example 30

3-[3-(2,5-Dimethyl-benzyl)-2-oxo-2,3-dihydro-benzoimidazol-1-yl]-hexanoic acid

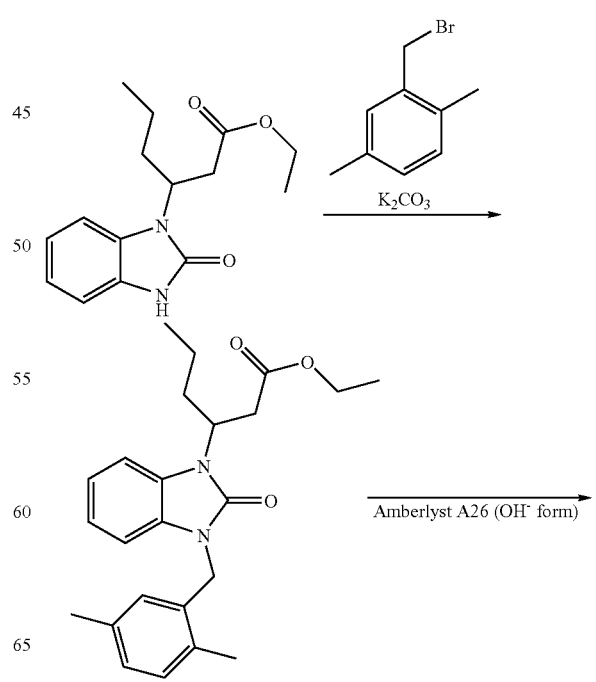

-continued

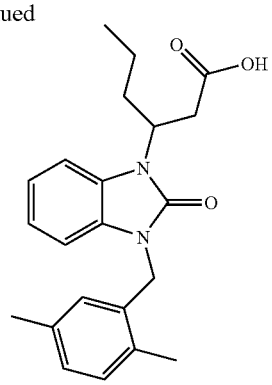

3-(2-Oxo-2,3-dihydro-benzoimidazol-1-yl)-hexanoic acid ethyl ester (40 mg, 0.145 mmol), prepared as described above, was dissolved in DMF (1 mL), and potassium carbonate (69 mg, 0.50 mmol) was added followed by 2-bromomethyl-1,4-dimethyl-benzene (56.3 mg, 0.28 mmol). The resulting mixture was heated at 80° C. for 4 h, cooled, filtered, and the solution was treated directly with the Amberlyst® resin (524 mg, 0.7 mmol). This reaction mixture was agitated overnight and the resin was then filtered and washed with several portions of methanol. The product was eluted by treating the resin with a 20% solution of formic acid in methanol (2×3 mL) and washing with methanol (2×3 mL). The combined eluant and final wash was evaporated to provide the title compound (25 mg, 47%). LCMS (ESMS): m/z 367 (M+H⁺).

Using methods similar to those described in the above example, the following analogs were also synthesized:

3-[3-(5-Chloro-2-difluoromethoxy-benzyl)-2-oxo-2,
3-dihydro-benzo imidazol-1-yl]-hexanoic acid.
LCMS (ESMS): m/z 439 (M+H⁺)

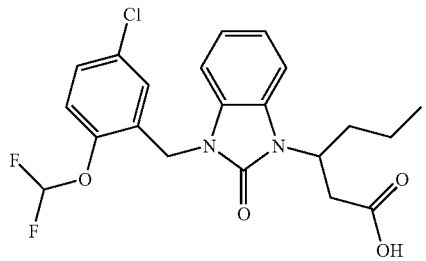 [SMILES: CCCC(CC(=O)O)n1c(=O)n(Cc2cc(Cl)ccc2OC(F)F)c2ccccc21]

3-[3-(5-Chloro-2-trifluoromethyl-benzyl)-2-oxo-2,3-
dihydro-benzoimidazol-1-yl]-hexanoic acid. LCMS
(ESMS): m/z 441 (M+H⁺)

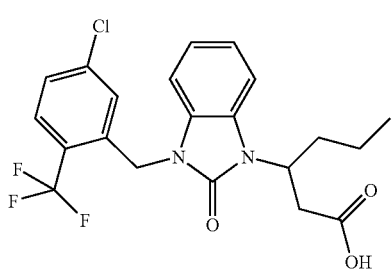 [SMILES: CCCC(CC(=O)O)n1c(=O)n(Cc2cc(Cl)ccc2C(F)(F)F)c2ccccc21]

3-{3-[2-bromo-5-(trifluoromethyl)benzyl]-2-oxo-2,
3-dihydro-1H-benzimidazol-1-yl}hexanoic acid.
LCMS (ESMS): m/z 485.7 (M+H⁺)

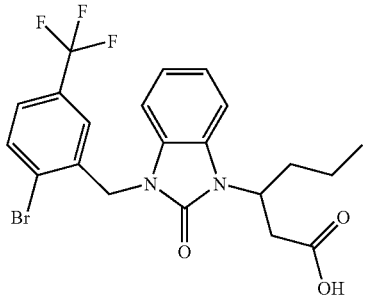 [SMILES: CCCC(CC(=O)O)n1c(=O)n(Cc2cc(C(F)(F)F)ccc2Br)c2ccccc21]

3-[2-oxo-3-(2,3,5-trichlorobenzyl)-2,3-dihydro-1H-
benzimidazol-1-yl]hexanoic acid. LCMS (ESMS):
m/z 441.0 (M+H⁺)

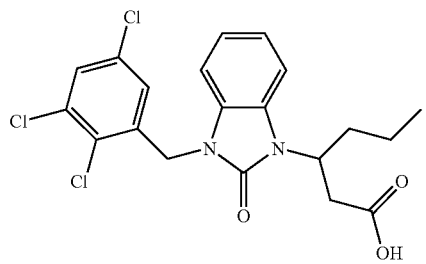 [SMILES: CCCC(CC(=O)O)n1c(=O)n(Cc2cc(Cl)cc(Cl)c2Cl)c2ccccc21]

Example 31

3-[3-(5-Bromo-2-methoxy-benzyl)-2-oxo-2,3-dihy-
dro-benzoimidazol-1-yl]-hexanoic acid

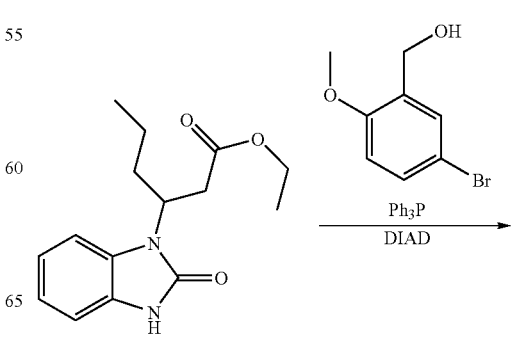

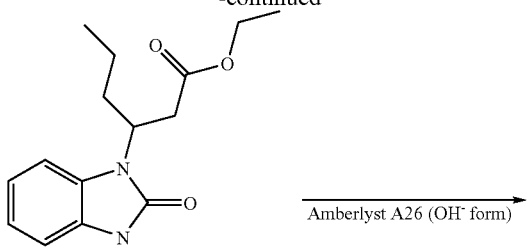

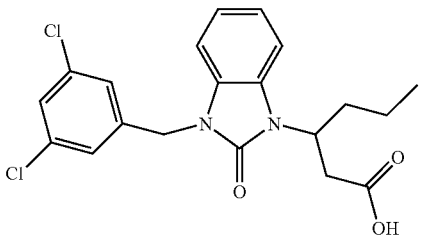 [SMILES: CCCC(CC(=O)O)n1c(=O)n(Cc2cc(Cl)cc(Cl)c2)c2ccccc21]

3-[3-(3,5-Dichloro-benzyl)-2-oxo-2,3-dihydro-benzoimidazol-1-yl]-hexanoic acid. LCMS (ESMS): m/z 407 (M+H+)

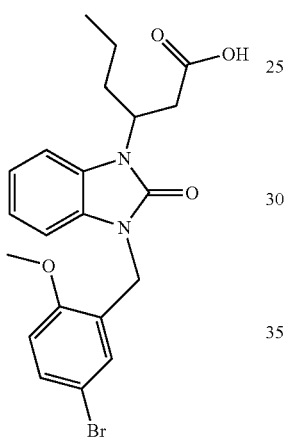

3-[3-(5-Bromo-benzo[b]thiophen-3-ylmethyl)-2-oxo-2,3-dihydro-benzoimidazol-1-yl]-hexanoic acid. LCMS (ESMS): m/z 473/5 (M+H+)

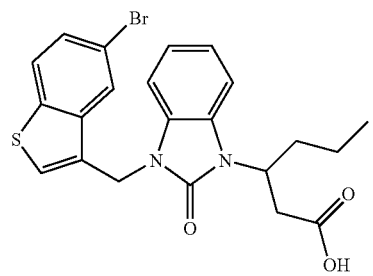 [SMILES: CCCC(CC(=O)O)n1c(=O)n(Cc2csc3ccc(Br)cc23)c2ccccc21]

3-[3-(1H-indol-3-ylmethyl)-2-oxo-2,3-dihydro-benzoimidazol-1-yl]-hexanoic acid. LCMS (ESMS): m/z 378 (M+H+)

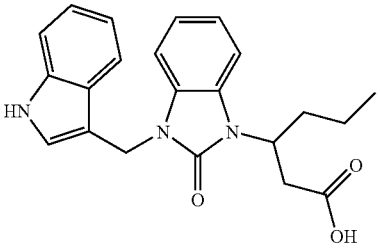 [SMILES: CCCC(CC(=O)O)n1c(=O)n(Cc2c[nH]c3ccccc23)c2ccccc21]

3-(2-Oxo-2,3-dihydro-benzoimidazol-1-yl)-hexanoic acid ethyl ester (96.7 mg, 0.35 mmol), prepared as described above, (5-bromo-2-methoxy-phenyl)-methanol (152 mg, 0.7 mmol) and triphenylphosphene (183.6, 0.7 mmol) were combined in a reaction vial and THF (1 mL) was added. The mixture was stirred until complete solution was attained, then cooled to 0° C., and diisopropylazodicarboxylate (0.136 mL, 0.7 mmol) was added dropwise. The reaction mixture was agitated at room temperature overnight, diluted with THF (2 mL) then treated directly with the Amberlyst® resin (3 g, 4 mmol). This reaction mixture was agitated overnight and the resin was then filtered and washed with DMF (2×3 mL) and several portions of methanol. The product was eluted by treating the resin with a 20% solution of formic acid in methanol (5 mL) and washing with methanol (3 mL). The combined eluant and final wash was evaporated to provide the title compound (154 mg, 99%). LCMS (ESMS): m/z 447/9 (M+H+).

Using methods similar to those described in the above example, the following analogs were also synthesized:

-[3-(1H-indol-3-ylmethyl)-2-oxo-2,3-dihydro-benzoimidazol-1-yl]-propionic acid. LCMS (ESMS): m/z 336 (M+H+)

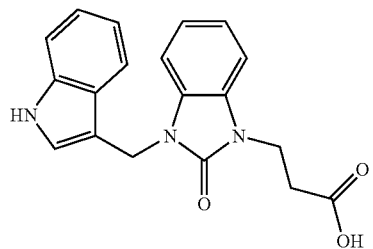 [SMILES: O=C(O)CCn1c(=O)n(Cc2c[nH]c3ccccc23)c2ccccc21]

3-{3-[(5-bromo-1-benzothien-3-yl)methyl]-2-oxo-2,
3-dihydro-1H-benzimidazol-1-yl}propanoic acid.
LCMS (ESMS): m/z 431,433 (M+H⁺)

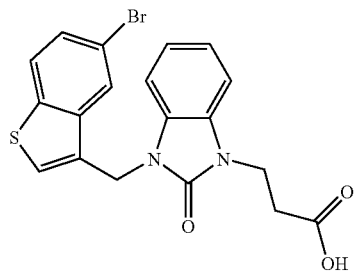 [SMILES: O=C(O)CCn1c(=O)n(Cc2csc3ccc(Br)cc23)c2ccccc21]

3-{3-[2-methyl-5-(trifluoromethyl)benzyl]-2-oxo-2,
3-dihydro-1H-benzimidazol-1-yl}hexanoic acid.
LCMS (ESMS): m/z 421.0 (M+H⁺)

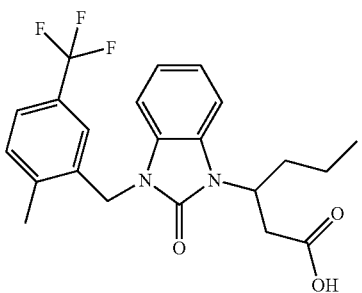 [SMILES: CCCC(CC(=O)O)n1c(=O)n(Cc2cc(C(F)(F)F)ccc2C)c2ccccc21]

3-[3-(2,3-dichlorobenzyl)-2-oxo-2,3-dihydro-1H-
benzimidazol-1-yl]hexanoic acid. LCMS (ESMS):
m/z 407.0 (M+H⁺)

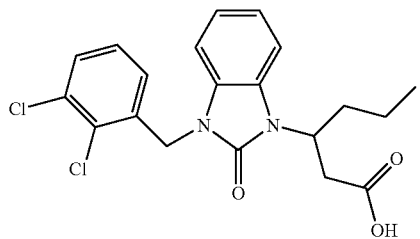 [SMILES: CCCC(CC(=O)O)n1c(=O)n(Cc2cccc(Cl)c2Cl)c2ccccc21]

3-[3-(2,5-dichlorobenzyl)-2-oxo-2,3-dihydro-1H-
benzimidazol-1-yl]hexanoic acid. LCMS (ESMS):
m/z407.0 (M+H⁺)

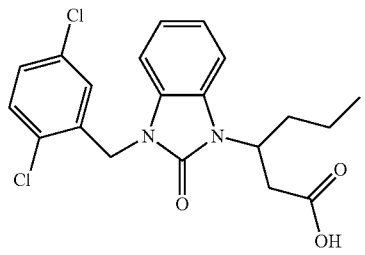 [SMILES: CCCC(CC(=O)O)n1c(=O)n(Cc2cc(Cl)ccc2Cl)c2ccccc21]

Example 32

3-[3-(4-Chloro-1H-indol-3-ylmethyl)-2-oxo-2,3-
dihydro-benzoimidazol-1-yl]-propionic acid

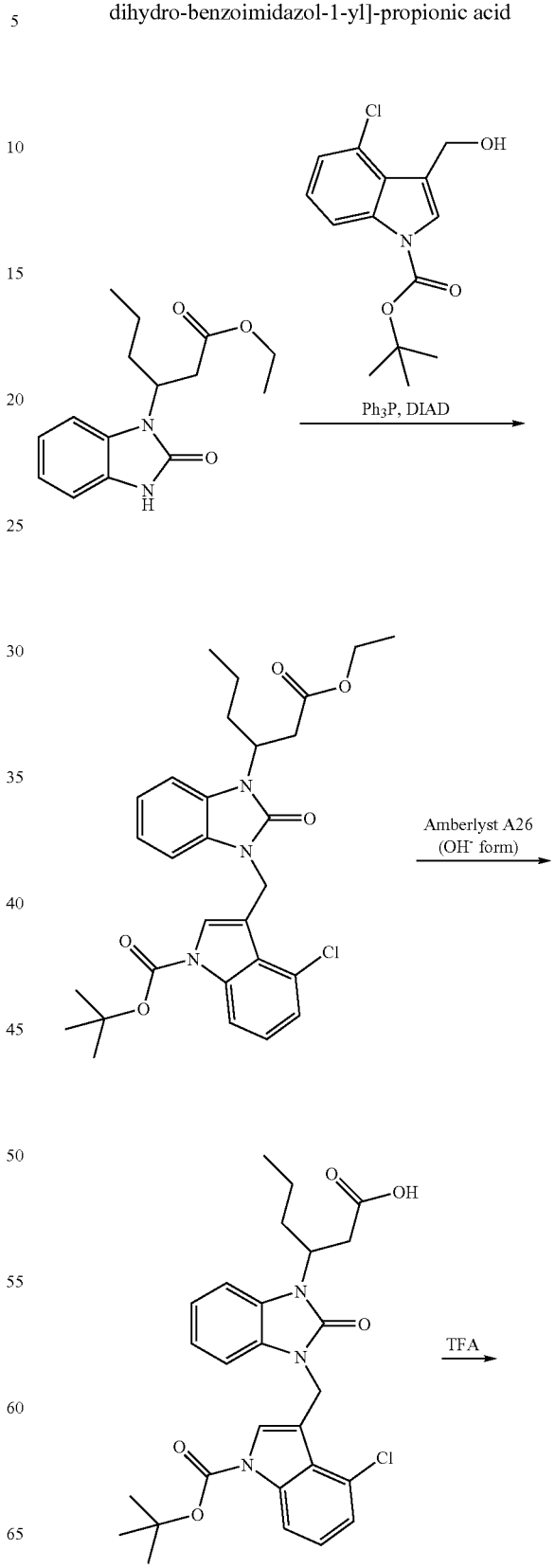

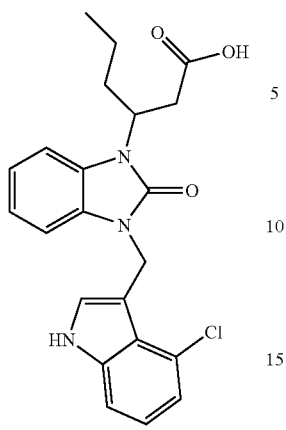

3-(2-Oxo-2,3-dihydro-benzoimidazol-1-yl)-hexanoic acid ethyl ester (80 mg, 0.29 mmol), prepared as described above, 4-chloro-3-hydroxymethyl-indole-1-carboxylic acid tert-butyl ester (282 mg, 1 mmol) and triphenylphosphene (223 mg, 0.85 mmol) were combined in a reaction vial and THF (1 mL) was added. The mixture was stirred until complete solution was attained, then cooled to 0° C., and diisopropylazodicarboxylate (0.165 mL, 0.85 mmol) was added dropwise. The reaction mixture was heated in the microwave at 130° C. for 20 minutes, cooled, then diluted with THF (1 mL) and treated directly with the Amberlyst® resin (2.2 g, 2.95 mmol). This reaction mixture was agitated overnight and the resin was then filtered and washed with DMF (2×3 mL) and several portions of methanol. The product was eluted by treating the resin with a 20% solution of formic acid in methanol (2×3 mL) and washing with methanol (3 mL). The combined eluant and final wash was evaporated and redissolved in dichloromethane (1 mL). To this solution was added TFA (0.2 mL) and the reaction mixture was agitated for 1 h. The solvent was evaporated and the residue was purified by preparative HPLC using an acetonitrile/water/formic acid gradient providing the title compound (8 mg, 7%) LCMS (ESMS): m/z 412 (M+H⁺).

Using methods similar to those described in the above example, the following analogs were also synthesized:

3-[3-(4-Bromo-1H-indol-3-ylmethyl)-2-oxo-2,3-dihydro-benzoimidazol-1-yl]-hexanoic acid. LCMS (ESMS): m/z 456.8 (M+H⁺)

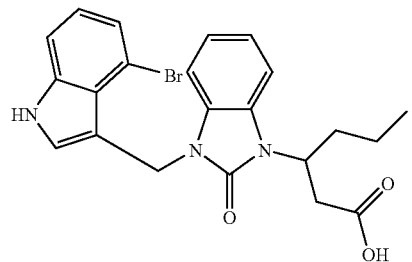 [SMILES: CCCC(CC(=O)O)n1c(=O)n(Cc2c[nH]c3cccc(Br)c23)c2ccccc21]

3-[3-(4-Chloro-1H-indol-3-ylmethyl)-2-oxo-2,3-dihydro-benzoimidazol-1-yl]-propionic acid. LCMS (ESMS): m/z 370 (M+H⁺)

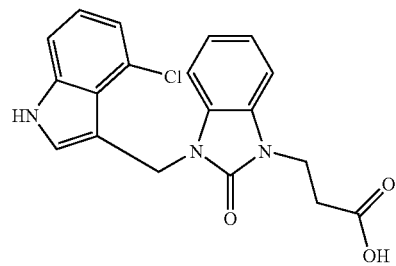 [SMILES: O=C(O)CCn1c(=O)n(Cc2c[nH]c3cccc(Cl)c23)c2ccccc21]

Example 33

3-[3-(1-benzothien-7-ylmethyl)-2-oxo-2,3-dihydro-1H-benzimidazol-1-yl]propanoic acid

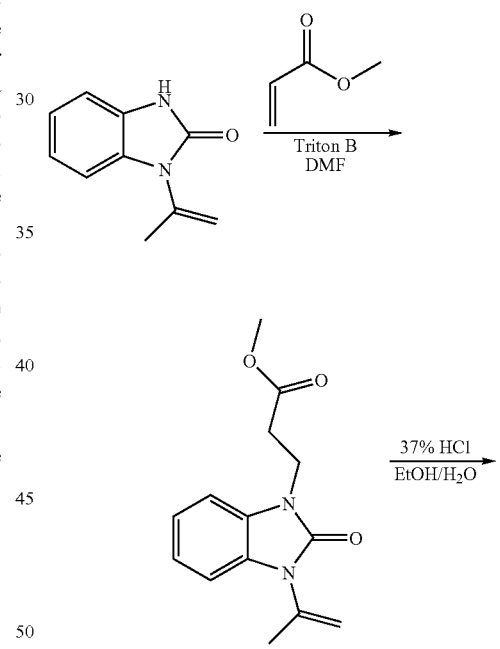

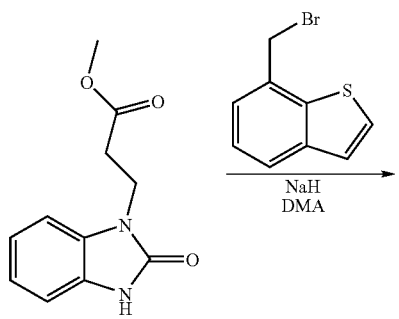

-continued

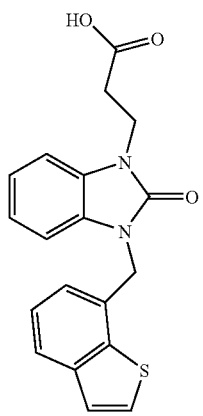

3-(3-Isopropenyl-2-oxo-2,3-dihydro-benzimidazol-1-yl)-propionic acid methyl ester To a stirred solution of 1-Isopropenyl-1,3-dihydro-benzimidazol-2-one (5 g, 28.7 mmol) in DMF (20 ml) was added methyl acrylate (2.8 ml, 31.6 mmol) followed by benzyltrimethylammonium hydroxide (Triton B, 40 wt % in MeOH, 3.2 ml). The resulting solution was stirred at ambient temperature until the reaction was complete. After this time the reaction was poured into water and ethyl acetate. The layers were separated and the aqueous phase was extracted twice more with ethyl acetate. The combined organic layers were dried (MgSO$_4$), filtered and concentrated to give the crude product which was purified via column chromatography (silica gel, 30% ethyl acetate/hexanes). The product-containing fractions were combined and concentrated to give 4.8 g (64%) of the desired product.

3-(2-Oxo-2,3-dihydro-benzimidazol-1-yl)-propionic acid methyl ester

To a stirred solution of 3-(3-Isopropenyl-2-oxo-2,3-dihydro-benzimidazol-1-yl)-propionic acid methyl ester (4.8 g, 18.4 mmol) in ethanol (30 ml) and water (30 ml) was added 37% hydrochloric acid (24 ml). The resulting solution was warmed to 60° C. for twenty minutes and cooled. The reaction was diluted with dichloromethane and water. The layers were separated and the organic phase was dried (Na$_2$SO$_4$), filtered and concentrated to give 3.5 g (86%) of the desired product as an oil which solidified on standing. Used without further purification.

3-[3-(1-benzothien-7-ylmethyl)-2-oxo-2,3-dihydro-1H-benzimidazol-1-yl]propanoic acid To a solution of 3-(2-Oxo-2,3-dihydro-benzimidazol-1-yl)-propionic acid methyl ester (200 mg, 0.91 mmol) in DMA (5 ml) was added sodium hydride (60% oil dispersion, 55 mg, 1.4 mmol). The resulting mixture was stirred for 10 minutes at ambient temperature after which time 7-bromomethyl-benzo[b]thiophene (206 mg, 0.91 mmol) was added. The reaction was heated at 120° C. in a microwave for 20 minutes. Upon cooling to ambient temperature the reaction was diluted with ethyl acetate and washed with NaHCO$_3$ (sat.) and brine. The aqueous phase was acidified using 1M HCl and extracted once with ethyl acetate. The organic phase was dried (MgSO$_4$), filtered and concentrated to give the crude product which was purified via column chromatography (silica gel, 5% methanol/dichloromethane). The product-containing fractions were combined and concentrated to give 20 mg (6%) of the desired product. LCMS (ESMS): m/z 353.41 (M+H$^+$).

The following compounds were synthesized using a similar procedure:

3-{3-[(1-methyl-1H-indol-3-yl)methyl]-2-oxo-2,3-dihydro-1H-benzimidazol-1-yl}propanoic acid. LCMS (ESMS): m/z 350.38 (M+H$^+$)

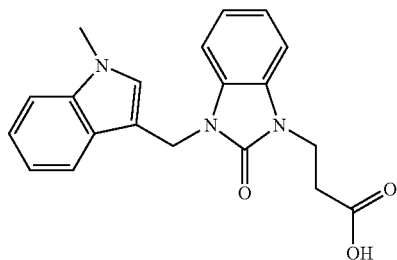 [SMILES: Cn1cc(Cn2c(=O)n(CCC(=O)O)c3ccccc32)c2ccccc21]

3-[3-(1,2-benzisothiazol-3-ylmethyl)-2-oxo-2,3-dihydro-1H-benzimidazol-1-yl]propanoic acid. LCMS (ESMS): m/z 354.40 (M+H$^+$)

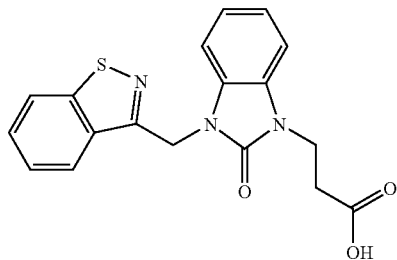 [SMILES: O=C(O)CCn1c(=O)n(Cc2nsc3ccccc23)c2ccccc21]

3-{3-[(6-methoxy-1-naphthyl)methyl]-2-oxo-2,3-dihydro-1H-benzimidazol-1-yl}propanoic acid. LCMS (ESMS): m/z 377.41 (M+H$^+$)

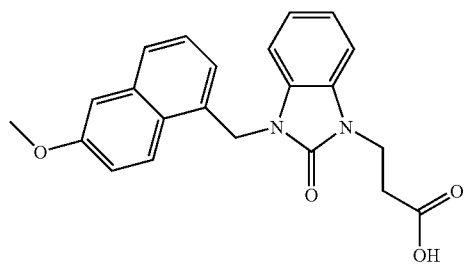 [SMILES: COc1ccc2c(Cn3c(=O)n(CCC(=O)O)c4ccccc43)cccc2c1]

287

3-{3-[(1-methyl-1H-indol-7-yl)methyl]-2-oxo-2,3-dihydro-1H-benzimidazol-1-yl}propanoic acid.
LCMS (ESMS): m/z 350.38 (M+H$^+$)

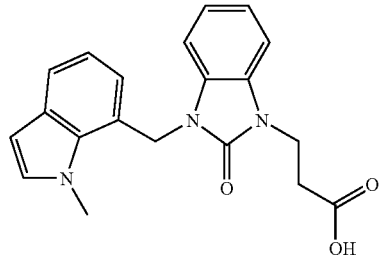 [SMILES: Cn1ccc2cccc(Cn3c(=O)n(CCC(=O)O)c4ccccc43)c21]

3-{3-[(1,3-dimethyl-1H-indol-7-yl)methyl]-2-oxo-2,3-dihydro-1H-benzimidazol-1-yl}propanoic acid.
LCMS (ESMS): m/z 364.41 (M+H$^+$)

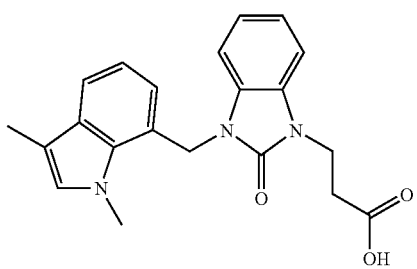 [SMILES: Cc1cn(C)c2c(Cn3c(=O)n(CCC(=O)O)c4ccccc43)cccc12]

Example 34

3-{3-[(6-hydroxy-1-naphthyl)methyl]-2-oxo-2,3-dihydro-1H-benzimidazol-1-yl}propanoic acid

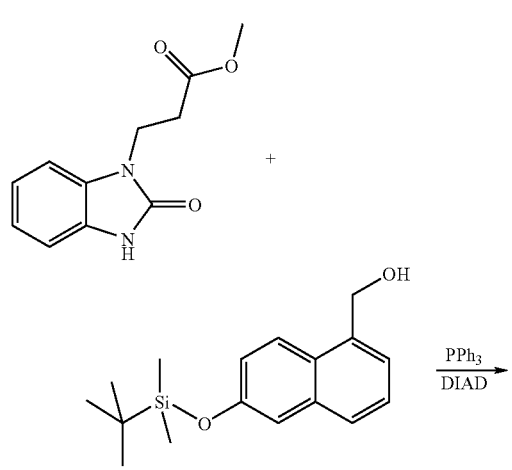

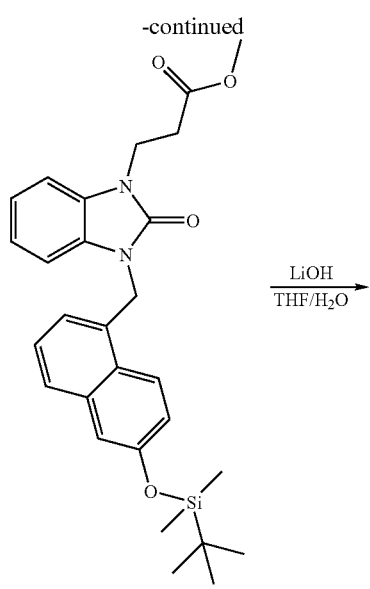

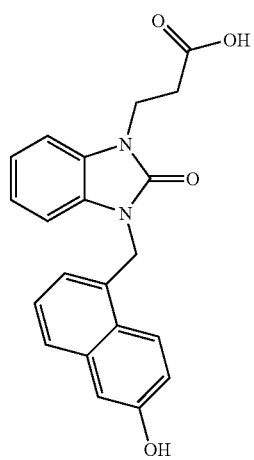

3-{3-[6-(tert-Butyl-dimethyl-silanyloxy)-naphthalen-1-ylmethyl]-2-oxo-2,3-dihydro-benzimidazol-1-yl}-propionic acid methyl ester To a stirred solution of 3-(2-oxo-2,3-dihydro-benzimidazol-1-yl)-propionic acid methyl ester (180 mg, 0.82 mmol) in THF (12 ml) was added [6-(tert-butyl-dimethyl-silanyloxy)-naphthalen-1-yl]-methanol (283 mg, 0.98 mmol) and triphenylphosphine (257 mg, 0.98 mmol). The DIAD (0.20 ml, 0.98 mmol) was then introduced in a dropwise manner and the resulting mixture was stirred at ambient temperature overnight. Silica gel was added and the reaction mixture was concentrated to dryness. The resulting solid was purified via column chromatography (silica gel, 40% ethyl acetate/hexanes) to give 240 mg (60%) of the desired product as an oil which solidified on standing.

3-{3-[(6-hydroxy-1-naphthyl)methyl]-2-oxo-2,3-dihydro-1H-benzimidazol-1-yl}propanoic acid To a stirred solution of 3-{3-[6-(tert-Butyl-dimethyl-silanyloxy)-naphthalen-1-ylmethyl]-2-oxo-2,3-dihydro-benzimidazol-1-yl}-propionic acid methyl ester (200 mg, 0.41 mmol) in THF (7 ml) and water (1 ml) was added lithium hydroxide monohydrate (26 mg, 0.61 mmol) at ambient temperature. Upon complete consumption of the starting material the reaction was diluted with water, ethyl acetate and 6N HCl (adjusted to pH=2). The layers were separated and the aqueous phase was extracted once with ethyl acetate. The combined organics were dried (MgSO$_4$), filtered and concentrated. The remaining residue was diluted with acetonitrile (3 ml) and allowed to stand over night. The resulting precipitated product was collected via filtration, washed with acetonitrile and dried on house vacuum to give 15 mg (10%) of the desired product. LCMS (ESMS): m/z 363.38 (M+H$^+$).

The following compounds were synthesized using a similar procedure:

3-{2-oxo-3-[(1,2,3-trimethyl-1H-indol-7-yl)methyl]-2,3-dihydro-1H-benzimidazol-1-yl}propanoic acid. LCMS (ESMS): m/z 378.44 (M+H$^+$)

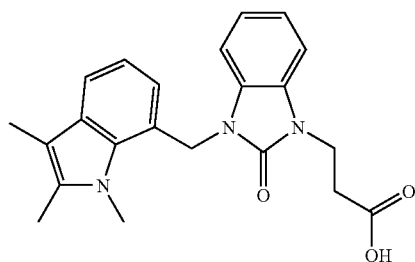 [SMILES: Cc1c(C)n(C)c2c(Cn3c(=O)n(CCC(=O)O)c4ccccc43)cccc12]

3-{3-[(8-bromo-1-naphthyl)methyl]-2-oxo-2,3-dihydro-1H-benzimidazol-1-yl}propanoic acid. LCMS (ESMS): m/z 427.28 (M+2H$^+$)

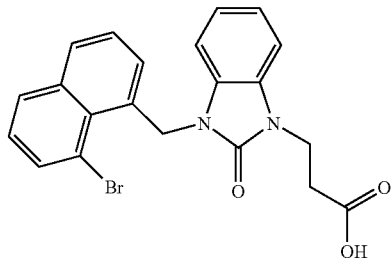 [SMILES: O=C(O)CCn1c(=O)n(Cc2cccc3cccc(Br)c23)c2ccccc21]

3-{3-[(4-methylpyrazolo[1,5-a]pyridin-3-yl)methyl]-2-oxo-2,3-dihydro-1H-benzimidazol-1-yl}propanoic acid. LCMS (ESMS): m/z 351.37 (M+H$^+$)

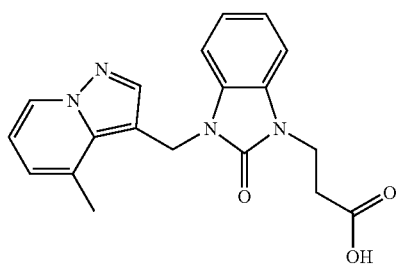 [SMILES: Cc1cccn2ncc(Cn3c(=O)n(CCC(=O)O)c4ccccc43)c12]

3-{3-[(5-chloro-1,2,3-trimethyl-1H-indol-7-yl)methyl]-2-oxo-2,3-dihydro-1H-benzimidazol-1-yl}propanoic acid. LCMS (ESMS): m/z 412.88 (M+H$^+$)

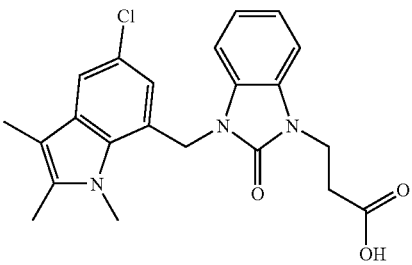 [SMILES: Cc1c(C)n(C)c2c(Cn3c(=O)n(CCC(=O)O)c4ccccc43)cc(Cl)cc12]

3-{3-[(5-methoxy-1,2,3-trimethyl-1H-indol-7-yl)methyl]-2-oxo-2,3-dihydro-1H-benzimidazol-1-yl}propanoic acid. LCMS (ESMS): m/z 408.30 (M+H$^+$)

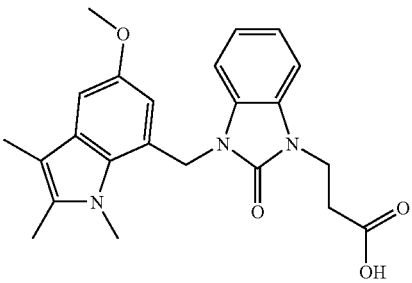 [SMILES: COc1cc(Cn2c(=O)n(CCC(=O)O)c3ccccc32)c2c(c1)c(C)c(C)n2C]

Example 35

3-[3-(1,2-benzisoxazol-3-ylmethyl)-2-oxo-2,3-dihydro-1H-benzimidazol-1-yl]hexanoic acid

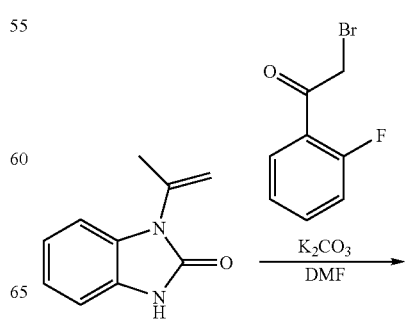

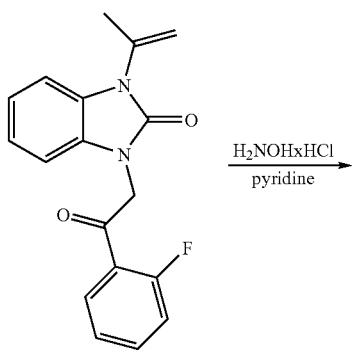

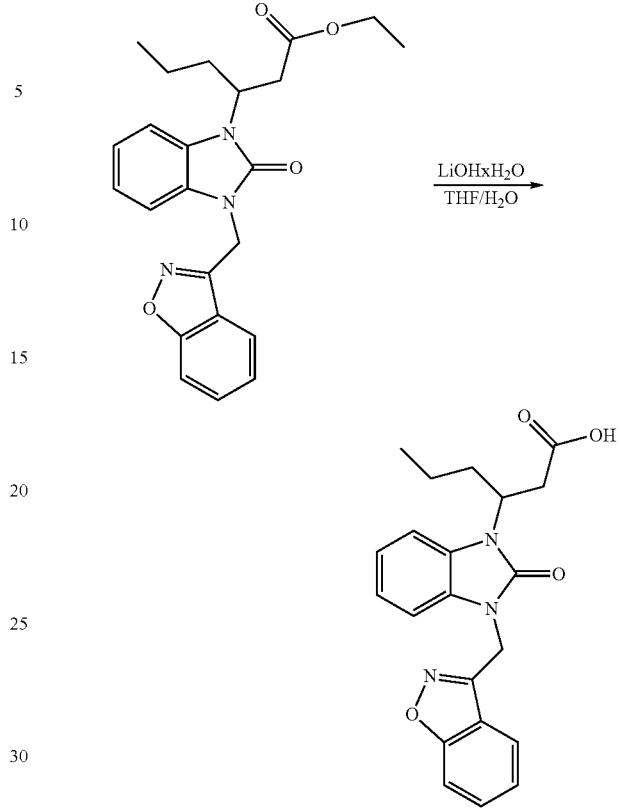

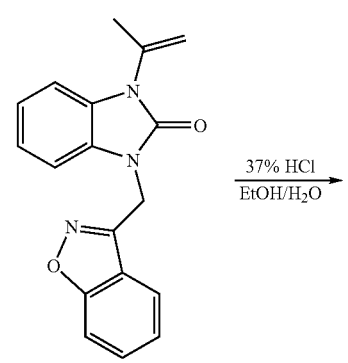

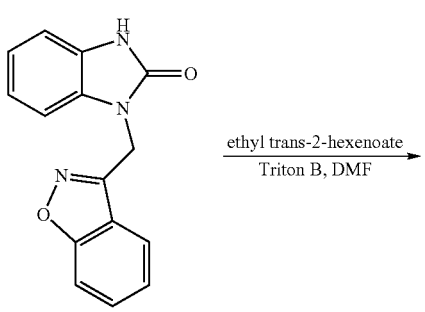

1-[2-(2-Fluoro-phenyl)-2-oxo-ethyl]-3-isopropenyl-1,3-dihydro-benzimidazol-2-one To a stirred solution of 1-isopropenyl-1,3-dihydro-benzimidazol-2-one (1 g, 5.7 mmol) in DMF (50 ml) was added potassium carbonate (1.6 g, 11.5 mmol) followed by 2-fluorophenacyl bromide (1.5 g, 6.9 mmol). The resulting mixture was warmed to 80° C. for 2 h and cooled to ambient temperature. The reaction was poured into water and ethyl acetate and the layers were separated. The aqueous phase was extracted with ethyl acetate (2×) and the combined organics were dried (MgSO$_4$). Filtration and concentration gave the crude product which was purified via column chromatography (silica gel, 50% EtOAc/hexanes). The product-containing fractions were combined and concentrated to give 1.6 g (90%) of the desired product.

1-{2-(2-Fluoro-phenyl)-2-[hydroxyimino]-ethyl}-3-isopropenyl-1,3-dihydro-benzimidazol-2-one To a stirred solution of 1-[2-(2-fluoro-phenyl)-2-oxo-ethyl]-3-isopropenyl-1,3-dihydro-benzimidazol-2-one (1.3 g, 4.2 mmol) in ethanol (50 ml) was added hydroxylamine hydrochloride (0.84 g, 12.2 mmol) followed by pyridine (1.7 ml, 21.0 mmol) at ambient temperature. The resulting mixture was warmed to 80° C. for 6 h, cooled to ambient temperature and concentrated. The remaining residue was diluted with water, 1M HCl and ethyl acetate. The layers were separated and the aqueous phase was extracted once more with ethyl acetate. The combined organics were dried (MgSO$_4$), filtered and concentrated to give the crude product which was purified via column chromatography (silica gel, 50% EtOAc/hexanes). The product-containing fractions were combined and concentrated to give 1.0 g (73%) of the desired product as an oil which solidified on standing.

1-1,2-Benzisoxazol-3-ylmethyl-3-isopropenyl-1,3-dihydro-benzimidazol-2-one

A 25 ml pear-shaped flask was charged with sodium hydride (60% oil dispersion, 68 mg, 1.7 mmol) which was washed with hexanes and then diluted with DME (3 ml). The 1-{2-(2-fluoro-phenyl)-2-[hydroxyimino]-ethyl}-3-isopropenyl-1,3-dihydro-benzimidazol-2-one (0.5 g, 1.5 mmol) was introduced as a DME (3 ml) solution in a dropwise manner. The resulting mixture was warmed to 85° C. for 20 h and cooled to ambient temperature. The reaction was diluted with water and the product was extracted into ethyl acetate (2×). The combined organics were dried (MgSO$_4$), filtered and concentrated to give the crude product which was purified via column chromatography (silica gel, 40% EtOAc/hexanes). The product-containing fractions were combined and concentrated to give 0.26 g (55%) of the desired product.

1-1,2-Benzisoxazol-3-ylmethyl-1,3-dihydro-benzimidazol-2-one

The 1-1,2-benzisoxazol-3-ylmethyl-3-isopropenyl-1,3-dihydro-benzimidazol-2-one (0.26 g, 0.85 mmol) was diluted with ethanol (2 ml), water (2 ml) and 37% HCl (1 ml). The resulting mixture was warmed to 60° C. for 1 h and cooled to ambient temperature. The reaction was diluted with water and the product was extracted into dichloromethane. The layers were separated and the organic phase was dried (MgSO$_4$). Filtration and concentration gave 0.20 g (89%) of the desired product which was used without further purification.

3-(3-1,2-Benzisoxazol-3-ylmethyl-2-oxo-2,3-dihydro-benzimidazol-1-yl)-hexanoic acid ethyl ester To a stirred solution of 1-1,2-benzisoxazol-3-ylmethyl-1,3-dihydro-benzimidazol-2-one (100 mg, 0.38 mmol) in DMF (5 ml) was added ethyl trans-2-hexenoate (80 mg, 0.57 mmol) followed by benzyltrimethylammonium hydroxide (Triton B, 40 wt % in MeOH, 17.0 ul). The resulting mixture was warmed to 60° C. for 12 h and cooled to ambient temperature. The reaction was diluted with NH$_4$Cl (sat.) and the product was extracted into ethyl acetate (2×). The combined organics were dried (MgSO$_4$), filtered and concentrated to give the crude product which was purified via column chromatography (silica gel, 5% EtOAc/dichloromethane). The product-containing fractions were combined and concentrated to give 70 mg (46%) of the desired product.

3-[3-(1,2-benzisoxazol-3-ylmethyl)-2-oxo-2,3-dihydro-1H-benzimidazol-1-yl]hexanoic acid To a stirred solution of 3-(3-1,2-benzisoxazol-3-ylmethyl-2-oxo-2,3-dihydro-benzimidazol-1-yl)-hexanoic acid ethyl ester (70 mg, 0.17 mmol) in THF (5 ml) and water (0.5 ml) was added lithium hydroxide monohydrate (22 mg, 0.52 mmol). Upon complete consumption of the starting material, the reaction was concentrated to low volume and diluted with water (20 ml) and acetic acid (0.5 ml). The resulting heterogeneous mixture was stirred for 1 h after which time the precipitated product was collected via filtration. The solid was washed with water and dried on house vacuum at 40° C. (18 h, over P$_2$O$_5$) to give 52 mg (80%) of the desired product. LCMS (ESMS): m/z 380.41 (M+H$^+$).

Example 36

3-{3-[(4-chloro-1,2,3-trimethyl-1H-indol-7-yl)methyl]-2-oxo-2,3-dihydro-1H-benzimidazol-1-yl}propanoic acid

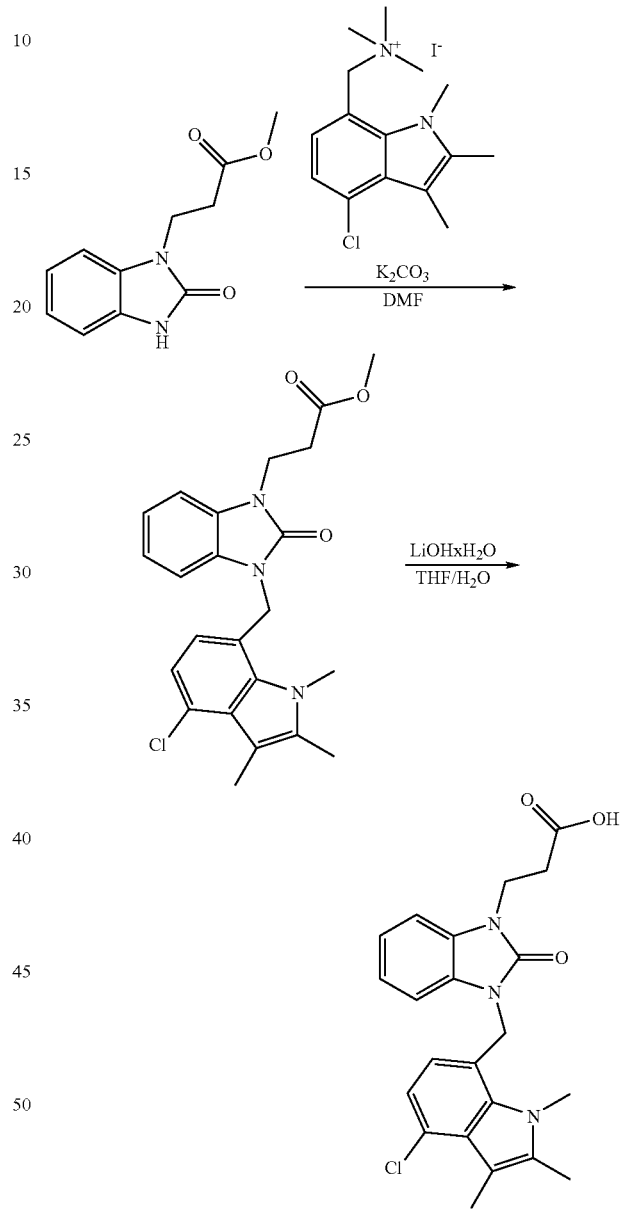

3-[3-(4-Chloro-1,2,3-trimethyl-1H-indol-7-ylmethyl)-2-oxo-2,3-dihydro-benzimidazol-1-yl]-propionic acid methyl ester To a stirred solution of 3-(2-oxo-2,3-dihydro-benzimidol-1-yl)-propionic acid methyl ester (50 mg, 0.23 mmol) in DMF (15 ml) was added (4-chloro-1,2,3-trimethyl-1H-indol-7-ylmethyl)-trimethyl-ammonium; iodide (107 mg, 0.27 mmol) followed by potassium carbonate (94 mg, 0.68 mmol). The resulting mixture was warmed at 100° C. over night and cooled to ambient temperature. The reaction was diluted with water and the resulting solids were removed via filtration. The filtrate was extracted with ethyl acetate (3×). The combined organics were dried (MgSO₄), filtered and concentrated to give the crude product which was purified via column chromatography (silica gel, 80% EtOAc/hexanes). The product-containing fractions were combined and concentrated to give 40 mg (41%) of the desired product.

3-{3-[(4-chloro-1,2,3-trimethyl-1H-indol-7-yl)methyl]-2-oxo-2,3-dihydro-1H-benzimidazol-1-yl}propanoic acid To a stirred solution of 3-[3-(4-chloro-1,2,3-trimethyl-1H-indol-7-ylmethyl)-2-oxo-2,3-dihydro-benzimidazol-1-yl]-propionic acid methyl ester (40 mg, 0.09 mmol) in THF (3 ml) and water (1 ml) was added lithium hydroxide monohydrate (10 mg, 0.24 mmol). The resulting mixture was stirred at ambient temperature until all of the starting material was consumed. After this time the reaction was concentrated to low volume and diluted with water (10 ml) and acetic acid (0.5 ml). The resulting heterogeneous mixture was stirred at ambient temperature for 18 h. The solid product was collected via filtration and suspended in acetonitrile. The product was collected once more via filtration and washed with minimal acetonitrile to give 5 mg (13%) of the desired product. LCMS (ESMS): m/z 412.88 (M+H⁺).

Example 37

3-{3-[(4-chloro-1,2,3-trimethyl-1H-indol-7-yl)methyl]-2-oxo-2,3-dihydro-1H-benzimidazol-1-yl}hexanoic acid

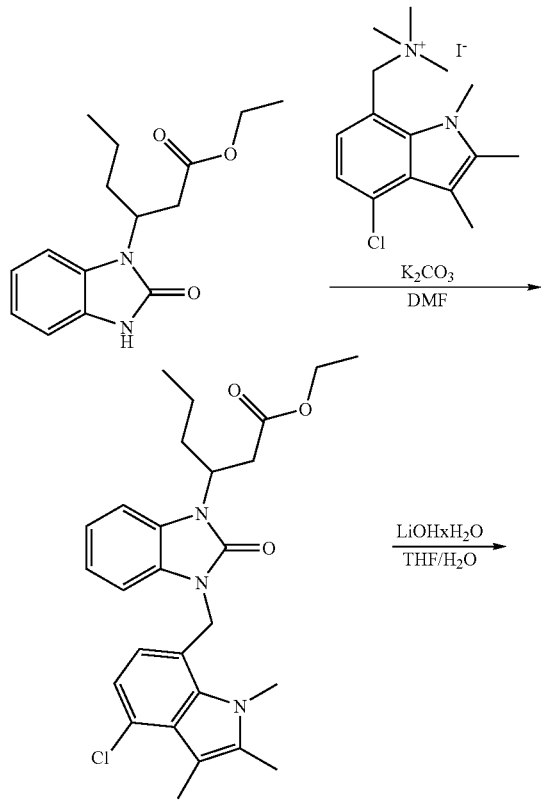

3-[3-(4-Chloro-1,2,3-trimethyl-1H-indol-7-ylmethyl)-2-oxo-2,3-dihydro-benzimidazol-1-yl]-hexanoic acid ethyl ester

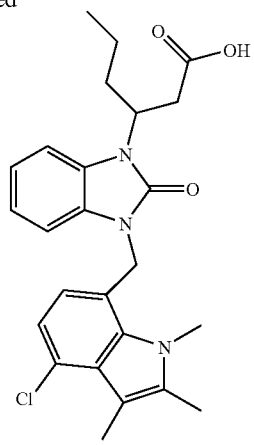

To a stirred solution of 3-(2-oxo-2,3-dihydro-benzimidazol-1-yl)-hexanoic acid ethyl ester (93 mg, 0.34 mmol) in DMF (10 ml) was added (4-chloro-1,2,3-trimethyl-1H-indol-7-ylmethyl)-trimethyl-ammonium; iodide (132 mg, 0.34 mmol) followed by potassium carbonate (140 mg, 1.01 mmol). The resulting mixture was warmed at 100° C. over night and cooled to ambient temperature. The reaction was diluted with water and ethyl acetate. The layers were separated and the organic phase was dried (MgSO₄), filtered and concentrated to give the crude product. Purification via preparative TLC (1 mm silica gel, 20% EtOAc/hexanes) gave 25 mg (15%) of the desired product.

3-{3-[(4-chloro-1,2,3-trimethyl-1H-indol-7-yl)methyl]-2-oxo-2,3-dihydro-1H-benzimidazol-1-yl}hexanoic acid To a stirred solution of 3-[3-(4-Chloro-1,2,3-trimethyl-1H-indol-7-ylmethyl)-2-oxo-2,3-dihydro-benzimidazol-1-yl]-hexanoic acid ethyl ester (25 mg, 0.05 mmol) in THF (5 ml) and water (1 ml) was added lithium hydroxide monohydrate (20 mg, 0.48 mmol). The resulting mixture was stirred at ambient temperature until all of the starting material was consumed. After this time the reaction was concentrated to low volume and diluted with water (5 ml) and acetic acid (0.2 ml). The resulting solid was collected via filtration and suspended in acetonitrile/water. The solid was collected once more via filtration and dried on house vacuum at 70° C. to give 10 mg (43%) of the desired product. LCMS (ESMS): m/z 454.96 (M+H⁺).

Example 38

3-{3-[(1,3-dimethyl-1H-indol-4-yl)methyl]-2-oxo-2,3-dihydro-1H-benzimidazol-1-yl}propanoic acid

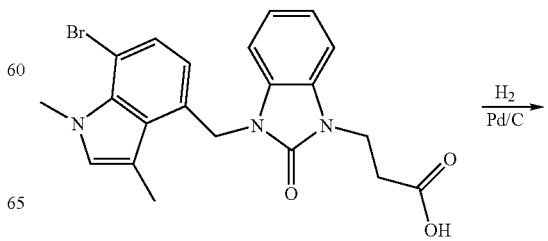

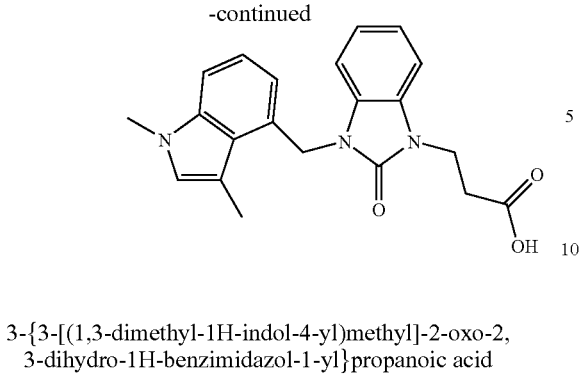

3-{3-[(1,3-dimethyl-1H-indol-4-yl)methyl]-2-oxo-2,3-dihydro-1H-benzimidazol-1-yl}propanoic acid A mixture of 3-[3-(7-Bromo-1,3-dimethyl-1H-indol-4-yl-methyl)-2-oxo-2,3-dihydro-benzimidazol-1-yl]-propionic acid (prepared using similar conditions as described in example 2, 65 mg, 0.15 mmol) and 10% Pd/C (50% wet, Degussa Type, 12 mg) in methanol (8 ml) was degassed and placed under hydrogen atmosphere (balloon). After stirring at ambient temperature over night, LCMS showed desired product as well as the methyl ester of the desired product. The catalyst was removed via filtration and the filtrate was concentrated to give the crude product. Purification via column chromatography (silica gel, 20-100% EtOAc/hexanes) gave the methyl ester which was dissolved into THF (2.5 ml) and water (0.5 ml) and treated with lithium hydroxide monohydrate (8 mg). Upon complete hydrolysis of the ester, the reaction was concentrated to low volume and the remaining residue was diluted with water and acetic acid. The resulting precipitate was collected via filtration, washed with water and dried on house vacuum to give 18 mg (34%) of the desired product. LCMS (ESMS): m/z 364.41 (M+H$^+$).

Example 39

3-[2-Oxo-3-(1,2,3-trimethyl-1H-indol-7-ylmethyl)-2,3-dihydro-benzoimidazol-1-yl]-hexanoic acid

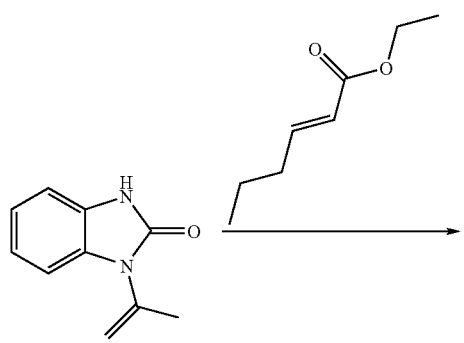

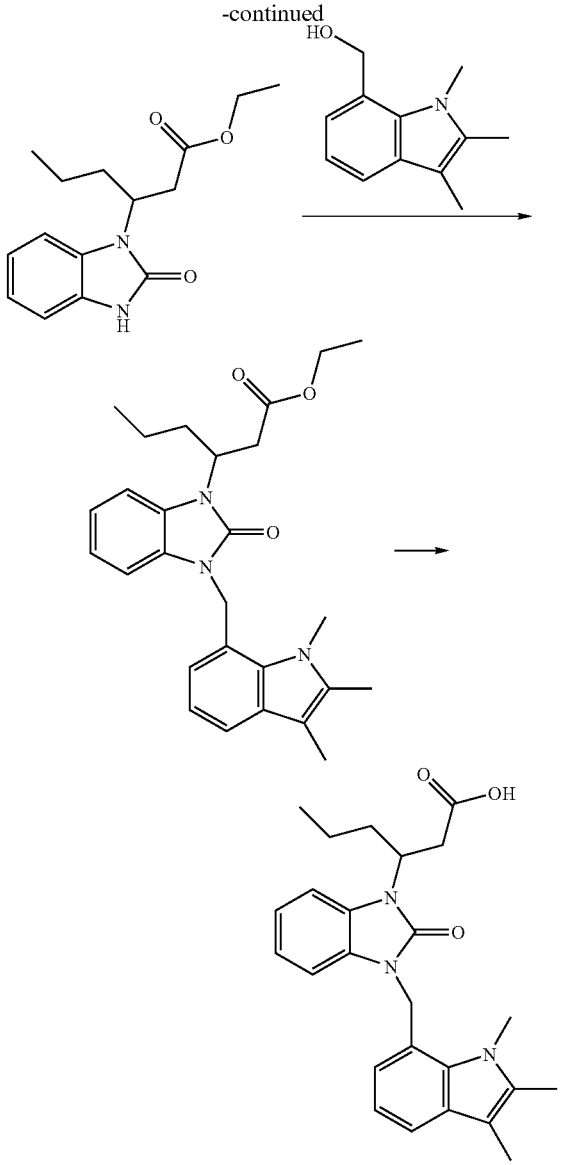

3-(3-Isopropenyl-2-oxo-2,3-dihydro-benzoimidazol-1-yl)-hexanoic acid ethyl ester To a solution of 1-isopropenyl-2-benzimidazolinone (2 g, 11.5 mmol) in DMF (10 mL) were added ethyl trans-2-hexenoate (2 g, 14 mmol) and the benzyltrimethylammonium hydroxide (40% in MeOH) (0.4 mL, 2.3 mmol) at room temperature. The solution was heated to 60 C for 12 hours. The solution was cooled down and sat.NH$_4$Cl sol was added. The solution was extracted with EtOAc and the combined organic layer was dried with MgSO$_4$ and filtered. The filtrate was concentrated and the residue was purified by CombiFlash with 20% EtOAc in Hexane to afford the desirable product 3-(3-Isopropenyl-2-oxo-2,3-dihydro-benzoimidazol-1-yl)-hexanoic acid ethyl ester (2 g, 55%) as an colorless oil.

3-(2-Oxo-2,3-dihydro-benzoimidazol-1-yl)-hexanoic acid ethyl ester 3-(3-Isopropenyl-2-oxo-2,3-dihydro-benzoimidazol-1-yl)-hexanoic acid ethyl ester (1 g, 3.2 mmol) was dissolved in MeOH (30 mL) and HCl (30 mL) solution at room temperature. The solution was heated to 60° C. for 2 hours. The solution was cooled down and was extracted with EtOAc. The combined organic layer was dried with MgSO₄ and was filtered. The filtrate was concentrated and the residue was purified by CombiFlash with 5% MeOH in CH₂Cl₂ as the eluent to afford the desirable product 3-(2-Oxo-2,3-dihydro-benzoimidazol-1-yl)-hexanoic acid ethyl ester (700 mg, 80%) as a colorless oil.

3-[2-Oxo-3-(1,2,3-trimethyl-1H-indol-7-ylmethyl)-2,3-dihydro-benzoimidazol-1-yl]hexanoic acid ethyl ester To a solution of 3-(2-Oxo-2,3-dihydro-benzoimidazol-1-yl)-hexanoic acid ethyl ester (100 mg, 0.36 mmol) in THF (10 mL) were added (1,2,3-Trimethyl-1H-indol-7-yl)-methanol (103 mg, 0.54 mmol), DIAD (diisoproyl azo-dicarboxylate) (0.14 mL, 0.7 mmol) and triphenylphosphine (95 mg, 0.36 mmol) at room temperature. The solution was stirred at the same temperatrue for 12 hours. The solution was filtered and the filtrate was concentrated. The residue was purified by combFlash with 10% EtOAc in Hexane as the eluent to afford the desirable product 3-[2-Oxo-3-(1,2,3-trimethyl-1H-indol-7-ylmethyl)-2,3-dihydro-benzoimidazol-1-yl]-hexanoic acid ethyl ester (80 mg, 49%) as a white foam.

3-[2-Oxo-3-(1,2,3-trimethyl-1H-indol-7-ylmethyl)-2,3-dihydro-benzoimidazol-1-yl]-hexanoic acid To a solution of 3-[2-Oxo-3-(1,2,3-trimethyl-1H-indol-7-ylmethyl)-2,3-dihydro-benzoimidazol-1-yl]-hexanoic acid ethyl ester (50 mg, 0.11 mmol) in 1,4-dioxane (5 mL) and H₂O (2 mL) was added LiOH (5.4 mg, 0.22 mmol). The solution was stirred at room temperature for 5 hours. The solution was concentrated and the residue was purified by CombiFlash with 10% MeOH in CH₂Cl₂ as the eluent to afford the desirable product 3-[2-Oxo-3-(1,2,3-trimethyl-1H-indol-7-ylmethyl)-2,3-dihydro-benzoimidazol-1-yl]-hexanoic acid (14.5 mg, 31%) as a white foam. LC-MS (M⁺+1): 420.21.

The following compound was prepared using a similar procedure.

3-[3-(8-Bromo-naphthalen-1-ylmethyl)-2-oxo-2,3-dihydro-benzoimidazol-1-yl]-hexanoic acid. LC-MS (M⁺+1): 469.04

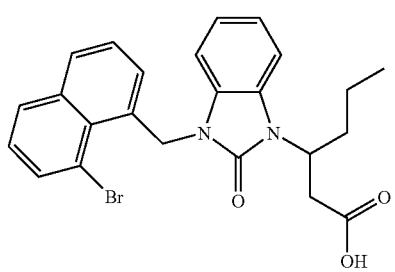 [SMILES: CCCC(CC(=O)O)n1c(=O)n(Cc2cccc3cccc(Br)c23)c2ccccc21]

3-{3-[(5-chloro-1,2,3-trimethyl-1H-indol-7-yl)methyl]-2-oxo-2,3-dihydro-1H-benzimidazol-1-yl}hexanoic acid. LC-MS (m⁺+1): 454.9

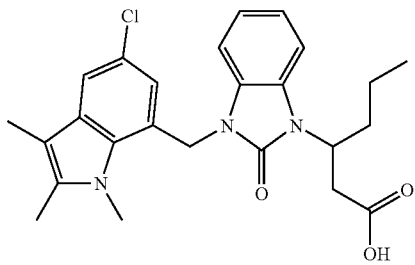 [SMILES: CCCC(CC(=O)O)n1c(=O)n(Cc2cc(Cl)cc3c(C)c(C)n(C)c23)c2ccccc21]

3-{3-[(5-fluoro-1,2,3-trimethyl-1H-indol-7-yl)methyl]-2-oxo-2,3-dihydro-1H-benzimidazol-1-yl}hexanoic acid. LC-MS (M⁺+1): 438.5

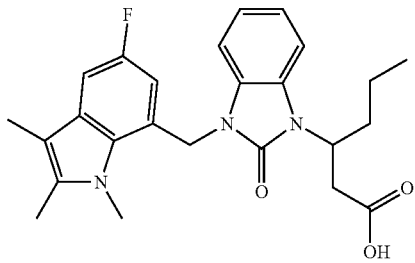 [SMILES: CCCC(CC(=O)O)n1c(=O)n(Cc2cc(F)cc3c(C)c(C)n(C)c23)c2ccccc21]

3-{3-[(5-chloro-1,3-dimethyl-1H-indol-7-yl)methyl]-2-oxo-2,3-dihydro-1H-benzimidazol-1-yl}hexanoic acid. LC-MS (M⁺+1): 440.25

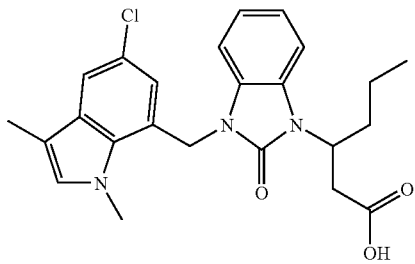 [SMILES: CCCC(CC(=O)O)n1c(=O)n(Cc2cc(Cl)cc3c(C)cn(C)c23)c2ccccc21]

2-({3-[(5-chloro-1,2,3-trimethyl-1H-indol-7-yl)methyl]-2-oxo-2,3-dihydro-1H-benzimidazol-1-yl}methyl)pentanoic acid. LC-MS (M⁺+1): 454.26

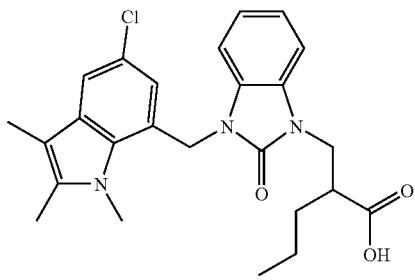 [SMILES: CCCC(Cn1c(=O)n(Cc2cc(Cl)cc3c(C)c(C)n(C)c23)c2ccccc21)C(=O)O]

301

3-{3-[(5-chloro-1-methyl-1H-indol-7-yl)methyl]-2-oxo-2,3-dihydro-1H-benzimidazol-1-yl}hexanoic acid. LC-MS (M⁺+1): 426.16

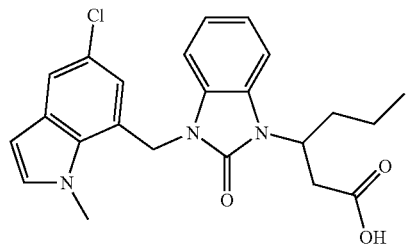 [SMILES: CCCC(CC(=O)O)n1c(=O)n(Cc2cc(Cl)cc3ccn(C)c23)c2ccccc21]

2-({3-[(5-chloro-1,2,3-trimethyl-1H-indol-7-yl)methyl]-2-oxo-2,3-dihydro-1H-benzimidazol-1-yl}methyl)butanoic acid. LC-MS (M⁺+1): 440.02

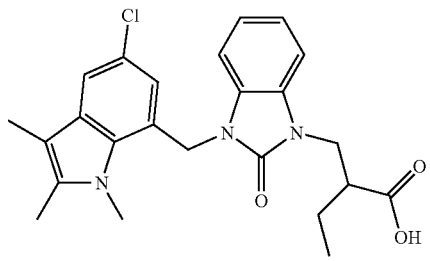 [SMILES: CCC(Cn1c(=O)n(Cc2cc(Cl)cc3c(C)c(C)n(C)c23)c2ccccc21)C(=O)O]

3-{3-[(5-chloro-1,2,3-trimethyl-1H-indol-7-yl)methyl]-2-oxo-2,3-dihydro-1H-benzimidazol-1-yl}-2-methylpropanoic acid. LC-MS (M⁺+1): 426.16

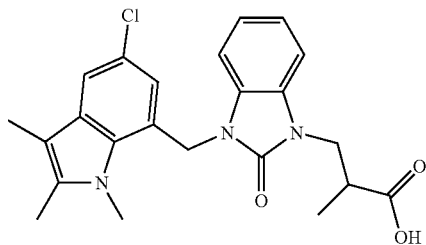 [SMILES: Cc1c(C)n(C)c2c(Cn3c(=O)n(CC(C)C(=O)O)c4ccccc43)cc(Cl)cc12]

3-{3-[(5-chloro-1,2,3-trimethyl-1H-indol-7-yl)methyl]-2-oxo-2,3-dihydro-1H-benzimidazol-1-yl}-2-phenylpropanoic acid. LC-MS (M⁺+1): 488.17

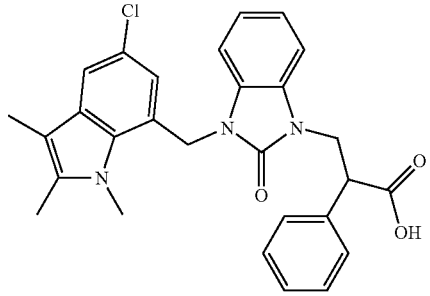 [SMILES: Cc1c(C)n(C)c2c(Cn3c(=O)n(CC(C(=O)O)c4ccccc4)c4ccccc43)cc(Cl)cc12]

302

Example 40

7-[3-(2-Carboxy-ethyl)-2-oxo-2,3-dihydro-benzoimidazol-1-ylmethyl]-1,2,3-trimethyl-1H-indole-6-carboxylic acid methyl ester

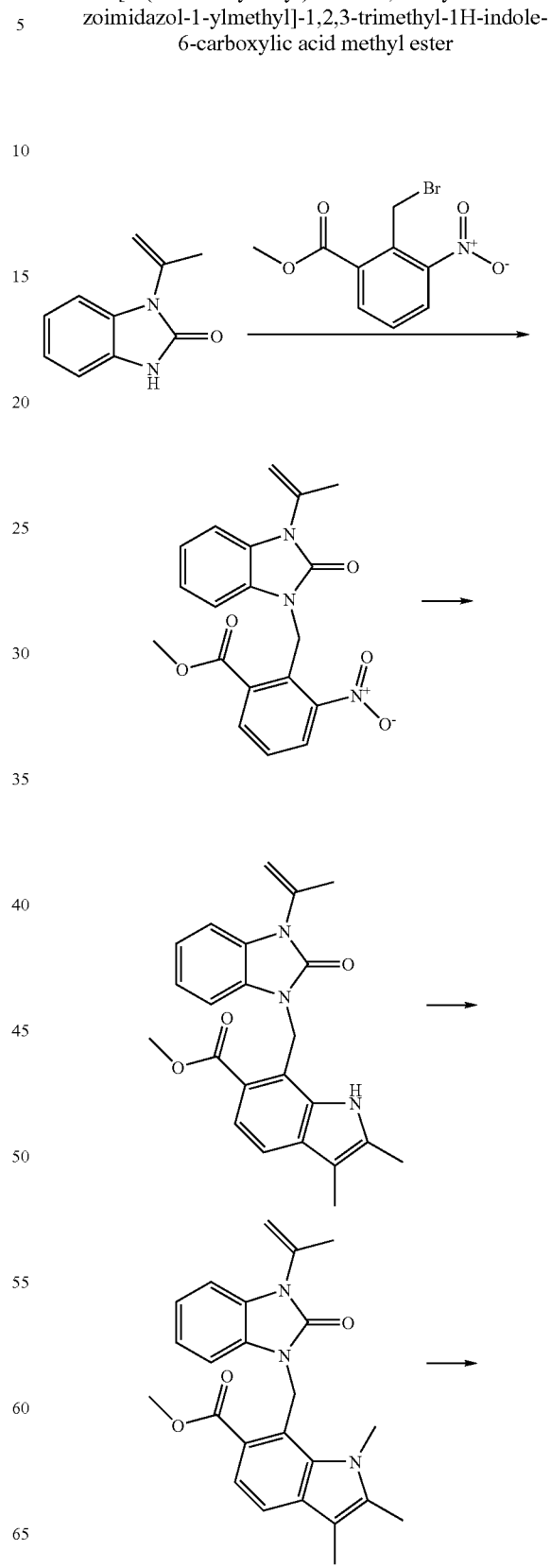

303
-continued

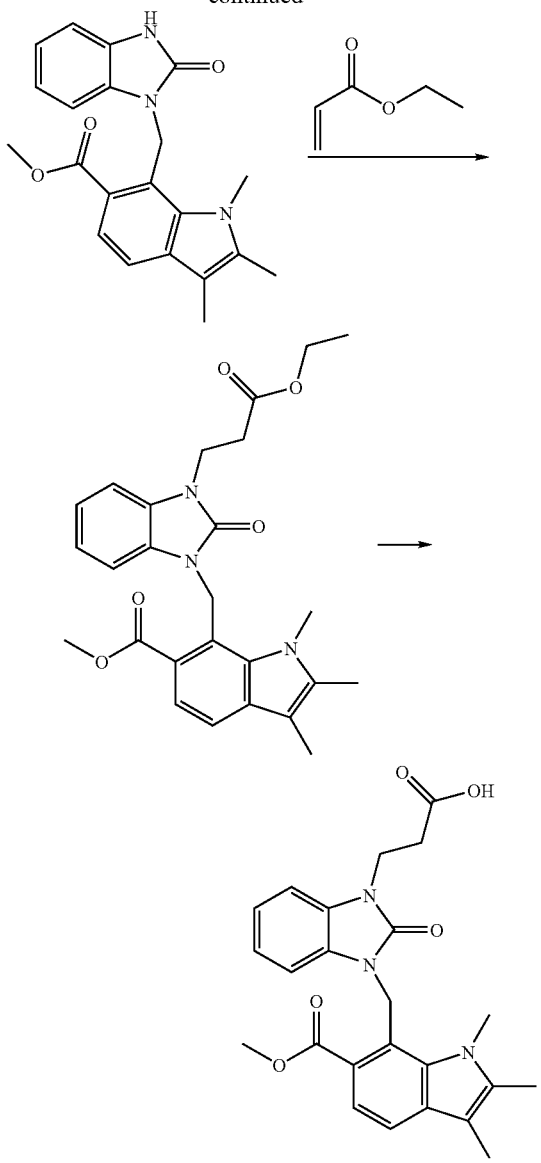

2-(3-Isopropenyl-2-oxo-2,3-dihydro-benzoimidazol-1-ylmethyl)-3-nitro-benzoic acid methyl ester To a solution of 1-isopropenyl-2-benzimidazolidinone (200 mg, 1.1 mmol) in DMF (10 mL) were added methyl-2-bromomethyl-3-nitrobenzoate (472 mg, 1.7 mmol) and K₂CO₃ (317 mg, 2.3 mmol) at room temperature. The solution was heated to 80 C for 2 hours. The solution was cooled down and sat. NH₄Cl solution was added. The solution was extracted with EtOAc. The combined organic layer was dried with MgSO₄ and was filtered. The filtrate was concentrated and the residue was purified by CombiFlash with 20% EtOAc in Hexane as the eluent to afford the desirable product 2-(3-Isopropenyl-2-oxo-2,3-dihydro-benzoimidazol-1-ylmethyl)-3-nitro-benzoic acid methyl ester (395 mg, 94%) as a pale yellow foam.

304

7-(3-Isopropenyl-2-oxo-2,3-dihydro-benzoimidazol-1-ylmethyl)-2,3-dimethyl-1H-indole-6-carboxylic acid methyl ester To a stirred solution of 2-(3-Isopropenyl-2-oxo-2,3-dihydro-benzoimidazol-1-ylmethyl)-3-nitro-benzoic acid methyl ester (1 g, 2.7 mmol) in THF was added 1-methyl-1-propenylmagnesium bromide solution (0.5M in THF) (16 mL. 8.6 mmol) at −50° C. (rapid dropwise addition) under nitrogen. Upon complete addition the reaction was stirred for 45 minutes (−50° C.) and quenched (NH₄Cl, sat.) and warmed to ambient temperature. Diluted with ether and separated the layers. The organic phase was washed with NH₄Cl (Sat., 2×). The organic phase was dried (MgSO₄), filtered and concentrated to give the crude product which was purified via CombiFlash with 10% EtOAc in hexane as the eluent to afford the desirable product 7-(3-lsopropenyl-2-oxo-2,3-dihydro-benzoimidazol-1-ylmethyl)-2,3-dimethyl-1H-indole-6-carboxylic acid methyl ester (350 mg, 33%) as a colorless oil.

7-(3-Isopropenyl-2-oxo-2,3-dihydro-benzoimidazol-1-ylmethyl)-1,2,3-trimethyl-1H-indole-6-carboxylic acid methyl ester To a solution of 7-(3-Isopropenyl-2-oxo-2,3-dihydro-benzoimidazol-1-ylmethyl)-2,3-dimethyl-1H-indole-6-carboxylic acid methyl ester (107 mg, 0.3 mmol) in THF (10 mL) was added NaH (60% in mineral oil) (22 mg, 0.55 mmol) at 0 C under nitrogen atmosphere. The solution was stirred at the same temperature for 15 minutes. MeI (0.034 mL, 0.55 mmol) was added and the solution was stirred at 0 C for 2 hour. Sat. NH₄Cl solution was added and the solution was extracted with EtOAc. The combined organic layer was dried with MgSO₄ and was filtered. The filtrate was concentrated and the residue was purified by CombiFlash with 10% EtOAc in Hexane as the eluent to afford the desirable product 7-(3-Isopropenyl-2-oxo-2,3-dihydro-benzoimidazol-1-ylmethyl)-1,2,3-trimethyl-1H-indole-6-carboxylic acid methyl ester (100 mg. 90%) as a colorless oil.

1,2,3-Trimethyl-7-(2-oxo-2,3-dihydro-benzoimidazol-1-ylmethyl)-1H-indole-6-carboxylic acid methyl ester 7-(3-Isopropenyl-2-oxo-2,3-dihydro-benzoimidazol-1-ylmethyl)-1,2,3-trimethyl-1H-indole-6-carboxylic acid methyl ester (100 mg. 0.25 mmol) was dissolved in MeOH (10 mL) and HCl (5 mL) solution at room temperature. The solution was heated to 60 C for 2 hours. The solution was cooled down and was extracted with EtOAc. The combined organic layer was dried with MgSO₄ and was filtered. The filtrate was concentrated and the residue was purified by CombiFlash with 10% EtOAc in hexane as the eluent to afford the desirable product 1,2,3-Trimethyl-7-(2-oxo-2,3-dihydro-benzoimidazol-1-ylmethyl)-1H-indole-6-carboxylic acid methyl ester (85 mg, 94%) as a colorless oil.

7-[3-(2-Ethoxycarbonyl-ethyl)-2-oxo-2,3-dihydro-benzoimidazol-1-ylmethyl]-1,2,3-trimethyl-1H-indole-6-carboxylic acid methyl ester To a stirred solution of 1,2,3-Trimethyl-7-(2-oxo-2,3-dihydro-benzoimidazol-1-ylmethyl)-1H-indole-6-carboxylic acid methyl ester (70 mg, 0.19 mmol) in DMF (10 mL) was added the methylacrylate (0.035 mL, 0.39 mmol) followed by the benzyltrimethylammonium hydroxide (40% in MeOH) (0.13 mL, 0.29 mmol). The resulting solution was stirred at ambient temperature for 2 h after which time the reaction appeared complete. The reaction was poured into water and EtOAc. The layers were separated and the aqueous phase was extracted with EtOAc (2×). The combined organics were dried with MgSO₄ and was filtered, concentrated. The residue was purified by CombiFlash with 20% EtOAc in Hexane as the eluent to afford the product 7-[3-(2-Ethoxycarbonyl-ethyl)-2-oxo-2,3-dihydro-benzoimidazol-1-ylmethyl]-1,2,3-trimethyl-1H-indole-6-carboxylic acid methyl ester (66 mg, 76%) as a colorless oil.

7-[3-(2-Carboxy-ethyl)-2-oxo-2,3-dihydro-benzoimidaml-1-ylmethyl]-1,2,3-trimethyl-1H-indole-6-carboxylic acid methyl ester To a solution of 7-[3-(2-Ethoxycarbonyl-ethyl)-2-oxo-2,3-dihydro-benzoimidazol-1-ylmethyl]-1,2,3-trimethyl-1H-indole-6-carboxylic acid methyl ester (60 mg, 0.13 mmol) in 1,4-dioxane (5 mL) and H₂O (2 mL) was added LiOH (6.4 mg). The solution was stirred at room temperature for 5 hours. The solution was concentrated and the residue was purified by CombiFlash with 10% MeOH in CH₂Cl₂ as the eluent to afford the desirable product 7-[3-(2-Carboxy-ethyl)-2-oxo-2,3-dihydro-benzoimidazol-1-ylmethyl]-1,2,3-trimethyl-1H-indole-6-carboxylic acid methyl ester (10 mg, 17%) as a white solid. LC-MS (M⁺): 435.36.

The following compound was prepared using a similar procedure.

3-{2-oxo-3-[(1,2,3,5-tetramethyl-1H-indol-7-yl)methyl]-2,3-dihydro-1H-benzimidazol-1-yl}propanoic acid. LCMS (M+1): 392.46

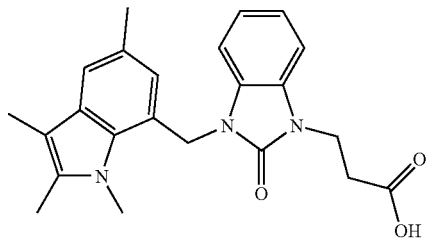 [SMILES: Cc1cc(Cn2c(=O)n(CCC(=O)O)c3ccccc32)c2c(c1)c(C)c(C)n2C]

Example 41

(S)-3-[3-(4-Methyl-1H-indol-3-ylmethyl)-2-oxo-2,3-dihydro-benzoimidazol-1-yl]-hexanoic acid

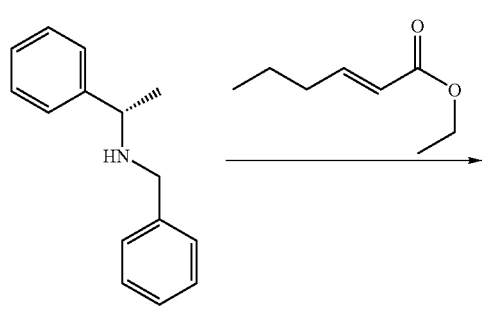

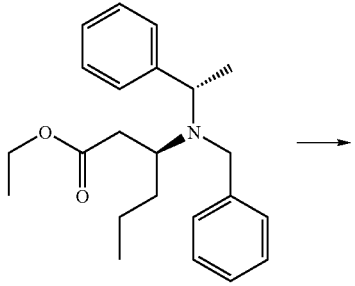

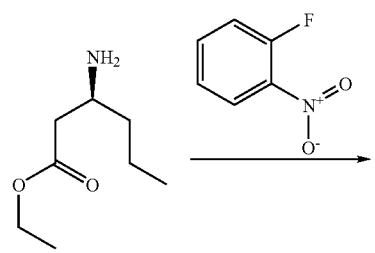

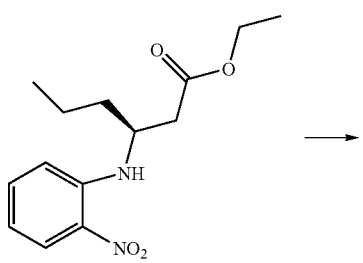

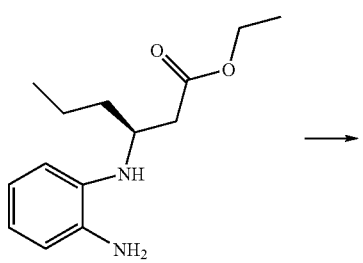

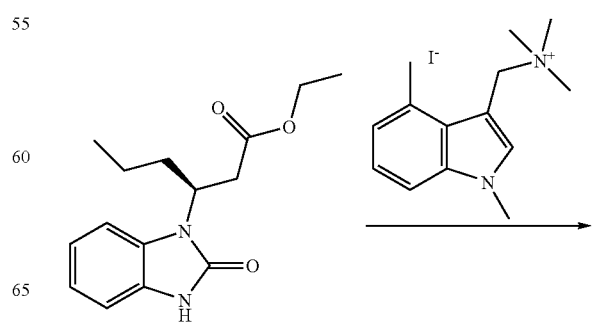

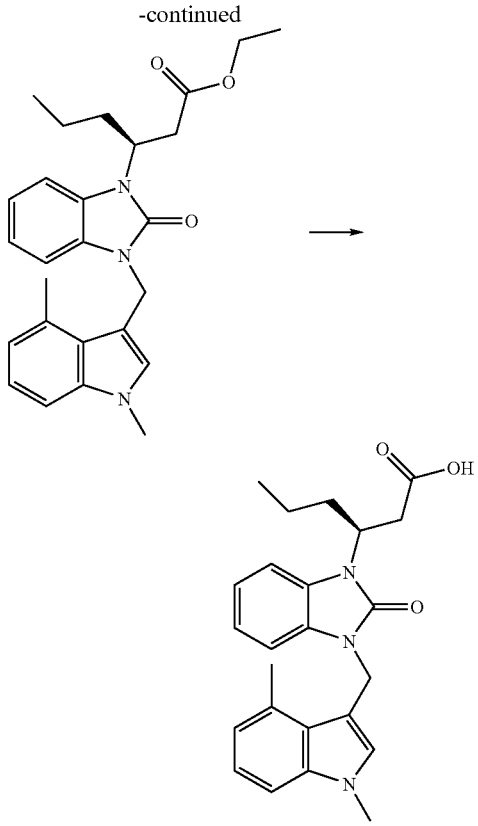

(S)-3-[Benzyl-((S)-1-phenyl-ethyl)-amino]-hexanoic acid ethyl ester

To a solution of (S)-(−)-N-benzyl-alpha-methyl-benzylamine (50 mL, 239 mmol) in THF (150 mL) at 0 C was added BuLi (2.5 M in THF) (100 mL, 250 mmol) under nitrogen atmosphere. The solution was cooled to −78 C and ethyl trans-2-hexenoate (16.6 g, 117 mmol) was added. The solution was stirred for 1 hour and Sat. NH$_4$Cl solution was added. The solution was warmed to room temperature and was extracted with EtOAc. The combined organic layer was dried with MgSO$_4$ and was filtered. The filtrate was concentrated and the residue was purified by CombiFlash with 5% EtOAc in Hexane as the eluent to afford the desirable product (S)-3-[Benzyl-((S)-1-phenyl-ethyl)-amino]-hexanoic acid ethyl ester (20.8 g, 50%) as a colorless oil.

(S)-3-Amino-hexanoic acid ethyl ester

To a solution of (S)-3-[Benzyl-((S)-1-phenyl-ethyl)-amino]-hexanoic acid ethyl ester (20.8 g, 59 mmol) in EtOH (50 mL) was added Pd(OH)$_2$ (20% in carbon) (2 g). The mixture was stirred under hydrogen atmosphere with 40 psi for 16 hours. The mixture was filtered and the filtrate was concentrated. The residue (8.2 g, 87%) was used in the next step of the synthesis without further purification.

(S)-3-(2-Nitro-phenylamino)-hexanoic acid ethyl ester

To a solution of 1-fluoro-2-nitrobenzene (500 mg, 3.5 mmol) in DMF (150 mL) were added (S)-3-Amino-hexanoic acid ethyl ester (600 mg, 3.8 mmol) and diisopropyl ethylamine (0.65 mL, 3.8 mmol). The solution was heated to 90 C for 16 hours. The solution was cooled down and was water (300 mL) was added. The solution was extracted with EtOAc and the combined organic layer was dried with MgSO$_4$. The mixture was filtered and the filtrate was concentrated. The residue was purified by CombiFlash with 5% EtOAc in Hexane as the eluent to afford the desirable product (S)-3-(2-Nitro-phenylamino)-hexanoic acid ethyl ester (795 mg, 80%) as a colorless oil.

(S)-3-(2-Amino-phenylamino)-hexanoic acid ethyl ester

To a solution of (S)-3-(2-Nitro-phenylamino)-hexanoic acid ethyl ester (795 mg, 2.8 mmol) in EtOH (20 mL) was added Pd/C (10% wt on carbon) (300 mg). The solution was stirred at room temperature for 3 hours. The solution was filtered and the filtrate was concentrated. The residue (683 mg, 96%) was used in the next step of the synthesis without further purification.

(S)-3-(2-Oxo-2,3-dihydro-benzoimidazol-1-yl)-hexanoic acid ethyl ester

To a solution of (S)-3-(2-Amino-phenylamino)-hexanoic acid ethyl ester (650 mg, 2.6 mmol) in THF (10 mL) was added carbonyl diimidazole [CDI] (842 mg, 5.2 mmol) at room temperature under nitrogen atmosphere. The solution was stirred at the same temperature for 12 hours. The solution was concentrated and the residue was purified by CombiFlash with 20% EtOAc in Hexane as the eluent to afford the desirable product (S)-3-(2-Oxo-2,3-dihydro-benzoimidazol-1-yl)-hexanoic acid ethyl ester (700 mg, 98%) as a colorless oil.

(S)-3-[3-(1,4-Dimethyl-1H-indol-3-ylmethyl)-2-oxo-2,3-dihydro-benzoimidazol-1-yl]-hexanoic acid ethyl ester To a solution of (S)-3-(2-Oxo-2,3-dihydro-benzoimidazol-1-yl)-hexanoic acid ethyl ester (700 mg, 2.5 mmol) in DMF (50 mL) were added (1,4-Dimethyl-1H-indol-3-ylmethyl)-trimethyl-amine iodide salt (1.3 g, 3.8 mmol) and K$_2$CO$_3$ (700 mg, 5.1 mmol) at room temperature under nitrogen atmosphere. The solution was heated to 100 C for 4 hours. The solution was cooled down and water was added. The solution was extracted with EtOAc and the combined organic layer was dried with MgSO$_4$. The solution was filtered and the filtrate was concentrated. The residue was purified by CombiFlash with 20% EtOAc in Hexane as the eluent to afford the desirable product (S)-3-[3-(1,4-Dimethyl-1H-indol-3-ylmethyl)-2-oxo-2,3-dihydro-benzoimidazol-1-yl]-hexanoic acid ethyl ester (737 mg, 67%) as a yellow foam.

(S)-3-[3-(1,4-Dimethyl-1H-indol-3-ylmethyl)-2-oxo-2,3-dihydro-benzoimidazol-1-yl]-hexanoic acid To a solution of (S)-3-[3-(1,4-Dimethyl-1H-indol-3-ylmethyl)-2-oxo-2,3-dihydro-benzoimidazol-1-yl]-hexanoic acid ethyl ester (4.2 g, 9.8 mmol) in 1,4-dioxane (100 mL) and water (10 mL) was added LiOH (234 mg, 9.8 mmol) at room temperature. The solution was stirred at the same temperature for 12 hours. The solution was concentrated and water was added to the residue. The solution was acidified by 12N HCl in an ice-bath. The solid that precipitated out from the solution was collected by filtration. The solid was dried under vacuum and was confirmed to be the desirable product (S)-

3-[3-(1,4-Dimethyl-1H-indol-3-ylmethyl)-2-oxo-2,3-dihydro-benzoimidazol-1-yl]-hexanoic acid (3.7 g, 92%). LC-MS (M⁺+1): 406.27.

The following compound was prepared following the similar procedure using appropriate starting material.

(3S)-3-{2-oxo-3-[(1,4,6-trimethyl-1H-indol-3-yl)methyl]-2,3-dihydro-1H-benzimidazol-1-yl}hexanoic acid. LCMS: m/z 420.28 (M+H⁺)

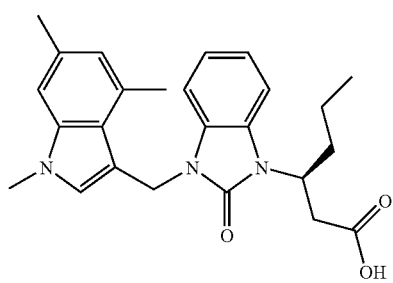 [SMILES: CCC[C@@H](CC(=O)O)n1c(=O)n(Cc2cn(C)c3cc(C)cc(C)c23)c2ccccc21]

Example 42

3-(3-naphtalen-2-ylmethyl-2-oxo-6-[(tetrahydrofuran-2-ylmethyl)carbamoyl]-2,3-dihydro-benzoimidazol-1-yl)propionic acid -continued

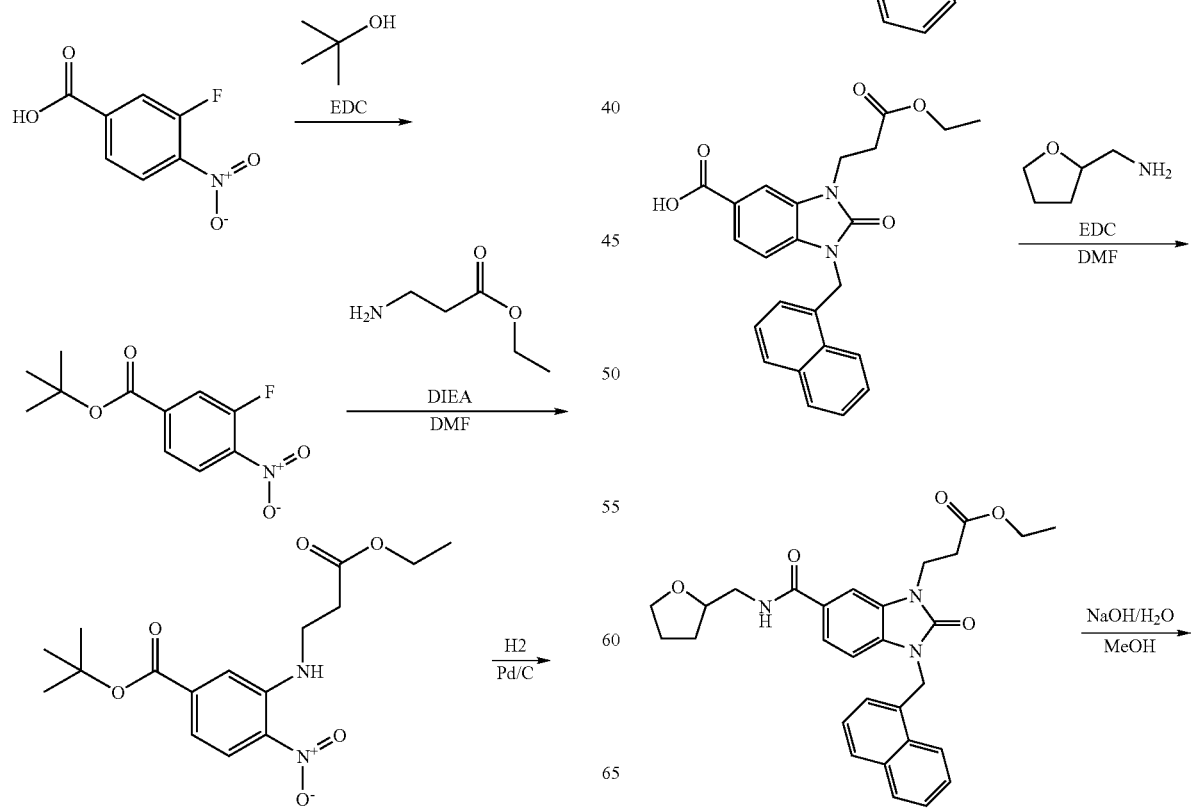

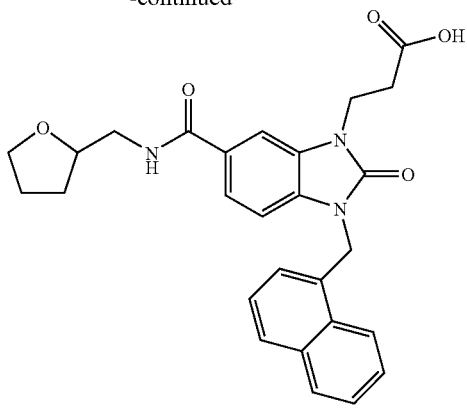

3-Fluoro-4-nitro-benzoic acid tert-butyl ester

A solution of 3-Fluoro-4-Nitro benzoic acid (2.00 g, 10.8 mmol) in 50% DMF/CH$_2$Cl$_2$ (60 ml) was put on ice for 15 minutes. To the solution EDC (2.1 g, 11 mmol) was added.

The solution was stirred in the cold for another 15 minutes. t-butanol (3.7 g, 50 mmol) was then added, followed by DMAP (100 mg). The solution was stirred at room temperature overnight. Upon completion (TLC), the reaction mixture was diluted with ethyl acetate (300 ml), washed with water then with 1N NaOH solution and finally with brine. The organic phase was evaporated to dryness. The residue was washed down a column eluded with 3% methanol in CH$_2$Cl$_2$. the pooled fractions were evaporated to dryness to give 2 g (77%) of the desired product.

3-(2-Ethoxycarbonyl-ethylamino)-4-nitro-benzoic acid tert-butyl ester 3-fluoro-4-nitro-benzoic acid tert-butyl ester (1 g, 4.14 mmol) and Beta-Alanine ethyl ester hydrochloride 1.037 g, 6.75 mmol) were dissolved in DMF (10 ml). To the solution DIEA 0.872 g, 6.75 mmol) was added and the mixture stirred at room temperature overnight. The reaction mixture was diluted with water (100 ml), extracted with Ethyl acetate 3×, dried over MgSO$_4$, filtered and evaporated to dryness to afford 1.2 g of solid was obtained (86%).

4-Amino-3-(2-Ethoxycarbonyl-ethylamino)-benzoic acid tert-butyl ester 3-(2-Ethoxycarbonyl-ethylamino)-4-nitro-benzoic acid tert-butyl ester (1.2 g, 3.55 mmol) was dissolved in ethanol (60 ml) to the solution Pd/C (10%) (300 mg) was added and the reaction mixture was stirred under Hydrogen (1 atmosphere) overnight. The reaction mixture was filtered through celite and evaporated to dryness to give 1 g (91%) of product.

3-(2-Ethoxycarbonyl-ethyl)-2-oxo-2,3-dihydro-1-H-bezoimidazole-5-carboxylic acid tert-butyl ester To a solution of 4-Amino-3-(2-Ethoxycarbonyl-ethylamino)-benzoic acid tert-butyl ester (900 mg, 2.92 mmol) in THF (20 ml) was added CDI (997 mg, 6 mmol). The solution was heated at 90 degrees for 30 minutes. The reaction mixture was evaporated to dryness, and then taken up in Ethyl Acetate. The organic phase was washed with brine, dried over MgSO$_4$, filtered, evaporated to dryness. The residue was purified by flash Chromatography eluded with 5% methanol in CH$_2$Cl$_2$. After evaporation of the desired fractions, 800 mg was obtained (82%).

3-(2-Ethoxycarbonyl-ethyl)-1-naphtalen-2-ylmethyl-2-oxo-2,3-dihydro-1-H-benzoimidazole-5-carboxylic acid tert-butyl ester 3-(2-Ethoxycarbonyl-ethyl)-2-oxo-2,3-dihydro-1-1-1-bezoimidazole-5-carboxylic acid tert-butyl ester (800 mg, 2.4 mmol) dissolved in DMF (15 ml) and put on ice for 15 minutes. To the solution NaH (87 mg, 3.6 mmol) was added portionwise. The resulting mixture was allowed to stir for another 20 minutes. The mixture was put on warm water until evolution of gas stopped. The ice bath was reintroduced and chloromethyl naphthalene dissolved in DMF (5 ml) was added slowly. The reaction mixture was then stirred at room temperature overnight. The reaction mixture was diluted with water, extracted (3×) with ethyl acetate, dried over MgSO$_4$, filtered, and evaporated to dryness. After purification by flash chromatography 850 mg was obtained (75%).

3-2-Ethoxycarbonyl-ethyl)1-naphtalen-2-ylmethyl-2oxo-2,3-dihydro-1-H-benzoimidazole-5-carboxylic acid 3-(2-Ethoxycarbonyl-ethyl)-1-naphtalen-2-ylmethyl-2-oxo-2,3-dihydro-1-H-benzoimidazole-5-carboxylic acid tert-butyl ester (900 mg, 1.9 mmol) was dissolved in 25% TFA in CH$_2$Cl$_2$ (100 ml). The solution was allowed to stand at room temperature for 4 hours. After complete disappearance of the starting material the solution was evaporated to dryness. The residue was re-dissolved in CH$_2$Cl$_2$ (100 ml) and evaporated to dryness. This was done 4 times. The residue was dried overnight under vacuum. 690 mg was obtained (87%).

3-{3-Naphtalen-2-ylmethyl-2-oxo-6-[(tetrahydro-furan-2-ylmethyl)-carbamoyl]-2'3-dihydro-benzoimidazol-1-yl}-propionic acid ethyl ester 3-2-Ethoxycarbonyl-ethyl)1-naphtalen-2-ylmethyl-2oxo-2,3-dihydro-1-H-benzoimidazole-5-carboxylic acid (100 mg, 0.24 mmol) was dissolved in DMF (3 ml). the solution was then put on ice. To the cold solution EDC (48 mg, 0.250 mmol) and HOBT (34 mg, 0.250 mmol) were added. After stirring the mixture on ice for 30 minutes, C-(tetrahydro-furan-2-yl)-methyl amine (25 mg, 0.250 mmol) was added. The reaction mixture was stirred at room temperature for 4 hours. TLC showed completion of the reaction. The reaction mixture was diluted with aqueous solution of Sodium bicarbonate, extracted with Ethyl acetate, washed with brine, dried over MgSO$_4$, filtered, and evaporated to dryness to give 106 mg (88%).

3-(3-naphtalen-2-ylmethyl-2-oxo-6-[(tetrahydro-furan-2-ylmethyl)carbamoyl]-2,3-dihydro-benzoimidazol-1-yl)propionic acid 3-{3-Naphtalen-2-ylmethyl-2-oxo-6-[(tetrahydro-furan-2-ylmethyl)-carbamoyl]-2'3-dihydro-benzoimidazol-1-yl}-propionic acid ethyl ester (100 mg, 0.2 mmol) was dissolved in methanol (2 ml). To the solution aqueous solution of sodium Hydroxide was added. The mixture was stirred at room temperature for 2 hours and evaporated to dryness. The reaction mixture was then taken up in water (10 ml) acidified with 1 N HCl, extracted with Ethyl acetate, washed with brine, dried over MgSO$_4$, filtered, evaporated to dryness. The residue was purified by flash chromatography eluded 5% methanol in CH$_2$Cl$_2$ to give 60 mg (60%) of the desired product. LCMS: m/z 473.52 (M+H$^+$).

The following compounds were synthesized using a similar procedure:

3-{6-[(2-hydroxyethyl)carbamoyl]-3-[(4-methyl-1-benzothien-3-ylmethyl]-2-oxo-2,3-dihydro-1H-benzimidazol-1-yl}propanoic acid. LCMS (ESMS): 453.51 (M+H$^+$)

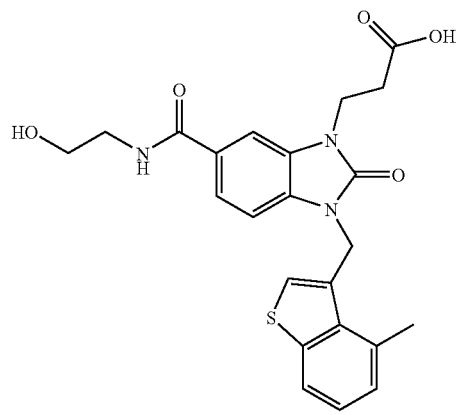 [SMILES: Cc1cccc2scc(Cn3c(=O)n(CCC(=O)O)c4cc(C(=O)NCCO)ccc43)c12]

3-{6-[(Benzypcarbamoyl]-3-[(4-methyl-1-benzothien-3-ylmethyl]-2-oxo-2,3-dihydro-1H-benzimidazol-1-yl}propanoic acid. LCMS (ESMS): 499.6 (M+H$^+$)

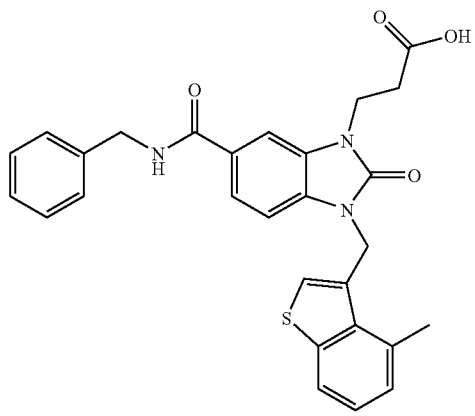 [SMILES: Cc1cccc2scc(Cn3c(=O)n(CCC(=O)O)c4cc(C(=O)NCc5ccccc5)ccc43)c12]

3-{6-{[2-(4-metoxyphenyl)ethyl]carbamoyl]-3-[(4-methyl-1-benzothien-3-ylmethyl]-2-oxo-2,3-dihydro-1H-benzimidazol-1-yl}propanoic acid. LCMS (ESMS): 543.54 (M$_+$H$^+$)

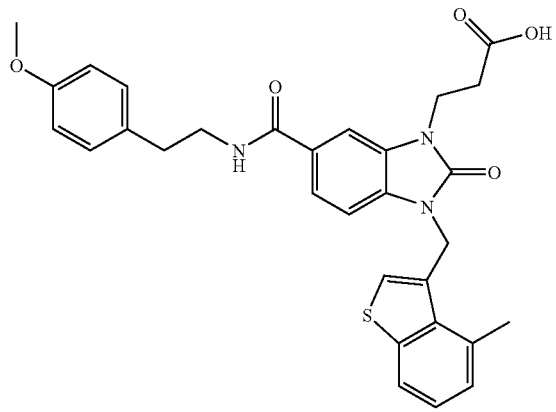 [SMILES: COc1ccc(CCNC(=O)c2ccc3c(c2)n(CCC(=O)O)c(=O)n3Cc2csc3cccc(C)c23)cc1]

3-{6-{[2-(2-metoxyphenyl)ethyl]carbamoyl]-3-[(1-naphtyl methyl]-2-oxo-2,3-dihydro-1H-benzimidazol-1-yl}propanoic acid. LCMS (ESMS): 523.54 (M+H$^+$)

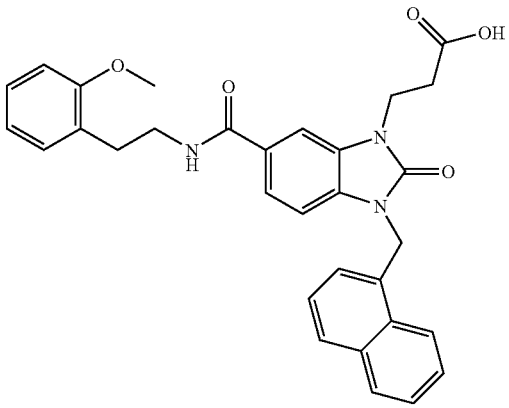 [SMILES: COc1ccccc1CCNC(=O)c1ccc2c(c1)n(CCC(=O)O)c(=O)n2Cc1cccc2ccccc12]

3-{6-{[3-hydroxypyrrolidin-1-yl)carbamoyl]-3-[(1-naphtyl methyl]-2-oxo-2,3-dihydro-1H-benzimidazol-1-yl}propanoic acid. LCMS (ESMS): 459.54 (M+H$^+$)

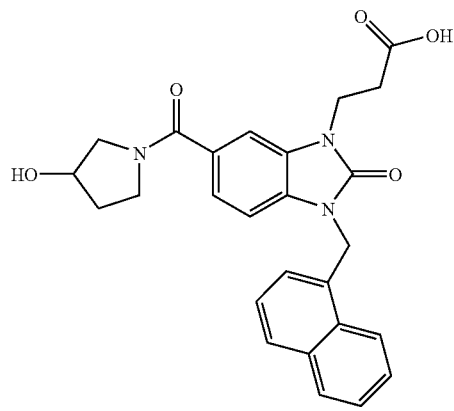 [SMILES: O=C(O)CCn1c(=O)n(Cc2cccc3ccccc23)c2ccc(C(=O)N3CCC(O)C3)cc21]

| 315 | 316 |
|---|---|
| 3-{6-{[2-(3-metoxyphenyl)ethyl]carbamoyl]-3-[(4-methyl-1-benzothien-3-ylmethyl]-2-oxo-2,3-dihydro-1H-benzimidazol-1-yl}propanoic acid. LCMS (ESMS): 543.54 (M+H+) | 3-{6-{[2-(3,4-dimetoxyphenyl)ethyl]carbamoyl]-3-[(1-naphylmethyl]-2-oxo-2,3-dihydro-1H-benzimidazol-1-yl}propanoic acid. LCMS (ESMS): 553.64 (M+H+) |

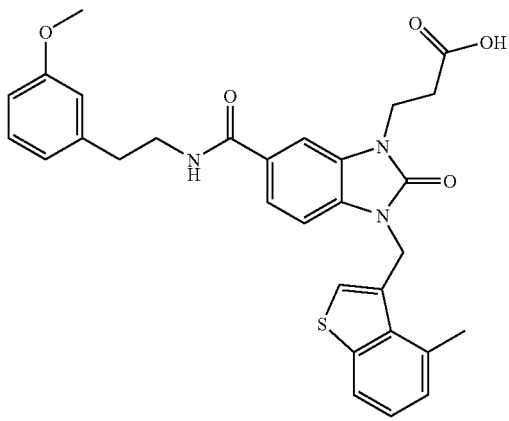 [SMILES: COc1cccc(CCNC(=O)c2ccc3c(c2)n(CCC(=O)O)c(=O)n3Cc2csc3cccc(C)c23)c1] 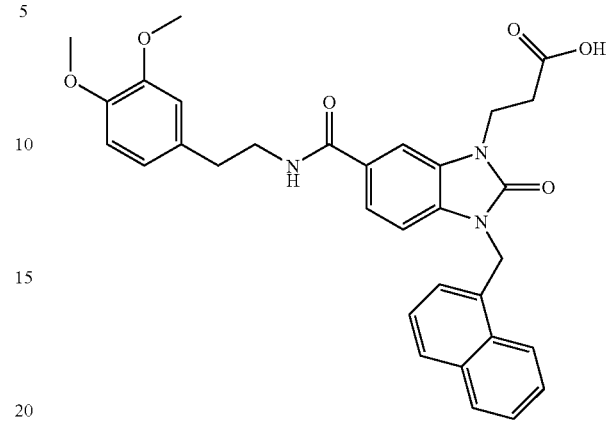

3-{6-{[2-(3-hydroxy-4-metoxyphenyl)ethyl]carbamoyl]-3-[(4-methyl-1-benzothien-3-ylmethyl]-2-oxo-2,3-dihydro-1H-benzimidazol-1-yl}propanoic acid. LCMS (ESMS): 559.64 (M+H+)

3-{6-{[2-(3-hydroxy-4-metoxyphenyl)ethyl]carbamoyl]-3-[(1-naphtylmethyl]-2-oxo-2,3-dihydro-1H-benzimidazol-1-yl}propanoic acid. LCMS (ESMS): 539.58 (M+H+)

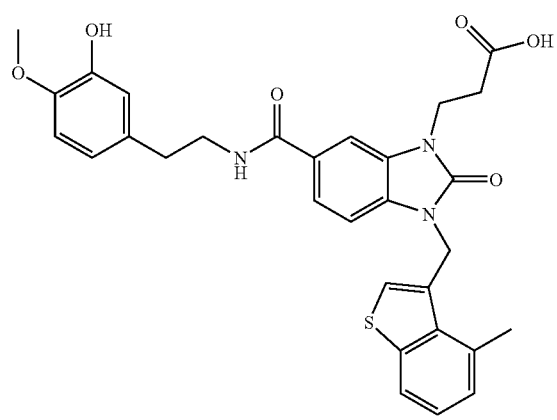 [SMILES: COc1ccc(CCNC(=O)c2ccc3c(c2)n(CCC(=O)O)c(=O)n3Cc2csc3cccc(C)c23)cc1O] 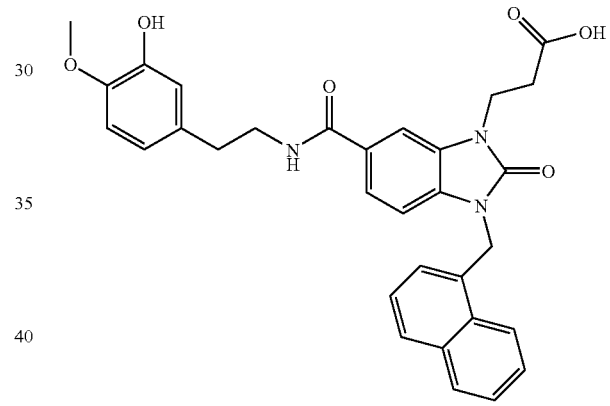

3-{6-{[2-(2-metoxyphenyl)ethyl]carbamoyl]-3-[(4-methyl-1-bezothien-3-ylmethyl]-2-oxo-2,3-dihydro-1H-benzimidazol-1-yl}propanoic acid. LCMS (ESMS): 543.64 (M+H+)

3-{6-{[2-(3,4-dimetoxyphenyl)ethyl]carbamoyl]-3-[(4-methyl-1-bezothien-3-ylmethyl]-2-oxo-2,3-dihydro-1H-benzimidazol-1-yl}propanoic acid. LCMS (ESMS): 573.64 (M+H+)

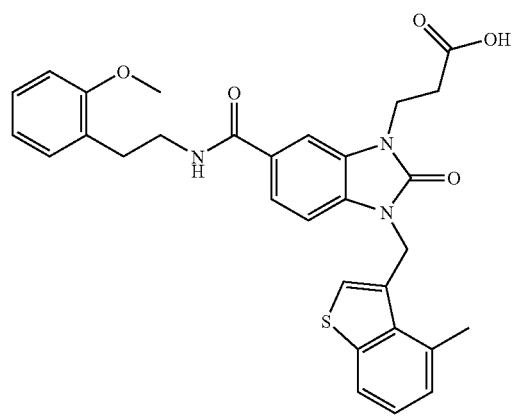 [SMILES: COc1ccccc1CCNC(=O)c1ccc2c(c1)n(CCC(=O)O)c(=O)n2Cc1csc2cccc(C)c12] 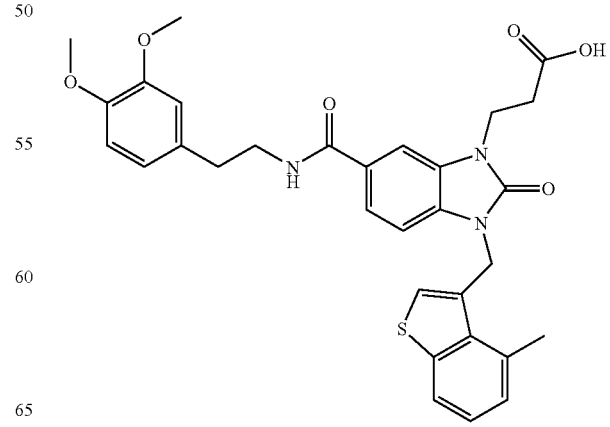

Example 43

3-[3-(1,2-Dimethyl-1H-indol-7-ylmethyl)-2-oxo-2,3-dihydro-benzimidazol-1-yl]-propionic acid

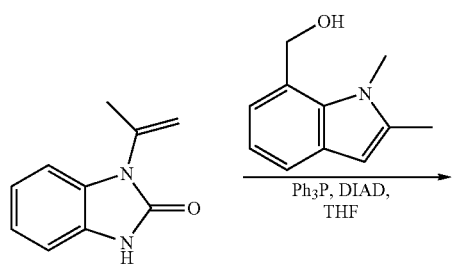

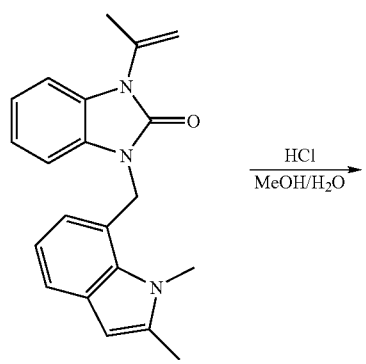

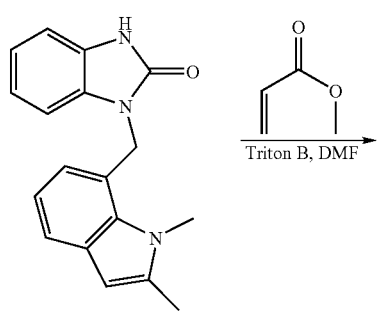

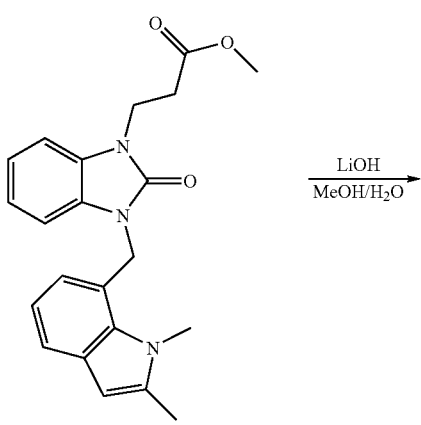

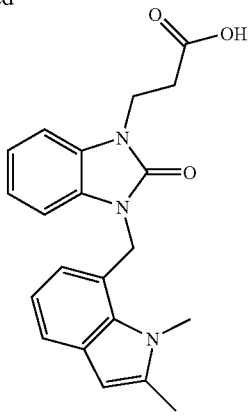

1-(1,2-Dimethyl-1H-indol-7-ylmethyl)-3-isopropenyl-1,3-dihydro-benzimidazol-2-one To a solution of 1-isopropenylbenzimidazolone (220 mg, 1.3 mmol) in dry THF (10 mL) are added triphenylphosphine (397 mg, 1.5 mmol) and (1,2-Dimethyl-1H-indol-7-yl)-methanol (220 mg, 1.3 mmol). Then diisopropyl azodicarboxylate (0.31 mL, 1.5 mmol) is added drop wise into the above solution at room temperature. The mixture is stirred for 16 hrs and then the solvent is removed under vacuum. The residue is purified by flash column chromatography using 10-30% EtOAc in hexanes to give 200 mg (48%) of 1-(1,2-dimethyl-1H-indol-7-ylmethyl)-3-isopropenyl-1,3-dihydro-benzimidazol-2-one.

1-(1,2-Dimethyl-1H-indol-7-ylmethyl)-1,3-dihydro-benzimidazol-2-one (1,2-dimethyl-1H-indol-7-ylmethyl)-3-isopropenyl-1,3-dihydro-benzimidazol-2-one (200 mg, 0.60 mmol) was suspended in ethanol (0.5 ml) and water (0.5 ml) and treated with 37% HCl (0.2 ml). The reaction was warmed to 60° C. for 1.5 h, cooled to room temperature and concentrated to low volume. The remaining residue was dissolved into DCM and sequentially washed with water and NaHCO$_3$ (sat.). The organic phase was dried (MgSO$_4$), filtered and concentrated to give 170 mg (97%) of 1-(1,2-dimethyl-1H-indol-7-ylmethyl)-1,3-dihydro-benzimidazol-2-one which was used without further purification.

3-[3-(1,2-Dimethyl-1H-indol-7-ylmethyl)-2-oxo-2,3-dihydro-benzimidazol-1-yl]-propionic acid methyl ester To a solution of 1-(1,2-dimethyl-1H-indol-7-ylmethyl)-1,3-dihydro-benzimidazol-2-one (170 mg, 0.58 mmol) in DMF (3.0 mL) are added methyl acrylate (0.06 mL, 0.6 mmol) and 40% benzyltrimethyl ammonium hydroxide in MeOH (0.06 mL, 0.15 mmol). The resulting mixture is stirred at room temperature for 18 h after which time water (20 mL) was added. The mixture is extracted with EtOAc (3×50 mL) and the organic layers are combined, dried over MgSO$_4$ and concentrated to give crude product. Purification by flash column chromatography using 20-50% EtOAc in Hexanes affords 90 mg (41%) of 3-[3-(1,2-dimethyl-1H-indol-7-ylmethyl)-2-oxo-2,3-dihydro-benzimidazol-1-yl]-propionic acid methyl ester.

3-[3-(1,2-Dimethyl-1H-indol-7-ylmethyl)-2-oxo-2,3-dihydro-benzimidazol-1-yl]-propionic acid To a stirred solution of 3-[3-(1,2-dimethyl-1H-indol-7-ylmethyl)-2-oxo-2,3-dihydro-benzimidazol-1-yl]-propionic acid methyl ester (90 mg, 0.24 mmol) in THF (3 ml) and water (0.5 ml) was added lithium hydroxide monohydrate (15 mg, 0.36 mmol). The reaction was stirred for 0.5 h and concentrated to low volume. The remaining residue was diluted with water and acetic acid (0.3 ml). The resulting suspension was stirred at ambient temperature overnight. The precipitate was collected via filtration, washed with water and then suspended in 1:1 acetonitrile/water. The solid precipitate was isolated via filtration and dried to give 65 mg (87%) of 3-[3-(1,2-dimethyl-1H-indol-7-ylmethyl)-2-oxo-2,3-dihydro-benzimidazol-1-yl]-propionic acid. LCMS (ESMS): m/z 364.41 (M+H).

Example 44

(2S)-2-{3-[(4-methyl-1-benzothien-3-yl)methyl]-2-oxo-2,3-dihydro-1H-benzimidazol-1-yl}propanoic acid

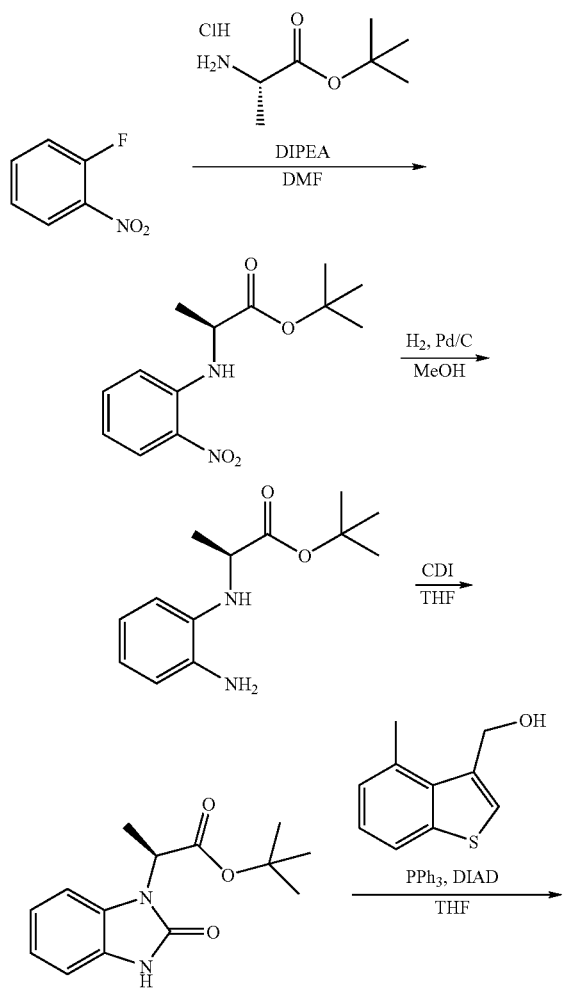

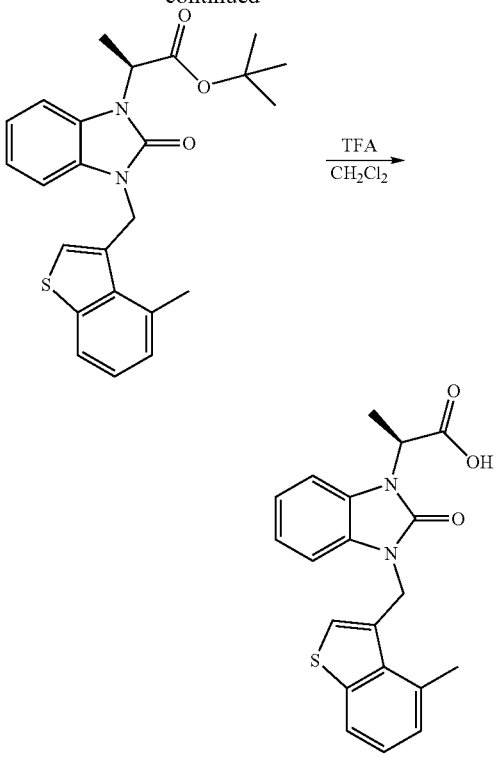

(S)-2-(2-Nitro-phenylamino)-propionic acid tert-butyl ester

To a solution of 2-fluoronitrobenzene (1.0 g, 7.09 mmol) in DMF (5 mL) were added H-ALA-OTBU HCl (2.6 g, 14.2 mmol) and DIPEA (2.5 mL, 14.2 mmol). The reaction mixture was stirred at room temperature over the weekend. The reaction mixture was then diluted with ethyl acetate and washed with water (×4). The organic phase was then dried over Na₂SO₄ and concentrated to afford 1.8 g (95%) of the desired product as orange oil. The resulting residue was used for the next reaction without further purification.

(S)-2-(2-Amino-phenylamino)-propionic acid tert-butyl ester

To a solution of (S)-2-(2-Nitro-phenylamino)-propionic acid tert-butyl ester (1.6 g, 6.0 mmol) in MeOH (20 mL) was added a slurry of 10% Pd/C (dry) (300 mg). The reaction mixture was degasses using house vacuum aspirator and then saturated with H₂ gas in balloon. The reaction mixture was stirred at room temperature for 16 h. The reaction mixture was then filtered through a celite and the filtrate was concentrated to afford 1.5 g (100%) of the desired product as a dark brown oily residue. This product was used for the next reaction without purification.

(S)-2-(2-Oxo-2,3-dihydro-benzimidazol-1-yl)-propionic acid tert-butyl ester To a solution of (S)-2-(2-Amino-phenylamino)-propionic acid tert-butyl ester (1.5 g, 6.3 mmol) in THF (10 mL) was added CDI (1.03 g, 6.3 mmol). The reaction mixture was stirred at room temperature for 1 h. When the reaction was completed, the reaction mixture was diluted with ethyl acetate and washed with water. The organic phase was dried over Na$_2$SO$_4$ and concentrated to afford 1.6 g of the desired product as an oily residue. The LCMS indicated only 40% purity; however, this product was used for the next reaction without further purification. LCMS (ESMS): m/z 263.38 (M+H$^+$).

(S)-2-[3-(4-Methyl-benzo[b]thiophen-3-ylmethyl)-2-oxo-2,3-dihydro-benzimidazol-1-yl]-propionic acid tert-butyl ester To a solution of (S)-2-(2-Oxo-2,3-dihydro-benzimidazol-1-yl)-propionic acid tert-butyl ester (0.3 g, 0.46 mmol), (4-Methyl-benzo[b]thiophen-3-yl)-methanol (0.12 g, 0.69 mmol), and triphenylphosphine (0.14 g, 0.55 mmol) was added dropwise DIAD (0.11 mL, 0.55 mmoL) at 0° C. The mixture was slowly warmed to room temperature and stirred for 2 h. The reaction mixture was diluted with ethyl acetate and washed with water (×2). The organic phase was dried over Na$_2$SO$_4$ and concentrated. The resulting residue was purified by silica gel prep TLC using 4:1 Hexanes:ethyl acetate as an eluent to afford 0.12 g (62%) of the desired product as a brownish oil. This product was not pure (~70% pure by 1H-NMR), but was used for the next reaction without further purification.

(2S)-2-{3-[(4-methyl-1-benzothien-3-yl)methyl]-2-oxo-2,3-dihydro-1H-benzimidazol-1-yl}propanoic acid To a solution of (S)-2-[3-(4-Methyl-benzo[b]thiophen-3-ylmethyl)-2-oxo-2,3-dihydro-benzimidazol-1-yl]-propionic acid tert-butyl ester (0.12 g, 0.28 mmol) in CH$_2$Cl$_2$ (5 mL) was added TFA (2 mL). The reaction mixture was stirred at room temperature for 3 h. When the reaction was complete, the reaction mixture was diluted with CH$_2$Cl$_2$ and washed with water. The organic phase was dried over Na$_2$SO$_4$ and concentrated. When a small amount of CH$_2$Cl$_2$ (~3 mL) was added to the resulting residue, a white solid came out of the solution. This solid was filtered and dried to afford 69 mg (66%) of the titled compound. LCMS (ESMS): m/z 367.23 (M+H$^+$).

The following compounds were synthesized following a similar procedure.

(2S)-3-methyl-2-{3-[(4-methyl-1-benzothien-3-yl)methyl]-2-oxo-2,3-dihydro-1H-benzimidazol-1-yl}butanoic acid. LCMS (ESMS): m/z 395.20 (M+H$^+$)

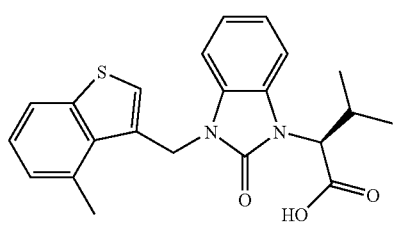 [SMILES: Cc1cccc2scc(Cn3c(=O)n([C@H](C(=O)O)C(C)C)c4ccccc43)c12]

(2S)-{3-[(4-methyl-1-benzothien-3-yl)methyl]-2-oxo-2,3-dihydro-1H-benzimidazol-1-yl}(phenyl)acetic acid. LCMS (ESMS): m/z 429.16 (M+H$^+$)

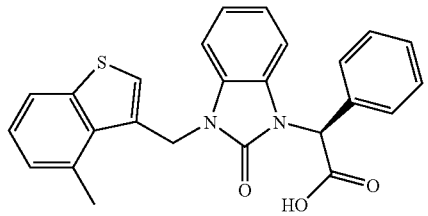 [SMILES: Cc1cccc2scc(Cn3c(=O)n([C@H](C(=O)O)c4ccccc4)c4ccccc43)c12]

Example 45

(2S)-2-{3-[(4-methyl-1-benzothien-3-yl)methyl]-2-oxo-2,3-dihydro-1H-benzimidazol-1-yl}pentanoic acid

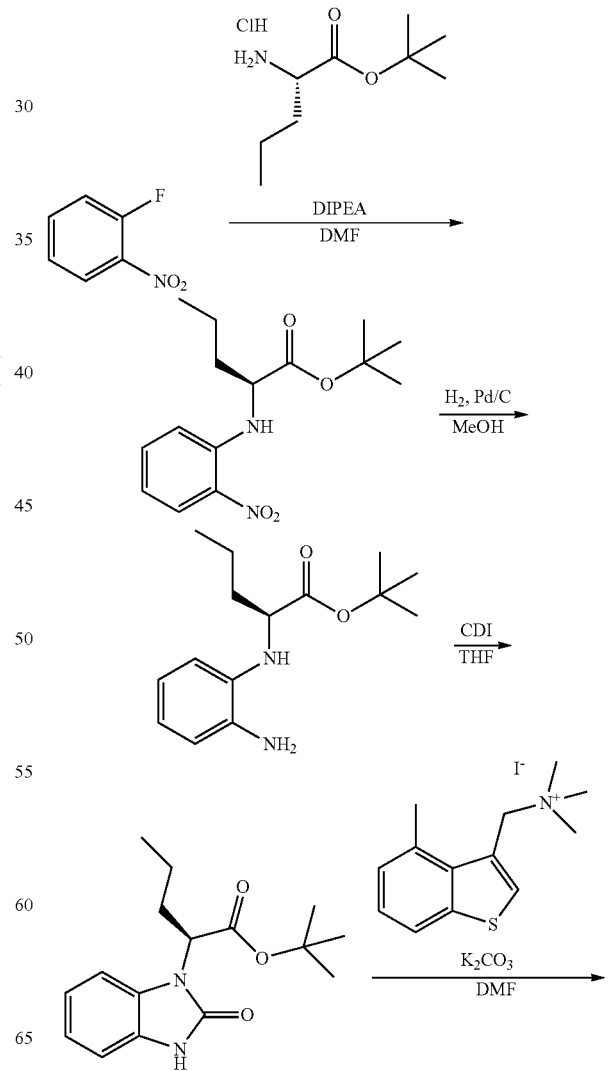

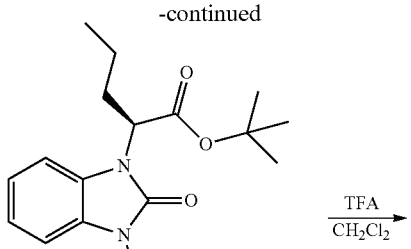

TFA / CH₂Cl₂

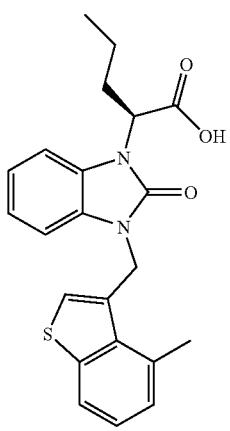 [SMILES: CCC[C@@H](C(=O)O)n1c(=O)n(Cc2csc3cccc(C)c23)c2ccccc21]

(S)-2-(2-Nitro-phenylamino)-pentanoic acid tert-butyl ester

To a solution of 2-fluoronitrobenzene (0.3 g, 2.1 mmol) in DMF (3 mL) were added (L)-NVA OTBU HCl (0.53 g, 2.6 mmol) and DIPEA (0.93 mL, 5.3 mmol). The reaction mixture was stirred at 70° C. overnight. The reaction mixture was then diluted with ethyl acetate and washed with water (×4). The organic phase was then dried over Na₂SO₄ and concentrated to afford 0.69 g (100%) of orange oil. The resulting residue was used for the next reaction without further purification.

(S)-2-(2-Amino-phenylamino)-pentanoic acid tert-butyl ester

To a solution of (S)-2-(2-Nitro-phenylamino)-pentanoic acid tert-butyl ester (0.69 g, 2.4 mmol) in MeOH (10 mL) was added a slurry of Pd/C (0.2 g) in MeOH (10 mL). The reaction mixture was degassed using house vacuum. The flask was saturated with H₂ and stirred under H₂ balloon for 2 h. When the reaction was completed, the mixture was filtered through a pad of celite and the filtrate was concentrated to afford 0.61 g (97%) of the desired product. The resulting residue was used for the next reaction without further purification.

(S)-2-(2-Oxo-2,3-dihydro-benzimidazol-1-yl)-pentanoic acid tert-butyl ester

To a solution of (S)-2-(2-Amino-phenylamino)-pentanoic acid tert-butyl ester (0.61 g, 2.3 mmol) in THF (8 mL) was added CDI (0.41 g, 2.5 mmol). The reaction mixture was stirred at room temperature for 3 h. When the reaction was complete, the reaction mixture was concentrated. The resulting residue was purified by silica gel prep TLC using 95:5 CH₂Cl₂:MeOH as an eluent to afford 0.51 g (76%) of the desired product as a brown solid. LCMS (ESMS): m/z 291.31 (M+H⁺).

(S)-2-[3-(4-Methyl-benzo[b]thiophen-3-ylmethyl)-2-oxo-2,3-dihydro-benzimidazol-1-yl]-pentanoic acid tert-butyl ester To a solution of (S)-2-(2-Oxo-2,3-dihydro-benzimidazol-1-yl)-pentanoic acid tert-butyl ester (0.1 g, 0.34 mmol) in DMF (2 mL) were added K₂CO₃ (0.1 g, 0.69 mmol) and trimethyl-(4-methyl-benzo[b]thiophen-3-ylmethyl)-ammonium iodide (0.24 g, 0.69 mmol). The reaction mixture was heated to 80° C. for 5 h. The reaction mixture was then diluted with ethyl acetate and washed with water (×4). The organic phase was dried over Na₂SO₄ and concentrated. The resulting residue was purified by silica gel prep TLC using 98:2 CH₂Cl₂:MeOH as an eluent to afford 0.11 g (71%) of the desired product as an oily residue. LCMS (ESMS): m/z 451.33 (M+H⁺).

To a solution of (S)-2-[3-(4-Methyl-benzo[b]thiophen-3-ylmethyl)-2-oxo-2,3-dihydro-benzimidazol-1-yl]-pentanoic acid tert-butyl ester (0.11 g, 0.24 mmol) in CH₂Cl₂ (2 mL) was added TFA (1 mL). The reaction mixture was stirred at room temperature for 2 h. When the reaction was complete, the reaction mixture was washed with water (×2). The organic phase was dried over Na₂SO₄ and concentrated. The resulting residue was purified by silica gel prep TLC using 95:5 CH₂Cl₂:MeOH as an eluent to afford 81 mg (84%) of the desired product as an off-white solid. LCMS (ESMS): m/z 395.09 (M+H⁺).

The following compound were prepared following a similar procedure.

(2S)-2-{3-[(4-methyl-1-benzothien-3-yl)methyl]-2-oxo-2,3-dihydro-1H-benzimidazol-1-yl}butanoic acid. LCMS (ESMS): m/z 381.09 (M+H⁺)

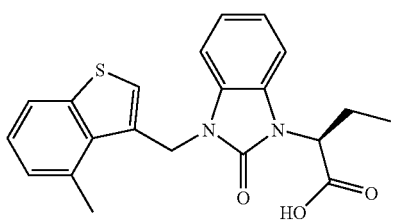 [SMILES: CC[C@@H](C(=O)O)n1c(=O)n(Cc2csc3cccc(C)c23)c2ccccc21]

Example 46

3-{5-anilino-3-[(1,4-dimethyl-1H-indol-3-yl)methyl]-2-oxo-2,3-dihydro-1H-benzimidazol-1-yl}hexanoic acid

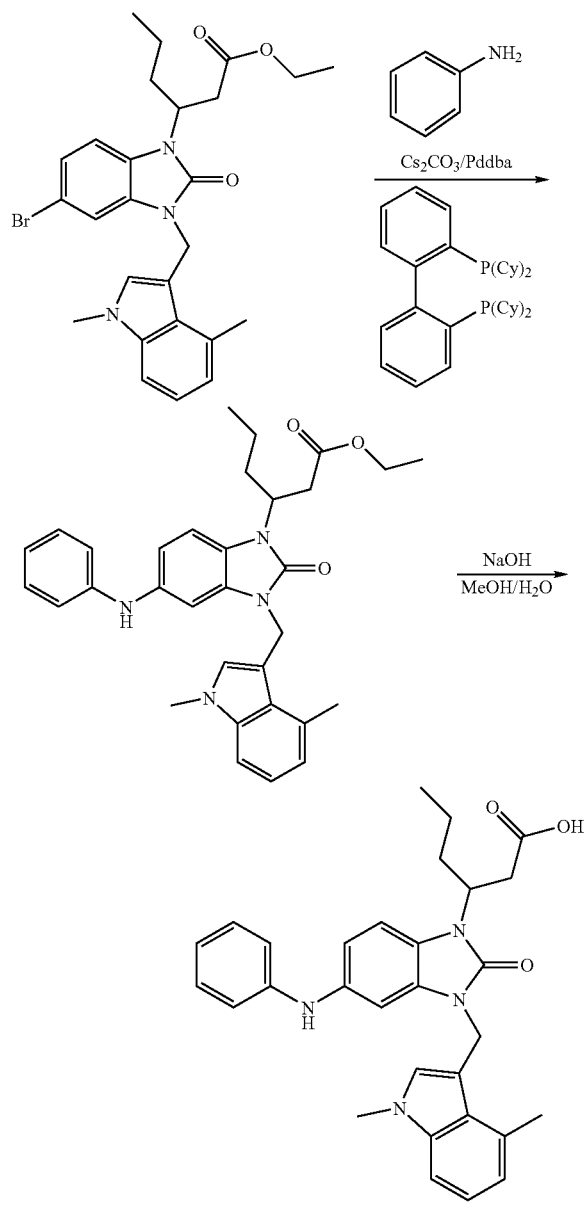

3-[3-1,4-Dimethyl-1H-indol-3-ylmethyl)-2-oxo-5-phenylamino-2,3-dihydro-benzoimidazol-1-yl]hexanoic acid Ethyl ester In a dry pressure bottle, 3-[5-bromo-3-(1,4-dimethyl-1H-indol-3-ylmethyl) 2-oxo-2,3-dihydro-benzoimidazol-1-yl]-hexanoic acid ethyl ester (200 mg, 0.390 mmol) was dissolved in 50% Toluene/NMP (10 ml). To the solution, 2-amino thiazole (59 mg, 0.585 mmol), Cesium carbonate (191 mg, 0.585 mmol), 2(dicyclohexylphosphino)biphenyl (14 mg, 0.040 mmo), tris (dibenzyledeneacetone)-dipalladium (0) 99 mg, 0.010 nmol) were added. The bottle was then purged for 5 minutes by passing a slow stream of argon through the mixture while stirring. As the bottle was ready to be capped, the argon flow was increased. After capping, the reaction vessel was then immersed in an oil bath heated to 100° C. for 18 hours. An aliquout was removed and checked by TLC. The cooled reaction mixture was then diluted with Ethyl Acetate (200 ml) and washed with water 3 times. The organic phase was again washed with 1N HCl (200 ml), followed with brine. The collected organic phase was dried over $MgSO_4$, filtered and evaporated to dryness to give an oil, which was purified by flash Chromatography, eluded with 30% to 50% ethyl acetate in Hexanes in 30 minutes to give 205 mg (35%) of 3-[3-1,4-Dimethyl-1H-indol-3-ylmethyl)-2-oxo-5-phenylamino-2,3-dihydro-benzoimidazol-1-yl]hexanoic acid Ethyl ester. LCMS (ESMS): m/z 524.65 (M+H).

3-[3-1,4-Dimethyl-1H-indol-3-ylmethyl)-2-oxo-5-phenylamino-2,3-dihydro-benzoimidazol-1-yl]hexanoic acid To a stirred solution of 3-[3-1,4-Dimethyl-1H-indol-3-ylmethyl)-2-oxo-5-phenylamino-2,3-dihydro-benzoimidazol-1-yl]hexanoic acid ethyl ester (50 mg, 0.95 mmol) in Methanol (5 ml) was added a concentrated solution of NaOH in water (2 ml). The mixture was stirred at RT for 2 hours. The reaction mixture was checked by TLC. The reaction mixture was then evaporated to dryness. The residue was diluted with water (10 ml) and acidified with 1N HCl (15 ml). The aqueous mixture was extracted with Ethyl Acetate (100 ml). The separated organic layer was dried over $MgSO_4$, filtered and evaporated to dryness. The residue obtained was purified by flash Chromatography eluded with 0 to 10% Methanol in Dichloro methane to give 20 mg (67.6%) of 3-[3-1,4-Dimethyl-1H-indol-3-ylmethyl)-2-oxo-5-phenylamino-2,3-dihydro-benzoimidazol-1-yl]hexanoic acid. LCMS (ESMS): m/z 496.60 (M+H).

The following compound was prepared following a similar procedure using appropriate starting materials.

3-{3-[(1,4-dimethyl-1H-indol-3-yl)methyl]-2-oxo-5-(1,3-thiazol-2-ylamino)-2,3-dihydro-1H-benzimidazol-1-yl}hexanoic acid. LCMS (ESMS): m/z 503.62 (M+H)

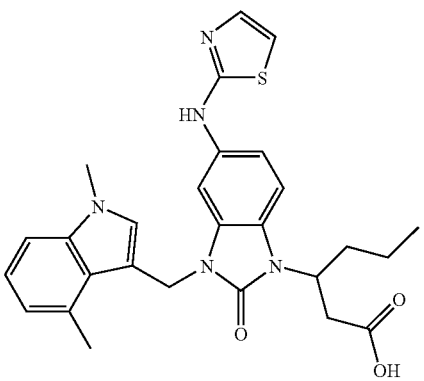 [SMILES: CCCC(CC(=O)O)n1c(=O)n(Cc2cn(C)c3cccc(C)c23)c2cc(Nc3nccs3)ccc21]

Example 47

(3S)-3-{5-(carbamoylamino)-3-[(1,4-dimethyl-1H-indol-3-yl)methyl]-2-oxo-2,3-dihydro-1H-benzimidazol-1-yl}hexanoic acid

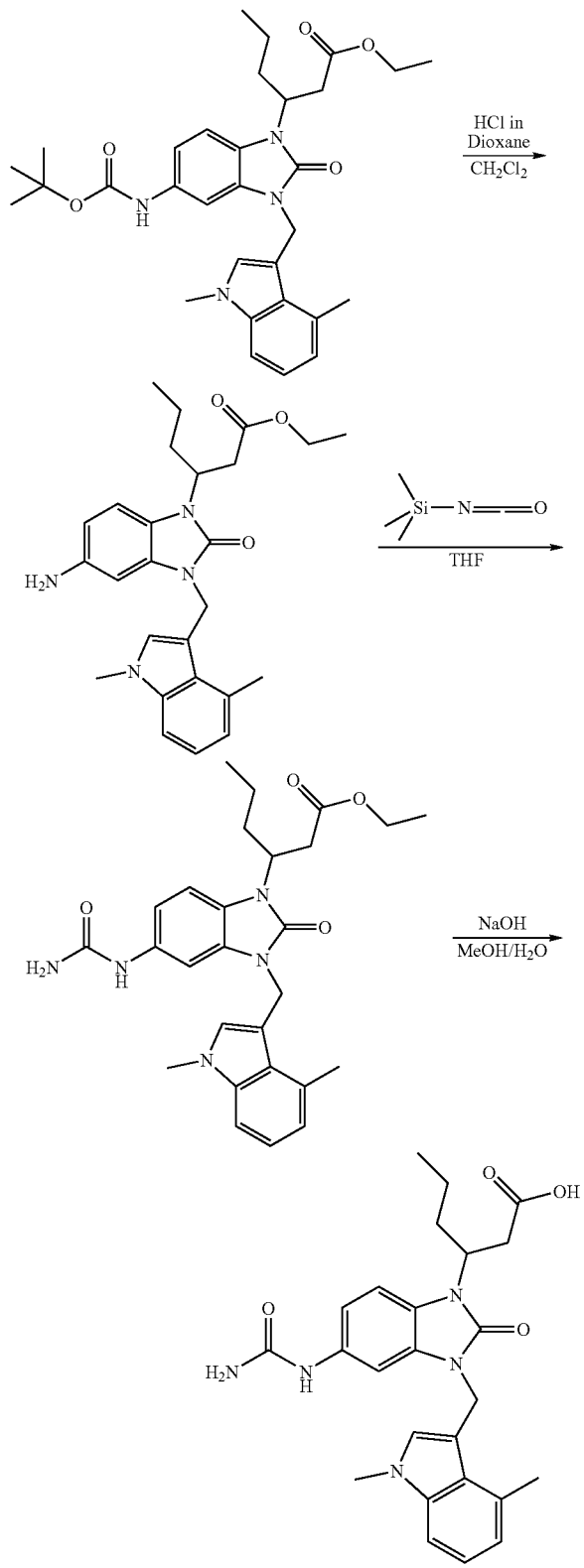

3-[5-Amino-3-(1,4-Dimethyl-1H-indol-3-ylmethyl)-2-oxo-2,3-dihydro-benzimidazol-1-yl]hexanoic acid ethyl ester 3-[5-tert-Butoxycarbonylamino-3-(1,4-Dimethyl-1H-indol-3-ylmethyl)-2-oxo-2,3-dihydro-benzoimidazol-1-yl] hexanoic acid: ethyl ester (350 mg, 0.638 mmol) was dissolved in Dichloro methane (5 ml) was put on ice for 20 minutes. To the cold solution 4N Dioxane/HCl (10 ml) was added and the mixture was stirred on ice for 2 hours. The solution was evaporated to dryness. The residue obtained was neutralized with and aqeous solution of Sodium Bicarbonate (25 ml), then extracted with Ehtyl acetate (200 ml). the organic phase was evaporated to dryness and purified by Flash Chromatography, eluded with 10% methanol in dichloromethane to give 280 mg (97.9%) of 3-[5-Amino-3-(1,4-Dimethyl-1H-indol-3-ylmethyl)-2-oxo-2,3-dihydro-benzoimidazol-1-yl]hexanoic acid ethyl ester. LCMS (ESMS): m/z 448.56 (M+H).

3-[3-1,4-Dimethyl-1H-indol-3-ylmethyl)-2-oxo-5-ureido-2,3-dihydro-benzoimidazol-1-yl]hexanoic acid ethyl ester To a solution of 3-[5-Amino-3-(1,4-Dimethyl-1H-indol-3-ylmethyl)-2-oxo-2,3-dihydro-benzoimidazol-1-yl]hexanoic acid: ethyl ester (50 mg, 0.111 mmol) in THF (30 ml) was added TMS isocynate (1.73 mg, 15 mmol). The solution was stirred at RT for 3 hours. The reaction was checked by LCMS. To the reaction mixture an aqeous solution of Sodium bicarbonate (60 ml) was added. The resulting mixture, stirred for another 30 minutes, was then extracted with Ethyl Acetate. The organic layer, dried over MgSO$_4$, was filtered and evaporated to dryness to give a dark residue. The residue was purified by prep TLC, eluded with 10% methanol in Dichloromethane to give 10 mg (18%) of 3-[3-1,4-Dimethyl-1H-indol-3-ylmethyl)-2-oxo-5-ureido-2,3-dihydro-benzoimidazol-1-yl]hexanoic acid ethyl ester. LCMS (ESMS): m/z 491.58 (M+H).

3-[3-1,4-Dimethyl-1H-indol-3-ylmethyl)-2-oxo-5-ureido-2,3-dihydro-benzoimidazol-1-yl]hexanoic acid To a solution of 3-[3-1,4-Dimethyl-1H-indol-3-ylmethyl)-2-oxo-5-ureido-2,3-dihydro-benzoimidazol-1-yl]hexanoic acid ethyl ester (10 mg, 0.020 mmol) in methanol (2 ml) was added a concentrated solution of Sodium Hydroxide in water (3 ml). The mixture was stirred at RT for 2 hours. The reaction was checked by TLC. The reaction mixture was evaporated to dryness. The residue was taken in water (3 ml), neutralized with 1N HCl (4 ml) and extracted with Ethyl acetate (100 ml). The organic layer was dried over MgSO$_4$, filtered and evaporated to dryness to give a light beige residue. The residue was purified by mass triggered HPLC to give 4 mg (42.4%) of 3-[3-1,4-Dimethyl-1H-indol-3-ylmethyl)-2-oxo-5-ureido-2,3-dihydro-benzoimidazol-1-yl]hexanoic acid. LCMS (ESMS): m/z 463.53 (M+H).

Example 48

Sodium (3S)-3-{3-[(1,4-dimethyl-1H-indol-3-yl)methyl]-2-oxo-2,3-dihydro-1H-benzimidazol-1-yl}hexanoate

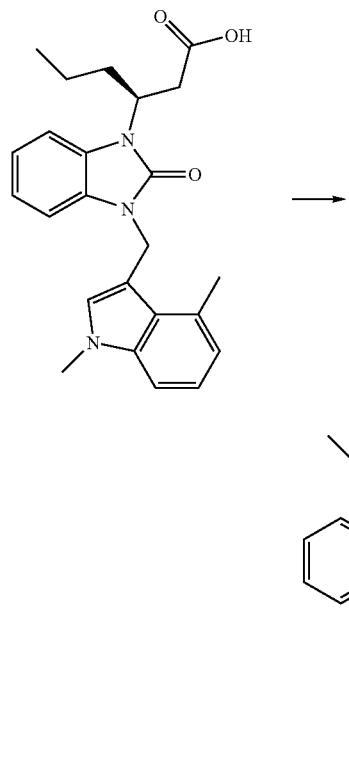

To a mixture of (S)-3-[3-(1,4-dimethyl-1H-indol-3-ylmethyl)-2-oxo-2,3-dihydro-benzimidazol-1-yl]-hexanoic acid (1.45 g, 3.6 mmol) in H₂O (25 mL) was added NaOH (1.041 M in THF) (3.1 mL, 3.2 mmol). The solution was stirred at room temperature for 2 hours. The solution was washed with EtOAc (30 mL×2) and the aqueous layer was lyophilized to give the desired sodium (S)-3-[3-(1,4-dimethyl-1H-indol-3-ylmethyl)-2-oxo-2,3-dihydro-benzimidazol-1-yl]-hexanoate (1.4 g, 91%) as a white solid. LCMS (ESMS):428.10 (M+H⁺).

Example 49

4-{3-[(1,4-dimethyl-1H-indol-3-yl)methyl]-2-oxo-2,3-dihydro-1H-benzimidazol-1-yl}pentanoic acid

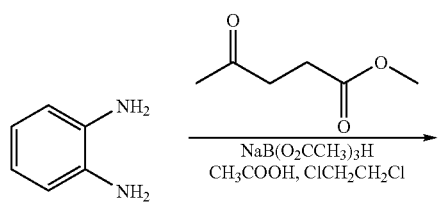

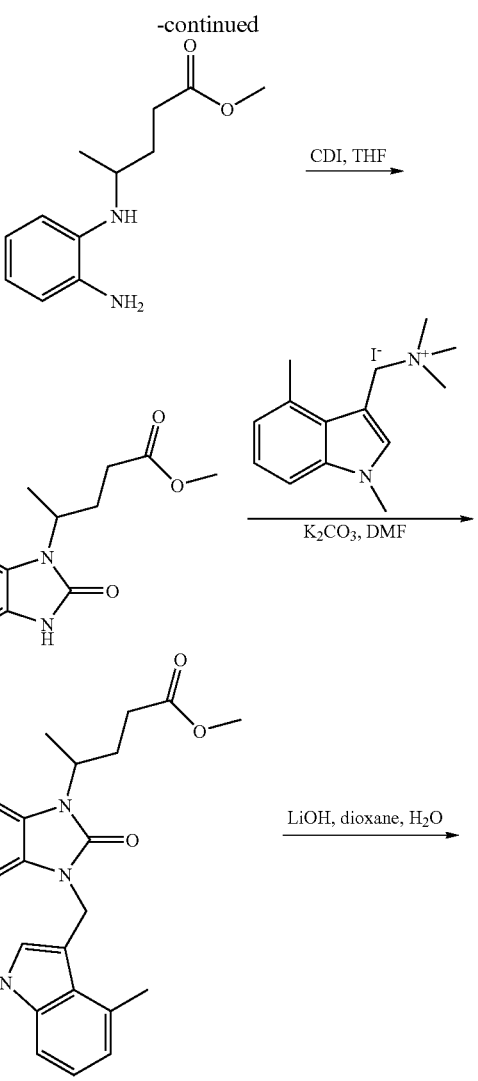

4-(2-Amino-phenylamino)-pentanoic acid methyl ester

To a mixture of 1,2-phenylenediamine (3.0 g, 27.7 mmol) and levulinic acid methyl ester (2.7 mL, 21.8 mmol) in 1,2- dichloroethane (25 mL) was added sodium triacetoxyborohydride (4.6 g, 21.7 mmol) and acetic acid (1.5 mL). The mixture was stirred at room temperature for 16 hours. The reaction mixture was diluted with EtOAc (100 mL) and washed with $H_2O$ (75 mL×3). The organic layer was dried over sodium sulfate and concentrated. The resulting residue was purified by CombiFlash with 40% EtOAc in Hexane as the eluent to afford the desired 4-(2-amino-phenylamino)-pentanoic acid methyl ester (1.05 g, 22%).

4-(2-Oxo-2,3-dihydro-benzimidazol-1-yl)-pentanoic acid methyl ester

To a solution of 4-(2-amino-phenylamino)-pentanoic acid methyl ester (1.05 g, 4.7 mmol) in THF (15 mL) was added 1,1'-carbonyldiimidazole (0.8 g, 4.9 mmol). The solution was stirred at room temperature for 16 hours. The reaction mixture was concentrated. The resulting residue was purified by CombiFlash with 50% EtOAc in Hexane as the eluent to afford the desired 4-(2-oxo-2,3-dihydro-benzimidazol-1-yl)-pentanoic acid methyl ester (1.1 g, 94%).

4-[3-(1,4-Dimethyl-3H-indol-3-ylmethyl)-2-oxo-2,3-dihydro-benzimidazol-1-yl]-pentanoic acid methyl ester To a mixture of 4-(2-oxo-2,3-dihydro-benzimidazol-1-yl)-pentanoic acid methyl ester (85 mg, 0.34 mmol) and (1,4-dimethyl-1H-indol-3-ylmethyl)-trimethylammonium iodide (175 mg, 0.51 mmol) in DMF (2.5 mL) was added $K_2CO_3$ (95 mg, 0.69 mmol). The mixture was stirred at 100° C. for 4 hours. The reaction mixture was allowed to cool to room temperature, diluted with EtOAc (50 mL) and washed with $H_2O$ (50 mL×3). The organic layer was dried over sodium sulfate and concentrated. The resulting residue was purified by CombiFlash with 25% EtOAc in Hexane as the eluent to afford the desired 4-[3-(1,4-dimethyl-3H-indol-3-ylmethyl)-2-oxo-2,3-dihydro-benzimidazol-1-yl]-pentanoic acid methyl ester (120 mg, 86%).

4-{3-[(1,4-dimethyl-1H-indol-3-yl)methyl]-2-oxo-2,3-dihydro-1H-benzimidazol-1-yl}pentanoic acid To a solution of 4-[3-(1,4-dimethyl-3H-indol-3-ylmethyl)-2-oxo-2,3-dihydro-benzimidazol-1-yl]-pentanoic acid methyl ester (120 mg, 0.3 mmol) in dioxane (2.5 ml) was added a solution of LiOH monohydrate (25 mg, 0.6 mmol) in $H_2O$ (2.5 mL). The solution was stirred at room temperature for 4 hours. The reaction mixture was quenched with 4M HCl in dioxane (250 □L) and concentrated. The resulting residue was purified by CombiFlash with 10% MeOH in dichloromethane as the eluent to afford the desired 4-{3-[(1,4-dimethyl-1H-indol-3-yl)methyl]-2-oxo-2,3-dihydro-1H-benzimidazol-1-yl}pentanoic acid (17 mg, 15%). LCMS (ESMS): 392.26 (M+H+).

Following compounds were synthesized using a similar procedure.

4-[3-(1,4-Dimethyl-1H-indol-3-ylmethyl)-2-oxo-2,3-dihydro-benzimidazol-1-yl]-heptanoic acid. LCMS (ESMS): 420.27 (M+H+)

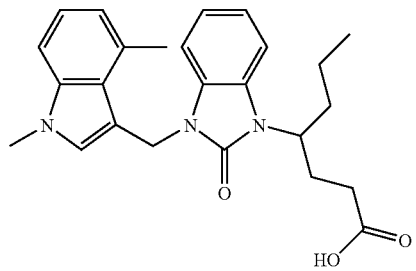 [SMILES: CCCC(CCC(=O)O)n1c(=O)n(Cc2cn(C)c3cccc(C)c23)c2ccccc21]

3-[3-(1,4-Dimethyl-1H-indol-3-ylmethyl)-2-oxo-2,3-dihydro-benzimidazol-1-yl]-2,2-dimethyl-butyric acid. LCMS (ESMS): 406.32 (M+H+)

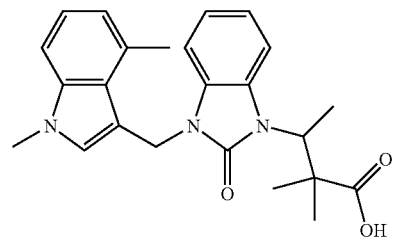 [SMILES: Cc1cccc2c1c(Cn1c(=O)n(C(C)C(C)(C)C(=O)O)c3ccccc31)cn2C]

Example 50

{1-[3-(1,4-Dimethyl-1H-indol-3-ylmethyl)-2-oxo-2,3-dihydro-benzimidazol-1-yl]-cyclohexyl}-acetic acid

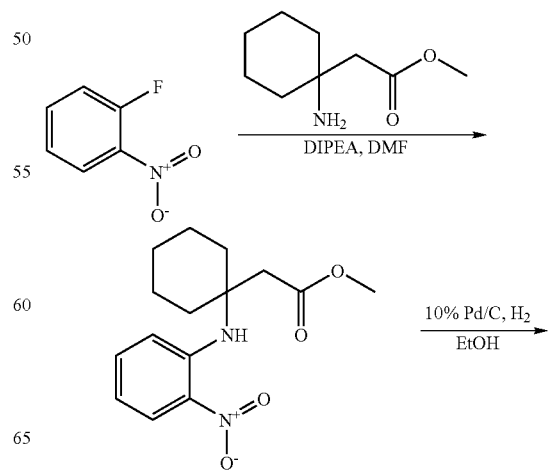

333
-continued

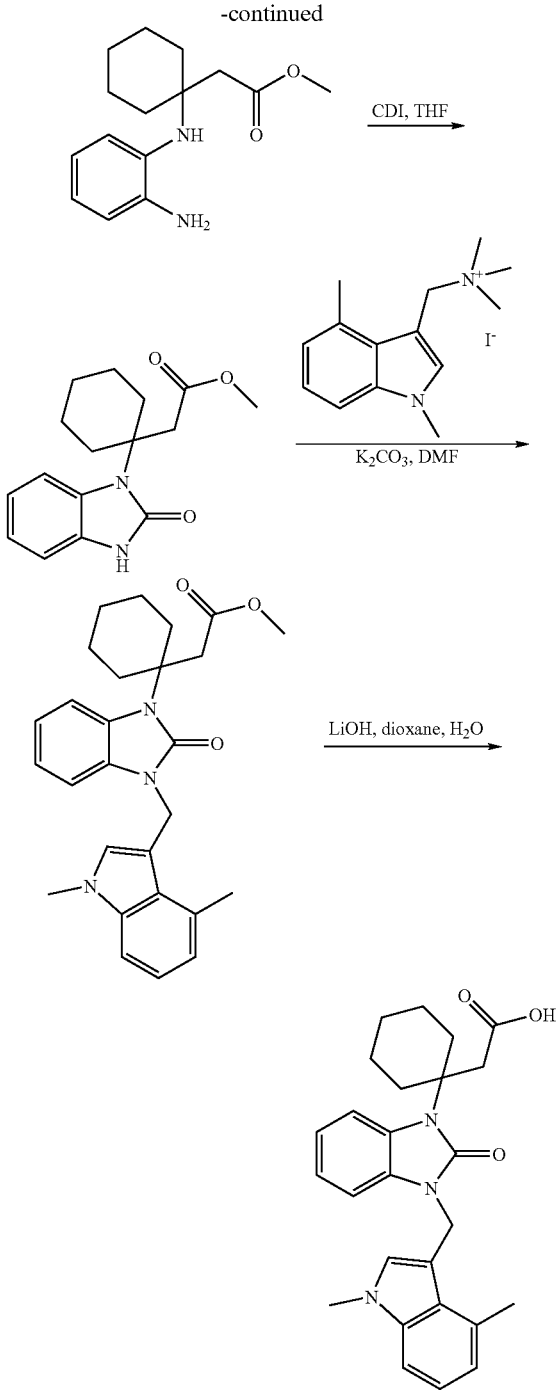

[1-(2-Nitro-phenylamino)-cyclohexyl]-acetic acid methyl ester

To a mixture of 1-fluoro-2-nitrobenzene (450 μL, 4.3 mmol) and (1-amino-cyclohexyl)-acetic acid methyl ester (880 mg, 5.2 mmol) in DMF (5 mL) was added DIPEA (1.0 mL, 5.7 mmol). The mixture was heated at 90° C. for 16 hours. The reaction mixture was allowed to cool to room temperature, diluted with EtOAc (50 mL) and washed with $H_2O$ (50 mL×3). The organic layer was dried over sodium sulfate and concentrated. The resulting residue was purified by CombiFlash with 20% EtOAc in Hexane as the eluent to afford the desired [1-(2-nitro-phenylamino)-cyclohexyl]-acetic acid methyl ester (230 mg, 19%).

[1-(2-Amino-phenylamino)-cyclohexyl]-acetic acid methyl ester

A mixture of [1-(2-nitro-phenylamino)-cyclohexyl]-acetic acid methyl ester (230 mg, 0.79 mmol), 10% Pd/C (80 mg) in EtOH (20 mL) under $H_2$ atmosphere at room temperature was stirred for 16 h. The reaction mixture was filtered and the organic layer was concentrated to give the desired [1-(2-amino-phenylamino)-cyclohexyl]-acetic acid methyl ester (205 mg, 99%).

[1-(2-Oxo-2,3-dihydro-benzimidazol-1-yl)-cyclohexyl]-acetic acid methyl ester

A mixture of [1-(2-amino-phenylamino)-cyclohexyl]-acetic acid methyl ester (205 mg, 0.79 mmol) in THF (5 mL) was added 1,1'-carbonyldiimidazole (180 mg, 1.11 mmol). The solution was stirred at room temperature for 16 hours. The reaction mixture was concentrated. The resulting residue was purified by CombiFlash with 50% EtOAc in Hexane as the eluent to afford the desired [1-(2-oxo-2,3-dihydro-benzimidazol-1-yl)-cyclohexyl]-acetic acid methyl ester (194 mg, 86%).

{1-[3-(1,4-Dimethyl-3H-indol-3-ylmethyl)-2-oxo-2,3-dihydro-benzimidazol-1-yl]-cyclohexyl}-acetic acid methyl ester To a mixture of [1-(2-oxo-2,3-dihydro-benzimidazol-1-yl)-cyclohexyl]-acetic acid methyl ester (115 mg, 0.40 mmol) and (1,4-dimethyl-1H-indol-3-ylmethyl)-trimethylammonium iodide (200 mg, 0.58 mmol) in DMF (2.5 mL) was added $K_2CO_3$ (110 mg, 0.80 mmol). The mixture was stirred at 100° C. for 4 hours. The reaction mixture was diluted with EtOAc (50 mL) and washed with $H_2O$ (50 mL×3). The organic layer was dried over sodium sulfate and concentrated. The resulting residue was purified by CombiFlash with 30% EtOAc in Hexane as the eluent to afford the desired {1-[3-(1,4-dimethyl-3H-indol-3-ylmethyl)-2-oxo-2,3-dihydro-benzimidazol-1-yl]-cyclohexyl}-acetic acid methyl ester (131 mg, 74%).

{1-[3-(1,4-Dimethyl-1H-indol-3-ylmethyl)-2-oxo-2,3-dihydro-benzimidazol-1-yl]-cyclohexyl}-acetic acid To a solution of {1-[3-(1,4-dimethyl-3H-indol-3-ylmethyl)-2-oxo-2,3-dihydro-benzimidazol-1-yl]-cyclohexyl}-acetic acid methyl ester (131 mg, 0.29 mmol) in dioxane (2.5 ml) was added a solution of LiOH monohydrate (25 mg, 0.60 mmol) in $H_2O$ (2.5 mL). The solution was stirred at room temperature for 4 hours. The reaction mixture was quenched with 4M HCl in dioxane (500 μL) and concentrated. The resulting residue was purified by CombiFlash with 3% MeOH in dichloromethane as the eluent to afford the desired {1-[3-(1,4-Dimethyl-1H-indol-3-ylmethyl)-2-oxo-2,3-dihydro-benzimidazol-1-yl]-cyclohexyl}-acetic acid (85 mg, 68%). LCMS (ESMS): 432.32 (M+H$^+$).

Following compounds were synthesized using a similar procedure.

3-[3-(1,4-Dimethyl-1H-indol-3-ylmethyl)-2-oxo-2,3-dihydro-benzimidazol-1-yl]-3-methyl-butyric acid. LCMS (ESMS): 392.26 (M+H⁺)

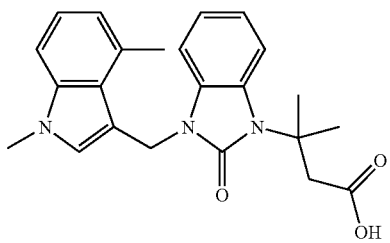 [SMILES: Cc1cccc2c1c(Cn1c(=O)n(C(C)(C)CC(=O)O)c3ccccc31)cn2C]

{1-[3-(1,4-Dimethyl-1H-indol-3-ylmethyl)-2-oxo-2,3-dihydro-benzimidazol-1-yl]-cyclopentyl}-acetic acid. LCMS (ESMS): 418.30 (M+H⁺)

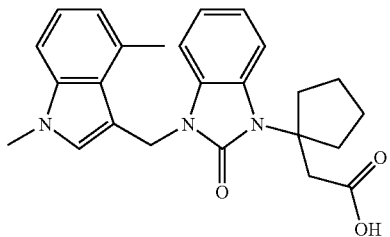 [SMILES: Cc1cccc2c1c(Cn1c(=O)n(C3(CC(=O)O)CCCC3)c3ccccc31)cn2C]

Example 51

3-{3-[(1,4-dimethyl-1H-indol-3-yl)methyl]-2-oxo-2,3-dihydro-1H-benzimidazol-1-yl}-4-methoxy-2,2-dimethylbutanoic acid

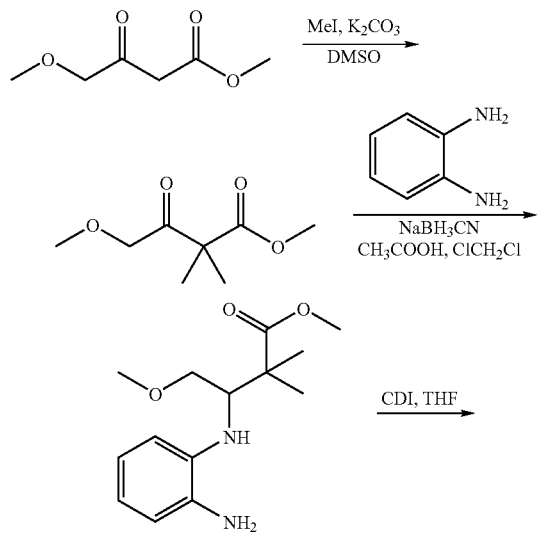

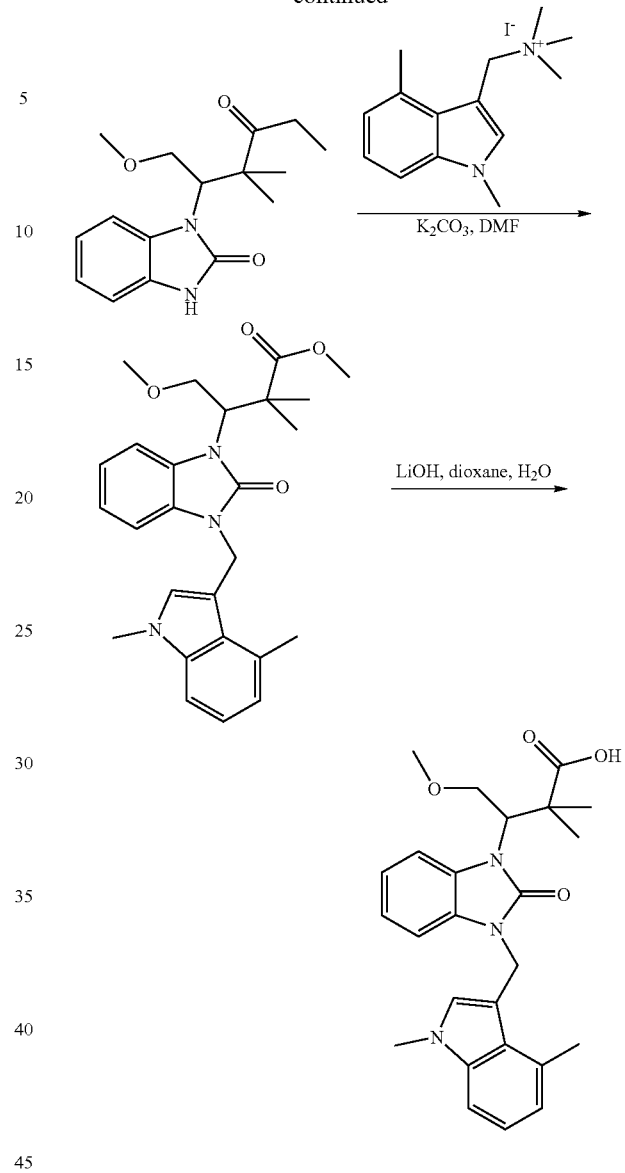

4-Methoxy-2,2-dimethyl-3-oxo-butyric acid methyl ester

To a solution of methyl 4-methoxyacetoacetate (2.0 mL, 15.5 mmol) and iodomethane (3.0 mL, 48.1 mmol) in DMSO (20 mL) was added potassium carbonate (4.7 g, 34.0 mmol). The mixture was stirred at room temperature for 16 hours. The reaction mixture was diluted with EtOAc (150 mL) and washed with H₂O (150 mL×3). The organic layer was dried over sodium sulfate and concentrated to afford the desired 4-methoxy-2,2-dimethyl-3-oxo-butyric acid methyl ester (2.7 g, 100%).

3-(2-Amino-phenylamino)-4-methoxy-2,2-dimethyl-butyric acid methyl ester

To a mixture of 1,2-phenylenediamine (900 mg, 8.3 mmol) and 4-methoxy-2,2-dimethyl-3-oxo-butyric acid methyl ester (1.7 g, 9.8 mmol) in MeOH (5 mL) was added sodium cyanoborohydride (700 mg, 11.1 mmol) and acetic acid (1.0 mL). The mixture was stirred at room temperature for 16 hours. The reaction mixture was diluted with EtOAc (100 mL) and washed with H₂O (75 mL×3). The organic layer was dried over sodium sulfate and concentrated. The resulting residue was purified by CombiFlash with 40% EtOAc in Hexane as the eluent to afford the desired 3-(2-amino-phenylamino)-4-methoxy-2,2-dimethyl-butyric acid methyl ester (550 mg, 25%).

4-Methoxy-2,2-dimethyl-3-(2-oxo-2,3-dihydro-benzimidazol-1-yl)-butyric acid methyl ester To a solution of 3-(2-amino-phenylamino)-4-methoxy-2,2-dimethyl-butyric acid methyl ester (550 mg, 2.1 mmol) in THF (25 mL) was added 1,1'-carbonyldiimidazole (500 mg, 3.1 mmol). The solution was stirred at room temperature for 16 hours. The reaction mixture was concentrated. The resulting residue was purified by CombiFlash with 75% EtOAc in Hexane as the eluent to afford the desired 4-methoxy-2,2-dimethyl-3-(2-oxo-2,3-dihydro-benzimidazol-1-yl)-butyric acid methyl ester (420 mg, 70%).

3-[3-(1,4-Dimethyl-3H-indol-3-ylmethyl)-2-oxo-2,3-dihydro-benzimidazol-1-yl]-4-methoxy-2,2-dimethyl-butyric acid methyl ester To a mixture of 4-methoxy-2,2-dimethyl-3-(2-oxo-2,3-dihydro-benzimidazol-1-yl)-butyric acid methyl ester (137 mg, 0.47 mmol) and (1,4-dimethyl-1H-indol-3-ylmethyl)-trimethylammonium iodide (225 mg, 0.65 mmol) in DMF (2.5 mL) was added K₂CO₃ (200 mg, 1.45 mmol). The mixture was stirred at 100° C. for 4 hours. The reaction mixture was allowed to cool to room temperature, diluted with EtOAc (50 mL) and washed with H₂O (50 mL×3). The organic layer was dried over sodium sulfate and concentrated. The resulting residue was purified by CombiFlash with 50% EtOAc in Hexane as the eluent to afford the desired 3-[3-(1,4-dimethyl-3H-indol-3-ylmethyl)-2-oxo-2,3-dihydro-benzimidazol-1-yl]-4-methoxy-2,2-dimethyl-butyric acid methyl ester (50 mg, 24%).

3-[3-(1,4-Dimethyl-3H-indol-3-ylmethyl)-2-oxo-2,3-dihydro-benzimidazol-1-yl]-4-methoxy-2,2-dimethyl-butyric acid To a solution of 3-[3-(1,4-dimethyl-3H-indol-3-ylmethyl)-2-oxo-2,3-dihydro-benzimidazol-1-yl]-4-methoxy-2,2-dimethyl-butyric acid methyl ester (50 mg, 0.11 mmol) in dioxane (2.5 ml) was added a solution of LiOH monohydrate (20 mg, 0.48 mmol) in H₂O (2.5 mL). The solution was stirred at 50° C. for 16 hours. The reaction mixture was allowed to cool to rt and quenched with 4M HCl in dioxane (500 □L) and concentrated. The resulting residue was purified by CombiFlash with 3% MeOH in dichloromethane as the eluent to afford the desired 3-[3-(1,4-dimethyl-3H-indol-3-ylmethyl)-2-oxo-2,3-dihydro-benzimidazol-1-yl]-4-methoxy-2,2-dimethyl-butyric acid (15 mg, 31%). LCMS (ESMS): 436.12 (M+H⁺).

Following compounds were synthesized using a similar procedure.

1-{1-[3-(1,4-Dimethyl-1H-indol-3-ylmethyl)-2-oxo-2,3-dihydro-benzimidazol-1-yl]-butyl}-cyclopropanecarboxylic acid. LCMS (ESMS): 432.32 (M+H)

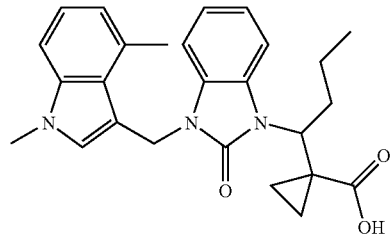 [SMILES: CCCC(n1c(=O)n(Cc2cn(C)c3cccc(C)c23)c2ccccc21)C1(C(=O)O)CC1]

3-[3-(1,4-Dimethyl-1H-indol-3-ylmethyl)-2-oxo-2,3-dihydro-benzimidazol-1-yl]-2,2-dimethyl-hexanoic acid. LCMS (ESMS): 434.30 (M+H⁺)

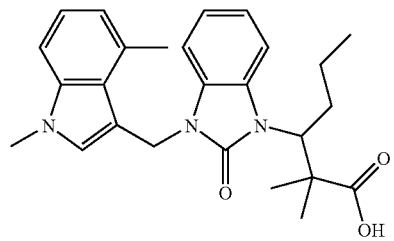 [SMILES: CCCC(n1c(=O)n(Cc2cn(C)c3cccc(C)c23)c2ccccc21)C(C)(C)C(=O)O]

Example 52

2-[3-(1,4-Dimethyl-1H-indol-3-ylmethyl)-2-oxo-2,3-dihydro-benzimidazol-1-yl]-2-methyl-propionic acid

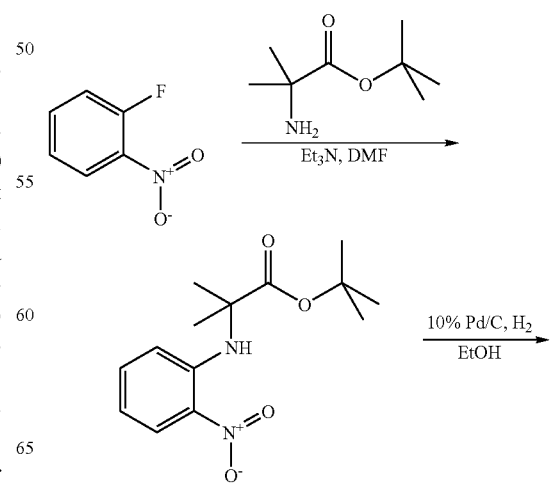

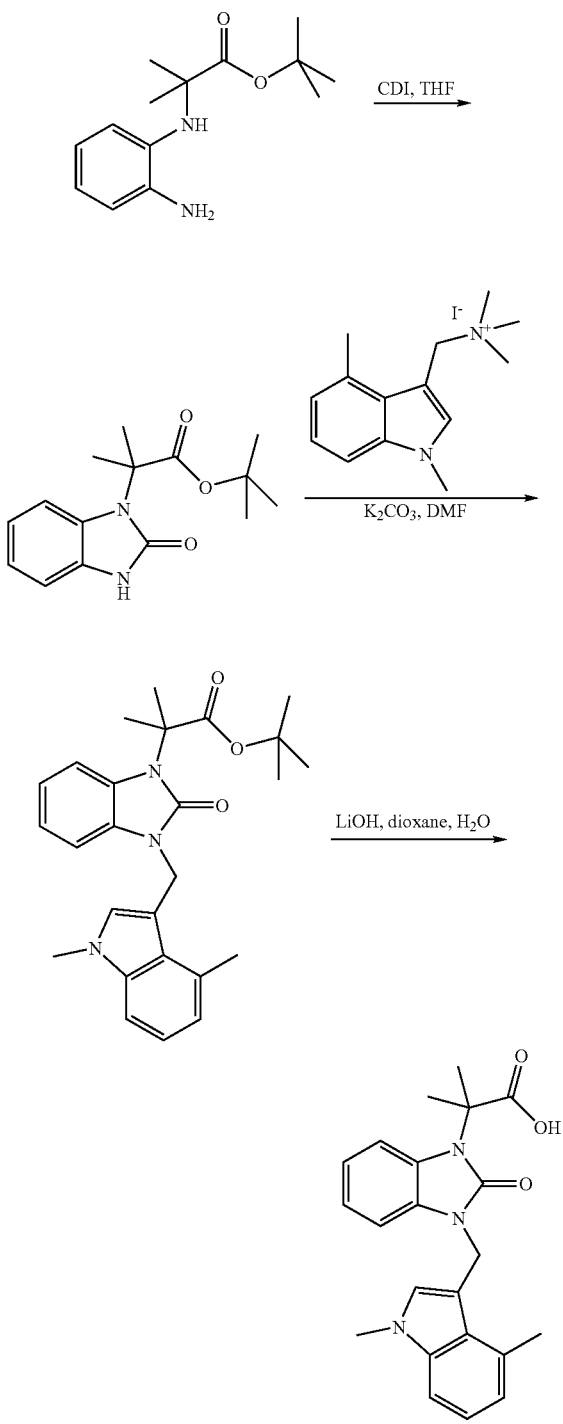

2-Methyl-2-(2-nitro-phenylamino)-propionic acid tert-butyl ester

To a mixture of 1-fluoro-2-nitrobenzene (485 µL, 4.6 mmol) and 2-amino-2-methyl-propionic acid tert-butyl ester hydrochloride (1.0 g, 5.1 mmol) in DMF (5 mL) was added Et$_3$N (1.3 mL, 9.3 mmol). The mixture was heated at 85° C. for 16 hours. The reaction mixture was allowed to cool to room temperature, diluted with EtOAc (50 mL) and washed with H$_2$O (50 mL×3). The organic layer was dried over sodium sulfate and concentrated. The resulting residue was purified by CombiFlash with 10% EtOAc in Hexane as the eluent to afford the desired 2-methyl-2-(2-nitro-phenylamino)-propionic acid tert-butyl ester (640 mg, 50%).

2-(2-Amino-phenylamino)-2-methyl-propionic acid tert-butyl ester

A mixture of 2-methyl-2-(2-nitro-phenylamino)-propionic acid tert-butyl ester (638 mg, 2.3 mmol), 10% Pd/C (110 mg) in EtOH (25 mL) under H$_2$ atmosphere at room temperature was stirred for 30 min. The reaction mixture was filtered and the organic layer was concentrated to give the desired 2-(2-amino-phenylamino)-2-methyl-propionic acid tert-butyl ester (570 mg, 100%).

2-Methyl-2-(2-oxo-2,3-dihydro-benzimidazol-1-yl)-propionic acid tert-butyl ester A mixture of 2-(2-amino-phenylamino)-2-methyl-propionic acid tert-butyl ester (570 mg, 2.3 mmol) in THF (25 mL) was added 1,1'-carbonyldiimidazole (560 mg, 3.5 mmol). The solution was stirred at room temperature for 16 hours. The reaction mixture was concentrated. The resulting residue was purified by CombiFlash with 50% EtOAc in Hexane as the eluent to afford the desired 2-methyl-2-(2-oxo-2,3-dihydro-benzimidazol-1-yl)-propionic acid tert-butyl ester (462 mg, 72%).

2-[3-(1,4-Dimethyl-3H-indol-3-ylmethyl)-2-oxo-2,3-dihydro-benzimidazol-1-yl]-2-methyl-propionic acid tert-butyl ester To a mixture of 2-methyl-2-(2-oxo-2,3-dihydro-benzimidazol-1-yl)-propionic acid tert-butyl ester (130 mg, 0.47 mmol) and (1,4-dimethyl-1H-indol-3-ylmethyl)-trimethylammonium iodide (250 mg, 0.73 mmol) in DMF (2.5 mL) was added K$_2$CO$_3$ (200 mg, 1.45 mmol). The mixture was stirred at 100° C. for 4 hours. The mixture was diluted with EtOAc (50 mL) and washed with H$_2$O (50 mL×3). The organic layer was dried over sodium sulfate and concentrated. The resulting residue was purified by CombiFlash with 30% EtOAc in Hexane as the eluent to afford the desired 2-[3-(1,4-dimethyl-3H-indol-3-ylmethyl)-2-oxo-2,3-dihydro-benzimidazol-1-yl]-2methyl-propionic acid tert-butyl ester (138 mg, 68%).

2-[3-(1,4-Dimethyl-3H-indol-3-ylmethyl)-2-oxo-2,3-dihydro-benzimidazol-1-yl]-2-methyl-propionic acid A solution of 2-[3-(1,4-dimethyl-3H-indol-3-ylmethyl)-2-oxo-2,3-dihydro-benzimidazol-1-yl]-2-methyl-propionic acid tert-butyl ester (138 mg, 0.32 mmol) in TFA (1.0 mL)

was stirred at room temperature for 1 hour. The reaction mixture was concentrated. The resulting residue was purified by CombiFlash with 10% MeOH in dichloromethane as the eluent to afford the desired 2-[3-(1,4-dimethyl-3H-indol-3-ylmethyl)-2-oxo-2,3-dihydro-benzimidazol-1-yl]-2-methyl-propionic acid (36 mg, 30%). LCMS (ESMS): 378.25 (M+H⁺).

Example 53

N-[(2-{3-[(4-methyl-1-benzothien-3-yl)methyl]-2-oxo-2,3-dihydro-1H-benzimidazol-1-yl}ethyl)carbamoyl]benzenesulfonamide

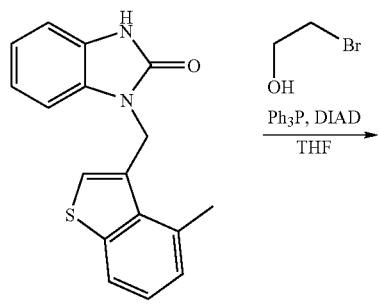

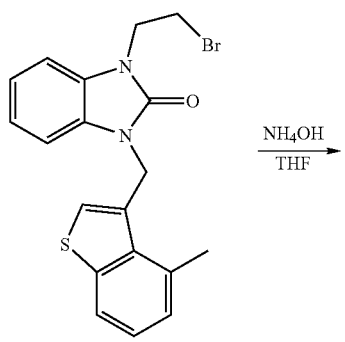

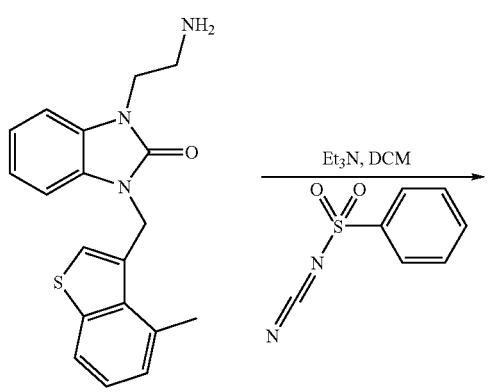

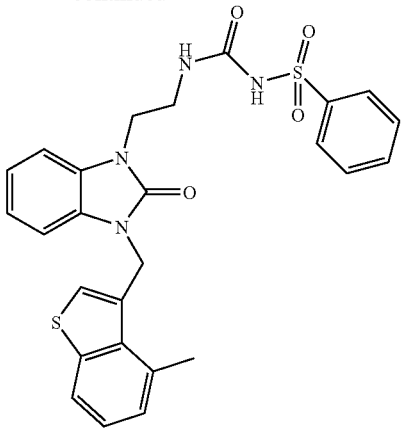

1-(2-Bromo-ethyl)-3-(4-methyl-benzo[b]thiophen-3-ylmethyl)-1,3-dihydro-benzimidazol-2-one To the stirred solution of 1-(4-Methyl-benzo[b]thiophen-3-ylmethyl)-1,3-dihydro-benzimidazol-2-one (100 mg, 0.34 mmol), 2-Bromo-ethanol (0.03 mL, 0.41 mmol) and triphenylphosphine (107 mg, 0.41 mmol) in THF (2.0 mL) is added DIAD (0.082 mL, 0.41 mmol) in a dropwise manner. The mixture is stirred at room temperature for 20 hr and then another 0.03 mL of 2-Bromo-ethanol, 107 mg of triphenylphosphine and 0.08 mL of DIAD are added. The reaction is continued for another 24 hr and then the solvent is removed under vacuum and the residue is purified by flash column chromatography to give 75 mg (55%) of 1-(2-Bromo-ethyl)-3-(4-methyl-benzo[b]thiophen-3-ylmethyl)-1,3-dihydro-benzimidazol-2-one.

1-(2-Amino-ethyl)-3-(4-methyl-benzo[b]thiophen-3-ylmethyl)-1,3-dihydro-benzimidazol-2-one 1-(2-Bromo-ethyl)-3-(4-methyl-benzo[b]thiophen-3-ylmethyl)-1,3-dihydro-benzimidazol-2-one (55 mg, 0.14 mmol) is dissolved in THF (1.5 mL) and NH₄OH (1.5 mL, 27% aqueous) is added into it at room temperature. The mixture is then stirred for 16 hr at 65° C. and another one week at room temperature. Then the solvents are removed under vacuum and the residue is washed with THF. The solid formed is filtered and rinsed with more THF to give 28 mg (61%) of 1-(2-Amino-ethyl)-3-(4-methyl-benzo[b]thiophen-3-ylmethyl)-1,3-dihydro-benzimidazol-2-one.

N-[(2-{3-[(4-methyl-1-benzothien-3-yl)methyl]-2-oxo-2,3-dihydro-1H-benzimidazol-1-yl}ethyl)carbamoyl]benzenesulfonamide 1-(2-Amino-ethyl)-3-(4-methyl-benzo[b]thiophen-3-ylmethyl)-1,3-dihydro-benzimidazol-2-one (28 mg, 0.083 mmol) is added into DCM (1.0 mL) at room temperature and triethylamine (0.014 mL, 0.10 mmol) is added. Then Benzenesulfonyl isocyanate (0.014 mL, 0.10 mmol) is added into the above reaction mixture. After stirring for 2 hr, another 0.014 mL of Benzenesulfonyl isocyanate is added and the mixture is further stirred for 30 min. Then 1.0 mL of 1.0M HCl is added along with 5 mL of water. The mixture is extracted with EtOAc (3×20 mL) and the organic layers are combined, dried (Na₂SO₄) and concentrated to give crude product. Purification by preparative TLC affords 33 mg (76%) of the title compound. LCMS (ESMS): m/z 521.17 (M+H⁺).

Example 54

(3S)-3-{3-[(1,4-dimethyl-1H-indol-3-yl)methyl]-2-oxo-2,3-dihydro-1H-benzimidazol-1-yl}-N-(phenylsulfonyl)hexanamide

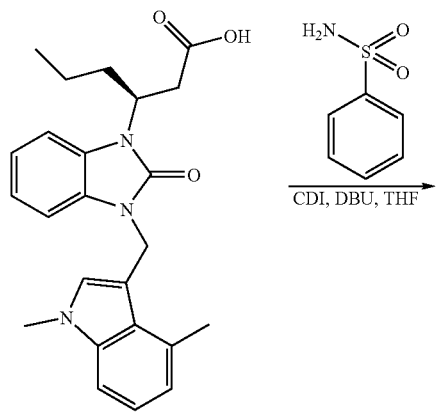

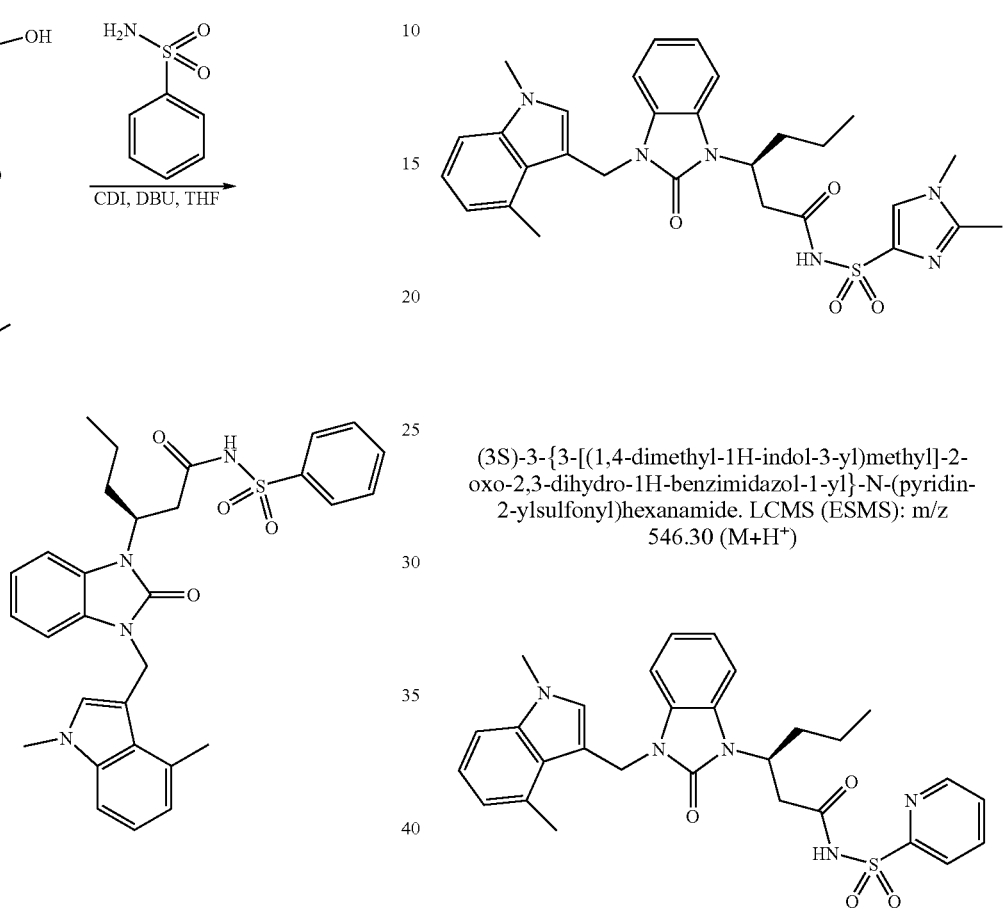

N-{(S)-3-[3-(1,4-Dimethyl-1H-indol-3-ylmethyl)-2-oxo-2,3-dihydro-benzimidazol-1-yl]-hexanoyl}-benzenesulfonamide (S)-3-[3-(1,4-Dimethyl-1H-indol-3-ylmethyl)-2-oxo-2,3-dihydro-benzimidazol-1-yl]-hexanoic acid (25 mg, 0.062 mmol) is dissolved THF (0.5 mL) and CDI (22 mg, 0.14 mmol) is added into it at room temperature. The mixture is stirred for 30 min and then it is heated at 55° C. for 1 hr. After the mixture is cooled down to room temperature, Benzenesulfonamide (19 mg, 0.12 mmol) is added and after 10 min, DBU (0.018 mL, 0.12 mmol) is added. The mixture is then stirred for 16 hr at room temperature. 1 mL of 1.0 M HCl is added followed by 10 mL of water. The mixture is extracted with EtOAc (3×20 mL) and the organic layers are combined, dried and concentrated to give crude product. Purification by Preparative TLC affords 16 mg (47%) of N-{(S)-3-[3-(1,4-Dimethyl-1H-indol-3-ylmethyl)-2-oxo-2,3-dihydro-benzimidazol-1-yl]-hexanoyl}-benzenesulfonamide. LCMS (ESMS): m/z 545.32 (M+H$^+$).

The following compounds are synthesized using the same procedure.

(3S)-N-[(1,2-dimethyl-1H-imidazol-4-yl)sulfonyl]-3-{3-[(1,4-dimethyl-1H-indol-3-yl)methyl]-2-oxo-2,3-dihydro-1H-benzimidazol-1-yl}hexanamide. LCMS (ESMS): m/z 563.35 (M+H$^+$)

(3S)-3-{3-[(1,4-dimethyl-1H-indol-3-yl)methyl]-2-oxo-2,3-dihydro-1H-benzimidazol-1-yl}-N-(pyridin-2-ylsulfonyl)hexanamide. LCMS (ESMS): m/z 546.30 (M+H$^+$)

(3S)-3-{3-[(1,4-dimethyl-1H-indol-3-yl)methyl]-2-oxo-2,3-dihydro-1H-benzimidazol-1-yl}-N-(methylsulfonyl)hexanamide. LCMS (ESMS): m/z 483.25 (M+H$^+$)

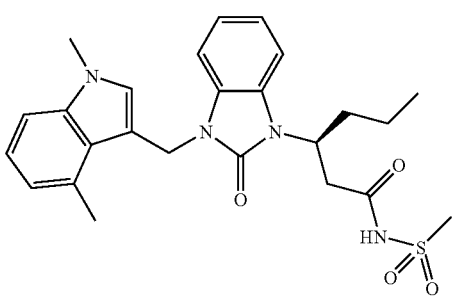 [SMILES: CCC[C@@H](CC(=O)NS(C)(=O)=O)n1c(=O)n(Cc2cn(C)c3cccc(C)c23)c2ccccc21]

| 345 | 346 |
|---|---|
| (3S)-N-(aminosulfonyl)-3-{3-[(1,4-dimethyl-1H-indol-3-yl)methyl]-2-oxo-2,3-dihydro-1H-benzimidazol-1-yl}hexanamide. LCMS (ESMS): m/z 484.23 (M+H$^+$) | (3S)-3-{3-[(1,4-dimethyl-1H-indol-3-yl)methyl]-2-oxo-2,3-dihydro-1H-benzimidazol-1-yl}-N-(ethylsulfonyl)hexanamide. LCMS (ESMS): m/z 497.29 (M+H$^+$) |

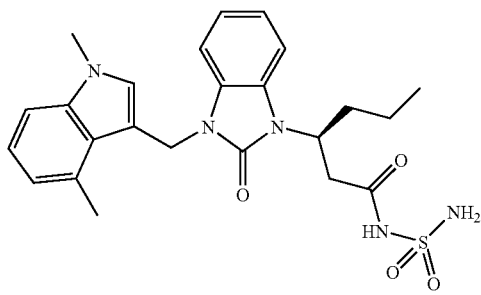 [SMILES: CCC[C@@H](CC(=O)NS(N)(=O)=O)n1c(=O)n(Cc2cn(C)c3cccc(C)c23)c2ccccc21] 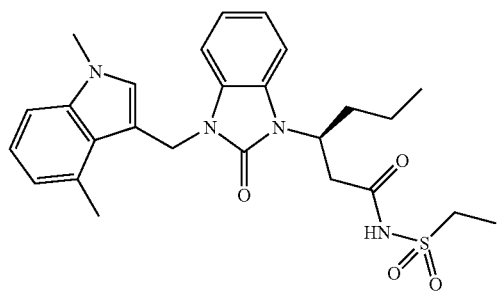

(3S)-3-{3-[(1,4-dimethyl-1H-indol-3-yl)methyl]-2-oxo-2,3-dihydro-1H-benzimidazol-1-yl}-N-[(1-methyl-1H-imidazol-4-yl)sulfonyl]hexanamide LCMS (ESMS): m/z 549.47 (M+H$^+$)

(3S)-N-(tert-butylsulfonyl)-3-{3-[(1,4-dimethyl-1H-indol-3-yl)methyl]-2-oxo-2,3-dihydro-1H-benzimidazol-1-yl}hexanamide. LCMS (ESMS): m/z 525.32 (M+H$^+$)

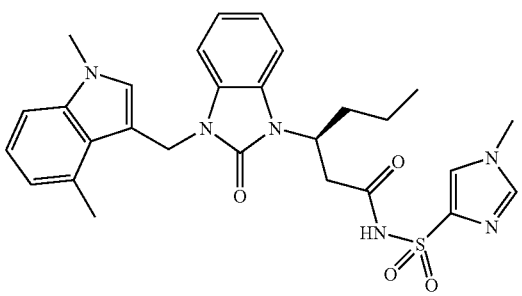 [SMILES: CCC[C@@H](CC(=O)NS(=O)(=O)c1cn(C)cn1)n1c(=O)n(Cc2cn(C)c3cccc(C)c23)c2ccccc21] 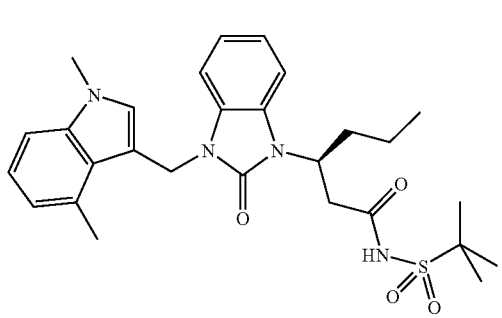

(3S)-3-{3-[(1,4-dimethyl-1H-indol-3-yl)methyl]-2-oxo-2,3-dihydro-1H-benzimidazol-1-yl}-N-(isopropylsulfonyl)hexanamide LCMS (ESMS): m/z 511.27 (M+H$^+$)

(3S)-N-cyano-3-{3-[(1,4-dimethyl-1H-indol-3-yl)methyl]-2-oxo-2,3-dihydro-1H-benzimidazol-1-yl}hexanamide. LCMS (ESMS): m/z 430.22 (M+H$^+$)

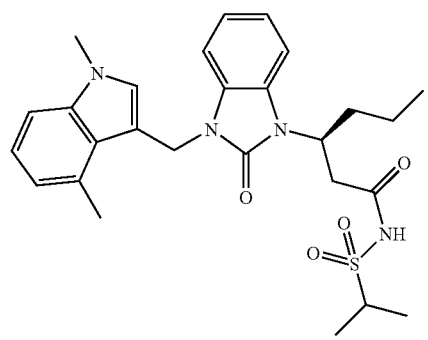 [SMILES: CCC[C@@H](CC(=O)NS(=O)(=O)C(C)C)n1c(=O)n(Cc2cn(C)c3cccc(C)c23)c2ccccc21] 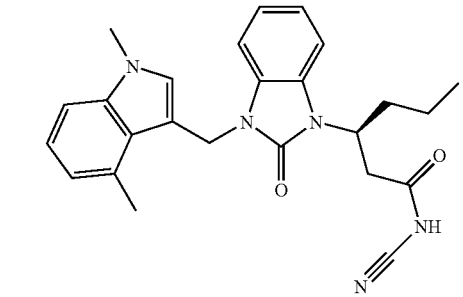 [SMILES: CCC[C@@H](CC(=O)NC#N)n1c(=O)n(Cc2cn(C)c3cccc(C)c23)c2ccccc21]

347

(3S)-N-(cyclopropylsulfonyl)-3-{3-[(1,4-dimethyl-1H-indol-3-yl)methyl]-2-oxo-2,3-dihydro-1H-benzimidazol-1-yl}hexanamide LCMS (ESMS): m/z 509.28 (M+H$^+$)

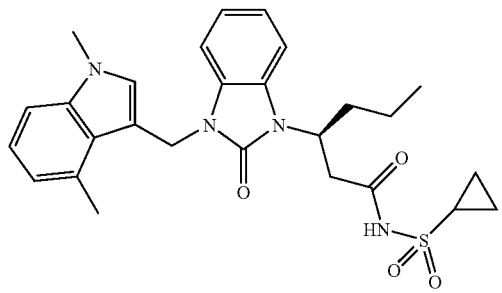 [SMILES: CCC[C@@H](CC(=O)NS(=O)(=O)C1CC1)n1c(=O)n(Cc2cn(C)c3cccc(C)c23)c2ccccc21]

Example 55

3-{3-[(1,4-dimethyl-1H-indol-3-yl)methyl]-2-oxo-2,3-dihydro-1H-benzimidazol-1-yl}-4-methoxybutanoic acid

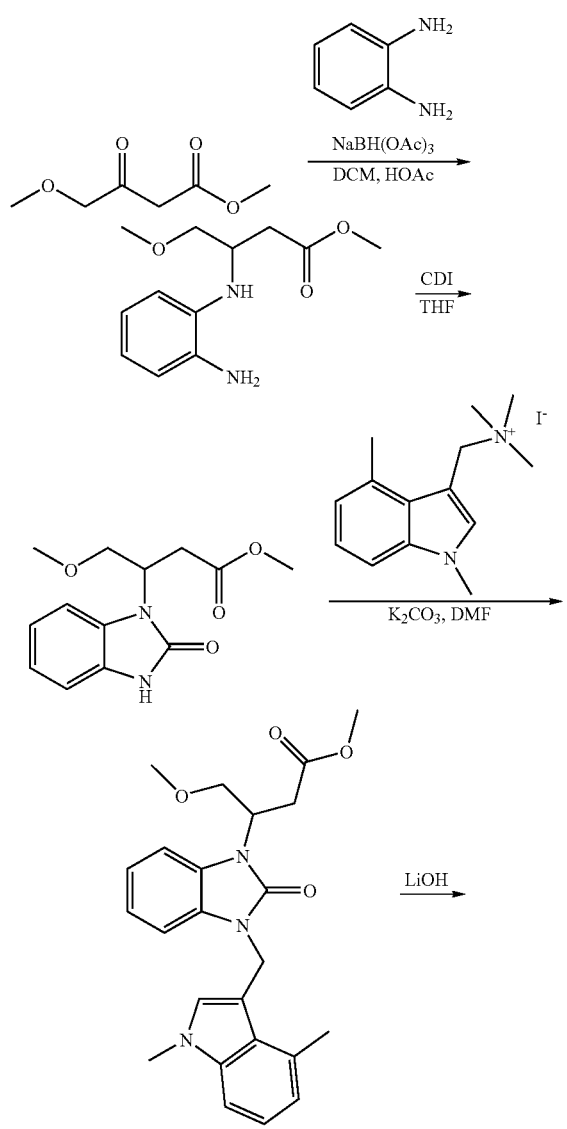

348

-continued

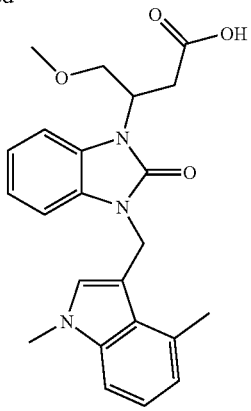

3-(2-Amino-phenylamino)-4-methoxy-butyric acid methyl ester

4-Methoxy-3-oxo-butyric acid methyl ester (0.67 mL, 5.0 mmol) and Benzene-1,2-diamine (560 mg, 5.5 mmol) are dissolved in DCM (20 mL) and HOAc (0.63 mL, 11 mmol) is added into it. The mixture is stirred for 6 hrs and then NaBH(OAC)$_3$ (3.7 g, 17 mmol) is added and the mixture is stirred for another 60 hr. Then 50 mL of sat. NaHCO$_3$ along with 50 mL of water are added and the mixture is extracted with EtOAc (3×100 mL). The organic layers are combined, dried and concentrated to give crude product. Purification by flash column chloromatography affords 320 mg (27%) of 3-(2-Amino-phenylamino)-4-methoxy-butyric acid methyl ester.

4-Methoxy-3-(2-oxo-2,3-dihydro-benzimidazol-1-yl)-butyric acid methyl ester

To a solution of 3-(2-Amino-phenylamino)-4-methoxy-butyric acid methyl ester (320 mg, 1.3 mmol) in THF (5.0 mL) is added CDT (440 mg, 2.7 mmol) at room temperature. The mixture is stirred at the same temperature for 16 hours. Then 5 mL of 1.0 M HCl solution is added along with 20 mL of water. The mixture is extracted with EtOAc (3×25 mL) and the organic layers are combined, dried and concentrated to give crude product. Purification by flash column chromatography affords 205 mg (58%) of 4-Methoxy-3-(2-oxo-2,3-dihydro-benzimidazol-1-yl)-butyric acid methyl ester.

3-[3-(1,4-Dimethyl-1H-indol-3-ylmethyl)-2-oxo-2,3-dihydro-benzimidazol-1-yl]-4-methoxy-butyric acid methyl ester To a solution of 4-Methoxy-3-(2-oxo-2,3-dihydro-benzimidazol-1-yl)-butyric acid methyl ester (205 mg, 0.78 mmol) in DMF (10 mL) are added (1,4-Dimethyl-1H-indol-3-ylmethyl)-trimethyl-ammonium iodide (470 mg, 1.4 mmol) and K$_2$CO$_3$ (210 mg, 1.6 mmol) at room temperature. The solution is heated to 100° C. for 5.5 hours. The solution is cooled down and 30 mL of water is added. The mixture is extracted with EtOAc (3×50 mL) and the organic layers are combined, washed with water (3×100 mL), dried with MgSO$_4$ and concentrated to give crude product. Purification by flash column chromatography affords 200 mg (61%) of 3-[3-(1,4-Dimethyl-1H-indol-3-ylmethyl)-2-oxo-2,3-dihydro-benzimidazol-1-yl]-4-methoxy-butyric acid methyl ester.

3-[3-(1,4-Dimethyl-1H-indol-3-ylmethyl)-2-oxo-2,3-dihydro-benzimidazol-1-yl]-4-methoxy-butyric acid To a solution of 3-[3-(1,4-Dimethyl-1H-indol-3-ylmethyl)-2-oxo-2,3-dihydro-benzimidazol-1-yl]-4-methoxy-butyric acid methyl ester (200 mg, 0.48 mmol) in 1,4-dioxane (2.0 mL) is added LiOH monohydrate (25 mg, 0.59 mmol) in water (2.0 mL) at room temperature. The solution is stirred at the same temperature for 2 hours. Then 1.0 mL of 1.0 M HCl solution is added along with 10 mL of water. Then the mixture is extracted with EtOAc (3×25 mL) and the organic layers are combined, dried and concentrated to give 190 mg (97%) of crude product. 30 mg of this crude is purified by preparative TLC to give 25 mg of 3-[3-(1,4-Dimethyl-1H-indol-3-ylmethyl)-2-oxo-2,3-dihydro-benzimidazol-1-yl]-4-methoxy-butyric acid. LCMS (ESMS): m/z 408.25 (M+H$^+$).

Example 56

3-{3-[(1,4-dimethyl-1H-indol-3-yl)methyl]-2-oxo-2,3-dihydro-1H-benzimidazol-1-yl}-4-methoxy-N-[(1-methyl-1H-imidazol-4-sulfonyl]butanamide

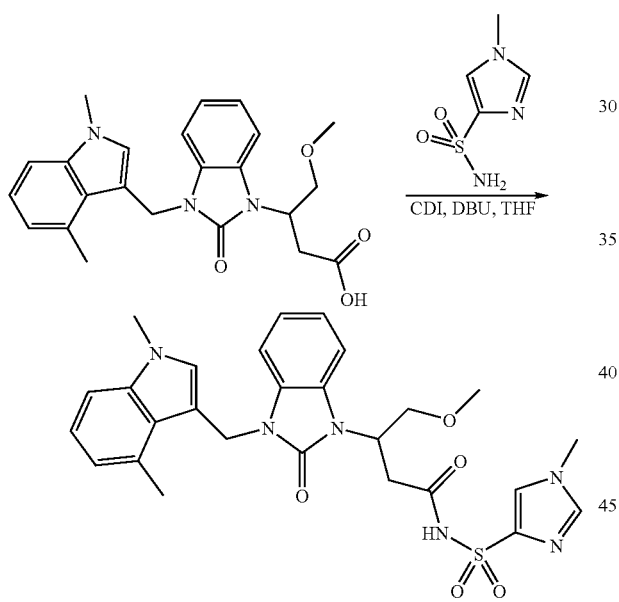

3-[3-(1,4-Dimethyl-1H-indol-3-ylmethyl)-2-oxo-2,3-dihydro-benzimidazol-1-yl]-4-methoxy-butyric acid (30 mg, 0.074 mmol) is dissolved THF (0.70 mL) and CDI (27 mg, 0.17 mmol) is added into it at room temperature. The mixture is heated at 55° C. for 1 hr. After the mixture is cooled down to room temperature, 1-Methyl-1H-imidazole-4-sulfonic acid amide (24 mg, 0.15 mmol) is added and after 10 min, DBU (0.022 mL, 0.15 mmol) is added. The mixture is stirred for 16 hr at room temperature. 2.0 mL of 1.0 M HCl is added followed by 20 mL of water. The mixture is extracted with EtOAc (3×25 mL) and the organic layers are combined, dried and concentrated to give crude product. Purification by flash column chromatography affords 17 mg (41%) of 1-Methyl-1H-imidazole-4-sulfonic acid {3-[3-(1,4-dimethyl-1H-indol-3-ylmethyl)-2-oxo-2,3-dihydro-benzimidazol-1-yl]-4-methoxy-butyryl}-amide. LCMS (ESMS): m/z 551.25 (M+H$^+$).

Example 57

2-{3-[(4-methyl-1-benzothien-3-yl)methyl]-2-oxo-2,3-dihydro-1H-benzimidazol-1-yl}pentane-1-sulfonic acid

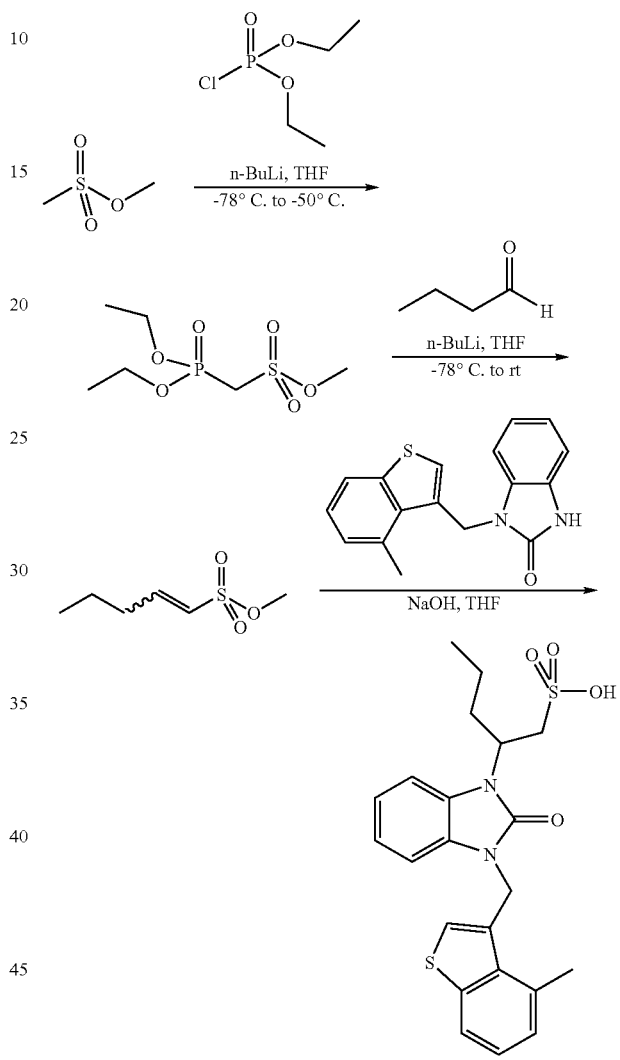

(Diethoxy-phosphoryl)-methanesulfonic acid methyl ester

Methanesulfonic acid methyl ester (0.43 mL, 5.0 mmol) is dissolved in THF (10 mL) and it is cooled down to −78° C. 1.6 M n-BuLi (3.4 mL, 5.5 mmol) in hexane is added into it dropwise and the mixture is stirred for 30 min at −78° C. Then Phosphorochloridic acid diethyl ester (0.41 mL, 2.8 mmol) is added dropwise into the mixture and it is then gradually warmed up to −50° C. in 2 hrs. 5 mL of sat. NH$_4$Cl and 20 mL of water are added and it is further warmed up to room temperature. The mixture is extracted with EtOAc (3×40 mL) and the organic layers are combined, dried (Na$_2$SO$_4$) and concentrated to give crude product. Purification by flash column chromatography affords 350 mg (53%) of (Diethoxy-phosphoryl)-methanesulfonic acid methyl ester.

Pent-1-ene-1-sulfonic acid methyl ester (Diethoxy-phosphoryl)-methanesulfonic acid methyl ester (150 mg, 0.61 mmol) is dissolved in THF (5.0 mL) and it is cooled down to −78° C. 1.6M nBuLi (0.46 mL, 0.73 mmol) in hexane is added into it dropwise. The mixture is stirred for 30 min at that temperature and Butyraldehyde (0.066 mL, 0.73 mmol) is added. Then mixture is gradually warmed up to room temperature in 3 hrs and the reaction is further stirred for 2 hr at room temperature. Then 30 mL of water is added and the mixture is extracted with EtOAc (3×50 mL). The organic layers are combined, dried and concentrated to give 100 mg (100%) of Pent-1-ene-1-sulfonic acid methyl ester.

2-[3-(4-Methyl-benzo[b]thiophen-3-ylmethyl)-2-oxo-2,3-dihydro-benzimidazol-1-yl]-pentane-1-sulfonic acid To a solution of 1-(4-Methyl-benzo[b]thiophen-3-ylmethyl)-1,3-dihydro-benzimidazol-2-one (50 mg, 0.17 mmol) in THF (1.0 mL) arc added Pent-1-ene-1-sulfonic acid methyl ester (56 mg, 0.34 mmol) and solid NaOH (14 mg, 0.34 mmol) in order. The resulting suspension is stirred at room temperature for 1 hr and it turned into a clear solution. Then 5 mL of sat.NH$_4$Cl is added along with 5 mL of water. The mixture is extracted with EtOAc (3×20 mL). The organic layers are combined, dried (MgSO$_4$) and concentrated to give crude product. Purification by flash column chromatography affords 11 mg (15%) of 2-[3-(4-Methyl-benzo[b]thiophen-3-ylmethyl)-2-oxo-2,3-dihydro-benzimidazol-1-yl]-pentane-1-sulfonic acid. LCMS (ESMS): m/z 445.13 (M+H$^+$).

Example 58

2-{3-[(1,4-dimethyl-1H-indol-3-yl)methyl]-2-oxo-2,3-dihydro-1H-benzimidazol-1-yl}benzoic acid

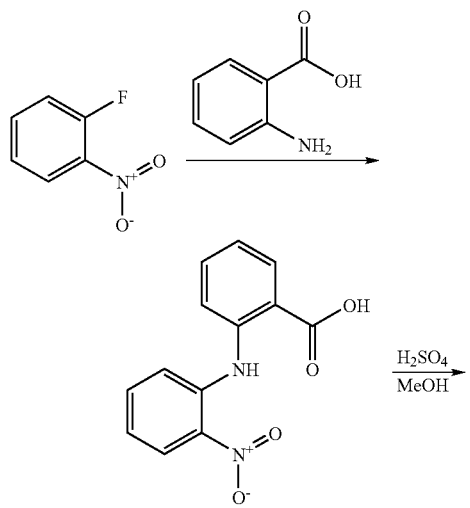

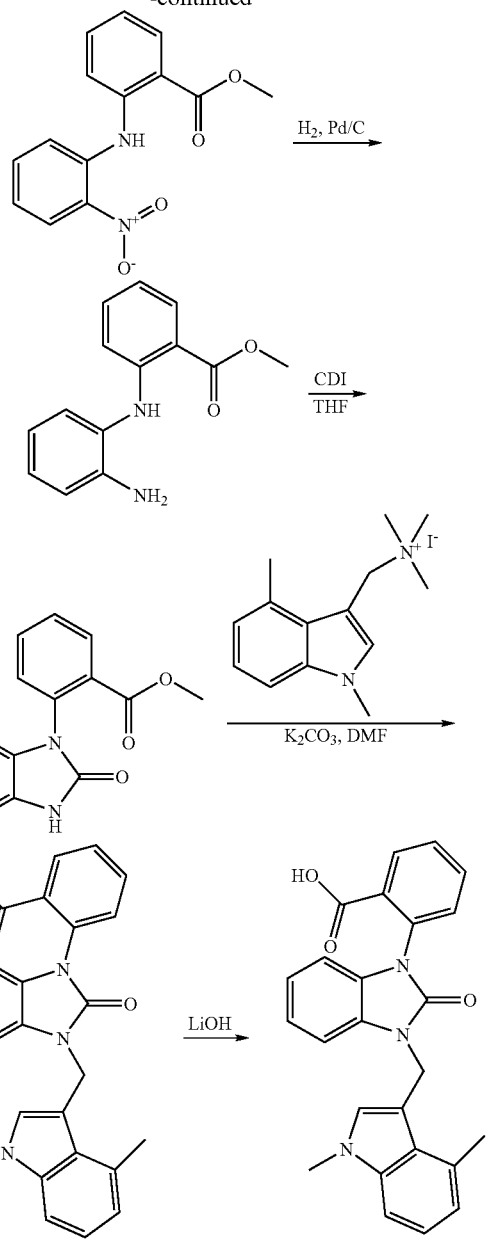

2-(2-Nitro-phenylamino)-benzoic acid

1-Fluoro-2-nitro-benzene (0.53 mL, 5.0 mmol), 2-Aminobenzoic acid (750 mg, 5.5 mmol) and Na$_2$CO$_3$ (420 mg, 4.0 mmol) are added together in reaction flask and the mixture is heated at 130° C. for 60 hrs. After it is cooled down to room temperature, 50 mL of water is added and HOAc is used to adjust the pH to slightly acidic. Then the mixture is extracted with EtOAc (3×50 mL) and the organic layers are combined, washed with water (3×50 mL), dried (Na$_2$SO$_4$) and concentrated to give crude product. Purifiction by flash column chromatography affords 560 mg (43%) of 2-(2-Nitro-phenylamino)-benzoic acid.

2-(2-Nitro-phenylamino)-benzoic acid methyl ester 2-(2-Nitro-phenylamino)-benzoic acid (560 mg, 2.2 mmol) is dissolved in methanol (10 mL) and concentrated H₂SO₄ (0.16 mL, 98%) is added into it. The mixture is then refluxed for 60 hr. After it is cooled down to room temperature, 100 mL of water is added and the pH of this solution is adjusted to pH 7 by adding 1.0 M NaOH aqueous solution. An orange solid is formed and it is filtered and rinsed with more water. Air drying of this orange solid affords 470 mg (80%) of 2-(2-Nitro-phenylamino)-benzoic acid methyl ester.

2-(2-Amino-phenylamino)-benzoic acid methyl ester 2-(2-Nitro-phenylamino)-benzoic acid methyl ester (200 mg, 0.74 mmol) is suspended in EtOAc (5.0 mL)) and 10% Pd/C wet (78 mg, 0.073 mmol) is added into it. A H₂ balloon is attached to the reaction flask and the reaction mixture is stirred under H₂ for 20 hrs. Then the Pd/C is filtered and the filtrated is concentrated to give 165 mg (93%) of 2-(2-Amino-phenylamino)-benzoic acid methyl ester.

2-(2-Oxo-2,3-dihydro-benzimidazol-1-yl)-benzoic acid methyl ester

To a solution of 2-(2-Amino-phenylamino)-benzoic acid methyl ester (75 mg, 0.31 mmol) in THF (1.0 mL) is added COI (100 mg, 0.62 mmol) at room temperature. The mixture is stirred at the same temperature for 16 hours. Then 3 mL of 1.0 M HCl solution is added along with 20 mL of water. The mixture is extracted with EtOAc (3×30 mL) and the organic layers are combined, dried and concentrated to give crude product. Purification by flash column chromatography affords 65 mg (78%) of 2-(2-Oxo-2,3-dihydro-benzimidazol-1-yl)-benzoic acid methyl ester.

2-[3-(1,4-Dimethyl-1H-indol-3-ylmethyl)-2-oxo-2,3-dihydro-benzimidazol-1-yl]-benzoic acid methyl ester To a solution of 2-(2-Oxo-2,3-dihydro-benzimidazol-1-yl)-benzoic acid methyl ester (30 mg, 0.11 mmol) in DMF (1.0 mL) are added (1,4-Dimethyl-1H-indol-3-ylmethyl)-trimethyl-ammonium iodide (46 mg, 0.13 mmol) and K₂CO₃ (31 mg, 0.22 mmol) at room temperature. The solution is heated to 60° C. for 16 hr and it is cooled down to room temperature for another 48 hr. Then 30 mL of water is added. The mixture is extracted with EtOAc (3×30 mL) and the combined organic layers are washed with water (3×100 mL), dried with Na₂SO₄ and concentrated to give crude product. Purification by preparative TLC affords 40 mg (86%) of 2-[3-(1,4-Dimethyl-1H-indol-3-ylmethyl)-2-oxo-2,3-dihydro-benzimidazol-1-yl]-benzoic acid methyl ester.
2-[3-(1,4-Dimethyl-1H-indol-3-ylmethyl)-2-oxo-2,3-dihydro-benzimidazol-1-yl]-benzoic acid To a solution of 2-[3-(1,4-Dimethyl-1H-indol-3-ylmethyl)-2-oxo-2,3-dihydro-benzimidazol-1-yl]-benzoic acid methyl ester (45 mg, 0.11 mmol) in 1,4-dioxane (1.0 mL) is added LiOH monohydrate (5.6 mg, 0.13 mmol) in water (0.1 mL) at room temperature. The solution is stirred at the same temperature for 16 hours. Then another 1.0 mg of LiOH monohydrate is added and the reaction is continued for another 2 hr. Then 0.5 mL of 1.0 M HCl is added along with 10 mL of water. The mixture is extracted with EtOAc (3×15 mL) and the organic layers are combined, dried and concentrated to give crude product. Purification by preparative TLC affords 41 mg (95%) of 2-[3-(1,4-Dimethyl-1H-indol-3-ylmethyl)-2-oxo-2,3-dihydro-benzimidazol-1-yl]-benzoic acid. LCMS (ESMS): m/z 412.17 (M+H⁺).

The following compounds are synthesized using the same procedure.

2-{3-[(1,4-dimethyl-1H-indol-3-yl)methyl]-2-oxo-2,3-dihydro-1H-benzimidazol-1-yl}-3-methoxybenzoic acid. LCMS (ESMS): m/z 442.06 (M+H⁺)

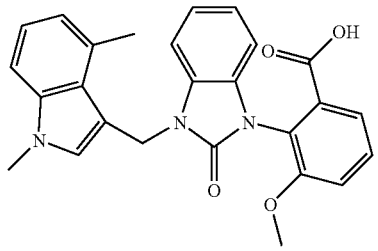 [SMILES: COc1cccc(C(=O)O)c1-n1c(=O)n(Cc2cn(C)c3cccc(C)c23)c2ccccc21]

2-{3-[(1,4-dimethyl-1H-indol-3-yl)methyl]-2-oxo-2,3-dihydro-1H-benzimidazol-1-yl}-3-methylbenzoic acid. LCMS (ESMS): m/z 426.04 (M+H⁺)

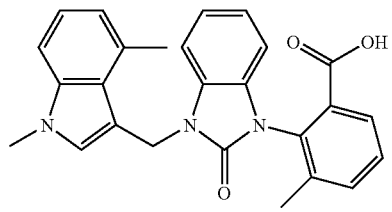 [SMILES: Cc1cccc(C(=O)O)c1-n1c(=O)n(Cc2cn(C)c3cccc(C)c23)c2ccccc21]

3-{3-[(1,4-dimethyl-1H-indol-3-yl)methyl]-2-oxo-2,3-dihydro-1H-benzimidazol-1-yl}-4-methoxybenzoic acid. LCMS (ESMS): m/z 442.18 (M+H⁺)

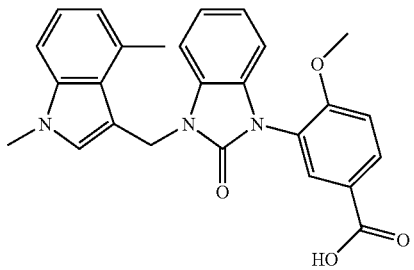 [SMILES: COc1ccc(C(=O)O)cc1-n1c(=O)n(Cc2cn(C)c3cccc(C)c23)c2ccccc21]

Example 59

1-[2-(1,1-dioxido-4-oxo-1,2,5-thiadiazolidin-2-yl)ethyl]-3-[(4-methyl-1-benzothien-3-yl)methyl]-1,3-dihydro-2H-benzimidazol-2-one

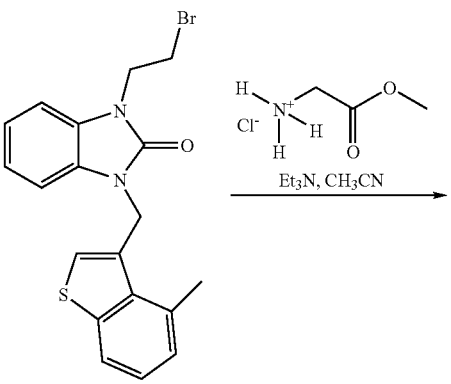

-continued

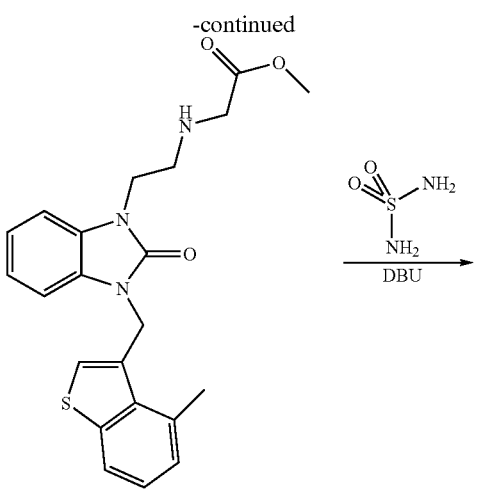

{2-[3-(4-Methyl-benzo[b]thiophen-3-ylmethyl)-2-oxo-2,3-dihydro-benzimidazol-1-yl]-ethylamino}-acetic acid methyl ester 1-(2-Bromo-ethyl)-3-(4-methyl-benzo[b]thiophen-3-ylmethyl)-1,3-dihydro-benzimidazol-2-one (30 mg, 0.075 mmol) is dissolved in $CH_3CN$ (0.5 mL)) and Methoxycarbonylmethyl-ammonium chloride (11 mg, 0.09 mmol) and $Et_3N$ (0.025 mL, 0.18 mmol) are added. The mixture is first stirred at room temperature for 16 hr. And then 11 mg of $Na_2CO_3$ is added and the mixture is stirred at room temperature for another 48 hr. Since the reaction is not completed, another 11 mg of Methoxycarbonylmethyl-ammonium chloride, 0.025 mL of $Et_3N$ and 11 mg of $Na_2CO_3$ are added. The mixture is then heated at 80° C. for 20 hrs. Then 10 mL of water is added and the mixture is extracted with EtOAc (3×15 mL). The organic layers are combined, dried and concentrated to give crude product. Purification by flash column chromatography affords 30 mg (98%) of {2-[3-(4-Methyl-benzo[b]thiophen-3-ylmethyl)-2-oxo-2,3-dihydro-benzimidazol-1-yl]-ethylamino}-acetic acid methyl ester.

1-(4-Methyl-benzo[b]thiophen-3-ylmethyl)-3-[2-(1,1,4-trioxo-1☐6-1,2,5-thiadiazolidin-2-yl)-ethyl]-1,3-dihydro-benzimidazol-2-one {2-[3-(4-Methyl-benzo[b]thiophen-3-ylmethyl)-2-oxo-2,3-dihydro-benzimidazol-1-yl]-ethylamino}-acetic acid methyl ester (30 mg, 0.073 mmol) and sulfamide (7.0 mg, 0.073 mmol) are added into the same reaction flask and DBU (0.1 mL, 0.67 mmol) is added into them. The neat reaction mixture is heated at 130° C. for 40 min. After it is cooled down to room temperature, 1.5 mL of 1.0M HCl solution is added along with 15 mL of water. The mixture is extracted with EtOAc (3×15 mL) and the organic layers are combined, dried and concentrated to give crude product. Purification by preparative TLC affords 14 mg (42%) of 1-(4-Methyl-benzo[b]thiophen-3-ylmethyl)-3-[2-(1,1,4-trioxo-1☐6-1,2,5-thiadiazolidin-2-yl)-ethyl]-1,3-dihydro-benzimidazol-2-one.
LCMS (ESMS): m/z 457.08 (M+H$^+$).

Example 60

2-{3-[(1,4-dimethyl-1H-indol-3-yl)methyl]-2-oxo-2,3-dihydro-1H-benzimidazol-1-yl}cyclopent-1-ene-1-carboxylic acid

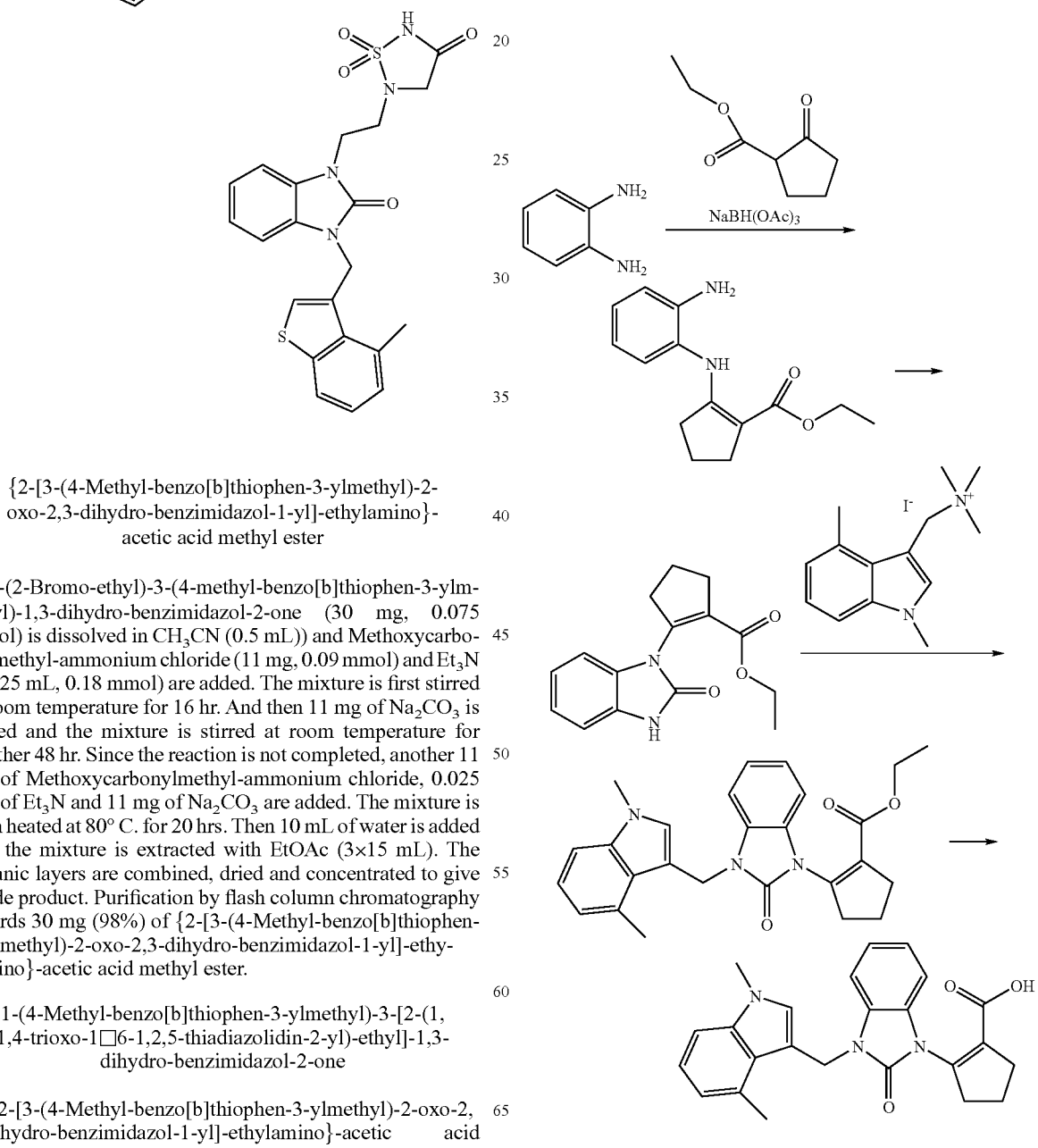

357

A solution of 500 mg (4.62 mmol) of 1,2-phenylenediamine and 0.7 mL (4.62 mmol) of ethyl 2-oxocyclopentane carboxylate in 5 mL, of dichloroethane was treated with 653 mg (3.08 mmol, 0.67 eq.) of sodium triacetoxyborohydride and 5 drops of acetic acid at room temperature. The resulting mixture was stirred at this temperature for h. Then the mixture was diluted with water and the organic layer was separated. The organic layer was dried over magnesium sulfate, filtered and concentrated. The residue was purified by flash chromatography to give 375 mg (33%) of desired compound as light tan solid.

A solution of 370 mg (1.5 mmol) of 2-(2-amino-phenylamino)-cyclopent-1-enecarboxylic acid ethyl ester and 483 mg (3.0 mmol, 2.0 eq.) of CDI in 10 mL of THF was stirred room temperature for 16 h. The resulting mixture was concentrated and the residue was purified by combiflash to give 120 mg (29%) of desired compound as light tan oil.

To a solution of 100 mg (0.37 mmol) of 2-(2-oxo-2,3-dihydro-benzimidazol-1-yl)-cyclopent-1-enecarboxylic acid ethyl ester in 5 mL of DMF was added 101 mg (0.73 mmol, 2.0 eq.) of potassium carbonate followed by 190 mg (0.55 mmol, 1.5 eq.) indole ammonium iodide at room temperature under nitrogen atmosphere. The resulting suspension was heated to 100° C. for 4 hours. The solution was cooled and stirred at RT over night. The reaction was poured into water and extracted with EtOAc (3x). The combined organics were washed with water, brine and dried (magnesium sulfate). Filtration and concentration gave the crude product which was absorbed onto silica gel and purified via CombiFlash to give 120 mg (76%) of the desired product as a light yellow oil.

A solution of 120 mg (0.28 mmol) of 2-[3-(1,4-dimethyl-1H-indol-3-ylmethyl)-2-oxo-2,3-dihydro-benzimidazol-1-yl]-cyclopent-1-enecarboxylic acid ethyl ester and 23 mg (0.56 mmol, 2.0 eq.) of lithium hydroxide monohydrate in 5 mL of methanol and 1 mL of water was stirred at room temperature for 2.5 days. Then the pH of the resulting mixture was adjusted to 3 with acetic acid and diluted with water. The precipitate was collected and washed with water. The isolated light pink solid was pumped overnight to give 94 mg (84%) of 2-[3-(1,4-dimethyl-1H-indol-3-ylmethyl)-2-oxo-2,3-dihydro-benzimidazol-1-yl]-cyclopent-1-enecarboxylic acid as a light pink solid.

Example 61

2-{3-[(1,4-dimethyl-1H-indol-3-yl)methyl]-2-oxo-2,3-dihydro-1H-benzimidazol-1-yl}cyclopentanecarboxylic acid

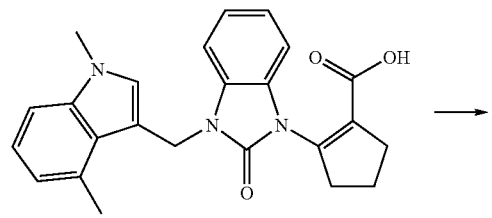

358

-continued

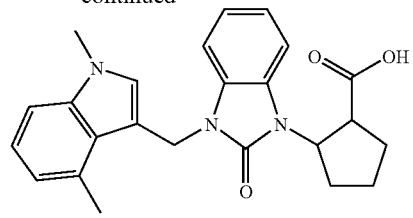

A mixture of 65 mg (0.16 mmol) of 2-{3-[(1,4-dimethyl-1H-indol-3-yl)methyl]-2-oxo-2,3-dihydro-1H-benzimidazol-1-yl}cyclopent-1-ene-1-carboxylic acid and 30 mg of 10% Pd/C in 3 mL of methanol was stirred at room temperature under hydrogen gas atmosphere (1 atom) for 16 h. The resulting mixture was filtered through Celite and the filtrate was concentrated. The residue was purified by combiflash to give 20 mg (31%) of 2-[3-(1,4-dimethyl-1H-indol-3-ylmethyl)-2-oxo-2,3-dihydro-benzimidazol-1-yl]-cyclopentanecarboxylic acid as a white solid.

Example 62

3-{3-[(2,3-dimethylindolizin-8-yl)methyl]-2-oxo-2,3-dihydro-1H-benzimidazol-1-yl}propanoic acid

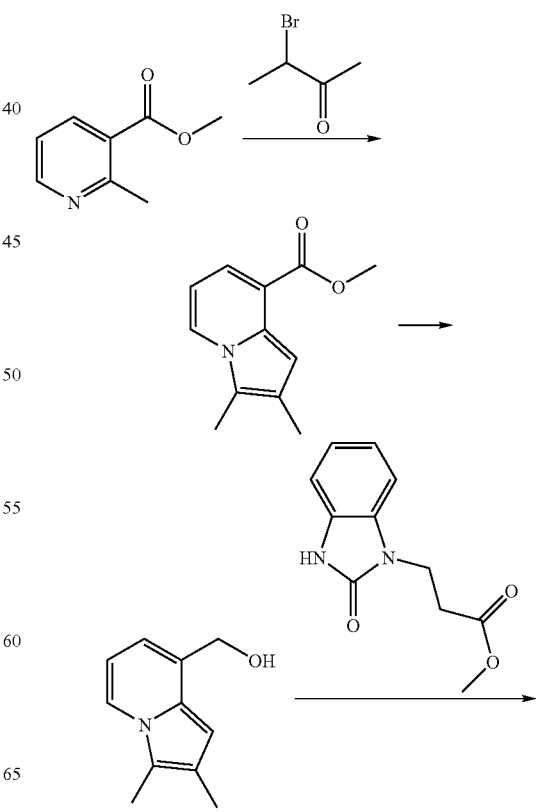

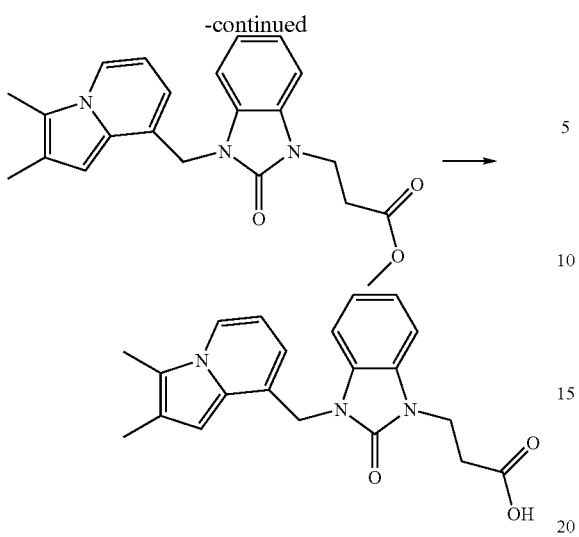

2,3-Dimethyl-indolizine-8-carboxylic acid methyl ester

A solution of methyl 2-methylnicotinate (4.9 g, 32.1 mmol) and 3-bromo-2-butanone (4.8 g, 32.1 mmol) in acetone (40 ml) were warmed to reflux for 3 d. Cooled to RT and partially purified the remaining residue via column chromatography (silica gel, 5-10% EtOAc/hexanes). The product-containing fractions were combined and concentrated to give the desired product.

(2,3-Dimethyl-indolizin-8-yl)-methanol

A solution of the 2,3-dimethyl-indolizine-8-carboxylic acid methyl ester (265 mg, 1.3 mmol) in ether (10 ml) was cooled to 0° C. and treated with LAH (1.0M in THF, 1.6 ml, 1.6 mmol, dropwise addition). After 3.5 h the reaction was quenched with sodium sulfate decahydrate (added in small portions until gas evolution ceased). The resulting mixture was stirred for 0.5 h and the precipitated solids were removed via filtration and washed with EtOAc. The combined filtrates were concentrated to give the product which was used without further purification.

3-[3-(2,3-Dimethyl-indolizin-8-ylmethyl)-2-oxo-2,3-dihydro-benzoimidazol-1-yl]-propionic acid methyl ester To a stirred solution of the 3-(2-oxo-2,3-dihydro-benzimidazol-1-yl)-propionic acid methyl ester (100 mg, 0.45 mmol) and (2,3-Dimethyl-indolizin-8-yl)-methanol (88 mg, 0.50 mmol) in THF (8 ml) was added triphenylphosphine (143 mg, 0.54 mmol) followed by DIAD (0.11 ml, 0.54 mmol, dropwise) at ambient temperature. After five minutes the reaction became dark brown and was consequently wrapped in aluminum foil. After stirring over night the reaction was treated with silica gel and concentrated. The remaining solid was purified via column chromatography (silica gel, 5-40% EtOAc/hexanes). The product-containing fractions were combined and concentrated to give the product which was used without further purification.

3-{3-[(2,3-dimethylindolizin-8-yl)methyl]-2-oxo-2,3-dihydro-1H-benzimidazol-1-yl}propanoic acid To a stirred solution of 3-[3-(2,3-dimethyl-indolizin-8-ylmethyl)-2-oxo-2,3-dihydro-benzoimidazol-1-yl]-propionic acid methyl ester (110 mg, 0.29 mmol) in THF (5 ml) and water (1.5 ml) was added lithium hydroxide monohydrate (25 mg, 0.58 mmol). After 1.5 h the reaction appeared complete (LC-MS) and was subsequently concentrated. The remaining residue was diluted with water (~12 ml) and acidified to pH~5 using HOAc (~5 drops). The resulting solid was dissolved into DCM and the layers were separated. The aqueous phase was extracted with DCM (1×) and the combined organics were concentrated. The remaining green residue was dissolved into a minimal volume of DCM and applied to a preparative TLC plate (1 mm). Eluted with 8% MeOH/DCM. The product-band was isolated and suspended in 5% MeOH/DCM. The silica gel was removed via filtration and washed with DCM. The combined filtrates were concentrated to give the desired product as a light green solid. LCMS (ESMS): m/z 364.24.

Example 63

3-{3-[(1-cyano-5-methylindolizin-3-yl)methyl]-2-oxo-2,3-dihydro-1H-benzimidazol-1-yl}hexanoic acid

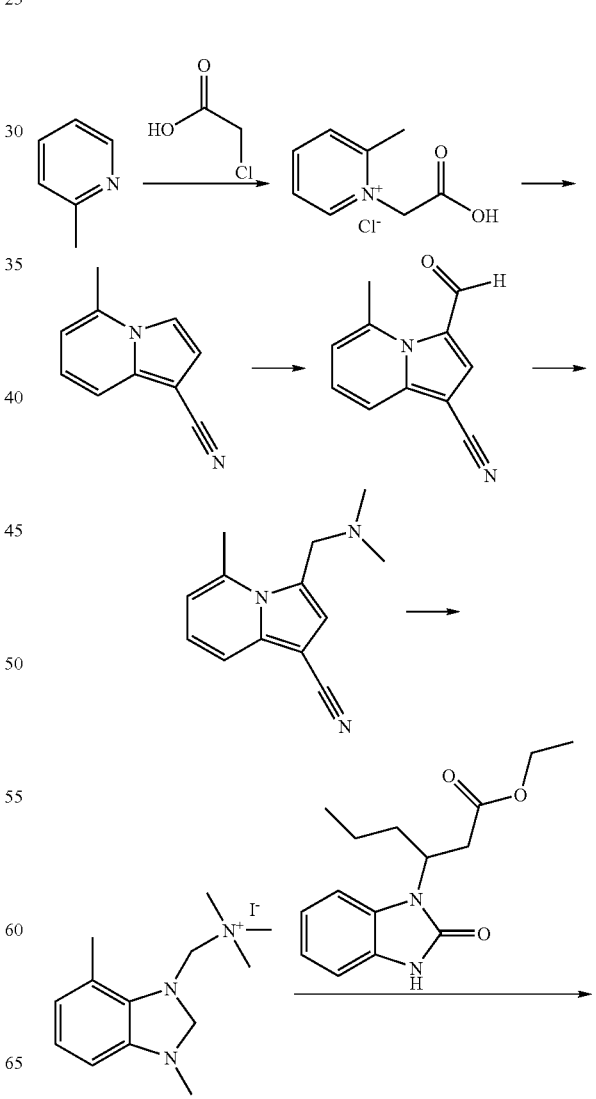

-continued

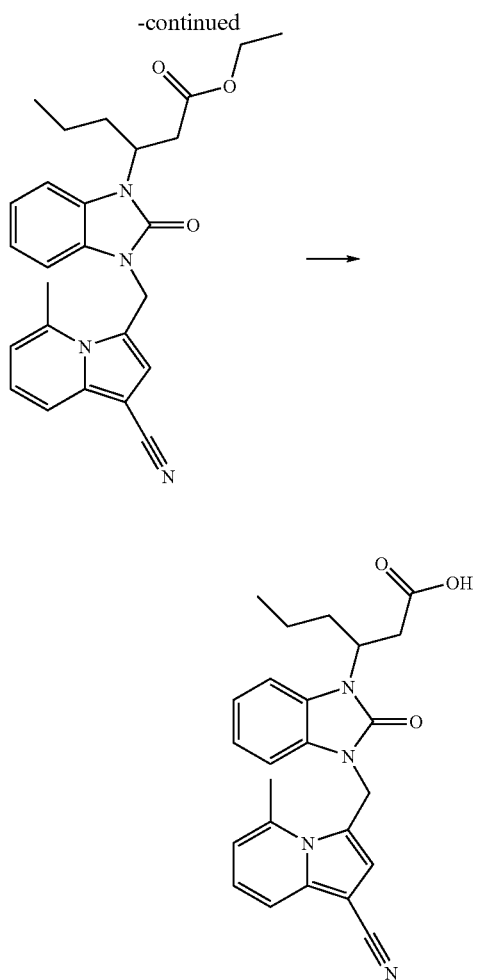

To a solution of 2-picoline (5.3 mL, 0.054 mol) in Et$_2$O (15 mL) was added chloroacetic acid (6 g, 0.064 mol) at room temperature. The solution was stirred at the same temperature for 12 hours. The solution was concentrated and the residue oil was used in the next step of the synthesis without further purification.

To a solution of crude 1-Carboxymethyl-2-methyl-pyridinium chloride (7 g, 0.037 mol) in toluene (50 mL) were added acrylonitrile (7.4 mL, 0.11 mol), MnO$_2$ (6.5 g, 0.075 mol) and Et$_3$N (2 mL) at room temperature under nitrogen atmosphere. The solution was heated to 90 C and was stirred at the same temperature for 12 hours. The solution was cooled down and was filtered to remove the excess MnO$_2$. The filtrate was concentrated and the residue was purified by CombiFlash with 10% EtOAc in Hexane to afford the desirable product 5-Methyl-indolizine-1-carbonitrile, CAS: 5-Methyl-indolizine-1-carbonitrile (3 g, 52%) as a white solid.

A solution of: 5-Methyl-indolizine-1-carbonitrile (200 mg, 1.28 mmol) in DMF (0.12 mL, 1.54 mmol) was cooled to ~5° C. under nitrogen. Pyrophosphoryl chloride (0.2 mL, 1.54 mmol) was then slowly introduced. Upon complete addition the cooling bath was removed and the reaction was allowed to warm to ambient temperature. After a total of 45 minutes the reaction was recooled to 5° C. and slowly quenched with 2N NaOH. The pH was adjusted to ~8. The solid that precipitate out from the solution was collected by filtration and was washed with water. The remaining white solid was dried in the oven and was confirmed to be the desirable product 3-Formyl-5-methyl-indolizine-1-carbonitrile, CAS: 3-Formyl-5-methyl-indolizine-1-carbonitrile (210 mg, 89%).

To a solution of 3-Formyl-5-methyl-indolizine-1-carbonitrile (200 mg, 1.09 mmol) in CH$_2$Cl$_2$ (10 mL) and dimethylamine (2M MeOH solution) (1.09 mL, 2.17 mmol) was added NaBH(OAc)$_3$ (460 mg, 2.17 mmol) at 0° C. Upon complete addition the cooling bath was removed and the reaction mixture was stirred at room temperature for 12 h. When the reaction was complete, the mixture was diluted with CH$_2$Cl$_2$ and washed with saturated NaHCO$_3$. The layers were separated and the organic phase was dried over MgSO$_4$, filtered and concentrated. The residue was purified by CombiFlash with 20% EtOAc in Hexane as the eluent to afford the desirable product 3-Dimethylaminomethyl-5-methyl-indolizine-1-carbonitrile, CAS: 3-Dimethylaminomethyl-5-methyl-indolizine-1-carbonitrile (150 mg, 65%) as a white solid.

To a stirred solution of 3-Dimethylaminomethyl-5-methyl-indolizine-1-carbonitrile (60 mg, 0.28 mmol) in acetonitrile (5 mL) was added iodomethane (0.02 mL, 0.34 mmol) at room temperature. The solution was stirred at the same temperature for 5 hours. The solution was concentrated and the resulting white solid was washed with small amount of acetonitrile (0.5 mL) and Et$_2$O was added. The white solid was collected by filtration and was washed with Et$_2$O. The white solid was confirmed to be the desirable product 3-trimethylaminomethyl-5-methyl-indolizine-1-carbonitrile iodide, CAS: 3-triimethylaminomethyl-5-methyl-indolizine-1-carbonitrile iodide (60 mg, 60%).

To a solution of 3-(2-Oxo-2,3-dihydro-benzimidazol-1-yl)-hexanoic acid ethyl ester (50 mg, 0.18 mmol) in DMF (5 mL) were added 3-trimethylaminomethyl-5-methyl-indolizine-1-carbonitrile iodide, CAS: 3-triimethylaminomethyl-5-methyl-indolizine-1-carbonitsile iodide (96 mg, 0.67 mmol) and K$_2$CO$_3$ (50 mg, 0.36 mmol) at room temperature under nitrogen atmosphere. The solution was heated to 100 C for 2 hours. The solution was cooled down and water was added. The solution was extracted with EtOAc and the combined organic layer was dried with MgSO$_4$. The solution was filtered and the filtrate was concentrated. The residue was purified by CombiFlash with 20% EtOAc in Hexane as the eluent to afford the desirable product 3-[3-(1-Cyano-5-methyl-indolizin-3-ylmethyl)-2-oxo-2,3-dihydro-benzoimidazol-1-yl]-hexanoic acid ethyl ester, CAS: 3-[3-(1-Cyano-5-methyl-indolizin-3-ylmethyl)-2-oxo-2,3-dihydro-benzimidazol-1-yl]-hexanoic acid ethyl ester (36 mg, 45%) as yellow foam.

To a solution of 3-[3-(1-Cyano-5-methyl-indolizin-3-ylmethyl)-2-oxo-2,3-dihydro-benzimidazol-1-yl]-hexanoic acid ethyl ester (30 mg, 0.067 mmol) in 1,4-dioxane (5 mL) and water (1 mL) was added LiOH (3.2 mg, 0.14 mmol) at room temperature. The solution was stirred at the same temperature for 12 hours. The solution was concentrated and water was added to the residue. The solution was acidified by 12N HCl in an ice-bath. The solid that precipitate out from the solution was collected by filtration. The solid was dried under vacuum and was confirmed to be the desirable product 1 (19 mg, 67%). LCMS (ESMS): m/z 417.28 (M+H$^+$).

The following compounds were prepared following a similar procedure using appropriate starting materials.

363
3-{3-[(1-cyano-5-methylindolizin-3-yl)methyl]-2-oxo-2,3-dihydro-1H-benzimidazol-1-yl}propanoic acid. LCMS (ESMS): m/z 375.21 (M+H$^+$)
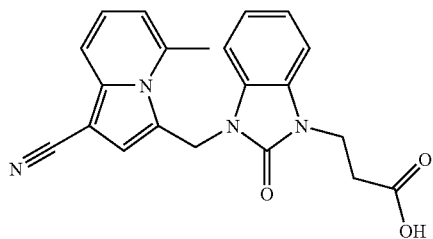 [SMILES: Cc1cccc2c(C#N)cc(Cn3c(=O)n(CCC(=O)O)c4ccccc43)n12]
3-{3-[(1-cyano-5,7-dimethylindolizin-3-yl)methyl]-2-oxo-2,3-dihydro-1H-benzimidazol-1-yl}hexanoic acid. LCMS (ESMS): m/z 431.07 (M+H$^+$)
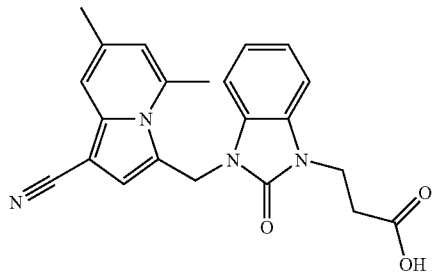 [SMILES: Cc1cc(C)n2c(Cn3c(=O)n(CCC(=O)O)c4ccccc43)cc(C#N)c2c1]
Example 64
3-{3-[(6,8-dichloro-3-methylindolizin-1-yl)methyl]-2-oxo-2,3-dihydro-1H-benzimidazol-1-yl}hexanoic acid
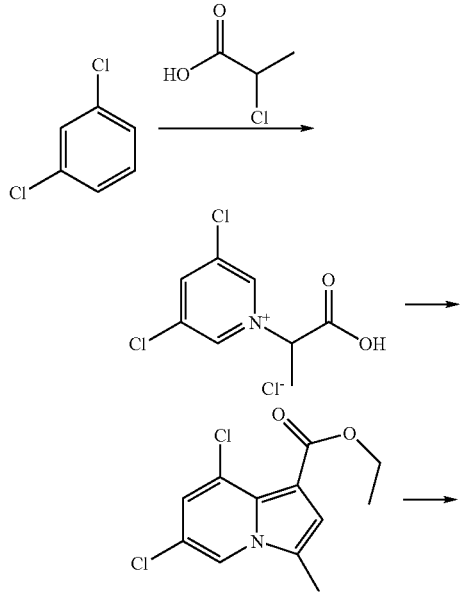
-continued
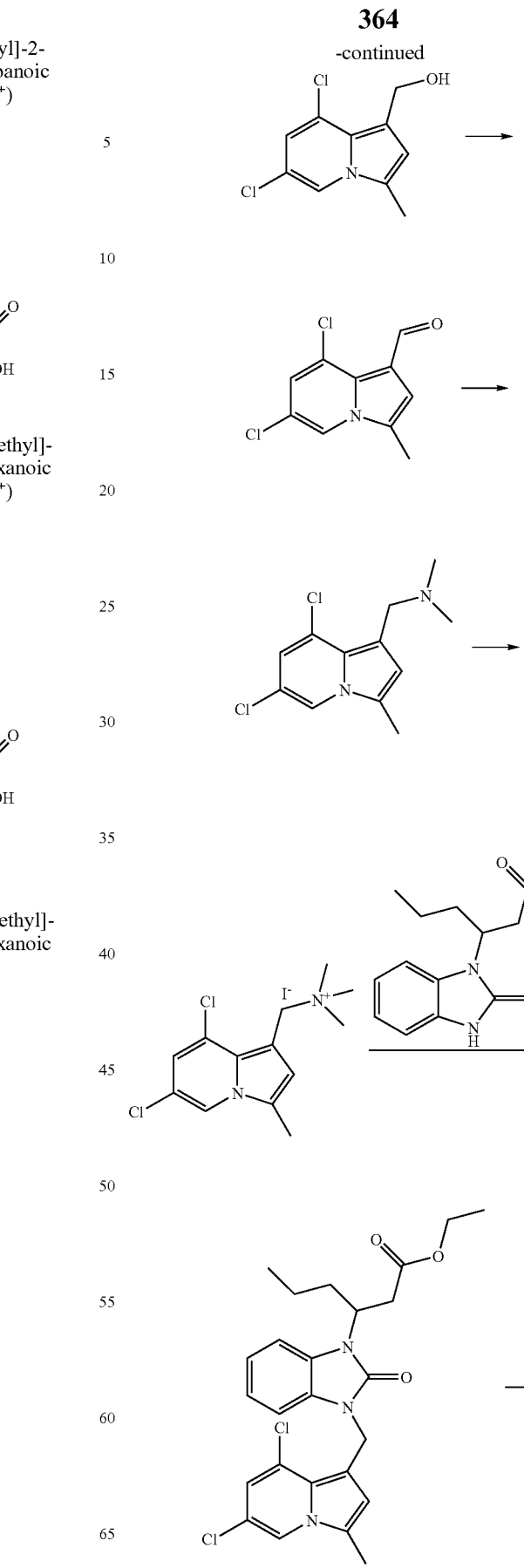

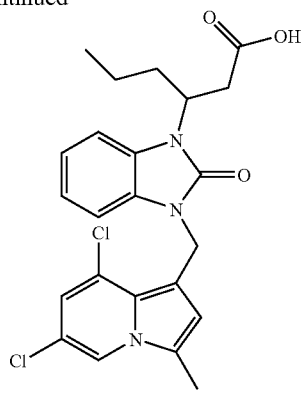

To a solution of 3,5-dichloropyridine (5 g, 0.034 mol) in Et₂O (10 mL) was added 2-chloropropionic acid (3.5 mL, 0.041 mol) at room temperature. The solution was stirred at the same temperature for 12 hours. The solution was concentrated and the residue oil was used in the next step of the synthesis without further purification.

To a solution of crude N-carbonylethyl-3,5-Dichloro-pyridinium chloride (10 g, 0.039 mol) in toluene (100 mL) were added ethyl acroylate (12.7 mL, 0.117 mol), MnO₂ (10.2 g, 0.117 mol) and Et₃N (5 mL) at room temperature under nitrogen atmosphere. The solution was heated to 90 C and was stirred at the same temperature for 12 hours. The solution was cooled down and was filtered to remove the excess MnO₂. The filtrate was concentrated and the residue was purified by CombiFlash with 10% EtOAc in Hexane to afford the desirable product 6,8-Dichloro-3-methyl-indolizine-1-carboxylic acid ethyl ester (150 mg, 1.4%) as a pale yellow foam.

To a solution of 6,8-Dichloro-3-methyl-indolizine-1-carboxylic acid ethyl ester (80 mg, 0.29 mmol) in Et₂O (10 mL) was added LAH (22.3 mg, 0.58 mmol) at 0 C under nitrogen atmosphere. The solution was warmed to room temperature. Sat. NaHCO₃ was added and the solution was extracted with EtOAc. The combined organic layer was dried with MgSO₄ and was filtered. The filtrate was concentrated and the residue was subjected to 1H-NMR analysis to confirm the presence of the desirable product (6,8-Dichloro-3-methyl-indolizin-1-yl)-methanol, CAS: (6,8-Dichloro-3-methyl-indolizin-1-yl)-methanol (60 mg, 89%).

To a solution of 6,8-Dichloro-3-methyl-indolizin-1-yl)-methanol (100 mg, 0.44 mmol) in acetone was added MnO₂ (75.5 mg, 0:87 mmol) at room temperature. The mixture was stirred at the same temperature for 3 hours. The solution was filtered and the filtrate was concentrated. The residue was purified by CombiFlash with 5% EtOAc in Hexane as the eluent to afford the desirable product 6,8-Dichloro-3-methyl-indolizine-1-carbaldehyde, CAS: 6,8-Dichloro-3-methyl-indolizine-1-carbaldehyde (50 mg, 50%) as a white solid.

To a solution of 6,8-Dichloro-3-methyl-indolizine-1-carbaldehyde (50 mg, 0.22 mmol) in CH₂Cl₂ (20 mL) and dimethylamine (2M methanol solution) (0.33 mL, 0.66 mmol) was added NaBH(OAc)₃ (232 mg, 1.1 mmol) at 0° C. Upon complete addition the cooling bath was removed and the reaction mixture was stirred at room temperature for 48 h. When the reaction was complete, the mixture was diluted with CH₂Cl₂ and washed with saturated NaHCO₃. The layers were separated and the organic phase was dried over MgSO₄, filtered and concentrated. The residue was used in the next step of the synthesis without purification.

To a stirred solution of crude (6,8-Dichloro-3-methyl-indolizin-1-ylmethyl)-dimethyl-amine (50 mg, 0.19 mmol) in acetonitrile (5 mL) was added iodomethane (0.04 mL, 0.58 mmol) at room temperature. The solution was stirred at the same temperature for 5 hours. The solution was concentrated and the resulting white solid was washed with small amount of acetonitrile (0.5 mL) and Et₂O was added. The white solid was collected by filtration and was washed with Et₂O. The white solid was confirmed to be the desirable product (6,8-Dichloro-3-methyl-indolizin-1-ylmethyl)-dimethyl-amine iodide (60 mg, 77%).

To a solution of 3-(2-Oxo-2,3-dihydro-benzimidazol-1-yl)-hexanoic acid ethyl ester (30 mg, 0.11 mmol) in DMF (10 mL) were added (6,8-Dichloro-3-methyl-indolizin-1-ylmethyl)-dimethyl-amine iodide, CAS: (6,8-Dichloro-3-methyl-indolizin-1-ylmethyl)-dimethyl-amine iodide (65 mg, 0.16 mmol). and K₂CO₃ (45 mg, 0.33 mmol) at room temperature under nitrogen atmosphere. The solution was heated to 100 C for 2 hours. The solution was cooled down and water was added. The solution was extracted with EtOAc and the combined organic layer was dried with MgSO₄. The solution was filtered and the filtrate was concentrated. The residue was purified by CombiFlash with 20% EtOAc in Hexane as the eluent to afford the desirable product 3-[3-(6,8-Dichloro-3-methyl-indolizin-1-ylmethyl)-2-oxo-2,3-dihydro-benzimidazol-1-yl]-hexanoic acid ethyl ester (20 mg, 38%) as a yellow foam.

To a solution of 3-[3-(6,8-Dichloro-3-methyl-indolizin-1-ylmethyl)-2-oxo-2,3-dihydro-benzimidazol-1-yl]-hexanoic acid ethyl ester (20 mg, 0.041 mmol) in 1,4-dioxane (5 mL) and water (1 mL) was added LiOH (2 mg, 0.082 mmol) at room temperature. The solution was stirred at the same temperature for 4 hours. The solution was concentrated and water was added to the residue. The solution was acidified by 12N HCl in an ice-bath. The solid that preciptate out from the solution was collected by filtration. The solid was dried under vacuum and was confirmed to be the desirable product. LCMS (ESMS): m/z 460.17 (M+H⁺).

Example 65

3-{3-[(3,8-dimethylindolizin-1-yl)methyl]-2-oxo-2,3-dihydro-1H-benzimidazol-1-yl}hexanoic acid

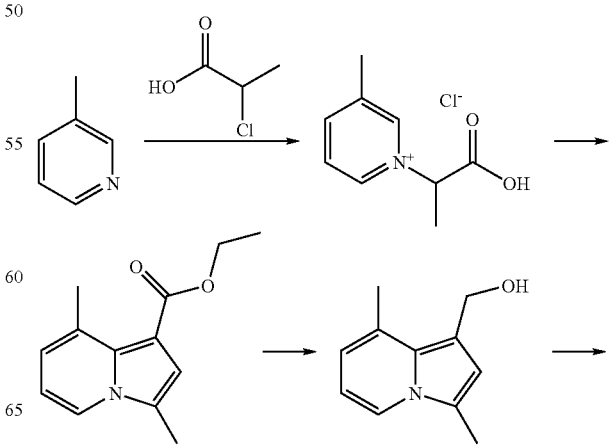

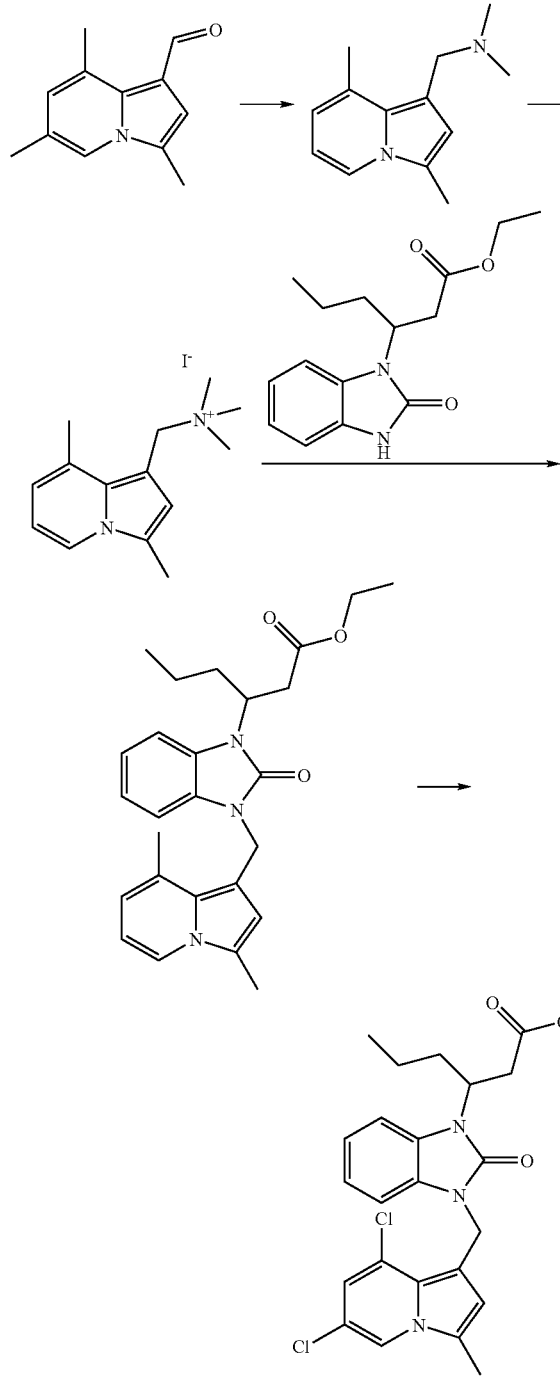

To a solution of 3-picoline (2 mL, 0.021 mol) in Et₂O (10 mL) was added 2-chloropropionic acid (2.1 mL, 0.025 mol) at room temperature. The solution was stirred at the same temperature for 12 hours. The solution was concentrated and the residue oil was used in the next of the synthesis without further purification.

To a solution of crude 1-(1-Carboxy-ethyl)-3-methyl-pyridinium; chloride (6 g, 0.03 mol) in toluene (100 mL) were added ethyl acroylate (9.7 mL, 0.089 mol), MnO₂ (7.8 g, 0.089 mol) and Et₃N (5 mL) at room temperature under nitrogen atmosphere. The solution was heated to 90 C and was stirred at the same temperature for 12 hours. The solution was cooled down and was filtered to remove the excess MnO₂. The filtrate was concentrated and the residue was purified by CombiFlash with 10% EtOAc in Hexane to afford the desirable product 3,8-Dimethyl-indolizine-1-carboxylic acid ethyl ester (735 mg, 11.4%).

To a solution of 3,8-Dimethyl-indolizine-1-carboxylic acid ethyl ester (700 mg, 3.2 mmol) in Et₂O (30 mL) was added LAH (244.5 mg, 6.4 mmol) at 0 C under nitrogen atmosphere. The solution was warmed to room temperature. Sat. NaHCO₃ was added and the solution was extracted with EtOAc. The combined organic layer was dried with MgSO₄ and was filtered. The filtrate was concentrated and the residue was subjected to 1H-NMR analysis to confirm the presence of the desirable product (3,8-Dimethyl-indolizin-1-yl)-methanol, CAS: (3,8-Dimethyl-indolizin-1-yl)-methanol (450 mg, 80%).

To a solution (3,8-Dimethyl-indolizin-1-yl)-methanol (600 mg, 3.4 mmol) in acetone (20 mL) was added MnO₂ (595 mg, 6.8 mmol) at room temperature. The mixture was stirred at the same temperature for 3 hours. The solution was filtered and the filtrate was concentrated. The residue was purified by CombiFlash with 5% EtOAc in Hexane as the eluent to afford the desirable product 3,8-Dimethyl-indolizine-1-carbaldehyde (400 mg, 67%) as a grey solid.

To a solution of 3,8-Dimethyl-indolizine-1-carbaldehyde (300 mg, 1.7 mmol) in CH₂Cl₂ (60 mL) and dimethylamine (2M methanol solution) (4.3 mL, 8.7 mmol) was added NaBH(OAc)₃ (1.8 g, 8.6 mmol) at 0° C. Upon complete addition the cooling bath was removed and the reaction mixture was stirred at room temperature for 12 h. When the reaction was complete, the mixture was diluted with CH₂Cl₂ and washed with saturated NaHCO₃. The layers were separated and the organic phase was dried over MgSO₄, filtered and concentrated. The residue was used in the next step of the synthesis without purification.

To a stirred solution of (3,8-Dimethyl-indolizin-1-ylmethyl)-dimethyl-amine (100 mg, 0.49 mmol) in acetonitrile (5 mL) was added iodomethane (0.1 mL, 1.5 mmol) at room temperature. The solution was stirred at the same temperature for 5 hours. The solution was concentrated and the resulting white solid was washed with small amount of acetonitrile (0.5 mL) and Et₂O was added. The white solid was collected by filtration and was washed with Et₂O. The reddish brown solid was used in the next step of the synthesis without further purification.

To a solution of 3-(2-Oxo-2,3-dihydro-benzimidazol-1-yl)-hexanoic acid ethyl ester (50 mg, 0.18 mmol) in DMF (10 mL) were added (3,8-Dimethyl-indolizin-1-ylmethyl)-trimethyl-ammonium; iodide, CAS: (3,8-Dimethyl-indolizin-1-ylmethyl)-trimethyl-ammonium; iodide (93.4 mg, 0.27 mmol) and K₂CO₃ (75 mg, 0.54 mmol) at room temperature under nitrogen atmosphere. The solution was heated to 100 C for 2 hours. The solution was cooled down and water was added. The solution was extracted with EtOAc and the combined organic layer was dried with MgSO₄. The solution was filtered and the filtrate was concentrated. The residue was purified by CombiFlash with 20% EtOAc in Hexane as the eluent to afford the desirable product 3-[3-(3,8-Dimethyl-indolizin-1-ylmethyl)-2-oxo-2,3-dihydro-benzimidazol-1-yl]-hexanoic acid ethyl ester (20 mg, 26%) as a colorless foam.

To a solution of 3-[3-(3,8-Dimethyl-indolizin-1-ylmethyl)-2-oxo-2,3-dihydro-benzimidazol-1-yl]-hexanoic acid ethyl ester (10 mg, 0.023 mmol) in 1,4-dioxane (5 mL) and water (1 mL) was added LiOH (1.1 mg, 0.046 mmol) at room temperature. The solution was stirred at the same temperature for 4 hours. The solution was concentrated and water was added to the residue. The solution was acidified by 12N HCl in an ice-bath. The solid that preciptate out from the solution was collected by filtration. The solid was dried under vacuum and was confirmed to be the desirable product. LCMS (ESMS): m/z 406.27 (M+H$^+$).

Example 66

3-{3-[(5-bromo-1-methyl-1H-indol-7-yl)methyl]-2-oxo-2,3-dihydro-1H-benzimidazol-1-yl}hexanoic acid

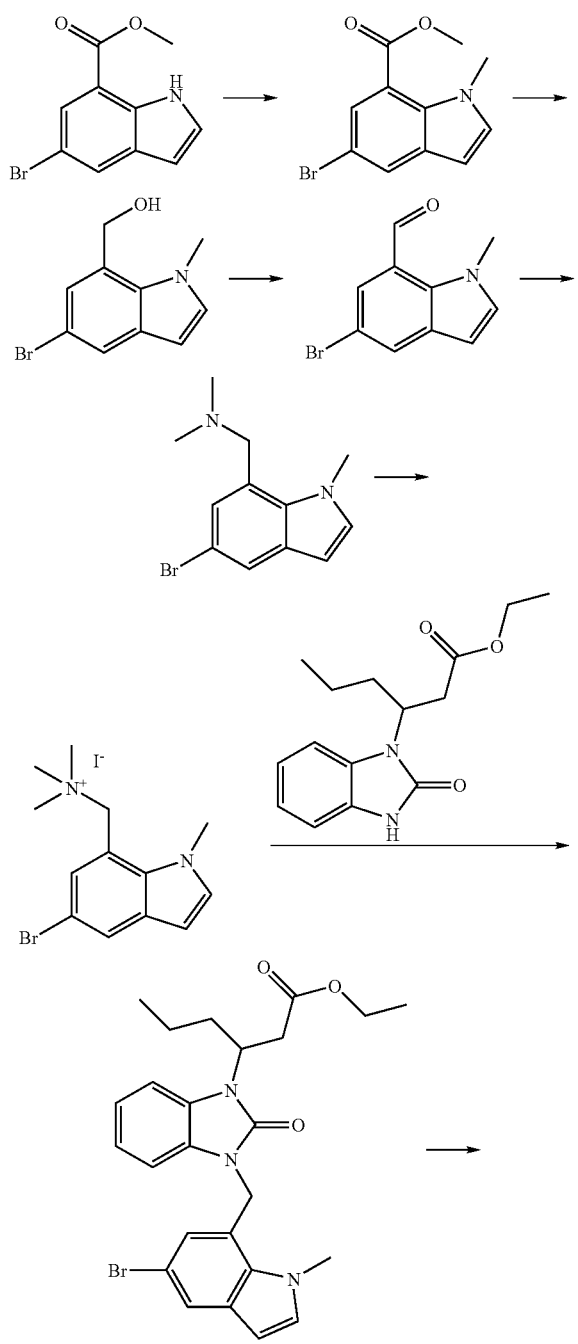

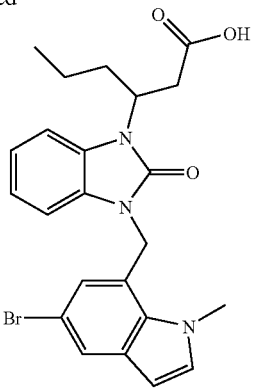

A solution of the 5-bromo-indole-7-carboxylic acid methyl ester (300 mg, 1.18 mmol) in DMF (15 mL) was cooled to 0° C. under nitrogen and treated with sodium hydride (60% in mineral oil) (56.6 gm, 1.4 mmol). After stirring for 15 minutes the iodomethane (0.08 mL, 1.3 mmol) was introduced and the cooling bath was removed (reaction became light purple). After 30 minutes the reaction was quenched with water (5 ml) and then concentrated to reduce the volume of DMF. The reaction was poured into water (1.6 L) and EtOAc (200 ml). The layers were separated and the aqueous phase was extracted with EtOAc (3×200 ml). The combined organics were washed with water (3×) and then dried (MgSO4). The solution was filtered and the filterate was concentrated. The residue was purfied by CombiFlash with 10% EtOAc in Hexane as the eluent to afford the desirable product 5-Bromo-1-methyl-1H-indole-7-carboxylic acid methyl ester (290 mg, 92%) as a white solid.

To a solution of 5-Bromo-1-methyl-1H-indole-7-carboxylic acid methyl ester (260 mg, 0.97 mmol) in Et$_2$O (50 mL) was added LAH (40.5 mg, 1.1 mmol) at 0 C under nitrogen atmosphere. The solution was warmed to room temperature. Sat. NaHCO$_3$ was added and the solution was extracted with EtOAc. The combined organic layer was dried with MgSO$_4$ and was filtered. The filtrate was concentrated and the residue was purified by CombiFlash with 50% EtOAc in Hexane as the eluent to afford the desirable product (5-Bromo-1-methyl-1H-indol-7-yl)-methanol (200 mg, 86%) as colorless oil.

To a solution of (5-Bromo-1-methyl-1H-indol-7-yl)-methanol (220 mg, 0.92 mmol) in acetone (20 mL) was added MnO$_2$ (239 mg, 2.7 mmol) at room temperature. The mixture was stirred at the same temperature for 3 hours. The solution was filtered and the filtrate was concentrated. The residue was purified by CombiFlash with 20% EtOAc in Hexane as the eluent to afford the desirable product 5-Bromo-1-methyl-1H-indole-7-carbaldehyde (177 mg, 81%) as a white solid.

To a solution of 5-Bromo-1-methyl-1H-indole-7-carbaldehyde (175 mg, 0.74 mmol) in CH$_2$Cl$_2$ (50 mL) and dimethylamine (2M methanol solution) (0.74 mL, 1.5 mmol) was added NaBH(OAc)$_3$ (467 mg, 2.2 mmol) at 0° C. Upon complete addition the cooling bath was removed and the reaction mixture was stirred at room temperature for 12 h. When the reaction was complete, the mixture was diluted with CH$_2$Cl$_2$ and washed with saturated NaHCO$_3$. The layers were separated and the organic phase was dried over MgSO$_4$, filtered and concentrated. The residue was used in the next step of the synthesis without purification.

To a stirred solution of crude (5-Bromo-1-methyl-1H-indol-7-ylmethyl)-dimethyl-amine (230 mg, 0.86 mmol) in acetonitrile (10 mL) was added iodomethane (0.06 mL, 1.0 mmol) at room temperature. The solution was stirred at the same temperature for 5 hours. The solution was concentrated and the resulting white solid was washed with small amount of acetonitrile (0.5 mL) and Et$_2$O was added. The white solid was collected by filtration and was washed with Et$_2$O. The white solid was used in the next step of the synthesis without further purification.

To a solution of 3-(2-Oxo-2,3-dihydro-benzimidazol-1-yl)-hexanoic acid ethyl ester (50 mg, 0.18 mmol) in DMF (10 mL) were added (5-Bromo-1-methyl-1H-indol-7-ylmethyl)-trimethyl-ammonium; iodide (111 mg, 0.27 mmol) and K$_2$CO$_3$ (75 mg, 0.54 mmol) at room temperature under nitrogen atmosphere. The solution was heated to 100 C for 2 hours. The solution was cooled down and water was added. The solution was extracted with EtOAc and the combined organic layer was dried with MgSO$_4$. The solution was filtered and the filtrate was concentrated. The residue was purified by CombiFlash with 20% EtOAc in Hexane as the eluent to afford the desirable product 3-[3-(5-Bromo-1-methyl-1H-indol-7-ylmethyl)-2-oxo-2,3-dihydro-benzimidazol-1-yl]-hexanoic acid ethyl ester (50 mg, 55%) as a colorless foam.

To a solution of 3-[3-(5-Bromo-1-methyl-1H-indol-7-ylmethyl)-2-oxo-2,3-dihydro-benzimidazol-1-yl]-hexanoic acid ethyl ester (10 mg, 0.02 mmol) in 1,4-dioxane (5 mL) and water (1 mL) was added LiOH (1 mg, 0.04 mmol) at room temperature. The solution was stirred at the same temperature for 4 hours. The solution was concentrated and water was added to the residue. The solution was acidified by 12N HCl in an ice-bath. The solid that precipitate out from the solution was collected by filtration. The solid was dried under vacuum and was confirmed to be the desirable product. LCMS (ESMS): m/z 471.17 (M+H$^+$).

Example 67

3-{3-[(5-bromo-1-methyl-2-oxo-2,3-dihydro-1H-indol-7-yl)methyl]-2-oxo-2,3-dihydro-1H-benzimidazol-1-yl}hexanoic acid

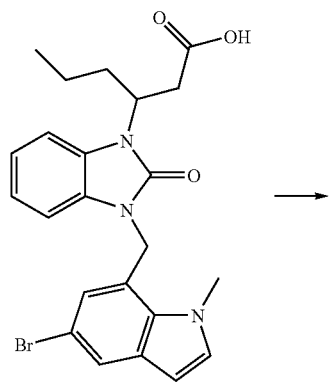

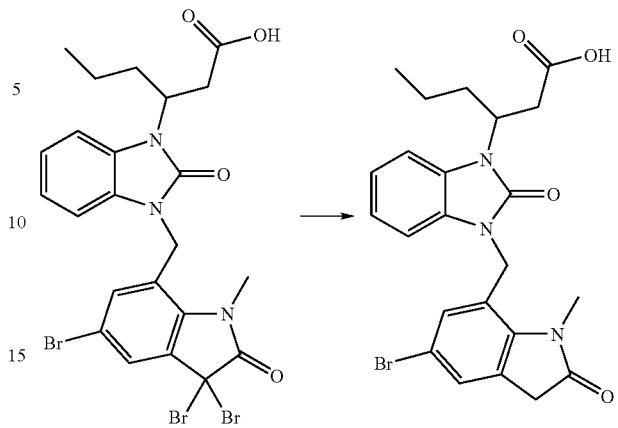

To a solution of 3-[3-(5-Bromo-1-methyl-1H-indol-7-ylmethyl)-2-oxo-2,3-dihydro-benzimidazol-1-yl]-hexanoic acid (20 mg, 0.04 mmol) in tBuOH (5 mL) was added NBS (15 mg, 0.085 mmol) at 40 C The solution was stirred at the same temperature for 1 hour. The solution was concentrated and the residue was purified by CombiFlash with 5% MeOH in CH$_2$Cl$_2$ as the eluent to afford the desirable product 3-[2-Oxo-3-(3,3,5-tribromo-1-methyl-2-oxo-2,3-dihydro-1H-indol-7-ylmethyl)-2,3-dihydro-benzimidazol-1-yl]hexanoic acid (20 mg, 73%) as colorless oil.

To a solution of 3-[2-Oxo-3-(3,3,5-tribromo-1-methyl-2-oxo-2,3-dihydro-1H-indol-7-ylmethyl)-2,3-dihydro-benzimidazol-1-yl]-hexanoic acid (20 mg, 0.031 mmol) in acetic acid (5 mL) was added Zinc powder (10 mg, 0.16 mmol) at room temperature. The mixture was stirred at the same temperature for 30 minutes. The mixture was filtered and the filtrate was concentrated. The residue was cool in an ice bath and water was added. The solid that precipitate out from the solution was collected by filtration and was washed with water. The white solid was dried in an oven and was confirmed to be the desirable product (8.9 mg, 59%). LCMS (ESMS): m/z 488.12 (M+H$^+$).

Example 68

3-{3-[(4,6-dimethyl-1,2-benzisothiazol-3-yl)methyl]-2-oxo-2,3-dihydro-1H-benzimidazol-1-yl}hexanoic acid

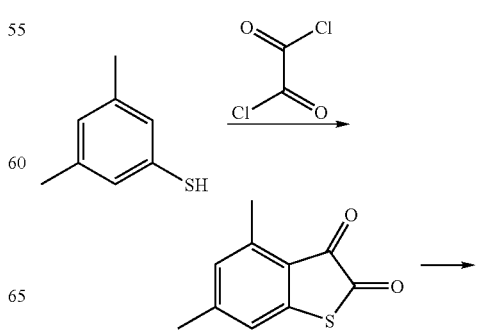

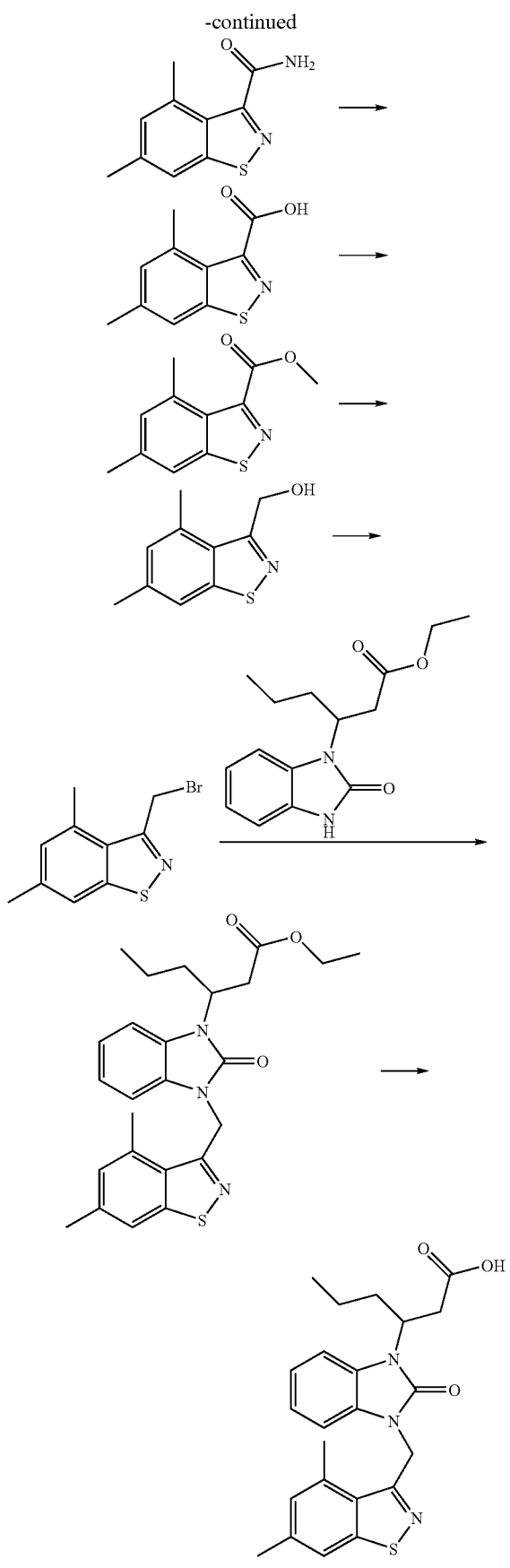

To a solution of AlCl$_3$ (0.4 g, 3.6 mmol) in CH$_2$Cl$_2$ (4 mL) at −20 C under nitrogen were added 3,5-dimethylbenzenethiol (1 g, 7.2 mmol) and oxalyl chloride (0.6 mL, 7.2 mmol) respectively. The solution was warmed to room temperature for 1 hour and was heated to 120 C in a microwave reactor for 15 minutes. The solution was cooled down and was pouled into crashed ice. The solution was extracted with CH$_2$Cl$_2$ and the organic layer was collected. The solution was dried with MgSO$_4$ and was filtered. The filtrate was concentrated and the residue was purified by Combi-Flash with 5% EtOAc in Hexane as the eluent to afford the desirable product 4,6-Dimethyl-benzo[b]thiophene-2,3-dione (500 mg, 35%).

To a solution of 4,6-Dimethyl-benzo[b]thiophene-2,3-dione (100 mg, 0.5 mmol) in NH$_3$ in MeOH (5 mL) was dropwisely added 30% H$_2$O$_2$ (0.17 mL, 1.6 mmol) at room temperature. The solution was stirred at the same temperature for 2 hours. The solution was concentrated and the residue was purified by CombiFlash with 20% EtOAc in Hexane as the eluent to afford the desirable product 4,6-Dimethyl-1,2-benzisothiazole-3-carboxylic acid amide (35 mg, 33%) as a pale red solid.

To a solution of 4,6-Dimethyl-1,2-benzisothiazole-3-carboxylic acid amide (20 mg, 0.097 mmol) in EtOH (10 mL) and H$_2$O (2 mL) was added KOH (11 mg, 0.19 mmol). The solution was heated to 85 C for 48 hours. The solution was cooled down and was placed in an ice bath. Conc HCl was added to adjust the pH of the solution to 2. The solid the precipitated out from the solution was collected by means of filtration. The white solid was dried and was confirmed to be the desirable product 4,6-Dimethyl-1,2-benzisothiazole-3-carboxylic acid (15 mg, 75%).

To a solution of 4,6-Dimethyl-1,2-benzisothiazole-3-carboxylic acid (10 mg, 0.048 mmol) in MeOH (5 mL) was added conc. H$_2$SO$_4$ (0.1 mL) at room temperature. The solution was heated up to 60 C for 24 hours. The solution was cooled down and was neutralized with sat. NaHCO$_3$. The solution was extracted with EtOAc. The combined organic layer was dried with MgSO$_4$ and was filtered. The filtrate was concentrated and the residue was purified by CombiFlash with 20% EtOAc in Hexane as the eluent to afford the desirable product 4,6-Dimethyl-benzo[d]isothiazole-3-carboxylic acid methyl ester, CAS: 4,6-Dimethyl-1,2-benzisothiazole-3-carboxylic acid methyl ester (10 mg, 94%) as colorless oil.

To a solution of 4,6-Dimethyl-1,2-benzisothiazole-3-carboxylic acid methyl ester (100 mg, 0.45 mmol) in THF (10 mL) was added LAH (34 mg, 0.9 mmol) at 0 C under nitrogen atmosphere. The solution was stirred at the same temperature for 1 hour. Sat. NaHCO$_3$ was added and the solution was extracted with EtOAc. The combined organic layer was dried with MgSO$_4$ and was filtered. The filtrate was concentrated and the residue was used in the next step of the synthesis without further purification.

To a solution of (4,6-Dimethyl-1,2-benzisothiazol-3-yl)-methanol (100 mg, 0.5 mmol) in CH$_2$Cl$_2$ (15 mL) were added PPh$_3$ (200 mg, 0.78 mmol) and CBr$_4$ (340 mg, 1 mmol) at room temperature. The solution was stirred at the same temperature for 1 hour. The solution was concentrated and the residue was purified by CombiFlash with 10% EtOAc in Hexane as the eluent to afford the desirable product 3-Bromomethyl-4,6-dimethyl-1,2-benzisothiazole (90 mg, 68%) as a white solid.

To a solution of 3-(2-Oxo-2,3-dihydro-benzimidazol-1-yl)-hexanoic acid ethyl ester (50 mg, 0.18 mmol) in DMF (10 mL) were added 3-Bromomethyl-4,6-dimethyl-benzo[d]isothiazole, CAS: 3-Bromomethyl-4,6-dimethyl-1,2-benzisothiazole (69.5 mg, 0.27 mmol) and K$_2$CO$_3$ (50 mg, 0.36 mmol) at room temperature under nitrogen atmosphere. The solution was heated to 100 C for 2 hours. The solution was cooled down and water was added. The solution was extracted with EtOAc and the combined organic layer was dried with MgSO₄. The solution was filtered and the filtrate was concentrated. The residue was purified by CombiFlash with 20% EtOAc in Hexane as the eluent to afford the desirable product 3-[3-(4,6-Dimethyl-1,2-benzisothiazol-3-ylmethyl)-2-oxo-2,3-dihydro-benzimidazol-1-yl]-hexanoic acid ethyl ester (45 mg, 55%) as colorless foam.

To a solution of product 3-[3-(4,6-Dimethyl-1,2-benzisothiazol-3-ylmethyl)-2-oxo-2,3-dihydro-benzimidazol-1-yl]-hexanoic acid ethyl ester (23 mg, 0.051 mmol)) in 1,4-dioxane (5 mL) and water (1 mL) was added LiOH (2.4 mg, 0.1 mmol) at room temperature. The solution was stirred at the same temperature for 4 hours. The solution was concentrated and water was added to the residue. The solution was acidified by 12N HCl in an ice-bath. The solid that preciptate out from the solution was collected by filtration. The solid was dried under vacuum and was confirmed to be the desirable product (10 mg, 46%). LCMS (ESMS): m/z 424.18 (M+H⁺).

The following compound was prepared following a similar procedure using appropriate starting material.

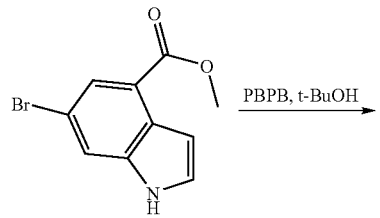

Example 69

3-{3-[(6-bromo-2-oxo-2,3-dihydro-1H-indol-4-yl)methyl]-2-oxo-2,3-dihydro-1H-benzimidazol-1-yl}hexanoic acid

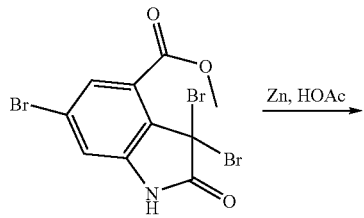

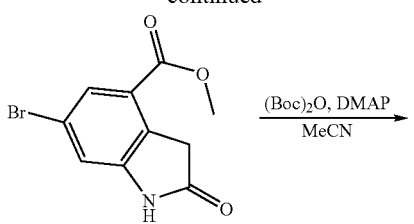

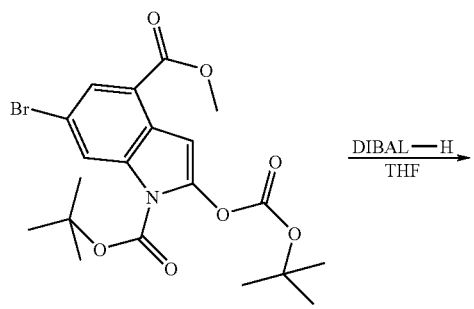

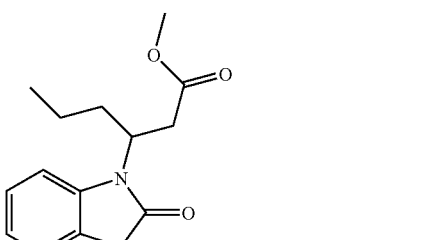

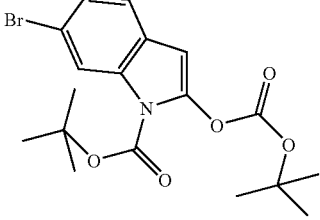

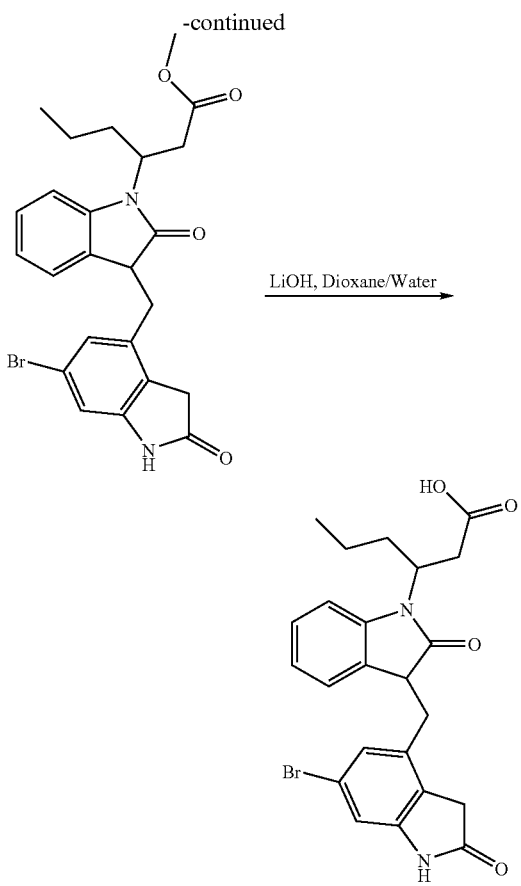

3,3,6-Tribromo-2-oxo-2,3-dihydro-1H-indole-4-carboxylic acid methyl ester

6-Bromo-1H-indole-4-carboxylic acid methyl ester 1.0 g (3.93 mmol, DE3525564) is dissolved in tert-butanol at 40° C. and then pyridinium bromide perbromide (4.0 g, 12.5 mmol) is added portion wise over 30 minutes. The reaction is stirred for two hours then the volatiles evaporated in vacuo and the residue taken up in 50 mL of ethyl acetate and 50 mL of water. The water layer is extracted with ethyl acetate (2×25 mL) and then the combined organic layers washed with brine, dried (MgSO$_4$) filtered and evaporated in vacuo to give the title compound (1.90 g, 3.77 mmol 95%). LCMS (ESMS): m/z 428.7 (M+H$^+$).

6-Bromo-2-oxo-2,3-dihydro-1H-indole-4-carboxylic acid methyl ester 3,3,6-Tribromo-2-oxo-2,3-dihydro-1H-indole-4-carboxylic acid methyl ester (5.90 g, 16.9 mmol) is suspended in glacial acetic acid (153 mL) and zinc dust (10 μM Mesh, 11.5 g, 169 mmol) is added over 5 minutes. The reaction is monitored by TLC and when complete (30 min) the reaction is filtered through celite and the filtrate washed with ethyl acetate. The combined filtrate and washings are evaporated in vacuo to yield an oil that is taken up in ethyl acetate (500 mL), washed with water (100 mL) and brine (100 mL). The organic layer is dried filtered and evaporated in vacuo to give the title compound that is recrystalized from ethyl acetate (2.2 g, 11.5 mmol 68%). LCMS (ESMS): m/z 271.3 (M+H$^+$).

6-Bromo-2-tert-butoxycarbonyloxy-indole-1,4-dicarboxylic acid 1-tert-butyl ester 4-methyl ester 6-Bromo-2-oxo-2,3-dihydro-1H-indole-4-carboxylic acid methyl ester 1 g 3.7 mmol and di tert butyldicarbonate (1.77 g, 8.14 mmol) is dissolved tetrahydrofuran (75 mL) and stirred at room temperature. DMAP (5 mg, 0.37 mmol) is added and the resulting solution stirred for 4 hours. The reaction is the evaporated in vacuo under low heat and the resulting solid purified on silica with hexanes ethyl acetate as the eluent to give the title compound (850 mg 1.8 mmol 49%). LCMS (ESMS): m/z 471.5(M+H$^+$).

6-Bromo-2-tert-butoxycarbonyloxy-4-hydroxymethyl-indole-1-carboxylic acid tert-butyl ester 6-Bromo-2-tert-butoxycarbonyloxy-indole-1,4-dicarboxylic acid 1-ten-butyl ester 4-methyl ester (280 mg, 0.59 mmol) is dissolved in tetrahydrofuran 3 mL and then purged with nitrogen and cooled to −78° C. (dry ice IPA). DIBAL-H (1M in hexanes 3.8 mL 3.8 mmol) is added to this stirring solution at −78 over the course of 5 minutes. Upon completion (3 hours) the reaction is quenched by the slow addition of saturated Rochelle's salt (50 mL) and the resulting slurry warmed to room temperature and stirred overnight. The product is extracted with dichloromethane (3×50 mL), dried (MgSO$_4$) filtered and evaporated in vacuo. Product purified on silica gel with dichloromethane methanol as the eluent (125 mg, 0.28 mmol 48%). LCMS (ESMS): m/z 443.7 (M+H$^+$).

6-Bromo-2-tert-butoxycarbonyloxy-4-[3-(1-methoxycarbonylmethyl-butyl)-2-oxo-2,3-dihydro-benzoimidazol-1-ylmethyl]-indole-1-carboxylic acid tert-butyl ester 6-Bromo-2-tert-butoxycarbonyloxy-4-hydroxymethyl-indole-1-carboxylic acid tert-butyl ester (220 mg, 0.50 mmol) is and 3-(2-Oxo-2,3-dihydro-benzoimidazol-1-yl)-hexanoic acid ethyl ester (151 mg, 0.55 mmol) is taken up in 5 mL of tetrahydrofuran and then triphenyl phosphine is added (157 mg, 0.6 mmol). The reaction is stirred at 0° C. and diisopropyl azodicarboxylate (116 □L, 0.6 mmol) is added drop wise to the reaction. The reaction is stirred at room temperature for 4 hours and then the solvent evaporated in vacuo. Product is purified by preparative TLC 3% methanol in dichloromethane to give the title compound (200 mg 0.28 mmol 57%). LCMS (ESMS): m/z 687.7 (M+H$^+$).

3-[3-(6-Bromo-2-oxo-2,3-dihydro-1H-indol-4-ylmethyl)-2-oxo-2,3-dihydro-benzoimidazol-1-yl]-hexanoic acid methyl ester 6-Bromo-2-tert-butoxycarbonyloxy-4-[3-(1-methoxycarbonylmethyl-butyl)-2-oxo-2,3-dihydro-benzoimidazol-1-ylmethyl]-indole-1-carboxylic acid tert-butyl ester (200 mg, 0.28 mmol) is dissolved in dichloromethane (5 mL) and then trifluoroacetic acid is added (2 mL). The reaction is stirred for 1 hour then evaporated in vacuo to give an oil that is purified by preparative reverse phase LC to give the title compound (63 mg 0.13 mmol 44%). LCMS (ESMS): m/z 487.6 (M+H$^+$).

3-[3-(6-Bromo-2-oxo-2,3-dihydro-1H-indol-4-ylmethyl)-2-oxo-2,3-dihydro-benzoimidazol-1-yl]-hexanoic acid 3-[3-(6-Bromo-2-oxo-2,3-dihydro-1H-indol-4-ylmethyl)-2-oxo-2,3-dihydro-benzoimidazol-1-yl]-hexanoic acid methyl ester 80 mg (0.16 mmol) is dissolved in 2.5 mL of dioxane and then lithium hydroxide (10 mg, 0.43 mmol in 1.5 mL of water) is added drop wise to the reaction mixture. The reaction is stirred at room temperature and monitored by LC/MS. Upon completion the reaction is acidified by the addition of 1N HCl, and diluted with 10 mL of water. A solid precipitated that is collected and dried to give the title compound (73 mg. 0.15 mmol 96%). LCMS (ESMS): m/z 473.1 (M+H$^+$).

Example 70

3-{3-[(5-chloro-2-oxo-2,3-dihydro-1,3-benzoxazol-7-yl)methyl]-2-oxo-2,3-dihydro-1H-benzimidazol-1-yl}hexanoic acid

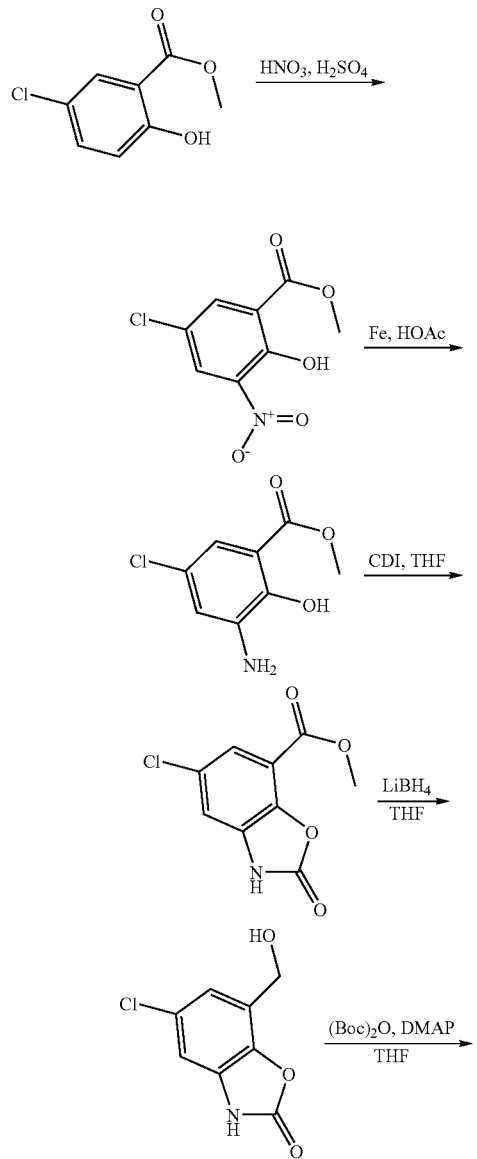

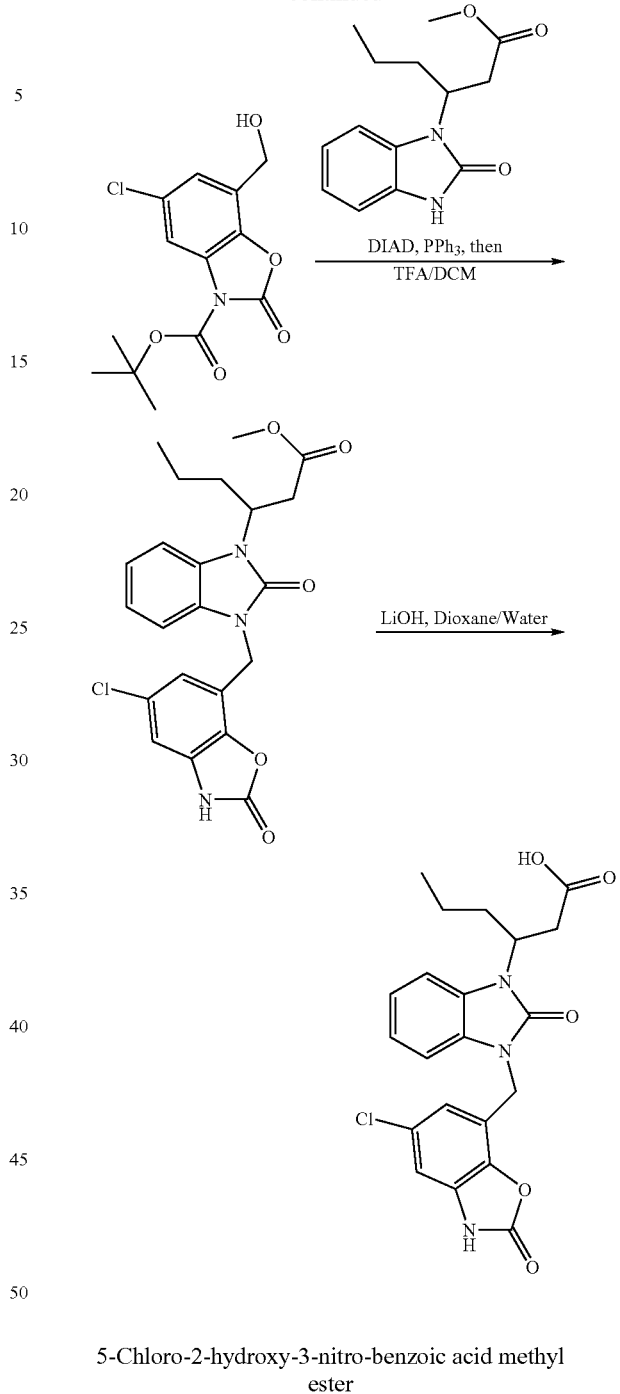

5-Chloro-2-hydroxy-3-nitro-benzoic acid methyl ester

Methyl-5-Chloro-2-hydroxylbenzoate (30 g, 160 mmol) is suspended in sulfuric acid (140 mL) and cooled to 0° C. in an ice bath. Nitric acid (13 mL) in sulfuric acid (30 mL) is added drop wise to the suspension over 30 minutes while maintaining the reaction temperature at 0° C. The reaction is warmed to room temperature and stirred for 4 hours. An additional 6 mL of nitric acid is added drop wise to the reaction over 30 minutes and the reaction is heated to 45° C. for 16 hours. The reaction is poured onto crushed ice, and the resulting yellow precipitate collected and washed with copious amount of water and dried in vacuo to give the title compound (33 g 142 mmol, 89%). LCMS (ESMS): m/z 232.7 (M+H$^+$).

3-Amino-5-chloro-2-hydroxy-benzoic acid methyl ester

5-Chloro-2-hydroxy-3-nitro-benzoic acid methyl ester 1 g (4.31 mmol) is dissolved in methanol (30 mL) and acetic acid (30 mL) and then iron powder is added (4.8 g, 86 mmol) at room temperature. The resulting suspension is stirred and heated to reflux for 1 hour. The reaction is allowed to cool to room temperature and then gravity filtered though a pad of celite. The celite cake is washed 3× with ethyl acetate (50 mL) and then the combined washings evaporated in vacuo. The oil is then taken up in ethyl acetate (250 mL) and washed with water (100 mL) and saturated sodium bicarbonate (100 mL). The organic layer is dried ($MgSO_4$), decolorized with charcoal, filtered and evaporated to give the title compound that is used without further purification (730 mg, 3.6 mmol, 84%). LCMS (ESMS): m/z 202.5 ($M+H^+$).

5-Chloro-2-oxo-2,3-dihydro-benzooxazole-7-carboxylic acid methyl ester

3-Amino-5-chloro-2-hydroxy-benzoic acid methyl ester 8 g (39.6 mmol) is dissolved in tetrahydrofuran 100 mL and carbonyl diimidazole (12.9 g, 79.3 mmol) is added. The reaction is heated to reflux for 2 hours and then cooled to room temperature. The reaction is evaporated in vacuo and then taken up in dichloromethane (200 mL) and then washed with HCl (2N, 50 mL 2×) and water (2×50 mL). The organic layer is dried ($Na_2SO_4$) filtered and evaporated in vacuo to give the title compound (8.2 g, 36 mmol, 91%). LCMS (ESMS): m/z 228.9 ($M+H^+$).

5-Chloro-7-hydroxymethyl-3H-benzooxazol-2-one

5-Chloro-2-oxo-2,3-dihydro-benzooxazole-7-carboxylic acid methyl ester (8 g, 35 mmol) is suspended in diethyl ether (100 mL) and tetrahydrofuran (410 mL) and cooled to zero. The reaction is purged with nitrogen and $LiBH_4$ (6.72 g, 310 mmol) is added portion wise to the reaction. The reaction is warmed to room temperature and stirred for 3 hours. Upon completion the reaction is cooled to 0° C. and quenched by the slow addition of saturated ammonium chloride (250 mL). Water is added to the reaction (500 mL) and the organic layer separated. The water layer is extracted with ethyl acetate (3×100 mL) and the combined organic layers are dried ($Na_2SO_4$) filtered and evaporated in vacuo. Product is purified on silica with dichloromethane methanol as the eluent to yield (4.2 g 31 mmol 60%) the title compound (4.2 g 31 mmol 60%). LCMS (ESMS): m/z 200.5 ($M+H^+$).

5-Chloro-7-hydroxymethyl-2-oxo-benzooxazole-3-carboxylic acid tert-butyl ester 5-Chloro-7-hydroxymethyl-3H-benzooxazol-2-one 1.3 g (6.5 mmol) is dissolved in tetrahydrofuran (30 mL) and cooled to zero. Di tert-butyl dicarbonate (1.2 g 5.41 mmol) is added portion wise over 5 minutes and then DMAP is added in one portion (6 mg, 0.05 mmol). The reaction is stirred at 0° C. and progress monitored by LC/MS. After 3 hours the reaction solvent is evaporated in vacuo and the resulting oil purified on silica gel with dichloromethane methanol as the eluent (1.9 g 6.34 mmol 97%). LCMS (ESMS): m/z 300.7 ($M+H^+$).

3-[3-(5-Chloro-2-oxo-2,3-dihydro-benzooxazol-7-ylmethyl)-2-oxo-2,3-dihydro-benzoimidazol-1-yl]-hexanoic acid methyl ester 5-Chloro-7-hydroxymethyl-2-oxo-benzooxazole-3-carboxylic acid tert-butyl ester 600 mg (2 mmol) is dissolved in tetrahydrofuran 1.5 mL and then 3-(2-Oxo-2,3-dihydro-benzoimidazol-1-yl)-hexanoic acid ethyl ester is added (608 mg (2.2 mmol). The reaction is cooled to 0° C. and then triphenylphosphine (630 mg, 2.4 mmol) is added followed by the drop wise addition of diisopropyl azodicarboxylate (465 μL, 2.40 mmol). The reaction is stirred for 15 minutes at 0° C. and then the solvents evaporated in vacuo. The compound is purified on silica with dichloromethane methanol as the eluent. This crude material is then taken up in dichloromethane (1.5 mL) and trifluoroacetic acid (500 uL) is added drop wise to the reaction. The reaction is stirred at room temperature and monitored by LC/MS. Upon completion the reaction is evaporated in vacuo and purified by preparative reverse phase LC to give the title compound 33 mg (0.07 mmol, 3.6%). LCMS (ESMS): m/z 444.9 ($M+H^+$).

3-[3-(5-Chloro-2-oxo-2,3-dihydro-benzooxazol-7-ylmethyl)-2-oxo-2,3-dihydro-benzoimidazol-1-yl]-hexanoic acid 3-[3-(5-Chloro-2-oxo-2,3-dihydro-benzooxazol-7-ylmethyl)-2-oxo-2,3-dihydro-benzoimidazol-1-yl]-hexanoic acid methyl ester (40 mg 0.08 mmol) is dissolved in 750 μL of 1,4 dioxane and then lithium hydroxide (5 mg in 750 μL of water) is added to the reaction. The reaction is stirred at room temperature for 1 hour and then acidified with 1N HCl. The product is extracted with ethyl acetate 3×1 mL) and the combined organic layers are dried, filtered and evaporated in vacuo. The crude material is purified by preparative reverse phase LC to give the title compound 20 mg (0.04 mmol, 54%). LCMS (ESMS): m/z 430.8 ($M+H^+$).

Example 71

3-{3-[4-amino-3-(trifluoromethoxy)benzyl]-2-oxo-2,3-dihydro-1H-benzimidazol-1-yl}hexanoic acid

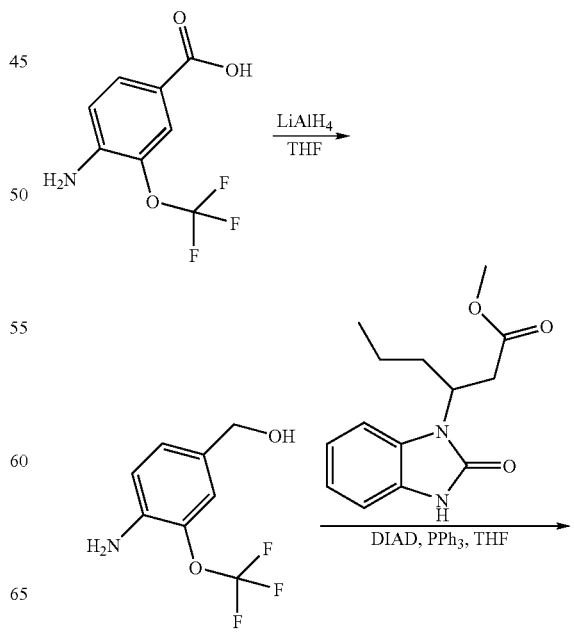

383

-continued

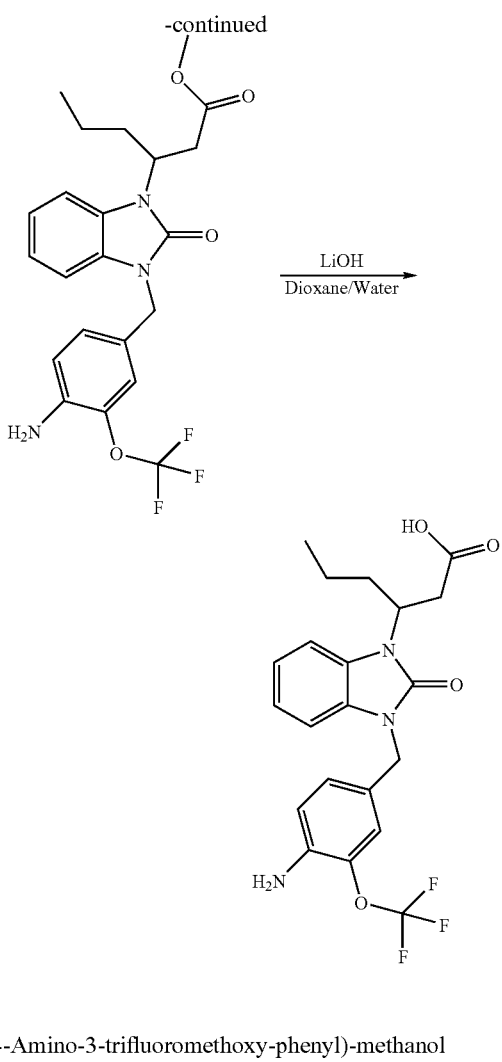

(4-Amino-3-trifluoromethoxy-phenyl)-methanol

4-Amino-3-(trifluoromethoxy)benzoic acid 2.0 g (9.04 mmol) is dissolved in 50 mL of THF. Lithium aluminium hydride (1.4 g, 36.2 mmol) is added portionwise over 10 minutes. A reflux condensor is attached and the reaction mixture is refluxed for 6 h at 80° C. It is cooled to room temperature and the Fieser work up is performed (1.4 mL of water, 1.4 mL 15% NaOH, 4.2 mL of water). The granular inorganic precipitate is filtered and washed with THF. The organic fractions is combined and dried over anhydrous $Na_2SO_4$. The solvent is evaporated and the residue is purified on silica, eluting with 0-10% methanol/dichloromethane to give the title compound (1.2 g, 5.79 mmol 64%). (ESMS): ink 208.3 (M+H$^+$).

3-[3-(4-Amino-3-trifluoromethoxy-benzyl)-2-oxo-2, 3-dihydro-benzimidazol-1-yl]-hexanoic acid ethyl ester (4-Amino-3-trifluoromethoxy-phenyl)-methanol (100 mg, 0.48 mmol) and 3-(2-Oxo-2,3-dihydro-benzoimidazol-1-yl)-hexanoic acid ethyl ester (133 mg, 0.48 mmol) is taken up in 4 mL of tetrahydrofuran and then triphenyl phosphine is added (190 mg, 0.72 mmol). The reaction is stirred at room temperature and DIAD (141 µL, 0.72 mmol) is, added dropwise to the reaction. The reaction is stirred at room temperature for 1 hour and then the solvent evaporated in vacuo.

384

Product is purified by preprative HPLC 30%-90% acetonitrile/water to give the title compound (20 mg, 0.04 mmol 9%). LCMS (ESMS): m/z 466.1 (M+H$^+$).

3-[3-(4-Amino-3-trifluoromethoxy-benzyl)-2-oxo-2, 3-dihydro-benzimidazol-1-yl]hexanoic acid 3-[3-(4-Amino-3-tri fluoromethoxy-benzyl)-2-oxo-2,3-dihydro-benzimidazol-1-yl]-hexanoic acid ethyl ester_20 mg (0.04 mmol) is dissolved in 1.5 mL of dioxane/water (1:1) and then lithium hydroxide (4.1 mg, 0.17 mmol) is added. The reaction is stirred at room temperature and monitord by LC/MS. Upon completion the reaction is acidified by the addition of 1N HCl. The solvent is evaporated and the residue partitioned between ethyl acetate (2 mL) and water (2 mL). The organic layer is dried over anhydrous sodium sulfate. The solvent is evaporated and the resulting solid is purified by Combi flash chromatography, eluting with 0-20% methanol/dichloromethane to give the title compound (18 mg, 0.04 mmol 95%). LCMS (ESMS): m/z 438.4 (M+H$^+$).

Example 72

3-{3-[(6-chloro-1H-indol-4-yl)methyl]-2-oxo-2,3-dihydro-1H-benzimidazol-1-yl}propanoic acid

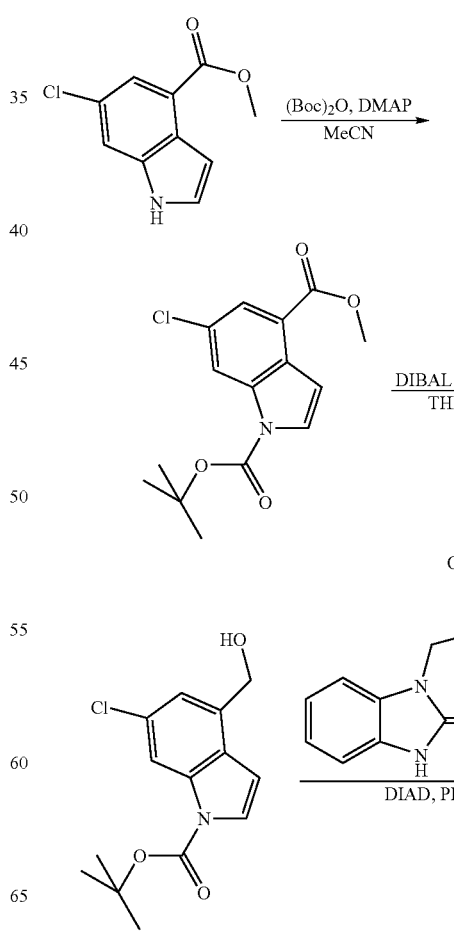

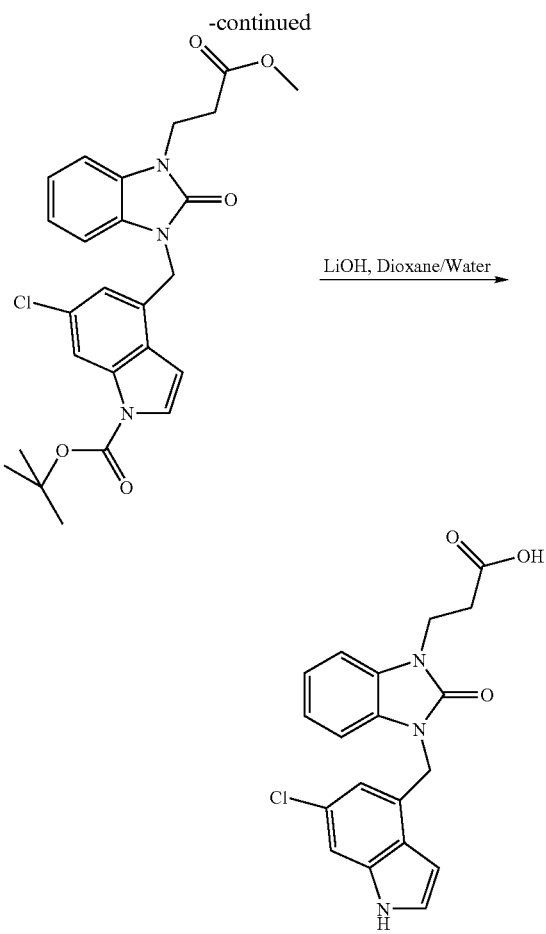

6-Chloro-indole-1,4-dicarboxylic acid 1-tert-butyl ester 4-methyl ester

6-Chloro-1H-indole-4-carboxylic acid methyl ester, 9 g (43 mmol, DE3525564) is dissolved in acetonitrile 140 mL and then di tert butyldicarbonate is added (11.24 g, 51.5 mmol). The reaction is stirred at room temperature and 180 mg (1.6 mmol) of DMAP is added. The reaction is stirred overnight for 16 hours then the solvent evaporated in vacuo. The resulting oil is taken up in ethyl acetate (500 mL) and washed with water (100 mL) citric acid (10%, 100 mL) and brine (100 mL). The organic layer is dried (Na$_2$SO$_4$) filtered and evaporated in vacuo to give the title compound (13.2 g, 43 mmol, 99%). LCMS (ESMS): m/z 310.7 (M+H$^+$).

6-Chloro-4-hydroxymethyl-indole-1-carboxylic acid tert-butyl ester

6-Chloro-indole-1,4-dicarboxylic acid 1-tert-butyl ester 4-methyl ester 13.2 g (42 mmol) is dissolved in 200 mL of dry tetrahydrofuran and cooled to −78° C. The reaction is equipped with a dropping funnel and the reaction purged with nitrogen. DIBAL-H (85 mL, 1.5 M/L 128 mmol) is added via a syringe to the dropping funnel and the reagent added over the course of 10 minutes. The reaction is stirred for 30 minutes then tested via LC/MS for completion. An additional two equivalents of DIBAL-H is added to the reaction via syringe and the reaction stirred for an additional hour. After 1 hour, the reaction is quenched by the slow addition of 500 mL of saturated Rochelle's salt, and slowly warmed to room temperature with stirring overnight. The resulting biphasic mixture is separated and the water layer extracted with DCM. The combined organic layers were dried (MgSO$_4$) filtered and evaporated in vacuo to give the title compound that is purified on silica gel with hexanes ethyl acetate as the eluent (9.5 g 34 mmol, 80%). LCMS (ESMS): m/z 282.9 (M+H$^+$).

6-Chloro-4-[3-(2-methoxycarbonyl-ethyl)-2-oxo-2,3-dihydro-benzoimidazol-1-ylmethyl]-indole-1-carboxylic acid tert-butyl ester 6-Chloro-4-hydroxymethyl-indole-1-carboxylic acid tert-butyl ester 350 mg, 1.24 mmol and 3-(2-Oxo-2,3-dihydro-benzimidazol-1-yl)-propionic acid methyl ester (300 mg 1.36 mmol, from Example 2) are dissolved in tetrahydrofuran 6.0 mL and triphenylphospine (630 mg 1.37 mmol) is added in one portion to the reaction. The reaction is cooled to 0° C. and then diisopropyl azodicarboxylate (265 μL 1.37 mmol) is added drop wise to the reaction over 5 minutes, and warmed to room temperature. The reaction is stirred for 15 minutes and then evaporated in vacuo, and purified on silica gel with hexanes ethyl acetate as the eluent to give the title compound (280 mg, 0.58 mmol, 47%). LCMS (ESMS): m/z 484.9 (M+H$^+$).

3-[3-(6-Chloro-1H-indol-4-ylmethyl)-2-oxo-2,3-dihydro-benzoimidazol-1-yl]-propionic acid 6-Chloro-4-[3-(2-methoxycarbonyl-ethyl)-2-oxo-2,3-dihydro-benzoimidazol-1-ylmethyl]-indole-1-carboxylic acid tert-butyl ester 270 mg (0.56 mmol) is taken up in dioxane 4 mL and then the lithium hydroxide 53 mg 2.23 mmol in water is added to the solution. The reaction is stirred for 2 hours and then made acidic by the addition of 1N HCl. The compound is then extracted into ethyl acetate and then the ethyl acetate is dried (MgSO$_4$) filtered and evaporated in vacuo. The oil is taken up in dichloromethane and TFA is added. The reaction is stirred for 1 hour and then evaporated in vacuo to give a solid that is taken up in ethyl acetate and precipitated with hexanes. The solid is collected and washed with hexanes to give the title compound (156 mg, 0.42 mmol, 76%). LCMS (ESMS): m/z 370.8 (M+H$^+$).

The following compound was prepared following a similar procedure using appropriate starting material.

3-{3-[(6-bromo-1H-indol-4-yl)methyl]-2-oxo-2,3-dihydro-1H-benzimidazol-1-yl}propanoic acid. LCMS (ESMS): m/z 414.4 (M+H$^+$)

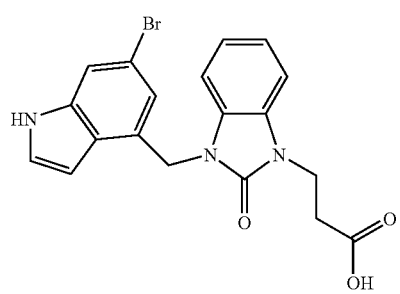 [SMILES: O=C(O)CCn1c(=O)n(Cc2cc(Br)cc3[nH]ccc23)c2ccccc21]

Example 73

3-{3-[(6-chloro-2-oxo-2,3-dihydro-1H-indol-4-yl)methyl]-2-oxo-2,3-dihydro-1H-benzimidazol-1-yl}propanoic acid

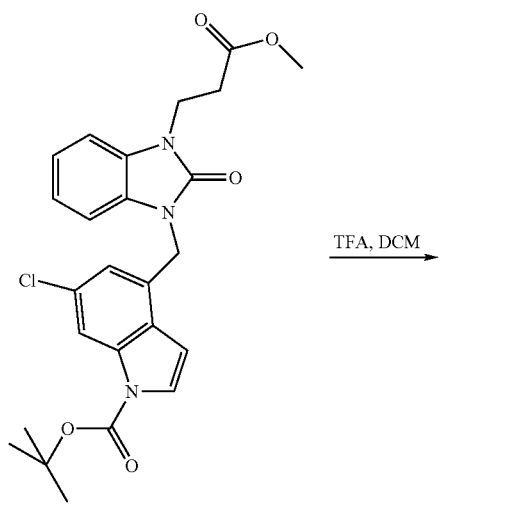

TFA, DCM →

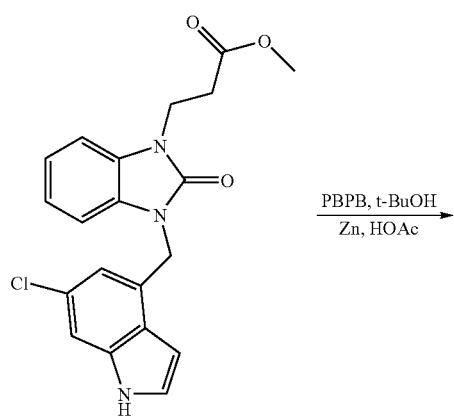

PBPB, t-BuOH / Zn, HOAc →

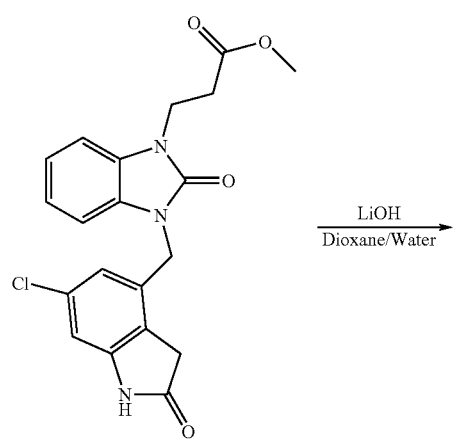

LiOH / Dioxane/Water →

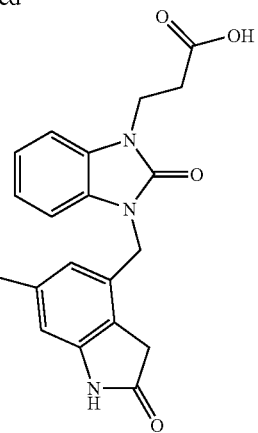

3-[3-(6-Chloro-1H-indol-4-ylmethyl)-2-oxo-2,3-dihydro-benzoimidazol-1-yl]-propionic acid methyl ester 6-Chloro-4-[3-(2-methoxycarbonyl-ethyl)-2-oxo-2,3-dihydro-benzoimidazol-1-ylmethyl]-indole-1-carboxylic acid tert-butyl ester (570 mg 1.1 mmol) is dissolved in 2.5 mL of dichloromethane and 2.5 mL of trifluoroacetic acid is added. The reaction is stirred for one hour, and then the solvent evaporated in vacuo to give an oil. The oil is taken up 3× in methanol and evaporated in vacuo to give the desired compound (450 mg, 1.1 mmol, 100%)

3-[3-(6-Chloro-2-oxo-2,3-dihydro-1H-indol-4-ylmethyl)-2-oxo-2,3-dihydro-benzoimidazol-1-yl]-propionic acid methyl ester 3-[3-(6-Chloro-1H-indol-4-ylmethyl)-2-oxo-2,3-dihydro-benzoimidazol-1-yl]-propionic acid methyl ester (248 mg, 0.64 mmol) is dissolved it tert-butanol (20 mL) at 40° C. The reaction is stirred and pyridiniumtrbromide is added portion wise over 5 minutes. The reaction is stirred for 10 minutes and concentrated in vacuo. The crude material is dissolved in acetic acid (10 mL) and zinc powder (211 mg, 3.2 mmol)is added to the reaction. The reaction is stirred at room temperature for one hour, then the solvent evaporated in vacuo. The residue is taken up in dimethyl sulfoxide and filtered. The crude material is purified by preparative reverse phase LC to give the title compound (34 mg 0.09 mmol, 36%).

3-[3-(6-Chloro-2-oxo-2,3-dihydro-1H-indol-4-ylmethyl)-2-oxo-2,3-dihydro-benzoimidazol-1-yl]-propionic acid 3-[3-(6-Chloro-2-oxo-2,3-dihydro-1H-indol-4-ylmethyl)-2-oxo-2,3-dihydro-benzoimidazol-1-yl]-propionic acid methyl ester (34 mg 0.09 mmol) is dissolved in dioxane water (2 mL/2 mL) and lithium hydroxide (18 mg, 0.45 mmol) is added in one portion. The reaction is stirred for one hour then the solvents evaporated in vacuo. The crude material is purified by preparative reverse phase LC to give the title compound (12 mg 0.03 mmol, 36%). LCMS (ESMS): m/z 387.1 (M+H$^+$).

The following compounds were prepared following a similar procedure using appropriate starting material.

3-{3-[(6-bromo-2-oxo-2,3-dihydro-1H-indol-4-yl)methyl]-2-oxo-2,3-dihydro-1H-benzimidazol-1-yl}propanoic acid. LCMS (ESMS): m/z 431.3 (M+H⁺)

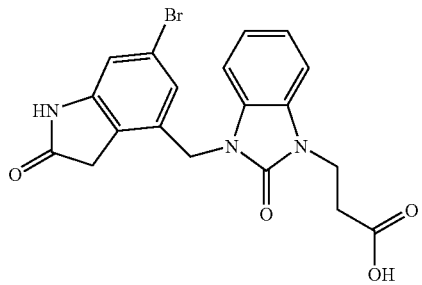 [SMILES: O=C(O)CCn1c(=O)n(Cc2cc(Br)cc3c2CC(=O)N3)c2ccccc21]

3-{3-[(6-chloro-2-oxo-2,3-dihydro-1H-indol-4-yl)methyl]-2-oxo-2,3-dihydro-1H-benzimidazol-1-yl}hexanoic acid. LCMS (ESMS): m/z 428.2 (M+H⁺).

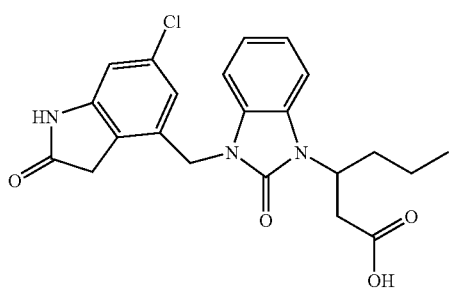 [SMILES: CCCC(CC(=O)O)n1c(=O)n(Cc2cc(Cl)cc3c2CC(=O)N3)c2ccccc21]

Example 74

3-{3-[(1,4-dimethyl-1H-indol-3-yl)methyl]-7-methyl-2-oxo-2,3-dihydro-1H-benzimidazol-1-yl}propanoic acid

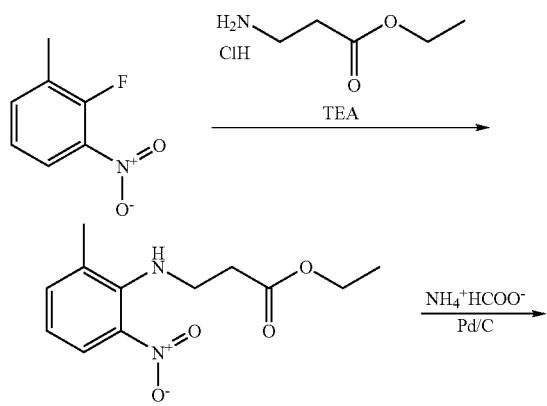

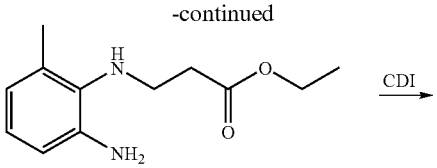

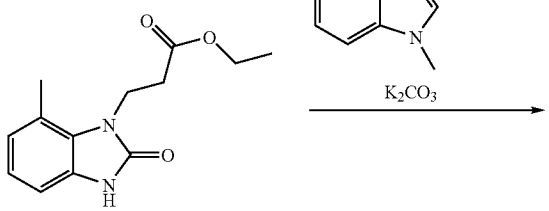

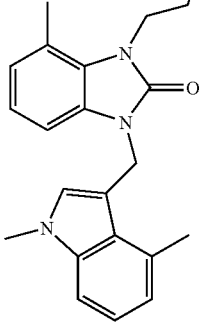

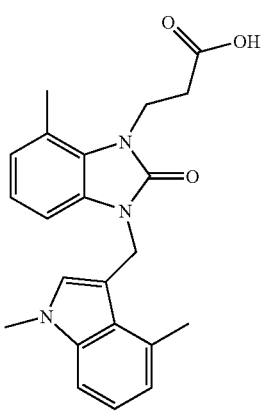 [SMILES: Cc1cccc2c1c(Cn1c(=O)n(CCC(=O)O)c3c(C)cccc31)cn2C]

1-Methyl-2-fluoro-3-nitro-benzene (465 mg, 3 mmol) was dissolved in DMF (6 mL) and 3-aminopropionic acid ethyl ester hydrochloride salt (735 mg, 4.6 mmol) was added followed by TEA (1.5 mL, 10.7 mmol). The reaction mixture was heated in the microwave at 130° C. for 1 h, cooled, diluted with water (100 mL) and extracted with dichloromethane (2×50 mL). The combined organic fractions were washed with 1 N HCl (30 mL), water (30 mL) and brine (30 mL), dried and evaporated to provide 3-(2-methyl-6-nitrophenylamino)-propionic acid ethyl ester (580 mg, 77% yield) which was used directly. This intermediate (101 mg, 0.4 mmol), ammonium formate (252 mg, 4 mmol) and Pd/C (5%, 5 mg) were combined in a reaction vial and methanol (1 mL) was added. The mixture was agitated at room temperature for 4 h, diluted with dichloromethane (5 mL) and filtered, and the mother liquors were concentrated to provide the crude product 3-(2-amino-6-methylphenylamino)-propionic acid ethyl ester which was used directly. This intermediate (37 mg, 0.17 mmol) was dissolved in dichoromethane (1 mL) and carbonyldiimidazole (34 mg, 0.21 mmol) was added. The resulting mixture was agitated at room temperature overnight then purified directly by preparative HPLC using an acetonitrile/water/formic acid gradient providing the intermediate 3-(7-methyl-2-oxo-2,3-dihydro-benzoimidazol-1-yl)-propionic acid ethyl ester (21 mg, 51% yield) which was used directly. This intermediate was dissolved in DMF (1 mL), and K$_2$CO$_3$ (69 mg, 0.5 mmol) was added followed by (1,4-dimethyl-1H-indol-3-ylmethyl)-trimethyl-ammonium iodide (137.7 mg, 0.4 mmol), prepared as described previously. The resulting mixture was heated at 65° C. overnight, cooled, filtered and the solution was treated directly with Amberlyst® A26 (OH—) (650 mg, 0.87 mmol). This reaction mixture was agitated overnight and the resin was filtered and washed with several portions of methanol. The product was eluted by treating the resin with a 20% solution of formic acid in methanol (2×2 mL) and washing with methanol (2 mL). The combined eluant and final wash was evaporated and the residue was purified by preparative HPLC using an acetonitrile/water/formic acid gradient providing the title compound (9 mg, 15% yield). LCMS (ESMS): m/z 378 (M+H).

Example 75

3-{7-bromo-3-[(1,4-dimethyl-1H-indol-3-yl)methyl]-2-oxo-2,3-dihydro-1H-benzimidazol-1-yl}propanoic acid

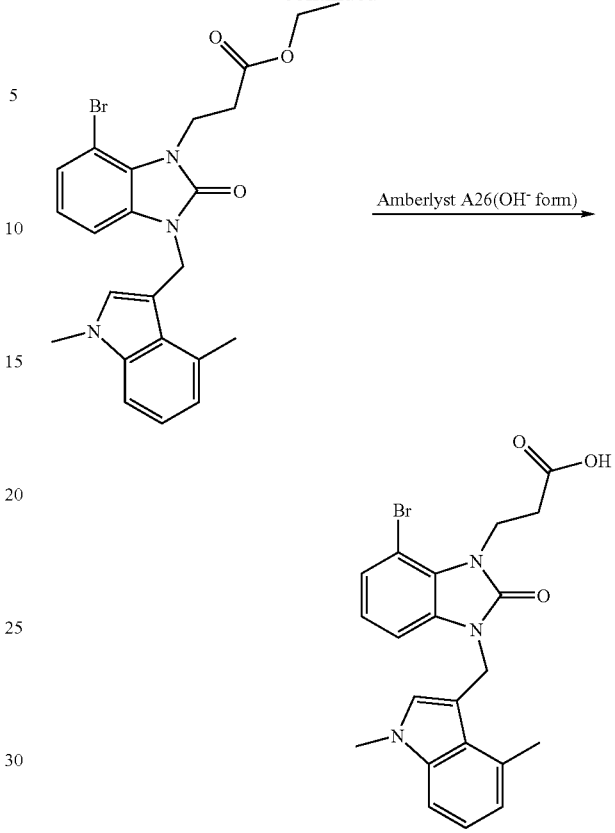

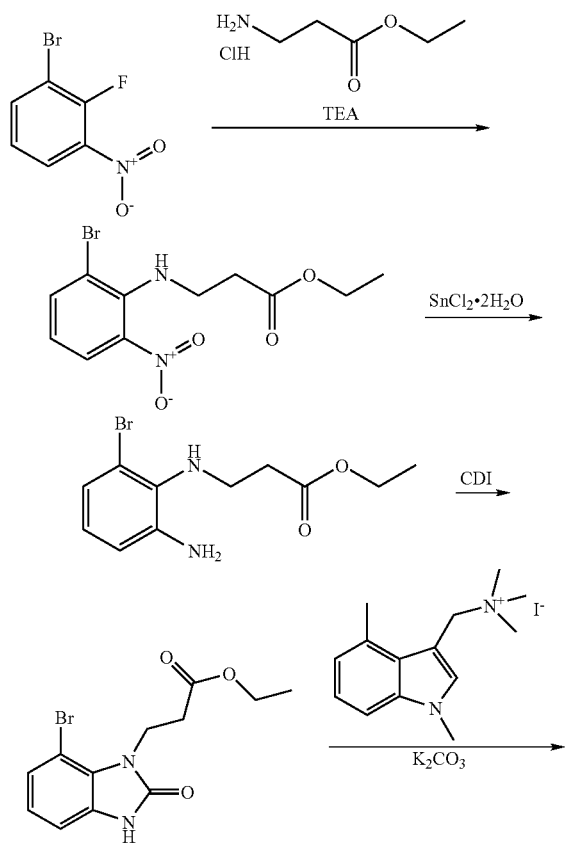

The intermediate 3-(2-bromo-6-nitrophenylamino)-propionic acid ethyl ester was prepared from 1-bromo-2-fluoro-3-nitrobenzene using methods similar to those described in Example 74. This intermediate (100 mg, 0.315 mmol) was dissolved in ethanol (10 mL) and SnCl$_2$.2H$_2$O (2.3 g, 10.2 mmol) was added. The resulting mixture was heated at 60° C. for 3 h, then added to an ice-cooled saturated solution of NaHCO$_3$ (25 mL). This mixture was extracted with ethyl acetate (4×4 mL), and the combined extracts were washed with water (1×10 mL) and brine (1×10 mL), dried and concentrated. The resulting crude product 3-(2-amino-6-bromophenylamino)-propionic acid ethyl ester was used directly and converted to the title compound using methods similar to those described in Example 74. LCMS (ESMS): m/z 442.4 (M+H).

Example 76

3-{3-[(1-ethyl-4-methyl-1H-indol-3-yl)methyl]-2-oxo-2,3-dihydro-1H-benzimidazol-1-yl}hexanoic acid

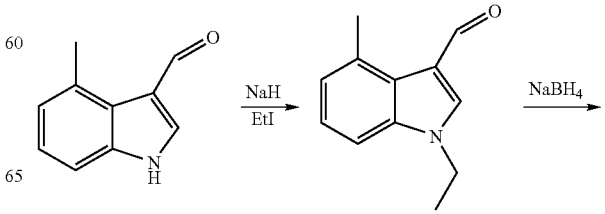

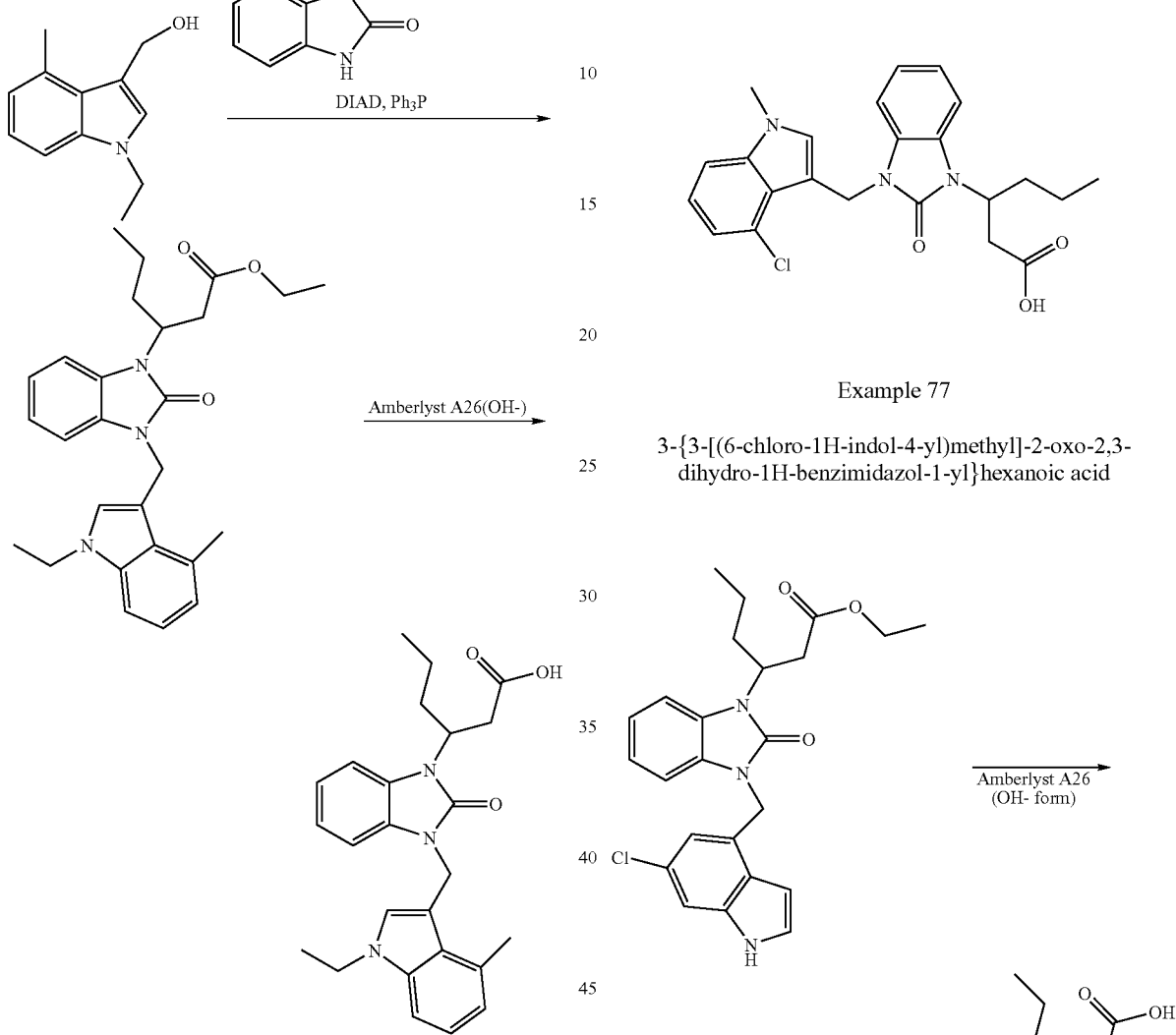

To a solution of 4-methyl-1H-indole-3-carbaldehyde (150 mg, 0.942 mmol) in dry DMF (1 mL) was added NaH (26 mg, 1.08 mmol) in 3 portions. When the evolution of gas was complete, the reaction vial was sealed and agitated for 5 m, after which time ethyl iodide (0.086 mL, 1.1 mmol) was added and agitation was continued overnight. The mixture was diluted with dichloromethane (10 mL), washed with water (2×5 mL), and brine (5 mL), dried and concentrated. This mixture was purified by flash chromatography using a gradient of ethyl acetate/hexane to provide 1-ethyl-4-methyl-1H-indole-3-carbaldehyde (111 mg, 63%). This intermediate (371 mg, 2 mmol) was dissolved in THF (3 mL) and NaBH$_4$ (38 mg, 5 mmol) was added followed by 3 drops of water. The reaction mixture was agitated for 4 h then added to a saturated solution of NaHCO$_3$ (10 mL). This mixture was stirred for 1 h and the intermediate, (1-ethyl-4-methyl-1H-indol-3-yl)-methanol was isolated by filtration and dried (330 mg, 88% yield). This intermediate was then converted to the title compound using methods similar to those described in Example 31. LCMS (ESMS): m/z 420 (M+H$^+$).

Using methods similar to those described in the above example, the following analog was also synthesized.

3-{3-[(4-chloro-1-methyl-1H-indol-3-yl)methyl]-2-oxo-2,3-dihydro-1H-benzimidazol-1-yl}hexanoic acid. LCMS (ESMS): m/z 426 (M+H)

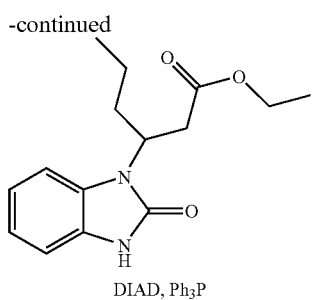

Example 77

3-{3-[(6-chloro-1H-indol-4-yl)methyl]-2-oxo-2,3-dihydro-1H-benzimidazol-1-yl}hexanoic acid 3-[3-(6-Chloro-1H-indol-4-ylmethyl)-2-oxo-2,3-dihydro-benzimidazol-1-yl]-hexanoic acid ethyl ester (100 mg, 0.23 mmol), prepared as described in example 72 using the appropriate reagents, was dissolved in methanol (1 mL) and treated with Amberlyst® A26 (OH— form) (1.2 g, 1.6 mmol). The resulting mixture was agitated 18 h. The mixture was filtered and the resin was washed with several portions of methanol. The product was eluted from the resin with 20% formic acid in methanol (2×2 mL). The solution was concentrated and purified by preparative HPLC using an acetonitrile/water/formic acid gradient to provide 50 mg (53%) of the title compound. LCMS (ESMS): m/z 412 (M+H).

Example 78

3-{3-[(6-chloro-1-methyl-1H-indol-4-yl)methyl]-2-oxo-2,3-dihydro-1H-benzimidazol-1-yl}hexanoic acid

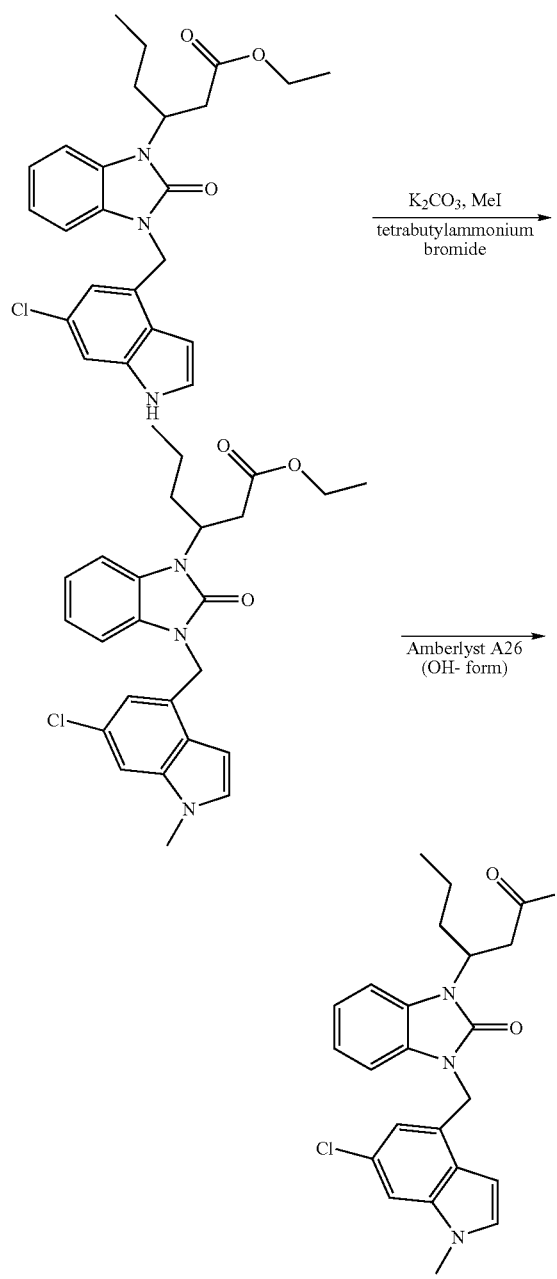

3-[3-(6-Chloro-1H-indol-4-ylmethyl)-2-oxo-2,3-dihydro-benzimidazol-1-yl]-hexanoic acid ethyl ester (300 mg, 0.68 mmol), prepared as described in example 72 using the appropriate reagents, was dissolved in acetonitrile (5 mL) and treated with $K_2CO_3$ (700 mg, 5.1 mmol), methyl iodide (0.31 mL, 5 mmol) and tetrabutylammonium bromide (161 mg, 0.5 mmol). The resulting mixture was heated at 65° C. for 60 h, filtered, and the solution was treated directly with Amberlyst® A26 (OH— form) (1.5 g, 2 mmol). This mixture was agitated for 18 h, filtered and the resin was washed with several portions of methanol. The product was eluted from the resin with 20% formic acid in methanol (2×2 mL). The eluant was concentrated and the residue was purified by preparative HPLC to provide 26 mg (9%) of the title compound. LCMS (ESMS): m/z 426 (M+H).

Example 79

3-{3-[(6-bromo-1-methyl-1H-indol-4-yl)methyl]-2-oxo-2,3-dihydro-1H-benzimidazol-1-yl}propanoic acid

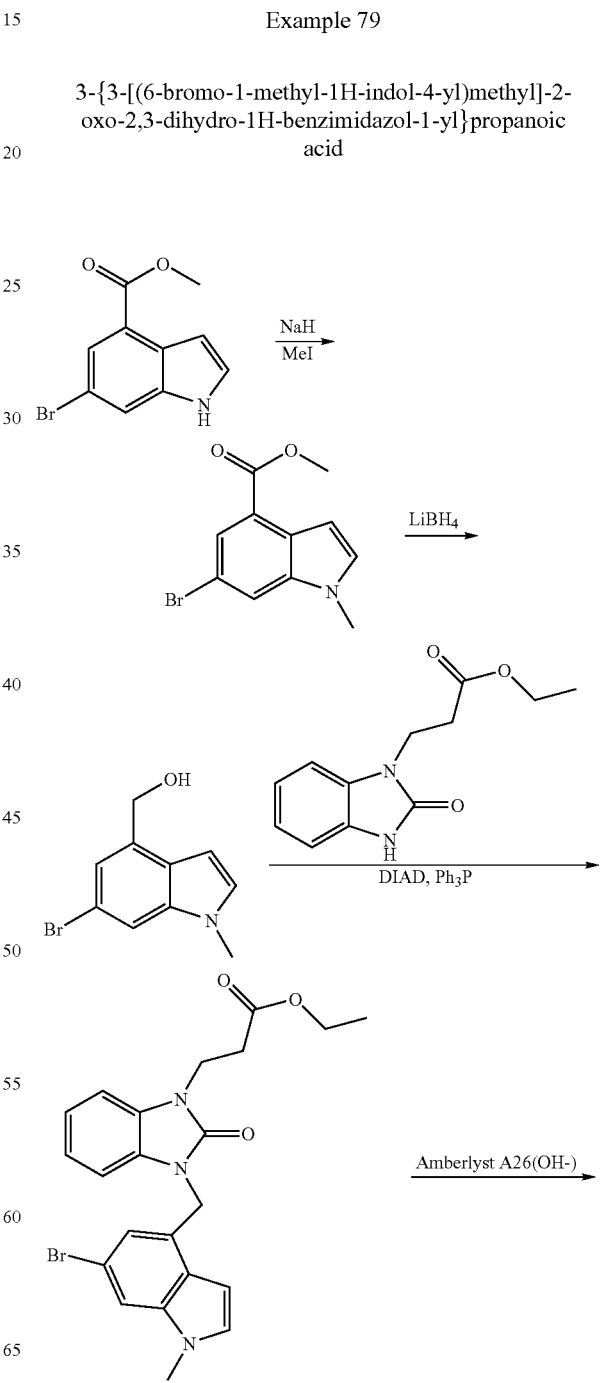

397

-continued

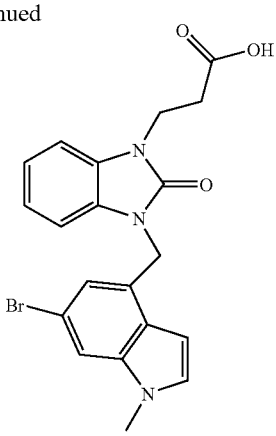

Sodium hydride (26.4 mg, 1.1 mmol) was dispersed in dry DMF (1.5 mL), and the mixture was cooled to 0° C. under an atmosphere of nitrogen. 6-Bromo-1H-indole-4-carboxylic acid methyl ester (254 mg, 1 mmol) was added dropwise as a solution in dry DMF (1 mL) and the resulting mixture was stirred at 0° C. for 30 m then purified directly by preparative HPLC using an acetonitrile/water/formic acid gradient to provide the desired intermediate (124 mg, 46% yield). Lithium borohydride (41 mg, 1.86 mmol) was dispersed in diethylether (5 mL). One drop of water was added followed by a solution of the above intermediate (120 mg, 0.45 mmol) in the same solvent (5 mL). The resulting mixture was agitated overnight then added to a saturated solution of $NaHCO_3$ (20 mL). The resulting mixture was stirred for 30 min then extracted with ethyl acetate (3×5 mL). The combined extracts were washed with brine (10 mL), dried and concentrated. The resulting crude intermediate, 6-bromo-1-methyl-1H-indol-4-yl)-methanol, was converted to the title compound using methods similar to those described in Example 31. LCMS (ESMS): m/z 428.30 (M+H).

The following compound was prepared following a similar procedure using appropriate starting material.

3-{3-[(6-bromo-1-methyl-1H-indol-4-y)methyl]-2-oxo-2,3-dihydro-1H-benzimidazol-1-yl}hexanoic acid. LCMS (ESMS): m/z 470.72 (M+H)

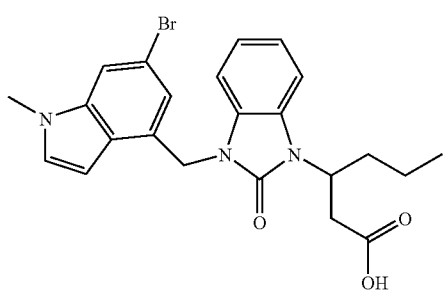 [SMILES: CCCC(CC(=O)O)n1c(=O)n(Cc2cc(Br)cc3c2ccn3C)c2ccccc21]

398

Example 80

3-{3-[(6-bromo-1-methyl-2-oxo-2,3-dihydro-1H-indol-4-yl)methyl]-2-oxo-2,3-dihydro-1H-benzimidazol-1-yl}hexanoic acid

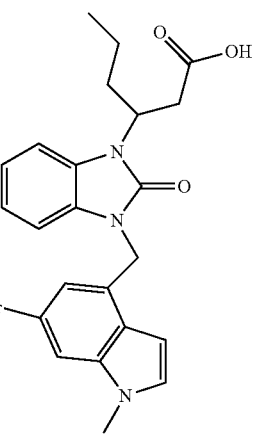

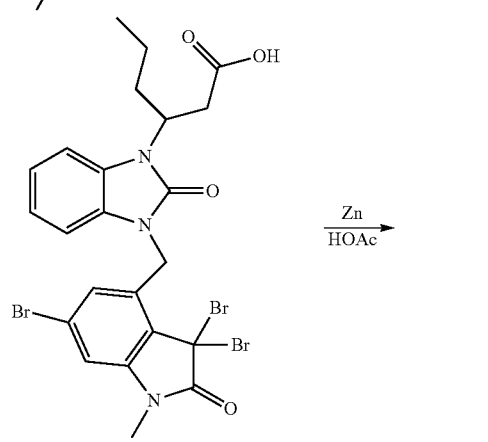

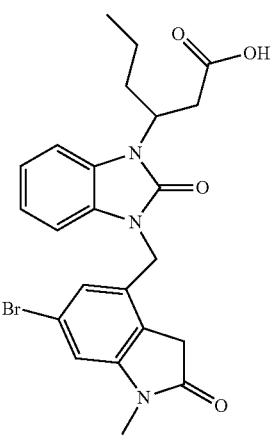

To a solution of 3-[3-(6-bromo-1-methyl-1H-indol-4-ylmethyl)-2-oxo-2,3-dihydro-benzimidazol-1-yl]-hexanoic acid (71 mg, 0.15 mmol) in THF (11 mL) was added t-BuOH (1 mL). A solution of NBS (58 mg, 0.32 mmol) in THF (0.5 mL) was added and the resulting mixture was stirred at ambient temperature for 15 m, concentrated and used directly. This crude intermediate was dissolved in acetic acid (1.5 mL). Zn powder (70 mg, 1.1 mmol) was added and the resulting mixture was agitated for 15 m. The reaction mixture was filtered and the mother liquors were concentrated and purified directly by preparative HPLC using an acetonitrile/water/formic acid gradient to provide 12 mg (25%) of the title compound. LCMS (ESMS): m/z 486.88 (M+H).

Example 81

3-{3-[(1-methyl-2-oxo-2,3-dihydro-1H-indol-4-yl)methyl]-2-oxo-2,3-dihydro-1H-benzimidazol-1-yl}hexanoic acid

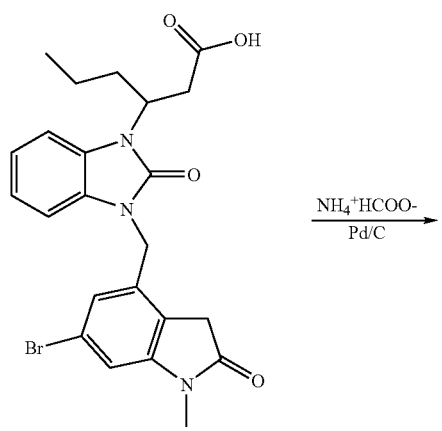

Example 82

3-{3-[(6-bromo-1H-indol-4-yl)methyl]-2-oxo-2,3-dihydro-1H-benzimidazol-1-yl}hexanoic acid

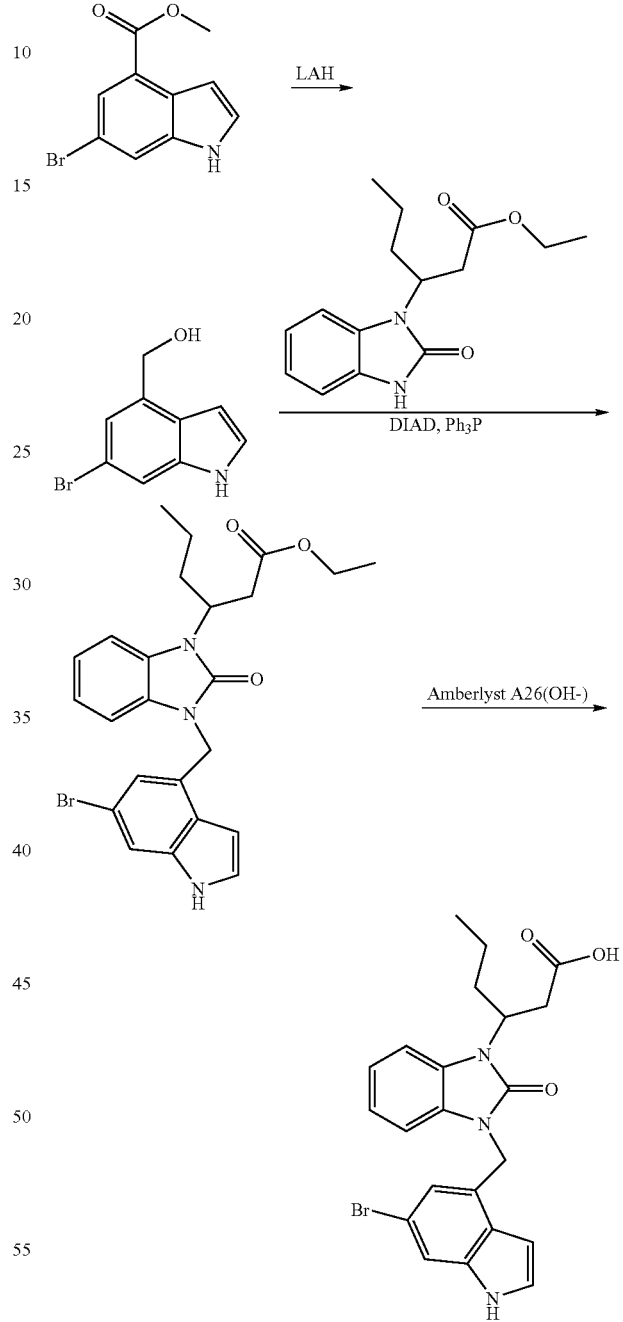

To a solution of 3-[3-(6-bromo-1-methyl-1H-indol-4-ylmethyl)-2-oxo-2,3-dihydro-benzimidazol-1-yl]-hexanoic acid (25 mg, 0.05 mmol) in methanol (2 mL) was added ammonium formate (150 mg, 2.4 mmol) and PdC 10% (5 mg). The resulting mixture was agitated for 60 h, filtered and concentrated. The resulting residue was dispersed in DCM (2 mL), filtered, and the filtrate was washed with DCM (1×2 mL). The mother liquors were concentrated and the residue was purified by preparative HPLC using an acetonitrile/water/formic acid gradient to provide 7 mg (35%) of the title compound. LCMS (ESMS): m/z 408 (M+H).

A solution of 6-bromo-1H-indole-4-carboxylic acid methyl ester (250 mg, 1 mmol) in THF (25 mL) was cooled to 0° C. and LAH (57 mg, 1.5 mmol) was added in portions under an atmosphere of $N_2$. The reaction mixture was stirred at 0° C. for 2 h, then added to a saturated solution of $NaHCO_3$ in portions. After stirring for 15 m, the mixture was extracted with ethyl acetate (3×15 mL) and the combined extracts were washed with brine, dried and concentrated to 220 mg of 6-bromo-1H-indol-4-yl)-methanol. This intermediate was then converted to the title compound using methods similar to those described in Example 31. LCMS (ESMS): m/z 456.8 (M+H).

Example 83

3-{3-[(6-methyl-1H-indol-4-yl)methyl]-2-oxo-2,3-dihydro-1H-benzimidazol-1-yl}hexanoic acid

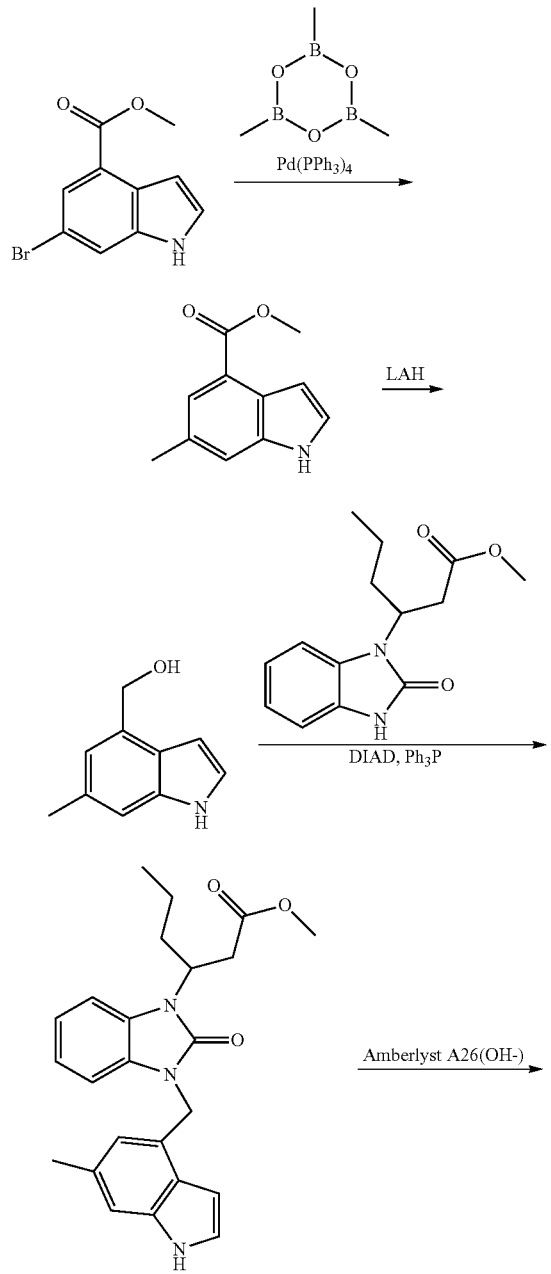

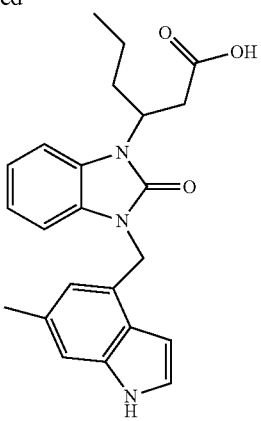

A reaction tube was charged with 6-bromo-1H-indole-4-carboxylic acid methyl ester (635 mg, 2.5 mmol) and Pd(PPh₃)₄ (15.7 mg, 0.06 mmol) followed by DMF (8 mL), trimethylboroxine (1.3 mL, 9.5 mmol), and an aqueous solution of Na₂CO₃ (2.75 mL, 4M, 11 mmol). The tube was sealed and the reaction mixture was heated in the microwave at 120° C. for 80 m. The reaction mixture was diluted with water (25 mL) and ethyl acetate (25 mL), filtered, and the mother liquors were isolated and washed with water (2×25 mL) and brine (1×25 mL), dried and concentrated. The residue was purified by flash chromatography using a gradient of ethyl acetate and hexane. The intermediate, 6-methyl-1H-indole-4-carboxylic acid methyl ester (238 mg, 50% yield) was isolated by evaporation of the solvent. A solution of this intermediate (238 mg, 1.26 mmol) in THF (10 mL) was cooled to 0° C. and LAH (77 mg, 2.0 mmol) was added in portions under an atmosphere of N₂. The reaction mixture was stirred at 0° C. for 2 h, then at ambient temperature for 18 h. An additional portion of LAH (40 mg, 1.05 mmol) was added and the reaction mixture was stirred an additional 3 h then added to a saturated solution of NaHCO₃ in portions. After stirring for 15 m, the mixture was extracted with ethyl acetate (3×15 mL) and the combined extracts were washed with brine, dried and concentrated to 174 mg of crude 6-methyl-1H-indol-4-yl)-methanol which was used directly. This intermediate was converted to the title compound using methods similar to those described in Example 31. LCMS (ESMS): m/z 392 (M+H).

Example 84

3-[3-(5-bromo-2-methylbenzyl)-2-oxo-2,3-dihydro-1H-benzimidazol-1-yl]hexanoic acid

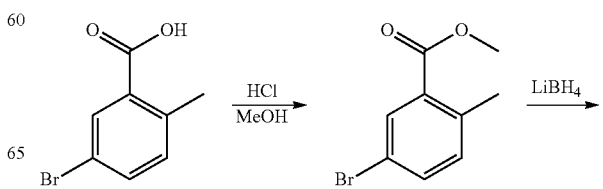

403
-continued

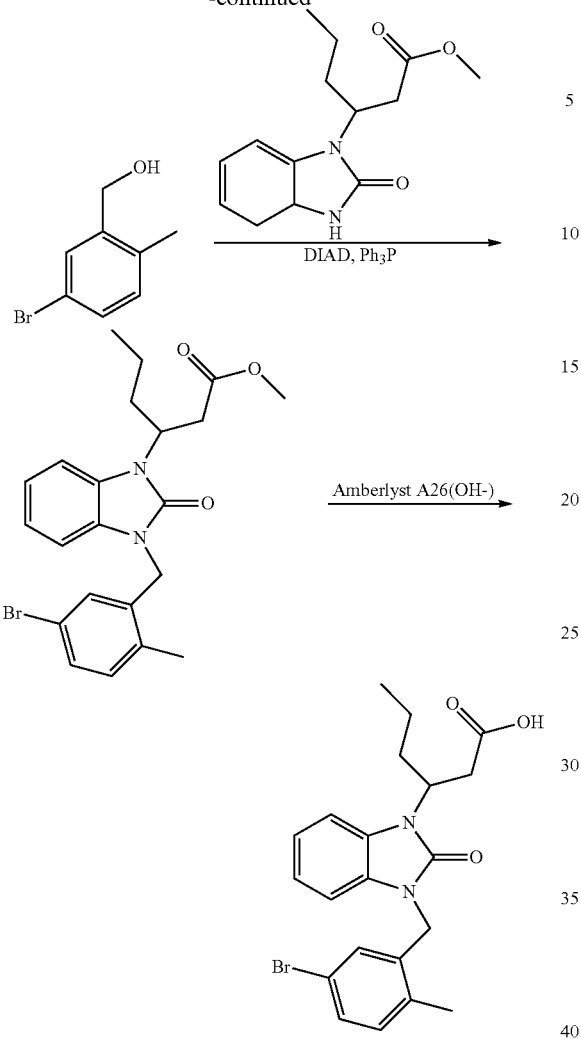

2-Methyl-5-bromobenzoic acid (360 mg, 1.67 mmol) was dissolved in methanol (10 mL). Concentrated HCl (0.25 mL) was added and the resulting mixture was agitated for 45 h at ambient temperature then 24 h at 60° C., after which time the mixture was concentrated to 358 mg of the intermediate which was used directly. To a solution of 2-methyl-5-bromobenzoic acid methyl ester (351 mg, 1.53 mmol) in diethyl ether (10 mL) was added LiBH$_4$ (200 mg, 9 mmol) followed by 3 drops of methanol, and the resulting mixture was agitated overnight. The reaction mixture was then diluted with a saturated solution of NaHCO$_3$. After stirring for ½ h, the mixture was extracted with ethyl acetate (2×20 mL) and the combined extracts were washed with brine, dried and concentrated to 236 mg of the desired intermediate 2-methyl-5-bromobenzylalcohol which was used directly. This intermediate was converted to the title compound using methods similar to those described in Example 31. LCMS (ESMS): m/z 431.33 (M+H).

The following compounds were prepared following a procedure using appropriate reagents.

404

3-[3-(5-chloro-2-methylbenzyl)-2-oxo-2,3-dihydro-1H-benzimidazol-1-yl]hexanoic acid. LCMS (ESMS): m/z 387 (M+H)

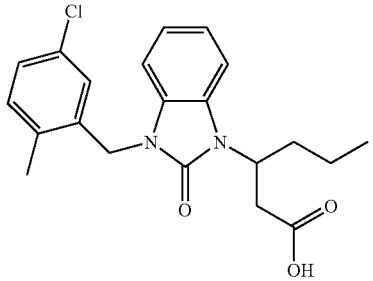 [SMILES: CCCC(CC(=O)O)n1c(=O)n(Cc2cc(Cl)ccc2C)c2ccccc21]

3-[3-(2-chloro-5-methylbenzyl)-2-oxo-2,3-dihydro-1H-benzimidazol-1-yl]hexanoic acid. LCMS (ESMS): m/z 387 (M+H)

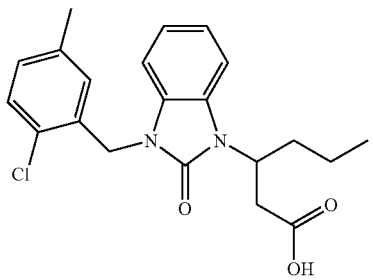 [SMILES: CCCC(CC(=O)O)n1c(=O)n(Cc2cc(C)ccc2Cl)c2ccccc21]

3-{3-[(3-bromo-1-naphthyl)methyl]-2-oxo-2,3-dihydro-1H-benzimidazol-1-yl}hexanoic acid. LCMS (ESMS): m/z 467.9 (M+H)

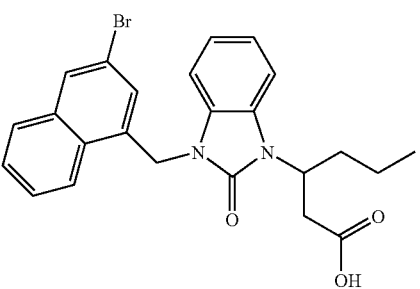 [SMILES: CCCC(CC(=O)O)n1c(=O)n(Cc2cc(Br)cc3ccccc23)c2ccccc21]

Example 85

3-{3-[(4-methyl-1H-indol-3-yl)methyl]-2-oxo-2,3-dihydro-1H-benzimidazol-1-yl}hexanoic acid

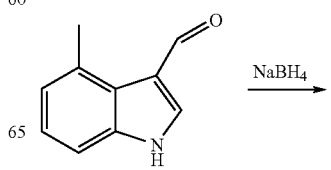

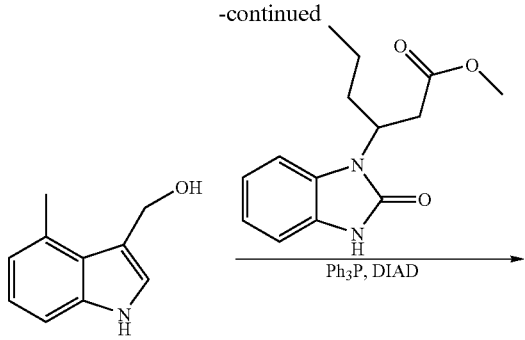
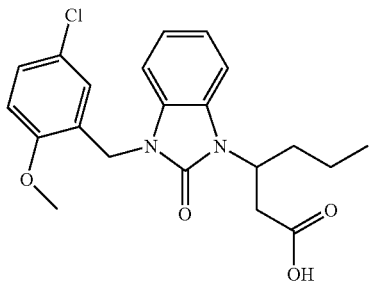 [SMILES: CCCC(CC(=O)O)n1c(=O)n(Cc2cc(Cl)ccc2OC)c2ccccc21]

3-[3-(5-chloro-2-methoxybenzyl)-2-oxo-2,3-dihydro-1H-benzimidazol-1-yl]hexanoic acid. LCMS (ESMS): m/z 403 (M+H)

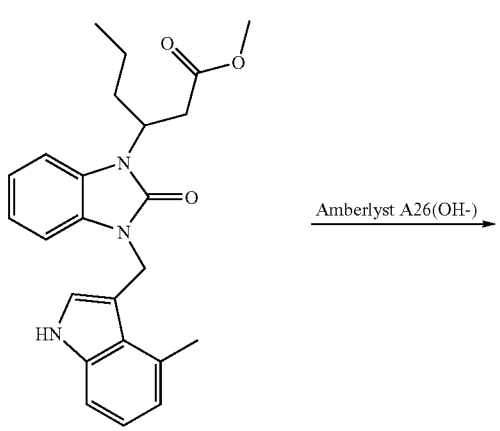

3-{3-[(5-bromo-1H-indol-3-yl)methyl]-2-oxo-2,3-dihydro-1H-benzimidazol-1-yl}hexanoic acid. LCMS (ESMS): m/z 456.8 (M+H)

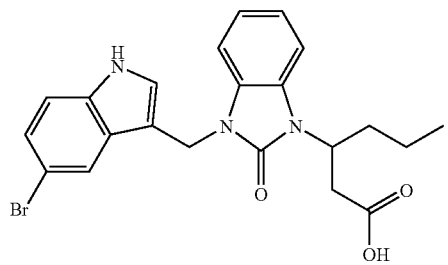 [SMILES: CCCC(CC(=O)O)n1c(=O)n(Cc2c[nH]c3ccc(Br)cc23)c2ccccc21]
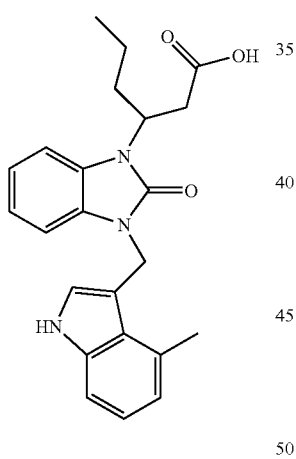

3-{3-[(4-fluoro-1-naphthyl)methyl]-2-oxo-2,3-dihydro-1H-benzimidazol-1-yl}hexanoic acid. LCMS (ESMS): m/z 407 (M+H)

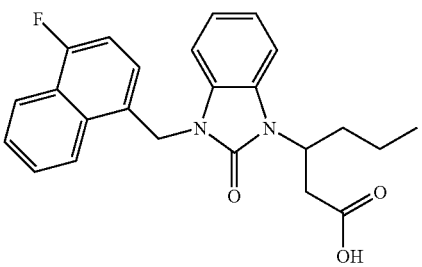 [SMILES: CCCC(CC(=O)O)n1c(=O)n(Cc2ccc(F)c3ccccc23)c2ccccc21]

To a solution of 4-methyl-1H-indole-3-carbaldehyde (159 mg, 1 mmol) in THF (3 mL) was added NaBH$_4$ (95 mg, 2.5 mmol) followed by three drops of water. The resulting mixture was agitated for 60 h then diluted with a saturated solution of NaHCO$_3$ (5 mL). This mixture was stirred for 15 m, diluted with water (10 mL) and extracted with DCM (2×10 mL). The combined extracts were washed with water and brine, dried and concentrated to the desired product, 4-methyl-1H-indol-3-yl)-methanol (140 mg, 87% yield) which was used directly. Using a method similar to that described in Example 31, this product was converted to the title compound. LCMS (ESMS): m/z 392 (M+H).

The following compound was prepared following a similar procedure using appropriate reagents.

Example 86

3-[3-(3-hydroxy-2,5-dimethylbenzyl)-2-oxo-2,3-dihydro-1H-benzimidazol-1-yl]hexanoic acid

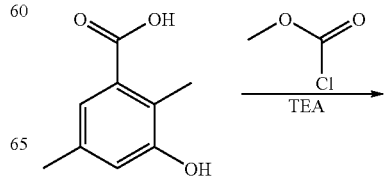

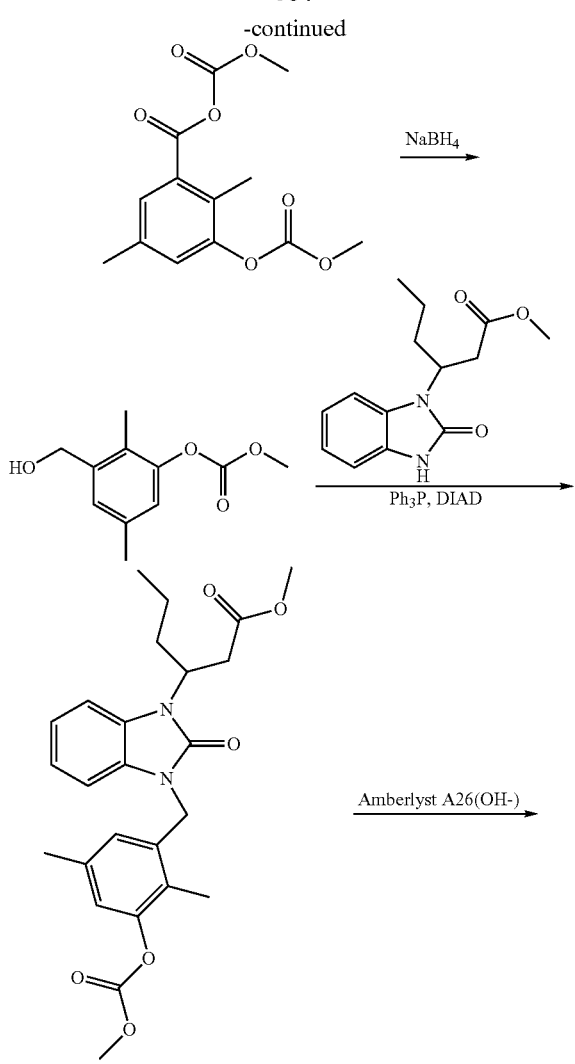

washed with 1N HCl (50 mL), NaHCO₃ (satd. aq., 50 mL), and brine (50 mL), dried and concentrated to 790 mg of an oil which was used directly. This intermediate (400 mg, 1.4 mmol) was dissolved in THF (5 mL) and NaBH₄ (300 mg, 7.9 mmol) was added followed by four drops of methanol. The resulting mixture was agitated for 30 m, then poured into a saturated solution of NaHCO₃ (25 mL). This mixture was then extracted with ethyl acetate (2×25 mL) and the combined extracts were washed with brine (25 mL), dried and concentrated to 252 mg of an oil which was purified by flash chromatography using and ethyl acetate/hexane gradient. The desired product, carbonic acid 3-hydroxymethyl-2,5-dimethyl-phenyl ester methyl ester, (190 mg, 64% yield) was recovered by evaporation of the solvents. This intermediate (185 mg, 0.88 mmol) was then combined with 3-(2-oxo-2,3-dihydro-benzimidazol-1-yl)-hexanoic acid methyl ester (231 mg, 0.88 mmol) and triphenylphosphine (236 mg, 0.9 mmol) in a reaction vial. Tetrahydrofuran (10 mL) was added and the resulting mixture was cooled to 0° C. Diisopropyl azodicarboxylate (0.174 mL, 0.9 mmol) was added dropwise and the resulting mixture was allowed to warm to room temperature and agitated overnight. This mixture was then diluted with methanol (5 mL), treated with Amberlyst®A26 (OH—) (6 g, 8 mmol) and agitated overnight. The resin was filtered and washed with several portions of DMF then methanol. The product was eluted from the resin by treatment with 10% formic acid in methanol (2×3 mL) then methanol (3 mL). The eluant was concentrated to 345 mg of an oil which was purified by preparative HPLC using an acetonitrile/water/formic acid gradient. The title compound (85 mg, 25%) was recovered by evaporation of the solvents. LCMS (ESMS): m/z 383 (M+H).

Example 87 trans-4-({3-[(4-methyl-1-benzothien-3-yl)methyl]-2-oxo-2,3-dihydro-1H-benzimidazol-1-yl}methyl)cyclohexanecarboxylic acid

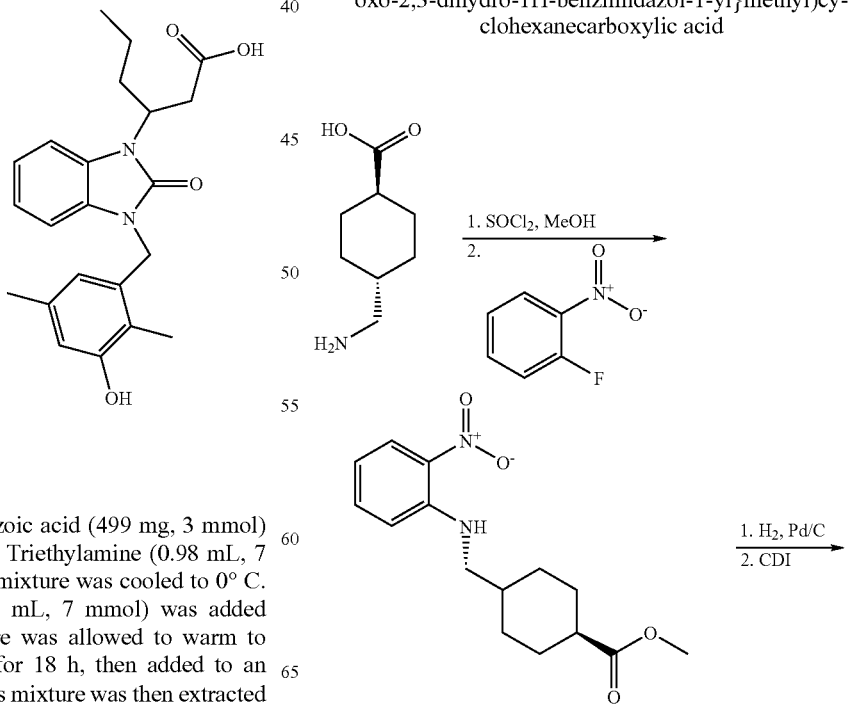

3-Hydroxy-2,5-dimethyl-benzoic acid (499 mg, 3 mmol) was dissolved in THF (10 mL). Triethylamine (0.98 mL, 7 mmol) was added, the reaction mixture was cooled to 0° C. and methylchloroformate (0.54 mL, 7 mmol) was added dropwise. The resulting mixture was allowed to warm to ambient temperature, agitated for 18 h, then added to an ice/water mixture (100 mL). This mixture was then extracted with ethyl acetate (2×50 mL) and the combined extracts were

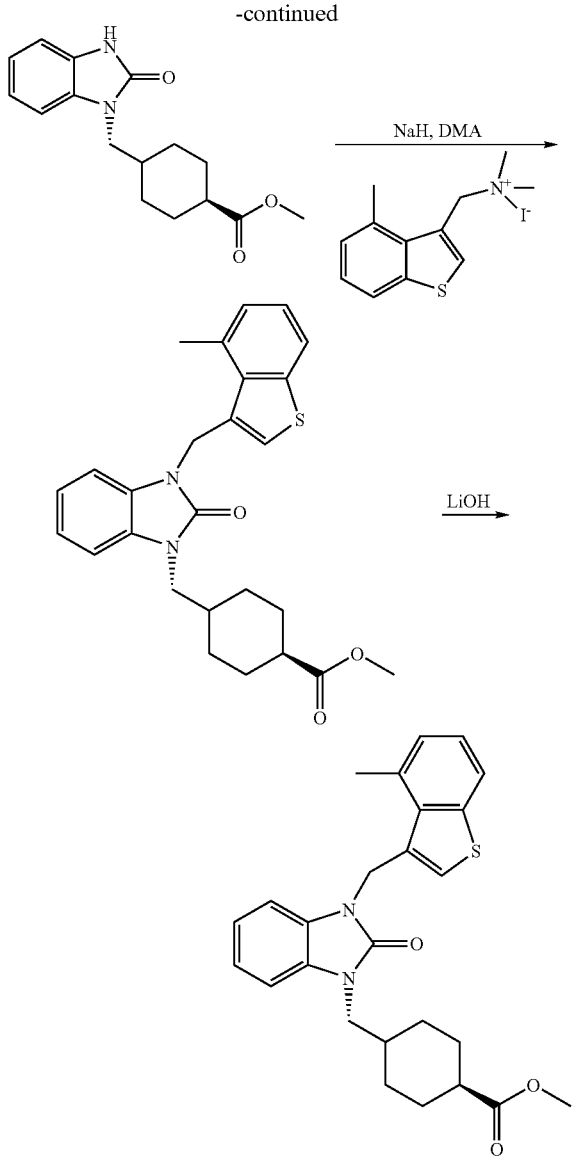

To a suspension of 4-[(2-nitro-phenylamino)-methyl]cyclohexanecarboxylic acid methyl ester (1.45 g, 4.96 mmol) in 40 ml of methanol was added 165 mg of Pd/C. The reaction flask was evacuated and backfill with $H_2$ (repeating this process 3 times). The reaction mixture was stirred at room temperature for 16 h. The crude product was filtered through celite and concentrated to yield 1.22 g (93.8%) of desired product.

To a solution of 4-[(2-amino-phenylamino)-methyl]cyclohexanecarboxylic acid methyl ester (610 mg, 2.33 mmol) in 25 ml of THF was added carbonyldiimidazole (566 mg, 3.49 mmol) at room temperature. The reaction solution was stirred at room temperature for 16 h. The solution was diluted with 50 ml of ethyl acetate and wash successively with 100 ml of sat. $NaHCO_3$ and 100 ml of brine. The organic layer was dried over $MgSO_4$, filtered and concentrated. The product (602 mg, 89.5%) was taken on without further purification.

To a solution of 4-(2-oxo-2,3-dihydro-benzoimidazol-1-ylmethyl)-cyclodexanecarboxylic acid methyl ester (200 mg, 0.694 mmol) in 1 ml of DMA was added NaH (0.042 g, 1.04 mmol) as a 60% dispersion in mineral oil. To the resulting suspension was added trimethyl-(4-methyl-benzothiophen-3-ylmethyl)-ammonium iodide (0.265 g, 0.763 mmol). The reaction mixture was stirred at room temperature for 15 min and was heated to 80 °C. and stirred at that temperature for 15 h. The solution was diluted with 25 ml of EtOAc and washed with 50 ml of $NaHCO_3$, 25 ml of water and 25 ml of brine. The organic layer was dried over $MgSO_4$, filtered and concentrated. The crude product was purified by combiflash eluting with a gradient of dicloromethane and methanol to yield 98 mg (31.5%) of desired. LCMS (ESMS): m/z 449 (M+H$^+$).

To a solution of 4-[3-(4-methyl-benzothiophen-3-ylmethyl)-2-oxo-2,3-dihydro-benzimidazol-1-ylmethyl]-cyclohexanecarboxylic acid methyl ester (78 mg, 0.174 mmol) in 2 ml of THF was added 1 ml methanol and 1 ml 1N LiOH. The reaction solution was stirred for 48 h at room temperature and then concentrated. The product was obtained by diluting with 5 ml of water, acidifing with glacial acetic acid, and collecting the resultant solid by filtration (62 mg, 0.143 mmol). LCMS (ESMS): m/z 433 (M−H$^+$).

Following compounds were synthesized using a similar procedure.

4-[3-(4-methyl-benzothiophen-3-ylmethyl)-2-oxo-2,3-dihydro-benzimidazol-1-ylmethyl]-cyclohexanecarboxylic acid A suspension of trans 4-aminomethyl cyclohexanecarboxylic acid (1.0 g, 6.98 mmol) in 20 ml of methanol was cooled to 0 °C. Thionyl chloride (2.03 ml, 27.9 mmol) was added dropwise over 10 min. The solution was stirred at room temperature for 16 h. The solution was concentrated and 1.32 g (97%) of a light yellow solid was obtained. The resulting 4-methoxycarbonylcylclohexylmethyl ammonium chloride (810 mg, 3.90 mmol) was added to a suspension of nitrofluorobenzene (500 mg, 3.54 mmol) and diisopropylethylamine (1.85 ml, 10.6 mmol) in 10 ml of DMA. The solution was heated at 80 °C. for 16 h. The reaction mixture was diluted with 50 ml of ethyl acetate and washed with 50 ml of sat. $NaHCO_3$. The organic layer was dried over $MgSO_4$, and filtered and concentrated. The product was obtained as 960 mg (92.7%) of a foam.

methyl (1R,3S)-3-{3-[(4-methyl-1-benzothien-3-yl)methyl]-2-oxo-2,3-dihydro-1H-benzimidazol-1-yl}cyclopentanecarboxylate. LCMS (ESMS): m/z 421 (M+H$^+$)

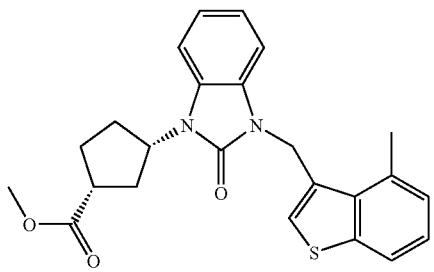 [SMILES: COC(=O)[C@@H]1CC[C@H](n2c(=O)n(Cc3csc4cccc(C)c34)c3ccccc32)C1]

411
(1R,3S)-3-{3-[(4-methyl-1-benzothien-3-yl)methyl]-2-oxo-2,3-dihydro-1H-benzimidazol-1-yl}cyclopentanecarboxylic acid. LCMS (ESMS): m/z 405 (M–H⁺)
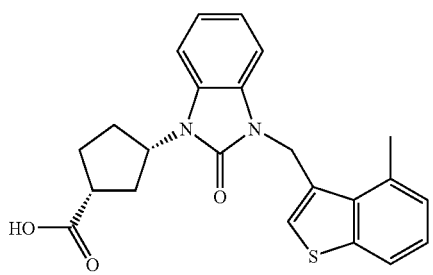 [SMILES: Cc1cccc2scc(Cn3c(=O)n([C@H]4CC[C@@H](C(=O)O)C4)c4ccccc43)c12]
Example 88
(S)-3-[3-(5-Bromo-2-oxo-2,3-dihydro-benzothiazol-7-ylmethyl)-2-oxo-2,3-dihydro-benzimidazol-1-yl]-hexanoic acid
412
-continued
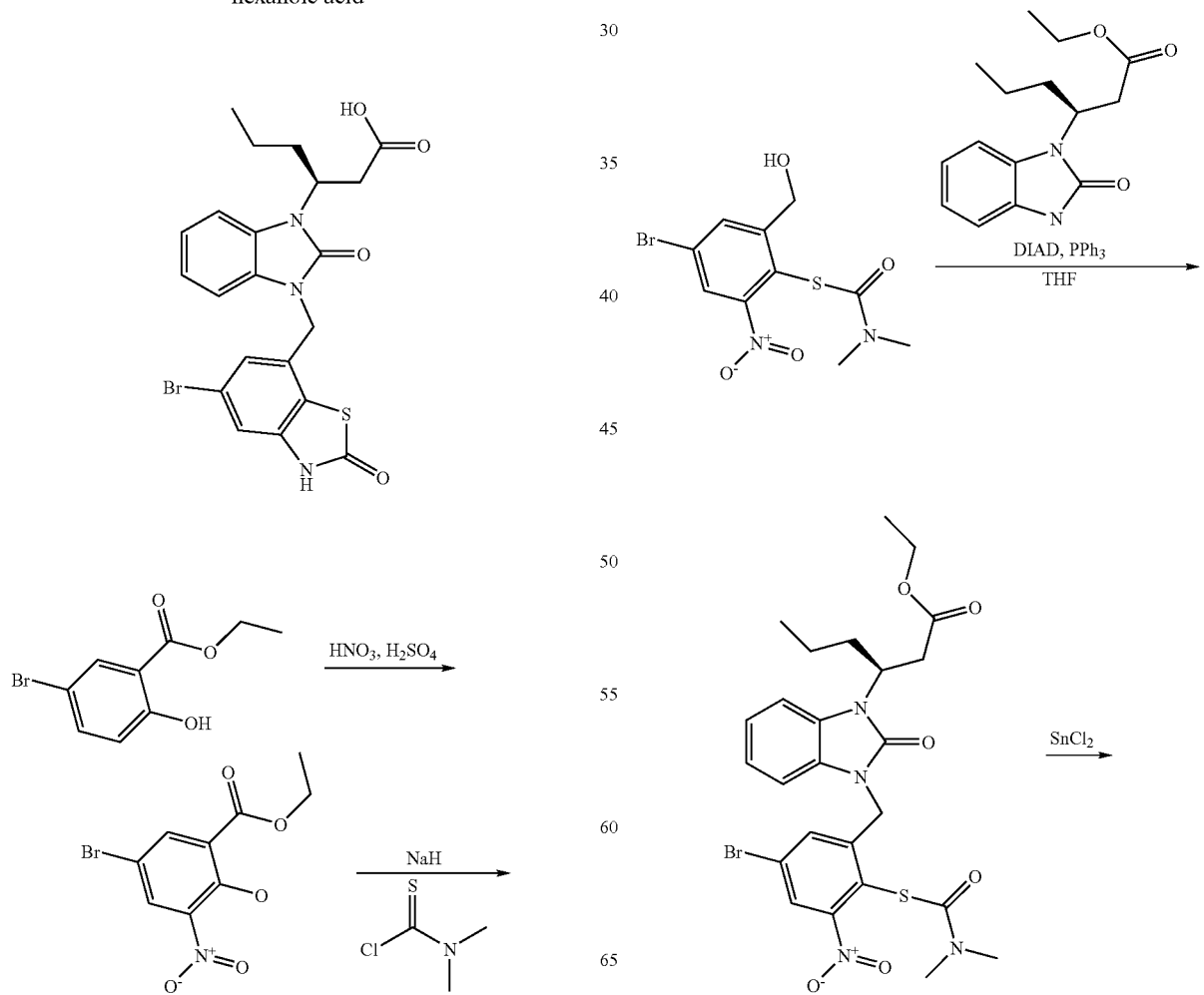

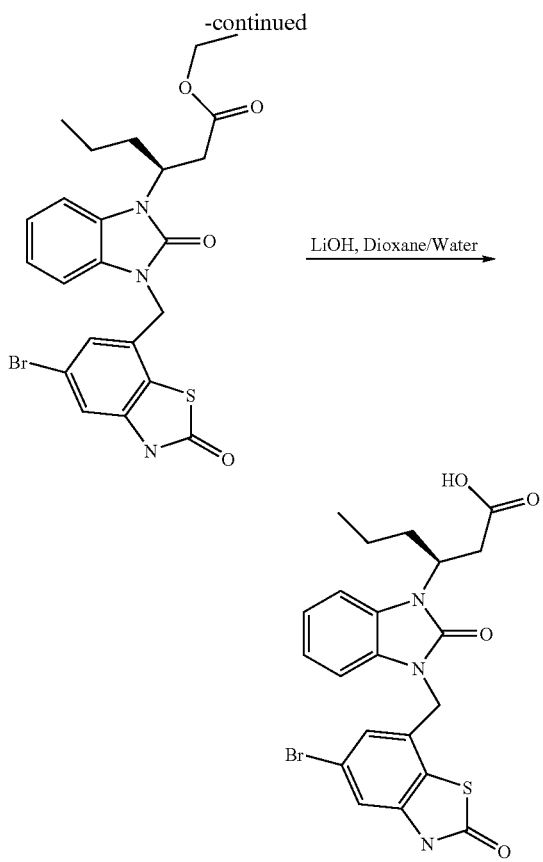

5-Bromo-2-hydroxy-3-nitro-benzoic acid ethyl ester

5-Bromo-2-hydroxy-benzoic acid ethyl ester (40 g, 214 mmol) is suspended in sulfuric acid (200 mL) and the reaction cooled to zero in an ice bath. The reaction is equipped with an overhead stirrer and then the nitric acid (20 mL) in sulfuric acid (40 mL) is added dropwise to the solution over the course of 30 minutes. After the addition the ice bath is removed and the reaction warmed to room temperature. The reaction is stirred at room temperature for 16 hours. When complete the reaction is poured onto crushed ice and the resulting yellow solid is collected by vacuum filtration and washed with ice cold water. The solid dried in vacuum over overnight to give the 45 g (91%) of title compound that is used without further purification. LCMS (ESMS): m/z 291.1 (M+H$^+$).

5-Bromo-2-dimethylthiocarbamoyloxy-3-nitro-benzoic acid ethyl ester

To a suspension of NaH (760 mg, 40%, 19 mmol) in DMF (50 mL) is added the 5-Bromo-2-hydroxy-3-nitro-benzoic acid ethyl ester (4.22 g, 18.2 mmol) portionwise over 5 minutes. After all the hydrogen gas is evolved the reaction is stirred for an additional 10 minutes and then an additional 100 mL, of dry DMF is added. The reaction is stirred at room temperature for 1 minute and dimethylthiocarbamoyl chloride (2.4 g, 18.9 mmol) is added over 5 minutes (Caution stench). The resulting reaction is stirred at room temperature for three days and then checked for completion by LC/MS. Reaction is quenched with water and extracted with ethyl acetate and dichloromethane to give 5.2 g (90%) of the crude product 80% pure, used without further purification. LCMS (ESMS): m/z 378.3 (M+H$^+$).

5-Bromo-2-dimethylcarbamoylsulfanyl-3-nitro-benzoic acid ethyl ester

5-Bromo-2-dimethylthiocarbamoyloxy-3-nitro-benzoic acid ethyl ester (6.2 g, 16.4 mmol) is taken up in 60 mL of NMP and placed into a round bottom flask. The reaction is heated at 100° C. for 6 hours at which time the LCMS showed 100% conversion. The reaction is poured into ether/ethyl acetate (1:1 350 mL) and then washed with water 2× (50 mL), Brine (50 mL) dried (MgSO$_4$) filtered and evaporated in vacuo to give 3.5 g (56%) of a yellow solids that is purified on silica with hexanes ethyl acetate as the eluent. LCMS (ESMS): m/z 378.4 (M+H$^+$).

Dimethyl-thiocarbamic acid S-(4-bromo-2-hydroxymethyl-6-nitro-phenyl)ester

5-Bromo-2-dimethylcarbamoylsulfanyl-3-nitro-benzoic acid ethyl ester (3.0 g, 9.4 mmol) is taken up in THF (40 mL)/diethyl ether (10 mL) and cooled to zero with an ice bath. Borane in THF (1M, 20 mL, 2.1 mmol) is added dropwise to the reaction and then the reaction warmed to room temperature. An additional equivalent of borane is added, and the reaction warmed to 45° C. The reaction is stirred at 45° C. for 4 hours and then the reaction cooled to zero and quenched by the slow addition of saturated NH$_4$Cl. The reaction is poured into water and then extracted with ethyl acetate. The combined organic layers were dried filtered and evaporated. The residue is purified on silica gel with DCM/MeOH as the eluent to afford 2.5 g (91%) of the title product. LCMS (ESMS): m/z 336.9 (M+H$^+$).

(S)-3-[3-(5-Bromo-2-dimethylcarbamoylsulfanyl-3-nitro-benzyl)-2-oxo-2,3-dihydro-benzimidazol-1-yl]-hexanoic acid ethyl ester Dimethyl-thiocarbamic acid S-(4-bromo-2-hydroxymethyl-6-nitro-phenyl) ester (250 mg, 0.74 mmol), triphenylphosphine (215 mg, 0.82 mmol) and (S)-3-(2-Oxo-2,3-dihydro-benzoimidazol-1-yl)-hexanoic acid ethyl ester (303 mg, 0.82 mmol,) are added to a flask with a N$_2$ line. Dry THF (6 mL) is added and the reaction is cooled to 0° C. DIAD (1 ml of THF, 0.82 mmol) is added dropwise over the course of 5 minutes to the reaction and the reaction is warmed slowly to room temperature. The reaction is stirred for 1 hour then evaporated in vacuo and directly purified on silica gel with dichloromethane methanol as the eluent. Reaction is re-purified via-preparative LC/MS to give 166 mg (37%) of the desired compound. LCMS (ESMS): m/z 594.4 (M+H$^+$).

(S)-3-[3-(5-Bromo-2-oxo-2,3-dihydro-benzothiazol-7-ylmethyl)-2-oxo-2,3-dihydro-benzimidazol-1-yl]-hexanoic acid ethyl ester (S)-3-[3-(5-Bromo -2-dimethylcarbamoylsulfanyl-3-nitro-benzyl)-2-oxo-2,3-dihydro-benzimidazol-1-yl]-hexanoic acid ethyl ester (70 mg, 0.11 mmol) is suspended in ethylacetate (0.5 mL)/ethanol (0.5 mL) and then tin chloride (133 mg, 0.6 mmol) is added. The resulting suspension is equipped with a reflux condenser and heated to 75° C. for 1 hour. Upon completion the reaction is cooled to room temperature and the solvents evaporated in vacuo. The resulting solid is taken up in ethyl acetate and the product is filtered. The solvent is evaporated in vacuo and the resulting solid is purified via prep reverse phase LC to give 33 mg (54%) of the title compound. LCMS (ESMS): m/z 519.7 (M+H$^+$).

(S)-3-[3-(5-Bromo-2-oxo-2,3-dihydro-benzothiazol-7-ylmethyl)-2-oxo-2,3-dihydro-benzimidazol-1-yl]-hexanoic acid (S)-3-[3-(5-Bromo-2-oxo-2,3-dihydro-benzothiazol-7-ylmethyl)-2-oxo-2,3-dihydro-benzimidazol-1-yl]-hexanoic acid ethyl ester (33 mg, 0.06 mmol) is dissolved in dioxane (3 mL) and then LiOH (8 mg, 0.3 mmol) in water (3 mL) is added to the reaction. The reaction is stirred for 1 hour then acidified with 4N HCl and the solvents evaporated in vacuo. The resulting crude solid is purified on reverse phase LC/MS to give 10 mg (32%) of the title compound as a white solid. LCMS (ESMS): m/z 491.8 (M+H$^+$).

METHODS OF USE

In accordance with the invention, there are provided methods of using the compounds as described herein and their pharmaceutically acceptable derivatives. The compounds used in the invention inhibit Chymase. Since Chymase is known to transform angiotensin I to angiotensin II and may contribute to activation of TGF-β, matrix proteases and cytokines, the inhibition of Chymase is an attractive means for preventing and treating a variety of diseases or conditions. Examples include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertenstion, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. The compounds of the invention may also be useful for the following procedures: coronary artery bypass grafting, percutaneous coronary intervention and stenting.

Other diseases within the scope of the invention include allergic rhinitis, dermatitis, asthma, chronic obstructive pulmonary disease (COPD), and pulmonary inflammation, asthma, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, traumatic arthritis, and sepsis. Reference in this regard may be made to U.S. Pat. Nos. 5,948,785 ; 6,271,238; 5,691,335; 5,814,631; 6,300,337; EP 1,099,690; U.S. Pat. No. 6,323,219; US 2005-0245536 A1; Fukami, et al., *Current Pharmaceutical Design* 1998, vol. 4, pp. 439-453.

As disclosed in the Background of the Invention, the compounds of the invention may contribute to activation of cytokines, they will therefore be useful for treating oncological diseases. Reference in this regard may be made to US 2005-0245536 A1. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Combinations with other therapeutics include but are not limited to: angiotensin II receptor blockers, angiotensin converting enzyme inhibitors, CETP inhibitors/apoA1 mimetics, adenosine diphosphate (P2Y12) inhibitors, direct thrombin inhibitors, aldosterone antagonists, factor Xa inhibitors, natriuretic peptides (ANP/BNP), renin inhibitors, anti-arrhythmics, Chymase inhibitors, HMG-CoA Reductase inhibitors (Statins), Rho kinase inhibitors, beta-blockers, Lipoprotein-associated phospholipase A2 inhibitors, cardiac glycosides, calcium channel blockers, diuretics, fibrates, Endothelin Receptor Antagonists, GPIIb/IIIa inhibitors, histone deacetylase inhibitors, heparins, nicotinic acid derivatives, vasopeptidase inhibitors, nitrites and nitrates, fatty acid oxidation inhibitors, oral anticoagulants, acyl-CoA:cholesterol acyltransferase inhibitors, thrombolytics, microsomal triglyceride transfer protein inhibitors, thiazolidinediones, adenosine receptor modulators, cholesterol absorbtion inhibitors, Advanced Glycation End products/receptor (AGE/RAGE) interaction modulators/blockers, acetyl salicylic acid, dipyridamole, gene therapy and cell therapy.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:
(i) preventing the disease-state from occurring in a patient, in particular, when such patient is genetically or otherwise predisposed to the disease-state but has not yet been diagnosed as having it;
(ii) inhibiting or ameliorating the disease-state in a patient, i.e., arresting or slowing its development; or
(iii) relieving the disease-state in a patient, i.e., causing regression or cure of the disease-state.

In vitro Assay for Inhibition of Chymase

Chymase assays were performed in a total volume of 15 μL in Corning black opaque 384-well microliter plates with a non-binding surface (Corning, N.Y.). The assay buffer was comprised of 20 mM Tris HCl pH 8.0, 50 mM NaCl, 0.01% CHAPS. The test compounds were serially diluted 3-fold with neat DMSO in a 96-well polypropylene plate from a 10 mM DMSO stock to give the 10 point dose response curve. 3 μL of the resulting DMSO solution were transferred to a 384-well polypropylene plate in duplicate, and 37 μL of assay buffer was added. Chymase was added to the assay plate in 3 uL of assay buffer followed by 2 uL of the appropriate compound dilution using a PlateMate Plus (Matrix Technologies Corp., Hudson, N.H.). The reaction was initiated by the addition of 10 uL rhodamine 110, bis-(succinoyl-1-alanyl-1-alanyl-1-prolyl-1-phenylalanylamide) (American Peptides, Sunnyvale, Calif.) in assay buffer containing 150 μM tris(2-carboxyethyl)phosphine (TCEP, Pierce Chemical, Rockford, Ill.) using a Multidrop (Thermo Electron Corp., Waltham, Mass.). Final assay concentrations were 500 pM chymase, 100 nM substrate, 100 μM TCEP, and 1% DMSO. The plates were incubated at 28° C. and 80% humidity for 1 hour, at which time the fluorescence was read on a Viewlux 1430 Microplate Imager (Perkin Elmer Life Sciences, Boston, Mass.) with 485 nm excitation, 530 nm emission, and a fluorescein dichroic mirror. The percentage of control values were calculated relative to assay blanks containing complete reaction minus chymase and a 100% control containing assay buffer with 1% DMSO in place of compound. IC50 values were obtained by fitting the data using XLFit4 (IDBS Software).

Preferred compounds of the invention have an activity of 1 microMolar or less.

All patent and literature references cited in this application are incorporated herein by reference in their entirety.

The invention claimed is:

1. A compound chosen from
N-[(2-fluorophenyl)sulfonyl]-3-{3-[(4-methyl-1-benzothien-3-yl)methyl]-2-oxo-2,3-dihydro-1H-benzimidazol-1-yl}hexanamide;
(3R)-3-{3-[(4-methyl-1-benzothien-3-yl)methyl]-2-oxo-2,3-dihydro-1H-benzimidazol-1-yl}-3-phenylpropanoic acid;
N-[(1,2-dimethyl-1H-imidazol-4-yl)sulfonyl]-3-{3-[(4-methyl-1-benzothien-3-yl)methyl]-2-oxo-2,3-dihydro-1H-benzimidazol-1-yl}hexanamide;
3-{3-[(4-methyl-1-benzothien-3-yl)methyl]-2-oxo-2,3-dihydro-1H-benzimidazol-1-yl}-N-(phenylsulfonyl)hexanamide;
(3S)-N-[1,2-dimethyl-1H-imidazol-4-yl)sulfonyl]-3-{3-[(1,4-dimethyl-1H-indol-3-yl)methyl]-2-oxo-2,3-dihydro-1H-benzimidazol-1-yl}hexanamide;
(3S)-3-{3-[(1,4-dimethyl-1H-indol-3-yl)methyl]-2-oxo-2,3-dihydro-1H-benzimidazol-1-yl}-N-(pyridin-2-ylsulfonyl)hexanamide;
2-({3-[(5-chloro-1,2,3-trimethyl-1H-indol-7-yl)methyl]-2-oxo-2,3-dihydro-1H-benzimidazol-1-yl}methyl)pentanoic acid;
3-{3-[(5-chloro-1,2,3-trimethyl-1H-indol-7-yl)methyl]-2-oxo-2,3-dihydro-1H-benzimidazol-1-yl}-2-phenylpropanoic acid;
(2S)-{3-[(4-methyl-1-benzothien-3-yl)methyl]-2-oxo-2,3-dihydro-1H-benzimidazol-1-yl}(phenyl)acetic acid;
N-[(4-fluorophenyl)sulfonyl]-3-{3-[(4-methyl-1-benzothien-3-yl)methyl]-2-oxo-2,3-dihydro-1H-benzimidazol-1-yl}hexanamide;
3-{3-[(4-methyl-1-benzothien-3-yl)methyl]-2-oxo-2,3-dihydro-1H-benzimidazol-1-yl}-N-[(1-methyl-1H-imidazol-4-yl)sulfonyl]hexanamide;
(3S)-3-{3-[(1,4-dimethyl-1H-indol-3-yl)methyl]-2-oxo-2,3-dihydro-1H-benzimidazol-1-yl}-N-[(1-methyl-1H-imidazol-4-yl)sulfonyl]hexanamide;
(3R)-3-{3-[(1,4-dimethyl-1H-indol-3-yl)methyl]-2-oxo-2,3-dihydro-1H-benzimidazol-1-yl}-3-phenylpropanoic acid;
(3S)-3-{6-methyl-3-[(4-methyl-1-benzothien-3-yl)methyl]-2-oxo-2,3-dihydro-1H-benzimidazol-1-yl}-5-phenylpentanoic acid;
3-{3-[(1,4-dimethyl-1H-indol-3-yl)methyl]-6-methyl-2-oxo-2,3-dihydro-1H-benzimidazol-1-yl}-N-(phenylsulfonyl)hexanamide;
3-{3-[(4-methyl-1-benzothien-3-yl)methyl]-2-oxo-2,3-dihydro-1H-benzimidazol-1-yl}-N-(pyridin-2-ylsulfonyl)hexanamide;
N-[(2-methoxyphenyl)sulfonyl]-3-{3-[(4-methyl-1-benzothien-3-yl)methyl]-2-oxo-2,3-dihydro-1H-benzimidazol-1-yl}hexanamide;
3-{3-[(4-methyl-1-benzothien-3-yl)methyl]-2-oxo-2,3-dihydro-1H-benzimidazol-1-yl}octanoic acid;
(3S)-3-{3-[(1,4-dimethyl-1H-indol-3-yl)methyl]-2-oxo-2,3-dihydro-1H-benzimidazol-1-yl}-N-(phenylsulfonyl)hexanamide;
(3R)-3-{3-[(1,4-dimethyl-1H-indol-3-yl)methyl]-6-methyl-2-oxo-2,3-dihydro-1H-benzimidazol-1-yl}-3-pyridin-3-ylpropanoic acid;
3-{3-[(4-methyl-1-benzothien-3-yl)methyl]-2-oxo-2,3-dihydro-1H-benzimidazol-1-yl}octanoic acid;
3-{3-[(1,4-dimethyl-1H-indol-3-yl)methyl]-5,6-dimethyl-2-oxo-2,3-dihydro-1H-benzimidazol-1-yl}hexanoic acid;
3-ethoxy-3-{3-[(4-methyl-1-benzothien-3-yl)methyl]-2-oxo-2,3-dihydro-1H-benzimidazol-1-yl}-N-(phenylsulfonyl)propanamide;
(3S)-3-{3-[(4-methyl-1-benzothien-3-yl)methyl]-2-oxo-2,3-dihydro-1H-benzimidazol-1-yl}-3-phenylpropanoic acid;
(3S)-N-(tert-butylsulfonyl)-3-{3-[(1,4-dimethyl-1H-indol-3-yl)methyl]-2-oxo-2,3-dihydro-1H-benzimidazol-1-yl}hexanamide;
2-({3-[(1,4-dimethyl-1H-indol-3-yl)methyl]-2-oxo-2,3-dihydro-1H-benzimidazol-1-yl}methyl)pentanoic acid;
(3S)-3-{2-oxo-3-[(1,4,6-trimethyl-1H-indol-3-yl)methyl]-2,3-dihydro-1H-benzimidazol-1-yl}hexanoic acid;
3-{3-[(4-methyl-1-benzothien-3-yl)methyl]-2-oxo-2,3-dihydro-1H-benzimidazol-1-yl}heptanoic acid;
N-[(3-fluorophenyl)sulfonyl]-3-{3-[(4-methyl-1-benzothien-3-yl)methyl]-2-oxo-2,3-dihydro-1H-benzimidazol-1-yl}hexanamide;
3-{6-methyl-3-[(4-methyl-1-benzothien-3-yl)methyl]-2-oxo-2,3-dihydro-1H-benzimidazol-1-yl}hexanoic acid;
3-ethoxy-3-{6-methyl-3-[(4-methyl-1-benzothien-3-yl)methyl]-2-oxo-2,3-dihydro-1H-benzimidazol-1-yl}propanoic acid;
3-{5,6-dimethyl-3-[(4-methyl-1-benzothien-3-yl)methyl]-2-oxo-2,3-dihydro-1H-benzimidazol-1-yl}-3-ethoxypropanoic acid;
(3S)-3-{3-[(4-methyl-1-benzothien-3-yl)methyl]-2-oxo-2,3-dihydro-1H-benzimidazol-1-yl}hexanoic acid;
3-{2-oxo-3-[(1,4,6-trimethyl-1H-indol-3-yl)methyl]-2,3-dihydro-1H-benzimidazol-1-yl}hexanoic acid;
N-[(4-methoxyphenyl)sulfonyl]-3-{3-[(4-methyl-1-benzothien-3-yl)methyl]-2-oxo-2,3-dihydro-1H-benzimidazol-1-yl}hexanamide;
3-{3-[(1,4-dimethyl-1H-indol-3-yl)methyl]-6-methyl-2-oxo-2,3-dihydro-1H-benzimidazol-1-yl}hexanoic acid;
N-(tert-butylsulfonyl)-3-{3-[(1,4-dimethyl-1H-indol-3-yl)methyl]-6-methyl-2-oxo-2,3-dihydro-1H-benzimidazol-1-yl}hexanamide;
3-{3-[(1,4-dimethyl-1H-indol-3-yl)methyl]-2-oxo-2,3-dihydro-1H-benzimidazol-1-yl}-2,2-dimethylhexanoic acid;
1-({3-[(1,4-dimethyl-1H-indol-3-yl)methyl]-2-oxo-2,3-dihydro-1H-benzimidazol-1-yl}methyl)cyclohexanecarboxylic acid;
3-ethoxy-3-{3-[(4-methyl-1-benzothien-3-yl)methyl]-2-oxo-2,3-dihydro-1H-benzimidazol-1-yl}propanoic acid;
N-[(3-methoxyphenyl)sulfonyl]-3-{3-[(4-methyl-1-benzothien-3-yl)methyl]-2-oxo-2,3-dihydro-1H-benzimidazol-1-yl}hexanamide;
3-{3-[(6-bromo-1H-indol-4-yl)methyl]-2-oxo-2,3-dihydro-1H-benzimidazol-1-yl}hexanoic acid;
2-({3-[(4,6-dimethyl-1,2-benzisothiazol-3-yl)methyl]-2-oxo-2,3-dihydro-1H-benzimidazol-1-yl}methyl)pentanoic acid;
(3S)-3-{3-[(1,4-dimethyl-1H-indol-3-yl)methyl]-2-oxo-2,3-dihydro-1H-benzimidazol-1-yl}hexanoic acid;

3-{3-[(1,4-dimethyl-1H-indol-3-yl)methyl]-2-oxo-2,3-dihydro-1H-benzimidazol-1-yl}-4-methoxy-N-[(1-methyl-1H-imidazol-4-yl)sulfonyl]butanamide;

3-{3-[(6-chloro-1H-indol-4-yl)methyl]-2-oxo-2,3-dihydro-1H-benzimidazol-1-yl}hexanoic acid;

(3S)-3-{3-[(4-methyl-1-benzothien-3-yl)methyl]-2-oxo-2,3-dihydro-1 H-benzimidazol-1-yl}-4-phenylbutanoic acid;

3-{3-[(4-methyl-1-benzothien-3-yl)methyl]-2-oxo-2,3-dihydro-1H-benzimidazol-1-yl}hexanoic acid;

3-{3-[(4-methyl-1-benzothien-3-yl)methyl]-2-oxo-2,3-dihydro-1H-benzimidazol-1-yl}-N-(pyridin-3-ylsulfonyl)hexanamide;

2-({3-[(5-chloro-1,2,3-trimethyl-1H-indol-7-yl)methyl]-2-oxo-2,3-dihydro-1H-benzimidazol-1-yl}methyl)butanoic acid;

2-{3-[(4-methyl-1-benzothien-3-yl)methyl]-2-oxo-2,3-dihydro-1H-benzimidazol-1-yl}pentane-1-sulfonic acid;

(3S)-3-{3-[(1,4-dimethyl-1H-indol-3-yl)methyl]-2-oxo-2,3-dihydro-1H-benzimidazol-1-yl}-N-(isopropylsulfonyl)hexanamide;

3-{3-[(1,4-dimethyl-1H-indol-3-yl)methyl]-2-oxo-2,3-dihydro-1H-benzimidazol-1-yl}hexanoic acid;

3-{3-[(1,4-dimethyl-1H-indol-3-yl)methyl]-2-oxo-5-(1,3-thiazol-2-ylamino)-2,3-dihydro-1H-benzimidazol-1-yl}hexanoic acid;

1-({3-[(5-chloro-1,2,3-trimethyl-1H-indol-7-yl)methyl]-2-oxo-2,3-dihydro-1H-benzimidazol-1-yl}methyl)cyclohexanecarboxylic acid;

N-(cyclopropylsulfonyl)-3-{3-[(4-methyl-1-benzothien-3-yl)methyl]-2-oxo-2,3-dihydro-1H-benzimidazol-1-yl}hexanamide;

5-methoxy-3-{3-[(4-methyl-1-benzothien-3-yl)methyl]-2-oxo-2,3-dihydro-1H-benzimidazol-1-yl}-5-oxopentanoic acid;

(3S)-N-cyano-3-{3-[(1,4-dimethyl-1H-indol-3-yl)methyl]-2-oxo-2,3-dihydro-1H-benzimidazol-1-yl}hexanamide;

3-{3-[(1,4-dimethyl-1H-indol-3-yl)methyl]-2-oxo-2,3-dihydro-1H-benzimidazol-1-yl}-3-ethoxypropanoic acid;

3-{5-bromo-3-[(1,4-dimethyl-1H-indol-3-yl)methyl]-2-oxo-2,3-dihydro-1H-benzimidazol-1-yl}hexanoic acid;

5-methyl-3-{3-[(4-methyl-1-benzothien-3-yl)methyl]-2-oxo-2,3-dihydro-1H-benzimidazol-1-yl}hexanoic acid;

(3S)-3-{3-[(1,4-dimethyl-1H-indol-3-yl)methyl]-2-oxo-2,3-dihydro-1H-benzimidazol-1-yl}-N-(ethylsulfonyl)hexanamide;

3-{3-[(4-methyl-1-benzothien-3-yl)methyl]-2-oxo-2,3-dihydro-1H-benzimidazol-1-yl}-N-(phenylsulfonyl)propanamide;

(3S)-N-(cyclopropylsulfonyl)-3-{3-[(1,4-dimethyl-1H-indol-3-yl)methyl]-2-oxo-2,3-dihydro-1H-benzimidazol-1-yl}hexanamide;

3-{3-[(4-methyl-1-benzothien-3-yl)methyl]-2-oxo-2,3-dihydro-1H-benzimidazol-1-yl}pentanedioic acid;

3-{3-[(5-chloro-1,2,3-trimethyl-1H-indol-7-yl)methyl]-2-oxo-2,3-dihydro-1H-benzimidazol-1-yl}hexanoic acid;

1-(1-{3-[(1,4-dimethyl-1H-indol-3-yl)methyl]-2-oxo-2,3-dihydro-1H-benzimidazol-1-yl}butyl)cyclopropanecarboxylic acid;

3-{3-[(3-bromo-1-naphthyl)methyl]-2-oxo-2,3-dihydro-1H-benzimidazol-1-yl}hexanoic acid;

3-{3-[(1-cyano-5,7-dimethylindolizin-3-yl)methyl]-2-oxo-2,3-dihydro-1H-benzimidazol-1-yl}hexanoic acid;

3-{3-[(5-chloro-1,2,3-trimethyl-1H-indol-7-yl)methyl]-2-oxo-2,3-dihydro-1H-benzimidazol-1-yl}propanoic acid;

N-[(2-{3-[(4-methyl-1-benzothien-3-yl)methyl]-2-oxo-2,3-dihydro-1H-benzimidazol-1-yl}ethyl)carbamoyl]benzenesulfonamide;

3-methoxy-3-{3-[(4-methyl-1-benzothien-3-yl)methyl]-2-oxo-2,3-dihydro-1H-benzimidazol-1-yl}propanoic acid;

3-{3-[(4-methyl-1-benzothien-3-yl)methyl]-2-oxo-2,3-dihydro-1H-benzimidazol-1-yl}-N-(methylsulfonyl)hexanamide;

(1-{3-[(1,4-dimethyl-1H-indol-3-yl)methyl]-2-oxo -2,3-dihydro-1H-benzimidazol-1-yl}cyclohexyl)acetic acid;

3-{3-[(5-chloro-1,3-dimethyl-1H-indol-7-yl)methyl]-2-oxo-2,3-dihydro-1H-benzimidazol-1-yl}hexanoic acid;

(3R)-3-{6-methyl-3-[(4-methyl-1-benzothien-3-yl)methyl]-2-oxo-2,3-dihydro-1H-benzimidazol-1-yl}-5-phenylpentanoic acid;

3-{3-[(1,4-dimethyl-1H-indol-3-yl)methyl]-6-methyl-2-oxo-2,3-dihydro-1H-benzimidazol-1-yl}-N-(ethylsulfonyl)hexanamide;

(3S)-3-{3-[(4,6-dimethyl-1,2-benzisothiazol-3-yl)methyl]-2-oxo-2,3-dihydro-1H-benzimidazol-1-yl}hexanoic acid;

N-[(2-{3-[(4-methyl-1-benzothien-3-yl)methyl]-2-oxo-2,3-dihydro-1H-benzimidazol-1-yl}ethyl)sulfonyl]benzamide;

(2S)-2-{3-[(4-methyl-1-benzothien-3-yl)methyl]-2-oxo-2,3-dihydro-1H-benzimidazol-1-yl}pentanoic acid;

3-{3-[(3,8-dimethylindolizin-1-yl)methyl]-2-oxo-2,3-dihydro-1H-benzimidazol-1-yl}hexanoic acid;

(3S)-N-(aminosulfonyl)-3-{3-[(1,4-dimethyl-1H-indol-3-yl)methyl]-2-oxo-2,3-dihydro-1H-benzimidazol-1-yl}hexanamide;

3-ethoxy-3-[3-(1-naphthylmethyl)-2-oxo-2,3-dihydro-1H-benzimidazol-1-yl]propanoic acid;

(3R)-3-{3-[(1,4-dimethyl-1H-indol-3-yl)methyl]-2-oxo-2,3-dihydro-1H-benzimidazol-1-yl}hexanoic acid;

(3R)-3-{3-[(4-methyl-1-benzothien-3-yl)methyl]-2-oxo-2,3-dihydro-1H-benzimidazol-1-yl}hexanoic acid;

2-({3-[(1,4-dimethyl-1H-indol-3-yl)methyl]-2-oxo -2,3-dihydro-1H-benzimidazol-1-yl}methyl)butanoic acid;

3-{3-[(4,6-dimethyl-1,2-benzisothiazol-3-yl)methyl]-2-oxo-2,3-dihydro-1H-benzimidazol-1-yl}hexanoic acid;

3-{3-[(4-methyl-1-benzothien-3-yl)methyl]-2-oxo-2,3-dihydro-1H-benzimidazol-1-yl}pentanoic acid;

1-({3-[(1,4-dimethyl-1H-indol-3-yl)methyl]-2-oxo -2,3-dihydro-1H-benzimidazol-1-yl}methyl)cyclopentanecarboxylic acid;

2-{3-[(4-methyl-1-benzothien-3-yl)methyl]-2-oxo-2,3-dihydro-1H-benzimidazol-1-yl}-N-(phenylsulfonyl)acetamide;

3-{3-[(1-ethyl-4-methyl-1H-indol-3-yl)methyl]-2-oxo-2,3-dihydro-1H-benzimidazol-1-yl}hexanoic acid;

3-{3-[(5-bromo-1-methyl-1H-indol-7-yl)methyl]-2-oxo-2,3-dihydro-1H-benzimidazol-1-yl}hexanoic acid;

3-{3-[(5-chloro-1,2,3-trimethyl-1H-indol-7-yl)methyl]-6-methyl-2-oxo-2,3-dihydro-1H-benzimidazol-1-yl}pentanoic acid;

3-{3-[(5-chloro-1,2,3-trimethyl-1H-indol-7-yl)methyl]-6-methyl-2-oxo-2,3-dihydro-1H-benzimidazol-1-yl}hexanoic acid;

(3S)-3-{3-[(1,4-dimethyl-1H-indol-3-yl)methyl]-2-oxo-2,3-dihydro-1H-benzimidazol-1-yl}-N-(methylsulfonyl)hexanamide;

3-{3-[(6,8-dichloro-3-methylindolizin-1-yl)methyl]-2-oxo-2,3-dihydro-1H-benzimidazol-1-yl}hexanoic acid;
4-{3-[(1,4-dimethyl-1H-indol-3-yl)methyl]-2-oxo-2,3-dihydro-1H-benzimidazol-1-yl}heptanoic acid;
(2S)-2-{3-[(4-methyl-1-benzothien-3-yl)methyl]-2-oxo-2,3-dihydro-1H-benzimidazol-1-yl}butanoic acid;
1-({3-[(5-chloro-1,2,3-trimethyl-1H-indol-7-yl)methyl]-2-oxo-2,3-dihydro-1H-benzimidazol-1-yl}methyl)cyclopentanecarboxylic acid;
2,2-dimethyl-3-{3-[(4-methyl-1-benzothien-3-yl)methyl]-2-oxo-2,3-dihydro-1H-benzimidazol-1-yl}propanoic acid;
5-hydroxy-3-{3-[(4-methyl-1-benzothien-3-yl)methyl]-2-oxo-2,3-dihydro-1H-benzimidazol-1-yl}pentanoic acid;
3-{3-[(6-bromo-2-oxo-2,3-dihydro-1H-indol-4-yl)methyl]-2-oxo-2,3-dihydro-1H-benzimidazol-1-yl}hexanoic acid;
3-[3-(1-naphthylmethyl)-2-oxo-2,3-dihydro-1H-benzimidazol-1-yl]hexanoic acid;
3-{3-[(6-bromo-1-methyl-1H-indol-4-yl)methyl]-2-oxo-2,3-dihydro-1H-benzimidazol-1-yl}hexanoic acid;
2-{3-[(1,4-dimethyl-1H-indol-3-yl)methyl]-2-oxo-2,3-dihydro-1H-benzimidazol-1-yl}cyclopent-1-ene-1-carboxylic acid;
3-{3-[(1,4-dimethyl-1H-indol-3-yl)methyl]-2-oxo-2,3-dihydro-1H-benzimidazol-1-yl}-4-methoxybutanoic acid;
3-{3-[5-chloro-1,2,3-trimethyl-1H-indol-7-yl)methyl]-2-oxo-2,3-dihydro-1H-benzimidazol-1-yl}-2-methylpropanoic acid;
(1-{3-[1,4-dimethyl-1H-indol-3-yl)methyl]-2-oxo-2,3-dihydro-1H-benzimidazol-1-yl}cyclopentyl)acetic acid;
3-{3-[1-cyano-5-methylindolizin-3-yl)methyl]-2-oxo-2,3-dihydro-1H-benzimidazol-1-yl}hexanoic acid;
2-{3-[(1,4-dimethyl-1H-indol-3-yl)methyl]-2-oxo-2,3-dihydro-1H-benzimidazol-1-yl}-3-methoxybenzoic acid;
3-{3-[5-chloro-1-methyl-1H-indol-7-yl)methyl]-2-oxo-2,3-dihydro-1H-benzimidazol-1-yl}hexanoic acid;
3-{7-bromo-3-[(1,4-dimethyl-1H-indol-3-yl)methyl]-2-oxo-2,3-dihydro-1H-benzimidazol-1-yl}propanoic acid;
5-methyl-3-[3-(1-naphthylmethyl)-2-oxo-2,3-dihydro-1H-benzimidazol-1-yl]hexanoic acid;
3-{3-[(6-methyl-1H-indol-4-yl)methyl]-2-oxo-2,3-dihydro-1H-benzimidazol-1-yl}hexanoic acid;
4-{3-[(4-methyl-1-benzothien-3-yl)methyl]-2-oxo-2,3-dihydro-1H-benzimidazol-1-yl}-N-(phenylsulfonyl)butanamide;
(2E)-3-{3-[(4-methyl-1-benzothien-3-yl)methyl]-2-oxo-2,3-dihydro-1H-benzimidazol-1-yl}acrylic acid;
3-{3-[(1,4-dimethyl-1H-indol-3-yl)methyl]-2-oxo-2,3-dihydro-1H-benzimidazol-1-yl}-2,2-dimethylbutanoic acid;
(2S)-3-methyl-2-{3-[(4-methyl-1-benzothien-3-yl)methyl]-2-oxo-2,3-dihydro-1H-benzimidazol-1-yl}butanoic acid;
3-{3-[(1,4-dimethyl-1H-indol-3-yl)methyl]-2-oxo-2,3-dihydro-1H-benzimidazol-1-yl}-4-methoxy-2,2-dimethylbutanoic acid;
3-[3-(1H-indol-3-ylmethyl)-2-oxo-2,3-dihydro-1H-benzimidazol-1-yl]hexanoic acid;
3-{3-[(1,4-dimethyl-1H-indol-3-yl)methyl]-2-oxo-2,3-dihydro-1H-benzimidazol-1-yl}-4-methoxybenzoic acid;
3-{2-oxo-3-[(1,2,3,5-tetramethyl-1H-indol-7-yl)methyl]-2,3-dihydro-1H-benzimidazol-1-yl}propanoic acid;
3-{3-[(4-methyl-1-benzothien-3-yl)methyl]-2-oxo-2,3-dihydro-1H-benzimidazol-1-yl}propanoic acid;
2-{3-[(1,4-dimethyl-1H-indol-3-yl)methyl]-2-oxo-2,3-dihydro-1H-benzimidazol-1-yl}benzoic acid;
3-{3-[(8-bromo-1-naphthyl)methyl]-2-oxo-2,3-dihydro-1H-benzimidazol-1-yl}hexanoic acid;
3-{3-[(4-methyl-1-benzothien-3-yl)methyl]-2-oxo-2,3-dihydro-1H-benzimidazol-1-yl}butanoic acid;
N-(isopropylsulfonyl)-3-{3-[(4-methyl-1-benzothien-3-yl)methyl]-2-oxo-2,3-dihydro-1H-benzimidazol-1-yl}propanamide;
N-[(2-{3-[(4-methyl-1-benzothien-3-yl)methyl]-2-oxo-2,3-dihydro-1H-benzimidazol-1-yl}ethyl)sulfonyl]acetamide;
3-{3-[(4-methyl-1H-indol-3-yl)methyl]-2-oxo-2,3-dihydro-1H-benzimidazol-1-yl}hexanoic acid;
(2S)-2-{3-[(4-methyl-1-benzothien-3-yl)methyl]-2-oxo-2,3-dihydro-1H-benzimidazol-1-yl}propanoic acid;
2-{3-[(1,4-dimethyl-1H-indol-3-yl)methyl]-2-oxo-2,3-dihydro-1H-benzimidazol-1-yl}-3-methylbenzoic acid;
3-{3-[(6-bromo-1H-indol-4-yl)methyl]-2-oxo-2,3-dihydro-1H-benzimidazol-1-yl}propanoic acid;
3-{3-[(4-methyl-1-benzothien-3-yl)methyl]-2-oxo-2,3-dihydro-1H-benzimidazol-1-yl}-N-(methylsulfonyl)propanamide;
3-{3-[(4-chloro-1-methyl-1H-indol-3-yl)methyl]-2-oxo-2,3-dihydro-1H-benzimidazol-1-yl}hexanoic acid;
3-{3-[(6-chloro-1H-indol-4-yl)methyl]-2-oxo-2,3-dihydro-1H-benzimidazol-1-yl}propanoic acid;
3-methoxy-3-[3-(1-naphthylmethyl)-2-oxo-2,3-dihydro-1H-benzimidazol-1-yl]propanoic acid;
4-{3-[(1,4-dimethyl-1H-indol-3-yl)methyl]-2-oxo-2,3-dihydro-1H-benzimidazol-1-yl}pentanoic acid;
3-{3-[(5-fluoro-1,2,3-trimethyl-1H-indol-7-yl)methyl]-2-oxo-2,3-dihydro-1H-benzimidazol-1-yl}hexanoic acid;
4-{3-[(4-methyl-1-benzothien-3-yl)methyl]-2-oxo-2,3-dihydro-1H-benzimidazol-1-yl}butanoic acid;
3-[3-(3-hydroxy-2,5-dimethylbenzyl)-2-oxo-2,3-dihydro-1H-benzimidazol-1-yl]hexanoic acid;
{3-[(4-methyl-1-benzothien-3-yl)methyl]-2-oxo-2,3-dihydro-1H-benzimidazol-1-yl}acetic acid;
2-{3-[(4-methyl-1-benzothien-3-yl)methyl]-2-oxo-2,3-dihydro-1H-benzimidazol-1-yl}ethanesulfonic acid;
3-{2-oxo-3-[(1,2,3-trimethyl-1H-indol-7-yl)methyl]-2,3-dihydro-1H-benzimidazol-1-yl}propanoic acid;
1-[(4-methyl-1-benzothien-3-yl)methyl]-3-[2-(1H-tetrazol-5-yl)ethyl]-1,3-dihydro-2H-benzimidazol-2-one;
3-{3-[(6-bromo-1-methyl-2-oxo-2,3-dihydro-1H-indol-4-yl)methyl]-2-oxo-2,3-dihydro-1H-benzimidazol-1-yl}hexanoic acid;
3-[2-oxo-3-(2,3,5-trichlorobenzyl)-2,3-dihydro-1H-benzimidazol-1-yl]hexanoic acid;
3-{2-oxo-3-[(1,2,3-trimethyl-1H-indol-7-yl)methyl]-2,3-dihydro-1H-benzimidazol-1-yl}hexanoic acid;
(1R,2R)-2-{3-[(1,4-dimethyl-1H-indol-3-yl)methyl]-2-oxo-2,3-dihydro-1H-benzimidazol-1-yl}cyclohexanecarboxylic acid;
3-(6-{[2-(3,4-dimethoxyphenyl)ethyl]carbamoyl}-3-[(4-methyl-1-benzothien-3-yl)methyl]-2-oxo-2,3-dihydro-1H-benzimidazol-1-yl)propanoic acid;
3-{3-[(1,4-dimethyl-1H-indol-3-yl)methyl]-2-oxo-2,3-dihydro-1H-benzimidazol-1-yl}-3-methylbutanoic acid;
3-{3-[(1,4-dimethyl-1H-indol-3-yl)methyl]-7-methyl-2-oxo-2,3-dihydro-1H-benzimidazol-1-yl}propanoic acid;
3-{3-[(8-bromo-1-naphthyl)methyl]-2-oxo-2,3-dihydro-1H-benzimidazol-1-yl}propanoic acid;

3-{3-[(1,4-dimethyl-1H-indol-3-yl)methyl]-2-oxo-2,3-dihydro-1H-benzimidazol-1-yl}propanoic acid;

2-{3-[(1,4-dimethyl-1H-indol-3-yl)methyl]-2-oxo-2,3-dihydro-1H-benzimidazol-1-yl}-2-methylpropanoic acid;

3-(6-{[2-(3-hydroxy-4-methoxyphenyl)ethyl]carbamoyl}-3-[(4-methyl-1-benzothien-3-yl)methyl]-2-oxo-2,3-dihydro-1H-benzimidazol-1-yl)propanoic acid;

3-{3-[(1,4-dimethyl-1H-indol-3-yl)methyl]-2-oxo-2,3-dihydro-1H-benzimidazol-1-yl}-2-methylpropanoic acid;

3-{3-[(6-chloro-1-methyl-1H-indol-4-yl)methyl]-2-oxo-2,3-dihydro-1H-benzimidazol-1-yl}hexanoic acid;

3-(6-{[2-(2-methoxyphenyl)ethyl]carbamoyl}-3-[(4-methyl-1-benzothien-3-yl)methyl]-2-oxo-2,3-dihydro-1H-benzimidazol-1-yl)propanoic acid;

3-{3-[(4-chloro-1H-indol-3-yl)methyl]-2-oxo-2,3-dihydro-1H-benzimidazol-1-yl}hexanoic acid;

3-({3-[(4-methyl-1-benzothien-3-yl)methyl]-2-oxo-2,3-dihydro-1H-benzimidazol-1-yl}methyl)benzoic acid;

2-{3-[(1,4-dimethyl-1H-indol-3-yl)methyl]-2-oxo-2,3-dihydro-1H-benzimidazol-1-yl}cyclopentanecarboxylic acid;

1-[2-(1,1-dioxido-4-oxo-1,2,5-thiadiazolidin-2-yl)ethyl]-3-[(4-methyl-1-benzothien-3-yl)methyl]-1,3-dihydro-2H-benzimidazol-2-one;

;3-[6-{[2-(3,4-dimethoxyphenyl)ethyl]carbamoyl}-3-(1-naphthylmethyl)-2-oxo-2,3-dihydro-lH-benzimidazol-1-yl]propanoic acid;

4-methyl-3-[3-(1-naphthylmethyl)-2-oxo-2,3-dihydro-1H-benzimidazol-1-yl]pentanoic acid;

3-[3-(5-bromo-2-methylbenzyl)-2-oxo-2,3-dihydro-1H-benzimidazol-1-yl]hexanoic acid;

3-[3-(2,5-dimethylbenzyl)-2-oxo-2,3-dihydro-1H-benzimidazol-1-yl]hexanoic acid;

3-{3-[(5-methoxy-1,2,3-trimethyl-1H-indol-7-yl)methyl]-2-oxo-2,3-dihydro-1H-benzimidazol-1-yl}propanoic acid;

trans-4-({3-[(4-methyl-1-benzothien-3-yl)methyl]-2-oxo-2,3-dihydro-1H-benzimidazol-1-yl}methyl)cyclohexanecarboxylic acid;

3-[3-(2,5-dichlorobenzyl)-2-oxo-2,3-dihydro-1H-benzimidazol-1-yl]hexanoic acid;

3-{3-[(6-chloro-2-oxo-2,3-dihydro-1H-indol-4-yl)methyl]-2-oxo-2,3-dihydro-1H-benzimidazol-1-yl}hexanoic acid;

3-{3-[(5-bromo-1-methyl-2-oxo-2,3-dihydro-1H-indol-7-yl)methyl]-2-oxo-2,3-dihydro-1H-benzimidazol-1-yl}hexanoic acid;

3-[3-(1-naphthylmethyl)-2-oxo-2,3-dihydro-1H-benzimidazol-1-yl]-N-(phenylsulfonyl)propanamide;

3-[6-{[2-(3-hydroxy-4-methoxyphenyl)ethyl]carbamoyl}-3-(1-naphthylmethyl)-2-oxo-2,3-dihydro-1H-benzimidazol-1-yl]propanoic acid;

(3S)-3-{5-(carbamoylamino)-3-[(1,4-dimethyl-1H-indol-3-yl)methyl]-2-oxo-2,3-dihydro-1H-benzimidazol-1-yl}hexanoic acid;

(3S)-3-{5-[(tert-butoxycarbonyl)amino]-3-[(1,4-dimethyl-1H-indol-3-yl)methyl]-2-oxo-2,3-dihydro-1H-benzimidazol-1-yl}hexanoic acid;

3-{6-(benzylcarbamoyl)-3-[(4-methyl-1-benzothien-3-yl)methyl]-2-oxo-2,3-dihydro-1H-benzimidazol-1-yl}propanoic acid;

3-{6-[(2-hydroxyethyl)carbamoyl]-3-[(4-methyl-1-benzothien-3-yl)methyl]-2-oxo-2,3-dihydro-1H-benzimidazol-1-yl}propanoic acid;

3-[3-(5-chloro-2-methylbenzyl)-2-oxo-2,3-dihydro-1H-benzimidazol-1-yl]hexanoic acid;

N-methyl-3-{3-[(4-methyl-1-benzothien-3-yl)methyl]-2-oxo-2,3-dihydro-1H-benzimidazol-1-yl}-N-(phenylsulfonyl)hexanamide;

3-(6-{[2-(4-methoxyphenyl)ethyl]carbamoyl}-3-[(4-methyl-1-benzothien-3-yl)methyl]-2-oxo-2,3-dihydro-1H-benzimidazol-1-yl)propanoic acid;

(2E)-3-[3-(1-naphthylmethyl)-2-oxo-2,3-dihydro-1H-benzimidazol-1-yl]acrylic acid;

3-[6-{[2-(2-methoxyphenyl)ethyl]carbamoyl}-3-(1-naphthylmethyl)-2-oxo-2,3-dihydro-1H-benzimidazol-1-yl]propanoic acid;

3-{6-[(3-hydroxypyrrolidin-1-yl)c arbonyl]-3-(1-naphthylmethyl)-2-oxo-2,3-dihydro-1H-benzimidazol-1-yl}propanoic acid;

3-{3-[(4-fluoro-1-naphthyl)methyl]-2-oxo-2,3-dihydro-1H-benzimidazol-1-yl}hexanoic acid;

3-(6-{[2-(3-methoxyphenyl)ethyl]carbamoyl 1-3-[(4-methyl-1-benzothien-3-yl)methyl]-2-oxo-2,3-dihydro-1H-benzimidazol-1-yl}propanoic acid;

3-{3-[5-chloro-2-(trifluoromethyl)benzyl]-2-oxo-2,3-dihydro-1H-benzimidazol-1 -yl}hexanoic acid;

3-{3-[(4-chloro-1,2,3-trimethyl-1H-indol-7-yl)methyl]-2-oxo-2,3-dihydro-1H-benzimidazol-1-yl}propanoic acid;

3-{3-(1-naphthylmethyl)-2-oxo-6-[(tetrahydrofuran-2-ylmethyl)carbamoyl]-2,3-dihydro-1H-benzimidazol-1-yl}propanoic acid;

3-{6-[(2-hydroxyethyl)carbamoyl]-3-(1-naphthylmethyl)-2-oxo-2,3-dihydro-1H-benzimidazol-1-yl}propanoic acid;

3-{[3-(1-naphthylmethyl)-2-oxo-2,3-dihydro-1H-benzimidazol-1-yl]methyl}benzoic acid;

3-[6-{[2-(1,3-dioxolan-2-yl)ethyl]carbamoyl}-3-(1-naphthylmethyl)-2-oxo-2,3-dihydro-1H-benzimidazol-1-yl]propanoic acid;

3-[6-{[2-(hydroxymethyl)piperidin-1-yl]carbonyl}-3-(1-naphthylmethyl)-2-oxo-2,3-dihydro-1H-benzimidazol-1-yl]propanoic acid;

3-{5-anilino-3-[(1,4-dimethyl-1H-indol-3-yl)methyl]-2-oxo-2,3-dihydro-1H-benzimidazol-1-yl}hexanoic acid;

3-{3-[(1-methyl-1H-indol-7-yl)methyl]-2-oxo-2,3-dihydro-1H-benzimidazol-1-yl}propanoic acid;

3-[6-({3-[acetyl(methyl)amino]pyrrolidin-1-yl}carbonyl)-3-(1-naphthylmethyl)-2-oxo-2,3-dihydro-1H-benzimidazol-1-yl]propanoic acid;

3-(6-{[2-(2-fluorophenyl)ethyl]carbamoyl}-3-[(4-methyl-1-benzothien-3-yl)methyl]-2-oxo-2,3-dihydro-1H-benzimidazol-1-yl)propanoic acid;

3-[6-{[(2S)-2-carbamoylpyrrolidin-1-yl]carbonyl}-3-(1-naphthylmethyl)-2-oxo-2,3-dihydro-1H-benzimidazol-1-yl]propanoic acid;

3-{6-[(3-carbamoylpiperidin-1-yl)carbonyl]-3-(1-naphthylmethyl)-2-oxo-2,3-dihydro-1H-benzimidazol-1-yl}propanoic acid;

3-{3-[2-methyl-5-(trifluoromethyl)benzyl]-2-oxo-2,3-dihydro-1H-benzimidazol-1-yl}hexanoic acid;

3-{3-[(1,3-dimethyl-1H-indol-7-yl)methyl]-2-oxo-2,3-dihydro-1H-benzimidazol-1-yl}propanoic acid;

3-(6-{[2-(2-chlorophenyl)ethyl]carbamoyl}-3-[(4-methyl-1-benzothien-3-yl)methyl]-2-oxo-2,3-dihydro-1H-benzimidazol-1-yl)propanoic acid;

3-{3-[(5-bromo-1-benzothien-3-yl)methyl]-2-oxo-2,3-dihydro-1H-benzimidazol-1-yl}hexanoic acid;

3-{6-[(1,1-dioxidotetrahydro-3-thienyl)carbamoyl]-3-(1-naphthylmethyl)-2-oxo-2,3-dihydro-1H-benzimidazol-1-yl}propanoic acid;

3-(6-{[2-(4-chlorophenyl)ethyl]carbamoyl}-3-[(4-methyl-1-benzothien-3-yl)methyl]-2-oxo-2,3-dihydro-1H-benzimidazol-1-yl)propanoic acid;

3-[6-cyano-3-(1-naphthylmethyl)-2-oxo-2,3-dihydro-1H-benzimidazol-1-yl]propanoic acid;

2-{3-[(4-methyl-1-benzothien-3-yl)methyl]-2-oxo-2,3-dihydro-1H-benzimidazol-1-yl}ethanesulfonamide;

N-(methylsulfonyl)-3-[3-(1-naphthylmethyl)-2-oxo-2,3-dihydro-1H-benzimidazol-1-yl]propanamide ;

3-{3-[(1,2-dimethyl-1H-indol-7-yl)methyl]-2-oxo-2,3-dihydro-1H-benzimidazol-1-yl}propanoic acid;

3-{3-[(4-methyl-1-benzothien-3-yl)methyl]-2-oxo-6-[(2-phenylethyl)carbamoyl]-2,3-dihydro-1H-benzimidazol-1-yl}propanoic acid;

3-{3-[(1-cyano-5-methylindolizin-3-yl)methyl]-2-oxo-2,3-dihydro-1H-benzimidazol-1-yl}propanoic acid;

3-{3-[(5-chloro-1-benzothien-3-yl)methyl]-2-oxo-2,3-dihydro-1H-benzimidazol-1-yl}propanoic acid;

3-{3-[(4-chloro-1,2,3-trimethyl-1H-indol-7-yl)methyl]-2-oxo-2,3-dihydro-1H-benzimidazol-1-yl}hexanoic acid;

3-(6-{[2-(3-fluorophenyl)ethyl]carbamoyl}-3-[(4-methyl-1-benzothien-3-yl)methyl]-2-oxo-2,3-dihydro-1H-benzimidazol-1-yl)propanoic acid;

3-{3-[(4-bromo-1H-indol-3-yl)methyl]-2-oxo-2,3-dihydro-1H-benzimidazol-1-yl}hexanoic acid;

3-{3-[(6-bromo-1-methyl-1H-indol-4-yl)methyl]-2-oxo-2,3-dihydro-1H-benzimidazol-1-yl}propanoic acid;

3-{3-[(6-hydroxy-1-naphthyl)methyl]-2-oxo-2,3-dihydro-1H-benzimidazol-1-yl}propanoic acid;

3-{3-(1-naphthylmethyl)-2-oxo-6-[(2-oxotetrahydrofuran-3-yl)carbamoyl]-2,3-dihydro-1H-benzimidazol-1-yl}propanoic acid;

3-(6-{[2-(3-chlorophenyl)ethyl]carbamoyl}-3-[(4-methyl-1-benzothien-3-yl)methyl]-2-oxo-2,3-dihydro-1H-benzimidazol-1-yl)propanoic acid;

3-[3-(3,5-dibromobenzyl)-2-oxo-2,3-dihydro-1H-benzimidazol-1-yl]hexanoic acid;

3-[3-(3,5-dichlorobenzyl)-2-oxo-2,3-dihydro-1H-benzimidazol-1-yl]hexanoic acid;

3-[6-({(2S)-2-hydroxy-1-(hydroxymethyl)-2-[4-(methylthio)phenyl]ethyl}carbamoyl)-3-(1-naphthylmethyl)-2-oxo-2,3-dihydro-1H-benzimidazol-1-yl]propanoic acid;

3-{3-[(5-chloro-2-oxo-2,3-dihydro-1,3-benzoxazol-7-yl)methyl]-2-oxo-2,3-dihydro-1H-benzimidazol-1-yl}hexanoic acid;

2-({3-[2-bromo-5-(trifluoromethyl)benzyl]-2-oxo-2,3-dihydro-1H-benzimidazol-1-yl}methyl)pentanoic acid;

3-{3-[2-bromo-5-(trifluoromethyl)benzyl]-2-oxo-2,3-dihydro-1H-benzimidazol-1-yl}hexanoic acid;

3-[6-{[(2S)-2-(hydroxymethyl)pyrrolidin-1-yl]carbonyl}-3-(1-naphthylmethyl)-2-oxo-2,3-dihydro-1H-benzimidazol-1-yl]propanoic acid;

3-[3-(1H-indol-3-ylmethyl)-2-oxo-2,3-dihydro-1H-benzimidazol-1-yl]propanoic acid;

3-{3-[(4-chloro-1H-indol-3-yl)methyl]-2-oxo-2,3-dihydro-1H-benzimidazol-1-yl}propanoic acid;

(R)-3-(4-Chloro-phenyl)-3-[(3-(1,4-dimethyl-1H-indol-3-ylmethyl)-2-oxo-2,3-dihydro-benzimidazol-1-yl]-propionic acid;

3-[3-(1,4-Dimethyl-1H-indol-3-ylmethyl)-2-oxo-2,3-dihydro-benzimidazol-1-yl]-2-hydroxymethyl-propionic acid;

3-[2-Oxo-3-(1,4,6-trimethyl-1H-indol-3-ylmethyl)-2,3-dihydro-benzimidazol-1-yl]-2-pyridin-3-yl-propionic acid;

(R)-3-[6-Cyano-2-oxo-3-(1,4,6-trimethyl-1H-indol-3-ylmethyl)-2,3-dihydro-benzimidazol-1-yl]-phenyl-propionic acid;

(R)-3-[6-Carbamoyl-2-oxo-3-(1,4,6-trimethyl-1H-indol-3-ylmethyl)-2,3-dihydro -benzimidazol-1-yl]-3-phenyl-propionic acid;

(R)-3-[6-Cyano-2-oxo-3-(1,4,6-trimethyl-1H-indol-3-ylmethyl)-2,3-dihydro-benzimidazol-1-yl]-3-(4-fluoro-phenyl)-propionic acid;

(R)-3-[6-Cyano-2-oxo-3-(1,4,5-trimethyl-1H-indol-3-ylmethyl)-2,3-dihydro-benzimidazol-1-yl]-3-(4-fluoro-phenyl)-propionic acid;

or the pharmaceutically acceptable salts thereof.

2. A pharmaceutical composition comprising a therapeutically effective amount of a compound according to claim 1 and one or more pharmaceutically acceptable carries and/or adjuvants.

\* \* \* \* \*